United States Patent
Abudayyeh et al.

(10) Patent No.: US 11,952,571 B2
(45) Date of Patent: *Apr. 9, 2024

(54) SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

(71) Applicant: Massachusetts Institute of Technology, Cambridge, MA (US)

(72) Inventors: Omar Abudayyeh, Cambridge, MA (US); Jonathan Gootenberg, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/487,744

(22) Filed: Oct. 16, 2023

(65) Prior Publication Data

US 2024/0067961 A1    Feb. 29, 2024

Related U.S. Application Data

(63) Continuation of application No. 18/066,223, filed on Dec. 14, 2022, now Pat. No. 11,827,881, which is a continuation of application No. 17/649,308, filed on Jan. 28, 2022, now Pat. No. 11,572,556, which is a continuation of application No. 17/451,734, filed on Oct. 21, 2021, now abandoned.

(60) Provisional application No. 63/222,550, filed on Jul. 16, 2021, provisional application No. 63/094,803, filed on Oct. 21, 2020.

(51) Int. Cl.
| | |
|---|---|
| *C12N 15/85* | (2006.01) |
| *A61K 31/7105* | (2006.01) |
| *C12N 9/12* | (2006.01) |
| *C12N 9/22* | (2006.01) |
| *C12N 15/10* | (2006.01) |
| *C12N 15/11* | (2006.01) |
| *C12N 15/113* | (2010.01) |
| *C12N 15/90* | (2006.01) |

(52) U.S. Cl.
CPC ........ *C12N 15/111* (2013.01); *A61K 31/7105* (2013.01); *C12N 9/1276* (2013.01); *C12N 9/22* (2013.01); *C12N 15/102* (2013.01); *C12N 15/113* (2013.01); *C12N 15/85* (2013.01); *C12N 15/907* (2013.01); *C12N 2310/20* (2017.05); *C12N 2310/3519* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 9,023,649 B2 | 5/2015 | Mali et al. | |
| 9,914,939 B2 | 3/2018 | Church et al. | |
| 10,113,163 B2 | 10/2018 | Liu et al. | |
| 10,125,361 B2 | 11/2018 | May et al. | |
| 11,193,123 B2 | 12/2021 | Halperin | |
| 11,299,731 B1 | 4/2022 | Held | |
| 11,352,623 B2 | 6/2022 | Halperin | |
| 11,447,770 B1 | 9/2022 | Liu et al. | |
| 11,572,556 B2 | 2/2023 | Abudayyeh | |
| 2011/0059502 A1 | 3/2011 | Chalasani | |
| 2014/0186958 A1 | 7/2014 | Zhang et al. | |
| 2014/0349400 A1 | 11/2014 | Noah et al. | |
| 2015/0071898 A1 | 3/2015 | Liu et al. | |
| 2018/0230464 A1 | 8/2018 | Zhong | |
| 2019/0055543 A1 | 2/2019 | Tran et al. | |
| 2019/0062734 A1 | 2/2019 | Cotta-Ramusino et al. | |
| 2019/0330619 A1 | 10/2019 | Smith et al. | |
| 2020/0109398 A1 | 4/2020 | Rubens | |
| 2022/0119848 A1 | 4/2022 | Doudna | |
| 2022/0145293 A1 | 5/2022 | Abudayyeh et al. | |
| 2022/0154224 A1 | 5/2022 | Abudayyeh et al. | |
| 2023/0135673 A1 | 5/2023 | Abudayyeh et al. | |
| 2023/0279391 A1 | 9/2023 | Abudayyeh et al. | |

FOREIGN PATENT DOCUMENTS

| | | | |
|---|---|---|---|
| WO | 2015035139 A2 | 3/2015 | |
| WO | 2015195798 A1 | 12/2015 | |
| WO | 2016205728 A1 | 12/2016 | |
| WO | 2017151719 A1 | 9/2017 | |

(Continued)

OTHER PUBLICATIONS

Anzalone, A., et al., "Programmable deletion, replacement, integration and inversion of large DNA sequences with twin prime editing," Nat. Biotechnol., 2022, 40(5):731-740.

(Continued)

*Primary Examiner* — Celine X Qian
(74) *Attorney, Agent, or Firm* — Lathrop GPM LLP; Laura A. Labeots

(57) ABSTRACT

This disclosure provides systems, methods, and compositions for site-specific genetic engineering using Programmable Addition via Site-Specific Targeting Elements (PASTE). PASTE comprises the addition of an integration site into a target genome followed by the insertion of one or more genes of interest or one or more nucleic acid sequences of interest at the site. PASTE combines gene editing technologies and integrase technologies to achieve unidirectional incorporation of genes in a genome for the treatment of diseases and diagnosis of disease.

25 Claims, 145 Drawing Sheets

Specification includes a Sequence Listing.

(56) References Cited

FOREIGN PATENT DOCUMENTS

| | | |
|---|---|---|
| WO | 2018049161 A1 | 3/2018 |
| WO | 2018049168 A1 | 3/2018 |
| WO | 20180165629 A1 | 9/2018 |
| WO | 2019051097 A1 | 3/2019 |
| WO | 2019118935 A1 | 6/2019 |
| WO | 2020047124 A1 | 3/2020 |
| WO | 2020191153 A2 | 9/2020 |
| WO | 2020191171 A1 | 9/2020 |
| WO | 2020191233 A1 | 9/2020 |
| WO | 2020191234 A1 | 9/2020 |
| WO | 2020191239 A1 | 9/2020 |
| WO | 2020191242 A1 | 9/2020 |
| WO | 2020191243 A1 | 9/2020 |
| WO | 2020191245 A1 | 9/2020 |
| WO | 2020191246 A1 | 9/2020 |
| WO | 2020191248 A1 | 9/2020 |
| WO | 2020191249 A1 | 9/2020 |
| WO | 2020247587 A1 | 12/2020 |
| WO | 2021046243 A2 | 3/2021 |
| WO | 2021072328 A1 | 4/2021 |
| WO | 2021138469 A1 | 7/2021 |
| WO | 2021188840 A1 | 9/2021 |
| WO | 2021226558 A1 | 11/2021 |
| WO | 2022067130 A2 | 3/2022 |
| WO | 2022087235 A1 | 4/2022 |
| WO | 2022098885 A1 | 5/2022 |

OTHER PUBLICATIONS

Chen, P., et al., "Enhanced prime editing systems by manipulating cellular determinants of editing outcomes," Cell, 2021, 184(22):5635-5652.e29.

Guilinger, J., et al., "Fusion of catalytically inactive Cas9 to FokI nuclease improves the specificity of genome modification," Nat. Biotechnol., 2014, 32(6):577-582.

Halperin, S., et al., "CRISPR-guided DNA polymerases enable diversification of all nucleotides in a tunable window," Nature, 2018, 560(7717):248-252. doi: 10.1038/s41586-018-0384-8.

Ioannidi, E., et al., "Drag-and-drop genome insertion without DNA cleavage with CRISPR-directed integrases," bioRxiv, 2021. doi: 10.1101/2021.11.01.466786.

Jiang, T., et al., "Deletion and replacement of long genomic sequences using prime editing," Nat. Biotechnol., 2022, 40(2):227-234.

Krzywkowski, T., et al., "Limited reverse transcriptase activity of phi29 DNA polymerase," Nucleic Acids Res., 2018, 46(7):3625-3632.

Lee, H. K., et al., "Simultaneous targeting of linked loci in mouse embryos using base editing," Sci. Rep., 2019, 9(1):1662.

Lin, Q., et al., "High-efficiency prime editing with optimized, paired pegRNAs in plants," Nat. Biotechnol., 2021, 39(8):923-927.

Marzec, M., et al., "Prime Editing: A New Way for Genome Editing," Trends Cell Biol., 2020, 30(4):257-259.

Mohr, G., et al., "A Reverse Transcriptase-Cas1 Fusion Protein Contains a Cas6 Domain Required for Both Crispr RNA Biogenesis and RNA Spacer Acquisition," Molecular Cell, 2018, 72(4):700-714, available at https://doi.org/10.1016/j.molcel.2018.09.013.

Nelson, J., et al., "Engineered pegRNAs improve prime editing efficiency," Nat. Biotechnol., 2022, 40(3):402-410. https://doi.org/10.1038/s41587-021-01039-7.

Pallarès-Masmitjà, M., et al., "Find and cut-and-transfer (FiCAT) mammalian genome engineering," Nat. Commun., 2021, 12(1):7071. https://doi.org/10.1038/s41467-021-27183-x.

Ran, F. A., et al., "Double Nicking by RNA-Guided CRISPR Cas9 for Enhanced Genome Editing Specificity," Cell, 2013, 154(6):1380-89.

Sharon, E., et al., "Functional Genetic Variants Revealed by Massively Parallel Precise Genome Editing," Cell, 2018, 175(2):544-557.e16.

Su, Y., et al., "Human DNA polymerase n has reverse transcriptase activity in cellular environments," J. Biol. Chem., 2019, 294(15):6073-6081.

Wang, J., et al., "Efficient targeted insertion of large DNA fragments without DNA donors," Nat. Methods, 2022, 19(3):331-340. https://doi.org/10.1038/s41592-022-01399-1.

Wang, Z., et al., "Optimized paired-sgRNA/Cas9 cloning and expression cassette triggers high-efficiency multiplex genome editing in kiwifruit," Plant Biotechnol. J., 2018, 16(8):1424-1433.

Xu, W., et al., "Multiplex Nucleotide Editing by High-Fidelity Cas9 Variants with Improved Efficiency in Rice," BMC Plant Biol., 2019, 19(1):511.

Yang, L., et al., "One Prime for All Editing," Cell, 2019, 179(7):1448-1450.

FLOTTE Human Gene Therapy, 2019, vol. 30, No. 2, pp. 1445-1446). (Year: 2019).

Anzalone et al., Nature 2019, vol. 576, 149-157, and methods and supplement. (Year: 2019).

Anzalone et al., Programmable Deletion, Replacement, Integration and Inversion of Large DNA Sequences with Twin Prime Editing, Nature Biotechnology, Dec. 9, 2021.

Innis et al., A Novel Bxb1 Integrase RMCE System for High Fidelity Site-Specific Integration of mAb Expression Cassette in CHO Cells, Biotechnology and BioEngineering, John Wiley, Hoboken, USA, vol. 114, No. 8, Mar. 14, 2017, pp. 1837-1846.

Merrick, et al., Serine Integrases: Advancing Synthetic Biology, ACS Synthetic Biology, vol. 7, No. 2, Jan. 9, 2018, pp. 299-310.

Lee et al., Conditional Targeting of Ispd Using Paired Cas9 Nickase and a Single DNA Template in Mice, FEBS Open Bio, vol. 4, No. 1, Jul. 1, 2014, pp. 637-642.

PCT Application No. PCT/US2021/056006, International Search Report and Written Opinion, dated Feb. 23, 2022, 20 pages.

Maeder et al., Development of a Gene-Editing Approach to Restore Vision Loss in Leber Congenital Amaurosis Type 10, Letters, Nature Medicine, 25, 229-233 (2019).

Anzalone, et al., Genome Editing with CRISPR-Cas Nucleases, Base Editors, Transposases and Prime Editors, Nat. Biotechnol. 38, 824-844 (2020).

Jiang et al., Deletion and Replacement of Long Genomic Sequences Using Prime Editing. Nat. Biotechnol. 1-8 (2021).

Hsu, P. D., Lander, E. S. & Zhang, F. Development and applications of CRISPR-Cas9 for genome engineering. Cell 157, 1262-1278 (2014).

Wright, A. V., Nuñez, J. K. & Doudna, J. A. Biology and Applications of CRISPR Systems: Harnessing Nature's Toolbox for Genome Engineering. Cell 164, 29-44 (2016).

Nami, F. et al. Strategies for In Vivo Genome Editing in Nondividing Cells. Trends Biotechnol. 36, 770-786 (2018).

Suzuki, K et al. In vivo genome editing via CRISPR/Cas9 mediated homology-independent targeted integration. Nature 540, 144-149 (2016).

Mali, P. et al. RNA-guided human genome engineering via Cas9. Science 339, 823-826 (2013).

Cong, L. et al. Multiplex genome engineering using CRISPR/Cas systems. Science 339, 819-823 (2013).

Rouet, P., Smih, F. & Jasin, M. Introduction of double-strand breaks into the genome of mouse cells by expression of a rare-cutting endonuclease. Mol. Cell. Biol. 14, 8096-8106 (1994).

Rudin, N., Sugarman, E. & Haber, J. E. Genetic and physical analysis of double-strand break repair and recombination in *Saccharomyces cerevisiae*. Genetics 122, 519-534 (1989).

Chapman, J. R., Taylor, M. R. G. & Boulton, S. J. Playing the end game: DNA double—strand break repair pathway choice. Mol. Cell 47, 497-510 (2012).

Geisinger, J. M. & Stearns, T. CRISPR/Cas9 treatment causes extended TP53-dependent cell cycle arrest in human cells. Nucleic Acids Res. 48, 9067-9081 (2020).

Wang, H. et al. Development of a Self-Restricting CRISPR-Cas9 System to Reduce Off-Target Effects. Mol Ther Methods Clin Dev 18, 390-401 (2020).

Kanca, O. et al. An efficient CRISPR-based strategy to insert small and large fragments of DNA using short homology arms. Elife 8, (2019).

(56) References Cited

OTHER PUBLICATIONS

Gaudelli, N. M. et al. Programmable base editing of A·T to G·C in genomic ONA without DNA cleavage. Nature 551, 464-471 (2017).
Komor, A. C., Kim, Y. B., Packer, M. S., Zuris, J. A. & Liu, D. R. Programmable editing of a target base in genomic DNA without double-stranded DNA cleavage. Nature 533, 420-424 (2016).
Rees, H. A. & Liu, D. R. Base editing: precision chemistry on the genome and transcriptome of living cells. Nat. Rev. Genet. 19, 770-788 (2018).
Anzalone, A. V. et al. Search-and-replace genome editing without double-strand breaks or donor DNA. Nature 576, 149-157 (2019).
Ivics, Z., Hackett, P. B., Plasterk, R. H. & Izsvák, Z. Molecular reconstruction of Sleeping Beauty, a Tc1-like transposon from fish, and its transposition in human cells. Cell 91, 501-510 (1997).
Choi, J. et al. Precise genomic deletions using paired prime editing. Nat. Biotechnol. 1-9 (2021).
Calos, M. P. The C31 Integrase System for Gene Therapy. Curr. Gene Ther. 6, 633-645 (2006).
Mulholland, C. B. et al. A modular open platform for systematic functional studies under physiological conditions. Nucleic Acids Res. 43, e112 (2015).
Ehrhardt, A., Engler, J. A., Xu, H., Cherry, A. M. & Kay, M. A. Molecular Analysis of Chromosomal Rearrangements in Mammalian Cells After øC31-Mediated Integration. Hum. Gene Ther. 17, 1077-1094 (2006).
Liu, J., Jeppesen, I., Nielsen, K. & Jensen, T. G. Phi c31 integrase induces chromosomal aberrations in primary human fibroblasts. Gene Ther. 13, 1188-1190 (2006).
Kovac, A. et al. RNA-guided retargeting of Sleeping Beauty transposition in human cells. Elife 9, (2020).
Ma, S. et al. Enhancing site-specific DNA integration by a Cas9 nuclease fused with a DNA donor-binding domain. Nucleic Acids Res. 48, 10590-10601 (2020).
Chen, S. P. & Wang, H. H. An Engineered Cas-Transposon System for Programmable and Site-Directed DNA Transpositions. CRISPR J 2, 376-394 (2019).
Bhatt, S. & Chalmers, R. Targeted DNA transposition using a dCas9-transposase fusion protein. bioRxiv 571653 (2019) doi:10.1101/571653.
Hew, B. E., Sato, R., Mauro, D., Stoytchev, I. & Owens, J. B. RNA-guided piggyBac transposition in human cells. Synth. Biol. 4, ysz018 (2019).
Chaikind, B., Bessen, J. L., Thompson, D. B., Hu, J. H. & Liu, D. R. A programmable Cas9-serine recombinase fusion protein that operates on DNA sequences in mammalian cells. Nucleic Acids Res. 44, 9758-9770 (2016).
Akopian, A., He, J., Boocock, M. R. & Stark, W. M. Chimeric recombinases with designed DNA sequence recognition. Proc. Natl. Acad. Sci. U. S. A. 100, 8688-8691 (2003).
Gordley, R. M., Smith, J. D., Gräslund, T. & Barbas, C. F., 3rd. Evolution of programmable zinc finger-recombinases with activity in human cells. J. Mol. Biol. 367, 802-813 (2007).
Mercer, A. C., Gaj, T., Fuller, R. P. & Barbas, C. F., 3rd. Chimeric TALE recombinases with programmable DNA sequence specificity. Nucleic Acids Res. 40, 11163-11172 (2012).
Gersbach, C. A., Gaj, T., Gordley, R. M., Mercer, A. C. & Barbas, C. F. Targeted plasmid integration into the human genome by an engineered zinc-finger recombinase. Nucleic Acids Res. 39, 7868-7878 (2011).
Prorocic, M. M. et al. Zinc-finger recombinase activities in vitro. Nucleic Acids Res. 39, 9316-9328 (2011).
Zhang, Q., Azarin, S. M. & Sarkar, C. A. Model-guided engineering of DNA sequences with predictable site-specific recombination rates. bioRxiv 2021.08.02.454698 (2021) doi:10.1101/2021.08.02.454698.
Peters, J. E., Makarova, K. S., Shmakov, S. & Koonin, E. V. Recruitment of CRISPR-Cas systems by Tn7-like transposons. Proc. Natl. Acad. Sci. U. S. A. 114, E7358-E7366 (2017).

Strecker, J. et al. RNA-guided DNA insertion with CRISPR-associated transposases. Science (2019) doi:10.1126/science.aax9181.
Klompe, S. E., Vo, P. L. H., Halpin-Healy, T. S. & Sternberg, S. H. Transposon-encoded CRISPR-Cas systems direct RNA-guided DNA integration. Nature 1 (2019).
Xu, Z. et al. Accuracy and efficiency define Bxb1 integrase as the best of fifteen candidate serine recombinases for the integration of DNA into the human genome. BMC Biotechnol. 13, 87 (2013).
Kay, M. A., He, C.-Y. & Chen, Z.-Y. A robust system for production of minicircle DNA vectors. Nat. Biotechnol. 28, 1287-1289 (2010).
Oscorbin, I. P., Wong, P. F., Boyarskikh, U. A., Khrapov, E. A. & Filipenko, M. L. The attachment of a DNA-binding Sso7d-like protein improves processivity and resistance to inhibitors of M-MuLV reverse transcriptase. FEBS Lett. 594, 4338-4356 (2020).
Ghosh, P., Kim, A. I. & Hatfull, G. F. The orientation of mycobacteriophage Bxb1 integration is solely dependent on the central dinucleotide of attP and attB. Mol. Cell 12, 1101-1111 (2003).
Keravala, A. et al. A diversity of serine phage integrases mediate site-specific recombination in mammalian cells. Molecular Genetics and Genomics vol. 276 (2006).
Singh, S., Ghosh, P. & Hatfull, G. F. Attachment site selection and identity in Bxb1 serine integrase-mediated site-specific recombination. PLoS Genet. 9, e1003490 (2013).
Jusiak, B. et al. Comparison of Integrases Identifies Bxb1-GA Mutant as the Most Efficient Site-Specific Integrase System in Mammalian Cells. ACS Synth. Biol. 8, 16-24 (2019).
Schwinn, M. K et al. CRISPR-Mediated Tagging of Endogenous Proteins with a Luminescent Peptide. ACS Chem. Biol. 13, 467-474 (2018).
Lin, S., Staahl, B. T., Alla, R. K. & Doudna, J. A. Enhanced homology-directed human genome engineering by controlled timing of CRISPR/Cas9 delivery. Elife 3, e04766 (2014).
Schnepp, B. C., Jensen, R. L., Chen, C.-L., Johnson, P. R. & Clark, K. R. Characterization of adeno-associated virus genomes isolated from human tissues. J. Virol. 79, 14793-14803 (2005).
Wold, W. S. M. & Toth, K. Adenovirus vectors for gene therapy, vaccination and cancer gene therapy. Curr. Gene Ther. 13, 421-433 (2013).
Wesselhoeft, R. A., Kowalski, P. S. & Anderson, D. G. Engineering circular RNA for potent and stable translation in eukaryotic cells. Nat. Commun. 9, 2629 (2018).
Azuma, H. et al. Robust expansion of human hepatocytes in Fah-/-/Rag2-/-/112rg-/- mice. Nat. Biotechnol. 25, 903-910 (2007).
Bateman, A. et al. UniProt: the universal protein knowledgebase in 2021. Nucleic Acids Res. (2020).
Amberger, J. S., Bocchini, C. A., Schiettecatte, F., Scott, A. F. & Hamosh, A. OMIM.org: Online Mendelian Inheritance in Man (OMIMQ®), an online catalog of human genes and genetic disorders. Nucleic Acids Res. 43, D789-98 (2015).
Ruan, J. et al. Efficient Gene Editing at Major CFTR Mutation Loci. Mol. Ther. Nucleic Acids 16, 73-81 (2019).
Mackay, D. S. et al. Screening of a large cohort of leber congenital amaurosis and retinitis pigmentosa patients identifies novel LCA5 mutations and new genotype-phenotype correlations. Hum. Mutat. 34, 1537-1546 (2013).
Marson, F. A. L., Bertuzzo, C. S. & Ribeiro, J. D. Classification of CFTR mutation classes. The Lancet. Respiratory medicine vol. 4 e37-e38 (2016).
Eyquem, J. et al. Targeting a CAR to the TRAC locus with CRISPR/Cas9 enhances tumour rejection. Nature 543, 113-117 (2017).
Tareen, A. & Kinney, J. B. Logomaker: beautiful sequence logos in Python. Bioinformatics 36, 2272-2274 (2020).
Su, Q., Sena-Esteves, M. & Gao, G. Purification of the recombinant Adenovirus by cesium chloride gradient centrifugation. Cold Spring Harb. Protoc. 2019, db.prot095547 (2019).
Brown et al., "Serine recombinases as tools for genome engineering." Methods, 2011; 53(4):372-9.
Hirano et al., "Site-specific recombinases as tools for heterologous gene integration." Appl. Microbiol. Biotechnol. 2011; 92(2):227-39.

(56) References Cited

OTHER PUBLICATIONS

Chavez and Calos, "Therapeutic applications of the ΦC31 integrase system." Curr. Gene Ther. 2011; 11(5):375-81.
Turan and Bode, "Site-specific recombinases: from tag-and-target-to tag-and-exchange-based genomic modifications." FASEB J. 2011; 25(12):4088-107.
Venken and Bellen, "Genome-wide manipulations of Drosophila melanogaster with transposons, Flp recombinase, and ΦC31 integrase." Methods Mol. Biol. 2012; 859:203-28.
Murphy, "Phage recombinases and their applications." Adv. Virus Res. 2012; 83:367-414.
Zhang et al., "Conditional gene manipulation: Creating a new biological era." J. Zhejiang Univ. Sci. B. 2012; 13(7):511-24.
Karpenshif and Bernstein, "From yeast to mammals: recent advances in genetic control of homologous recombination." DNA Repair (Amst). 2012; 1; 11(10):781-8.
Groth et al., "Phage integrases: biology and applications." J. Mol. Biol. 2004; 335, 667-678.
Gordley et al., "Synthesis of programmable integrases." Proc. Natl. Acad. Sci. USA. 2009; 106, 5053-5058.
Moss, W. N. et al., RNA Biol. 2011, 8(5), 714-718.
Burke, W. D. et al., Molecular Biology and Evolution 2003, 20(8), 1260-1270).
Wang et al., 2010, Genome Res. 20, 19-27.
Bannert and Kurth, 2006, Proc. Natl. Acad. USA 101, 14572-14579.
Lander et al., 2001, Nature 409, 860-921; Hua-Van et al., 2011, Biol. Dir. 6, 19.
Graham et al. (1973) Virology, 52: 456.
Anzalone et al., Programmable Large DNA Deletion, Replacement, Integration, and Inversion with Twin Prime Editing and Site-Specific Recombinases, https://doi.org/10.1101/2021.11.01.466790.
Gaj, et al., Genome-Editing Technologies: Principles and Applications, Cold Spring Harbor Perspectives in Biology 2016;8:a023754.
Ata-Abadi, "Construction of a new minicircle DNA carrying an enhanced green florescent protein reporter gene for efficient expression into mammalian cell lines", Mol. Biol. Rep., 2015, 42: 1175-1185.

PASTE ACTB (cytoskeletal) literature
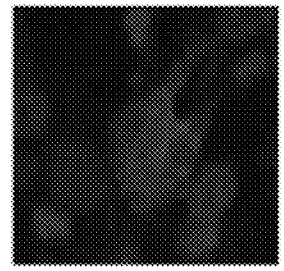 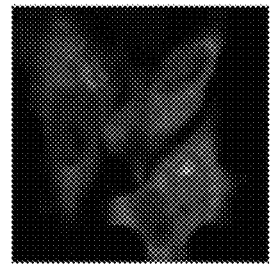
SUPT16H (nucleus)
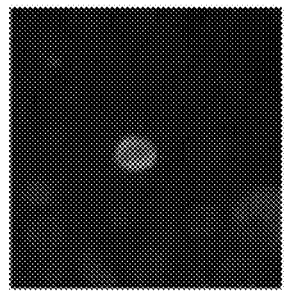 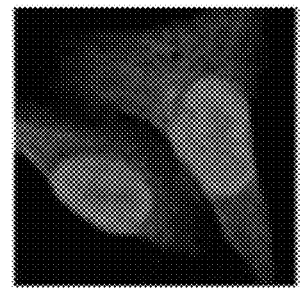
FIG. 28A PASTE  literature
NOLC1 (fibrillar center)
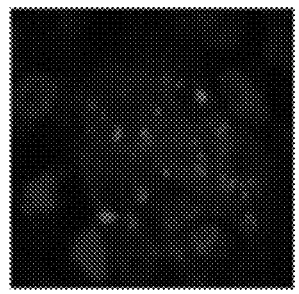 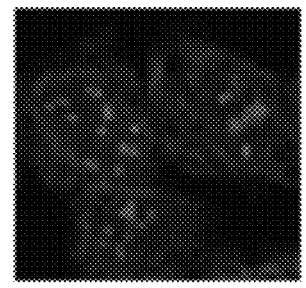
SRRM2 (nuclear speckles)
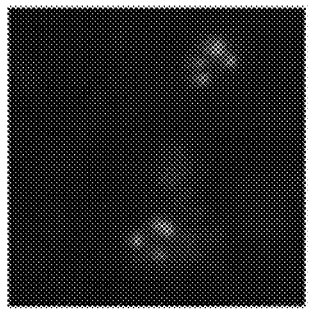 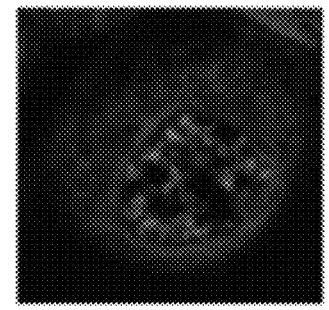
FIG. 28B PASTE literature
LMNB1 (nuclear membrane)
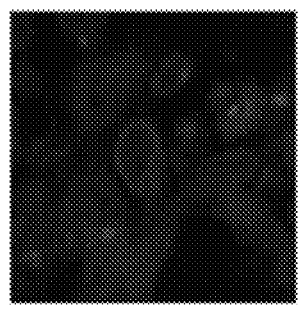 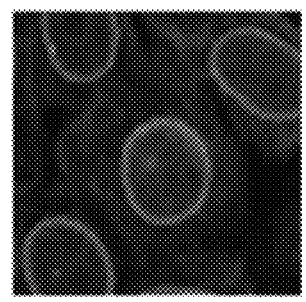
DEPDC4 (aggresome)
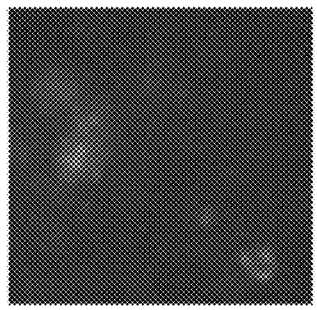 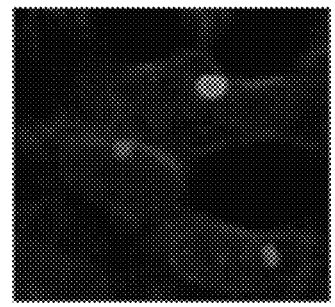
FIG. 28C

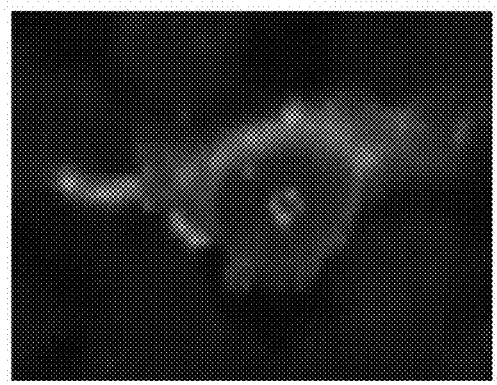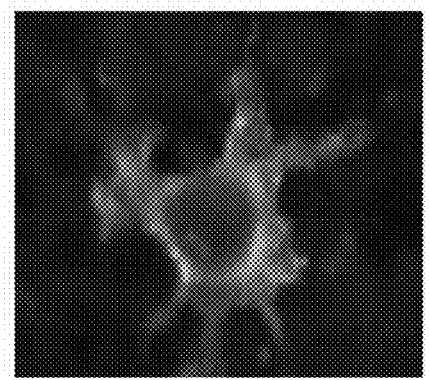
FIG. 28F

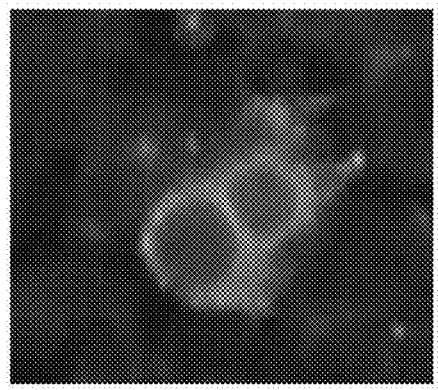 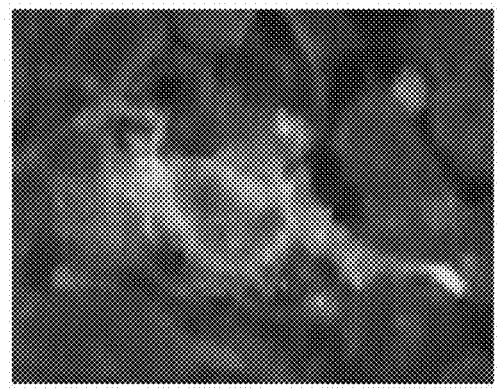
FIG. 28G

PASTE pegRNA Design
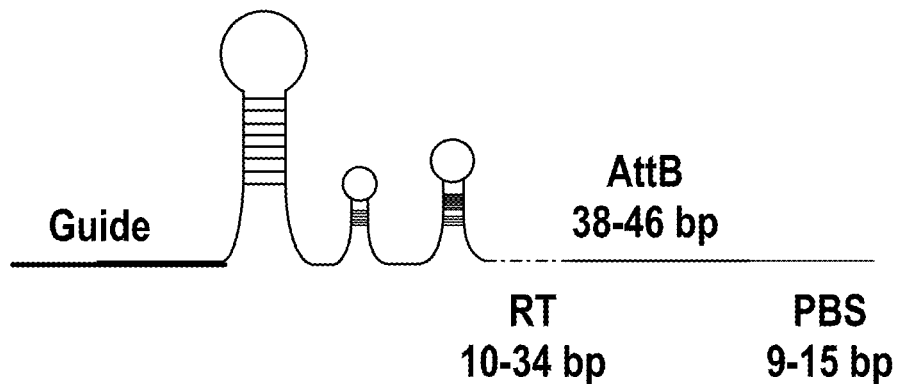
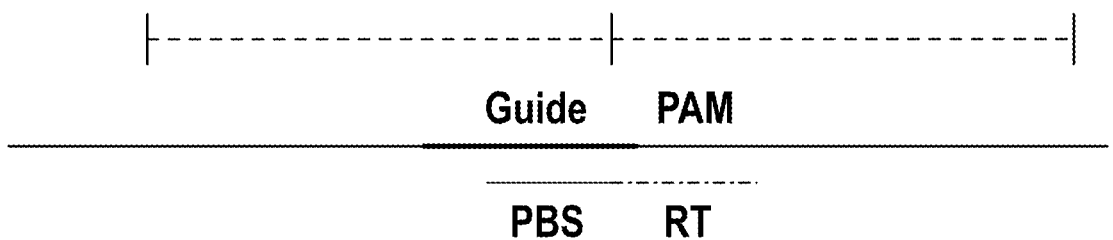
Target Considerations
FIG. 31A

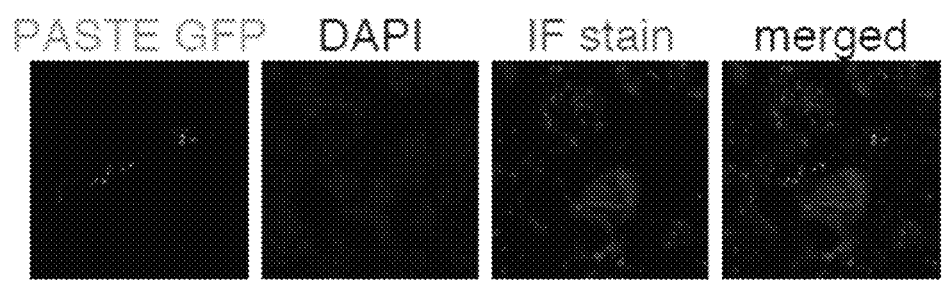
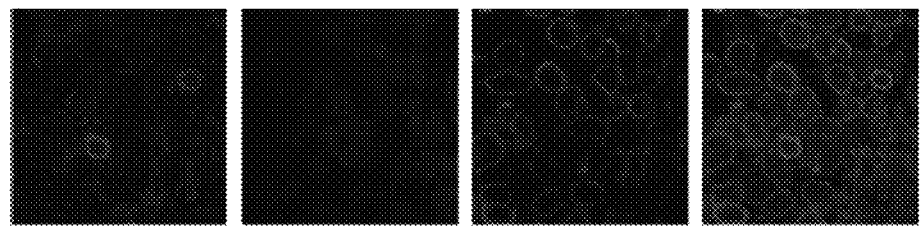
FIG. 34E

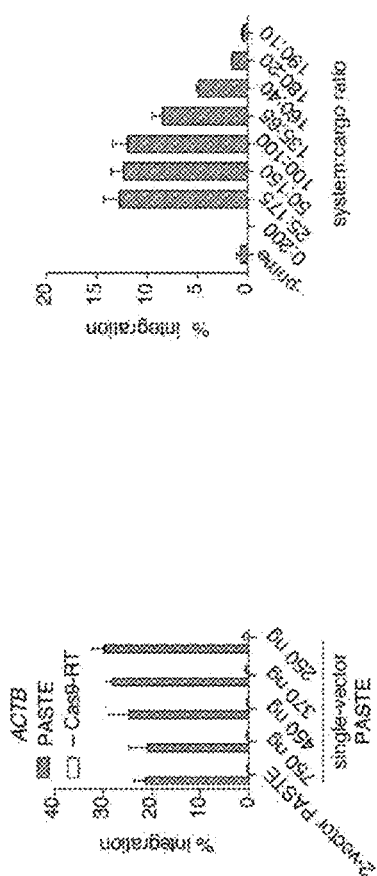
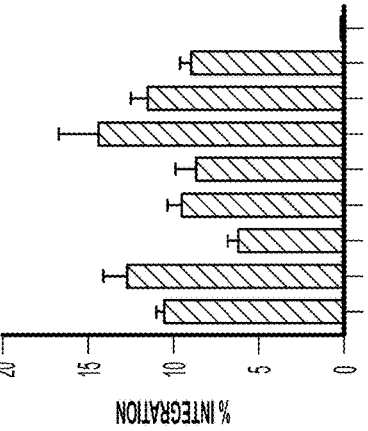

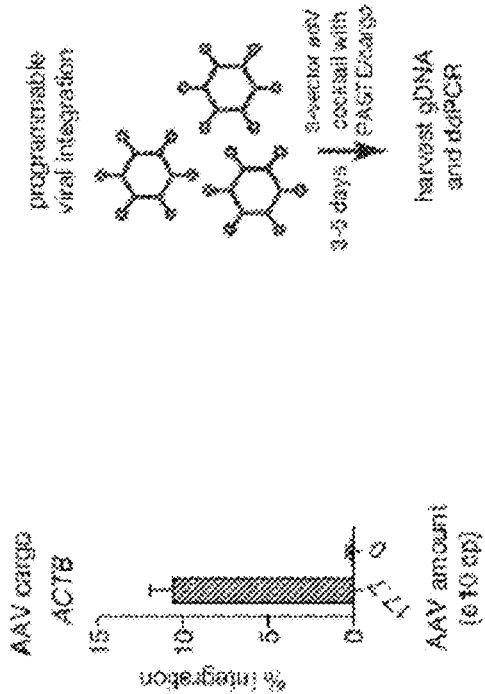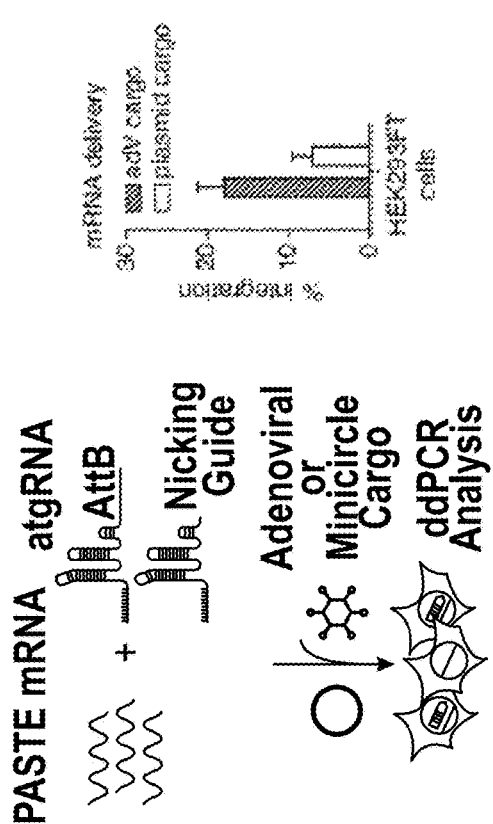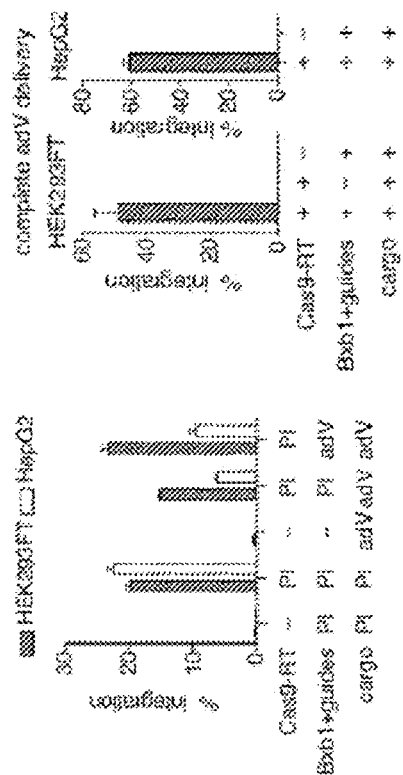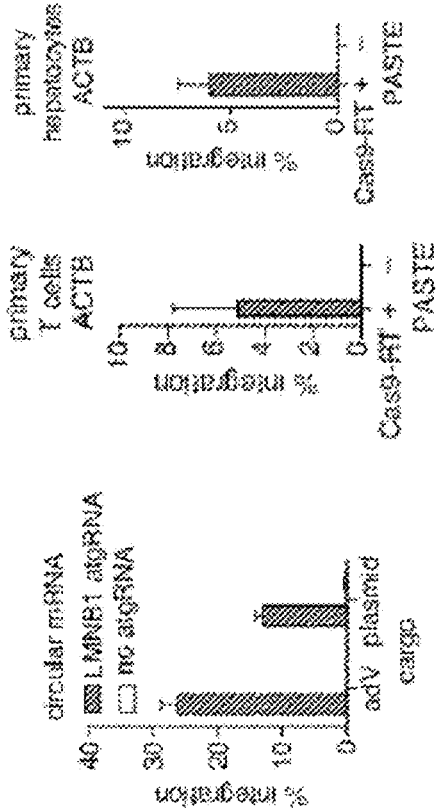

```
SEQUENCE LISTING

Sequence total quantity: 431
SEQ ID NO: 1            moltype = DNA  length = 34
FEATURE                 Location/Qualifiers
misc_feature            1..34
                        note = Description of Artificial Sequence: Synthetic
                        oligonucleotide
misc_feature            1..34
                        note = Lox71
source                  1..34
                        mol_type = other DNA
                        organism = synthetic construct
SEQUENCE: 1
ataacttcgt ataatgtatg ctatacgaac ggta                                   34

SEQ ID NO: 2            moltype = DNA  length = 34
FEATURE                 Location/Qualifiers
misc_feature            1..34
                        note = Description of Artificial Sequence: Synthetic
                        oligonucleotide
misc_feature            1..34
                        note = Lox66
source                  1..34
                        mol_type = other DNA
                        organism = synthetic construct
SEQUENCE: 2
taccgttcgt ataatgtatg ctatacgaag ttat                                   34

SEQ ID NO: 3            moltype = DNA  length = 46
FEATURE                 Location/Qualifiers
misc_feature            1..46
                        note = Description of Artificial Sequence: Synthetic
                        oligonucleotide
misc_feature            1..46
                        note = AttB
source                  1..46
```

```
                            mol_type = other DNA
                            organism = synthetic construct
SEQUENCE: 3
ggccggcttg tcgacgacgg cggtctccgt cgtcaggatc atccgg          46

SEQ ID NO: 4               moltype = DNA  length = 46
FEATURE                    Location/Qualifiers
misc_feature               1..46
                           note = Description of Artificial Sequence: Synthetic
                             oligonucleotide
misc_feature               1..46
                           note = AttP
source                     1..46
                           mol_type = other DNA
                           organism = synthetic construct
SEQUENCE: 4
ccggatgatc ctgacgacgg agaccgccgt cgtcgacaag ccggcc          46

SEQ ID NO: 5               moltype = DNA  length = 38
FEATURE                    Location/Qualifiers
misc_feature               1..38
                           note = Description of Artificial Sequence: Synthetic
                             oligonucleotide
misc_feature               1..38
                           note = AttB-TT
source                     1..38
                           mol_type = other DNA
                           organism = synthetic construct
SEQUENCE: 5
ggcttgtcga cgacggcgtt ctccgtcgtc aggatcat                   38

SEQ ID NO: 6               moltype = DNA  length = 52
FEATURE                    Location/Qualifiers
misc_feature               1..52
                           note = Description of Artificial Sequence: Synthetic
                             oligonucleotide
misc_feature               1..52
                           note = AttP-TT
source                     1..52
                           mol_type = other DNA
                           organism = synthetic construct
SEQUENCE: 6
gtggtttgtc tggtcaacca ccgcgttctc agtggtgtac ggtacaaacc ca   52

SEQ ID NO: 7               moltype = DNA  length = 38
FEATURE                    Location/Qualifiers
misc_feature               1..38
                           note = Description of Artificial Sequence: Synthetic
                             oligonucleotide
misc_feature               1..38
                           note = AttB-AA
source                     1..38
                           mol_type = other DNA
                           organism = synthetic construct
SEQUENCE: 7
ggcttgtcga cgacggcgaa ctccgtcgtc aggatcat                   38

SEQ ID NO: 8               moltype = DNA  length = 52
FEATURE                    Location/Qualifiers
misc_feature               1..52
                           note = Description of Artificial Sequence: Synthetic
                             oligonucleotide
misc_feature               1..52
                           note = AttP-AA
source                     1..52
                           mol_type = other DNA
                           organism = synthetic construct
SEQUENCE: 8
gtggtttgtc tggtcaacca ccgcgaactc agtggtgtac ggtacaaacc ca   52

SEQ ID NO: 9               moltype = DNA  length = 38
FEATURE                    Location/Qualifiers
misc_feature               1..38
                           note = Description of Artificial Sequence: Synthetic
                             oligonucleotide
misc_feature               1..38
                           note = AttB-CC
source                     1..38
                           mol_type = other DNA
```

```
                        organism = synthetic construct
SEQUENCE: 9
ggcttgtcga cgacggcgcc ctccgtcgtc aggatcat                          38

SEQ ID NO: 10           moltype = DNA   length = 52
FEATURE                 Location/Qualifiers
misc_feature            1..52
                        note = Description of Artificial Sequence: Synthetic
                         oligonucleotide
misc_feature            1..52
                        note = AttP-CC
source                  1..52
                        mol_type = other DNA
                        organism = synthetic construct
SEQUENCE: 10
gtggtttgtc tggtcaacca ccgcgccctc agtggtgtac ggtacaaacc ca          52

SEQ ID NO: 11           moltype = DNA   length = 38
FEATURE                 Location/Qualifiers
misc_feature            1..38
                        note = Description of Artificial Sequence: Synthetic
                         oligonucleotide
misc_feature            1..38
                        note = AttB-GG
source                  1..38
                        mol_type = other DNA
                        organism = synthetic construct
SEQUENCE: 11
ggcttgtcga cgacggcggg ctccgtcgtc aggatcat                          38

SEQ ID NO: 12           moltype = DNA   length = 52
FEATURE                 Location/Qualifiers
misc_feature            1..52
                        note = Description of Artificial Sequence: Synthetic
                         oligonucleotide
misc_feature            1..52
                        note = AttP-GG
source                  1..52
                        mol_type = other DNA
                        organism = synthetic construct
SEQUENCE: 12
gtggtttgtc tggtcaacca ccgcgggctc agtggtgtac ggtacaaacc ca          52

SEQ ID NO: 13           moltype = DNA   length = 38
FEATURE                 Location/Qualifiers
misc_feature            1..38
                        note = Description of Artificial Sequence: Synthetic
                         oligonucleotide
misc_feature            1..38
                        note = AttB-TG
source                  1..38
                        mol_type = other DNA
                        organism = synthetic construct
SEQUENCE: 13
ggcttgtcga cgacggcgtg ctccgtcgtc aggatcat                          38

SEQ ID NO: 14           moltype = DNA   length = 52
FEATURE                 Location/Qualifiers
misc_feature            1..52
                        note = Description of Artificial Sequence: Synthetic
                         oligonucleotide
misc_feature            1..52
                        note = AttP-TG
source                  1..52
                        mol_type = other DNA
                        organism = synthetic construct
SEQUENCE: 14
gtggtttgtc tggtcaacca ccgcgtgctc agtggtgtac ggtacaaacc ca          52

SEQ ID NO: 15           moltype = DNA   length = 38
FEATURE                 Location/Qualifiers
misc_feature            1..38
                        note = Description of Artificial Sequence: Synthetic
                         oligonucleotide
misc_feature            1..38
                        note = AttB-GT
source                  1..38
                        mol_type = other DNA
                        organism = synthetic construct
```

```
SEQUENCE: 15
ggcttgtcga cgacggcggt ctccgtcgtc aggatcat                           38

SEQ ID NO: 16           moltype = DNA  length = 52
FEATURE                 Location/Qualifiers
misc_feature            1..52
                        note = Description of Artificial Sequence: Synthetic
                          oligonucleotide
misc_feature            1..52
                        note = AttP-GT
source                  1..52
                        mol_type = other DNA
                        organism = synthetic construct
SEQUENCE: 16
gtggtttgtc tggtcaacca ccgcggtctc agtggtgtac ggtacaaacc ca           52

SEQ ID NO: 17           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-CT
source                  1..38
                        mol_type = other DNA
                        organism = synthetic construct
SEQUENCE: 17
ggcttgtcga cgacggcgct ctccgtcgtc aggatcat                           38

SEQ ID NO: 18           moltype = DNA  length = 52
FEATURE                 Location/Qualifiers
misc_feature            1..52
                        note = Description of Artificial Sequence: Synthetic
                          oligonucleotide
misc_feature            1..52
                        note = AttP-CT
source                  1..52
                        mol_type = other DNA
                        organism = synthetic construct
SEQUENCE: 18
gtggtttgtc tggtcaacca ccgcgctctc agtggtgtac ggtacaaacc ca           52

SEQ ID NO: 19           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-CA
source                  1..38
                        mol_type = other DNA
                        organism = synthetic construct
SEQUENCE: 19
ggcttgtcga cgacggcgca ctccgtcgtc aggatcat                           38

SEQ ID NO: 20           moltype = DNA  length = 52
FEATURE                 Location/Qualifiers
misc_feature            1..52
                        note = Description of Artificial Sequence: Synthetic
                          oligonucleotide
misc_feature            1..52
                        note = AttP-CA
source                  1..52
                        mol_type = other DNA
                        organism = synthetic construct
SEQUENCE: 20
gtggtttgtc tggtcaacca ccgcgcactc agtggtgtac ggtacaaacc ca           52

SEQ ID NO: 21           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-TC
source                  1..38
                        mol_type = other DNA
                        organism = synthetic construct
SEQUENCE: 21
```

```
ggcttgtcga cgacggcgtc ctccgtcgtc aggatcat                        38

SEQ ID NO: 22          moltype = DNA   length = 52
FEATURE                Location/Qualifiers
misc_feature           1..52
                       note = Description of Artificial Sequence: Synthetic
                       oligonucleotide
misc_feature           1..52
                       note = AttP-TC
source                 1..52
                       mol_type = other DNA
                       organism = synthetic construct
SEQUENCE: 22
gtggtttgtc tggtcaacca ccgcgtcctc agtggtgtac ggtacaaacc ca          52

SEQ ID NO: 23          moltype = DNA   length = 38
FEATURE                Location/Qualifiers
misc_feature           1..38
                       note = Description of Artificial Sequence: Synthetic
                       oligonucleotide
misc_feature           1..38
                       note = AttB-GA
source                 1..38
                       mol_type = other DNA
                       organism = synthetic construct
SEQUENCE: 23
ggcttgtcga cgacggcgga ctccgtcgtc aggatcat                        38

SEQ ID NO: 24          moltype = DNA   length = 52
FEATURE                Location/Qualifiers
misc_feature           1..52
                       note = Description of Artificial Sequence: Synthetic
                       oligonucleotide
misc_feature           1..52
                       note = AttP-GA
source                 1..52
                       mol_type = other DNA
                       organism = synthetic construct
SEQUENCE: 24
gtggtttgtc tggtcaacca ccgcggactc agtggtgtac ggtacaaacc ca          52

SEQ ID NO: 25          moltype = DNA   length = 38
FEATURE                Location/Qualifiers
misc_feature           1..38
                       note = Description of Artificial Sequence: Synthetic
                       oligonucleotide
misc_feature           1..38
                       note = AttB-AG
source                 1..38
                       mol_type = other DNA
                       organism = synthetic construct
SEQUENCE: 25
ggcttgtcga cgacggcgag ctccgtcgtc aggatcat                        38

SEQ ID NO: 26          moltype = DNA   length = 52
FEATURE                Location/Qualifiers
misc_feature           1..52
                       note = Description of Artificial Sequence: Synthetic
                       oligonucleotide
misc_feature           1..52
                       note = AttP-AG
source                 1..52
                       mol_type = other DNA
                       organism = synthetic construct
SEQUENCE: 26
gtggtttgtc tggtcaacca ccgcgagctc agtggtgtac ggtacaaacc ca          52

SEQ ID NO: 27          moltype = DNA   length = 38
FEATURE                Location/Qualifiers
misc_feature           1..38
                       note = Description of Artificial Sequence: Synthetic
                       oligonucleotide
misc_feature           1..38
                       note = AttB-AC
source                 1..38
                       mol_type = other DNA
                       organism = synthetic construct
SEQUENCE: 27
ggcttgtcga cgacggcgac ctccgtcgtc aggatcat                        38
```

```
SEQ ID NO: 28           moltype = DNA  length = 52
FEATURE                 Location/Qualifiers
misc_feature            1..52
                        note = Description of Artificial Sequence: Synthetic
                          oligonucleotide
misc_feature            1..52
                        note = AttP-AC
source                  1..52
                        mol_type = other DNA
                        organism = synthetic construct
SEQUENCE: 28
gtggtttgtc tggtcaacca ccgcgacctc agtggtgtac ggtacaaacc ca            52

SEQ ID NO: 29           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-AT
source                  1..38
                        mol_type = other DNA
                        organism = synthetic construct
SEQUENCE: 29
ggcttgtcga cgacggcgat ctccgtcgtc aggatcat                            38

SEQ ID NO: 30           moltype = DNA  length = 52
FEATURE                 Location/Qualifiers
misc_feature            1..52
                        note = Description of Artificial Sequence: Synthetic
                          oligonucleotide
misc_feature            1..52
                        note = AttP-AT
source                  1..52
                        mol_type = other DNA
                        organism = synthetic construct
SEQUENCE: 30
gtggtttgtc tggtcaacca ccgcgatctc agtggtgtac ggtacaaacc ca            52

SEQ ID NO: 31           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-GC
source                  1..38
                        mol_type = other DNA
                        organism = synthetic construct
SEQUENCE: 31
ggcttgtcga cgacggcggc ctccgtcgtc aggatcat                            38

SEQ ID NO: 32           moltype = DNA  length = 52
FEATURE                 Location/Qualifiers
misc_feature            1..52
                        note = Description of Artificial Sequence: Synthetic
                          oligonucleotide
misc_feature            1..52
                        note = AttP-GC
source                  1..52
                        mol_type = other DNA
                        organism = synthetic construct
SEQUENCE: 32
gtggtttgtc tggtcaacca ccgcggcctc agtggtgtac ggtacaaacc ca            52

SEQ ID NO: 33           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-CG
source                  1..38
                        mol_type = other DNA
                        organism = synthetic construct
SEQUENCE: 33
ggcttgtcga cgacggcgcg ctccgtcgtc aggatcat                            38
```

-continued

```
SEQ ID NO: 34            moltype = DNA  length = 52
FEATURE                  Location/Qualifiers
misc_feature             1..52
                         note = Description of Artificial Sequence: Synthetic
                         oligonucleotide
misc_feature             1..52
                         note = AttB-CG
source                   1..52
                         mol_type = other DNA
                         organism = synthetic construct
SEQUENCE: 34
gtggtttgtc tggtcaacca ccgcgcgctc agtggtgtac ggtacaaacc ca          52

SEQ ID NO: 35            moltype = DNA  length = 38
FEATURE                  Location/Qualifiers
misc_feature             1..38
                         note = Description of Artificial Sequence: Synthetic
                         oligonucleotide
misc_feature             1..38
                         note = AttB-TA
source                   1..38
                         mol_type = other DNA
                         organism = synthetic construct
SEQUENCE: 35
ggcttgtcga cgacggcgta ctccgtcgtc aggatcat                          38

SEQ ID NO: 36            moltype = DNA  length = 52
FEATURE                  Location/Qualifiers
misc_feature             1..52
                         note = Description of Artificial Sequence: Synthetic
                         oligonucleotide
misc_feature             1..52
                         note = AttP-TA
source                   1..52
                         mol_type = other DNA
                         organism = synthetic construct
SEQUENCE: 36
gtggtttgtc tggtcaacca ccgcgtactc agtggtgtac ggtacaaacc ca          52

SEQ ID NO: 37            moltype = DNA  length = 45
FEATURE                  Location/Qualifiers
misc_feature             1..45
                         note = Description of Artificial Sequence: Synthetic
                         oligonucleotide
misc_feature             1..45
                         note = C-31-B
source                   1..45
                         mol_type = other DNA
                         organism = synthetic construct
SEQUENCE: 37
tgcgggtgcc agggcgtgcc cttgggctcc ccgggcgcgt actcc                  45

SEQ ID NO: 38            moltype = DNA  length = 42
FEATURE                  Location/Qualifiers
misc_feature             1..42
                         note = Description of Artificial Sequence: Synthetic
                         oligonucleotide
misc_feature             1..42
                         note = C31-P
source                   1..42
                         mol_type = other DNA
                         organism = synthetic construct
SEQUENCE: 38
gtgccccaac tggggtaacc tttgagttct ctcagttggg gg                     42

SEQ ID NO: 39            moltype = DNA  length = 57
FEATURE                  Location/Qualifiers
misc_feature             1..57
                         note = Description of Artificial Sequence: Synthetic
                         oligonucleotide
misc_feature             1..57
                         note = R4-B
source                   1..57
                         mol_type = other DNA
                         organism = synthetic construct
SEQUENCE: 39
gcgcccaagt tgcccatgac catgccgaag cagtggtaga agggcaccgg cagacac     57

SEQ ID NO: 40            moltype = DNA  length = 70
```

```
FEATURE                 Location/Qualifiers
misc_feature            1..70
                        note = Description of Artificial Sequence: Synthetic
                          oligonucleotide
misc_feature            1..70
                        note = R4-P
source                  1..70
                        mol_type = other DNA
                        organism = synthetic construct
SEQUENCE: 40
aggcatgttc cccaaagcga taccacttga agcagtggta ctgcttgtgg gtacactctg    60
cgggtgatga                                                          70

SEQ ID NO: 41           moltype = DNA  length = 60
FEATURE                 Location/Qualifiers
misc_feature            1..60
                        note = Description of Artificial Sequence: Synthetic
                          oligonucleotide
misc_feature            1..60
                        note = BT1-B
source                  1..60
                        mol_type = other DNA
                        organism = synthetic construct
SEQUENCE: 41
gtccttgacc aggtttttga cgaaagtgat ccagatgatc cagctccaca ccccgaacgc    60

SEQ ID NO: 42           moltype = DNA  length = 63
FEATURE                 Location/Qualifiers
misc_feature            1..63
                        note = Description of Artificial Sequence: Synthetic
                          oligonucleotide
misc_feature            1..63
                        note = BT1-P
source                  1..63
                        mol_type = other DNA
                        organism = synthetic construct
SEQUENCE: 42
ggtgctgggt tgttgtctct ggacagtgat ccatgggaaa ctactcagca ccaccaatgt    60
tcc                                                                 63

SEQ ID NO: 43           moltype = DNA  length = 50
FEATURE                 Location/Qualifiers
misc_feature            1..50
                        note = Description of Artificial Sequence: Synthetic
                          oligonucleotide
misc_feature            1..50
                        note = Bxb-B
source                  1..50
                        mol_type = other DNA
                        organism = synthetic construct
SEQUENCE: 43
tcggccggct tgtcgacgac ggcggtctcc gtcgtcagga tcatccgggc               50

SEQ ID NO: 44           moltype = DNA  length = 58
FEATURE                 Location/Qualifiers
misc_feature            1..58
                        note = Description of Artificial Sequence: Synthetic
                          oligonucleotide
misc_feature            1..58
                        note = Bxb-P
source                  1..58
                        mol_type = other DNA
                        organism = synthetic construct
SEQUENCE: 44
gtcgtggttt gtctggtcaa ccaccgcggt ctcagtggtg tacggtacaa accccgac     58

SEQ ID NO: 45           moltype = DNA  length = 46
FEATURE                 Location/Qualifiers
misc_feature            1..46
                        note = Description of Artificial Sequence: Synthetic
                          oligonucleotide
misc_feature            1..46
                        note = TG1-B
source                  1..46
                        mol_type = other DNA
                        organism = synthetic construct
SEQUENCE: 45
gatcagctcc gcgggcaaga ccttctcctt cacggggtgg aaggtc                   46
```

```
SEQ ID NO: 46           moltype = DNA  length = 67
FEATURE                 Location/Qualifiers
misc_feature            1..67
                        note = Description of Artificial Sequence: Synthetic
                        oligonucleotide
misc_feature            1..67
                        note = TG1-P
source                  1..67
                        mol_type = other DNA
                        organism = synthetic construct
SEQUENCE: 46
tcaaccccgt tccagcccaa cagtgttagt ctttgctctt acccagttgg gcgggatagc    60
ctgcccg                                                              67

SEQ ID NO: 47           moltype = DNA  length = 57
FEATURE                 Location/Qualifiers
misc_feature            1..57
                        note = Description of Artificial Sequence: Synthetic
                        oligonucleotide
misc_feature            1..57
                        note = C1-B
source                  1..57
                        mol_type = other DNA
                        organism = synthetic construct
SEQUENCE: 47
aacgattttc aaaggatcac tgaatcaaaa gtattgctca tccacgcgaa attttc        57

SEQ ID NO: 48           moltype = DNA  length = 57
FEATURE                 Location/Qualifiers
misc_feature            1..57
                        note = Description of Artificial Sequence: Synthetic
                        oligonucleotide
misc_feature            1..57
                        note = C1-P
source                  1..57
                        mol_type = other DNA
                        organism = synthetic construct
SEQUENCE: 48
aatatttag gtatatgatt ttgtttatta gtgtaaataa cactatgtac ctaaaat        57

SEQ ID NO: 49           moltype = DNA  length = 53
FEATURE                 Location/Qualifiers
misc_feature            1..53
                        note = Description of Artificial Sequence: Synthetic
                        oligonucleotide
misc_feature            1..53
                        note = C370-B
source                  1..53
                        mol_type = other DNA
                        organism = synthetic construct
SEQUENCE: 49
tgtaaaggag actgataatg gcatgtacaa ctatactcgt cggtaaaaag gca           53

SEQ ID NO: 50           moltype = DNA  length = 52
FEATURE                 Location/Qualifiers
misc_feature            1..52
                        note = Description of Artificial Sequence: Synthetic
                        oligonucleotide
misc_feature            1..52
                        note = C370-P
source                  1..52
                        mol_type = other DNA
                        organism = synthetic construct
SEQUENCE: 50
taaaaaaata cagcgttttt catgtacaac tatactagtt gtagtgccta aa            52

SEQ ID NO: 51           moltype = DNA  length = 56
FEATURE                 Location/Qualifiers
misc_feature            1..56
                        note = Description of Artificial Sequence: Synthetic
                        oligonucleotide
misc_feature            1..56
                        note = K38-B
source                  1..56
                        mol_type = other DNA
                        organism = synthetic construct
SEQUENCE: 51
gagcgccgga tcagggagtg gacggcctgg gagcgctaca cgctgtggct gcggtc        56
```

| | |
|---|---|
| SEQ ID NO: 52 | moltype = DNA length = 56 |
| FEATURE | Location/Qualifiers |
| misc_feature | 1..56 |
| | note = Description of Artificial Sequence: Synthetic oligonucleotide |
| misc_feature | 1..56 |
| | note = K38-P |
| source | 1..56 |
| | mol_type = other DNA |
| | organism = synthetic construct |

SEQUENCE: 52
ccctaatacg caagtcgata actctcctgg gagcgttgac aacttgcgca ccctga      56

| | |
|---|---|
| SEQ ID NO: 53 | moltype = DNA length = 68 |
| FEATURE | Location/Qualifiers |
| misc_feature | 1..68 |
| | note = Description of Artificial Sequence: Synthetic oligonucleotide |
| misc_feature | 1..68 |
| | note = RB-B |
| source | 1..68 |
| | mol_type = other DNA |
| | organism = synthetic construct |

SEQUENCE: 53
tctcgtggtg gtggaaggtg ttggtgcggg gttggccgtg gtcgaggtgg ggtggtggta      60
gccattcg                                                              68

| | |
|---|---|
| SEQ ID NO: 54 | moltype = DNA length = 69 |
| FEATURE | Location/Qualifiers |
| misc_feature | 1..69 |
| | note = Description of Artificial Sequence: Synthetic oligonucleotide |
| misc_feature | 1..69 |
| | note = RV-P |
| source | 1..69 |
| | mol_type = other DNA |
| | organism = synthetic construct |

SEQUENCE: 54
gcacaggtgt agtgtatctc acaggtccac ggttggccgt ggactgctga agaacattcc      60
acgccagga                                                             69

| | |
|---|---|
| SEQ ID NO: 55 | moltype = DNA length = 65 |
| FEATURE | Location/Qualifiers |
| misc_feature | 1..65 |
| | note = Description of Artificial Sequence: Synthetic oligonucleotide |
| misc_feature | 1..65 |
| | note = SPBC-B |
| source | 1..65 |
| | mol_type = other DNA |
| | organism = synthetic construct |

SEQUENCE: 55
agtgcagcat gtcattaata tcagtacaga taaagctgta tctcctgtga acacaatggg      60
tgcca                                                                 65

| | |
|---|---|
| SEQ ID NO: 56 | moltype = DNA length = 55 |
| FEATURE | Location/Qualifiers |
| misc_feature | 1..55 |
| | note = Description of Artificial Sequence: Synthetic oligonucleotide |
| misc_feature | 1..55 |
| | note = SPBC-P |
| source | 1..55 |
| | mol_type = other DNA |
| | organism = synthetic construct |

SEQUENCE: 56
aaagtagtaa gtatcttaaa aaacagataa agctgtatat taagatactt actac      55

| | |
|---|---|
| SEQ ID NO: 57 | moltype = DNA length = 54 |
| FEATURE | Location/Qualifiers |
| misc_feature | 1..54 |
| | note = Description of Artificial Sequence: Synthetic oligonucleotide |
| misc_feature | 1..54 |
| | note = TP901-B |
| source | 1..54 |
| | mol_type = other DNA |
| | organism = synthetic construct |

SEQUENCE: 57

```
tgataattgc aacacaatt aacatctcaa tcaaggtaaa tgcttttcg tttt            54

SEQ ID NO: 58           moltype = DNA   length = 54
FEATURE                 Location/Qualifiers
misc_feature            1..54
                        note = Description of Artificial Sequence: Synthetic
                        oligonucleotide
misc_feature            1..54
                        note = TP901-P
source                  1..54
                        mol_type = other DNA
                        organism = synthetic construct
SEQUENCE: 58
aattgcgagt ttttatttcg tttatttcaa ttaaggtaac taaaaaactc cttt           54

SEQ ID NO: 59           moltype = DNA   length = 68
FEATURE                 Location/Qualifiers
misc_feature            1..68
                        note = Description of Artificial Sequence: Synthetic
                        oligonucleotide
misc_feature            1..68
                        note = Wbeta-B
source                  1..68
                        mol_type = other DNA
                        organism = synthetic construct
SEQUENCE: 59
aaggtagcgt caacgatagg tgtaactgtc gtgtttgtaa cggtacttcc aacagctggc     60
gtttcagt                                                             68

SEQ ID NO: 60           moltype = DNA   length = 68
FEATURE                 Location/Qualifiers
misc_feature            1..68
                        note = Description of Artificial Sequence: Synthetic
                        oligonucleotide
misc_feature            1..68
                        note = Wbeta-P
source                  1..68
                        mol_type = other DNA
                        organism = synthetic construct
SEQUENCE: 60
tagtttaaa gttggttatt agttactgtg atatttatca cggtacccaa taccaatga      60
atatttga                                                             68

SEQ ID NO: 61           moltype = DNA   length = 57
FEATURE                 Location/Qualifiers
misc_feature            1..57
                        note = Description of Artificial Sequence: Synthetic
                        oligonucleotide
misc_feature            1..57
                        note = A118-B
source                  1..57
                        mol_type = other DNA
                        organism = synthetic construct
SEQUENCE: 61
tgtaactttt tcggatcaag ctatgaagga cgcaaagagg gaactaaaca cttaatt       57

SEQ ID NO: 62           moltype = DNA   length = 57
FEATURE                 Location/Qualifiers
misc_feature            1..57
                        note = Description of Artificial Sequence: Synthetic
                        oligonucleotide
misc_feature            1..57
                        note = A118-P
source                  1..57
                        mol_type = other DNA
                        organism = synthetic construct
SEQUENCE: 62
ttgtttagtt cctcgttttc tctcgttgga agaagaagaa acgagaaact aaaatta       57

SEQ ID NO: 63           moltype = DNA   length = 63
FEATURE                 Location/Qualifiers
misc_feature            1..63
                        note = Description of Artificial Sequence: Synthetic
                        oligonucleotide
misc_feature            1..63
                        note = BL3-B
source                  1..63
                        mol_type = other DNA
                        organism = synthetic construct
```

```
                                   -continued
SEQUENCE: 63
caacctgttg acatgtttcc acagacaact cacgtggagg tagtcacggc ttttacgtta     60
gtt                                                                  63

SEQ ID NO: 64           moltype = DNA  length = 61
FEATURE                 Location/Qualifiers
misc_feature            1..61
                        note = Description of Artificial Sequence: Synthetic
                         oligonucleotide
misc_feature            1..61
                        note = BL3-P
source                  1..61
                        mol_type = other DNA
                        organism = synthetic construct
SEQUENCE: 64
gagaatactg ttgaacaatg aaaaactagg catgtagaag ttgtttgtgc actaacttta     60
a                                                                    61

SEQ ID NO: 65           moltype = DNA  length = 120
FEATURE                 Location/Qualifiers
misc_feature            1..120
                        note = Description of Artificial Sequence: Synthetic
                         polynucleotide
misc_feature            1..120
                        note = MR11-B
source                  1..120
                        mol_type = other DNA
                        organism = synthetic construct
SEQUENCE: 65
acaggtcaac acatcgcagt tatcgaacaa tcttcgaaaa tgtatggagg cacttgtatc     60
aatataggat gtataccttc gaagacactt gtacatgatg gattagaagg caaatccttt    120

SEQ ID NO: 66           moltype = DNA  length = 120
FEATURE                 Location/Qualifiers
misc_feature            1..120
                        note = Description of Artificial Sequence: Synthetic
                         polynucleotide
misc_feature            1..120
                        note = MR11-P
source                  1..120
                        mol_type = other DNA
                        organism = synthetic construct
SEQUENCE: 66
caaaataaaa aacattgatt tttattaact tcttttgtgc ggaactacga acagttcatt     60
aatacgaagt gtacaaactt ccatacaaaa ataaccacga caattaagac gtggtttcta   120

SEQ ID NO: 67           moltype = DNA  length = 17
FEATURE                 Location/Qualifiers
misc_feature            1..17
                        note = Description of Artificial Sequence: Synthetic
                         oligonucleotide
misc_feature            1..17
                        note = AttL
source                  1..17
                        mol_type = other DNA
                        organism = synthetic construct
SEQUENCE: 67
attatttctc accctga                                                   17

SEQ ID NO: 68           moltype = DNA  length = 17
FEATURE                 Location/Qualifiers
misc_feature            1..17
                        note = Description of Artificial Sequence: Synthetic
                         oligonucleotide
misc_feature            1..17
                        note = AttR
source                  1..17
                        mol_type = other DNA
                        organism = synthetic construct
SEQUENCE: 68
atcatctccc acccgga                                                   17

SEQ ID NO: 69           moltype = DNA  length = 34
FEATURE                 Location/Qualifiers
misc_feature            1..34
                        note = Description of Artificial Sequence: Synthetic
                         oligonucleotide
misc_feature            1..34
                        note = Vox
```

```
source                 1..34
                       mol_type = other DNA
                       organism = synthetic construct
SEQUENCE: 69
aataggtctg agaacgccca ttctcagacg tatt                              34

SEQ ID NO: 70          moltype = DNA  length = 34
FEATURE                Location/Qualifiers
misc_feature           1..34
                       note = Description of Artificial Sequence: Synthetic
                        oligonucleotide
misc_feature           1..34
                       note = FRT
source                 1..34
                       mol_type = other DNA
                       organism = synthetic construct
SEQUENCE: 70
gaagttccta tactttctag agaataggaa cttc                              34

SEQ ID NO: 71          moltype = DNA  length = 5881
FEATURE                Location/Qualifiers
misc_feature           1..5881
                       note = Description of Artificial Sequence: Synthetic
                        polynucleotide
misc_feature           1..5881
                       note = Cre Recombinase Expression Plasmid
source                 1..5881
                       mol_type = other DNA
                       organism = synthetic construct
SEQUENCE: 71
ggtcgacatt gattattgac tagttattaa tagtaatcaa ttacgggtc attagttcat    60
agcccatata tggagttccg cgttacataa cttacggtaa atggcccgcc tggctgaccg   120
cccaacgacc cccgcccatt gacgtcaata atgacgtatg ttcccatagt aacgccaata   180
gggactttcc attgacgtca atgggtggag tatttacggt aaactgccca cttggcagta   240
catcaagtgt atcatatgcc aagtacgccc cctattgacg tcaatgacgg taaatggccc   300
gcctggcatt atgcccagta catgacctta tgggactttc ctacttggca gtacatctac   360
gtattagtca tcgctattac catggtcgag gtgagcccca cgttctgctt cactctcccc   420
atctcccccc cctccccacc cccaattttg tatttattta ttttttaatt attttgtgca   480
gcgatggggg cggggggggg ggggggcgcg ccaggcggg gggggggggg ggggggggg    540
gggggggggg gggcggggg gggcggcggc agccaatcag agcggcgcgc tccgaaagtt   600
tccttttatg gcgaggcggc ggcggcggcg ccctataaa aagcgaagcg cgcggcgggc   660
gggagtcgct gcgcgctgcc ttcgccccgt gccccgctcc gccgccgcct cgcgccgccc   720
gccccggctc tgactgaccg cgttactccc acaggtgagc gggcgggacg gcccttctcc   780
tccgggctgt aattagcgct tggtttaatg acggcttgtt tcttttctgt ggctgcgtga   840
aagccttgag gggctccggg agggcccttt gtgcggggggg agcggctcgg ggggtgcgtg   900
cgtgtgtgtg tgcgtgggga gcgccgcgtg cggctccgcg ctgcccggcg gctgtgagcg   960
ctgcgggcgc ggcgcggggc tttgtgcgct ccgcagtgtg cgcgagggga gcgcggccgg  1020
gggcggtgcc ccgcggtgcg ggggggggctg cgagggaac aaaggctgcg tgcgggtgt  1080
gtgcgtgggg gggtgagcag gggtgtggg cgcgtcggtc gggctgcaac ccccctgca  1140
cccccctccc cgagttgctg agcacggccc ggcttcgggt gcgggctcc gtacggggcg  1200
tggcgcgggg ctcgccgtgc cgggcgggggg gtggccgcag gtggggtgc cggggggtgg  1260
ggggccgcct cgggccgggg agggctcggg ggaggggcgc ggcggccccc ggagcgccgg  1320
cggctgtcga ggcgcggcga gccgcagcca ttgccttta tggtaatcgt gcgagagggc  1380
gcagggactt cctttgtccc aaatctgtgc ggagccgaaa tctgggaggc gccgccgcac  1440
ccctctagc gggcgcgggg cgaagcggtg cggcgccggc aggaaggaaa tgggcgggga  1500
gggccttcgt gcgtcgccgc gccgccgtcc ccttctccct ctccagcctc ggggctgtcc  1560
gcgggggggac ggctgccttc ggggggggacg gggcagggcg gggttcggct tctggcgtgt  1620
gaccggcggc tctagagcct ctgctaacca tgttcatgcc ttcttctttt tcctacagct  1680
cctgggcaac gtgctggtta ttgtgctgtc tcatcatttt ggcaaagaat tctgagccgc  1740
caccatggcc aattactga ccgtacacca aaatttgcct gcattaccgg tcgatgcaac  1800
gagtgatgag gttcgcaaga acctgatgga catgttcagg gatcgccagg cgttttctga  1860
gcatacctgg aaaatgcttc tgtccgtttg ccggtcgtgg gcggcatggt gcaagttgaa  1920
taaccggaaa tggtttcccg cagaacctga agatgttcgc gattatcttc tatatcttca  1980
ggcgcgcggt ctggcagtaa aaactatcca gcaacatttg ggccagctaa acatgcttca  2040
tcgtcggtcc gggctgccac gaccaagtga cagcaatgct gtttcactgg ttatgcggcg  2100
gatccgaaaa gaaaacgttg atgccggtga acgtgcaaaa caggctctag cgttcgaacg  2160
cactgatttc gaccaggttc gttcactcat ggaaaatagc gatcgctgcc aggatatacg  2220
taatctggca tttctgggga ttgcttataa caccctgtta cgtatagccg aaattgccag  2280
gatcagggtt aaagatatct cacgtactga cggtgggaga tgttaatcc atattgggca  2340
aacgaaaacg ctggttagca ccgcaggtgt agagaaggca cttagcctgg ggtaactaa  2400
actggtcgag cgatggattt ccgtctctgg tgtagctgat gatccgaata actacctgtt  2460
ttgccgggtc agaaaaaatg gtgttgccgc gccatctgcc accagccagc tatcaactcg  2520
cgccctggaa gggattttg aagcaactca tcgattgatt tacggcgcta aggatgactc  2580
tggtcagaga tacctggcct ggtctggaca cagtgcccgt gtcggagccg cgcagatat  2640
ggcccgcgct ggagtttcaa taccggagat catgcaagct ggtggctgga ccaatgtaaa  2700
tattgtcatg aactatatcc gtaacctgga tagtgaaaca ggggcaatgg tgcgcctgct  2760
ggaagatggc gatggaccgg tggaacaaaa acttattct gaagaagatc tgtgatagcg  2820
gccgcactcc tcaggtgcag gctgcctatc agaaggtggt ggctggtgtg gccaatgccc  2880
tggctcacaa ataccactga atctttttc cctctgccaa aaattatggg gacatcatga  2940
```

```
agccccttga gcatctgact tctggctaat aaaggaaatt tatttttcatt gcaatagtgt 3000
gttggaattt tttgtgtctc tcactcggaa ggacatatgg gagggcaaat catttaaaac 3060
atcagaatga gtatttggtt tagagtttgg caacatatgc ccatatgctg ctgccatga  3120
acaaaggttg gctataaaga ggtcatcagt atatgaaaca gcccctgct gtccattcct  3180
tattccatag aaaagccttg acttgaggtt agatttttt tatattttgt tttgtgttat  3240
ttttttcttt aacatcccta aaattttcct tacatgtttt actagccaga ttttttcctcc 3300
tctcctgact actcccagtc atagctgtcc ctcttctctt atggagatcc ctcgacctgc 3360
agcccaagct tggcgtaatc atggtcatag ctgtttcctg tgtgaaattg ttatccgctc 3420
acaattccac acaacatacg agccggaagc ataaagtgta aagcctgggg tgcctaatga 3480
gtgagctaac tcacattaat tgcgttgcgc tcactgcccg ctttccagtc gggaaacctg 3540
tcgtgccagc ggatccgcat ctcaattagt cagcaaccat agtcccgccc ctaactccgc 3600
ccatcccgcc cctaactccg cccagttccg cccattctcc gccccatggc tgactaattt 3660
tttttattta tgcagaggcc gaggccgcct cggcctctga gctattccag aagtagtgag 3720
gaggctttt tggaggccta ggcttttgca aaaagctaac ttgtttattg cagcttataa 3780
tggttacaaa taaagcaata gcatcacaaa tttcacaaat aaagcatttt tttcactgca 3840
ttctagttgt ggtttgtcca aactcatcaa tgtatcttat catgtctgga tccgctgcat 3900
taatgaatcg gccaacgcgc ggggagaggc ggtttgcgta ttgggcgctc ttccgcttcc 3960
tcgctcactg actcgctgcg ctcggtcgtt cggctgcggc gagcggtatc agctcactca 4020
aaggcggtaa tacggttatc cacagaatca ggggataacg caggaaagaa catgtgagca 4080
aaaggccagc aaaaggccag gaaccgtaaa aaggccgcgt tgctggcgtt tttccatagg 4140
ctccgccccc ctgacgagca tcacaaaaat cgacgctcaa gtcagaggtg gcgaaacccg 4200
acaggactat aaagatacca ggcgtttccc cctggaagct ccctcgtgcg ctctcctgtt 4260
ccgaccctgc cgcttaccgg atacctgtcc gcctttctcc cttcgggaag cgtggcgctt 4320
tctcatagct cacgctgtag gtatctcagt tcggtgtagg tcgttcgctc caagctgggc 4380
tgtgtgcacg aaccccccgt tcagcccgac cgctgcgcct tatccggtaa ctatcgtctt 4440
gagtccaacc cggtaagaca cgacttatcg ccactggcag cagccactgg taacaggatt 4500
agcagagcga ggtatgtagg cggtgctaca gagttcttga agtggtggcc taactacggc 4560
tacactagaa gaacagtatt tggtatctgc gctctgctga gccagttac cttcggaaaa 4620
agagttggta gctcttgatc cggcaaacaa accaccgctg gtagcggtgg ttttttgtt  4680
tgcaagcagc agattacgcg cagaaaaaaa ggatctcaag aagatccttt gatcttttct 4740
acggggtctg acgctcagtg gaacgaaaac tcacgttaag ggattttggt catgagatta 4800
tcaaaaagga tcttcaccta gatcctttta aattaaaaat gaagttttaa atcaatctaa 4860
agtatatatg agtaaacttg gtctgacagt taccaatgct taatcagtga ggcacctatc 4920
tcagcgatct gtctatttcg ttcatccata gttgcctgac tccccgtcgt gtagataact 4980
acgatacggg agggcttacc atctggcccc agtgctgcaa tgataccgcg agacccacgc 5040
tcaccggctc cagatttatc agcaataaac cagccagccg aaggccga gcgcagaagt 5100
ggtcctgcaa ctttatccgc ctccatccag tctattaatt gttgccggga agctagagta 5160
agtagttcgc cagttaatag tttgcgcaac gttgttgcca ttgctacagg catcgtggtg 5220
tcacgctcgt cgtttggtat ggcttcattc agctccggtt cccaacgatc aaggcgagtt 5280
acatgatccc ccatgttgtg caaaaaagcg gttagctcct tcggtcctcc gatcgttgtc 5340
agaagtaagt tggccgcagt gttatactc atggttatgg cagcactgca taattctctt 5400
actgtcatgc catccgtaag atgcttttct gtgactggtg agtactcaac caagtcattc 5460
tgagaatagt gtatgcggcg accgagttgc tcttgcccgg cgtcaatacg ggataataccc 5520
gcgccacata gcagaacttt aaaagtgctc atcattggaa aacgttcttc ggggcgaaaa 5580
ctctcaagga tcttaccgct gttgagatcc agttcgatgt aacccactcg tgcacccaac 5640
tgatcttcag catcttttac tttcaccagc gtttctgggt gagcaaaaac aggaaggcaa 5700
aatgccgcaa aaaagggaat aagggcgaca cggaaatgtt gaatactcat actcttcctt 5760
tttcaatatt attgaagcat ttatcagggt tattgtctca tgagcggata catatttgaa 5820
tgtatttaga aaaataaaca aataggggtt ccgcgcacat ttccccgaaa agtgccacct 5880
g                                                                5881
```

SEQ ID NO: 72          moltype = DNA   length = 4915
FEATURE                Location/Qualifiers
misc_feature           1..4915
                       note = Description of Artificial Sequence: Synthetic
                       polynucleotide
misc_feature           1..4915
                       note = GFP-Lox66-Cre expression plasmid
source                 1..4915
                       mol_type = other DNA
                       organism = synthetic construct
SEQUENCE: 72

```
agctctgatc aagagacagg atgaggatcg tttcgcatga ttgaacaaga tggattgcac  60
gcaggttctc cggccgcttg ggtggagagg ctattcggct atgactggc acaacagaca  120
atcggctgct ctgatgccgc cgtgttccgg ctgtcagcgc aggggcgccc ggttcttttt  180
gtcaagaccg acctgtccgg tgccctgaat gaactgcaag acgaggcagc gcggctatcg  240
tggctggcca cgacgggcgt tccttgcgca gctgtgctcg acgttgtcac tgaagcggga  300
agggactggc tgctattggg cgaagtgccg gggcaggatc tcctgtcat ctacaccttg  360
ctcctgccga gaaagtatcc atcatggctg atgcaatgcg gcggctgcat acgcttgatc  420
cggctacctg cccattcgac caccaagcga aacatcgcat cgagcgagca cgtactcgga  480
tggaagccgg tcttgtcgat caggatgatc tggacgaaga gcatcagggg ctcgcgccag  540
ccgaactgtt cgccaggctc aaggcgagca tgcccgacgg cgaggatctc gtcgtgaccc  600
atggcgatgc ctgcttgccg aatatcatgg tggaaaatgg ccgcttttct ggattcatcg  660
actgtggccg gctgggtgtg gcggaccgct atcaggacat agcgttggct acccgtgata  720
ttgctgaaga gcttggcggc gaatgggctg accgcttcct cgtgctttac ggtatcgccg  780
ctcccgattc gcagcgcatc gccttctatc gccttcttga cgagttcttc tgaattatta  840
actcgagatc cactagagtg tggcggccgc attcttataa tcagcatcat gatgtggtac  900
cacatcatga tgctgattac ccccaactga gagaactcaa aggttacccc agttggggcg  960
ggcccacaaa taaagcaata gcatcacaaa tttcacaaat aaagcatttt tttcactgca 1020
```

```
ttctagttgt ggtttgtcca aactcatcga gctcgagatc tggcgaaggc gatgggggtc    1080
ttgaaggcgt gctggtactc cacgatgccc agctcggtgt tgctgtgcag ctcctccacg    1140
cggcggaagg cgaacatggg gcccccgttc tgcaggatgc tggggtggat ggcgctcttg    1200
aagtgcatgt ggctgtccac cacgaagctg tagtagccgc cgtcgcgcag gctgaaggtg    1260
cgggcgaagc tgcccaccag cacgttatcg cccatgggtc gcaagtgctc cacggtggcg    1320
ttgctgcgga tgatcttgtc ggtgaagatc acgctgtcct cggggaagcc ggtgcccacc    1380
accttgaagt cgccgatcac gcggccggcc tcgtagcggt agctgaagct cacgtgcagc    1440
acgccgccgt cctcgtactt ctcgatgcgg gtgttggtgt agccgccgtt gttgatggcg    1500
tgcaggaagg ggttctcgta gccgctgggg taggtgccga agtggtagaa gccgtagccc    1560
atcacgtggc tcagcaggta ggggctgaag gtcagggcgc ctttggtgct cttcatcttg    1620
ttggtcatgc ggccctgctc gggggtgccc tctccgccgc ccaccagctc gaactccacg    1680
ccgttcaggg tgccggtgat gcggcactcg atcttcatgg cgggcatggt ggcgaccggt    1740
agcgctagcg gcttcggata acttcgtata gcatacatta tacgaacggt aagcgctacc    1800
gccggcatac ccaagtgaag ttgctcgcag cttatatcg cgcccgggga gcccaaggc     1860
acgccctggc accgcggccg ctgagtctcg accatcatca tcatcatcat tgagtttatc    1920
tgggataaca gggtaatgtc atctaggat aacagggtat gtcatctggg ataacagggt     1980
aatgtatcta gggataacag ggtaatgtca tctgggataa cagggtaatg tcatctaggg    2040
ataacagggt atgtcatctg ggataacagg gtaatgtatc tagggataac agggtaatgt    2100
catctgggat aacagggtaa tgtcatctag gataacagg gtatgtcatc tgggataaca     2160
gggtaatgta tctagggata acagggtaat gtcatctggg ataacagggt aatgtcatct    2220
agggataaca gggtatgtca tctggataaa cagggtaatg tatctaggga taacagggta    2280
atgtcatctg ggataacagg gtaatgtcat ctagggataa cagggtatgt catctgggat    2340
aacagggtaa tgtatctagg gataacaggg taatgtcatc tgggataaca gggtaatgtc    2400
atctagggat aacagggtat gtcatctggg ataacagggt aatgtatcta gggataacag    2460
ggtaatgtca tctgggataa cagggtaatg tcatctaggg ataacagggt aaatgtcatc    2520
tagggataac agggtaatgt catctaggga taacagggta atgtcatcag gataacagg     2580
gtaatgtcat ctagggataa cagggtaatg tatcgccagc gtcgcacagc atgtttgctt    2640
gtcgccgtcg cgtctgtcac atctttccg ccagcagtta gggattagcg tcttaagctg     2700
gcgcgaggac caacgtatca gccaggcgaa gctgcttttg agcaccaccc ggatgcctat    2760
cgccaccgtc ggtcgcaatg ttggttttga cgatcaactc tatttctcgc gggtatttaa    2820
aaaatgcacc ggggccagcc cgagcgagtt ccgtgccggt tgtgaagaaa aagtgaatga    2880
tgtagccgtc aagttgtcat aattggtaac gaatcagaca attgacggct tgacggagta    2940
gcatagggtt tgcagaatcc ctgcttcgtc catttgacag gcacattatg catgccgctt    3000
cgccttcgcg cgcgaattga tctgctgcct cgcgcgtttc ggtgatgacg gtgaaaacct    3060
ctgacacatg cagctcccgg agacggtcac agcttgtctg taagcggatg ccgggagcga    3120
acaagcccgt cagggcgcgt cagcgggtgt tggcgggtgt cggggcgcag ccatgaccca    3180
gtcacgtagc gatagcggag tgtatactgg cttaactatg cggcatcaga gcagattgta    3240
ctgagagtgc accatatgcg gtgtgaaata ccgcacagat gcgtaaggag aaaataccgc    3300
atcaggcgct cttccgcttc ctcgctcact gactcgctgc gctcggtcgt tcggctgcgg    3360
cgagcggtat cagctcactc aaaggcggta atacggttat ccacagaatc aggggataac    3420
gcaggaaaga acatgtgagc aaaaggccag caaaaggcca ggaaccgtaa aaaggccgcg    3480
ttgctggcgt ttttccatag gctccgcccc cctgacgagc atcacaaaaa tcgacgctca    3540
agtcagaggt ggcgaaaccc gacaggacta taaagatacc aggcgtttcc ccctggaagc    3600
tccctcgtgc gctctcctgt tccgaccctg ccgcttaccg gatacctgtc gcctttctc    3660
ccttcgggaa gcgtggcgct ttctcatagc tcacgctgta ggtatctcag ttcggtgtag    3720
gtcgttcgct ccaagctggg ctgtgtgcac gaaccccccg ttcagcccga ccgctgcgcc    3780
ttatccggta actatcgtct tgagtccaac ccggtaagac acgacttatc gccactggca    3840
gcagccactg gtaacaggat tagcagagcg aggtatgtag gcggtgctac agagttcttg    3900
aagtggtggc ctaactacgg ctacactaga aggacagtat ttggtatctg cgctctgctg    3960
aagccagtta ccttcggaaa aagagttggt agctcttgat ccggcaaaca aaccaccgct    4020
ggtagcggtg gttttttgt ttgcaagcag cagattacgc gcagaaaaaa aggatctcaa    4080
gaagatcctt tgatcttttc tacggggtct gacgctcagt ggaacgaaaa ctcacgttaa    4140
gggattttgg tcatgagcgg atacatattt gaatgtattt agaaaaataa acaaaagagt    4200
ttgtagaaac gcaaaaaggc catccgtcag gatggccttc tgcttaattt gatgcctggc    4260
agtttatggc gggcgtcctg cccgccaccc tccgggccgt tgcttcgcaa cgttcaaatc    4320
cgctcccggc ggatttgtcc tactcaggag agcgttcacc gacaaacaac agataaaacg    4380
aaaggcccag tctttcgact gagcctttcg ttttatttga tgcctggcag ttccctactc    4440
tcgcatggga gacccccaca ctaccatcgg cgctacggcg tttcacttct gagttcggca    4500
tggggtcagg tgggaccacc gcgctactgc cgccaggcaa attctgtttt atcagaccgc    4560
ttctgcgttc tgatttaatc tgtatcaggc tgaaaatctt ctctcatccg ccaaacagc    4620
caagctggag accgtttggc cccctcgag cacgtagaaa gccagtccgc agaaacggtg     4680
ctgacccccg atgaatgtca gctactgggc tatctggaca agggaaaacg caagcgcaaa    4740
gagaaagcag gtagcttgca gtgggcttac atgcgatagc tagactgggc ggttttatg     4800
gacagcaagc gaaccggaat tgccagctgg ggcgccctct ggtaaggttg ggaagccctg    4860
caaagtaaac tggatggctt tctcgccgcc aaggatctga tggcgcaggg gatca         4915

SEQ ID NO: 73         moltype = DNA   length = 10815
FEATURE               Location/Qualifiers
misc_feature          1..10815
                      note = Description of Artificial Sequence: Synthetic
                      polynucleotide
misc_feature          1..10815
                      note = pCMV-PE2-P2A-Cre
source                1..10815
                      mol_type = other DNA
                      organism = synthetic construct
SEQUENCE: 73
acgcgttgac attgattatt gactagttat taatagtaat caattacggg gtcattagtt       60
catagcccat atatggagtt ccgcgttaca taacttacgg taaatggccc gcctggctga      120
```

```
ccgcccaacg accccccgccc attgacgtca ataatgacgt atgttcccat agtaacgcca   180
atagggactt tccattgacg tcaatgggtg gagtatttac ggtaaactgc ccacttggca   240
gtacatcaag tgtatcatat gccaagtacg cccctattg acgtcaatga cggtaaatgg    300
cccgcctggc attatgccca gtacatgacc ttatgggact ttcctacttg gcagtacatc   360
tacgtattag tcatcgctat taccatggtg atgcggtttt ggcagtacat caatgggcgt   420
ggatagcggt ttgactcacg gggatttcca agtctccacc ccattgacgt caatgggagt   480
ttgttttggc accaaaatca acgggacttt ccaaaatgtc gtaacaactc cgccccattg   540
acgcaaatgg gcggtaggcg tgtacggtgg gaggtctata taagcagagc tggtttagtg   600
aaccgtcaga tccgctagag atccgcggcc gctaatacga ctcactatag ggagagccac   660
caccatgaaa cggacagccg acggaagcga gttcgagtca ccaaagaaga agcggaaagt   720
cgacaagaag tacagcatcg gcctggacat cggcaccaac tctgtgggct gggccgtgat   780
caccgacgag tacaaggtgc ccagcaagaa attcaaggtg ctgggcaaca ccgaccggca   840
cagcatcaag aagaacctga tcggagccct gctgttcgac agcggcgaaa cagccgaggc   900
caccccggct gaagagaaccg ccagaagaag atacaccaga cggaagaacc ggatctgcta   960
tctgcaagag atcttcagca acgagatggc caaggtggac gacagcttct tccacagact  1020
ggaagagtcc ttcctggtgg aagaggataa gaagcacgag cggcacccca tcttcggcaa  1080
catcgtggac gaggtggcct accacgagaa gtaccccacc atctaccacc tgagaaagaa  1140
actggtggac agcaccgaca aggccgacct gcggctgatc tatctggccc tggcccacat  1200
gatcaagttc cggggccact tcctgatcga gggcgacctg aaccccgaca cagcgacgt   1260
ggacaagctg ttcatccagc tggtgcagac ctacaaccag ctgttcgagg aaaaccccat  1320
caacgccagc ggcgtggacg ccaaggccat cctgtctgcc agactgagca gagcagacg   1380
gctggaaaat ctgatcgccc agctgcccgg cgagaagaag aaggcctgt tcggaaacct   1440
gattgccctg agcctgggcc tgaccccaa cttcaagagc aacttcgacc tggccgagga   1500
tgccaaactg cagctgagca aggacaccta cgacgacgc ctggacaacc tgctggccca   1560
gatcggcgac cagtacgccg acctgtttct ggccgccaag aacctgtccg acgccatcct  1620
gctgagcgac atcctgagag tgaaccacga gatcaccaag gccccctga gcgcctctat  1680
gatcaagaga tacgacgagc accaccagga cctgaccctg ctgaaagctc tcgtcggca   1740
gcagctgcct gagaagtaca agagattttt cttcgaccag agcaagaacg gctacgccgg  1800
ctacattgac ggcggagcca gccaggaaga gttctacaag ttcatcaagc ccatcctgga  1860
aaagatggac ggcaccgagg aactgctcgt gaagctgaac agagaggacc tgctgcggaa  1920
gcagcggacc ttcgacaacg gcagcatccc ccaccagatc cacctgggag agctgcacgc  1980
cattctgcgg cggcaggaag attttttaccc attcctgaag gacaaccggg aaaagatcga  2040
gaagatcctg accttccgca tcccctacta cgtgggccct ctggccaggg aaacagcag   2100
attcgcctgg atgaccagaa agagcgagga aaccatcacc ccctggaact tcgaggaagt  2160
ggtggacaag ggcgcttccg cccagagctt catcgagcgg atgaccaact tcgataagaa  2220
cctgcccaac gagaaggtgc tgcccaagca cagcctgctg tacgagtact tcaccgtgta  2280
taacgagctg accaaagtga atacgtgac cgagggaatg agaaagcccg ccttcctgag  2340
cggcgagcag aaaaaggcca tcgtggacct gctgttcaag accaaccgga agtgaccgt   2400
gaagctgctg aaagaggact acttcaagaa aatcgagtgc ttcgactccg tggaaatctc  2460
cggcgtggaa gatcggttca acgcctcccct gggcacatac cacgatctgc tgaaaattat  2520
caaggacaag gacttcctgg acaatgagga aaacgaggac atttctggaag atatcgtgct  2580
gaccctgaca ctgtttgagg acagagagat gatcgaggaa cggctgaaaa cctatgccca  2640
cctgttcgac gacaaagtga tgaagcagct gaagcggcga agataccccg gctggggcca  2700
gctgagccgg aagctgatca acggcatccg ggacaagcag tccggcaaga caatcctgga  2760
tttcctgaag tccgacggct tcgccaacag aaacttcatg cagctgatcc acgacgacag  2820
cctgaccttt aaagaggaca tccagaaagc ccaggtgtcc ggccagggcg atagcctgca  2880
cgagcacatt gccaatctgg ccggcagccc cgccattaag aagggcatcc tgcagacagt  2940
gaaggtggtg gacgagctcg tgaaagtgat gggccggcac aagcccgaga acatcgtgat  3000
cgaaatggcc agagagaacc agaccaccca agggacag aagaacagcc gcgagagaat   3060
gaagcggatc gaagagggca tcaaagagct gggcagccag atcctgaaag aacacccgt   3120
ggaaaacacc cagctgcaga acgagaagct gtacctgtac tacctgcaga atgggcggga  3180
tatgtacgtg gaccaggaac tggacatcaa ccggctgtcc gactacgatg tggacgctat  3240
cgtgcctcag agctttctga aggacgactc catcgacaac aaggtgctga ccagaagcga  3300
caagaaccgg ggcaagagcg acaacgtgcc ctccgaagag gtcgtgaaga agtgaagaa   3360
ctactggcgg cagctgctga acgccaagct gattacccag agaaagttcg acaatctgac  3420
caaggccgga gaggcggcc tgagcgaact ggataaggcc ggcttcatca agagacagct   3480
ggtgaaaacc cggcagatca aaagcacgt ggcacagatc ctggactccc ggatgaacac   3540
taagtacgac gagaatgaca agctgatccg ggaagtgaaa gtgatcaccc tgaagtccaa  3600
gctggtgtcc gattttcgga aggattcca gttttacaaa gtgcgcgaga tcaacaacta  3660
ccaccacgca cacgacgct acctgaacgc cgtcgtgggaa accgccctga tcaaaaagta  3720
ccctaagctg gaaagcgagt tcgtgtacgg cgactacaag gtgtacgacg tgcggaagat  3780
gatcgccaag agcgagcagg aaatcggcaa ggctaccgcc agtacttct tctacagcaa   3840
catcatgaac ttttttcaaga ccgagattac cctggccaac ggcgagatcc ggaagcggcc  3900
tctgatcgaa acaaacggcg aaacggggga gatcgtgtgg gataagggcc gggattttgc  3960
caccgtgcgg aaaagtgctga gcatgcccca gtgaatatc gtgaaaaaga ccgaggtgca   4020
gacaggcggc ttcagcaaag agtctatcct gcccaagagg aacagcgata gctgatcgc   4080
cagaaagaag gactgggacc ctaagaagta cggcggcttc gacagcccca ccgtggccta  4140
ttctctgtgctg gtggtggcca aagtggaaaa gggcaagtcc aagaaactga agagtgtgaa  4200
agagctgctg gggatcacca tcatggaaag aagcagcttc gagaagaatc ccatcgactt  4260
tctggaagcc aagggctaca aagaagtgaa aaaggacctg atcatcaagc tgcctaagta  4320
ctccctgttc gagctggaaa acggccggaa gagaatgctg gcctctgccg gcgaactgca  4380
gaagggaaac gaactggccc tgccctccaa atatgtgaac ttcctgtacc tggccagcca  4440
ctatgagaag ctgaagggct cccccgagga taatgagcag aaacagcgt tgtggaaca   4500
gcacaagcac tacctggacg agatcatcga gcagatcagt gagttcagca agagagtgat  4560
cctggccgac gctaatctgg acaaagtgct gtccgcctac aacaagcacc gggataagcc  4620
catcagagag caggccgaga atcatccga cctgttacc ctgaccaatc tgggagcccc   4680
tgccgccttc aagtactttg acaccaccat cgaccgaag aggtacacca gcaccaaaga  4740
ggtgctggac gccacccga tccaccagag catcaccggc ctgtacgaga cacggatcga  4800
cctgtctcag ctgggaggtg actctggagg atctagcgga ggatcctctg gcagcgagac  4860
```

```
accaggaaca agcgagtcag caacaccaga gagcagtggc ggcagcacgcg cggcagcag    4920
caccctaaat atagaagatg agtatccggct acatgagacc tcaaaagagc cagatgtttc    4980
tctagggtcc acatggctgt ctgattttcc tcaggcctgg gcggaaaccg ggggcatggg    5040
actggcagtt cgccaagctc ctctgatcat acctctgaaa gcaacctcta cccccgtgtc    5100
cataaacaa tacccatgt cacaagaagc cagactgggg atcaagccac acatacagag    5160
actgttggac cagggaatac tggtaccctg ccagtccccc tggaacacgc ccctgctacc    5220
cgttaagaaa ccagggacta atgattatag gcctgtccag gatctgagag aagtcaacaa    5280
gcgggtggaa gacatccacc ccaccgtgcc caacccttac aacctcttga gcgggctccc    5340
accgtcccac cagtggtaca ctgtgcttga tttaaaggat gccttttct gcctgagact    5400
ccacccacc agtcagcctc tcttcgcctt tgagtggaga gatccagaga tgggaatctc    5460
aggacaattg acctggacca gactcccaca gggtttcaaa aacagtccca ccctgtttaa    5520
tgaggcactg cacagagacc tagcagactt ccggatccag cacccagact tgatcctgct    5580
acagtacgtg gatgacttac tgctggccgc cacttctgag ctagactgcc aacaaggtac    5640
tcgggccctg ttacaaaccc tagggaacct cgggtatccg gcctcggcca agaaagccca    5700
aatttgccag aaacaggtca agtatctggg gtatcttcta aaagagggtc agagatggct    5760
gactgaggcc agaaaagaga ctgtgatggg gcagcctact ccgaagaccc ctcgacaact    5820
aagggagttc ctagggaagg caggcttctg tcgcctcttc atccctgggt ttgcagaaat    5880
ggcagccccc ctgtaccctc tcaccaaacc ggggactcta tttaattggg gcccagacca    5940
acaaaaggcc tatcaagaaa tcaagcaagc tcttctaact gccccagccc tggggttgcc    6000
agatttgact aagcccttg aactctttgt cgacgagaag cagggctacg ccaaaggtgt    6060
cctaacgcaa aaactgggac cttggcgtcg gccggtggcc tacctgtcca aaaagctaga    6120
cccagtagca gctgggtggc cccttgcct acggatggca gcagccattg ccgtactgac    6180
aaaggatgca ggcaagctaa ccatgggaca gccactagtc attctggccc ccatgcagt    6240
agaggcacta gtcaaacaac cccccgaccg ctggctttcc aacgcccgga tgactcacta    6300
tcaggccttg cttttggaca cggaccgggt ccagttcgga ccggtggtag ccctgaaccc    6360
ggctacgctg ctcccactgc ctgaggaagg gctgcaacac aactgccttg atatcctggc    6420
cgaagcccac ggaacccgac ccgacctaac ggaccagccg ctcccagacg ccgaccacac    6480
ctggtacacg gatggaagca gtctcttaca agagggacag cgtaaggcgg gagctgcggt    6540
gaccaccgag accgaggtaa tctgggctaa agccctgcca gccgggacat ccgctcagcg    6600
ggctgaactg atagcactca cccaggccct aaagatggca gaaggtaaga agctaaatgt    6660
ttatactgat agccgttatg cttttgctac tgcccatatc catggagaaa tatacagaag    6720
gcgtgggtgg ctcacatcag aaggcaaaga gatcaaaaat aaagacgaga tcttggccct    6780
actaaaagcc ctctttctgc ccaaaagact tagcataatc cattgtccag acatcaaaa    6840
gggacacagc gccgaggcta gaggcaaccg gatggctgac caagcggccg gaaaggcagc    6900
catcacagag actccagaca cctctaccct cctcataaga aattcatcac cctctggcg    6960
ctcaaaaaga accgccgacg gcagcgaatt cgagcccaag aagaaggaga aagtcggaag    7020
cggagcgtact aacttcagcc tgctgaagca ggctggcgac gtggaggaga accctggacc    7080
taatttactg accgtacacc aaaatttgcc tgcattaccg gtcgatgcaa cgagtgatga    7140
ggttcgcaag aacctgatgg acatgttcag ggatcgccag gcgttttctg agcatacctg    7200
gaaaatgctt ctgtccgttt gccggtcgtg ggcggcatgg tgcaagttga ataaccggaa    7260
atggtttccc gcagaacctg aagatgttcg cgattatctt ctatatcttc aggcgcgcgg    7320
tctggcagta aaaactatcc agcaacattt gggccagcta acatgcttc atcgtcggtc    7380
cgggctgcca cgaccaagtg acagcaatgc tgtttcactg gttatgcggc ggatccgaaa    7440
agaaaacgtt gatgccggtg aacgtgcaaa acaggctcta gcgttcgaac gcactgattt    7500
cgaccaggtt cgttcactca tggaaaatag cgatcgctgc caggatatac gtaatctggc    7560
atttctgggg attgcttata acaccctgtt acgtatagcc gaaattgcca ggatcagggt    7620
taaagatatc tcacgtactg acggtgggag aatgttaatc catatttgta gaacgaaaac    7680
gctggttagc accgcaggtg tagagaaggc acttagcctg ggggtaacta aactggtcga    7740
gcgatggatt tccgtctctg gtgtagctga tgatccgaat aactaccgt tttgccgggt    7800
cagaaaaaat ggtgttgccg cgccatctgc caccagccag ctatcaactc gcgccctga    7860
agggatttt gaagcaactc atcgattgat ttacgcgct aaggatgact ctggtcagag    7920
ataccctggcc tggtctggac acagtgcccg tgtcggagcc gcgcgagata tggcccgcgc    7980
tggagtttca ataccggaga tcatgcaagc tggtggctgg accaatgtaa atattgtcat    8040
gaactatatc cgtaacctgg atagtgaaac aggggcaatg gtgcgcctgc tggaagatgg    8100
cgattaattt aaacccgctg atcagcctcg actgtgcctt ctagttgcca gccatctgtt    8160
gtttgcccct ccccgtgcc ttccttgacc ctggaaggtg ccactccac tgtcctttcc    8220
taataaaatg agaaaattgc atcgcattgt ctgagtaggt gtcattctat tctgggggt    8280
gggtgggggc aggacagcaa gggggaggat tgggaagaca atagcaggca tgctgggat    8340
gcggtgggct ctatggcttc tgaggcggaa agaaccagct ggggctcgat accgtcgacc    8400
tctagctaga gcttggcgta atcatggtca tagctgtttc ctgtgtgaaa ttgttatccg    8460
ctcacaattc cacacaacat acgagccgga agcataaagt gtaaagccta gggtgcctaa    8520
tgagtgagct aactcacatt aattgcgttg cgctcactgc ccgctttcca gtcgggaaac    8580
ctgtcgtgcc agctgcatta atgaatcggc caacgcgcgg ggagaggcgg tttgcgtatt    8640
gggcgctctt ccgcttcctc gctcactgac tcgctgccgt cggtcgttcg gctgcggcga    8700
gcggtatcag ctcactcaaa ggcggtaata cggttatcca cagaatcagg ggataacgca    8760
ggaaagaaca tgtgagcaaa aggccagcaa aaggccagga accgtaaaaa ggccgcgttg    8820
ctggcgtttt tccataggct ccgccccct gacgagcatc acaaaatcg acgctcaagt    8880
cagaggtggc gaaacccgac aggactataa agataccagg cgtttccccc tggaagctcc    8940
ctcgtgcgct ctcctgttcc gaccctgccg cttaccggat acctgtccgc ctttctccct    9000
tcggaagcg tggcgcttt tcatagctca cgctgtaggt atctcagttc ggtgtaggtc    9060
gttcgctcca agctgggctg tgtgcacgaa ccccccgttc agcccgaccg ctgcgcctta    9120
tccggtaact atcgtcttga gtccaacccg gtaagacacg acttatcgcc actggcagca    9180
gccactggta acaggattag cagagcgagg tatgtaggcg gtgctacaga gttcttgaag    9240
tggtggccta actacggcta cactagaaga acagtatttg gtatctgcgc tctgctgaag    9300
ccagttacct tcggaaaaag agttggtagc tcttgatccg gcaaacaaac caccgctggt    9360
agcggtggtt tttttgtttg caagcagcag attacgcgca gaaaaaaagg atctcaagaa    9420
gatcctttga tcttttctac ggggtctgac gctcagtgga acgaaaactc acgttaaggg    9480
attttggtca tgagattatc aaaaaggatc ttcacctaga tccttttaaa ttaaaaatga    9540
agttttaaat caatctaaag tatatatgag taaacttggt ctgacagtta ccaatgctta    9600
```

```
atcagtgagg cacctatctc agcgatctgt ctatttcgtt catccatagt tgcctgactc  9660
cccgtcgtgt agataactac gatacgggag ggcttaccat ctggccccag tgctgcaatg  9720
ataccgcgag acccacgctc accggctcca gatttatcag caataaacca gccagccgga  9780
agggccgagc gcagaagtgg tcctgcaact ttatccgcct ccatccagtc tattaattgt  9840
tgccgggaag ctagagtaag tagttcgcca gttaatagtt tgcgcaacgt tgttgccatt  9900
gctacaggca tcgtggtgtc acgctcgtcg tttggtatgg cttcattcag ctccggttcc  9960
caacgatcaa ggcgagttac atgatccccc atgttgtgca aaaaagcggt tagctccttc 10020
ggtcctccga tcgttgtcag aagtaagttg gccgcagtgt tatcactcat ggttatggca 10080
gcactgcata attctcttac tgtcatgcca tccgtaagat gcttttctgt gactggtgag 10140
tactcaacca agtcattctg agaatagtgt atgcggcgac cgagttgctc ttgcccggcg 10200
tcaatacggg ataataccgc gccacatagc agaactttaa aagtgctcat cattggaaaa 10260
cgttcttcgg ggcgaaaact ctcaaggatc ttaccgctgt tgagatccag ttcgatgtaa 10320
cccactcgtg cacccaactg atcttcagca tcttttactt tcaccagcgt ttctgggtga 10380
gcaaaaacag gaaggcaaaa tgccgcaaaa aagggaataa gggcgacacg gaaatgttga 10440
atactcatac tcttcctttt tcaatattat tgaagcattt atcagggtta ttgtctcatg 10500
agcggataca tatttgaatg tatttagaaa aataaacaaa tagggggttcc gcgcacattt 10560
ccccgaaaag tgccacctga cgtcgacgga tcggagatc gatctcccga tcccctaggg 10620
tcgactctca gtacaatctg ctctgatgcc gcatagttaa gccagtatct gctccctgct 10680
tgtgtgttgg aggtcgctga gtagtgcgcg agcaaaattt aagctacaac aaggcaaggc 10740
ttgaccgaca attgcatgaa gaatctgctt agggttaggc gttttgcgct gcttcgcgat 10800
gtacgggcca gatat                                                  10815

SEQ ID NO: 74           moltype = DNA  length = 20
FEATURE                 Location/Qualifiers
misc_feature            1..20
                        note = Description of Artificial Sequence: Synthetic
                         oligonucleotide
misc_feature            1..20
                        note = +90ngRNA guide sequence
source                  1..20
                        mol_type = other DNA
                        organism = synthetic construct
SEQUENCE: 74
gtcaaccagt atcccggtgc                                                 20

SEQ ID NO: 75           moltype = DNA  length = 96
FEATURE                 Location/Qualifiers
misc_feature            1..96
                        note = Description of Artificial Sequence: Synthetic
                         oligonucleotide
misc_feature            1..96
                        note = +90ngRNA
source                  1..96
                        mol_type = other DNA
                        organism = synthetic construct
SEQUENCE: 75
gtcaaccagt atcccggtgc gttttagagc tagaaatagc aagttaaaat aaggctagtc     60
cgttatcaac ttgaaaaagt ggcaccgagt cggtgc                               96

SEQ ID NO: 76           moltype = DNA  length = 4968
FEATURE                 Location/Qualifiers
misc_feature            1..4968
                        note = Description of Artificial Sequence: Synthetic
                         polynucleotide
misc_feature            1..4968
                        note = GFP minicircle template (before cleavage)
source                  1..4968
                        mol_type = other DNA
                        organism = synthetic construct
SEQUENCE: 76
tgatcccctg cgccatcaga tccttggcgg cgagaaagcc atccagttta ctttgcaggg     60
cttcccaacc ttaccagagg gcgccccagc tggcaattcc ggttcgcttg ctgtccataa    120
aaccgcccag tctagctatc gccatgtaag cccactgcaa gctacctgct ttctctttgc    180
gcttgcgttt tcccttgtcc agatagccca gtagctgaca ttcatccggg tcagcaccg    240
tttctgcgga ctggctttct acgtgctcga gggggggccaa acggtctcca gcttggcgtgt    300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca atccgccgg gagcggattt    600
gaacgttgcg aagcaacggc ccggagggtg cgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atccttttttt tctgcgcgta atctgctgct tgcaaacaaa aaaaccaccg ctaccagcgg    900
tggtttgttt gccggatcaa gagctaccaa ctctttttcc gaaggtaact ggcttcagca    960
gagcgcagat accaaatact gtccttctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
```

|     |     |     |     |     |      |
| --- | --- | --- | --- | --- | ---- |
| agcggtcggg | ctgaacgggg | ggttcgtgca | cacagcccag | cttggagcga | acgacctaca | 1200 |
| ccgaactgag | atacctacag | cgtgagctat | gagaaagcgc | cacgcttccc | gaagggagaa | 1260 |
| aggcggacag | gtatccggta | agcggcaggg | tcggaacagg | agagcgcacg | agggagcttc | 1320 |
| caggggggaaa | cgcctggtat | ctttatagtc | ctgtcgggtt | tcgccacctc | tgacttgagc | 1380 |
| gtcgattttt | gtgatgctcg | tcagggggc | ggagcctatg | gaaaaacgcc | agcaacgcgg | 1440 |
| ccttttttacg | gttcctggcc | ttttgctggc | cttttgctca | catgttcttt | cctgcgttat | 1500 |
| cccctgattc | tgtggataac | cgtattaccg | cctttgagtg | agctgatacc | gctcgccgca | 1560 |
| gccgaacgac | cgagcgcagc | gagtcagtga | gcgaggaagc | ggaagagcgc | ctgatgcggt | 1620 |
| attttctcct | tacgcatctg | tgcggtattt | cacaccgcat | atggtgcact | ctcagtacaa | 1680 |
| tctgctctga | tgccgcatag | ttaagccagt | atacactccg | ctatcgctac | gtgactgggt | 1740 |
| catggctgcg | ccccgacacc | cgccaacacc | cgctgacgcg | ccctgacggg | cttgtctgct | 1800 |
| cccggcatcc | gcttacagac | aagctgtgac | cgtctccggg | agctgcatgt | gtcagaggtt | 1860 |
| ttcaccgtca | tcaccgaaac | gcgcgaggca | gcagatcaat | tcgcgcgcga | aggcgaagcg | 1920 |
| gcatgcataa | tgtgcctgtc | aaatggacga | agcagggatt | ctgcaaaccc | tatgctactc | 1980 |
| cgtcaagccg | tcaattgtct | gattcgttac | caattatgac | aacttgacgg | ctacatcatt | 2040 |
| cacttttttct | tcacaaccgg | cacggaactc | gctcgggctg | gccccggtgc | attttttaaa | 2100 |
| tacccgcgag | aaatagagtt | gatcgtcaaa | accaacattg | cgaccgacgg | tggcgatagg | 2160 |
| catccggttg | gtgctcaaaa | gcagcttcgc | ctggctgata | cgttggtcct | gcgccagct | 2220 |
| taagacgcta | atccctaact | gctggcgaa | aagatgtgac | agacgcgacg | gcgacaagca | 2280 |
| aacatgctgt | gcgacgctgg | cgatacatta | ccctgttatc | cctagatgac | attaccctgt | 2340 |
| tatcccagat | gacattaccc | tgttatccct | agatgacatt | accctgttat | ccctagatga | 2400 |
| catttaccct | gttatcccta | gatgacatta | ccctgttatc | ccagatgaca | ttaccctgtt | 2460 |
| atccctagat | acattaccct | gttatcccag | atgacatacc | ctgttatccc | tagatgacat | 2520 |
| taccctgtta | tccagatgca | cattaccctg | ttatccctag | atacattacc | ctgttatccc | 2580 |
| agatgacata | ccctgttatc | cctagatgac | attaccctgt | atcccagat | gacattaccc | 2640 |
| tgttatccct | agatacatta | ccctgttatc | ccagatgaca | taccctgtta | tcccagatg | 2700 |
| acattaccct | gttatcccag | atgcattac | cctgttatcc | ctagatacat | taccctgtta | 2760 |
| tcccagatga | cataccctgt | tatccctaga | tgacattacc | ctgttatccc | agatgacatt | 2820 |
| accctgttat | ccctagatac | attaccctgt | tatcccagat | gacataccct | gttatcccta | 2880 |
| gatgacatta | ccctgttatc | ccagatgaca | ttaccctagt | atccctagtt | acattaccct | 2940 |
| gttatcccag | atgcataccc | ctgttatccc | tagatgacat | taccctgtta | tcccagataa | 3000 |
| actcaatgat | gatgatgatg | atggtcgaga | ctcagcggcc | gcggtgccag | ggcgtgccct | 3060 |
| tgggctcccc | gggcgcgact | ataagctgcg | agcaacttca | cttgggtatg | ccggcggtag | 3120 |
| cgcttaccgt | tcgtataatg | tatgctatac | gaagttatcc | gaagccgtca | gcggtggtct | 3180 |
| gtctggtcaa | ccaccgcggt | ctcagtggtg | tacggtacaa | acccagctac | cggtcgccac | 3240 |
| catgcccgcc | atgaagatcg | agtgccgcat | caccggcacc | ctgaacgcg | tggagttcga | 3300 |
| gctggtgggc | ggcggagagg | gcacccccga | gcagggccgc | atgaccaaca | agatgaagag | 3360 |
| caccaaaggc | gccctgacct | tcagcccta | cctgctgagc | cacgtgatgg | gctacggctt | 3420 |
| ctaccacttc | ggcaacctac | ccagcgcta | cgagaaccca | ttcctgcacg | ccatcaacaa | 3480 |
| cggcggctac | accaacaccc | gcatcgagaa | gtacgaggac | ggcggcgtgc | tgcacgtgag | 3540 |
| cttcagctac | cgctacgagg | ccggccgcgt | gatcggcgac | ttcaaggtgg | tgggcaccgg | 3600 |
| cttccccgag | gacagcgtga | tcttcaccga | caagatcatc | gcagcaacg | ccaccgtgga | 3660 |
| gcacctgcac | cccatgggcg | ataacgtgct | ggtgggcagc | ttcgccgca | ccttcagcct | 3720 |
| gcgcgacggc | ggctactaca | gcttcgtggt | ggacagccac | atgcacttca | agagcgccat | 3780 |
| ccaccccagc | atcctgcaga | acgggggccc | catgttcgcc | ttcgccgcg | tggaggagct | 3840 |
| gcacagcaac | accgagctgg | gcatcgtgga | gtaccagcac | gccttcaaga | cccccatcgc | 3900 |
| cttcgccaga | tctcgagctc | gatgagtttg | gacaaaccaa | aactagaatg | cagtgaaaaa | 3960 |
| aatgctttat | ttgtgaaatt | tgtgatgcta | ttgctttatt | tgtgggcccg | cccaactgtg | 4020 |
| ggtaaccttt | gagttctctc | agttgggggt | aatcagcatc | atgatgtggt | accacatcat | 4080 |
| gatgctgatt | ataagaatgc | ggccgccaca | ctctagtgga | tctcgagtta | ataattcaga | 4140 |
| agaactcgtc | aagaaggcga | tagaaggcga | tgcgctgcga | atcgggagcg | gcgataccgt | 4200 |
| aaagcacgag | gaagcggtca | gcccattcgc | cgccaagctc | ttcagcaata | tcacgggtag | 4260 |
| ccaacgctat | gtcctgatag | cggtccgcca | cacccagccg | gccacagtcg | atgaatccag | 4320 |
| aaaagcggcc | attttccacc | atgatattcg | gcaagcaggc | atcgccatgg | gtcacgacga | 4380 |
| gatcctcgcc | gtcgggcatg | ctcgccttga | gcctggcgaa | cagttcggct | ggcgcgagcc | 4440 |
| cctgatgctc | ttcgtccaga | tcatcctgat | cgacaagacc | ggcttccatc | cgagtacgtg | 4500 |
| ctcgctcgat | gcgatgtttc | gcttggtggt | cgaatgggca | ggtagccgga | tcaagcgtat | 4560 |
| gcagccgccg | cattgcatca | gccatgatgg | atactttctc | ggcaggagca | aggtgtagat | 4620 |
| gacatggaga | tcctgccccg | gcacttcgcc | caatagcagc | cagtccctc | ccgcttcagt | 4680 |
| gacaacgtcg | agcacagctg | cgcaaggaac | gcccgtcgtg | gccagccacg | atagccgcgc | 4740 |
| tgcctcgtct | tgcagttcat | tcagggcacc | ggacaggtcg | gtcttgacaa | aaagaaccgg | 4800 |
| gcgcccctgc | gctgacagcc | ggaacacggc | ggcatcagag | cagccgattg | tctgttgtgc | 4860 |
| ccagtcatag | ccgaatagcc | tctccaccca | agcggccgga | gaacctgcgt | gcaatccatc | 4920 |
| ttgttcaatc | atgcgaaacg | atcctcatcc | tgtctcttga | tcagagct | | 4968 |

```
SEQ ID NO: 77          moltype = DNA   length = 4855
FEATURE                Location/Qualifiers
misc_feature           1..4855
                       note = Description of Artificial Sequence: Synthetic
                        polynucleotide
misc_feature           1..4855
                       note = GLuc minicircle template
source                 1..4855
                       mol_type = other DNA
                       organism = synthetic construct
SEQUENCE: 77
tgatcccctg cgccatcaga tccttggcgg cgagaaagcc atccagttta ctttgcaggg    60
cttcccaacc ttaccagagg gcgccccagc tggcaattcc ggttcgcttg ctgtccataa   120
aaccgcccag tctagctatc gccatgtaag cccactgcaa gctacctgct ttctctttgc   180
```

```
gcttgcgttt tcccttgtcc agatagccca gtagctgaca ttcatccggg gtcagcaccg    240
tttctgcgga ctggctttct acgtgctcga gggggggccaa acggtctcca gcttggctgt   300
tttggcggat gagagaagat tttcagcctg atacagatta aatcagaacg cagaagcggt   360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca aatccgccgg gagcggattt    600
gaacgttgcg aagcaacggc ccggaggtg gcgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atcctttttt tctgcgcgta atctgctgct tgcaaacaaa aaaaccaccg ctaccagcgg    900
tggtttgttt gccggatcaa gagctaccaa ctctttttcc gaaggtaact ggcttcagca    960
gagcgcagat accaaatact gtcctctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
agcggtcggg ctgaacgggg ggttcgtgca cacagcccag cttggagcga acgacctaca   1200
ccgaactgag atacctacag cgtgactat gagaaagcgc cacgcttccc gaagggagaa    1260
aggcggacag gtatccgta agcggcaggg tcggaacagg agagcgcacg agggagcttc   1320
caggggggaaa cgcctggtat ctttatagtc ctgtcgggtt tcgccacctc tgacttgagc   1380
gtcgattttt gtgatgctcg tcaggggggc ggagcctatg gaaaaacgcc agcaacgcgg   1440
cctttttacg gttcctggcc ttttgctggc cttttgctca catgttcttt cctgcgttat   1500
cccctgattc tgtggataac cgtattaccg cctttgagtg agctgatacc gctcgccgca   1560
gccgaacgac cgagcgcagc gagtcagtga gcgaggaagc ggaagagcgc ctgatgcggt   1620
attttctcct tacgcatctg tgcggtattt cacaccgcat atggtgcact ctcagtacaa   1680
tctgctctga tgccgcatag ttaagccagt atacactccg ctatcgctac gtgactgggt   1740
catggctgcg ccccgacacc cgccaacacc cgctgacgcg ccctgacggg cttgtctgct   1800
cccggcatcc gcttacagac aagctgtgac cgtctccggg agctgcatgt gtcagaggtt   1860
ttcaccgtca tcaccgaaac gcgcgaggca gcagatcaat tcgcgcgcga aggcgaagcg   1920
gcatgcataa tgtgcctgtc aaatggacga agcagggatt ctgcaaaccc tatgctactc   1980
cgtcaagccg tcaattgtct gattcgttac caattatgac aacttgacgg ctacatcatt   2040
cacttttttct tcacaaccgg cacggaactc gctcgggctg gccccggtgc atttttaaa   2100
tacccgcgag aaatagagtt gatcgtcaaa accaacattg cgaccgacgg tggcgatagg   2160
catccggggtg gtgctcaaaa gcagcttcgc ctggctgata cgttggtcct cgcgccagct   2220
taagcgcta atccctaact gctggcgaa aagatgtgac agacgcgacg gcgacaagca    2280
aacatgctgt gcgacgctgg cgatacatta ccctgttatc cctagatgac attaccctgt   2340
tatcccagat gacattaccc tgttatccct agatgacatt accctgttat ccctagatga   2400
catttaccct gttatcccta gatgacatta ccctgttatc cagatgaca ttaccctgtt   2460
atccctagat acattaccct gttatcccag atgacatac tagatgacat                 2520
taccctgtta tcccagatga cattaccctg ttatccctag atacattacc ctgttatccc   2580
agatgacata ccctgttatc cctagatgac attaccctgt tatcccagat gacattaccc   2640
tgttatccct agatacatta ccctgttatc cagatgaca taccctgtta tcccctagatg   2700
acattaccct gttatcccag atgacattac cctgttatcc tagatacat tccccctgtta   2760
tcccagatga catacccctgt tatccctaga tgacattacc ctgttatccc agatgacatt   2820
accctgttat ccctagatac attccccctgt tatcccagat gacatacccct gttatccctaa   2880
gatgacatta ccctgttatc ccagatgaca ttaccctgtt atccctagat acattaccct   2940
gttatcccag atgacatacc ctgttatccc tagatgacat taccctgtta tcccagataa   3000
actcaatgat gatgatgatg atggtcgaga ctcagcggcc gcggtgccag ggcgtgccct   3060
tgggctcccc gggcgcgact ataagctgcg agcaacttca cttgggtatg ccggcggtag   3120
cgcttaccgt tcgtataatg tatgctatac gaagttatcc gaagccgcta gcggtggttt   3180
gtctgtcaa ccaccgcggt ctcagtggtg tacggtacaa acccactacc ggtcgccacc   3240
atgggagtca aagttctgtt tgccctgatc tgcatcgctg tggccgaggc caagcccacc   3300
gagaacaacg aagacttcaa catcgtggcg gtgccagca acttcgcgac cacggatctc   3360
gatgctgacc gcgggaagtt gcccggcaag aagctgccgc tggaggtgct caaagagatg   3420
gaagccaatg cccggaaagc tggctgcacc aggggctgtc tgatctgcct gtcccacatc   3480
aagtgcacgc ccaagatgaa gaagttcatc ccaggacgct gccacaccta cgaaggcgac   3540
aaaagagtccg cacagggcgg cataggcgag cgatcgtcg acattcctga gattcctggg   3600
ttcaaggact tggagcccat ggagcagttc atcgcacagg tcgatctgtg tgtggactgc   3660
acaactggct gcctcaaagg gcttgccaac gtgcagtgtt ctgacctgct caagaagtgg   3720
ctgccgcaac gctgtgcgac ctttgccagc aagatccagg gcaggtggaa caagatcaag   3780
ggggccggtg gtgactaagc ggagctcgat gagtttggac aaaccacaac tagaatgcag   3840
tgaaaaaaat gctttattg tgaaattgt gatgctattg ctttatttgt gggccccgccc   3900
caactggggt aaccctgag ttctctcagt tgggggtaat cagcatcatg atgtggtacc   3960
acatcatgat gctgattata agaatgcggc gccacactc tagtggatct aagttataa    4020
attcagaaga actcgtcaag aaggcgatag aaggcgatgc gctgcgaatc gggagcggcg   4080
ataccgtaaa gcacgaggaa gcggtcagcc cattcgccgc caagctcttc agcaatatca   4140
cgggtagcca acgctatgtc ctgatagcgg tccgccacac ccagccggcc acagtcgatg   4200
aatccagaaa agcggccatt tccaccatg atattcggca agcaggcatc gccatgggtc   4260
acgacgagat cctcgccgtc gggcatgctc gccttgagcc tggcgaacag ttcggctgg   4320
gcgagcccct gatgctcttc gtccagatca tcctgatcga caagaccggc ttccatccga   4380
gtacgtgctc gctcgatgcg atgtttcgct tggtggtcga atgggcaggt agccggatca   4440
agcgtatgca gccgccgcat tgcatcagcc atgatggata cttctcggc aggagcaagg   4500
tgtagatgac atggagatcc tgccccggca cttcgcccaa tagcagccag tcccttcccg   4560
cttcagtgac aacgtcgagc acagctgcgc aaggaacgcc cgtcgtggcc agccacgata   4620
gccgcgctgc ctcgtcttgc agttcattca gggcaccgga caggtcggtc ttgacaaaaaa   4680
gaaccgggcg cccctgcgct gacagccgga acacggcggc atcagagcag ccgattgtct   4740
gttgtgccca gtcatagccg aatagcctct ccacccaagc ggccgagaa cctgcgtgca   4800
atccatcttg ttcaatcatg cgaaacgatc ctcatcctgt ctcttgatca gagct         4855
```

| | | |
|---|---|---|
| SEQ ID NO: 78 | moltype = DNA length = 38 | |
| FEATURE | Location/Qualifiers | |
| misc_feature | 1..38 | |
| | note = Description of Artificial Sequence: Synthetic oligonucleotide | |
| misc_feature | 1..38 | |
| | note = pseudo-attP | |
| source | 1..38 | |
| | mol_type = other DNA | |
| | organism = synthetic construct | |

SEQUENCE: 78
```
ccccaactgg ggtaaccttt gagttctctc agttgggg                              38
```

| | | |
|---|---|---|
| SEQ ID NO: 79 | moltype = DNA length = 194 | |
| FEATURE | Location/Qualifiers | |
| misc_feature | 1..194 | |
| | note = Description of Artificial Sequence: Synthetic polynucleotide | |
| misc_feature | 1..194 | |
| | note = Albumin-pegRNA-SERPIN | |
| source | 1..194 | |
| | mol_type = other DNA | |
| | organism = synthetic construct | |

SEQUENCE: 79
```
gactgaaact tcacagaata gttttagagc tagaaatagc aagttaaaat aaggctagtc       60
cgttatcaac ttgaaaaagt ggcaccgagt cggtgcttgg gatagttatg aattcaatct      120
tcaaccctat ccggatgatc ctgacgacgg agaccgccgt cgtcgacaag ccggcctctg      180
tgaagtttca gtca                                                        194
```

| | | |
|---|---|---|
| SEQ ID NO: 80 | moltype = DNA length = 189 | |
| FEATURE | Location/Qualifiers | |
| misc_feature | 1..189 | |
| | note = Description of Artificial Sequence: Synthetic polynucleotide | |
| misc_feature | 1..189 | |
| | note = Albumin-pegRNA-CPS1 | |
| source | 1..189 | |
| | mol_type = other DNA | |
| | organism = synthetic construct | |

SEQUENCE: 80
```
gactgaaact tcacagaata gttttagagc tagaaatagc aagttaaaat aaggctagtc       60
cgttatcaac ttgaaaaagt ggcaccgagt cggtgcttgg gatagttatg aattcaatct      120
tcaaccctat ccggatgatc ctgacgacgg agaccgccgt cgtcgacaag ccggcctctg      180
tgaagtttc                                                              189
```

| | | |
|---|---|---|
| SEQ ID NO: 81 | moltype = DNA length = 177 | |
| FEATURE | Location/Qualifiers | |
| misc_feature | 1..177 | |
| | note = Description of Artificial Sequence: Synthetic polynucleotide | |
| misc_feature | 1..177 | |
| | note = 34bp lox71 pegRNA | |
| source | 1..177 | |
| | mol_type = other DNA | |
| | organism = synthetic construct | |

SEQUENCE: 81
```
ggcccagact gagcacgtga gttttagagc tagaaatagc aagttaaaat aaggctagtc       60
cgttatcaac ttgaaaaagt ggcaccgagt cggtgctgga ggaagcaggg cttcctttcc     120
tctgccatca taccgttcgt atagcataca ttatacgaag ttatcgtgct cagtctg        177
```

| | | |
|---|---|---|
| SEQ ID NO: 82 | moltype = DNA length = 177 | |
| FEATURE | Location/Qualifiers | |
| misc_feature | 1..177 | |
| | note = Description of Artificial Sequence: Synthetic polynucleotide | |
| misc_feature | 1..177 | |
| | note = 34bp lox66 pegRNA | |
| source | 1..177 | |
| | mol_type = other DNA | |
| | organism = synthetic construct | |

SEQUENCE: 82
```
ggcccagact gagcacgtga gttttagagc tagaaatagc aagttaaaat aaggctagtc       60
cgttatcaac ttgaaaaagt ggcaccgagt cggtgctgga ggaagcaggg cttcctttcc     120
tctgccatca ataacttcgt atagcataca ttatacgaac ggtacgtgct cagtctg        177
```

| | | |
|---|---|---|
| SEQ ID NO: 83 | moltype = DNA length = 20 | |
| FEATURE | Location/Qualifiers | |
| misc_feature | 1..20 | |
| | note = Description of Artificial Sequence: Synthetic | |

```
                                    oligonucleotide
misc_feature                        1..20
                                    note = gRNA2
source                              1..20
                                    mol_type = other DNA
                                    organism = synthetic construct
SEQUENCE: 83
ggcccagact gagcacgtga                                                 20

SEQ ID NO: 84           moltype = DNA  length = 184
FEATURE                 Location/Qualifiers
misc_feature            1..184
                        note = Description of Artificial Sequence: Synthetic
                         polynucleotide
source                  1..184
                        mol_type = other DNA
                        organism = synthetic construct
SEQUENCE: 84
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggccgga tgatcctgac gacggagacc gccgtcgtcg acaagccggc ctgagctgcg  180
agaa                                                               184

SEQ ID NO: 85           moltype = DNA  length = 179
FEATURE                 Location/Qualifiers
misc_feature            1..179
                        note = Description of Artificial Sequence: Synthetic
                         polynucleotide
source                  1..179
                        mol_type = other DNA
                        organism = synthetic construct
SEQUENCE: 85
gctattctcg cagctcacca gttttagagc tagaaatagc aagttaaaat aaggctagtc   60
cgttatcaac ttgaaaaagt ggcaccgagt cggtgcgagt cggtgcgacg agcgcggcga  120
tatcatcatc catggcacaa ttaacatctc aatcaaggta aatgcttgag ctgcgagaa   179

SEQ ID NO: 86           moltype = DNA  length = 179
FEATURE                 Location/Qualifiers
misc_feature            1..179
                        note = Description of Artificial Sequence: Synthetic
                         polynucleotide
source                  1..179
                        mol_type = other DNA
                        organism = synthetic construct
SEQUENCE: 86
gctattctcg cagctcacca gttttagagc tagaaatagc aagttaaaat aaggctagtc   60
cgttatcaac ttgaaaaagt ggcaccgagt cggtgcgagt cggtgcgacg agcgcggcga  120
tatcatcatc catggagcat ttaccttgat tgagatgtta attgtgtgag ctgcgagaa   179

SEQ ID NO: 87           moltype = DNA  length = 182
FEATURE                 Location/Qualifiers
misc_feature            1..182
                        note = Description of Artificial Sequence: Synthetic
                         polynucleotide
source                  1..182
                        mol_type = other DNA
                        organism = synthetic construct
SEQUENCE: 87
gctattctcg cagctcacca gttttagagc tagaaatagc aagttaaaat aaggctagtc   60
cgttatcaac ttgaaaaagt ggcaccgagt cggtgcgagt cggtgcgacg agcgcggcga  120
tatcatcatc catggcaggt ttttgacgaa agtgatccag atgatccagt gagctgcgag  180
aa                                                                 182

SEQ ID NO: 88           moltype = DNA  length = 182
FEATURE                 Location/Qualifiers
misc_feature            1..182
                        note = Description of Artificial Sequence: Synthetic
                         polynucleotide
source                  1..182
                        mol_type = other DNA
                        organism = synthetic construct
SEQUENCE: 88
gctattctcg cagctcacca gttttagagc tagaaatagc aagttaaaat aaggctagtc   60
cgttatcaac ttgaaaaagt ggcaccgagt cggtgcgagt cggtgcgacg agcgcggcga  120
tatcatcatc catggctgga tcatctggat cactttcgtc aaaaacctgt gagctgcgag  180
aa                                                                 182

SEQ ID NO: 89           moltype = DNA  length = 96
FEATURE                 Location/Qualifiers
```

```
misc_feature           1..96
                       note = Description of Artificial Sequence: Synthetic
                         oligonucleotide
source                 1..96
                       mol_type = other DNA
                       organism = synthetic construct
SEQUENCE: 89
gaagccggcc ttgcacatgc gttttagagc tagaaatagc aagttaaaat aaggctagtc    60
cgttatcaac ttgaaaaagt ggcaccgagt cggtgc                              96

SEQ ID NO: 90          moltype = DNA   length = 164
FEATURE                Location/Qualifiers
misc_feature           1..164
                       note = Description of Artificial Sequence: Synthetic
                         polynucleotide
source                 1..164
                       mol_type = other DNA
                       organism = synthetic construct
SEQUENCE: 90
gaagccggcc ttgcacatgc gttttagagc tagaaatagc aagttaaaat aaggctagtc    60
cgttatcaac ttgaaaaagt ggcaccgagt cggtgcatat catcatccat ggtaccgttc   120
gtatagcata cattatacga agttattgag ctgcgagaat agcc                    164

SEQ ID NO: 91          moltype = DNA   length = 172
FEATURE                Location/Qualifiers
misc_feature           1..172
                       note = Description of Artificial Sequence: Synthetic
                         polynucleotide
source                 1..172
                       mol_type = other DNA
                       organism = synthetic construct
SEQUENCE: 91
gaagccggcc ttgcacatgc gttttagagc tagaaatagc aagttaaaat aaggctagtc    60
cgttatcaac ttgaaaaagt ggcaccgagt cggtgcgacg agcgcggcga tatcatcatc   120
catggtaccg ttcgtatagc atacattata cgaagttatt gagctgcgag aa           172

SEQ ID NO: 92          moltype = DNA   length = 189
FEATURE                Location/Qualifiers
misc_feature           1..189
                       note = Description of Artificial Sequence: Synthetic
                         polynucleotide
source                 1..189
                       mol_type = other DNA
                       organism = synthetic construct
SEQUENCE: 92
gctattctcg cagctcacca gttttagagc tagaaatagc aagttaaaat aaggctagtc    60
cgttatcaac ttgaaaaagt ggcaccgagt cggtgctcga cgacgagcgc ggcgatatca   120
tcatccatgg ccggatgatc ctgacgacgg agaccgccgt cgtcgacaag ccggcctgag   180
ctgcgagaa                                                           189

SEQ ID NO: 93          moltype = DNA   length = 181
FEATURE                Location/Qualifiers
misc_feature           1..181
                       note = Description of Artificial Sequence: Synthetic
                         polynucleotide
source                 1..181
                       mol_type = other DNA
                       organism = synthetic construct
SEQUENCE: 93
gctattctcg cagctcacca gttttagagc tagaaatagc aagttaaaat aaggctagtc    60
cgttatcaac ttgaaaaagt ggcaccgagt cggtgcgagc gcggcgatat catcatccat   120
ggccggatga tcctgacgac ggagaccgcc gtcgtcgaca gccggcctg agctgcgaga   180
a                                                                   181

SEQ ID NO: 94          moltype = DNA   length = 178
FEATURE                Location/Qualifiers
misc_feature           1..178
                       note = Description of Artificial Sequence: Synthetic
                         polynucleotide
source                 1..178
                       mol_type = other DNA
                       organism = synthetic construct
SEQUENCE: 94
gctattctcg cagctcacca gttttagagc tagaaatagc aagttaaaat aaggctagtc    60
cgttatcaac ttgaaaaagt ggcaccgagt cggtgccgcg gcgatatcat catccatggc   120
cggatgatcc tgacgacgga gaccgccgtc gtcgacaagc cggcctgagc tgcgagaa     178

SEQ ID NO: 95          moltype = DNA   length = 175
FEATURE                Location/Qualifiers
```

```
misc_feature              1..175
                          note = Description of Artificial Sequence: Synthetic
                              polynucleotide
source                    1..175
                          mol_type = other DNA
                          organism = synthetic construct
SEQUENCE: 95
gctattctcg cagctcacca gttttagagc tagaaatagc aagttaaaat aaggctagtc    60
cgttatcaac ttgaaaaagt ggcaccgagt cggtgcggcg atatcatcat ccatggccgg   120
atgatcctga cgacggagac cgccgtcgtc gacaagccgg cctgagctgc gagaa        175

SEQ ID NO: 96              moltype = DNA   length = 171
FEATURE                   Location/Qualifiers
misc_feature              1..171
                          note = Description of Artificial Sequence: Synthetic
                              polynucleotide
source                    1..171
                          mol_type = other DNA
                          organism = synthetic construct
SEQUENCE: 96
gctattctcg cagctcacca gttttagagc tagaaatagc aagttaaaat aaggctagtc    60
cgttatcaac ttgaaaaagt ggcaccgagt cggtgcatat catcatccat ggccggatga   120
tcctgacgac ggagaccgcc gtcgtcgaca agccggcctg agctgcgaga a            171

SEQ ID NO: 97              moltype = DNA   length = 194
FEATURE                   Location/Qualifiers
misc_feature              1..194
                          note = Description of Artificial Sequence: Synthetic
                              polynucleotide
source                    1..194
                          mol_type = other DNA
                          organism = synthetic construct
SEQUENCE: 97
gctattctcg cagctcacca gttttagagc tagaaatagc aagttaaaat aaggctagtc    60
cgttatcaac ttgaaaaagt ggcaccgagt cggtgctcga cgacgagcgc ggcgatatca   120
tcatccatgg ccggatgatc ctgacgacgg agaccgccgt cgtcgacaag ccggcctgag   180
ctgcgagaat agcc                                                     194

SEQ ID NO: 98              moltype = DNA   length = 189
FEATURE                   Location/Qualifiers
misc_feature              1..189
                          note = Description of Artificial Sequence: Synthetic
                              polynucleotide
source                    1..189
                          mol_type = other DNA
                          organism = synthetic construct
SEQUENCE: 98
gctattctcg cagctcacca gttttagagc tagaaatagc aagttaaaat aaggctagtc    60
cgttatcaac ttgaaaaagt ggcaccgagt cggtgcgacg agcgcggcga tcatcatc    120
catggccgga tgatcctgac gacggagacc gccgtcgtcg acaagccggc ctgagctgcg   180
agaatagcc                                                           189

SEQ ID NO: 99              moltype = DNA   length = 176
FEATURE                   Location/Qualifiers
misc_feature              1..176
                          note = Description of Artificial Sequence: Synthetic
                              polynucleotide
source                    1..176
                          mol_type = other DNA
                          organism = synthetic construct
SEQUENCE: 99
gctattctcg cagctcacca gttttagagc tagaaatagc aagttaaaat aaggctagtc    60
cgttatcaac ttgaaaaagt ggcaccgagt cggtgcatat catcatccat ggccggatga   120
tcctgacgac ggagaccgcc gtcgtcgaca agccggcctg agctgcgaga atagcc       176

SEQ ID NO: 100             moltype = DNA   length = 194
FEATURE                   Location/Qualifiers
misc_feature              1..194
                          note = Description of Artificial Sequence: Synthetic
                              polynucleotide
source                    1..194
                          mol_type = other DNA
                          organism = synthetic construct
SEQUENCE: 100
gctgtctccg ccgcccgcca gttttagagc tagaaatagc aagttaaaat aaggctagtc    60
cgttatcaac ttgaaaaagt ggcaccgagt cggtgcctgc ccatccgcgg cggcacgggg   120
gtcgcagtcg ccatgccgga tgatcctgac gacggagacc gccgtcgtcg acaagccggc   180
ccgggcggcg gaga                                                     194
```

```
SEQ ID NO: 101            moltype = DNA   length = 189
FEATURE                   Location/Qualifiers
misc_feature              1..189
                          note = Description of Artificial Sequence: Synthetic
                          polynucleotide
source                    1..189
                          mol_type = other DNA
                          organism = synthetic construct
SEQUENCE: 101
gctgtctccg ccgcccgcca gttttagagc tagaaatagc aagttaaaat aaggctagtc    60
cgttatcaac ttgaaaaagt ggcaccgagt cggtgccatc cgcggcggca cggggtcgc   120
agtcgccatg ccggatgatc ctgacgacgg agaccgccgt cgtcgacaag ccggcccggg   180
cggcggaga                                                           189

SEQ ID NO: 102            moltype = DNA   length = 184
FEATURE                   Location/Qualifiers
misc_feature              1..184
                          note = Description of Artificial Sequence: Synthetic
                          polynucleotide
source                    1..184
                          mol_type = other DNA
                          organism = synthetic construct
SEQUENCE: 102
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgccgga tgatcctgac gacgagacc gccgtcgtcg acaagccggc ccgggcggcg   180
gaga                                                                184

SEQ ID NO: 103            moltype = DNA   length = 179
FEATURE                   Location/Qualifiers
misc_feature              1..179
                          note = Description of Artificial Sequence: Synthetic
                          polynucleotide
source                    1..179
                          mol_type = other DNA
                          organism = synthetic construct
SEQUENCE: 103
gctgtctccg ccgcccgcca gttttagagc tagaaatagc aagttaaaat aaggctagtc    60
cgttatcaac ttgaaaaagt ggcaccgagt cggtgcggca cggggtcgc agtcgccatg   120
ccggatgatc ctgacgacgg agaccgccgt cgtcgacaag ccggcccggg cggcggaga   179

SEQ ID NO: 104            moltype = DNA   length = 174
FEATURE                   Location/Qualifiers
misc_feature              1..174
                          note = Description of Artificial Sequence: Synthetic
                          polynucleotide
source                    1..174
                          mol_type = other DNA
                          organism = synthetic construct
SEQUENCE: 104
gctgtctccg ccgcccgcca gttttagagc tagaaatagc aagttaaaat aaggctagtc    60
cgttatcaac ttgaaaaagt ggcaccgagt cggtgcgggg gtcgcagtcg ccatgccgga   120
tgatcctgac gacggagacc gccgtcgtcg acaagccggc ccgggcggcg gaga          174

SEQ ID NO: 105            moltype = DNA   length = 199
FEATURE                   Location/Qualifiers
misc_feature              1..199
                          note = Description of Artificial Sequence: Synthetic
                          polynucleotide
source                    1..199
                          mol_type = other DNA
                          organism = synthetic construct
SEQUENCE: 105
gctgtctccg ccgcccgcca gttttagagc tagaaatagc aagttaaaat aaggctagtc    60
cgttatcaac ttgaaaaagt ggcaccgagt cggtgcctgc ccatccgcgg cggcacgggg   120
gtcgcagtcg ccatgccgga tgatcctgac gacggagacc gccgtcgtcg acaagccggc   180
ccgggcggcg gagacagcg                                                199

SEQ ID NO: 106            moltype = DNA   length = 194
FEATURE                   Location/Qualifiers
misc_feature              1..194
                          note = Description of Artificial Sequence: Synthetic
                          polynucleotide
source                    1..194
                          mol_type = other DNA
                          organism = synthetic construct
SEQUENCE: 106
gctgtctccg ccgcccgcca gttttagagc tagaaatagc aagttaaaat aaggctagtc    60
cgttatcaac ttgaaaaagt ggcaccgagt cggtgccatc cgcggcggca cggggtcgc   120
```

-continued

```
agtcgccatg ccggatgatc ctgacgacgg agaccgccgt cgtcgacaag ccggcccggg   180
cggcggagac agcg                                                      194

SEQ ID NO: 107              moltype = DNA   length = 189
FEATURE                     Location/Qualifiers
misc_feature                1..189
                            note = Description of Artificial Sequence: Synthetic
                            polynucleotide
source                      1..189
                            mol_type = other DNA
                            organism = synthetic construct
SEQUENCE: 107
gctgtctccg ccgcccgcca gttttagagc tagaaatagc aagttaaaat aaggctagtc   60
cgttatcaac ttgaaaaagt ggaccgagt cggtgcgcgg cggcacgggg gtcgcagtcg   120
ccatgccgga tgatcctgac gacggagacc gccgtcgtcg acaagccggc ccgggcggcg   180
gagacagcg                                                           189

SEQ ID NO: 108              moltype = DNA   length = 184
FEATURE                     Location/Qualifiers
misc_feature                1..184
                            note = Description of Artificial Sequence: Synthetic
                            polynucleotide
source                      1..184
                            mol_type = other DNA
                            organism = synthetic construct
SEQUENCE: 108
gctgtctccg ccgcccgcca gttttagagc tagaaatagc aagttaaaat aaggctagtc   60
cgttatcaac ttgaaaaagt ggcaccgagt cggtgcggca cggggtcgc agtcgccatg   120
ccggatgatc ctgacgacgg agaccgccgt cgtcgacaag ccggcccggg cggcggagac   180
agcg                                                                184

SEQ ID NO: 109              moltype = DNA   length = 179
FEATURE                     Location/Qualifiers
misc_feature                1..179
                            note = Description of Artificial Sequence: Synthetic
                            polynucleotide
source                      1..179
                            mol_type = other DNA
                            organism = synthetic construct
SEQUENCE: 109
gctgtctccg ccgcccgcca gttttagagc tagaaatagc aagttaaaat aaggctagtc   60
cgttatcaac ttgaaaaagt ggcaccgagt cggtgcgggg gtcgcagtcg ccatgccgga   120
tgatcctgac gacggagacc gccgtcgtcg acaagccggc ccgggcggcg gagacagcg    179

SEQ ID NO: 110              moltype = DNA   length = 96
FEATURE                     Location/Qualifiers
misc_feature                1..96
                            note = Description of Artificial Sequence: Synthetic
                            oligonucleotide
source                      1..96
                            mol_type = other DNA
                            organism = synthetic construct
SEQUENCE: 110
gcgtggtggg gccgccagcg gttttagagc tagaaatagc aagttaaaat aaggctagtc   60
cgttatcaac ttgaaaaagt ggcaccgagt cggtgc                              96

SEQ ID NO: 111              moltype = DNA   length = 180
FEATURE                     Location/Qualifiers
misc_feature                1..180
                            note = Description of Artificial Sequence: Synthetic
                            polynucleotide
source                      1..180
                            mol_type = other DNA
                            organism = synthetic construct
SEQUENCE: 111
gctattctcg cagctcacca gttttagagc tagaaatagc aagttaaaat aaggctagtc   60
cgttatcaac ttgaaaaagt ggcaccgagt cggtgcgacg agcgcggcga tatcatcatc   120
catgggatg atcctgacga cggagaccgc cgtcgtcgac aagccggtga gctgcgagaa   180

SEQ ID NO: 112              moltype = DNA   length = 178
FEATURE                     Location/Qualifiers
misc_feature                1..178
                            note = Description of Artificial Sequence: Synthetic
                            polynucleotide
source                      1..178
                            mol_type = other DNA
                            organism = synthetic construct
SEQUENCE: 112
gctattctcg cagctcacca gttttagagc tagaaatagc aagttaaaat aaggctagtc   60
```

-continued

```
cgttatcaac ttgaaaaagt ggcaccgagt cggtgcgacg agcgcggcga tatcatcatc   120
catgggatga tcctgacgac ggagaccgcc gtcgtcgaca agccgtgagc tgcgagaa     178

SEQ ID NO: 113          moltype = DNA   length = 176
FEATURE                 Location/Qualifiers
misc_feature            1..176
                        note = Description of Artificial Sequence: Synthetic
                         polynucleotide
source                  1..176
                        mol_type = other DNA
                        organism = synthetic construct
SEQUENCE: 113
gctattctcg cagctcacca gttttagagc tagaaatagc aagttaaaat aaggctagtc   60
cgttatcaac ttgaaaaagt ggcaccgagt cggtgcgacg agcgcggcga tatcatcatc   120
catggatgat cctgacgacg gagaccgccg tcgtcgacaa gcctgagctg cgagaa       176

SEQ ID NO: 114          moltype = DNA   length = 174
FEATURE                 Location/Qualifiers
misc_feature            1..174
                        note = Description of Artificial Sequence: Synthetic
                         polynucleotide
source                  1..174
                        mol_type = other DNA
                        organism = synthetic construct
SEQUENCE: 114
gctattctcg cagctcacca gttttagagc tagaaatagc aagttaaaat aaggctagtc   60
cgttatcaac ttgaaaaagt ggcaccgagt cggtgcgacg agcgcggcga tatcatcatc   120
catggtgatc ctgacgacgg agaccgccgt cgtcgacaag ctgagctgcg agaa         174

SEQ ID NO: 115          moltype = DNA   length = 182
FEATURE                 Location/Qualifiers
misc_feature            1..182
                        note = Description of Artificial Sequence: Synthetic
                         polynucleotide
source                  1..182
                        mol_type = other DNA
                        organism = synthetic construct
SEQUENCE: 115
gctgtctccg ccgcccgcca gttttagagc tagaaatagc aagttaaaat aaggctagtc   60
cgttatcaac ttgaaaaagt ggcaccgagt cggtgcgcgg cggcacgggg gtcgcagtcg   120
ccatgcggat gatcctgacg acggagaccg ccgtcgtcga caagccggcc gggcggcgga   180
ga                                                                  182

SEQ ID NO: 116          moltype = DNA   length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 116
gctgtctccg ccgcccgcca gttttagagc tagaaatagc aagttaaaat aaggctagtc   60
cgttatcaac ttgaaaaagt ggcaccgagt cggtgcgcgg cggcacgggg gtcgcagtcg   120
ccatgggatg atcctgacga cggagaccgc cgtcgtcgaa agccggcgg gcggcggaga   180

SEQ ID NO: 117          moltype = DNA   length = 178
FEATURE                 Location/Qualifiers
misc_feature            1..178
                        note = Description of Artificial Sequence: Synthetic
                         polynucleotide
source                  1..178
                        mol_type = other DNA
                        organism = synthetic construct
SEQUENCE: 117
gctgtctccg ccgcccgcca gttttagagc tagaaatagc aagttaaaat aaggctagtc   60
cgttatcaac ttgaaaaagt ggcaccgagt cggtgcgcgg cggcacgggg gtcgcagtcg   120
ccatggatga tcctgacgac ggagaccgcc gtcgtcgaca agccgcgggc ggcggaga     178

SEQ ID NO: 118          moltype = DNA   length = 176
FEATURE                 Location/Qualifiers
misc_feature            1..176
                        note = Description of Artificial Sequence: Synthetic
                         polynucleotide
source                  1..176
                        mol_type = other DNA
                        organism = synthetic construct
SEQUENCE: 118
gctgtctccg ccgcccgcca gttttagagc tagaaatagc aagttaaaat aaggctagtc   60
```

```
cgttatcaac ttgaaaaagt ggcaccgagt cggtgcgcgg cggcacgggg gtcgcagtcg    120
ccatgatgat cctgacgacg gagaccgccg tcgtcgacaa gcccgggcgg cggaga        176

SEQ ID NO: 119          moltype = DNA   length = 189
FEATURE                 Location/Qualifiers
misc_feature            1..189
                        note = Description of Artificial Sequence: Synthetic
                         polynucleotide
source                  1..189
                        mol_type = other DNA
                        organism = synthetic construct
SEQUENCE: 119
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt    120
ccgccccgga tgatcctgac gacggagacc gccgtcgtcg acaagccggc ctcctccagg    180
caatacgcg                                                            189

SEQ ID NO: 120          moltype = DNA   length = 184
FEATURE                 Location/Qualifiers
misc_feature            1..184
                        note = Description of Artificial Sequence: Synthetic
                         polynucleotide
source                  1..184
                        mol_type = other DNA
                        organism = synthetic construct
SEQUENCE: 120
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt    120
ccgccccgga tgatcctgac gacggagacc gccgtcgtcg acaagccggc ctcctccagg    180
caat                                                                 184

SEQ ID NO: 121          moltype = DNA   length = 182
FEATURE                 Location/Qualifiers
misc_feature            1..182
                        note = Description of Artificial Sequence: Synthetic
                         polynucleotide
source                  1..182
                        mol_type = other DNA
                        organism = synthetic construct
SEQUENCE: 121
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt    120
ccgcccggat gatcctgacg acggagaccg ccgtcgtcga caagccggct cctccaggca    180
at                                                                   182

SEQ ID NO: 122          moltype = DNA   length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 122
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt    120
ccgccggatg atcctgacga cggagaccgc cgtcgtcgac aagccggtcc tccaggcaat    180

SEQ ID NO: 123          moltype = DNA   length = 178
FEATURE                 Location/Qualifiers
misc_feature            1..178
                        note = Description of Artificial Sequence: Synthetic
                         polynucleotide
source                  1..178
                        mol_type = other DNA
                        organism = synthetic construct
SEQUENCE: 123
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt    120
ccgccgatga tcctgacgac ggagaccgcc gtcgtcgaca agccgtcctc caggcaat     178

SEQ ID NO: 124          moltype = DNA   length = 176
FEATURE                 Location/Qualifiers
misc_feature            1..176
                        note = Description of Artificial Sequence: Synthetic
                         polynucleotide
source                  1..176
                        mol_type = other DNA
                        organism = synthetic construct
```

```
SEQUENCE: 124
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccatgat cctgacgacg gagaccgccg tcgtcgacaa gcctcctcca ggcaat       176

SEQ ID NO: 125          moltype = DNA  length = 97
FEATURE                 Location/Qualifiers
misc_feature            1..97
                        note = Description of Artificial Sequence: Synthetic
                         oligonucleotide
source                  1..97
                        mol_type = other DNA
                        organism = synthetic construct
SEQUENCE: 125
gagccgagca cgaggggata cgttttagag ctagaaatag caagttaaaa taaggctagt    60
ccgttatcaa cttgaaaaag tggcaccgag tcggtgc                             97

SEQ ID NO: 126          moltype = DNA  length = 167
FEATURE                 Location/Qualifiers
misc_feature            1..167
                        note = Description of Artificial Sequence: Synthetic
                         polynucleotide
source                  1..167
                        mol_type = other DNA
                        organism = synthetic construct
SEQUENCE: 126
gctattctcg cagctcacca gttttagagc tagaaatagc aagttaaaat aaggctagtc    60
cgttatcaac ttgaaaaagt ggcaccgagt cggtgcggcg atatcatcat ccatggatga   120
tcctgacgac ggagaccgcc gtcgtcgaca agcctgagct gcgagaa                 167

SEQ ID NO: 127          moltype = DNA  length = 162
FEATURE                 Location/Qualifiers
misc_feature            1..162
                        note = Description of Artificial Sequence: Synthetic
                         polynucleotide
source                  1..162
                        mol_type = other DNA
                        organism = synthetic construct
SEQUENCE: 127
gctattctcg cagctcacca gttttagagc tagaaatagc aagttaaaat aaggctagtc    60
cgttatcaac ttgaaaaagt ggcaccgagt cggtgctatc atcatccatg gatgatcctg   120
acgacggaga ccgccgtcgt cgacaagcct gagctgcgag aa                      162

SEQ ID NO: 128          moltype = DNA  length = 157
FEATURE                 Location/Qualifiers
misc_feature            1..157
                        note = Description of Artificial Sequence: Synthetic
                         polynucleotide
source                  1..157
                        mol_type = other DNA
                        organism = synthetic construct
SEQUENCE: 128
gctattctcg cagctcacca gttttagagc tagaaatagc aagttaaaat aaggctagtc    60
cgttatcaac ttgaaaaagt ggcaccgagt cggtgctcat ccatggatga tcctgacgac   120
ggagaccgcc gtcgtcgaca agcctgagct gcgagaa                            157

SEQ ID NO: 129          moltype = DNA  length = 163
FEATURE                 Location/Qualifiers
misc_feature            1..163
                        note = Description of Artificial Sequence: Synthetic
                         polynucleotide
source                  1..163
                        mol_type = other DNA
                        organism = synthetic construct
SEQUENCE: 129
gctattctcg cagctcacca gttttagagc tagaaatagc aagttaaaat aaggctagtc    60
cgttatcaac ttgaaaaagt ggcaccgagt cggtgcggcg atatcatcat ccatggatga   120
tcctgacgac ggagaccgcc gtcgtcgaca agcctgagct gcg                     163

SEQ ID NO: 130          moltype = DNA  length = 158
FEATURE                 Location/Qualifiers
misc_feature            1..158
                        note = Description of Artificial Sequence: Synthetic
                         polynucleotide
source                  1..158
                        mol_type = other DNA
                        organism = synthetic construct
SEQUENCE: 130
gctattctcg cagctcacca gttttagagc tagaaatagc aagttaaaat aaggctagtc    60
```

```
cgttatcaac ttgaaaaagt ggcaccgagt cggtgctatc atcatccatg gatgatcctg   120
acgacggaga ccgccgtcgt cgacaagcct gagctgcg                            158

SEQ ID NO: 131         moltype = DNA   length = 153
FEATURE                Location/Qualifiers
misc_feature           1..153
                       note = Description of Artificial Sequence: Synthetic
                       polynucleotide
source                 1..153
                       mol_type = other DNA
                       organism = synthetic construct
SEQUENCE: 131
gctattctcg cagctcacca gttttagagc tagaaatagc aagttaaaat aaggctagtc   60
cgttatcaac ttgaaaaagt ggcaccgagt cggtgctcat ccatggatga tcctgacgac   120
ggagaccgcc gtcgtcgaca agcctgagct gcg                                 153

SEQ ID NO: 132         moltype = DNA   length = 167
FEATURE                Location/Qualifiers
misc_feature           1..167
                       note = Description of Artificial Sequence: Synthetic
                       polynucleotide
source                 1..167
                       mol_type = other DNA
                       organism = synthetic construct
SEQUENCE: 132
gctgtctccg ccgcccgcca gttttagagc tagaaatagc aagttaaaat aaggctagtc   60
cgttatcaac ttgaaaaagt ggcaccgagt cggtgccggg ggtcgcagtc gccatgatga   120
tcctgacgac ggagaccgcc gtcgtcgaca agcccgggcg gcggaga                 167

SEQ ID NO: 133         moltype = DNA   length = 162
FEATURE                Location/Qualifiers
misc_feature           1..162
                       note = Description of Artificial Sequence: Synthetic
                       polynucleotide
source                 1..162
                       mol_type = other DNA
                       organism = synthetic construct
SEQUENCE: 133
gctgtctccg ccgcccgcca gttttagagc tagaaatagc aagttaaaat aaggctagtc   60
cgttatcaac ttgaaaaagt ggcaccgagt cggtgcgtcg cagtcgccat gatgatcctg   120
acgacggaga ccgccgtcgt cgacaagccc gggcggcgga ga                      162

SEQ ID NO: 134         moltype = DNA   length = 157
FEATURE                Location/Qualifiers
misc_feature           1..157
                       note = Description of Artificial Sequence: Synthetic
                       polynucleotide
source                 1..157
                       mol_type = other DNA
                       organism = synthetic construct
SEQUENCE: 134
gctgtctccg ccgcccgcca gttttagagc tagaaatagc aagttaaaat aaggctagtc   60
cgttatcaac ttgaaaaagt ggcaccgagt cggtgcagtc gccatgatga tcctgacgac   120
ggagaccgcc gtcgtcgaca agcccgggcg gcggaga                             157

SEQ ID NO: 135         moltype = DNA   length = 163
FEATURE                Location/Qualifiers
misc_feature           1..163
                       note = Description of Artificial Sequence: Synthetic
                       polynucleotide
source                 1..163
                       mol_type = other DNA
                       organism = synthetic construct
SEQUENCE: 135
gctgtctccg ccgcccgcca gttttagagc tagaaatagc aagttaaaat aaggctagtc   60
cgttatcaac ttgaaaaagt ggcaccgagt cggtgccggg ggtcgcagtc gccatgatga   120
tcctgacgac ggagaccgcc gtcgtcgaca agcccgggcg gcg                     163

SEQ ID NO: 136         moltype = DNA   length = 158
FEATURE                Location/Qualifiers
misc_feature           1..158
                       note = Description of Artificial Sequence: Synthetic
                       polynucleotide
source                 1..158
                       mol_type = other DNA
                       organism = synthetic construct
SEQUENCE: 136
gctgtctccg ccgcccgcca gttttagagc tagaaatagc aagttaaaat aaggctagtc   60
cgttatcaac ttgaaaaagt ggcaccgagt cggtgcgtcg cagtcgccat gatgatcctg   120
```

```
acgacggaga ccgccgtcgt cgacaagccc gggcggcg                            158

SEQ ID NO: 137          moltype = DNA   length = 153
FEATURE                 Location/Qualifiers
misc_feature            1..153
                        note = Description of Artificial Sequence: Synthetic
                         polynucleotide
source                  1..153
                        mol_type = other DNA
                        organism = synthetic construct
SEQUENCE: 137
gctgtctccg ccgcccgcca gttttagagc tagaaatagc aagttaaaat aaggctagtc   60
cgttatcaac ttgaaaaagt ggcaccgagt cggtgcagtc gccatgatga tcctgacgac  120
ggagaccgcc gtcgtcgaca agcccgggcg gcg                               153

SEQ ID NO: 138          moltype = DNA   length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 138
gagaagcggc gtccggggct agttttagag ctagaaatag caagttaaaa taaggctagt   60
ccgttatcaa cttgaaaaag tggcaccgag tcggtgctct ttgtccagag tcacagccat  120
accggatgat cctgacgacg agaccgccgc tcgtcgacaa gccggccccc cggacgccgc  180

SEQ ID NO: 139          moltype = DNA   length = 179
FEATURE                 Location/Qualifiers
misc_feature            1..179
                        note = Description of Artificial Sequence: Synthetic
                         polynucleotide
source                  1..179
                        mol_type = other DNA
                        organism = synthetic construct
SEQUENCE: 139
gggcacgggg ccatgtacaa gttttagagc tagaaatagc aagttaaaat aaggctagtc   60
cgttatcaac ttgaaaaagt ggcaccgagt cggtgcggcg tcggcagccc gatcccgttg  120
ccggatgatc ctgacgacgg agaccgccgt cgtcgacaag ccggcctaca tggccccgt   179

SEQ ID NO: 140          moltype = DNA   length = 185
FEATURE                 Location/Qualifiers
misc_feature            1..185
                        note = Description of Artificial Sequence: Synthetic
                         polynucleotide
source                  1..185
                        mol_type = other DNA
                        organism = synthetic construct
SEQUENCE: 140
gtgtcaggtg gggcggggct agttttagag ctagaaatag caagttaaaa taaggctagt   60
ccgttatcaa cttgaaaaag tggcaccgag tcggtgcgct ggctcctccc ctggcaccat  120
accggatgat cctgacgacg gagaccgccg tcgtcgacaa gccggccccc cgccccacct  180
gacac                                                              185

SEQ ID NO: 141          moltype = DNA   length = 184
FEATURE                 Location/Qualifiers
misc_feature            1..184
                        note = Description of Artificial Sequence: Synthetic
                         polynucleotide
source                  1..184
                        mol_type = other DNA
                        organism = synthetic construct
SEQUENCE: 141
gagtgggtca gacgagcagg agttttagag ctagaaatag caagttaaaa taaggctagt   60
ccgttatcaa cttgaaaaag tggcaccgag tcggtgcgat ggagggctgc atggggagg   120
agtcgccgga tgatcctgac gacggagacc gccgtcgtcg acaagccggc ctgctcgtct  180
gacc                                                               184

SEQ ID NO: 142          moltype = DNA   length = 97
FEATURE                 Location/Qualifiers
misc_feature            1..97
                        note = Description of Artificial Sequence: Synthetic
                         oligonucleotide
source                  1..97
                        mol_type = other DNA
                        organism = synthetic construct
SEQUENCE: 142
gcagccaccc gctctcggcc cgttttagag ctagaaatag caagttaaaa taaggctagt   60
```

```
ccgttatcaa cttgaaaaag tggcaccgag tcggtgc                              97

SEQ ID NO: 143           moltype = DNA   length = 97
FEATURE                  Location/Qualifiers
misc_feature             1..97
                         note = Description of Artificial Sequence: Synthetic
                         oligonucleotide
source                   1..97
                         mol_type = other DNA
                         organism = synthetic construct
SEQUENCE: 143
gtgtagtcag gccgctcacc cgttttagag ctagaaatag caagttaaaa taaggctagt    60
ccgttatcaa cttgaaaaag tggcaccgag tcggtgc                              97

SEQ ID NO: 144           moltype = DNA   length = 97
FEATURE                  Location/Qualifiers
misc_feature             1..97
                         note = Description of Artificial Sequence: Synthetic
                         oligonucleotide
source                   1..97
                         mol_type = other DNA
                         organism = synthetic construct
SEQUENCE: 144
gctgacaagt ctacggaacc tgttttagag ctagaaatag caagttaaaa taaggctagt    60
ccgttatcaa cttgaaaaag tggcaccgag tcggtgc                              97

SEQ ID NO: 145           moltype = DNA   length = 96
FEATURE                  Location/Qualifiers
misc_feature             1..96
                         note = Description of Artificial Sequence: Synthetic
                         oligonucleotide
source                   1..96
                         mol_type = other DNA
                         organism = synthetic construct
SEQUENCE: 145
gctcctccag cgccttgacc gttttagagc tagaaatagc aagttaaaat aaggctagtc    60
cgttatcaac ttgaaaaagt ggcaccgagt cggtgc                               96

SEQ ID NO: 146           moltype = DNA   length = 20
FEATURE                  Location/Qualifiers
misc_feature             1..20
                         note = Description of Artificial Sequence: Synthetic
                         oligonucleotide
source                   1..20
                         mol_type = other DNA
                         organism = synthetic construct
SEQUENCE: 146
gctattctcg cagctcacca                                                 20

SEQ ID NO: 147           moltype = DNA   length = 20
FEATURE                  Location/Qualifiers
misc_feature             1..20
                         note = Description of Artificial Sequence: Synthetic
                         oligonucleotide
source                   1..20
                         mol_type = other DNA
                         organism = synthetic construct
SEQUENCE: 147
agaagcggcg tccggggcta                                                 20

SEQ ID NO: 148           moltype = DNA   length = 20
FEATURE                  Location/Qualifiers
misc_feature             1..20
                         note = Description of Artificial Sequence: Synthetic
                         oligonucleotide
source                   1..20
                         mol_type = other DNA
                         organism = synthetic construct
SEQUENCE: 148
gggcacgggg ccatgtacaa                                                 20

SEQ ID NO: 149           moltype = DNA   length = 20
FEATURE                  Location/Qualifiers
misc_feature             1..20
                         note = Description of Artificial Sequence: Synthetic
                         oligonucleotide
source                   1..20
                         mol_type = other DNA
                         organism = synthetic construct
```

```
SEQUENCE: 149
gcgtattgcc tggaggatgg                                                   20

SEQ ID NO: 151          moltype = DNA   length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 150
tgtcaggtgg ggcggggcta                                                   20

SEQ ID NO: 151          moltype = DNA   length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 151
agtgggtcag acgagcagga                                                   20

SEQ ID NO: 152          moltype = DNA   length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 152
gctgtctccg ccgcccgcca                                                   20

SEQ ID NO: 153          moltype = DNA   length = 96
FEATURE                 Location/Qualifiers
misc_feature            1..96
                        note = Description of Artificial Sequence: Synthetic
                         oligonucleotide
source                  1..96
                        mol_type = other DNA
                        organism = synthetic construct
SEQUENCE: 153
gctattctcg cagctcacca gttttagagc tagaaatagc aagttaaaat aaggctagtc       60
cgttatcaac ttgaaaaagt ggcaccgagt cggtgc                                 96

SEQ ID NO: 154          moltype = DNA   length = 184
FEATURE                 Location/Qualifiers
misc_feature            1..184
                        note = Description of Artificial Sequence: Synthetic
                         polynucleotide
misc_difference         148..149
                        note = CG, GC, AT, TA, GG, TT, GA, AG, CC, TC, CT, AA, TG,
                         GT, CA, or AC
source                  1..184
                        mol_type = other DNA
                        organism = synthetic construct
SEQUENCE: 154
gctattctcg cagctcacca gttttagagc tagaaatagc aagttaaaat aaggctagtc       60
cgttatcaac ttgaaaaagt ggcaccgagt cggtgcgacg agcgcggcga tatcatcatc      120
catgccggat gatcctgacg acggagnnc gccgtcgtcg acaagccggc ctgagctgcg      180
agaa                                                                   184

SEQ ID NO: 155          moltype = DNA   length = 183
FEATURE                 Location/Qualifiers
misc_feature            1..183
                        note = Description of Artificial Sequence: Synthetic
                         polynucleotide
source                  1..183
                        mol_type = other DNA
                        organism = synthetic construct
SEQUENCE: 155
gctattctcg cagctcacca gttttagagc tagaaatagc aagttaaaat aaggctagtc       60
cgttatcaac ttgaaaaagt ggcaccgagt cggtgcgacg agcgcggcga tatcatcatc      120
catgccggat gatcctgacg acggagaccg ccgtcgtcga caagccggcc tgagctgcga      180
gaa                                                                    183
```

```
SEQ ID NO: 156          moltype = DNA   length = 183
FEATURE                 Location/Qualifiers
misc_feature            1..183
                        note = Description of Artificial Sequence: Synthetic
                        polynucleotide
source                  1..183
                        mol_type = other DNA
                        organism = synthetic construct
SEQUENCE: 156
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catgccggat gatcctgacg acggagagcg ccgtcgtcga caagccggcc tgagctgcga   180
gaa                                                                 183

SEQ ID NO: 157          moltype = DNA   length = 189
FEATURE                 Location/Qualifiers
misc_feature            1..189
                        note = Description of Artificial Sequence: Synthetic
                        polynucleotide
source                  1..189
                        mol_type = other DNA
                        organism = synthetic construct
SEQUENCE: 157
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccgga tgatcctgac gacggagtcc gccgtcgtcg acaagccggc ctcctccagg    180
caatacgcg                                                           189

SEQ ID NO: 158          moltype = DNA   length = 189
FEATURE                 Location/Qualifiers
misc_feature            1..189
                        note = Description of Artificial Sequence: Synthetic
                        polynucleotide
source                  1..189
                        mol_type = other DNA
                        organism = synthetic construct
SEQUENCE: 158
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgccgga tgatcctgac gacggagctc gccgtcgtcg acaagccggc ccgggcggcg   180
gagacagcg                                                           189

SEQ ID NO: 159          moltype = DNA   length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 159
gtcacctcca atgactaggg                                                20

SEQ ID NO: 160          moltype = DNA   length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 160
gggcaaccac aaacccacga                                                20

SEQ ID NO: 161          moltype = DNA   length = 194
FEATURE                 Location/Qualifiers
misc_feature            1..194
                        note = Description of Artificial Sequence: Synthetic
                        polynucleotide
source                  1..194
                        mol_type = other DNA
                        organism = synthetic construct
SEQUENCE: 161
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggctatg ccggatgatc ctgacgacgg agtccgccgt cgtcgacaag ccggccctag   180
ctgagctgcg agaa                                                     194

SEQ ID NO: 162          moltype = DNA   length = 189
```

```
FEATURE                 Location/Qualifiers
misc_feature            1..189
                        note = Description of Artificial Sequence: Synthetic
                        polynucleotide
source                  1..189
                        mol_type = other DNA
                        organism = synthetic construct
SEQUENCE: 162
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgccg gatgatcctg acgacggagt ccgccgtcgt cgacaagccg ccctatgag    180
ctgcgagaa                                                           189

SEQ ID NO: 163          moltype = DNA   length = 184
FEATURE                 Location/Qualifiers
misc_feature            1..184
                        note = Description of Artificial Sequence: Synthetic
                        polynucleotide
source                  1..184
                        mol_type = other DNA
                        organism = synthetic construct
SEQUENCE: 163
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggccgga tgatcctgac gacggagtcc gccgtcgtcg acaagccggc ctgagctgcg   180
agaa                                                                184

SEQ ID NO: 164          moltype = DNA   length = 179
FEATURE                 Location/Qualifiers
misc_feature            1..179
                        note = Description of Artificial Sequence: Synthetic
                        polynucleotide
source                  1..179
                        mol_type = other DNA
                        organism = synthetic construct
SEQUENCE: 164
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggggatg atcctgacga cggagtccgc cgtcgtcgaa agccgtgag ctgcgagaa     179

SEQ ID NO: 165          moltype = DNA   length = 174
FEATURE                 Location/Qualifiers
misc_feature            1..174
                        note = Description of Artificial Sequence: Synthetic
                        polynucleotide
source                  1..174
                        mol_type = other DNA
                        organism = synthetic construct
SEQUENCE: 165
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgatc ctgacgacgg agtccgccgt cgtcgacaag ctgagctgcg agaa         174

SEQ ID NO: 166          moltype = DNA   length = 169
FEATURE                 Location/Qualifiers
misc_feature            1..169
                        note = Description of Artificial Sequence: Synthetic
                        polynucleotide
source                  1..169
                        mol_type = other DNA
                        organism = synthetic construct
SEQUENCE: 166
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggatcct gacgacggag tccgccgtcg tcgacatgag ctgcgagaa               169

SEQ ID NO: 167          moltype = DNA   length = 164
FEATURE                 Location/Qualifiers
misc_feature            1..164
                        note = Description of Artificial Sequence: Synthetic
                        polynucleotide
source                  1..164
                        mol_type = other DNA
                        organism = synthetic construct
SEQUENCE: 167
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggcctga cgacggagtc cgccgtcgtc gtgagctgcg agaa                    164
```

| SEQ ID NO: 168 | moltype = DNA length = 159 |
|---|---|
| FEATURE | Location/Qualifiers |
| misc_feature | 1..159 |
| | note = Description of Artificial Sequence: Synthetic polynucleotide |
| source | 1..159 |
| | mol_type = other DNA |
| | organism = synthetic construct |

SEQUENCE: 168
```
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgacg acggagtccg ccgtcgtgag ctgcgagaa                          159
```

| SEQ ID NO: 169 | moltype = DNA length = 154 |
|---|---|
| FEATURE | Location/Qualifiers |
| misc_feature | 1..154 |
| | note = Description of Artificial Sequence: Synthetic polynucleotide |
| source | 1..154 |
| | mol_type = other DNA |
| | organism = synthetic construct |

SEQUENCE: 169
```
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggacgac ggagtccgcc gtgagctgcg agaa                               154
```

| SEQ ID NO: 170 | moltype = DNA length = 149 |
|---|---|
| FEATURE | Location/Qualifiers |
| misc_feature | 1..149 |
| | note = Description of Artificial Sequence: Synthetic polynucleotide |
| source | 1..149 |
| | mol_type = other DNA |
| | organism = synthetic construct |

SEQUENCE: 170
```
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catgggacgg agtccgtgag ctgcgagaa                                     149
```

| SEQ ID NO: 171 | moltype = DNA length = 144 |
|---|---|
| FEATURE | Location/Qualifiers |
| misc_feature | 1..144 |
| | note = Description of Artificial Sequence: Synthetic polynucleotide |
| source | 1..144 |
| | mol_type = other DNA |
| | organism = synthetic construct |

SEQUENCE: 171
```
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggcggag ttgagctgcg agaa                                          144
```

| SEQ ID NO: 172 | moltype = DNA length = 182 |
|---|---|
| FEATURE | Location/Qualifiers |
| misc_feature | 1..182 |
| | note = Description of Artificial Sequence: Synthetic polynucleotide |
| source | 1..182 |
| | mol_type = other DNA |
| | organism = synthetic construct |

SEQUENCE: 172
```
gaagccggcc ttgcacatgc gttttagagc tagaaatagc aagttaaaat aaggctagtc    60
cgttatcaac ttgaaaaagt ggcaccgagt cggtgctcga cgacgagcgc ggcgatatca   120
tcatccatgg taccgttcgt atagcataca ttatacgaag ttattgagct gcgagaatag   180
cc                                                                  182
```

| SEQ ID NO: 173 | moltype = DNA length = 177 |
|---|---|
| FEATURE | Location/Qualifiers |
| misc_feature | 1..177 |
| | note = Description of Artificial Sequence: Synthetic polynucleotide |
| source | 1..177 |
| | mol_type = other DNA |
| | organism = synthetic construct |

SEQUENCE: 173
```
gaagccggcc ttgcacatgc gttttagagc tagaaatagc aagttaaaat aaggctagtc    60
cgttatcaac ttgaaaaagt ggcaccgagt cggtgcgacg agcgcggcga tatcatcatc   120
catggtaccg ttcgtatagc atacattata cgaagttatt gagctgcgag aatagcc      177
```

```
SEQ ID NO: 174           moltype = DNA   length = 177
FEATURE                  Location/Qualifiers
misc_feature             1..177
                         note = Description of Artificial Sequence: Synthetic
                         polynucleotide
source                   1..177
                         mol_type = other DNA
                         organism = synthetic construct
SEQUENCE: 174
gaagccggcc ttgcacatgc gttttagagc tagaaatagc aagttaaaat aaggctagtc    60
cgttatcaac ttgaaaaagt ggcaccgagt cggtgctcga cgacgagcgc ggcgatatca   120
tcatccatgg taccgttcgt atagcataca ttatacgaag ttattgagct gcgagaa      177

SEQ ID NO: 175           moltype = DNA   length = 159
FEATURE                  Location/Qualifiers
misc_feature             1..159
                         note = Description of Artificial Sequence: Synthetic
                         polynucleotide
source                   1..159
                         mol_type = other DNA
                         organism = synthetic construct
SEQUENCE: 175
gaagccggcc ttgcacatgc gttttagagc tagaaatagc aagttaaaat aaggctagtc    60
cgttatcaac ttgaaaaagt ggcaccgagt cggtgcatat catcatccat ggtaccgttc   120
gtatagcata cattatacga agttattgag ctgcgagaa                          159

SEQ ID NO: 176           moltype = DNA   length = 96
FEATURE                  Location/Qualifiers
misc_feature             1..96
                         note = Description of Artificial Sequence: Synthetic
                         oligonucleotide
source                   1..96
                         mol_type = other DNA
                         organism = synthetic construct
SEQUENCE: 176
ccccacgatg gagggaaga gttttagagc tagaaatagc aagttaaaat aaggctagtc     60
cgttatcaac ttgaaaaagt ggcaccgagt cggtgc                              96

SEQ ID NO: 177           moltype = DNA   length = 96
FEATURE                  Location/Qualifiers
misc_feature             1..96
                         note = Description of Artificial Sequence: Synthetic
                         oligonucleotide
source                   1..96
                         mol_type = other DNA
                         organism = synthetic construct
SEQUENCE: 177
ccttctcctg gagccgcgac gttttagagc tagaaatagc aagttaaaat aaggctagtc    60
cgttatcaac ttgaaaaagt ggcaccgagt cggtgc                              96

SEQ ID NO: 178           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 178
gtggtttgtc tggtcaacca ccgcggtctc agtggtgtac ggtacaaacc ca            52

SEQ ID NO: 179           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 179
tgggtttgta ccgtacacca ctgagaccgc ggtggttgac cagacaaacc ac            52

SEQ ID NO: 180           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
```

```
                    organism = synthetic construct
SEQUENCE: 180
gtggtttgtc tggtcaacca ccgcgcgctc agtggtgtac ggtacaaacc ca            52

SEQ ID NO: 181          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 181
tgggtttgta ccgtacacca ctgagcgcgc ggtggttgac cagacaaacc ac            52

SEQ ID NO: 182          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 182
gtggtttgtc tggtcaacca ccgcggcctc agtggtgtac ggtacaaacc ca            52

SEQ ID NO: 183          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 183
tgggtttgta ccgtacacca ctgaggccgc ggtggttgac cagacaaacc ac            52

SEQ ID NO: 184          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 184
gtggtttgtc tggtcaacca ccgcgatctc agtggtgtac ggtacaaacc ca            52

SEQ ID NO: 185          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 185
tgggtttgta ccgtacacca ctgagatcgc ggtggttgac cagacaaacc ac            52

SEQ ID NO: 186          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 186
gtggtttgtc tggtcaacca ccgcgtactc agtggtgtac ggtacaaacc ca            52

SEQ ID NO: 187          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 187
```
tgggtttgta ccgtacacca ctgagtacgc ggtggttgac cagacaaacc ac          52

SEQ ID NO: 188         moltype = DNA   length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 188
gtggtttgtc tggtcaacca ccgcgggctc agtggtgtac ggtacaaacc ca          52

SEQ ID NO: 189         moltype = DNA   length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 189
tgggtttgta ccgtacacca ctgagcccgc ggtggttgac cagacaaacc ac          52

SEQ ID NO: 190         moltype = DNA   length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 190
gtggtttgtc tggtcaacca ccgcgttctc agtggtgtac ggtacaaacc ca          52

SEQ ID NO: 191         moltype = DNA   length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 191
tgggtttgta ccgtacacca ctgagaacgc ggtggttgac cagacaaacc ac          52

SEQ ID NO: 192         moltype = DNA   length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 192
gtggtttgtc tggtcaacca ccgcggactc agtggtgtac ggtacaaacc ca          52

SEQ ID NO: 193         moltype = DNA   length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 193
tgggtttgta ccgtacacca ctgagtccgc ggtggttgac cagacaaacc ac          52

SEQ ID NO: 194         moltype = DNA   length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 194
gtggtttgtc tggtcaacca ccgcgagctc agtggtgtac ggtacaaacc ca          52

```
SEQ ID NO: 195          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 195
tgggtttgta ccgtacacca ctgagctcgc ggtggttgac cagacaaacc ac          52

SEQ ID NO: 196          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 196
gtggtttgtc tggtcaacca ccgcgccctc agtggtgtac ggtacaaacc ca          52

SEQ ID NO: 197          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 197
tgggtttgta ccgtacacca ctgagggcgc ggtggttgac cagacaaacc ac          52

SEQ ID NO: 198          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 198
gtggtttgtc tggtcaacca ccgcgtcctc agtggtgtac ggtacaaacc ca          52

SEQ ID NO: 199          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 199
tgggtttgta ccgtacacca ctgaggacgc ggtggttgac cagacaaacc ac          52

SEQ ID NO: 200          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 200
gtggtttgtc tggtcaacca ccgcgctctc agtggtgtac ggtacaaacc ca          52

SEQ ID NO: 201          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 201
tgggtttgta ccgtacacca ctgagagcgc ggtggttgac cagacaaacc ac          52

SEQ ID NO: 202          moltype = DNA  length = 52
FEATURE                 Location/Qualifiers
```

```
misc_feature            1..52
                        note = Description of Artificial Sequence: Synthetic
                           oligonucleotide
source                  1..52
                        mol_type = other DNA
                        organism = synthetic construct
SEQUENCE: 202
gtggtttgtc tggtcaacca ccgcgaactc agtggtgtac ggtacaaacc ca          52

SEQ ID NO: 203          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 203
tgggtttgta ccgtacacca ctgagttcgc ggtggttgac cagacaaacc ac          52

SEQ ID NO: 204          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 204
gtggtttgtc tggtcaacca ccgcgcactc agtggtgtac ggtacaaacc ca          52

SEQ ID NO: 205          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 205
tgggtttgta ccgtacacca ctgagtgcgc ggtggttgac cagacaaacc ac          52

SEQ ID NO: 206          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 206
gtggtttgtc tggtcaacca ccgcgacctc agtggtgtac ggtacaaacc ca          52

SEQ ID NO: 207          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 207
tgggtttgta ccgtacacca ctgaggtcgc ggtggttgac cagacaaacc ac          52

SEQ ID NO: 208          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 208
gtggtttgtc tggtcaacca ccgcgtgctc agtggtgtac ggtacaaacc ca          52

SEQ ID NO: 209          moltype = DNA  length = 52
FEATURE                 Location/Qualifiers
misc_feature            1..52
                        note = Description of Artificial Sequence: Synthetic
```

```
                              oligonucleotide
source                        1..52
                              mol_type = other DNA
                              organism = synthetic construct
SEQUENCE: 209
tgggtttgta ccgtacacca ctgagcacgc ggtggttgac cagacaaacc ac          52

SEQ ID NO: 210                moltype = DNA   length = 46
FEATURE                       Location/Qualifiers
misc_feature                  1..46
                              note = Description of Artificial Sequence: Synthetic
                              oligonucleotide
source                        1..46
                              mol_type = other DNA
                              organism = synthetic construct
SEQUENCE: 210
ggccggcttg tcgacgacgg cggtctccgt cgtcaggatc atccgg                 46

SEQ ID NO: 211                moltype = DNA   length = 46
FEATURE                       Location/Qualifiers
misc_feature                  1..46
                              note = Description of Artificial Sequence: Synthetic
                              oligonucleotide
source                        1..46
                              mol_type = other DNA
                              organism = synthetic construct
SEQUENCE: 211
ccggatgatc ctgacgacgg agaccgccgt cgtcgacaag ccggcc                 46

SEQ ID NO: 212                moltype = DNA   length = 46
FEATURE                       Location/Qualifiers
misc_feature                  1..46
                              note = Description of Artificial Sequence: Synthetic
                              oligonucleotide
source                        1..46
                              mol_type = other DNA
                              organism = synthetic construct
SEQUENCE: 212
ggccggcttg tcgacgacgg cgaactccgt cgtcaggatc atccgg                 46

SEQ ID NO: 213                moltype = DNA   length = 46
FEATURE                       Location/Qualifiers
misc_feature                  1..46
                              note = Description of Artificial Sequence: Synthetic
                              oligonucleotide
source                        1..46
                              mol_type = other DNA
                              organism = synthetic construct
SEQUENCE: 213
ccggatgatc ctgacgacgg agttcgccgt cgtcgacaag ccggcc                 46

SEQ ID NO: 214                moltype = DNA   length = 46
FEATURE                       Location/Qualifiers
misc_feature                  1..46
                              note = Description of Artificial Sequence: Synthetic
                              oligonucleotide
source                        1..46
                              mol_type = other DNA
                              organism = synthetic construct
SEQUENCE: 214
ggccggcttg tcgacgacgg cggactccgt cgtcaggatc atccgg                 46

SEQ ID NO: 215                moltype = DNA   length = 46
FEATURE                       Location/Qualifiers
misc_feature                  1..46
                              note = Description of Artificial Sequence: Synthetic
                              oligonucleotide
source                        1..46
                              mol_type = other DNA
                              organism = synthetic construct
SEQUENCE: 215
ccggatgatc ctgacgacgg agtccgccgt cgtcgacaag ccggcc                 46

SEQ ID NO: 216                moltype = DNA   length = 46
FEATURE                       Location/Qualifiers
misc_feature                  1..46
                              note = Description of Artificial Sequence: Synthetic
                              oligonucleotide
source                        1..46
```

```
                         mol_type = other DNA
                         organism = synthetic construct
SEQUENCE: 216
ggccggcttg tcgacgacgg cgcactccgt cgtcaggatc atccgg              46

SEQ ID NO: 217           moltype = DNA   length = 46
FEATURE                  Location/Qualifiers
misc_feature             1..46
                         note = Description of Artificial Sequence: Synthetic
                           oligonucleotide
source                   1..46
                         mol_type = other DNA
                         organism = synthetic construct
SEQUENCE: 217
ccggatgatc ctgacgacgg agtgcgccgt cgtcgacaag ccggcc              46

SEQ ID NO: 218           moltype = DNA   length = 46
FEATURE                  Location/Qualifiers
misc_feature             1..46
                         note = Description of Artificial Sequence: Synthetic
                           oligonucleotide
source                   1..46
                         mol_type = other DNA
                         organism = synthetic construct
SEQUENCE: 218
ggccggcttg tcgacgacgg cgtactccgt cgtcaggatc atccgg              46

SEQ ID NO: 219           moltype = DNA   length = 46
FEATURE                  Location/Qualifiers
misc_feature             1..46
                         note = Description of Artificial Sequence: Synthetic
                           oligonucleotide
source                   1..46
                         mol_type = other DNA
                         organism = synthetic construct
SEQUENCE: 219
ccggatgatc ctgacgacgg agtacgccgt cgtcgacaag ccggcc              46

SEQ ID NO: 220           moltype = DNA   length = 46
FEATURE                  Location/Qualifiers
misc_feature             1..46
                         note = Description of Artificial Sequence: Synthetic
                           oligonucleotide
source                   1..46
                         mol_type = other DNA
                         organism = synthetic construct
SEQUENCE: 220
ggccggcttg tcgacgacgg cgagctccgt cgtcaggatc atccgg              46

SEQ ID NO: 221           moltype = DNA   length = 46
FEATURE                  Location/Qualifiers
misc_feature             1..46
                         note = Description of Artificial Sequence: Synthetic
                           oligonucleotide
source                   1..46
                         mol_type = other DNA
                         organism = synthetic construct
SEQUENCE: 221
ccggatgatc ctgacgacgg agctcgccgt cgtcgacaag ccggcc              46

SEQ ID NO: 222           moltype = DNA   length = 46
FEATURE                  Location/Qualifiers
misc_feature             1..46
                         note = Description of Artificial Sequence: Synthetic
                           oligonucleotide
source                   1..46
                         mol_type = other DNA
                         organism = synthetic construct
SEQUENCE: 222
ggccggcttg tcgacgacgg cgggctccgt cgtcaggatc atccgg              46

SEQ ID NO: 223           moltype = DNA   length = 46
FEATURE                  Location/Qualifiers
misc_feature             1..46
                         note = Description of Artificial Sequence: Synthetic
                           oligonucleotide
source                   1..46
                         mol_type = other DNA
                         organism = synthetic construct
```

```
SEQUENCE: 223
ccggatgatc ctgacgacgg agcccgccgt cgtcgacaag ccggcc                    46

SEQ ID NO: 224          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 224
ggccggcttg tcgacgacgg cgcgctccgt cgtcaggatc atccgg                    46

SEQ ID NO: 225          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 225
ccggatgatc ctgacgacgg agcgcgccgt cgtcgacaag ccggcc                    46

SEQ ID NO: 226          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 226
ggccggcttg tcgacgacgg cgtgctccgt cgtcaggatc atccgg                    46

SEQ ID NO: 227          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 227
ccggatgatc ctgacgacgg agcacgccgt cgtcgacaag ccggcc                    46

SEQ ID NO: 228          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 228
ggccggcttg tcgacgacgg cgacctccgt cgtcaggatc atccgg                    46

SEQ ID NO: 229          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 229
ccggatgatc ctgacgacgg aggtcgccgt cgtcgacaag ccggcc                    46

SEQ ID NO: 230          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 230
ggccggcttg tcgacgacgg cggcctccgt cgtcaggatc atccgg                    46
```

```
SEQ ID NO: 231          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 231
ccggatgatc ctgacgacgg aggccgccgt cgtcgacaag ccggcc            46

SEQ ID NO: 232          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 232
ggccggcttg tcgacgacgg cgccctccgt cgtcaggatc atccgg            46

SEQ ID NO: 233          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 233
ccggatgatc ctgacgacgg agggcgccgt cgtcgacaag ccggcc            46

SEQ ID NO: 234          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 234
ggccggcttg tcgacgacgg cgtcctccgt cgtcaggatc atccgg            46

SEQ ID NO: 235          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 235
ccggatgatc ctgacgacgg aggacgccgt cgtcgacaag ccggcc            46

SEQ ID NO: 236          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 236
ggccggcttg tcgacgacgg cgatctccgt cgtcaggatc atccgg            46

SEQ ID NO: 237          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 237
ccggatgatc ctgacgacgg agatcgccgt cgtcgacaag ccggcc            46

SEQ ID NO: 238          moltype = DNA  length = 46
```

```
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 238
ggccggcttg tcgacgacgg cgctctccgt cgtcaggatc atccgg            46

SEQ ID NO: 239          moltype = DNA   length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 239
ccggatgatc ctgacgacgg agagcgccgt cgtcgacaag ccggcc            46

SEQ ID NO: 240          moltype = DNA   length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 240
ggccggcttg tcgacgacgg cgttctccgt cgtcaggatc atccgg            46

SEQ ID NO: 241          moltype = DNA   length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 241
ccggatgatc ctgacgacgg agaacgccgt cgtcgacaag ccggcc            46

SEQ ID NO: 242          moltype = DNA   length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 242
ggcttgtcga cgacggcggt ctccgtcgtc aggatcat                     38

SEQ ID NO: 243          moltype = DNA   length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 243
atgatcctga cgacggagac cgccgtcgtc gacaagcc                     38

SEQ ID NO: 244          moltype = DNA   length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 244
ggcttgtcga cgacggcgaa ctccgtcgtc aggatcat                     38

SEQ ID NO: 245          moltype = DNA   length = 38
FEATURE                 Location/Qualifiers
misc_feature            1..38
```

```
                        note = Description of Artificial Sequence: Synthetic
                        oligonucleotide
source                  1..38
                        mol_type = other DNA
                        organism = synthetic construct
SEQUENCE: 245
atgatcctga cgacggagtt cgccgtcgtc gacaagcc                               38

SEQ ID NO: 246          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 246
ggcttgtcga cgacggcgga ctccgtcgtc aggatcat                               38

SEQ ID NO: 247          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 247
atgatcctga cgacggagtc cgccgtcgtc gacaagcc                               38

SEQ ID NO: 248          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 248
ggcttgtcga cgacggcgca ctccgtcgtc aggatcat                               38

SEQ ID NO: 249          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 249
atgatcctga cgacggagtg cgccgtcgtc gacaagcc                               38

SEQ ID NO: 250          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 250
ggcttgtcga cgacggcgta ctccgtcgtc aggatcat                               38

SEQ ID NO: 251          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 251
atgatcctga cgacggagta cgccgtcgtc gacaagcc                               38

SEQ ID NO: 252          moltype = DNA  length = 38
FEATURE                 Location/Qualifiers
misc_feature            1..38
                        note = Description of Artificial Sequence: Synthetic
                        oligonucleotide
```

```
source                  1..38
                        mol_type = other DNA
                        organism = synthetic construct
SEQUENCE: 252
ggcttgtcga cgacggcgag ctccgtcgtc aggatcat                              38

SEQ ID NO: 253          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 253
atgatcctga cgacggagct cgccgtcgtc gacaagcc                              38

SEQ ID NO: 254          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 254
ggcttgtcga cgacggcggg ctccgtcgtc aggatcat                              38

SEQ ID NO: 255          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 255
atgatcctga cgacggagcc cgccgtcgtc gacaagcc                              38

SEQ ID NO: 256          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 256
ggcttgtcga cgacggcgcg ctccgtcgtc aggatcat                              38

SEQ ID NO: 257          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 257
atgatcctga cgacggagcg cgccgtcgtc gacaagcc                              38

SEQ ID NO: 258          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 258
ggcttgtcga cgacggcgtg ctccgtcgtc aggatcat                              38

SEQ ID NO: 259          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
```

```
                        organism = synthetic construct
SEQUENCE: 259
atgatcctga cgacggagca cgccgtcgtc gacaagcc                              38

SEQ ID NO: 260          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 260
ggcttgtcga cgacggcgac ctccgtcgtc aggatcat                              38

SEQ ID NO: 261          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 261
atgatcctga cgacggaggt cgccgtcgtc gacaagcc                              38

SEQ ID NO: 262          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 262
ggcttgtcga cgacggcggc ctccgtcgtc aggatcat                              38

SEQ ID NO: 263          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 263
atgatcctga cgacggaggc cgccgtcgtc gacaagcc                              38

SEQ ID NO: 264          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 264
ggcttgtcga cgacggcgcc ctccgtcgtc aggatcat                              38

SEQ ID NO: 265          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 265
atgatcctga cgacggaggg cgccgtcgtc gacaagcc                              38

SEQ ID NO: 266          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 266
```

```
ggcttgtcga cgacggcgtc ctccgtcgtc aggatcat                           38

SEQ ID NO: 267          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 267
atgatcctga cgacggagga cgccgtcgtc gacaagcc                           38

SEQ ID NO: 268          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 268
ggcttgtcga cgacggcgat ctccgtcgtc aggatcat                           38

SEQ ID NO: 269          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 269
atgatcctga cgacggagat cgccgtcgtc gacaagcc                           38

SEQ ID NO: 270          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 270
ggcttgtcga cgacggcgct ctccgtcgtc aggatcat                           38

SEQ ID NO: 271          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 271
atgatcctga cgacggagag cgccgtcgtc gacaagcc                           38

SEQ ID NO: 272          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 272
ggcttgtcga cgacggcgtt ctccgtcgtc aggatcat                           38

SEQ ID NO: 273          moltype = DNA  length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 273
atgatcctga cgacggagaa cgccgtcgtc gacaagcc                           38
```

| | | |
|---|---|---|
| SEQ ID NO: 274 | moltype = DNA length = 34 | |
| FEATURE | Location/Qualifiers | |
| misc_feature | 1..34 | |
| | note = Description of Artificial Sequence: Synthetic oligonucleotide | |
| source | 1..34 | |
| | mol_type = other DNA | |
| | organism = synthetic construct | |
| SEQUENCE: 274 | | |
| taccgttcgt ataatgtatg ctatacgaag ttat | | 34 |
| | | |
| SEQ ID NO: 275 | moltype = DNA length = 34 | |
| FEATURE | Location/Qualifiers | |
| misc_feature | 1..34 | |
| | note = Description of Artificial Sequence: Synthetic oligonucleotide | |
| source | 1..34 | |
| | mol_type = other DNA | |
| | organism = synthetic construct | |
| SEQUENCE: 275 | | |
| ataacttcgt atagcataca ttatacgaac ggta | | 34 |
| | | |
| SEQ ID NO: 276 | moltype = DNA length = 34 | |
| FEATURE | Location/Qualifiers | |
| misc_feature | 1..34 | |
| | note = Description of Artificial Sequence: Synthetic oligonucleotide | |
| source | 1..34 | |
| | mol_type = other DNA | |
| | organism = synthetic construct | |
| SEQUENCE: 276 | | |
| ataacttcgt ataatgtatg ctatacgaac ggta | | 34 |
| | | |
| SEQ ID NO: 277 | moltype = DNA length = 34 | |
| FEATURE | Location/Qualifiers | |
| misc_feature | 1..34 | |
| | note = Description of Artificial Sequence: Synthetic oligonucleotide | |
| source | 1..34 | |
| | mol_type = other DNA | |
| | organism = synthetic construct | |
| SEQUENCE: 277 | | |
| taccgttcgt atagcataca ttatacgaag ttat | | 34 |
| | | |
| SEQ ID NO: 278 | moltype = DNA length = 27 | |
| FEATURE | Location/Qualifiers | |
| misc_feature | 1..27 | |
| | note = Description of Artificial Sequence: Synthetic oligonucleotide | |
| source | 1..27 | |
| | mol_type = other DNA | |
| | organism = synthetic construct | |
| SEQUENCE: 278 | | |
| tttaccttga ttgagatgtt aattgtg | | 27 |
| | | |
| SEQ ID NO: 279 | moltype = DNA length = 27 | |
| FEATURE | Location/Qualifiers | |
| misc_feature | 1..27 | |
| | note = Description of Artificial Sequence: Synthetic oligonucleotide | |
| source | 1..27 | |
| | mol_type = other DNA | |
| | organism = synthetic construct | |
| SEQUENCE: 279 | | |
| cacaattaac atctcaatca aggtaaa | | 27 |
| | | |
| SEQ ID NO: 280 | moltype = DNA length = 50 | |
| FEATURE | Location/Qualifiers | |
| misc_feature | 1..50 | |
| | note = Description of Artificial Sequence: Synthetic oligonucleotide | |
| source | 1..50 | |
| | mol_type = other DNA | |
| | organism = synthetic construct | |
| SEQUENCE: 280 | | |
| gcgagttttt atttcgttta tttcaattaa ggtaactaaa aaactccttt | | 50 |
| | | |
| SEQ ID NO: 281 | moltype = DNA length = 50 | |
| FEATURE | Location/Qualifiers | |

```
misc_feature            1..50
                        note = Description of Artificial Sequence: Synthetic
                            oligonucleotide
source                  1..50
                        mol_type = other DNA
                        organism = synthetic construct
SEQUENCE: 281
aaaggagttt tttagttacc ttaattgaaa taaacgaaat aaaaactcgc            50

SEQ ID NO: 282          moltype = DNA   length = 34
FEATURE                 Location/Qualifiers
misc_feature            1..34
                        note = Description of Artificial Sequence: Synthetic
                            oligonucleotide
source                  1..34
                        mol_type = other DNA
                        organism = synthetic construct
SEQUENCE: 282
ctggatcatc tggatcactt tcgtcaaaaa cctg                             34

SEQ ID NO: 283          moltype = DNA   length = 34
FEATURE                 Location/Qualifiers
misc_feature            1..34
                        note = Description of Artificial Sequence: Synthetic
                            oligonucleotide
source                  1..34
                        mol_type = other DNA
                        organism = synthetic construct
SEQUENCE: 283
caggtttttg acgaaagtga tccagatgat ccag                             34

SEQ ID NO: 284          moltype = DNA   length = 57
FEATURE                 Location/Qualifiers
misc_feature            1..57
                        note = Description of Artificial Sequence: Synthetic
                            oligonucleotide
source                  1..57
                        mol_type = other DNA
                        organism = synthetic construct
SEQUENCE: 284
ttcgggtgct gggttgttgt ctctggacag tgatccatgg gaaactactc agcacca    57

SEQ ID NO: 285          moltype = DNA   length = 57
FEATURE                 Location/Qualifiers
misc_feature            1..57
                        note = Description of Artificial Sequence: Synthetic
                            oligonucleotide
source                  1..57
                        mol_type = other DNA
                        organism = synthetic construct
SEQUENCE: 285
tggtgctgag tagtttccca tggatcactg tccagagaca acaacccagc acccgaa    57

SEQ ID NO: 286          moltype = DNA   length = 24
FEATURE                 Location/Qualifiers
misc_feature            1..24
                        note = Description of Artificial Sequence: Synthetic
                            oligonucleotide
source                  1..24
                        mol_type = other DNA
                        organism = synthetic construct
SEQUENCE: 286
aaaagtgtgg gctgcaggat ctga                                        24

SEQ ID NO: 287          moltype = DNA   length = 22
FEATURE                 Location/Qualifiers
misc_feature            1..22
                        note = Description of Artificial Sequence: Synthetic
                            oligonucleotide
source                  1..22
                        mol_type = other DNA
                        organism = synthetic construct
SEQUENCE: 287
ggagctggca gctgtcaatg cc                                          22

SEQ ID NO: 288          moltype = DNA   length = 21
FEATURE                 Location/Qualifiers
misc_feature            1..21
                        note = Description of Artificial Sequence: Synthetic
```

```
                        oligonucleotide
source                  1..21
                        mol_type = other DNA
                        organism = synthetic construct
SEQUENCE: 288
agtcaatgcc gctctcgtgg a                                              21

SEQ ID NO: 289          moltype = DNA  length = 21
FEATURE                 Location/Qualifiers
misc_feature            1..21
                        note = Description of Artificial Sequence: Synthetic
                        oligonucleotide
source                  1..21
                        mol_type = other DNA
                        organism = synthetic construct
SEQUENCE: 289
cagcgggctc agctgatagc a                                              21

SEQ ID NO: 290          moltype = DNA  length = 21
FEATURE                 Location/Qualifiers
misc_feature            1..21
                        note = Description of Artificial Sequence: Synthetic
                        oligonucleotide
source                  1..21
                        mol_type = other DNA
                        organism = synthetic construct
SEQUENCE: 290
cggatggcta accaagcggc c                                              21

SEQ ID NO: 291          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 291
cccggcttcc tttgtcc                                                   17

SEQ ID NO: 292          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 292
gaactccacg ccgttca                                                   17

SEQ ID NO: 293          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 293
cccggcttcc tttgtcc                                                   17

SEQ ID NO: 294          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 294
aaccacaact agaatgcagt ga                                             22

SEQ ID NO: 295          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 295
cccggcttcc tttgtcc                                                   17
```

```
SEQ ID NO: 296          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 296
gaactccacg ccgttca                                                        17

SEQ ID NO: 297          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 297
cccggcttcc tttgtcc                                                        17

SEQ ID NO: 298          moltype = DNA   length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 298
aaccacaact agaatgcagt ga                                                  22

SEQ ID NO: 299          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 299
cccggcttcc tttgtcc                                                        17

SEQ ID NO: 300          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 300
gaactccacg ccgttca                                                        17

SEQ ID NO: 301          moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 301
tccttatcac ggtcccgctc g                                                   21

SEQ ID NO: 302          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 302
gaactccacg ccgttca                                                        17

SEQ ID NO: 303          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 303
cgtcgacaac ggtagtg                                                        17
```

```
SEQ ID NO: 304            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 304
gaactccacg ccgttca                                                         17

SEQ ID NO: 305            moltype = DNA  length = 18
FEATURE                   Location/Qualifiers
misc_feature              1..18
                          note = Description of Artificial Sequence: Synthetic primer
source                    1..18
                          mol_type = other DNA
                          organism = synthetic construct
SEQUENCE: 305
tcgcgtgatt ctcggaac                                                        18

SEQ ID NO: 306            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 306
gaactccacg ccgttca                                                         17

SEQ ID NO: 307            moltype = DNA  length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 307
gggcggtaag tggttagttt                                                      20

SEQ ID NO: 308            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 308
gaactccacg ccgttca                                                         17

SEQ ID NO: 309            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 309
aagaggcgga gccagta                                                         17

SEQ ID NO: 310            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 310
gaactccacg ccgttca                                                         17

SEQ ID NO: 311            moltype = DNA  length = 19
FEATURE                   Location/Qualifiers
misc_feature              1..19
                          note = Description of Artificial Sequence: Synthetic primer
source                    1..19
                          mol_type = other DNA
                          organism = synthetic construct
SEQUENCE: 311
```
ctcccttctc ccggtgccc                                                    19

SEQ ID NO: 312          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 312
gaactccacg ccgttca                                                      17

SEQ ID NO: 313          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 313
cccggcttcc tttgtcc                                                      17

SEQ ID NO: 314          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 314
gaactccacg ccgttca                                                      17

SEQ ID NO: 315          moltype = DNA   length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 315
gggcggtaag tggttagttt                                                   20

SEQ ID NO: 316          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 316
gaactccacg ccgttca                                                      17

SEQ ID NO: 317          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 317
cgtcgacaac ggtagtg                                                      17

SEQ ID NO: 318          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 318
gaactccacg ccgttca                                                      17

SEQ ID NO: 319          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct

```
SEQUENCE: 319
aagaggcgga gccagta                                                    17

SEQ ID NO: 320           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 320
gaactccacg ccgttca                                                    17

SEQ ID NO: 321           moltype = DNA  length = 19
FEATURE                  Location/Qualifiers
misc_feature             1..19
                         note = Description of Artificial Sequence: Synthetic primer
source                   1..19
                         mol_type = other DNA
                         organism = synthetic construct
SEQUENCE: 321
ctcccttctc ccggtgccc                                                  19

SEQ ID NO: 322           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 322
gaactccacg ccgttca                                                    17

SEQ ID NO: 323           moltype = DNA  length = 21
FEATURE                  Location/Qualifiers
misc_feature             1..21
                         note = Description of Artificial Sequence: Synthetic primer
source                   1..21
                         mol_type = other DNA
                         organism = synthetic construct
SEQUENCE: 323
tccttatcac ggtcccgctc g                                               21

SEQ ID NO: 324           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 324
gaactccacg ccgttca                                                    17

SEQ ID NO: 325           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 325
cccggcttcc tttgtcc                                                    17

SEQ ID NO: 326           moltype = DNA  length = 18
FEATURE                  Location/Qualifiers
misc_feature             1..18
                         note = Description of Artificial Sequence: Synthetic primer
source                   1..18
                         mol_type = other DNA
                         organism = synthetic construct
SEQUENCE: 326
ggcctgccag caggagga                                                   18

SEQ ID NO: 327           moltype = DNA  length = 17
FEATURE                  Location/Qualifiers
misc_feature             1..17
                         note = Description of Artificial Sequence: Synthetic primer
source                   1..17
                         mol_type = other DNA
```

```
                        organism = synthetic construct
SEQUENCE: 327
cccggcttcc tttgtcc                                                         17

SEQ ID NO: 328          moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 328
ggtgtgcagt cacattggta aagcc                                                25

SEQ ID NO: 329          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 329
cccggcttcc tttgtcc                                                         17

SEQ ID NO: 330          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 330
gatgggtcta gtccagctaa ag                                                   22

SEQ ID NO: 331          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 331
cccggcttcc tttgtcc                                                         17

SEQ ID NO: 332          moltype = DNA  length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 332
gagagacaag gctgcaca                                                        18

SEQ ID NO: 333          moltype = DNA  length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 333
ccaggtgaga gtcagggtag tgttca                                               26

SEQ ID NO: 334          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 334
gaactccacg ccgttca                                                         17

SEQ ID NO: 335          moltype = DNA  length = 23
FEATURE                 Location/Qualifiers
misc_feature            1..23
                        note = Description of Artificial Sequence: Synthetic primer
source                  1..23
```

```
                            mol_type = other DNA
                            organism = synthetic construct
SEQUENCE: 335
agggaccttt gcctgtgtga gtc                                               23

SEQ ID NO: 336              moltype = DNA  length = 17
FEATURE                     Location/Qualifiers
misc_feature                1..17
                            note = Description of Artificial Sequence: Synthetic primer
source                      1..17
                            mol_type = other DNA
                            organism = synthetic construct
SEQUENCE: 336
gaactccacg ccgttca                                                      17

SEQ ID NO: 337              moltype = DNA  length = 21
FEATURE                     Location/Qualifiers
misc_feature                1..21
                            note = Description of Artificial Sequence: Synthetic primer
source                      1..21
                            mol_type = other DNA
                            organism = synthetic construct
SEQUENCE: 337
tcagctctgt gctgaggcga a                                                 21

SEQ ID NO: 338              moltype = DNA  length = 17
FEATURE                     Location/Qualifiers
misc_feature                1..17
                            note = Description of Artificial Sequence: Synthetic primer
source                      1..17
                            mol_type = other DNA
                            organism = synthetic construct
SEQUENCE: 338
gaactccacg ccgttca                                                      17

SEQ ID NO: 339              moltype = DNA  length = 32
FEATURE                     Location/Qualifiers
misc_feature                1..32
                            note = Description of Artificial Sequence: Synthetic primer
source                      1..32
                            mol_type = other DNA
                            organism = synthetic construct
SEQUENCE: 339
aagccatctc ccagaatatc tgcttagaaa tg                                     32

SEQ ID NO: 340              moltype = DNA  length = 17
FEATURE                     Location/Qualifiers
misc_feature                1..17
                            note = Description of Artificial Sequence: Synthetic primer
source                      1..17
                            mol_type = other DNA
                            organism = synthetic construct
SEQUENCE: 340
gaactccacg ccgttca                                                      17

SEQ ID NO: 341              moltype = DNA  length = 25
FEATURE                     Location/Qualifiers
misc_feature                1..25
                            note = Description of Artificial Sequence: Synthetic primer
source                      1..25
                            mol_type = other DNA
                            organism = synthetic construct
SEQUENCE: 341
gagaggagca acagtgagca tgatg                                             25

SEQ ID NO: 342              moltype = DNA  length = 17
FEATURE                     Location/Qualifiers
misc_feature                1..17
                            note = Description of Artificial Sequence: Synthetic primer
source                      1..17
                            mol_type = other DNA
                            organism = synthetic construct
SEQUENCE: 342
gaactccacg ccgttca                                                      17

SEQ ID NO: 343              moltype = DNA  length = 32
FEATURE                     Location/Qualifiers
misc_feature                1..32
                            note = Description of Artificial Sequence: Synthetic primer
```

```
                                source           1..32
                                                 mol_type = other DNA
                                                 organism = synthetic construct
SEQUENCE: 343
aagccatctc ccagaatatc tgcttagaaa tg                                           32

SEQ ID NO: 344                  moltype = DNA   length = 17
FEATURE                         Location/Qualifiers
misc_feature                    1..17
                                note = Description of Artificial Sequence: Synthetic primer
source                          1..17
                                mol_type = other DNA
                                organism = synthetic construct
SEQUENCE: 344
gaactccacg ccgttca                                                            17

SEQ ID NO: 345                  moltype = DNA   length = 25
FEATURE                         Location/Qualifiers
misc_feature                    1..25
                                note = Description of Artificial Sequence: Synthetic primer
source                          1..25
                                mol_type = other DNA
                                organism = synthetic construct
SEQUENCE: 345
gagaggagca acagtgagca tgatg                                                   25

SEQ ID NO: 346                  moltype = DNA   length = 17
FEATURE                         Location/Qualifiers
misc_feature                    1..17
                                note = Description of Artificial Sequence: Synthetic primer
source                          1..17
                                mol_type = other DNA
                                organism = synthetic construct
SEQUENCE: 346
gaactccacg ccgttca                                                            17

SEQ ID NO: 347                  moltype = DNA   length = 17
FEATURE                         Location/Qualifiers
misc_feature                    1..17
                                note = Description of Artificial Sequence: Synthetic primer
source                          1..17
                                mol_type = other DNA
                                organism = synthetic construct
SEQUENCE: 347
cccggcttcc tttgtcc                                                            17

SEQ ID NO: 348                  moltype = DNA   length = 22
FEATURE                         Location/Qualifiers
misc_feature                    1..22
                                note = Description of Artificial Sequence: Synthetic primer
source                          1..22
                                mol_type = other DNA
                                organism = synthetic construct
SEQUENCE: 348
ggctatgaac taatgacccc gt                                                      22

SEQ ID NO: 349                  moltype = DNA   length = 17
FEATURE                         Location/Qualifiers
misc_feature                    1..17
                                note = Description of Artificial Sequence: Synthetic primer
source                          1..17
                                mol_type = other DNA
                                organism = synthetic construct
SEQUENCE: 349
cccggcttcc tttgtcc                                                            17

SEQ ID NO: 350                  moltype = DNA   length = 18
FEATURE                         Location/Qualifiers
misc_feature                    1..18
                                note = Description of Artificial Sequence: Synthetic primer
source                          1..18
                                mol_type = other DNA
                                organism = synthetic construct
SEQUENCE: 350
ggcctgccag caggagga                                                           18

SEQ ID NO: 351                  moltype = DNA   length = 17
FEATURE                         Location/Qualifiers
misc_feature                    1..17
```

```
                     note = Description of Artificial Sequence: Synthetic primer
source               1..17
                     mol_type = other DNA
                     organism = synthetic construct
SEQUENCE: 351
cccggcttcc tttgtcc                                                    17

SEQ ID NO: 352       moltype = DNA  length = 25
FEATURE              Location/Qualifiers
misc_feature         1..25
                     note = Description of Artificial Sequence: Synthetic primer
source               1..25
                     mol_type = other DNA
                     organism = synthetic construct
SEQUENCE: 352
ggtgtgcagt cacattggta aagcc                                           25

SEQ ID NO: 353       moltype = DNA  length = 52
FEATURE              Location/Qualifiers
misc_feature         1..52
                     note = Description of Artificial Sequence: Synthetic
                     oligonucleotide
source               1..52
                     mol_type = other DNA
                     organism = synthetic construct
SEQUENCE: 353
acactctttc cctacacgac gctcttccga tctccgacct cggctcacag cg             52

SEQ ID NO: 354       moltype = DNA  length = 53
FEATURE              Location/Qualifiers
misc_feature         1..53
                     note = Description of Artificial Sequence: Synthetic
                     oligonucleotide
source               1..53
                     mol_type = other DNA
                     organism = synthetic construct
SEQUENCE: 354
acactctttc cctacacgac gctcttccga tctaccgacc tcggctcaca gcg            53

SEQ ID NO: 355       moltype = DNA  length = 54
FEATURE              Location/Qualifiers
misc_feature         1..54
                     note = Description of Artificial Sequence: Synthetic
                     oligonucleotide
source               1..54
                     mol_type = other DNA
                     organism = synthetic construct
SEQUENCE: 355
acactctttc cctacacgac gctcttccga tctgaccgac ctcggctcac agcg           54

SEQ ID NO: 356       moltype = DNA  length = 55
FEATURE              Location/Qualifiers
misc_feature         1..55
                     note = Description of Artificial Sequence: Synthetic
                     oligonucleotide
source               1..55
                     mol_type = other DNA
                     organism = synthetic construct
SEQUENCE: 356
acactctttc cctacacgac gctcttccga tcttgaccga cctcggctca cagcg          55

SEQ ID NO: 357       moltype = DNA  length = 56
FEATURE              Location/Qualifiers
misc_feature         1..56
                     note = Description of Artificial Sequence: Synthetic
                     oligonucleotide
source               1..56
                     mol_type = other DNA
                     organism = synthetic construct
SEQUENCE: 357
acactctttc cctacacgac gctcttccga tctctgaccg acctcggctc acagcg         56

SEQ ID NO: 358       moltype = DNA  length = 57
FEATURE              Location/Qualifiers
misc_feature         1..57
                     note = Description of Artificial Sequence: Synthetic
                     oligonucleotide
source               1..57
                     mol_type = other DNA
```

```
                            organism = synthetic construct
SEQUENCE: 358
acactctttc cctacacgac gctcttccga tctactgacc gacctcggct cacagcg      57

SEQ ID NO: 359          moltype = DNA  length = 58
FEATURE                 Location/Qualifiers
misc_feature            1..58
                        note = Description of Artificial Sequence: Synthetic
                        oligonucleotide
source                  1..58
                        mol_type = other DNA
                        organism = synthetic construct
SEQUENCE: 359
acactctttc cctacacgac gctcttccga tcttactgac cgacctcggc tcacagcg     58

SEQ ID NO: 360          moltype = DNA  length = 59
FEATURE                 Location/Qualifiers
misc_feature            1..59
                        note = Description of Artificial Sequence: Synthetic
                        oligonucleotide
source                  1..59
                        mol_type = other DNA
                        organism = synthetic construct
SEQUENCE: 360
acactctttc cctacacgac gctcttccga tctgtactga ccgacctcgg ctcacagcg    59

SEQ ID NO: 361          moltype = DNA  length = 51
FEATURE                 Location/Qualifiers
misc_feature            1..51
                        note = Description of Artificial Sequence: Synthetic
                        oligonucleotide
source                  1..51
                        mol_type = other DNA
                        organism = synthetic construct
SEQUENCE: 361
gtgactggag ttcagacgtg tgctcttccg atctccaccc agccagctcc c            51

SEQ ID NO: 362          moltype = DNA  length = 51
FEATURE                 Location/Qualifiers
misc_feature            1..51
                        note = Description of Artificial Sequence: Synthetic
                        oligonucleotide
source                  1..51
                        mol_type = other DNA
                        organism = synthetic construct
SEQUENCE: 362
acactctttc cctacacgac gctcttccga tctccggtgg cgcattgcca c            51

SEQ ID NO: 363          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 363
acactctttc cctacacgac gctcttccga tctaccggtg gcgcattgcc ac           52

SEQ ID NO: 364          moltype = DNA  length = 53
FEATURE                 Location/Qualifiers
misc_feature            1..53
                        note = Description of Artificial Sequence: Synthetic
                        oligonucleotide
source                  1..53
                        mol_type = other DNA
                        organism = synthetic construct
SEQUENCE: 364
acactctttc cctacacgac gctcttccga tctgaccggt ggcgcattgc cac          53

SEQ ID NO: 365          moltype = DNA  length = 54
FEATURE                 Location/Qualifiers
misc_feature            1..54
                        note = Description of Artificial Sequence: Synthetic
                        oligonucleotide
source                  1..54
                        mol_type = other DNA
                        organism = synthetic construct
SEQUENCE: 365
```

```
acactctttc cctacacgac gctcttccga tcttgaccgg tggcgcattg ccac          54

SEQ ID NO: 366          moltype = DNA   length = 55
FEATURE                 Location/Qualifiers
misc_feature            1..55
                        note = Description of Artificial Sequence: Synthetic
                          oligonucleotide
source                  1..55
                        mol_type = other DNA
                        organism = synthetic construct
SEQUENCE: 366
acactctttc cctacacgac gctcttccga tctctgaccg gtggcgcatt gccac         55

SEQ ID NO: 367          moltype = DNA   length = 56
FEATURE                 Location/Qualifiers
misc_feature            1..56
                        note = Description of Artificial Sequence: Synthetic
                          oligonucleotide
source                  1..56
                        mol_type = other DNA
                        organism = synthetic construct
SEQUENCE: 367
acactctttc cctacacgac gctcttccga tctactgacc ggtggcgcat tgccac        56

SEQ ID NO: 368          moltype = DNA   length = 57
FEATURE                 Location/Qualifiers
misc_feature            1..57
                        note = Description of Artificial Sequence: Synthetic
                          oligonucleotide
source                  1..57
                        mol_type = other DNA
                        organism = synthetic construct
SEQUENCE: 368
acactctttc cctacacgac gctcttccga tcttactgac cggtggcgca ttgccac       57

SEQ ID NO: 369          moltype = DNA   length = 58
FEATURE                 Location/Qualifiers
misc_feature            1..58
                        note = Description of Artificial Sequence: Synthetic
                          oligonucleotide
source                  1..58
                        mol_type = other DNA
                        organism = synthetic construct
SEQUENCE: 369
acactctttc cctacacgac gctcttccga tctgtactga ccggtggcgc attgccac      58

SEQ ID NO: 370          moltype = DNA   length = 54
FEATURE                 Location/Qualifiers
misc_feature            1..54
                        note = Description of Artificial Sequence: Synthetic
                          oligonucleotide
source                  1..54
                        mol_type = other DNA
                        organism = synthetic construct
SEQUENCE: 370
gtgactggag ttcagacgtg tgctcttccg atctcagagt ccagcttggg ccca          54

SEQ ID NO: 371          moltype = DNA   length = 20
FEATURE                 Location/Qualifiers
misc_feature            1..20
                        note = Description of Artificial Sequence: Synthetic
                          oligonucleotide
source                  1..20
                        mol_type = other DNA
                        organism = synthetic construct
SEQUENCE: 371
gatattttcc cagctcacca                                                20

SEQ ID NO: 372          moltype = DNA   length = 20
FEATURE                 Location/Qualifiers
misc_feature            1..20
                        note = Description of Artificial Sequence: Synthetic
                          oligonucleotide
source                  1..20
                        mol_type = other DNA
                        organism = synthetic construct
SEQUENCE: 372
tctattctcc cagctcccca                                                20
```

```
SEQ ID NO: 373              moltype = DNA  length = 40
FEATURE                     Location/Qualifiers
misc_feature                1..40
                            note = Description of Artificial Sequence: Synthetic
                            oligonucleotide
source                      1..40
                            mol_type = other DNA
                            organism = synthetic construct
SEQUENCE: 373
agcggcttct gtctctgtga gtgagctggc ggtctccgtc                              40

SEQ ID NO: 374              moltype = DNA  length = 43
FEATURE                     Location/Qualifiers
misc_feature                1..43
                            note = Description of Artificial Sequence: Synthetic
                            oligonucleotide
source                      1..43
                            mol_type = other DNA
                            organism = synthetic construct
SEQUENCE: 374
gactagccca cgctccggtt ctgagccgcg acggcggtct ccg                          43

SEQ ID NO: 375              moltype = DNA  length = 41
FEATURE                     Location/Qualifiers
misc_feature                1..41
                            note = Description of Artificial Sequence: Synthetic
                            oligonucleotide
source                      1..41
                            mol_type = other DNA
                            organism = synthetic construct
SEQUENCE: 375
cccagggtcc catgcgctcc ccggccctga cggcggtctc c                            41

SEQ ID NO: 376              moltype = AA  length = 2560
FEATURE                     Location/Qualifiers
REGION                      1..2560
                            note = Description of Artificial Sequence: Synthetic
                            polypeptide
source                      1..2560
                            mol_type = protein
                            organism = synthetic construct
SEQUENCE: 376
MKRTADGSEF ESPKKKRKVD KKYSIGLDIG TNSVGWAVIT DEYKVPSKKF KVLGNTDRHS    60
IKKNLIGALL FDSGETAEAT RLKRTARRRY TRRKNRICYL QEIFSNEMAK VDDSFFHRLE   120
ESFLVEEDKK HERHPIFGNI VDEVAYHEKY PTIYHLRKKL VDSTDKADLR LIYLALAHMI   180
KFRGHFLIEG DLNPDNSDVD KLFIQLVQTY NQLFEENPIN ASGVDAKAIL SARLSKSRRL   240
ENLIAQLPGE KKNGLFGNLI ALSLGLTPNF KSNFDLAEDA KLQLSKDTYD DDLDNLLAQI   300
GDQYADLFLA AKNLSDAILL SDILRVNTEI TKAPLSASMI KRYDEHHQDL TLLKALVRQQ   360
LPEKYKEIFF DQSKNGYAGY IDGGASQEEF YKFIKPILEK MDGTEELLVK LNREDLLRKQ   420
RTFDNGSIPH QIHLGELHAI LRRQEDFYPF LKDNREKIEK ILTFRIPYYV GPLARGNSRF   480
AWMTRKSEET ITPWNFEEVV DKGASAQSFI ERMTNFDKNL PNEKVLPKHS LLYEYFTVYN   540
ELTKVKYVTE GMRKPAFLSG EQKKAIVDLL FKTNRKVTVK QLKEDYFKKI ECFDSVEISG   600
VEDRFNASLG TYHDLLKIIK DKDFLDNEEN EDILEDIVLT LTLFEDREMI EERLKTYAHL   660
FDDKVMKQLK RRRYTGWGRL SRKLINGIRD KQSGKTILDF LKSDGFANRN FMQLIHDDSL   720
TFKEDIQKAQ VSGQGDSLHE HIANLAGSPA IKKGILQTVK VVDELVKVMG RHKPENIVIE   780
MARENQTTQK GQKNSRERMK RIEEGIKELG SQILKEHPVE NTQLQNEKLY LYYLQNGRDM   840
YVDQELDINR LSDYDVDAIV PQSFLKDDSI DNKVLTRSDK NRGKSDNVPS EEVVKKMKNY   900
WRQLLNAKLI TQRKFDNLTK AERGGLSELD KAGFIKRQLV ETRQITKHVA QILDSRMNTK   960
YDENDKLIRE VKVITLKSKL VSDFRKDFQF YKVREINNYH HAHDAYLNAV VGTALIKKYP  1020
KLESEFVYGD YKVYDVRKMI AKSEQEIGKA TAKYFFYSNI MNFFKTEITL ANGEIRKRPL  1080
IETNGETGEI VWDKGRDFAT VRKVLSMPQV NIVKKTEVQT GGFSKESILP KRNSDKLIAR  1140
KKDWDPKKYG GFDSPTVAYS VLVVAKVEKG KSKKLKSVKE LLGITIMERS SFEKNPIDFL  1200
EAKGYKEVKK DLIIKLPKYS LFELENGRKR MLASAGELQK GNELALPSKY VNFLYLASHY  1260
EKLKGSPEDN EQKQLFVEQH KHYLDEIIEQ ISEFSKRVIL ADANLDKVLS AYNKHRDKPI  1320
REQAENIIHL FTLTNLGAPA AFKYFDTTID RKRYTSTKEV LDATLIHQSI TGLYETRIDL  1380
SQLGGDSGGS SGGSSGSETP GTSESATPES SGSETPGTSE SATPESSGSE TPGTSESATP  1440
ESSGGSSGGS STLNIEDEYR LHETSKEPDV SLGSTWLSDF PQAWAETGGM GLAVRQAPLI  1500
IPLKATSTPV SIKQYPMSQE ARLGIKPHIQ RLLDQGILVP CQSPWNTPLL PVKKPGTNDY  1560
RPVQDLREVN KRVEDIHPTV PNPYNLLSGP PPSHQWYTVL DLKDAFFCLR LHPTSQPLFA  1620
FEWRDPEMGI SGQLTWTRLP QGFKNSPTLF NEALHRDLAD FRIQHPDLIL LQYVDDLLLA  1680
ATSELDCQQG TRALLQTLGN LGYRASAKKA QICQKQVKYL GYLLKEGQRW LTEARKETVM  1740
GQPTPKTPRQ LREFLGKAGF CRLFIPGFAE MAAPLYPLTK PGTLFNWGPD QQKAYQEIKQ  1800
ALLTAPALGL PDLTKPFELF VDEKQGYAKG VLTQKLGPWR RPVAYLSKKL DPVAAGWPPC  1860
LRMVAAIAVL TKDAGKLTMG QPLVILAPHA VEALVKQPPD RWLSNARMTH YQALLLDTDR  1920
VQFGPVVALN PATLLPLPEE GLQHNCLDGT GGGGVTVKFK YKGEELEVDI SKIKKVWRVG  1980
KMISFTYDDN GKTGRGAVSE KDAPKELLQM LEKSGKSSGG SKRTADGSEF EPKKKRKVGG  2040
GGSPKKKRKV YPDVPDYAG SRALVVIRLS RVTDATTSPE RQLESCQQLC AQRGWDVVGV  2100
AEDLDVSGAV DPFDRKRRPN LARWLAFEEQ PFDVIVAYRV DRLTRSIRHL QQLVHWAEDH  2160
KKLVVSATEA HFDTTTPFAA VVIALMGTVA QMELEAIKER NRSAAHFNIR AGKYRGSLPP  2220
```

```
WGYLPTRVDG EWRLVPDPVQ RERILEVYHR VVDNHEPLHL VAHDLNRRGV LSPKDYFAQL    2280
QGREPQGREW SATALKRSMI SEAMLGYATL NGKTVRDDDG APLVRAEPIL TREQLEALRA    2340
ELVKTSRAKP AVSTPSLLLR VLFCAVCGEP AYKFAGGGRK HPRYRCRSMG FPKHCGNGTV    2400
AMAEWDAFCE EQVLDLLGDA ERLEKWVAG  SDSAVELAEV NAELVDLTSL IGSPAYRAGS    2460
PQREALDARI AALAARQEEL EGLEARPSGW EWRETGQRPF GDWWREQDTAA KNTWLRSMNV   2520
RLTFDVRGGL TRTIDFGDLQ EYEQHLRLGS VVERLHTGMS                         2560

SEQ ID NO: 377          moltype = DNA   length = 7680
FEATURE                 Location/Qualifiers
misc_feature            1..7680
                        note = Description of Artificial Sequence: Synthetic
                        polynucleotide
source                  1..7680
                        mol_type = other DNA
                        organism = synthetic construct
SEQUENCE: 377
atgaaacgga cagccgacgg aagcgagttc gagtcaccaa agaagaagcg aaagtcgac    60
aagaagtaca gcatcggcct ggacatcggc accaactctg tgggctgggc cgtgatcacc    120
gacgagtaca aggtgcccag caagaaattc aaggtgctgg gcaacaccga ccggcacagc    180
atcaagaaga acctgatcgg agccctgctg ttcgacagcg gcgaaacagc cgaggccacc    240
cggctgaaga gaaccgccag aagaagatac accagacgga gaaccggat  ctgctatctg    300
caagagatct tcagcaacga gatggccaag gtggacgaca gcttcttcca cagactggaa    360
gagtccttcc tggtggaaga ggataagaag cacgagcggc accccatctt cggcaacatc    420
gtggacgagg tggcctacca cgagaagtac cccaccatct accacctgag aaagaaactg    480
gtggacagca ccgacaaggc cgacctgcgg ctgatctatc tggccctggc ccacatgatc    540
aagttccggg gccacttcct gatcgagggc gacctgaacc cggacaacag cgacgtggac    600
aagctgttca tccagctggt gcagacctac aaccagctgt tcgaggaaaa ccccatcaac    660
gccagcggcg tggacgccaa ggccatcctg tctgccagac tgagcaagag cagacggctg    720
gaaaatctga tcgcccagct gcccggcgag aagaagaatg gcctgttcgg aaacctgatt    780
gccctgagcc tgggcctgac ccccaacttc aagagcaact tcgacctggc cgaggatgcc    840
aaactgcagc tgagcaagga cacctacgac gacgacctgg acaacctgct ggcccagatc    900
ggcgaccagt acgccgacct gtttctggcc gccaagaacc tgtccgacgc catcctgctg    960
agcgacatcc tgagagtgaa caccgagatc accaaggccc ccctgagcgc ctctatgatc    1020
aagagatacg acgagcacca ccaggacctg acccctgctga aagctctcgt gcggcagcta    1080
ctgcctgaga agtacaaaga gattttcttc gaccagagca agaacggcta cgccggctac    1140
attgacggcg gagccagcca ggaagagttc tacaagttca tcaagcccat cctggaaaag    1200
atggacggca ccgaggaact gctcgtgaag ctgaacagag aggacctgct gcggaagcag    1260
cggaccttcg acaacggcag catcccccac cagatccacc tgggagagct gcacgccatt    1320
ctgcggcggg aggaagattt tacccattc  ctgaaggaca accggaaaa  gctgagaag    1380
atcctgacct tccgcatccc ctactacgtg ggccctctgg ccaggggaaa cagcagattc    1440
gcctggatga ccagaaagag cgaggaaacc atcaccccct ggaacttcga ggaagtggtg    1500
gacaaggcgc cttccgccca gagcttcatc gagcggatga ccaacttcga taagaacctg    1560
cccaacagca aggtgctgcc caagcacagc ctgctgtacg agtacttcac cgtgtataac    1620
gagctgacca aagtgaaata cgtgaccgag ggaatgagaa agcccgcctt cctgagcggc    1680
gagcagaaaa aggccatcgt ggacctgctg ttcaagacca ccggaaagt  gaccgtgaag    1740
cagctgaaag gagactactt caagaaaatc gagtgcttcg actccgtgga aatctccggc    1800
gtggaagatc ggttcaacgc ctccctgggc acataccacg atctgctgaa aattatcaag    1860
gacaaggact tcctggacaa tgaggaaaac gaggacattc tggaagatat cgtgctgacc    1920
ctgacactgt ttgaggacag agagatgatc gaggaacggc tgaaaccta  tgcccacctg    1980
ttcgacgaca aagtgatgaa gcagctgaag cggcggagat acaccggctg gggcaggctg    2040
agccggaagc tgatcaacgg catccgggac aagcagtccg gcaagacaat cctggatttc    2100
ctgaagtccg acggcttcgc caacagaaac ttcatgcagc tgatccacga cgacagcctg    2160
accttttaaag aggacatcca gaaagcccag gtgtccggcc agggcgatag cctgcacgag    2220
cacattgcca atctggccgg cagccccgcc attaagaagg gcatcctgca gacagtgaag    2280
gtggtggacg agctcgtgaa agtgatgggc cggcacaagc ccgagaacat cgtgatcgaa    2340
atggccagag agaaccagac cacccagaag ggacagaaga acagccgcga gagaatgaag    2400
cggatcgaag agggcatcaa agagctgggc agccagatcc tgaaagaaca ccccgtggaa    2460
aacacccagc tgcagaacga gaagctgtac ctgtactacc tgcagaatgg gcgggatatg    2520
tacgtggacc aggaactgga catcaaccgg ctgtccgact acgatgtgga ccgctatcgg    2580
cctcagagct ttctgaagga cgactccatc gacaacaagg tgctgaccag aagcgacaag    2640
aaccgggggca agagcgacaa cgtgccctcc gaagaggtcg tgaagaagat gaagaactac    2700
tggcggcagc tgctgaacgc caagctgatt acccagagaa agttcgacaa tctgaccaag    2760
gccgagagag cggcctgag  cgaactggat aaggccggct tcatcaagag acagctggtg    2820
gaaacccgac agatcacaaa gcacgtggca cagatcctgg actcccggat gaacactaag    2880
tacgacgaga atgacaagct gatccggaa  gtgaaagtga tcaccctgaa gtccaagctg    2940
gtgtccgatt ccggaagga  tttcagtttt acaaagtgc  gcgagatcaa caactaccac    3000
cacgcccacg acgcctacct gaacgccgtc gtgggaaccg ccctgatcaa aaagtaccct    3060
aagctggaaa gcgagttcgt gtacggcgac tacaaggtgt acgacgtgcg gaagatgatc    3120
gccaagagcg agcaggaaat cggcaaggct accgccaagt acttcttcta cagcaacatc    3180
atgaacttt  tcaagaccga gattaccctg gccaacggcg agatccggaa gcggcctctg    3240
atcgagacaa acggcgaaac cggggagatc gtgtgggata agggccggga ttttgccacc    3300
gtgcggaaag tgctgagcat gccccaagtg aatatcgtga aaagaccga  ggtgcagaca    3360
ggcggcttca gcaaagagtc tatcctgccc aagaggaaca gcgataagct gatcgccaga    3420
aagaaggact gggaccctaa gaagtacggc ggcttcgaca gccccaccgt ggcctattct    3480
gtgctggtgg tggccaaagt ggaaaagggc aagtccaaga aactgaagag tgtgaaagag    3540
ctgctgggga tcaccatcat ggaaagaagc agcttcgaga gaatcccat  cgactttctg    3600
gaagccaagg gctacaaaga agtgaaaaag gacctgatca tcaagctgcc taagtactcc    3660
ctgttcgagc tggaaacgg  ccggaagaga atgctggcct gccggcga   actgcagaag    3720
ggaaacgaac tggcctgcc  ctccaaatat gtgaacttcc tgtacctggc cagccactat    3780
```

-continued

```
gagaagctga agggctcccc cgaggataat gagcagaaac agctgtttgt ggaacagcac   3840
aagcactacc tggacgagat catcgagcag atcagcgagt tctccaagag agtgatcctg   3900
gccgacgcta atctggacaa agtgctgtcc gcctacaaca agcaccggga taagcccatc   3960
agagagcagg ccgagaatat catccacctg tttaccctga ccaatctggg agccctgcc    4020
gccttcaagt actttgacac caccatcgac cggaagagat acaccagcac caaagaggtg   4080
ctggacgcca ccctgatcca ccagagcatc accggcctgt acgacacacg gatcgacctg   4140
tctcagctgg gaggtgactc tggaggatct agcggaggat cctctggcag cgagacacca   4200
ggaacaagcg agtcagcaac accagagagc tctggtagcg agacacccgg taccagtgaa   4260
agcgccacgc cagaaagcag tgggagtgag actccgggta catctgaatc agcgacaccg   4320
gaatcaagtg gcggcagcag cggcggcagc agcaccctaa atataagaga tgagtatcga   4380
ctacatgaga cctcaaaaga gccagatgtt tctctagggt ccacatggct gtctgatttt   4440
cctcaggcct gggcggaaac cggggggcatg ggactgcag ttcgccaagc tcctctgatc    4500
atacctctga aagcaaacct tacccccgtg tccataaaac aatacccat gtcacaagaa   4560
gccagactgg ggatcaagcc ccacatacag agactgttgg accaggaat actggtaccc    4620
tgccagtccc cctggaacac gcccctgcta cccgttaaga aaccaggac taatgattat    4680
aggcctgtcc aggatctgag agaagtcaac aagcgggtgg aagacatcca ccccaccgtg   4740
cccaacccctt acaacctctt gagcgggccc ccaccgtccc accagtggta cactgtgctt   4800
gatttaaagg atgcctttt ctgcctgaga ctccaccca cagtcagcc tctcttcgcc     4860
tttgagtgga gagatccaga gatgggaatc tcaggacaat tgacctggac cagactccca   4920
cagggtttca aaaacagtcc caccctgttt aatgaggcac tgcacagaga cctagcagac   4980
ttccggatcc agcacccaga cttgatcctg ctacagtacg tggatgactt actgctggcc   5040
gccacttctg agctagactg ccaacaaggt actcggggcc tgttacaaac cctagggaac   5100
ctcgggtatc gggcctcggc caagaaagcc caaatttgcc agaaacaggt caagtatctg   5160
gggtatcttc taaagagggg tcagagatgg ctgactgagg ccagaaaaga gactgtgatg   5220
gggcagccta ctccgaagac ccctcgacaa ctaagggagt tcctagggaa ggcaggcttc   5280
tgtcgcctct tcatccctgg gttttgcaaa atggcagccc ccctgtaccc tctcaccaaa   5340
ccggggactc tgtttaattg gggcccagac caacaaaagg cctatcaaga aatcaagcaa   5400
gctcttctaa ctgccccagc cctggggttg ccagatttga ctaagccctt tgaactcttt   5460
gtcgacgaga agcagggcta cgccaaaggt gtcctaacgc aaaaactggg accttggcgt   5520
cggccggtgg cctacctgtc caaaaagcta gacccagtag cagctgggtg gccccctttgc   5580
ctacggatgg tagcagccat tgccgtactg acaaaggatg caggcaagct aaccatggga   5640
cagccactag tcattctggc ccccatgca gtagaggcac tagtcaaaca accccccgac   5700
cgctggccttt ccaacgcccg gatgactcac tatcaggcct tgcttttgga cacggaccgg   5760
gtccagttcg gaccggtggt agccctgaac ccggctacgc tgctccact gcctgaggaa   5820
gggctgcaac acaactgcct tgatgggaca ggtggcggtg gtgtcaccgt caagttcaag   5880
tacaagggtg aggaacttga agttgatatt agcaaaatca agaaggtttg gcgcgttggt   5940
aaaatgatat ctttttactta tgacgacaac ggcaagacag gtagaggggc agtgtctgag   6000
aaagacgccc ccaaggagct gttgcaaatg ttggaaaagt ctgggaaaaa gtctggcggc   6060
tcaaaaagaa ccgccgacgg cagcgaattc gagcccaaga agaagaggaa agtcggaggt   6120
ggcgggagcc caaaaaagaa aagaaagtg tatccctatg atgtcccga ttatgccggt    6180
tcaagagccc tggtcgtgat tagactgagc cgagtgacag acgccaccac aagtcccgag   6240
agacagctgg aatcatgcca gcagctctgt gctcagcggg gttgggatgt ggtcggcgtg   6300
gcagaggatc tggacgtgag cggggccgtc gatccattcg acagaaagag gagggccaac   6360
ctggcaagat ggctcgcttt cgaggaacag ccctttgatg tgatcgtcgc ctacagagtg   6420
gaccggctga cccgctcaat tcgacatctc cagcagctgg tgcattgggc tgaggaccac   6480
aagaaactgt tggtcagcgc aacagaagcc cacttcgata ctaccacacc ttttgccgct   6540
gtggtcatcg cactgatggg cactgtggcc cagatgggct tcgaagctat caaggagcga   6600
aacaggagcg cagcccattt caatattagg gccggtaaat acagaggctc cctgccccct   6660
tggggatatc tccctaccag ggtgatggg gagtggagac tggtgccaga ccccgtccag   6720
agagagcgga ttctggaagt gtaccacaga gtggtcgata ccacgaacc actccatctg   6780
gtggcacacg acctgaatag acgcggcgtg ctctctccaa aggattattt tgctcagctg   6840
cagggaagag agccacaggg aagagaatg agtgctactg cactgaagag atctatgatc   6900
agtgaggcta tgctgggtta cgcaacactc aatggcaaaa ctgtccggga cgatgacgga   6960
gcccctctgt tgagggctga gccattctc accagagagc agctcgaagc tctgcgggca   7020
gaactggtca agactagtcg cgccaaacct gccgtgagca ccccaagcct gctcctgagg   7080
gtgctgttct gcgccgtctg tggagagcca gcatacaagt ttgccggcgg agggcgcaaa   7140
catcccgct atcgatgcag gagcatgggg ttccctaagc actgtggaaa cgggacagtg   7200
gccatggctg agtgggacgc cttttgcgag aacaggtgc tggatctcct gggtgacgct   7260
gagcggctgg aaaagtgtg ggtggcagga tctgactccg ctgtggagct ggcagaagtc   7320
aatgccgagc tcgtggatct gacttccctc atcggatctc ctgcatatag actgggtcc    7380
ccacagagag aagctctgga cgcacgaatt gctgcactcg ctgctagaca ggaggaactg   7440
gagggcctgg aggccaggcc ctctggatgg gagtggcgag aaaccggaca gaggtttggg   7500
gattggtgga gggagcagga caccgcagcc aagaacacat ggctgagatc catgaatgtc   7560
cggctcacat tcgacgtgcg cggtggcctg actcgaacca tcgattttgg cgacctgcag   7620
gagtatgaac agcacctgag actggggctcc gtggtcgaaa gactgcacac tggatgtcc    7680
```

SEQ ID NO: 378  moltype = AA length = 1367
FEATURE    Location/Qualifiers
REGION     1..1367
        note = Description of Artificial Sequence: Synthetic
        polypeptide
source     1..1367
        mol_type = protein
        organism = synthetic construct
SEQUENCE: 378

```
DKKYSIGLDI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
```

```
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASQSF  IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDAI   840
VPQSFLKDDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD              1367

SEQ ID NO: 379           moltype = AA   length = 576
FEATURE                  Location/Qualifiers
REGION                   1..576
                         note = Description of Artificial Sequence: Synthetic
                         polypeptide
source                   1..576
                         mol_type = protein
                         organism = synthetic construct
SEQUENCE: 379
LNIEDEYRLH ETSKEPDVSL GSTWLSDFPQ AWAETGGMGL AVRQAPLIIP LKATSTPVSI    60
KQYPMSQEAR LGIKPHIQRL LDQGILVPCQ SPWNTPLLPV KKPGTNDYRP VQDLREVNKR   120
VEDIHPTVPN PYNLLSGPPP SHQWYTVLDL KDAFFCLRLH PTSQPLFAFE WRDPEMGISG   180
QLTWTRLPQG FKNSPTLFNE ALHRDLADFR IQHPDLILLQ YVDDLLLAAT SELDCQQGTR   240
ALLQTLGNLG YRASAKKAQI CQKQVKYLGY LLKEGQRWLT EARKETVMGQ PTPKTPRQLR   300
EFLGKAGFCR LFIPGFAEMA APLYPLTKPG TLFNWGPDQQ KAYQEIKQAL LTAPALGLPD   360
LTKPFELFVD EKQGYAKGVL TQKLGPWRRP VAYLSKKLDP VAAGWPPCLR MVAAIAVLTK   420
DAGKLTMGQP LVILAPHAVE ALVKQPPDRW LSNARMTHYQ ALLLDTDRVQ FGPVVALNPA   480
TLLPLPEEGL QHNCLDGTGG GGVTVKFKYK GEELEVDISK IKKVWRVGKM ISFTYDDNGK   540
TGRGAVSEKD APKELLQMLE KSGKKSGGSK RTADGS                             576

SEQ ID NO: 380           moltype = AA   length = 500
FEATURE                  Location/Qualifiers
REGION                   1..500
                         note = Description of Artificial Sequence: Synthetic
                         polypeptide
source                   1..500
                         mol_type = protein
                         organism = synthetic construct
SEQUENCE: 380
SRALVVIRLS RVTDATTSPE RQLESCQQLC AQRGWDVVGV AEDLDVSGAV DPFDRKRRPN    60
LARWLAFEEQ PFDVIVAYRV DRLTRSIRHL QQLVHWAEDH KKLVVSATEA HFDTTTPFAA   120
VVIALMGTVA QMELEAIKER NRSAAHFNIR AGKYRGSLPP WGYLPTRVDG EWRLVPDPVQ   180
RERILEVYHR VVDNHEPLHL VAHDLNRRGV LSPKDYFAQL QGREPQGREW SATALKRSMI   240
SEAMLGYATL NGKTVRDDDG APLVRAEPIL TREQLEALRA ELVKTSRAKP AVSTPSLLLR   300
VLFCAVCGEP AYKFAGGGRK HPRYRCRSMG FPKHCGNLPV AMAEWDAFCE EQVLDLLGDA   360
ERLEKVWVAG SDSAVELAEV NAELVDLTSL IGSPAYRAGS PQREALDARI AALAARQEEL   420
EGLEARPSGW EWRETGQRFG DWWREQDTAA KNTWLRSMNV RLTFDVRGGL TRTIDFGDLQ   480
EYEQHLRLGS VVERLHTGMS                                                500

SEQ ID NO: 381           moltype = DNA   length = 11344
FEATURE                  Location/Qualifiers
misc_feature             1..11344
                         note = Description of Artificial Sequence: Synthetic
                         polynucleotide
source                   1..11344
                         mol_type = other DNA
                         organism = synthetic construct
SEQUENCE: 381
ccgaaaagtg ccacctgacg tcgacggatc gggagatcga tctcccgatc ccctagggtc    60
gactctcagt acaatctgct ctgatgccgc atagttaagc cagtatctgc tccctgcttg   120
tgtgttggag gtcgctgagt agtgcgcgag caaaatttaa gctacaacaa ggcaaggctt   180
gaccgacaat gcatgaagaa atctgcttag ggttaggcgt tttgcgctgc ttcgcgatgt   240
acgggccaga tatacgcgtt gacattgatt attgactagt tattaatagt aatcaattac   300
ggggtcatta gttcatagcc catatatgga gttccgcgtt acataactta cggtaaatgg   360
cccgcctggc tgaccgccca acgacccccg cccattgacg tcaataatga cgtatgttcc   420
catagtaacg ccaatagggA ctttccattg acgtcaatgg gtggagtatt tacggtaaac   480
tgcccacttg gcagtacatc aagtgtatca tatgccaagt acgccccta ttgacgtcaa   540
tgacggtaaa tggcccgcct ggcattatgc ccagtacatg accttatggg actttcctac   600
ttggcagtac atctacgtat tagtcatcgc tattaccatg gtgatgcggt tttggcagta   660
```

```
catcaatggg cgtggatagc ggtttgactc acggggattt ccaagtctcc accccattga    720
cgtcaatggg agtttgtttt ggcaccaaaa tcaacgggac tttccaaaat gtcgtaacaa    780
ctccgcccca ttgacgcaaa tgggcggtag gcgtgtacgg tgggaggtct atataagcag    840
agctggttta gtgaaccgtc agatccgcta gagatccgcg gccgctaata cgactcacta    900
tagggagagc cgccaccatg aaacggacag ccgacgaagg cgagttcgag tcaccaaaga    960
agaagcggaa agtcgacaag aagtacagca tcggcctgga catcggcacc aactctgtgg   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggcg   1140
aaacagccga ggccacccgg ctgaagagaa ccgccagaag aagatacacc agacggaaga   1200
accggatctg ctatctgcaa gagatcttca gcaacgagat ggccaaggtg gacgacagct   1260
tcttccacag actggaagag tccttcctgg tggaagagga taagaagcac gagcggcacc   1320
ccatcttcgg caacatcgtg gacgaggtgg cctaccacga aagtaccccc accatctacc   1380
acctgagaaa gaaactggtg gacagcaccg acaaggccga cctgcggctg atctatctgg   1440
ccctgcccca catgatcaag ttccgggggcc acttcctgat cgagggcgac ctgaaccccg   1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagagcag acggctggaa aatctgatcg cccagctgcc cggcgagaag aagaatggcc   1680
tgttcggaaa cctgattgcc ctgagcctgg gcctgacccc caacttcaag agcaacttcg   1740
acctggccga ggatgccaaa ctgcagctga gcaaggacac ctacgacgag gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggcccccc   1920
tgagcgcctc tatgatcaag agatacgacg agcaccacca agatctgacc ctgctgaaag   1980
ctctcgtgcg gcagcagctg cctgagaagt acaaagagat tttcttcgac cagagcaaga   2040
acggctacgc cggctacatt gacggcgagg ccagccagga gagttctac aagttcatca   2100
agcccatcct ggaaaagatg gacggcaccg aggaactgct cgtgaagctg aacagagagg   2160
acctgctgcg gaagcagcgg accttcgaca acggcagcat cccccaccag atccacctgg   2220
gagagctgca cgccattctg cggcggcagg aagattttta cccattcctg aaggacaacc   2280
gggaaaagat cgaaaagatc ctgacctttc gcatccccta ctacgtgggc cctctggcca   2340
ggggaaacag cagattcgcc tggatgacca gaaagagcga ggaaaccatc accccctgga   2400
acttcgagga agtggtggac aagggcgctt ccgcccagga cttcatcgag cggatgacca   2460
acttcgataa gaacctgccc aacgagaagg tgctgcccaa gcacagcctg ctgtacgagt   2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgact   2700
ccgtggaaat ctccggcgtg gaagatcggt tcaacgcctc cctgggcaca taccacgatc   2760
tgctgaaaat tatcaaggac aaggacttcc tggacaatga ggaaaacgag gacattctgg   2820
aagatatcgt gctgaccctg acactgtttg aggacagaga gatgatcgag gaacggctga   2880
aaacctatgc ccacctgttc gacgacaaag tgatgaagca gctgaagcgg cggagataca   2940
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaaagagg acatccagaa agcccaggtg tccgccagg    3120
gcgatagcct gcacgagcac attgccaatc tggccggcag ccccgccatt aagaagggca   3180
tcctgcagac agtgaaggtg gtggacgagc tcgtgaaagt gatgggccgg cacaagccga   3240
agaacatcgt gatcgaaatg gccagagaga accagaccac ccagaaggga cagaagaaca   3300
gccgcgagag aatgaagcgg atcgagaggg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggaaat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt gcctccgaa gaggtcgtga    3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa acccggcaga tcacaaagca cgtggcacag atcctggact   3780
cccggatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgccgtcgtg ggaaccgcca   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aacttttca agaccgagat taccctggcc aacggcgaga   4140
tccggaagcg gcctctgatc gagacaaacg gcgaaaccgg ggatcgtg tgggataagg    4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgcagaaag aaggactggg acctaagaa gtacggcggc ttcgacagcc     4380
ccaccgtggc ctattctgtg ctggtggtgg ccaaagtgga aaagggcaag tccaagaaac   4440
tgaagagtgt gaaagagctg ctggggatca ccatcatgga aagaagcagc ttcgagaaga   4500
atcccatcga ctttctggaa gccaaggcgt caaagaagt gaaaaaggac ctgatcatca    4560
agctgcctaa gtactccctg ttcgagctgg aaaacggccg gaagagaatg ctggcctctg   4620
ccggcgaact gcagaaggga acgaactggg ccctgccctc caaatatgtg aacttcctgt   4680
acctggccag ccactatgag aagctgaagg ctccccga ggataatgag cagaaacagc      4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctgct ggaggatcc    5100
ctggcagcga gacaccagga acaagcgagt cagcaacacc agagagcagt ggcggagcca   5160
gcggcggcag cagcacccta aatatagaag atgagtatcg gctacatgag acctcaaaag   5220
agccagatgt ttctctaggg tccacatggc tgtctgattt tcctcaggcc tgggcggaaa   5280
ccgggggcat gggactggca gttcgccaag ctcctctgat catacctctg aaagcaacct   5340
ctaccccccgt gtccataaaa caatacccca tgtcacaaga agccagactg gggatcaagc   5400
```

```
cccacataca gagactgttg gaccagggaa tactggtacc ctgccagtcc ccctggaaca    5460
cgccctgct  acccgttaag aaaccaggga ctaatgatta taggcctgtc caggatctga    5520
gagaagtcaa caagcgggtg gaagacatcc accccaccgt gcccaaccct tacaacctct    5580
tgagcgggct cccaccgtcc caccagtggt acactgtgct tgatttaaag gatgcctttt    5640
tctgcctgag actccacccc accagtcagc ctctcttcag ctttgagtgg agagatccga    5700
agatgggaat ctcaggacaa ttgacctgga ccagactccc acaggggttc aaaaacagtc    5760
ccaccctgtt taatgaggca ctgcacagag acctagcaga cttccggatc cagcacccag    5820
acttgatcct gctacagtac gtggatgact tactgctggc cgccacttct gagctagact    5880
gccaacaagg tactcgggcc ctgttacaaa ccctagggaa cctcgggtat cgggcctcgg    5940
ccaagaaagc ccaaatttgc cagaaacagg tcaagtatct ggggtatctt ctaaaagagg    6000
gtcagagatg gctgactgag gccagaaaag agactgtgat ggggcagcct actccgaaga    6060
ccctcgaca actaagggag ttcctaggga aggcaggctt ctgtcgcctc ttcatccctg     6120
ggtttgcaga aatggcagcc ccctgtacc ctctcaccaa accgggact ctgtttaatt      6180
ggggcccaga ccaacaaaag gcctatcaag aaatcaagca agctcttcta actgcccag     6240
ccctgggggtt gccagatttg actaagccct tgaactctt tgtcgacgag aagcagggct    6300
acgccaaagg tgtcctaacg caaaaactgg gaccttggcg tcggccggtg gcctacctgt    6360
ccaaaaagct agacccagta gcagctgggt ggccccttg cctacggatg gtagcagcca     6420
ttgccgtact gacaaaggat gcaggcaagc taaccatggg acagccacta gtcattctgg    6480
cccccccatgc agtagaggca ctagtcaaac aaccccccga ccgctggctt tccaacgccc   6540
ggatgactca ctatcaggcc ttgcttttgg acacggaccg ggtccagttc ggaccggtgg    6600
tagccctgaa cccggctacg ctgctccac tgcctgagga agggctgcaa cacaactgcc     6660
ttgatatcct ggccgaagcc cacgaaaccc gacccgacct aacggaccag ccgctcccag    6720
acgccgacca cacctggtac acggatgaa gcagtctctt acaagaggga cagcgtaagg     6780
cgggagctgc ggtgaccacc gagaccgagg taatctgggc taaagccctg ccagccggga    6840
catccgctca gcgggctgaa ctgatagcac tcacccaggc cctaaagatg gcagaaggta    6900
agaagctaaa tgtttatact gatagccgtt atgcttttgc tactgcccat atccatggag    6960
aaatatacag aaggcgtggg tggctcacat cagaaggcaa agagatcaaa aataaagacg    7020
agatcttggc cctactaaaa gccctctttc tgcccaaaag acttagcata atccattgtc    7080
caggacatca aaagggacac agcgccgagg ctagaggcaa ccggatggct gaccaagcgg    7140
cccgaaaagc agccatcaca gagactccag acacctctac cctcctcata gaaaattcat    7200
caccctctgg cggctcaaaa agaaccgccg acggcagcga attcgagccc aagaagaaga    7260
ggaaagtcgg aagcggagct actaacttca gcctgctgaa gcaggctggc gacgtggagg    7320
agaaccctgg acctccaaaa aagaaaagaa aagtgtatcc ctatgatgtc cccgattatg    7380
ccggttcaag agccctggtc gtgattagac tgagccgagt gacagacgcc accacaagtc    7440
ccgagagaca gctggaatca tgccagcagc tctgtgctca gcggggttgg gatgtggtcg    7500
gcgtggcaga ggatcggac gtgagcgggg ccgtcgatcc attcgacaga aagaggaggc      7560
ccaacctggc aagatggctc gctttcgagg aacagccctt tgatgtgatc gtcgcctaca    7620
gagtggaccg gctgacccgc tcaattcgac atctccagca gctggtgcat tgggctgagg    7680
accacaagaa actggtggtc agcgcaacag aagcccactt cgatactacc acaccttttg    7740
ccgctgtggt catcgcactg atgggcactg tggcccagat ggagctcgaa gctatcaagg    7800
agcgaaacag gagcgcagcc catttcaata ttagggccgg taaatacaga ggctccctgc    7860
cccttgggg atatctccct accagggtgg atggggagtg gagactggtg ccagacccccg   7920
tccagagaca gcggattctg gaagtgtacc acagagtggt cgataaccac gaaccactcc    7980
atctggtggc acacgacctg aatagacgcg gcgtgctctc tccaaaggat tattttgctc    8040
agctgcaggg aagagagcca caggaagag aatggagtgc tactgcactg aagagatcta     8100
tgatcagtga ggctatgctg ggttacgcaa cactcaatgg caaaactgtc cgggacgatg    8160
acggagcccc tctggtgagg gctgagccta ttctcaccag agagcagctc gaagctctgc    8220
gggcagaact ggtcaagact agtcgcgcca aacctgccgt gagcacccca agcctgctcc    8280
tgagggtgct gttctgcgcc gtctgtggag agccagcata caagtttgcc ggcggagggc    8340
gcaaacatcc ccgctatcga tgcaggagca tgggttccc taagcactgt ggaaacggga    8400
cagtggccat ggctgagtgg gacgcctttt gcgaggaaca ggtgctggat ctcctgaggg    8460
acgctgagcg gctggaaaaa gtgtgggtgg caggatctga ctccgctgtg gagctggcag    8520
aagtcaatgc cgagctcgtg gatctgactt ccctcatcgg atctcctgca tatagagctg    8580
ggtccccaca gagagaagct ctggacgcac gaattgctgc actcgctgct agacaggagg    8640
aactggaggg cctggaggcc aggccctctg gatgggagtg gcgagaaacc ggacagaggt    8700
ttggggattg gtggagggag caggacaccg cagccaagaa cacatggctg agatccatga    8760
atgtccggct cacattcgac gtgcgcggtg gcctgactcg aaccatcgat tttggcgacc    8820
tgcaggagta tgaacagcac ctgagactgg ggtccgtggt cgaaagactg cacactggga    8880
tgtcctaggt ttaaacccgc tgatcagcct cgactgtgcc tttctagttgc cagccatctg   8940
ttgtttgccc ctcccccgtg ccttccttga ccctgggaag tgccactccc actgtccttt    9000
cctaataaaa tgagaaaatt gcatcgcatt gtctgagtag gtgtcattct attctggggg    9060
gtggggtggg gcaggacagc aagggggagg attgggaaga caatagcagg catgctgggg    9120
atgcggtggg ctctatggct tctgaggcgg aaagaaccag ctgggctcg ataccgtcga     9180
cctctagcta gagcttggcg taatcatggt catagctgtt tcctgtgtga aattgttatc    9240
cgctcacaat tccacacaac atacgagccg aagcataaa gtgtaaagcc tagggtgcct      9300
aatgagtgag ctaactcaca ttaattgcgt tgcgctcact gcccgctttc cagtcgggaa    9360
acctgtcgtg ccagctgcat taatgaatcg gccaacgcgc ggggagaggc ggtttgcgta    9420
ttgggcgctc ttccgcttcc tcgctcactg actcgctgcg ctcggtcgtt cggctgcggc    9480
gagcggtatc agctcactca aaggcggtaa tacggttatc cacagaatca ggggataacg    9540
caggaaagaa catgtgagca aaaggccagc aaaaggccag gaaccgtaaa aaggccgcgt    9600
tgctggcgtt tttccatagg ctccgccccc ctgacgagca tcacaaaaat cgacgctcaa    9660
gtcagaggtg gcgaaacccg acaggactat aaagatacca ggcgtttccc cctggaagct    9720
ccctcgtgcg ctctcctgtt ccgaccctgc cgcttaccgg atacctgtcc gcctttctcc    9780
cttcgggaag cgtggcgctt tctcatagct cacgctgtag gtatctcagt tcggtgtagg    9840
tcgttcgctc caagctgggc tgtgtgcacg aaccccccgt tcagcccgac cgctgcgcct    9900
tatccggtaa ctatcgtctt gagtccaacc cggtaagaca cgacttatcg ccactggcag    9960
cagccactgg taacaggatt agcagagcga ggtatgtagg cggtgctaca gagttcttga   10020
agtggtggcc taactacggc tacactagaa gaacagtatt tggtatctgc gctctgctga   10080
agccagttac cttcggaaaa agagttggta gctcttgatc cggcaaacaa accaccgctg   10140
```

```
gtagcggtgg ttttttttgtt tgcaagcagc agattacgcg cagaaaaaaa ggatctcaag   10200
aagatccttt gatcttttct acggggtctg acgctcagtg gaacgaaaac tcacgttaag   10260
ggattttggt catgagatta tcaaaaagga tcttcaccta gatccttta aattaaaaat    10320
gaagttttaa atcaatctaa agtatatatg agtaaacttg gtctgacagt taccaatgct   10380
taatcagtga ggcacctatc tcagcgatct gtctatttcg ttcatccata gttgcctgac   10440
tccccgtcgt gtagataact acgatacggg agggcttacc atctggcccc agtgctgcaa   10500
tgataccgcg agacccacgc tcaccggctc cagatttatc agcaataaac cagccagccg   10560
gaagggccga gcgcagaagt ggtcctgcaa ctttatccgc ctccatccag tctattaatt   10620
gttgccggga agctagagta agtagttcgc cagttaatag tttgcgcaac gttgttgcca   10680
ttgctacagg catcgtggtg tcacgctcgt cgtttggtat ggcttcattc agctccggtt   10740
cccaacgatc aaggcgagtt acatgatccc ccatgttgtg caaaaaagcg gttagctcct   10800
tcggtcctcc gatcgttgtc agaagtaagt tggccgcagt gttatcactc atggttatgg   10860
cagcactgca taattctctt actgtcatgc catccgtaag atgcttttct gtgactggtg   10920
agtactcaac caagtcattc tgagaatagt gtatgcggcg accgagttgc tcttgcccgg   10980
cgtcaatacg ggataatacc gcgccacata gcagaacttt aaaagtgctc atcattggaa   11040
aacgttcttc ggggcgaaaa ctctcaagga tcttaccgct gttgagatcc agttcgatgt   11100
aacccactcg tgcacccaac tgatcttcag catcttttac tttcaccagc gtttctgggt   11160
gagcaaaaac aggaaggcaa aatgccgcaa aaaagggaat aagggcgaca cggaaatgtt   11220
gaatactcat actcttcctt tttcaatatt attgaagcat ttatcagggt tattgtctca   11280
tgagcggata catatttgaa tgtatttaga aaaataaaca aataggggtt ccgcgcacat   11340
ttcc                                                               11344

SEQ ID NO: 382          moltype = DNA   length = 9753
FEATURE                 Location/Qualifiers
misc_feature            1..9753
                        note = Description of Artificial Sequence: Synthetic
                         polynucleotide
source                  1..9753
                        mol_type = other DNA
                        organism = synthetic construct
SEQUENCE: 382
ccgaaaagtg ccacctgacg tcgacggatc gggagatcga tctcccgatc ccctagggtc   60
gactctcagt acaatctgct ctgatgccgc atagttaagc cagtatctgc tccctgcttg   120
tgtgttggag gtcgctgagt agtgcgcgag caaaatttaa gctacaacaa ggcaaggctt   180
gaccgacaat tgcatgaaga atctgcttag ggttaggcgt tttgcgctgc ttcgcgatgt   240
acgggccaga tatacgcgtt gacattgatt attgactagt tattaatagt aatcaattac   300
ggggtcatta gttcatagcc catatatgga gttccgcgtt acataactta cggtaaatgg   360
cccgcctggc tgaccgccca acgacccccg cccattgacg tcaataatga cgtatgttcc   420
catagtaacg ccaataggga cttttccatt acgtcaatgg gtggagtatt tacggtaaac   480
tgcccacttg gcagtacatc aagtgtatca tatgccaagt acgccccctat tgacgtcaa   540
tgacggtaaa tggcccgcct ggcattatgc ccagtacatg accttatggg actttcctac   600
ttggcagtac atctacgtat tagtcatcgc tattaccatg gtgatgcggt tttggcagta   660
catcaatgtg cgtggatagc ggtttgactc acggggattt ccaagtctcc accccattga   720
cgtcaatggg agtttgtttt ggcaccaaaa tcaacgggac tttccaaaat gtcgtaacaa   780
ctccgcccca ttgacgcaaa tgggcggtag gcgtgtacgg tgggaggtct atataagcag   840
agctggttta gtgaaccgtc agatccgcta gagatccgcg gccgctaata cgactcacta   900
tagggagagc cgccaccatg aaacggagag ccgcaggaag tgagttcgaa tcaccaaaga   960
agaagcggaa agtcgacaag aagtacagca tcggcctgga catcggcacc aactctgtgg   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggcg   1140
aaacagccga ggccacccgg ctgaagagaa ccgccagaag aagatacacc agacggaaga   1200
accggatctg ctatctgcaa gagatcttca gcaacgagat ggccaaggtg gacgacagct   1260
tcttccacag actggaagag tccttcctgg tggaagagga taagaagcac gagcggcacc   1320
ccatcttcgg caacatcgtg gacgaggtgg cctaccacga gaagtacccc accatctacc   1380
acctgagaaa gaaactggtg gacagcaccg acaaggccga cctgcggctg atctatctgg   1440
ccctggccca catgatcaag ttccggggcc acttcctgat cgagggcgac ctgaaccccg   1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagagcag acggctggaa aatctgatcg cccagctgcc cggcgagaag aagaatggcc   1680
tgttcggaaa cctgattgcc ctgagcctgg gcctgacccc caacttcaag agcaacttcg   1740
acctggccga ggatgccaaa ctgcagctga gcaaggacac ctacgacgac gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggcccccc   1920
tgagcgcctc tatgatcaag agatacgacg agcaccacca ggacctgacc ctgctgaaag   1980
ctctcgtgcg gcagcagctg cctgagaagt acaaagagat tttcttcgac cagagcaaga   2040
acggctacgc cggctacatt gacggcggag ccagccagga agagttctac aagttcatca   2100
agcccatcct ggaaaagatg gacggcaccg aggaactgct cgtgaagctg aacagagagg   2160
acctgctgcg gaagcagcgg accttcgaca acggcagcat cccccaccag atccacctgg   2220
gagagctgca cgccattctg cggcgccaga aagattttta cccattcctg aaggacaacc   2280
gggaaaagat cgagaagatc ctgaccttcc gcatcccta ctacgtggcc cctctgccca   2340
ggggaaacag cagattcgcc tggatgacca aaagagcga ggaaaccatc accccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgact   2700
ccgtggaaat ctcggcgtg gaagatcggt tcaacgcctc cctgggcaca taccacgatc   2760
tgctgaaaat tatcaaggac aaggacttcc tggacaatga ggaaacgag acattctgg   2820
aagatatcgt gctgaccctg acactgtttg aggacagaga gatgatcgag gaacggctga   2880
```

```
aaacctatgc ccacctgttc gacgacaaag tgatgaagca gctgaagcgg cggagataca   2940
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaga accagaccac ccagaaggga cagaagaaca   3300
gccgcgagag aatgaagcgg atcgaagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt gccctccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa acccggcaga tcacaaagca cgtggcacag atcctggact   3780
cccggatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgccgtcgtg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aacttttca agaccgagat taccctggcc aacggcgaga   4140
tccggaagcg gcctctgatc gagacaaacg gcgaaacgtg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggccaa tccaagaaac   4440
tgaagagtgt gaaagagctg ctggggatca ccatcatgga aagaagcagc ttcgagaaga   4500
atcccatcga ctttctggaa gccaagggct acaaagaagt gaaaaaggac ctgatcatca   4560
agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccag ccactatgag aagctgaagg gctcccccga ggataatgag cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctagc ggaggatcct   5100
ctggcagcga gacaccagga acaagcgagt cagcaacacc agagagcagt ggcggcagca   5160
gcggccggca cagcaccta aatatagaag atgagtatcg gctacatgga acctcaaaag   5220
agccagatgt ttctctaggg tccacatggc tgtctgattt tcctcaggcc tgggcggaaa   5280
ccggggcat gggactggca gttcgccaag ctccctgat catacctctg aaagcaacct   5340
ctaccccgt gtccataaaa caataccca tgtcacaaga agccagactg gggatcaagc   5400
cccacataca gagactgttg gaccaggaa tactggtacc ctgccagtcc ccctggaaca   5460
cgccctgct acccgttaag aaaccaggga ctaatgatta taggcctgtc caggatctga   5520
gagaagtcaa caagcgggtg gaagacatcc accccaccgt gcccaaccct tacaacctct   5580
tgagcgggct cccaccgtcc caccagtggt acactgtgct tgatttaaag gatgcctttt   5640
tctcctgag actccacccc accagtcagc ctctcttcgc ctttgagtgg agagatccag   5700
agatgggaat ctcaggacaa ttgacctgga ccagactccc acaggggttc aaaaacagtc   5760
ccaccctgtt taatgaggca ctgcacagag acctagcaga cttccggatc cagcacccag   5820
acttgatcct gctacagtac gtggatgact tactgctggc cgccacttct gagctagact   5880
gccaacaagg tactcgggcc ctgttacaaa ccctagggaa cctcgggtat cgggcctctg   5940
ccaagaaagc ccaaatttgc cagaaacagg tcaagtatct ggggtatctt ctaaaagagg   6000
gtcagagatg gctgactgag gccagaaag agactgtgat ggggcagcct actccgaaga   6060
cccctcgaca actaagggag ttcctaggga aggcaggctt ctgtcgcctc ttcatccctg   6120
ggttgcagaa aatggcagcc ccctgtacc tctccaccaa accgggggact ctgtttaatt   6180
ggggcccaga ccaacaaaag gcctatcaag aaatcaagca agctcttcta actgcccag   6240
ccctgggtt gccagatttg actaagccct ttgaactctt tgtcgacgag aagcagggct   6300
acgccaaagg tgtcctaacg caaaactgg gaccttggcg tcggccggtg gcctacctgt   6360
ccaaaaagct agacccagta gcagctgggt ggccccttg cctacggatg gtagcagcca   6420
ttgccgtact gacaaaggat gcaggcaagc taaccatggg acagccactc gtcattctgg   6480
cccccatgc agtagaggca ctagtcaaac acccccga ccgctggctt tccaacgccc   6540
ggatgactca ctatcaggcc ttgctttttgg acacggaccg ggtccagttc ggaccggtgg   6600
tagccctgaa cccggctacg ctgctccac tgcctgagga agggctgcaa cacaactgcc   6660
ttgatatcct ggccgaagcc cacggaacc gacccgcct accgctcccag   6720
acgccgacca cacctggtac acggatgaa gcagtctctt acaagaggga cagcgtaagg   6780
cgggagctgc ggtgaccacc gagaccgagg taatctgggc taaagccctg ccagccggga   6840
catccgctca gcgggctgaa ctgatagcac tcacccaggc cctaaagatg gcagaagta   6900
agaagctaaa tgtttatact gatagccgtt atgcttttgc tactgcccat atccatgag   6960
aaatatacag aaggcgtggg tggctcacat cagaaggcaa agagatcaaa aataaagacg   7020
agatcttggc cctactaaaa gcctctttc tgcccaaaag acttagcata atccattgtc   7080
caggacatca aaagggacac agcgccgagg ctagaggcaa ccggatggct gaccaagcgg   7140
cccgaaaggc agccatcaca gagactccag acacctctac cctcctcata gaaaattcat   7200
caccctctgg cggctcaaaa agaaccgcg acggcagcga attcgagccc aagaagaaga   7260
ggaaagtcta accggtcatc aaccaccatca ccattgagtt taaacccgct gatcagcctc   7320
gactgtgcct tctagttgcc agccatctgt tgtttgcccc tcccccgtgc cttccttgac   7380
cctgaaggt gccactccca ctgtccttttc ctaataaaat gagaaaattg catcgcattg   7440
tctgagtagg tgtcattcta ttctgggggg tggggtgggg caggacagca agggggagga   7500
ttgggaagac aatagcaggc atgctgggga tgcggtgggc tctatggctt ctgaggcgga   7560
aagaaccagc tggggctcga taccgtcgac ctctagctag agcttggcgt aatcatggtc   7620
```

```
atagctgttt cctgtgtgaa attgttatcc gctcacaatt ccacacaaca tacgagccgg  7680
aagcataaag tgtaaagcct agggtgccta atgagtgagc taactcacat taattgcgtt  7740
gcgctcactg cccgctttcc agtcgggaaa cctgtcgtgc cagctgcatt aatgaatcgg  7800
ccaacgcgcg gggagaggcg gtttgcgtat tgggcgctct tccgcttcct cgctcactga  7860
ctcgctgcgc tcggtcgttc ggctgcggcg agcggtatca gctcactcaa aggcggtaat  7920
acggttatcc acagaatcag gggataacgc aggaaagaac atgtgagcaa aaggccagca  7980
aaaggccagg aaccgtaaaa aggccgcgtt gctggcgttt ttccataggc tccgcccccc  8040
tgacgagcat cacaaaaatc gacgctcaag tcagaggtgg cgaaacccga caggactata  8100
aagataccag gcgtttcccc ctggaagctc cctcgtgcgc tctcctgttc cgaccctgcc  8160
gcttaccgga tacctgtccg cctttctccc ttcgggaagc gtggcgcttt ctcatagctc  8220
acgctgtagg tatctcagtt cggtgtaggt cgttcgctcc aagctgggct gtgtgcacga  8280
acccccegtt cagcccgacc gctgcgcctt atccggtaac tatcgtcttg agtccaaccc  8340
ggtaagacac gacttatcgc cactggcagc agccactggt aacaggatta gcagagcgag  8400
gtatgtaggc ggtgctacag agttcttgaa gtggtggcct aactacggct acactagaag  8460
aacagtattt ggtatctgcg ctctgctgaa gccagttacc ttcggaaaaa gagttggtag  8520
ctcttgatcc ggcaaacaaa ccaccgctgg tagcggtggt ttttttgttt gcaagcagca  8580
gattacgcgc agaaaaaaag gatctcaaga agatcctttg atcttttcta cggggtctga  8640
cgctcagtgg aacgaaaact cacgttaagg gattttggtc atgagattat caaaaaggat  8700
cttcacctag atccttttaa attaaaaatg aagttttaaa tcaatctaaa gtatatatga  8760
gtaaacttgg tctgacagtt accaatgctt aatcagtgag gcacctatct cagcgatctg  8820
tctatttcgt tcatccatag ttgcctgact ccccgtcgtg tagataacta cgatacggga  8880
gggcttacca tctggcccca gtgctgcaat gataccgcga gaacacgctc accggctcc  8940
agatttatca gcaataaacc agccagccgg aagggccgag cgcagaagtg gtcctgcaac  9000
tttatccgcc tccatccagt ctattaattg ttgccgggaa gctagagtaa gtagttcgcc  9060
agttaatagt ttgcgcaacg ttgttgccat tgctacaggc atcgtggtgt cacgctcgtc  9120
gtttggtatg gcttcattca gctccggttc caacgatcag gagttacatg atgatcccca  9180
catgttgtgc aaaaaagcgg ttagctcctt cggtcctccg atcgttgtca gaagtaagtt  9240
ggccgcagtg ttatcactca tggttatggc agcactgcat aattctctta ctgtcatgcc  9300
atccgtaaga tgcttttctg tgactggtga gtactcaacc aagtcattct gagaatagtg  9360
tatgcggcga ccgagttgct cttgcccggc gtcaatacgg gataataccg cgccacatag  9420
cagaacttta aaagtgctca tcattggaaa acgttcttcg gggcgaaaac tctcaaggat  9480
cttaccgctg ttgagatcca gttcgatgta acccactcgt gcacccaact gatcttcagc  9540
atcttttact ttcaccagcg tttctgggtg agcaaaaaca ggaaggcaaa atgccgcaaa  9600
aaagggaata agggcgacac ggaaatgttg aatactcata ctcttccttt ttcaatatta  9660
ttgaagcatt tatcagggtt attgtctcat gagcggatac atatttgaat gtatttagaa  9720
aaataaacaa ataggggttc cgcgcacatt tcc                               9753
```

```
SEQ ID NO: 383          moltype = DNA   length = 11433
FEATURE                 Location/Qualifiers
misc_feature            1..11433
                        note = Description of Artificial Sequence: Synthetic
                        polynucleotide
source                  1..11433
                        mol_type = other DNA
                        organism = synthetic construct
SEQUENCE: 383
ccgaaaagtg ccacctgacg tcgacggatc gggagatcga tctcccgatc ccctagggtc    60
gactctcagt acaatctgct ctgatgccgc atagttaagc cagtatctgc tccctgcttg   120
tgtgttggag gtcgctgagt agtgcgcgag caaaatttaa gctacaacaa ggcaaggctt   180
gaccgacaat gcatgaaga atctgcttag ggttaggcgt tttgcgctgc ttcgcgatgt   240
acgggccaga tatacgcgtt gacattgatt attgactagt tattaatagt aatcaattac   300
ggggtcatta gttcatagcc catatatgga gttccgcgtt acataactta cggtaaatgg   360
cccgcctggc tgaccgccca acgacccccg cccattgacg tcaataatga cgtatgttcc   420
catagtaacg ccaataggga cttttccatt acgtcaatgg gtggagtatt tacggtaaac   480
tgcccacttg gcagtacatc aagtgtatca tatgccaagt acgcccccta ttgacgtcaa   540
tgacggtaaa tggcccgcct ggcattatgc ccagtacatg accttatggg actttcctac   600
ttggcagtac atctacgtat tagtcatcgc tattaccatg gtgatgcggt tttggcagta   660
catcaatggg cgtggatagc ggtttgactc acggggattt ccaagtctcc accccattga   720
cgtcaatggg agtttgtttt ggcaccaaaa tcaacgggac tttccaaaat gtcgtaacaa   780
ctccgcccca ttgacgcaaa tgggcggtag cgtgtacggt gggaggtct atataagcag   840
agctggttta gtgaaccgtc agatccgcta gagatccgcg gccgctaata cgactcacta   900
tagggagagc cgccaccatg cccgcggcta gagggtgaa gcttgacggt ggaaaacgga   960
cagccgacgg aagcgagttc gagtcaccaa agaagaagcg gaaagtcgac aagaagtaca  1020
gcatcggcct ggacatcggc accaactctg tgggctggcc cgtgatcacc gacgagtaca  1080
aggtgcccag caagaaattc aaggtgctgg gcaacaccga ccggcacagc atcaagaaga  1140
acctgatcgg agccctgctg ttcgacagcg gcgaaacagc cgaggccacc cggctgaaga  1200
gaaccgccaa gaagaagatac accagacgga gaaccggatc tgctatctg caagagatct  1260
tcagcaacga gatggccaag gtggacgaca gcttcttcca cagactggaa gagtccttcc  1320
tggtggaaga ggataagaag cacgagcggc acccccatct tggcaacatc gtggacgagg  1380
tggcctacca cgagaagtac cccaccatct accacctgag aaagaaactg gtggacagca  1440
ccgacaaggc cgacctgcgg ctgatctatc tggccctggc ccacatgatc aagttccggg  1500
gccacttcct gatcgagggc gacctgaacc ccgacaacag cgacgtggac aagctgttca  1560
tccagctggt gcagacctac aaccagctgt tcgaggaaaa ccccatcaac gccagcggcg  1620
tggacgccaa ggccatcctg tctgccgac tgagcaagag ccggagactg gaaaatctga  1680
tcgcccagct gcccggcgag aagaagaatg gcctgttcgg aaacctgatt gccctgagcc  1740
tgggcctgac ccccaacttc aagagcaact tcgacctggc cgaggatgcc aaactgcagc  1800
tgagcaagga cacctacgac gacgacctgg acaacctgct ggcccagatc ggcgaccagt  1860
acgccgacct gtttctggcc gccaagaacc tgtccgacgc catcctgctg agcgacatcc  1920
tgagagtgaa caccgagatc accaaggccc ccctgagcgc ctctatgatc aagagatacg  1980
```

```
acgagcacca ccaggacctg accctgctga aagctctcgt gcggcagcag ctgcctgaga    2040
agtacaaaga gattttcttc gaccagagca agaacggcta cgccggctac attgacggcg    2100
gagccagcca ggaagagttc tacaagttca tcaagcccat cctggaaaag atggacggca    2160
ccgaggaact gctcgtgaag ctgaacagag aggacctgct gcggaagcag cggaccttcg    2220
acaacggcag catcccccac cagatccacc tgggagagct gcacgccatt ctgcggcggc    2280
aggaagattt ttacccattc ctgaaggaca accgggaaaa gatcgagaag atcctgacct    2340
tccgcatccc ctactacgtg ggccctctgg ccagggaaaa cagcagattc gcctggatga    2400
ccagaaagag cgaggaaacc atcaccccct ggaacttcga ggaagtggtg gacaagggcg    2460
cttccgccca gagcttcatc gagcggatga ccaacttcga taagaacctg cccaacgaga    2520
aggtgctgcc caagcacagc ctgctgtacg agtacttcac cgtgtataac gagctgacca    2580
aagtgaaata cgtgaccgag ggaatgagaa agcccgcctt cctgagcggc gagcagaaaa    2640
aggccatcgt ggacctgctg ttcaagacca accggaaagt gaccgtgaag cagctgaaag    2700
aggactactt caagaaaatc gagtgcttcg actccgtgga aatctccggc gtggaagatc    2760
ggttcaacgc ctccctgggc acataccacg atctgctgaa aattatcaag gacaaggact    2820
tcctggacaa tgaggaaaac gaggacattc tggaagatat cgtgctgacc ctgacactgt    2880
ttgaggacag agagatgatc gaggaacggc tgaaaaccta tgcccacctg ttcgacgaca    2940
aagtgatgaa gcagctgaag cggcgcgaga tacaccggctg gggcaggctg agccggaagc    3000
tgatcaacgg catcccgggac aagcagtccg caagacaat cctggatttc ctgaagtccg    3060
acggcttcgc caacagaaac ttcatgcagc tgatccacga cgacagcctg accttttaaag    3120
aggacatcca gaaagcccag gtgtccggcc agggcgatag cctgcacgag cacattgcca    3180
atctggccgg cagcccgccc attaagaagg gcatcctgca gacagtgaag gtggtggacg    3240
agctcgtgaa agtgatggcc cggcacaagc ccgagaacat cgtgatcgaa atggccagag    3300
agaaccagac cacccagaag ggacagaaga acagccgcga gagaatgaag cggatcgaag    3360
agggcatcaa agagctgggc agccagatcc tgaaagaaca cccgtggaa acacccagc    3420
tgcagaacga gaagctgtac ctgtactacc tgcagaatgg cgggatatg tacgtggacc    3480
aggaactgga catcaaccgg ctgtccgact acgatgtgga cgctcatcgtg cctcagagct    3540
ttctgaagga cgactccatc gacaacaagg tgctgaccag aagcgacaag aaccggggca    3600
agagcgacaa cgtgccctcc gaagaggtcg tgaagaagat gaagaactac tggcggcagc    3660
tgctgaacgc caagctgatt acccagagaa agttcgacaa tctgaccaag gccgagagag    3720
gcggcctgag cgaactggat aaggccggct tcatcaagag acagctggtg gaaacccggc    3780
agatcacaaa gcacgtggca cagatcctgg actcccggat gaacactaag tacgacgagg    3840
atgacaagct gatccgggaa gtgaaagtga tcacctgaa gtccaagctg gtgtccgatt    3900
tccggaagga tttccagttt tacaaagtgc gcgagatcaa caactaccac cacgcccacg    3960
acgcctacct gaacgccgtc gtgggaaccg ccctgatcaa aaagtaccct aagctggaaa    4020
gcgagttcgt gtacggcgac tacaaggtgt acgacgtgcg gaagatgatc gccaagagcg    4080
agcaggaaat cggcaaggct accgccaagt acttcttcta cagcaacatc atgaactttt    4140
tcaagaccga gattaccctg gccaacggcg agatccggaa gcggcctctg atcgagacaa    4200
acggcgaaac cggggagatc gtgtgggata agggccgga ttttgccacc gtgcggaaag    4260
tgctggcat gccccaagtg aatatcgtga aaaagaccga ggtgcagaca ggcggcttca    4320
gcaaagagtc tatcctgccc aagaggaaca gcgataagct gatcgccaga aagaaggact    4380
gggaccctaa gaagtacggc ggcttcgaca gccccaccgt ggcctattct gtgctggtgg    4440
tggccaaagt ggaaaagggc aagtccaaga aactgaagag tgtgaaagag ctgctgggga    4500
tcaccatcat ggaaagaagc cgcttctgga gaatcccat cgactttctg gaagccaagg    4560
gctacaaaga agtgaaaaag gacctgatca tcaagctgcc taagtactcc ctgttcgagc    4620
tggaaaacgg ccggaagaga atgctggcct ctgccggcga actgcagaag ggaaacgaac    4680
tggccctgcc ctcaaaatat gtgaacttcc tgtacctggc cagccactat gagaagctga    4740
agggctcccc cgaggataat gagcagaaac agctgttttgt ggaacagcac aagcactacc    4800
tggacgagat catcgagcag atcagcgagt tctccaagag agtgatcctg gccgacgcta    4860
atctggacaa agtgctgtcc gcctacaaca agcaccggga taagcccatc agagagcagg    4920
ccgagaatat catccaccctg tttaccctga ccaatctggg agccctgcc gccttcaagt    4980
actttgacac caccatcgac cggaagaggt acaccagcac caaagaggtg ctggacgcca    5040
ccctgatcca ccagagcatc accggcctgt acgagacacg gatcgacctg tctcagctgg    5100
gaggtgactc tggaggatct agcggaggat cctctggcag cgagcacacca ggaacaagcg    5160
agtcagcaac accagagagc agtggcggca gcggcggcgg cagcagcacc ctaaatatag    5220
aagtagagta tcggctacat gagacctcaa aagagccgaa tgtttctcta gggtccacat    5280
ggctgtctga ttttcctcag gcctgggcgg aaaccggggg catgggactg gcagttcgcc    5340
aagctcctct gatcataccct ctgaaagcaa cctctacccc cgtgtccata aaacaatacc    5400
ccatgtcaca agaagccaga ctggggatca agccccacat acagagactg ttggaccagg    5460
gaatatggta ccctgccagt cccccctgaa cacgcccctg ctaccgttta agaaaccagg    5520
gactaatgat tataggcctg tccaggatct gagagaagtc aacaagcggg tggaagacat    5580
ccaccccacc gtgccaacc cttacaaccct cttgagcggg ctccaccgt cccaccagtg    5640
gtacactgtg cttgatttaa aggatgcctt tttctgcctg agactccacc ccaccagtca    5700
gcctctcttc gcctttgagt ggagagatcc agagatggga atctcaggac aattgacctg    5760
gaccagactcc ccacagggtt tcaaaaacag tcccacccctg tttaatgaag cactgcacag    5820
agcctagca gacttccgga tccagcaccc agacttgatc ctgctacagt acgtggatga    5880
cttactgctg gccgccactt ctgagctaga ctgccaacaa ggtactcggg ccctgttaca    5940
aaccctaggg aacctcgggt atcgggcctc ggccaagaaa gcccaaattt gccagaaaca    6000
ggtcaagtat ctggggtatc ttctaaaaga gggtcagaga tggctgactg aggccagaaa    6060
agagactgtg atggggcagc ctactccgaa gacccgctga caactaaggg agttcctagg    6120
gaaggcaggc ttctgtcgcc tcttcatccc tgggttttgca gaaatggcag ccccccttgta    6180
ccctctcacc aaaccgggga ctctgtttaa ttggggccca gaccaacaaa aggcctatca    6240
agaaatcaag caagctcttc taactgcccc agccctgggg ttgccagatt tgactaagcc    6300
cttttgaactc tttgtcgacg agaagcaggg ctacgccaaa ggtgtcctaa cgcaaaaact    6360
gggaccttgg cgtcggccgg tcctacct gtccaaaaag ctagacccag tagcagctgg    6420
gtggcccct tgcctacgga tggtagcagc cattgccgta ctgacaaagg atgcaggcaa    6480
gctaaccatg ggacagccac tagtcattct ggccccccat gcagtagagg cactagtcaa    6540
acaaccccc gaccgctggc tttcaacgc ccggatgact cactatcagg ccttgctttt    6600
ggacacggac cgggtccagt tcggaccggt ggtagccctg aacccggcta cgctgctccc    6660
actgcctgag gaagggctgc aacacaactg ccttgatatc ctggccgaag cccacggaac    6720
```

```
ccgacccgac ctaacggacc agccgctccc agacgccgac cacacctggt acacggatgg   6780
aagcagtctc ttacaagagg gacagcgtaa ggcgggagct gcggtgacca ccgagaccga   6840
ggtaatctgg gctaaagccc tgccagccgg gacatccgct cagcgggctg aactgatagc   6900
actcacccag gccctaaaga tggcagaagg taagaagcta aatgtttata ctgatagccg   6960
ttatgctttt gctactgccc atatccatgg agaaatatac agaaggcgtg ggtggctcac   7020
atcagaaggc aaagagatca aaaataaaga cgagatcttg gccctactaa aagccctctt   7080
tctgcccaaa agacttagca taatccattg tccaggacat caaaagggac acagcgccga   7140
ggctagaggc aaccggatgg ctgaccaagc ggcccgaaag gcagccatca cagagactcc   7200
agacacctct accctcctca tagaaaattc atcaccctct ggcggctcaa aaagaaccgc   7260
cgacggcagc gaaaaaagaa ccgctgactc tcaacattcc acacctccaa aaaccaagcg   7320
aaaagtggaa ttcgagccca agaagaagag gaaagtcgga agcggagcta ctaacttcag   7380
cctgctgaag caggctggcg acgtggagga gaaccctgga cctccaaaaa agaaaagaaa   7440
agtgtatccc tatgatgtcc ccgattatgc cggttcaaga gccctggtcg tgattagact   7500
gagccgagtg acagacgcca ccacaagtcc cgagagacag ctggaatcat gccagcagct   7560
ctgtgctcag cggggtttgg gatgtggtcg cgtggcagag gatctggacg tgagcggggc   7620
cgtcgatcca ttcgacagaa agaggaggcc caacctggca agatggctcg ctttcgagga   7680
acagcccttt gatgtgatcg tcgcctacag agtggaccgg ctgaccgct caattcgaca   7740
tctccagcag ctggtgcatt gggctgagga ccacaagaaa ctggtggtca gcgcaacaga   7800
agcccacttc gatactacca caccttttgc cgctgtggtc atcgcactga tgggcactgt   7860
ggcccagatg gagctcgaag ctatcaagga gcgaaacagg agcgcagccc atttcaatat   7920
tagggccggt aaatacagag gctccctgcc cccttgggga tatctcccta ccagggtgga   7980
tgggagtgg agactggtgc cagacccccgt ccagagacg cggattctgg aagtgtacca   8040
cagagtggtc gataaccacg aaccactcca tctggtggca cacgacctga atagacgcgg   8100
cgtgctctct ccaaaggatt attttgctca gctgcaggga agagagcac agggaagaga   8160
atggagtgct actgcactga agagatctat gatcagtgag gctatgctgg ttacgcaac   8220
actcaatggc aaaactgtcc gggacgatga cggagccct ctggtgaggg ctgagcctat   8280
tctcaccaga gagcagctcg aagctctgcg ggcagaactg gtcaagacta gtcgcgccaa   8340
acctgccgtg agcaccccaa gcctgctcct gaggtgctg ttctgcgccg tctgtggaga   8400
gccagcatac aagtttgccg gcggagggcg caaacatccc cgctatcgat gcaggagcat   8460
gggttccct aagcactgtg gaaacggac agtggccatg gctgagtggg acgcctttg   8520
cgaggaacag gtgctggatc tcctgggtga cgctgagcgg ctggaaaaag tgtgggtggc   8580
aggatctgac tccgctgtgg agctggcaga agtcaatgcc gagctcgtgg atctgacttc   8640
cctcatcgga tctcctgcat atagagctgg gtccccacag agagaagctc tggacgcacg   8700
aattgctgca ctcgctgcta gacaggagga actgagggc ctggaggcca ggccctctgg   8760
atgggagtgg cgagaaaccg gacagaggtt tgggattgg tggaggggagg aggaccgc    8820
agccaagaac acatggctga gatccatgaa tgtccggctc acattcgacg tgcgcggtgg   8880
cctgactcga accatcgatt ttggcgacct gcaggagtat gaacagcacc tgagactggg   8940
gtccgtggtc gaaagactgc acactgggat gtcctaggtt taaacccgct gatcagcctc   9000
gactgtgcct tctagttgcc agccatctgt tgtttgcccc tccccgtgc cttccttgac   9060
cctgaaggt gccactccca ctgtccttc ctaataaaat gagaaaattg catcgcattg   9120
tctgagtagg tgtcattcta ttctgggggg tgggtgggg caggacagca aggggagga   9180
ttgggaagac aatagcaggc atgctgggga tgcggtgggc tctatggctt ctgaggcgga   9240
aagaaccagc tggggctcga taccgtcgac ctctagctag agcttggcgt aatcatggtc   9300
atagctgttt cctgtgtgaa attgttatcc gctcacaatt ccacacaaca tacgagccgg   9360
aagcataaag tgtaaagcct agggtgccta atgagtgagc taactcacat taattgcgtt   9420
gcgctcactg cccgctttcc agtcgggaaa cctgtcgtgc cagctgcatt aatgaatcgg   9480
ccaacgcgcg gggagaggcg gtttgcgtat tgggcgctct tccgcttcct cgctcactga   9540
ctcgctgcgc tcggtcgttc ggctgcggcg agcggtatca gctcactcaa aggcggtaat   9600
acggttatcc acagaatcag gggataacgc aggaaagaac atgtgagcaa aaggccagca   9660
aaaggccagg aaccgtaaaa aggccgcgtt gctggcgttt ttccataggc tccgccccc   9720
tgacgagcat cacaaaaatc gacgctcaag tcagaggtgg cgaaacccga caggactata   9780
aagataccag gcgtttcccc ctggaagctc cctcgtgcgc tctcctgttc cgacccctgcc   9840
gcttaccgga tacctgtccg cctttctccc ttcgggaagc gtggcgcttt ctcatagctc   9900
acgctgtagg tatctcagtt cggtgtaggt cgttcgctcc aagctgggct gtgtgcacga   9960
acccccgtt cagcccgacc gctgcgcctt atccggtaac tatcgtcttg agtccaaccc  10020
ggtaagacac gacttatcgc cactggcagc agccactggt aacaggatta gcagagcgag  10080
gtatgtaggc ggtgctacag agttcttgaa gtggtggcct aactacggct acactagaag  10140
aacagtattt ggtatctgcg ctctgctgaa gccagttacc ttcggaaaaa gagttggtag  10200
ctcttgatcc ggcaaacaaa ccaccgctgg tagcggtggt ttttttgttt gcaagcagca  10260
gattacgcgc agaaaaaaag gatctcaaga agatcctttg atcttttcta cggggtctga  10320
cgctcagtgg aacgaaaact cacgttaagg gattttggtc atgagattat caaaaaggat  10380
cttcacctag atccttttaa attaaaaatg aagttttaaa tcaatctaaa gtatatatga  10440
gtaaacttgg tctgacagtt accaatgctt aatcagtgag gcacctatct cagcgatctg  10500
tctatttcgt tcatccatag ttgcctgact ccccgtcgtg tagataacta cgatacggga  10560
gggcttacca tctggccca gtgctgcaat gataccgcga gacccacgct caccggctcc  10620
agatttatca gcaataaacc agccagccgg aaggccgag cgcagaagtg gtcctgcaac  10680
tttatccgcc tccatccagt ctattaattg ttgccgggaa gctagagtaa gtagttcgcc  10740
agttaatagt ttgcgcaacg ttgttgccat tgctacaggc atcgtggtgt cacgctcgtc  10800
gtttggtatg gcttcattca gctccggttc ccaacgatca aggcgagtta catgatcccc  10860
catgttgtgc aaaaaagcgg ttagctcctt cggtcctccg atcgttgtca gaagtaagtt  10920
ggccgcagtg ttatcactca tggttatggc agcactgcat aattctctta ctgtcatgcc  10980
atccgtaaga tgcttttctg tgactggtga gtactcaacc aagtcattct gagaatagtg  11040
tatgcggcga ccgagttgct cttgcccggc gtcaatacgg gataataccg cgccacatag  11100
cagaacttta aaagtgctca tcattggaaa acgttcttcg gggcgaaaac tctcaaggat  11160
cttaccgctg ttgagatcca gttcgatgta acccactcgt gcacccaact gatcttcagc  11220
atcttttact ttcaccagcg tttctgggtg agcaaaaaca ggaagcaaa atgccgcaaa  11280
aaagggaata agggcgacac ggaaatgttg aatactcata ctcttccttt ttcaatatta  11340
ttgaagcatt tatcagggtt attgtctcat gagcggatac atatttgaat gtatttagaa  11400
aaataaacaa ataggggttc cgcgcacatt tcc                               11433
```

```
SEQ ID NO: 384           moltype = DNA  length = 11056
FEATURE                  Location/Qualifiers
misc_feature             1..11056
                         note = Description of Artificial Sequence: Synthetic
                         polynucleotide
source                   1..11056
                         mol_type = other DNA
                         organism = synthetic construct
SEQUENCE: 384
ccgaaaagtg ccacctgacg tcgacggatc gggagatcga tctcccgatc ccctagggtc   60
gactctcagt acaatctgct ctgatgccgc atagttaagc cagtatctgc tccctgcttg  120
tgtgttggag gtcgctgagt agtgcgcgag caaaatttaa gctacaacaa ggcaaggctt  180
gaccgacaat tgcatgaaga atctgcttag ggttaggcgt tttgcgctgc ttcgcgatgt  240
acggccaga tatacgcgtt gacattgatt attgactagt tattaatagt aatcaattac  300
ggggtcatta gttcatagcc catatatgga gttccgcgtt acataactta cggtaaatgg  360
cccgcctggc tgaccgccca cgacccccg cccattgacg tcaataatga cgtatgttcc  420
catagtaacg ccaataggga cttttccattg acgtcaatga gtggagtatt tacggtaaac  480
tgcccacttg gcagtacatc aagtgtatca tatgccaagt acgccccta ttgacgtcaa  540
tgacggtaaa tggcccgcct ggcattatgc ccagtacatg accttatggg actttcctac  600
ttggcagtac atctacgtat tagtcatcgc tattaccatg gtgatgcggt tttggcagta  660
catcaatggg cgtggatagc ggtttgactc acggggattt ccaagtctcc accccattga  720
cgtcaatggg agtttgtttt ggcaccaaaa tcaacgggac tttccaaaat gtcgtaacaa  780
ctccgcccca ttgacgcaaa tgggcggtag gcgtgtacgg tgggaggtct atataagcag  840
agctggttta gtgaaccgtc agatccgcta gagatccgcg ccgctaata cgactcacta  900
tagggagagc cgccaccatg aaacggacag cgagttcgau tcaccaaaga  960
agaagcggaa agtcgacaag aagtacagca tcggcctgga catcggcacc aactctgtgg 1020
gctgggcgt gatcaccgac gagtacaagg tgcccagcaa gaaattcaag gtgctgggca 1080
acaccgaccg gcacagcatc aagaagaacc tgatcggagc cctgctgttc gacagcggcg 1140
aaacagccga ggccaccccg gctgaagagaa ccgccaagaa gatacacc agacggaaga 1200
accggatctg ctatctgcaa gagatcttca gcaacgagat ggccaaggtg gacgacagct 1260
tcttccacag actggaagag tccttcctgg tggaagagga taagaagcac gagcggcacc 1320
ccatcttcgg caacatcgtg gacgaggtgg cctaccacga gaagtacccc accatctacc 1380
acctgagaaa gaaactggtg gacagcaccg acaaggcga cctgcggctg atctatctgg 1440
ccctggccca catgatcaag ttccgggggcc acttcctgat cgagggcgac ctgaacccca 1500
acaacagcga cgtggacaag ctgttcatcc agctggtgca gacctacaac cagctgttcg 1560
aggaaaaccc catcaacgcc agcggcgtgg acgccaaggc catcctgtct gccagactga 1620
gcaagagcag acggctggaa aatctgatcg cccagctgcc cggcgagaag aagaatggcc 1680
tgttcggaaa cctgattgcc ctgagccttgg gcctgacccc caacttcaag agcaacttcg 1740
acctggccga ggatgccaaa ctgcagctga gcaaggacac ctacgacgac gacctggaca 1800
acctgctggc ccagatcggc gaccagtacg ccgacctgtt tctggccgcc aagaacctgt 1860
ccgacgccat cctgctgagc gacatcctga gagtgaacac cgagatcacc aaggcccccc 1920
tgagcgcctc tatgatcaag agatacgacg agcaccacca ggacctgact cctgctgaaag 1980
ctctcgtgcg gcagcagctg cctgagaagt acaaagagat tttcttcgac cagagcaaga 2040
acggctacgc cggctacatt gacggcgagc cagccagga agttctac aagttcatca 2100
agcccatcct ggaaaagatg gacggcaccg aggaactgct cgtgaagctg aacagagagg 2160
acctgctgcg gaagcagcgg accttcgaca cggcagcat cccccaccag atccacctgg 2220
gagagctgca cgccattctg cggcggcagg aagattttta cccattcctg aaggacaacc 2280
gggaaaagat cgaaaagatc ctgacctttc gcatccccta ctacgtgggc cctctggcca 2340
ggggaaacag cagattcgcc tggatgacca aaaagagcga ggaaaccatc accccctgga 2400
acttcgagga agtggtggac aagggcgctt ccgcccagag cttcatcgag cggatgacca 2460
acttcgataa gaacctgccc aacgagaagg tgctgcccaa gcacagcctg ctgtacgagt 2520
acttcaccgt gtataacgag ctgaccaaag tgaaatacgt gaccgaggga atgagaaagc 2580
ccgccttcct gagcggcgag cagaaaaagg ccatcgtgga cctgctgttc aagaccaacc 2640
ggaaagtgac cgtgaagcag ctgaaagagg actacttcaa gaaaatcgag tgcttcgact 2700
ccgtggaaat ctccggcgtg gaagatcggt tcaacgcctc cctgggcaca taccacgatc 2760
tgctgaaaat tatcaaggac aaggacttcc tggacaatga ggaaaacgag gacattctgg 2820
aagatatcgt gctgaccctg acactgtttg aggacagaga gatgatcgag gaacggctga 2880
aaacctatgc ccacctgttc gacgacaaag tgatgaagca gctgaagcgg cggagataca 2940
ccggctgggg caggctgagc cggaagctga tcaacggcat ccgggacaag cagtccggca 3000
agacaatcct ggatttcctg aagtccgacg gcttcgccaa cagaaacttc atgcagctga 3060
tccacgacga cagcctgacc tttaaagagg acatccagaa agcccaggtg tccggccagg 3120
gcgatagcct gcacgagcac attgccaatc tggccggcag ccccgccatt aagaagggca 3180
tcctgcagac agtgaaagtg gtggacgagc tcgtgaaagt gatgggccgg cacaagccca 3240
agaacatcgt gatcgaaatg gccagagaga accagaccac ccagaaggga cagaagaaca 3300
gccgcgagag aatgaagcgg atcgaagagg gcatcaaaga gctgggcagc cagatcctga 3360
aagaacaccc cgtggaaaac acccagctgc agaacgagaa gctgtacctg tactacctgc 3420
agaatgggcg ggatatgtac gtggaccagg aactggacat caaccggctg tccgactacg 3480
atgtggacgc tatcgtgcct cagagctttc tgaaggacga ctccatcgac aacaaggtgc 3540
tgaccagaag cgacaagaac cggggcaaga gcgacaacgt gccctccgaa gaggtcgtga 3600
agaagatgaa gaactactgg cggcagctgc tgaacgccaa gctgattacc cagagaaagt 3660
tcgacaatct gaccaaggcc gagagaggcg gcctgagcga actggataag gccggcttca 3720
tcaagagaca gctggtggaa accggcagaa tcacaaagca cgtggcacag atcctggact 3780
cccggatgaa cactaagtac gacgagaatg acaaactgat ccgggaagtg aaagtgatca 3840
ccctgaagtc caagctggtg tccgatttcc gaaggatttt ccagtttac aaagtgcgcg 3900
agatcaacaa ctaccaccac gcccacgacg cctacctgaa cgccgtcgtg ggaaccgccc 3960
tgatcaaaaa gtaccctaag ctggaaagcg agttcgtgta cggcgactac aaggtgtacg 4020
acgtgcggaa gatgatcgcc aagagcgagc aggaaatcgg caaggctacc gccaagtact 4080
tcttctacag caacatcatg aacttttttca agaccgagat taccctggcc aacggcgaga 4140
```

```
tccggaagcg gcctctgatc gagacaaacg gcgaaaccgg ggagatcgtg tgggataagg    4200
gccgggattt tgccaccgtg cggaaagtgc tgagcatgcc ccaagtgaat atcgtgaaaa    4260
agaccgaggt gcagacaggc ggcttcagca aagagtctat cctgcccaag aggaacagcg    4320
ataagctgat cgccagaaag aaggactggg accctaagaa gtacggcggc ttcgacagcc    4380
ccaccgtggc ctattctgtg ctggtggtgt ccaaagtgga aaagggcaag tccaagaaac    4440
tgaagagtgt gaaagagctg ctggggatca ccatcatgga aagaagcagc ttcgagaaga    4500
atcccatcga ctttctggaa gccaagggct acaaagaagt gaaaaaggac ctgatcatca    4560
agctgcctaa gtactccctg ttcgagctgg aaaacggccg gaagagaatg ctggcctctg    4620
ccggcgaact gcagaaggga aacgaactgg ccctgccctc caaatatgtg aacttcctgt    4680
acctggccag ccactatgag aagctgaagg gctcccccga ggataatgag cagaaacagc    4740
tgtttgtgga acagcacaag cactacctgg acgagatcat cgagcagatc agcgagttct    4800
ccaagagagt gatcctggcc gacgctaatc tggacaaagt gctgtccgcc tacaacaagc    4860
accgggataa gcccatcaga gagcaggccg agaatatcat ccacctgttt accctgacca    4920
atctgggagc ccctgccgcc ttcaagtact ttgacaccac catcgaccgg aagaggtaca    4980
ccagcaccaa agaggctgctg gacgccaccc tgatccacca gagcatcacc ggcctgtacg    5040
agacacggat cgacctgtct cagctgggag gtgactctgg aggatctagc ggaggatcct    5100
ctggcagcga gacaccagga acaagcgagt cagcaacacc agagagctct ggtagcgaga    5160
cacccggtac cagtgaaagc gccacgccag aaagcagtgg gagtgagact ccgggtacat    5220
ctgaatcagc gacaccggaa tcaagtggcg gcagcagcag cggcagcagc acctaaata    5280
tagaagatga gtatcggcta catgagacct caaaagagcc agatgtttct ctagggtcca    5340
catggctgtc tgatttcct caggcctggg cggaaaccgg gggcatggga ctggcagttc    5400
gccaagctcc tctgatcata ctctgaaag caacctctac ccccgtgtcc ataaaacaat    5460
accccatgtc acaagaagcc agactgggga tcaagcccca catacagaca ctgttggacc    5520
agggaatact ggtaccctgc cagtcccct ggaacacgcc cctgctaccc gttaagaaac    5580
cagggactaa tgattatagg cctgtccagg atctgagaga agtcaacaag cgggtggaag    5640
acatccaccc caccgtgccc aacccttaca acctcttgg cgggccccca ccgtcccacc    5700
agtggtacac tgtgcttgat ttaaaggatg ccttttttctg cctgagactc caccccacca    5760
gtcagcctct cttcgccttt gagtggagag atccagagat gggaatctca ggacaattga    5820
cctgaccag actccacag ggtttcaaaa acagtcccac cctgtttaat gaggcactgc    5880
acagacct agcagacttc cggatccagc acccagactt gatcctgcta cagtacgtgg    5940
atgacttact gctggccgcc acttctgagc tagactgcca acaaggtact cgggccctgt    6000
tacaaaccct agggaacctc gggatcgggg cctcggccaa gaaagcccaa atttgccaga    6060
aacaggtcaa gtatctgggg tatcttctaa aagagggtca gagatggctg actgaggcca    6120
gaaagagac tgtgatgggg cagcctactc cgaagacccc tcgacaacta agggagttcc    6180
tagggaaggc aggcttctgt cgcctcttca tccctgggt tgcagaaatg gcagccccc    6240
tgtaccctct caccaaaccg gggactctgt taattgggg cccagaccaa caaaaggcct    6300
atcaagaat caagcaagct cttctaactg ccccagccct gggggtgcca gatttgacta    6360
agcccttga actctttgtc gacgagaagc agggctacgc caaaggtgtc ctaacgcaaa    6420
aactggacc ttggcgtcgg ccggtggcct acctgtccaa aaagctagac ccagtagcag    6480
ctggtggcc cccttgccta cggatggtag cagccattgc cgtactgaca aaggatgcag    6540
gcaagctaac catgggacag ccactagtca ttctggcccc ccatgcagta gaggcactag    6600
tcaaacaacc ccccgaccgc tggcttttcca acgccggat gactcactat caggccttgc    6660
ttttgacac ggaccggtc cagttcggac cggtggtagc cctgaacccg gctacgctgc    6720
tcccactgcc tgaggaaggg ctgcaacaca actgccttga tgggacaggt ggcggtggtg    6780
tcaccgtcaa gttcaagtac aagggtgagg aacttgaagt tgatattagc aaaatcaaga    6840
aggtttggcg cgttggtaaa atgatatctt ttacttatga cgacaacggc aagacaggta    6900
gagggcagt gtctgagaaa gacgcccca aggagctgtt gcaaatgttg gaaaagtctg    6960
ggaaaaagtc tggcgggctca aaaagaaccg ccgacggcag cgaattcgag cccaagaaga    7020
agaggaaagt cggaggtggc gggagcccaa aaaagaaaag aaaagtgtat ccctatgatg    7080
tccccgatta tgccggttca agagccctgg tcgtgattag actgagccga gtgacagacg    7140
ccaccacaag tccccgagaa cagctggaat catgccacgc gctctgtgct cagcgggctt    7200
gggatgtggt cggcgtggca gaggatctgc acgtgagcgg ggccgtcgat ccattcgaca    7260
gaaagaggag gcccaacctg gcaagatggc tcgctttcga ggaacagccc tttgatgtga    7320
tcgtcgccta cagagtggac cggctgaccc gctcaattcg acatctccag cagctggtgc    7380
attggcgtga ggaccacaag aaactggctg tcagcgcaac agaagcccac ttcgatacta    7440
ccacaccttt tgccgctgtg gtcatcgcac tgatgggcac tgtggccagg atggagctgg    7500
aagctatcaa ggagcgaaac aggagcgcag cccatttcaa tattagggcc ggtaaataca    7560
gaggctccct gccccttgg ggatatctcc ctaccagggt ggatggggag tggagactgg    7620
tgccagaccc cgtccagaga gagcggattc tggaagtgta cagccgagtg gtcgataacc    7680
acgaaccact ccatctggtg gcacacgacc tgaatagacg cggcagtgtc tctccaaagg    7740
attatttttgc tcagctgcag ggaagagagc cacaggaag agaatggagt gctactgcac    7800
tgaagagatc tatgatcagt gaggctatgc tgggttacgc aacactcaat ggcaaaactg    7860
tccgggacga tgacggagcc cctctggtga gggctgagc tattctcacc agagagcagc    7920
tcgaagtct gcgggcagaa ctggtcaaga ctagtccgcc caaacctgcc gtgagcaccc    7980
caagcctgct cctgagggtg ctgttctgcg ccgtctgtgg agagccagca tacaagtttg    8040
ccggcggagg gcgcaaacat ccccgctatc gatgcaggag catggggttc cctaagcact    8100
gtggaaacgg gacagtggcc atggctgagt gggacgcctt ttgcgaggaa caggtgctgg    8160
atctcctggg tgacgctgag cggctggaaa agtgtgggt ggcaggatct gactccgctg    8220
tggagctgac agaagtcaat gccgagctcg tggatctgca ttccctcatc ggatctctgc    8280
catatagagc tgggtcccca cagagagaag ctctggacgc acgaattgct gcactcgctg    8340
ctagacagga ggaactggag ggctggagg ccaggccctc tggatgggag tggcgagaaa    8400
ccggacagag gtttggggat tggtggaggg agcaggacac cgcagccaag aacacatggc    8460
tgagatccat gaatgtccgg ctcacattcg acgtgcgcgg tggcctgact cgaaccatcg    8520
attttggcga cctgcaggag tatgaacagc acctgagact ggggtccgtg gtcgaaagac    8580
tgcacactgg gatgtcctag gtttaaaccc gctgatcagc ctcgactgtg ccttctagtt    8640
gccagccatc tgttgtttgc ccctcccccg tgccttcctt gaccctggaa ggtgccactc    8700
ccactgtcct ttcctaataa aatgagaaaa ttgcatcgca ttgtctgagt aggtgtcatt    8760
ctattctggg gggtggggtg gggcaggaca gcaagggga ggattgggaa gacaatagca    8820
ggcatgctgg ggatgcggtg ggctctatgg cttctgaggc ggaaagaacc agctggggct    8880
```

```
cgataccgtc gacctctagc tagagcttgg cgtaatcatg gtcatagctg tttcctgtgt   8940
gaaattgtta tccgctcaca attccacaca acatacgagc cggaagcata agtgtaaag   9000
cctagggtgc ctaatgagtg agctaactca cattaattgc gttgcgctca ctgcccgctt   9060
tccagtcggg aaacctgtcg tgccagctgc attaatgaat cggccaacgc gcggggagag   9120
gcggtttgcg tattgggcgc tcttccgctt cctcgctcac tgactcgctg cgctcggtcg   9180
ttcggctgcg gcgagcggta tcagctcact caaaggcggt aatacggtta tccacagaat   9240
caggggataa cgcaggaaag aacatgtgag caaaaggcca gcaaaaggcc aggaaccgta   9300
aaaaggccgc gttgctggcg tttttccata ggctccgccc ccctgacgag catcacaaaa   9360
atcgacgctc aagtcagagg tggcgaaacc cgacaggact ataaagatac caggcgtttc   9420
cccctggaag ctccctcgtg cgctctcctg ttccgaccct gccgcttacc ggatacctgt   9480
ccgcctttct cccttcggga agcgtggcgc tttctcatag ctcacgctgt aggtatctca   9540
gttcggtgta ggtcgttcgc tccaagctgg gctgtgtgca cgaaccccc gttcagcccg   9600
accgctgcgc cttatccggt aactatcgtc ttgagtccaa cccggtaaga cacgacttat   9660
cgccactggc agcagccact ggtaacagga ttagcagagc gaggtatgta ggcggtgcta   9720
cagagttctt gaagtggtgg cctaactacg gctacactag aagaacagta tttggtatct   9780
gcgctctgct gaagccagtt accttcggaa aaagagttgg tagctcttga tccggcaaac   9840
aaaccaccgc tggtagcggt ggtttttttg tttgcaagca gcagattacg cgcagaaaaa   9900
aaggatctca agaagatcct ttgatctttt ctacggggtc tgacgctcag tggaacgaaa   9960
actcacgtta agggattttg gtcatgagat tatcaaaaag gatcttcacc tagatccttt   10020
taaattaaaa atgaagtttt aaatcaatct aaagtatata tgagtaaact tggtctgaca   10080
gttaccaatg cttaatcagt gaggcaccta tctcagcgat ctgtctattt cgttcatcca   10140
tagttgcctg actccccgtc gtgtagataa ctacgatacg ggagggctta ccatctggcc   10200
ccagtgctgc aatgataccg cgagacccac gctcaccggc tccagattta tcagcaataa   10260
accagccagc cggaagggcc gagcgcagaa gtggtcctgc aactttatcc gcctccatcc   10320
agtctattaa ttgttgccgg gaagctagag taagtagttc gccagttaat agtttgcgca   10380
acgttgttgc cattgctaca ggcatcgtgg tgtcacgctc gtcgtttggt atggcttcat   10440
tcagctccgg ttcccaacga tcaaggcgag ttacatgatc ccccatgttg tgcaaaaaag   10500
cggttagctc cttcggtcct ccgatcgttg tcagaagtaa gttggccgca gtgttatcac   10560
tcatggttat ggcagcactg cataattctc ttactgtcat gccatccgta agatgctttt   10620
ctgtgactgg tgagtactca accaagtcat tctgagaata gtgtatgcgg cgaccgagtt   10680
gctcttgccc ggcgtcaata cgggataata ccgcgccaca tagcagaact ttaaaagtgc   10740
tcatcattgg aaaacgttct cggggcgaaa actctcaag gatcttaccg ctgttgagat   10800
ccagttcgat gtaacccact cgtgcaccca actgatcttc agcatctttt actttcacca   10860
gcgtttctgg gtgagcaaaa acaggaaggc aaaatgccgc aaaaaaggga ataagggcga   10920
cacggaaatg ttgaatactc atactcttcc ttttcaata ttattgaagc atttatcagg   10980
gttattgtct catgagcgga tacatatttg aatgtattta gaaaaataaa caaatagggg   11040
ttccgcgcac atttcc                                                    11056

SEQ ID NO: 385          moltype = DNA   length = 2367
FEATURE                 Location/Qualifiers
misc_feature            1..2367
                        note = Description of Artificial Sequence: Synthetic
                        polynucleotide
source                  1..2367
                        mol_type = other DNA
                        organism = synthetic construct
SEQUENCE: 385
tgttgagatc cagttcgatg taacccactc gtgcacccaa ctgatcttca gcatctttta    60
ctttcaccag cgtttctggg tgagcaaaaa caggaaggca aaatgccgca aaaaagggaa   120
taagggcgac acgaaatgt tgaatactca tactcttcct ttttcaatat tattgaagca   180
tttatcaggg ttattgtctc atgagcggat acatatttga atgtatttag aaaaataaac   240
aaatagggt tccgcgcaca tttccccgaa aagtgccacc tgacgtcgct agctgtacaa   300
aaaagcaggc tttaaaggaa ccaattcagt cgactggatc cggtaccaag gtcgggcagg   360
aagagggcct atttcccatg attccttcat atttgcatat acgatacaag gctgttagag   420
agataattag aattaatttg actgtaaaca caaagatatt agtacaaaat acgtgacgta   480
gaaagtaata atttcttggg tagtttgcag ttttaaaatt atgttttaaa atggactatc   540
atatgcttac cgtaacttga agtatttcg atttcttggc tttatatatc ttgtggaaag   600
gacgaaacac cgctattctc gcagctcacc agttttagag ctagaaatag caagttaaaa   660
taaggctagt ccgttatcaa cttgaaaaag tggcaccgag tcggtgcgac gagcgcggcg   720
atatcatcat ccatggccgg atgatcctga cgacggagac cgccgtcgtc gacaagccgg   780
cctgagctgc gagaatttt ttaagcttgg gccgctcgag gtacctctct acatatgaca   840
tgtgagcaaa aggccagcaa aaggccagga accgtaaaaa ggccgcgttg ctggcgtttt   900
tccataggct ccgcccccct gacgagcatc acaaaaatcg acgctcaagt cagaggtggc   960
gaaacccgac aggactataa agataccagg cgtttccccc tggaagctcc ctcgtgcgct  1020
ctcctgttcc gaccctgccg cttaccggat acctgtccgc ctttctccct tcgggaagcg  1080
tggcgctttc tcatagctca cgctgtaggt atctcagttc ggtgtaggtc gttcgctcca  1140
agctgggctg tgtgcacgaa ccccccgttc agcccgaccg ctgcgcctta tccggtaact  1200
atcgtcttga gtccaacccg gtaagacacg acttatcgcc actggcagca gccactggta  1260
acaggattag cagagcgagg tatgtaggcg gtgctacaga gttcttgaag tggtggccta  1320
actacggcta cactagaaga acagtatttg gtatctgcgc tctgctgaag ccagttacct  1380
tcggaaaaag agttggtagc tcttgatccg gcaaacaaac caccgctggt agcggtggtt  1440
tttttgtttg caagcagcag attacgcgca gaaaaaaagg atctcaagaa gatcctttga  1500
tcttttctac ggggtctgac gctcagtgga acgaaaactc acgttaaggg attttggtca  1560
tgagattatc aaaaaggatc ttcacctaga tccttttaaa attaaaaatga agttttaat  1620
caatctaaag tatatatgag taaacttggt ctgacagtta ccaatgctta atcagtgagg  1680
cacctatctc agcgatctgt ctatttcgtt catccatagt tgcctgactc cccgtcgtgt  1740
agataactac gatacgggag ggcttaccat ctggccccag tgctgcaatg ataccgcgag  1800
atccacgctc accggctcca gatttatcag caataaacca gccaggagga gggccgagc  1860
gcagaagtgg tcctgcaact ttatccgcct ccatccagtc tattaattgt tgccgggaag  1920
```

```
ctagagtaag tagttcgcca gttaatagtt tgcgcaacgt tgttgccatt gctacaggca   1980
tcgtggtgtc acgctcgtcg tttggtatgg cttcattcag ctccggttcc aacgatcaa    2040
ggcgagttac atgatccccc atgttgtgca aaaaagcggt tagctccttc ggtcctccga   2100
tcgttgtcag aagtaagttg gccgcagtgt tatcactcat ggttatggca gcactgcata   2160
attctcttac tgtcatgcca tccgtaagat gcttttctgt gactggtgag tactcaacca   2220
agtcattctg agaatagtgt atgcggcgac cgagttgctc ttgcccggcg tcaatacggg   2280
ataataccgc gccacatagc agaactttaa aagtgctcat cattggaaaa cgttcttcgg   2340
ggcgaaaact ctcaaggatc ttaccgc                                       2367
```

| | |
|---|---|
| SEQ ID NO: 386 | moltype = DNA  length = 2280 |
| FEATURE | Location/Qualifiers |
| misc_feature | 1..2280 |
| | note = Description of Artificial Sequence: Synthetic polynucleotide |
| source | 1..2280 |
| | mol_type = other DNA |
| | organism = synthetic construct |

```
SEQUENCE: 386
ctccatccag tctattaatt gttgccggga agctagagta agtagttcgc cagttaatag    60
tttgcgcaac gttgttgcca ttgctacagg catcgtggtg tcacgctcgt cgtttggtat   120
ggcttcattc agctccggtt cccaacgatc aaggcgagtt acatgatccc catgttgtg   180
caaaaaagcg ttagctcctt cggtcctcc gatcgttgtc agaagtaagt tggccgcagt   240
gttatcactc atggttatgg cagcactgca taattctctt actgtcatgc catccgtaag   300
atgcttttct gtgactggtg agtactcaac caagtcattc tgagaatagt gtatgcggcg   360
accgagttgc tcttgcccgg cgtcaatacg ggataatacc gcgccacata gcagaacttt   420
aaaagtgctc atcattggaa aacgttcttc ggggcgaaaa ctctcaagga tcttaccgct   480
gttgagatcc agttcgatgt aacccactcg tgcacccaac tgatcttcag catcttttac   540
tttcaccagc gtttctgggt gagcaaaaac aggaaggcaa aatgccgcaa aaaagggaat   600
aagggcgaca cggaaatgtt gaatactcat actcttcctt tttcaatatt attgaagcat   660
ttatcagggt tattgtctca tgagcggata catatttgaa tgtatttaga aaataaaaca   720
aataggggtt ccgcgcacat ttccccgaaa agtgccacct gacgtcgcta gctgtacaaa   780
aaagcaggct ttaaaggaac caattcagtc gactggatcc ggtaccaagg tcgggcagga   840
agagggccta tttcccatga ttccttcata tttgcatata cgatacaagg ctgttagaga   900
gataattaga attaatttga ctgtaaacac aaagatatta gtacaaaata cgtgacgtag   960
aaagtaataa tttcttgggt agtttgcagt tttaaaatta tgttttaaaa tggactatca   1020
tatgcttacc gtaacttgaa agtatttcga tttcttggct ttatatatct tgtggaaagg   1080
acgaaacacc gaagccggcc ttgcacatgc gtttagagc tagaaatagc aagttaaaat   1140
aaggctagtc cgttatcaac ttgaaaaagt ggcaccgagt cggtgcgttt ttttaagctt   1200
gggccgctcg aggtacctct ctacatatga catgtgagca aaaggccagc aaaaggccag   1260
gaaccgtaaa aaggccgcgt tgctggcgtt tttccatagg ctccgccccc ctgacgagca   1320
tcacaaaaat cgacgctcaa gtcagaggtg gcgaaacccg acaggactat aaagatacca   1380
ggcgtttccc cctggaagct ccctcgtgcg ctctcctgtt ccgaccctgc cgcttaccgg   1440
atacctgtcc gcctttctcc cttcgggaag cgtggcgctt tctcatagct cacgctgtag   1500
gtatctcagt tcggtgtagg tcgttcgctc caagctgggc tgtgtgcacg aaccccccgt   1560
tcagcccgac cgctgcgcct tatccggtaa ctatcgtctt gagtccaacc cggtaagaca   1620
cgacttatcg ccactggcag cagccactgg taacaggatt agcagagcga ggtatgtagg   1680
cggtgctaca gagttcttga agtggtggcc taactacggc tacactagaa gaacagtatt   1740
tggtatctgc gctctgctga agccagttac cttcggaaaa agagttggta gctcttgatc   1800
cggcaaacaa accaccgctg gtagcggtgg tttttttgtt tgcaagcagc agattacgcg   1860
cagaaaaaaa ggatctcaag aagatccttt gatcttttct acgggtctg acgctcagtg   1920
gaacgaaaac tcacgttaag ggattttggt catgagatta tcaaaaagga tcttcaccta   1980
gatcctttta aattaaaaat gaagttttaa atcaatctaa agtatatatg agtaaacttg   2040
gtctgacagt taccaatgct taatcagtga ggcacctatc tcagcgatct gtctatttcg   2100
ttcatccata gttgcctgac tccccgtcgt gtagataact acgatacggg agggcttacc   2160
atctggcccc agtgctgcaa tgataccgcg agatccacgc tcaccggctc cagatttatc   2220
agcaataaac cagccagccg gaagggccga gcgcagaagt ggtcctgcaa ctttatccgc   2280
```

| | |
|---|---|
| SEQ ID NO: 387 | moltype = DNA  length = 6386 |
| FEATURE | Location/Qualifiers |
| misc_feature | 1..6386 |
| | note = Description of Artificial Sequence: Synthetic polynucleotide |
| source | 1..6386 |
| | mol_type = other DNA |
| | organism = synthetic construct |

```
SEQUENCE: 387
tgagcgcaac gcaattaatg tgagttagct cactcattag gcaccccagg ctttacactt    60
tatgcttccg gctcgtatgt tgtgtggaat tgtgagcgga taacaatttc acacaggaaa   120
cagctatgac catgaggcgc gccggattcg acattgatta attaatagta     180
atcaattacg gggtcattag ttcatagccc atatatggag ttccgcgtta caaacttac    240
ggtaaatggc ccgcctggct gaccgcccaa cgacccccgc ccattgacgt caataatgac   300
gtatgttccc atagtaacgc caatagggac tttccattga cgtcaatggg tggagtattt   360
acggtaaact gcccacttgg cagtacatca agtgtatcat atgccaagta cgccccctat   420
tgacgtcaat gacggtaaat ggcccgcctg gcattatgcc cagtacatga cctttatggga   480
cttcctact tggcagtaca tctacgtatt agtcatcgct attaccatgg tcgaggtgag   540
ccccacgttc tgcttcactc tccccatctc ccccccctcc ccacccccaa ttttgtattt   600
atttatttt taattatttt gtgcagcgat ggggcgggg ggggggggg ggcgcgcgcc   660
rggsggggsg gggsgggsg rggggsgggg sgggsgagg cggagaggtg cggcggcagc   720
caatcagagc ggcgcgctcc gaaagtttcc ttttatggcg aggcggcggc ggcggcggcc   780
```

```
ctataaaaag cgaagcgcgc ggcgggcggg agtcgctgcg cgctgccttc gcccgtgcc    840
ccgctccgcc gccgcctcgc gccgcccgcc ccggctctga ctgaccgcgt tactcccaca    900
ggtgagcggg cgggacggcc cttctcctcc gggctgtaat tagcgcttgg tttaatgacg    960
gcttgtttct tttctgtggc tgcgtgaaag ccttgagggg ctccgggagg gcccttgtg   1020
cgggggagc ggctcggggg gtgcgtgcgt gtgtgtgtgc gtggggagcg ccgcgtgcgg   1080
ctccgcgctg cccggcggct gtgagcgctg cgggcgcggc gcggggcttt gtgcgctccg   1140
cagtgtgcgc gaggggagcg cggccggggg cggtgccccg cggtgcgggg ggggctgcga   1200
ggggaacaaa ggctgcgtgc ggggtgtgtg cgtgggggg tgagcagggg gtgtgggcgc   1260
gtcggtcggg ctgcaacccc ccctgcaccc ccctccccga gttgctgagc acggcccggc   1320
ttcgggtgcg gggctccgta cggggcgtgg cgcggggctc gccgtgccgg ccgggggtg   1380
gcggcaggtg ggggtgccgg gcggggcggg gccgcctcgg gccggggagg gctcggggga   1440
ggggcgcggc ggccccggga gcgccggcgg ctgtcgaggc gcggcgagcc gcagccattg   1500
cctttatgg taatcgtgcg agagggcgca gggacttcct ttgtcccaaa tctgtgcgga   1560
gccgaaatct gggaggcgcc gccgcacccc ctctagcggg cgcggggcga agcggtgcgg   1620
cgccggcagg aaggaaatgg gcggggaggg ccttcgtgcg tcgccgcgcc gccgtcccct   1680
tctccctctc cagcctcggg gctgtccgcg gggggacggc tgccttcggg ggggacgggg   1740
cagggcgggg ttcggcttct ggcgtgtgac cggcggctct agagcctctg ctaaccatgt   1800
tcatgccttc ttctttttcc tacagatcct taattaataa tacgactcac tatagggggt   1860
cgacccgcca ccatgccaaa aaagaaaaga aaagtgtatc cctatgatgt ccccgattat   1920
gccggttcaa gagcccctgg cgtgattaga ctgagccgag tgacagacgc caccacaagt   1980
cccgagagac agctggaatc atgccagcag ctctgtgctc agcggggttg ggatgtggtc   2040
ggcgtggcag aggatctgga ctgagcggg gccgtcgatc cattcgacag aaagaggagg   2100
cccaacctgg caagatggct cgcttttcgag aacagccct ttgatgtgat cgtcgcctac   2160
agagtggacc ggctgacccg ctcaattcga catctccagc agctggtgca ttgggctgag   2220
gaccacaaga aactggtggt cagcgcaaca gaagcccact tcgatactac cacacctttt   2280
gccgctgtgg tcatcgcact gatgggcact gtggccgaca gtggctcga agctatcaag   2340
gagcgaaaca ggagcgcagc ccatttcaat attagggccg gtaaatacag aggctccctg   2400
ccccccttggg gatatctccc taccagggtg gatggggagt ggagactggt gccagacccc   2460
gtccagagag agcggattct ggaagtgtac cacagagtgg tcgataacca cgaaccactc   2520
catctggtgg cacacgacct gaatagacgc ggcgtgctct ctccaaagga ttattttgct   2580
cagctgcagg gaagagagcc acagggaaga gaatggagtg ctactgcact gaagagatct   2640
atgatcagtg aggctatgct gggttacgca acactcaatg gcaaaactgt ccgggacgat   2700
gacggagccc ctctggtgag ggctgagcct attctcacca gagagcagct cgaagctctg   2760
cgggcagaac tggtcaagac tagtcgcgcc aaacctgccg tgacaccccc aagcctgtc   2820
ctgagggtgc tgttctgcgc cgtctgtgga gagccagcat acaagtttgc cggcggaggg   2880
cgcaaacatc cccgctatcg atgcaggagc atggggttcc ctaagcactg tggaaacggg   2940
acagtggcca tggctgagtg ggacgccttt tgcgaggaac aggtgctgga tcctctgggt   3000
gacgctgagc ggctggaaaa agtgtgggtg gcaggatctg actccgctgt ggagctggca   3060
gaagtcaatg ccgagctcgt ggatctgact tccctcatcg aatcttcctgc atatagagct   3120
gggtccccac agagagaagc tctgacgca cgaattgctg cactcgctgc tagacaggag   3180
gaactcccag ggcctggagc caggccctcct ggatggggagt ggcagagaaa cggacagagg   3240
tttgggggatt ggtggaggga gcaggacacc gcagccaaga acacatggct gagatccatg   3300
aatgtccggc tcacattcga cgtgcgcggt ggcctgactc gaaccatcga tttttggcgac   3360
ctgcaggagt atgaacagca cctgagactg gggtccgtgg tcgaaagact gcacactggg   3420
atgtcctagg tcagagctcg ctgatcagcc tcgactgtgc cttctagttg ccagccatct   3480
gttgtttgcc cctcccccgt gccttccttg acccctgaag gtgccactcc cactgtcctt   3540
tcctaataaa atgaggaaat tgcatcgcat tgtctgagta ggtgtcattc tattctgggg   3600
ggtgggtgg ggcaggacag caaggggag gattgggaag acaatagcag gcatgctggg   3660
gatgcggtgg gctctatggc ttctgaggcg gaaagaacca gctggggctc gagatccact   3720
agttctagcc tcgaggctag agcggccgcc actggccgtc gttttacaac gtcgtgactg   3780
ggaaaaccct ggcgttaccc aacttaatcg ccttgcagca catccccctt tcgccagctg   3840
gcgtaatage gaagaggccc gcaccgatcg cccttcccaa cagttgcgca gcctgaatgg   3900
cgaatgggac gcgccctgta gcggcgcatt aagcgcggcg ggtgtggtgg ttacgcgcag   3960
cgtgaccgct acacttgcca gcgccctagc gcccgctcct ttcgctttct tcccttcctt   4020
tctccgccacg ttcgccggct ttccccgtca agctctaaat cggggggctcc ctttagggtt   4080
ccgatttagt gctttacggc acctcgaccc caaaaaactt gattagggtg atggttcacg   4140
tagtgggcca tcgccctgat agacggtttt tcgccctttg acgttggagt ccacgttctt   4200
taatagtgga ctcttgttcc aaactggaac aacactcaac cctatctcgg tctattcttt   4260
tgatttataa gggattttgc cgatttcggc ctattggtta aaaaatgagc tgatttaaca   4320
aaaatttaac gcgaattttta acaaaatatt aacgcttacr mktymsrtks smcwttymgg   4380
sgaaatgtgc gcggaacccc tatttgttta ttttcctaaa tacattcaaa tatgtatccg   4440
ctcatgagac aataaccctg ataaatgctt caataatatt gaaaaggaa gagtatgagt   4500
attcaacatt tccgtgtcgc ccttattccc ttttttgcgg catttgcct tcctgttttt   4560
gctcacccag aaacgctggt gaaagtaaaa gatgctgaag atcagttggg tgcacgagtg   4620
ggttacatcg aactggatct caacagcggt aagatccttg agagttttcg ccccgaagaa   4680
cgttttccaa tgatgagcac ttttaaagtt ctgctatgtg gcgcggtatt atcccgtatt   4740
gacgccggc aagagcaact cggtcgccgc atacactatt ctcagaatga cttggttgag   4800
tactcaccag tcacagaaaa gcatcttacg gatggcatga cagtaagaga attatgcagt   4860
gctgccataa ccatgagtga taacactgcg gccaacttac ttctgacaac gatcggagga   4920
ccgaaggagc taaccgcttt tttgcacaac atgggggatc atgtaactcg ccttgatcgt   4980
tgggaaccgg agctgaatga agccatacca aacgacgagc gtgacaccac gatgcctgta   5040
gcaatggcaa caacgttgcg caaactatta actggcgaac tacttactct agcttcccgg   5100
caacaattaa tagactggat ggaggcggat aaagttgcag gaccacttct gcgctcggcc   5160
cttccggctg gctggtttat tgctgataaa tctggagccg gtgagcgtgg gtctcgcggt   5220
atcattgcag cactgggcc agatggtaag ccctcccgta tcgtagttat ctacacgacg   5280
gggagtcagg caactatgga tgaacgaaat agacagatcg ctgagatagg tgcctcactg   5340
attaagcatt ggtaactgtc agaccaagtt tactcatata tactttagat tgatttaaaa   5400
cttcattttt aatttaaaag gatctaggtg aagatccttt ttgataatct catgaccaaa   5460
atcccttaac gtgagttttc gttccactga gcgtcagacc ccgtagaaaa gatcaaagga   5520
```

```
tcttcttgag atcctttttt tctgcgcgta atctgctgct tgcaaacaaa aaaaccaccg   5580
ctaccagcgg tggtttgttt gccggatcaa gagctaccaa ctcttttcc gaaggtaact    5640
ggcttcagca gagcgcagat accaaatact gttcttctag tgtagccgta gttaggccac   5700
cacttcaaga actctgtagc accgcctaca tacctcgctc tgctaatcct gttaccagtg   5760
gctgctgcca gtggcgataa gtcgtgtctt accgggttgg actcaagacg atagttaccg   5820
gataaggcgc agcggtcggg ctgaacgggg ggttcgtgca cacagcccag cttggagcga   5880
acgacctaca ccgaactgag atacctacag cgtgagctat gagaaagcgc cacgcttccc   5940
gaagggagaa aggcggacag gtatccgta  agcggcaggg tcggaacagg agagcgcacg   6000
agggagcttc caggggaaa  cgcctggtat ctttatagtc ctgtcgggtt tcgccacctc   6060
tgacttgagc gtcgattttt gtgatgctcg tcagggggg  ggagcctatg gaaaaacgcc   6120
agcaacgcgg ccttttacg  gttcctggcc ttttgctggc cttttgctca catgttcttt   6180
cctgcgttat ccctgattc  tgtggataac cgtattaccg cctttgagtg agctgatacc   6240
gctcgccgca gccgaacgac cgagcgcagc gagtcagtga gcgaggaagc ggaagagcgc   6300
ccaatacgca aaccgcctct ccccgcgcgt tggccgattc attaatgcag ctggcacgac   6360
aggtttcccg actggaaagc gggcag                                        6386

SEQ ID NO: 388       moltype = DNA  length = 6317
FEATURE              Location/Qualifiers
misc_feature         1..6317
                     note = Description of Artificial Sequence: Synthetic
                     polynucleotide
source               1..6317
                     mol_type = other DNA
                     organism = synthetic construct
SEQUENCE: 388
gattcgacat tgattattga ctagttatta atagtaatca attacggggt cattagttca   60
tagcccatat atggagttcc gcgttacata acttacggta aatggcccgc ctggctgacc   120
gcccaacgac ccccgcccat tgacgtcaat aatgacgtat gttcccatag taacgccaat   180
agggactttc cattgacgtc aatgggtgga gtatttacgg taaactgccc acttggcagt   240
acatcaagtg tatcatatgc caagtacgcc ccctattgac gtcaatgacg gtaaatggcc   300
cgcctggcat tatgcccagt acatgacctt atgggacttt cctacttggc agtacatcta   360
cgtattagtc atcgctatta ccatggtcga ggtgagcccc acgttctgct tcactctccc   420
catctccccc cctccccac  ccccaatttt gtatttattt atttttaat  tattttgtgc   480
agcgatgggg gcgggggggg gggggggcg  cgcgccrggs ggggsgggs  ggggsgrggg   540
gsggggsggg gsgaggcgga gaggtgcggc ggcagccaat cagagcgggc cgctccgaaa   600
gtttccttt  atggcgaggc ggcggcggcg gcggcccat  aaaaagcgaa gcgcgcggcg   660
ggcgggagtc gctgcgcgct gccttcgccc cgtcccgc  tccgccgccg cctcgcgccg   720
cccgcccgg  ctctgactga ccgcgttact cccacaggtg agcgggcggg acggcccttc   780
tcctccgcc  tgtaattagc gcttggttta atgacggctt gtttcttttc tgtgctgcg   840
tgaaagcctt gaggggctcc gggagggccc tttgtgcggg gggagcggct cgggggggtgc   900
gtgcgtgtgt gtgtgcgtgg ggagcgccgc gtgcggctcc gcgctgcccg gcggctgtga   960
gcgctgcggg cgcggcgcgg ggctttgtgc gctccgcagt gtgcgcgagg ggagcgcggc   1020
cggggggggt gccccgcggt gcggggggg  ctgcgagggg aacaaaggct gcgtgcgggg   1080
tgtgtgcgtg gggggggtgag cagggggtgt gggcgcgtcg gtcgggctgc aacccccct   1140
gcaccccct  ccccgagttg ctgagcacgg cccggcttcg ggtgcgggc  tccgtacggg   1200
gcgtggcgcg ggctcgccg  tgccgggcgg ggggtggcgg caggtggggg tgccgggcgg   1260
ggcggggccg cctcgggccg gggagggctc gggggagggg cgcggcgccg cccggagccg   1320
cggcggctgt cgaggcgcgg cgagccgcag ccattgcctt ttatggtaat cgtgcgagag   1380
ggcgcaggga cttcctttgt cccaaatctg tgccgagccg aaatctggga ggcgccgccg   1440
cacccccctc agcgggcgcg gggcgaagcg gtgcggcgcc ggcaggaagg aaatgggcgg   1500
ggagggcctt cgtgcgtcgc cgcgccgccg tcccctttc  cctctccagc ctcgggggct   1560
tccgcggggg gacggctgcc ttcggggggg acggggcagg gcggggttcg gcttctggcg   1620
tgtgaccggc ggctctagag cctctgctaa ccatgttcat gccttcttct ttttcctaca   1680
gatccttaat taataatacg actcactata ggggtcgac  ccgccaccat gacagcgcca   1740
aagaaaaaga ggaaggtcat gaccaagaaa gtggccatct atactagagt gagcacaacg   1800
aatcaggccg aggaggggtt ctctattgac gagcaaatcg atcgtctgac caagtacgcg   1860
gaagcaatgg gctggcaagt cagcgacact tacaccgatg ctgggttctc cggcgccaaa   1920
ctggaaaggc ctgccatgca gcggctgatt acgacattg  agaacaaggc ctttgataca   1980
gtgctcgtat acaagctcga caggctccagc cgatctgtgc gggacacgct ttacctcgta   2040
aaggatgttt tcactaagaa taaaatcgac ttcattagtc tgaacgaatc cattgacacc   2100
agctcagcta tgggctctct gttcctgacc atcctgagcg ctatcaatga gtttgagagg   2160
gagaatataa aggagcgcat gacaatggga aagctgggta gagcgaagtc cgggaaatct   2220
atgatgtgga ccaagaccgc ttttggatac taccacaata ggaagacggg cattctggag   2280
atcgtgccct tgcaggcaac catcgttgag cagatcttca ccgactacct gagcggaata   2340
tctctcacga agttgcgaga taagctgaat gagagcggac acattggcaa ggatattcct   2400
tggtcatata gaaccctccg ccaaactctg gataatccgg tgtactgcgg ttacatcaag   2460
ttcaaagaca gcctcttcga gggaatgcat aaacctatca ttccatacga gacatacctg   2520
aaagtccaaa aggaactcga agagcgccag caacagactt acgaacggaa taataatccc   2580
aggcctttcc aggccaaata tgctgtgcc  gcatggcaa  gatgcggata ctgcgggcga   2640
ccactcaaga ttgtgcttgg ccataaacgg aaggatggaa gcagaaccat gaaatatcac   2700
tgcgcaaacc gctttccaag gaaaacgaag gggattaccg tgtacaatga caacaaaaaa   2760
tgtgatagcg gaacctacga tctgtccaac ttggaaaaca ccgtcattga catttaatt   2820
ggatttcagg aaaataatga cagccttctg aagattatca cgggaacaa  tcagccgatt   2880
ctggacactt catctttcaa aaaacagatc tctcagattg ataagaaaat tcagaaaaat   2940
tccgattta  acctcaatga tttcataacg atggatgagc tgaaggaccg gaccgacagt   3000
ttgcaggccg agaagaaact gctgaaagca aagatctccg agaacaagtt caatgacagt   3060
accgatgtct tcgagttggt gaagaccag  ctgggtagta tcccaatcaa cgagttgagc   3120
tatgacaata agaagaagat tgttaataac ctggtgagca agtggacgt  gaccgctgat   3180
aacgtggata ttatcttcaa gttccagctg gcctgagtca gagctcgctg atcagcctcg   3240
```

```
actgtgcctt ctagttgcca gccatctgtt gtttgcccct cccccgtgcc ttccttgacc    3300
ctggaaggtg ccactcccac tgtcctttcc taataaaatg aggaaattgc atcgcattgt    3360
ctgagtaggt gtcattctat tctgggggt ggggtggggc aggacagcaa ggggggaggat    3420
tgggaagaca atagcaggca tgctggggat gcggtgggct ctatggcttc tgaggcggaa    3480
agaaccagct ggggctcgag atccactagt tctagcctga aggctagagc ggccgccact    3540
ggccgtcgtt ttacaacgtc gtgactggga aaaccctggc gttacccaac ttaatcgcct    3600
tgcagcacat ccccctttcg ccagctggcg taatagcgaa gaggcccgca ccgatcgccc    3660
ttcccaacag ttgcgcagcc tgaatggcga atgggacgcg ccctgtagcg cgcattaag    3720
cgcggcgggt gtggtggtta cgcgcagcgt gaccgctaca cttgccagcg ccctagcgcc    3780
cgctcctttc gctttcttcc cttcctttct cgccacgttc gccggctttc cccgtcaagc    3840
tctaaatcgg gggctccctt tagggttccg atttagtgct ttacggcacc tcgaccccaa    3900
aaaacttgat tagggtgatg gttcacgtag tgggccatcg ccctgataga cggttttcg    3960
cccttttgacg ttggagtcca cgttctttaa tagtggactc ttgttccaaa ctggaacaac    4020
actcaaccct atctcggtct attctttga tttataaggg attttgccga tttcggccta    4080
ttggttaaaa aatgagctga tttaacaaaa atttaacgcg aattttaaca aaatattaac    4140
gcttacrmkt ymsrtkssmc wttymggsga aatgtgcgcg gaaccccat ttgtttattt    4200
ttctaaatac attcaaatat gtatccgctc atgagacaat aaccctgata aatgcttcaa    4260
taatattgaa aaaggaagag tatgagtatt caacatttcc gtgtcgccct tattccctt    4320
tttgcggcat tttgccttcc tgttttgct cacccagaaa cgctggtgaa agtaaaagat    4380
gctgaagatc agttgggtgc acgagtggg tacatcgaac tggatctcaa cagcggtaag    4440
atccttgaga gttttcgccc cgaagaacgt tttccaatga tgagcacttt taagttctg    4500
ctatgtggcg cggtattatc ccgtattgac gccgggcaag agcaactcgg tcgccgcata    4560
cactattctc agaatgactt ggttgagtac tcaccagtca cagaaaagca tcttacggat    4620
ggcatgacag taagagaatt atgcagtgct gccataacca tgagtgataa cactgcggcc    4680
aacttacttc tgacaacgat cggaggaccg aaggagctaa ccgcttttt gcacaacatg    4740
ggggatcatg taactcgcct tgatcgttgg gaaccggagc tgaatgaagc cataccaaac    4800
gacgagcgtg acaccacgat gcctgtagca atggcaacaa cgttgcgcaa actattaact    4860
ggcgaactac ttactctagc ttcccggcaa caattaatag actggatgga ggcggataaa    4920
gttgcaggac cacttctgcg ctcggccctt ccggctggct ggtttattgc tgataaatct    4980
ggagccggtg agcgtgggtc tcgcggtatc attgcagcac tggggccaga tggtaagcc    5040
tcccgtatcg tagttatcta cacgacgggg agtcaggcaa ctatggatga acgaaataga    5100
cagatcgctg agataggtgc ctcactgatt aagcattggt aactgtcaga ccaagtttac    5160
tcatatatac tttagattga tttaaaactt cattttaat ttaaaggat ctaggtgaag    5220
atccttttg ataatctcat gaccaaaatc ccttaacgtg agttttcgtt ccactgagcg    5280
tcagaccccg tagaaaagat caaaggatct tcttgagatc cttttttct gcgcgtaatc    5340
tgctgcttgc aaacaaaaaa accaccgcta ccagcggtgg tttgtttgcc ggatcaagag    5400
ctaccaactc ttttttccgaa ggtaactggc ttcagcagag cgcagatacc aaatactgtt    5460
cttctagtgt agccgtagtt aggccaccac ttcaagaact ctgtagcacc gcctacatac    5520
ctcgctctgc taatcctgtt accagtggct gctgccagtg gcgataagtc gtgtcttacc    5580
gggttggact caagacgata gttaccggat aaggcgcagc ggtcgggctg aacggggggt    5640
tcgtgcacac agcccagctt ggagcgaacg acctacaccg aactgagata cctacagcgt    5700
gagctatgag aaagcgccac gcttcccgaa gggagaaagg cggacaggta tccggtaagc    5760
ggcagggtcg gaacaggaga gcgcacgagg gagcttccag ggggaaacgc ctggtatctt    5820
tatagtcctg tcgggtttcg ccacctctga cttgagcgtc gatttttgtg atgctcgtca    5880
gggggggcgga gcctatgaa aaacgccagc aacgcggcct ttttacggtt cctggccttt    5940
tgctggcctt ttgctcacat gttctttcct gcgttatccc ctgattctgt ggataaccgt    6000
attaccgcct ttgagtgagc tgataccgct cgccgcagcc gaacgaccga gcgcagcgag    6060
tcagtgagcg aggaagcgga agagcgccca atacgcaaac cgcctctccc cgcgcgttgg    6120
ccgattcatt aatgcagctg gcacgacagg tttcccgact ggaaagcggg cagtgagcgc    6180
aacgcaatta atgtgagtta gctcactcat taggcacccc aggctttaca ctttatgctt    6240
ccggctcgta tgttgtgtgg aattgtgagc ggataacaat ttcacacagg aaacagctat    6300
gaccatgagg cgcgccg                                                  6317
```

```
SEQ ID NO: 389          moltype = DNA   length = 6638
FEATURE                 Location/Qualifiers
misc_feature            1..6638
                        note = Description of Artificial Sequence: Synthetic
                        polynucleotide
source                  1..6638
                        mol_type = other DNA
                        organism = synthetic construct
SEQUENCE: 389
gattcgacat tgattattga ctagttatta atagtaatca attacgggt cattagttca    60
tagcccatat atggagttcc gcgttacata acttacggta aatggcccgc ctggctgacc    120
gcccaacgac ccccgcccat tgacgtcaat aatgacgtat gttcccatag taacgccaat    180
agggactttc cattgacgtc aatgggtgga gtatttacgg taaactgccc acttggcagt    240
acatcaagtg tatcatatgc caagtacgcc ccctattgac gtcaatgacg gtaaatggcc    300
cgcctggcat tatgcccagt acatgacctt atgggacttt cctacttggc agtacatcta    360
cgtattagtc atcgctatta ccatggtcga ggtgagccc acgttctgct tcactctccc    420
catctccccc ccctccccac ccccaatttt gtatttattt attttttaat tattttgtgc    480
agcgatgggg gcgggggggg gggggggcg cgcgccrggs ggggsgggs ggggsgrggg    540
gsggggsggg gsgaggcgga gaggtgcggc ggcagccaat cagagcggcg cgctccgaaa    600
gtttcctttt atgcgaggc ggcggcgcg gcggccctat aaaagcgaa gcgcgcggcg    660
ggcgggagtc gctgcgcgct gccttcgccc cgtgccccgc tccgccgccg cctccgcgcg    720
cccgccccgc ctctgactga ccgcgttact cccacaggtg agcgggcggg acggcccttc    780
tcctccggc tgtaattagc gcttggttta atgacggctt gtttcttttc tgtggctgcg    840
tgaaagcctt gaggggctcc gggagggccc tttgtgcggg ggagcggct cgggggtgc    900
gtgcgtgtgt gtgtgcgtgg ggagcgccgc gtgcggctcc gcgctgcccg gcggctgtga    960
gcgctgcggg cgcggcgcgg ggctttgtgc gctccgcagt gtgcgcgagg ggagcgcggc    1020
```

```
cgggggcggt gccccgcggt gcggggcggg ctgcgagggg aacaaaggct gcgtgcgggg      1080
tgtgtgcgtg gggggtgag caggggtgt gggcgcgtcg gtcgggctgc aaccccccct       1140
gcacccccct ccccgagttg ctgagcacgg cccggcttcg ggtgcgggc tccgtacggg      1200
gcgtggcgcg gggctcgccg tgccgggcgg ggggtggcgg caggtggggg tgccgggcgg     1260
ggcggggccg cctcggggcg ggagggctc gggggaggg cgcggccggcc cccggagccg     1320
cggcggctgt cgaggcgcgg cgagccgcag ccattgcctt ttatggtaat cgtgcgagag    1380
ggcgcaggga cttcctttgt cccaaatctg tgcggagccg aaatctggga ggcgccgccg   1440
cacccctct agcgggcgcg gggcgaagcg gtgcggcgcc ggcaggaagg aaatgggcgg     1500
ggagggcctt cgtgcgtcgc cgcgccgccg tccccttctc cctctccagc ctcggggctg    1560
tccgcggggg gacggctgcc ttcggggggg acggggcagg gcggggttcg gcttctggcg   1620
tgtgaccggc ggctctagag cctctgctaa ccatgttcat gccttcttct ttttcctaca   1680
gatccttaat taataatacg actcactata ggggtcgac ccgccaccat gcccaagaag     1740
aaacggaaag tgatgagccc ctttatcgcc ccggacgtgc ccgagcacct cctgacact     1800
gtgcgcgtct ttctgtacgc ccgtcagagt aaaggacggt cagatggatc tgacgtgcc    1860
accgaagcac agctcgctgc cggacgggcc cttgttgcct caagaaacgc acaaggggga    1920
gctagatggg tggtggcggg cgaattcgtg gatgtgggca gatcagggtg ggacccgaat   1980
gtgacacgcg ccgacttcga aagaatgatg ggcgaggtgc gcgccggtga gggagacgta  2040
gtggtggtta atgaactgag tcgccttacg aggaagggcg cccacgaggc tctggagatc   2100
gataacgaac tcaaaaaaca cggtgtgcgc ttcatgagcg tgctggaacc attcctggat 2160
accagcaccc caatcggtgt cgcgatcttt gccctgattg ccgcgctcgc taaacaggat    2220
tcagacctta aagctgagcg gctgaagggg gctaaagatg agatcgctgc cttgggggt    2280
gtgcacagct catctgcgcc attcggcatg agggcggtca gaaagaaagt ggataacctg   2340
gtcatatctg ttctggagcc tgatgaggac aaccccggacc acgttgagct tgtgaacgg   2400
atggctaaga tgtctttcga aggcgtcagc gataacgcaa ttgccacaac atttgagaag  2460
gagaaaatcc cctctccggg gatggctgag agacgagcca cggagaagag gcttgcttct    2520
attaaggcac ggaggctcaa tggccgccgaa aagccgatca tgtggcggcc gcagacagtt    2580
agatggattc ttaaccatcc cgcgattggt ggattcgcat tcgagcgggt gaaacacgga    2640
aaagcccaca tcaacgtgat acgaagagat cccggcggca aaccccttac ccctcacact   2700
ggtatcctgt ctggatccaa gtggttgaaa ctccaggaga agaagcgg gaaaaatctc    2760
tccgaccgca aaccaggtgc cgaagtggaa cctacgctgc tttccgggtg gagattctg   2820
ggatgtcgga tatgcggtgg gtcaatgggc cagtcccaag ggggccgtaa gaggaatgga 2880
gacttggctg agggcaatta catgtgtgca aacccaaagg ggcacggcgg tctgagcgtc  2940
aagaggtctg agcttgatga attcgtggca tcaaaagtct gggccaggtt gcgcacggct  3000
gacatggagg atgaacatga ccaagcatgg attgcagctg cagctgaacg gtttgcttg    3060
cagcacgacc tggcggggt agctgacgag cgacggaagg aacaagctca cctggataac    3120
gttcggagat caataaaaga tctccaggcg gataggaagg caggtctcta cgtgggacgc    3180
gaagaactgg agacctggcg cagtaccgtc ctgcaatata ggagctacga ggctgagtgt    3240
actactaggt tggctgagct ggatgaaaaa atgaatggat ccaccccggt gccttcagaa   3300
tggtttagcg gcgaggaccc aaccgcggaa ggaggcatat ggcgagctg ggatgtctat    3360
gagcgccggg agtttctcag ctttttttg gactccgtaa tggttgacag ggcagacat   3420
cctgaaacca agaatatat accattgaaa gaccgggtga ccttaaagtg gcggagctg    3480
ttaaaggaag aggatgaagc aagcgaggcc acagaacggg agctggcagc tctttaggtc    3540
agagctcgct gatcagcctc gactgtgcct tctagttgcc agccatctgt tgtttgcccc    3600
tcccccgtgc cttccttgac cctggaaggt gccactccca ctgtcctttc ctaataaaat    3660
gaggaaattg catcgcattg tctgagtagg tgtcattcta ttctgggggg tggggtggg   3720
caggacagca agggggagga ttgggaagac aatagcaggc atgctgggga tgcggtgggc    3780
tctatgcctt ctgaggcgaa aagaaccgac tggggctcga gatccactag ttctagcctc    3840
gaggctagag cggccgccac tggccgtcgt tttacaacgt cgtgactggg aaaaccctgg    3900
cgttacccaa cttaatcgcc ttgcagcaca tccccctttc gccagctggc gtaatagcga    3960
agaggcccgc accgatcgcc cttcccaaca gttgcgcagc ctgaatgcg aatgggacg     4020
gccctgtagc ggcgcattaa gcgcggcggg tgtggtggtt acgcgcagcg tgaccgctac    4080
acttgccagc gccctagcgc ccgctccttt cgctttcttc ccttcctttc tcgccacgtt   4140
cgccggcttt cccgtcaag ctctaaatcg ggggctccct ttagggttcc gatttagtgc   4200
tttacgcgac ctcgacccca aaaaacttga ttagggtgat ggttcacgta gtgggccatc   4260
gccctgatag acggttttc gccctttgac gttggagtcc acgttcttta atagtggact    4320
cttgttccaa actggaacaa cactcaaccc tatctcggtc tattcttttg atttataagg    4380
gattttgccg atttcggcct attggttaaa aatgagctg atttaacaaa atttaacgc     4440
gaattttaac aaaatattaa cgcttacrmk tymsrtkssm cwttymggsg aaatgtgcgc    4500
ggaacccccta tttgtttatt tttctaaata cattcaaata tgtatccgct catgagacaa    4560
taaccctgat aaatgcttca ataatattga aaaaggaaga gtatgagtat tcaacatttc    4620
cgtgtcgccc ttattccctt ttttgcggca ttttgccttc ctgttttgc tcacccagaa     4680
acgctggtga agtaaaaga tgctgaagat cagttgggtg cacgagtggg ttacatcgaa    4740
ctggatctca acagcggtaa gatccttgag agttttcgcc ccgaagaacg ttttccaatg    4800
atgagcactt ttaaagttct gctatgtggc gcggtattat cccgtattga cgccgggcaa    4860
gagcaactcg gtcgccgcat acactattct cagaatgact tggttgagta ctcaccagtc   4920
acagaaaagc atcttacgga tggcatgaca gtaagagaat tatgcagtgc tgccataacc    4980
atgagtgata acactgcggc caacttactt ctgacaacga tcgaggacc gaaggagcta   5040
accgcttttt tgcacaacat ggggggatcat gtaactcgcc ttgatcgttg ggaaccggag   5100
ctgaatgaag ccataccaaa tgacgagcgt gacaccacga tgcctgtagc aatggcaaca    5160
acgttgcgca aactattaac tggcgaacta cttactctag cttcccggca acaattaata    5220
gactggatgg aggcggataa agttgcagga ccacttctgc gctcggccct tccggctggc    5280
tggtttattg ctgataaatc tggagccggt gagcgtggt ctcgcggtat cattgcagca    5340
ctggggccag atggtaagcc ctcccgtatc gtagttatct acacgacggg gagtcaggca    5400
actatggatg aacgaaatag acagatcgct gagataggtg cctcactgat taagcattgg    5460
taactgtcag accaagttta ctcatatata ctttagattg atttaaaact tcatttttaa    5520
tttaaaagga tctaggtgaa gatccttttt gataatctca tgaccaaaat cccttaacgt    5580
gagttttcgt tccactgagc gtcagacccc gtagaaaaga tcaaaggatc ttcttgagat    5640
ccttttttc tgcgcgtaat ctgctgcttg caaacaaaaa aaccaccgct accagcggtg    5700
gtttgtttgc cggatcaaga gctaccaact cttttttccga aggtaactgg cttcagcaga    5760
```

```
gcgcagatac caaatactgt tcttctagtg tagccgtagt taggccacca cttcaagaac    5820
tctgtagcac cgcctacata cctcgctctg ctaatcctgt taccagtggc tgctgccagt    5880
ggcgataagt cgtgtcttac cgggttggac tcaagacgat agttaccgga taaggcgcag    5940
cggtcgggct gaacgggggg ttcgtgcaca cagcccagct tggagcgaac gacctacacc    6000
gaactgagat acctacagcg tgagctatga gaaagcgcca cgcttcccga agggagaaag    6060
gcggacaggt atccggtaag cggcagggtc ggaacaggag agcgcacgag ggagcttcca    6120
gggggaaacg cctggtatct ttatagtcct gtcgggtttc gccacctctg acttgagcgt    6180
cgattttgt gatgctcgtc aggggggcgg agcctatgga aaaacgccag caacgcggcc    6240
tttttacggt tcctggcctt ttgctggcct tttgctcaca tgttctttcc tgcgttatcc    6300
cctgattctg tggataaccg tattaccgcc tttgagtgag ctgataccgc tcgccgcagc    6360
cgaacgaccg agcgcagcga gtcagtgagc gaggaagcgg aagagcgccc aatacgcaaa    6420
ccgcctctcc ccgcgcgttg gccgattcat taatgcagct ggcacgacag gtttcccgac    6480
tggaaagcgg gcagtgagcg caacgcaatt aatgtgagt agctcactca ttaggcaccc    6540
caggctttac actttatgct tccggctcgt atgttgtgtg gaattgtgag cggataacaa    6600
tttcacacag gaaacagcta tgaccatgag gcgcgccg                            6638

SEQ ID NO: 390         moltype = DNA  length = 9530
FEATURE                Location/Qualifiers
misc_feature           1..9530
                       note = Description of Artificial Sequence: Synthetic
                       polynucleotide
source                 1..9530
                       mol_type = other DNA
                       organism = synthetic construct
SEQUENCE: 390
taatcagcat catgatgtgg taccacatca tgatgctgat tataagaatg cggccgccac      60
actctagtgg atctcgagtt aataattcag aagaactcgt caagaaggcg atagaaggcg     120
atgcgctgcg aatcgggagc ggcgataccg taaagcacga ggaagcggtc agcccattcg     180
ccgccaagct cttcagcaat atcacgggta gccaacgcta tgtcctgata gcggtccgcc     240
acacccagcc ggccacagtc gatgaatcca gaaaagcggc catttccac catgatattc      300
ggcaagcagg catcgccatg ggtcacgacg agatcctcgc cgtcgggcat gctcgccttg     360
agcctggcga acagttcggc tggcgcgagc ccctgatgct cttcgtccag atcatcctga     420
tcgacaagac cggcttccat ccgagtacgt gctcgctcga tgcgatgttt cgcttggtgg     480
tcgaatgggc aggtagccgg atcaagcgta tgcagccgcc gcattgcatc agccatgatg     540
gatactttct cggcaggagc aaggtgtaga tgacatggag atcctgcccc ggcacttcgc     600
ccaatagcag ccagtccctt cccgcttcag tgacaacgtc gagcacagct gcgcaaggaa     660
cgcccgtcgt ggccagccac gatagccgcg ctgcctcgtc ttgcagttca ttcagggcac     720
cggacaggtc ggtcttgaca aaaagaaccg ggcgccctg cgctgacagc cggaacacgg     780
cggcatcaga gcagccgatt gtctgttgtg cccagtcata gccgaatagc ctctccaacc     840
aagcggccgg agaacctgcg tgcaatccat cttgttcaat catgcgaaac gatcctcatc     900
ctgtctcttg atcagagctt gatccctgc gccatcagat ccttggcggc gagaaagcca     960
tccagtttac tttgcagggc ttcccaacct taccagaggg cgccccagct ggcaattccg    1020
gttcgcttgc tgtccataaa accgcccagt ctagctatcg ccatgtaagc ccactgcaag    1080
ctacctgctt tctctttgcg cttgcgtttt cccttgtcca gatagcccag tagctgacat    1140
tcatccgggg tcagcaccgt ttctgcggac tggctttcta cgtgctcgag gggggccaaa    1200
cggtctccag cttggctgtt ttggcggatg agagaagatt tcagcctgga tacagattaa    1260
atcagaacgc agaagcggtc tgataaaaca gaatttgcct ggcggcagta gcgcggtggt    1320
cccacctgac cccatgccga actcagaagt gaaacgccgt agcgccgatg gtagtgtggg    1380
gtctccccat gcgagagtag ggaactgcca ggcatcaaat aaaacgaaag gctcagtcga    1440
aagactgggc ctttcgtttt atctgttgtt tgtcggtgaa cgctctcctg agtaggacaa    1500
atccgccggg agcggatttg aacgttgcga gcaacggcc cggagggtgg cgggcaggac    1560
gcccgccata aactgccagg catcaaatta gcagaaggc catcctgacg gatggccttt    1620
ttgcgtttct acaaactctt tgtttatttt ttctaaatac attcaaatat gtatccgctc    1680
atgaccaaaa tcccttaacg tgagttttcg ttccactgag cgtcagaccc cgtagaaaag    1740
atcaaaggat cttcttgaga tcctttttt ctgcgcgtaa tctgctgctt gcaaacaaaa    1800
aaaccaccgc taccagcggt ggtttgtttg ccggatcaag agctaccaac tcttttccg    1860
aagtaactg gcttcagcag agcgcagata ccaaatactg tccttctagt gtagccgtag    1920
ttaggccacc acttcaagaa ctctgtagca ccgcctacat acctcgctct gctaatcctg    1980
ttaccagtgg ctgctgccag tggcgataag tcgtgtctta ccgggttgga ctcaagacga    2040
tagttaccgg ataaggcgca gcggtcgggc tgaacggggg gttcgtgcac acagcccagc    2100
ttggagcgaa cgacctacac cgaactgaga tacctacagc gtgagctatg agaaagcgcc    2160
acgcttcccg aagggagaaa ggcggacagg tatccggtaa gcggcagggt cggaacagga    2220
gagcgcacga gggagcttcc agggggaaac gcctggtatc tttatagtcc tgtcgggttt    2280
cgccacctct gacttgagcg tcgatttttg tgatgctcgt caggggggcg gagcctatgg    2340
aaaaacgcca gcaacgcggc cttttacgg ttcctggcct tttgctggcc ttttgctcac    2400
atgttctttc ctgcgttatc ccctgattct gtggataacc gtattaccgc ctttgagtga    2460
gctgataccg ctcgccgcag ccgaacgacc gagcgcagcg agtcagtgag cgaggaagcg    2520
gaagagcgcc tgatgcggta ttttctcctt acgcatctgt gcggtatttc acaccgcata    2580
tggtgcactc tcagtacaat ctgctctgat gccgcatagt taagccagta tacactccgc    2640
tatcgctacg tgactgggtc atggctgcgc cccgacaccc gccaacaccc gctgacgcgc    2700
cctgacgggg ttgtctgctc ccggcatccg cttacagaca agctgtgacc gtctccggga    2760
gctgcatgtg tcagaggttt tcaccgtcat caccgaaacg cgcgaggcag cagatcaatt    2820
cgcgcgcgaa ggcgaagcgg catgcataat gtgcctgtca atggacgaa gcagggattc    2880
tgcaaaccct atgctactcc gtcaagccgt caattgtctg attcgttacc aattatgaca    2940
acttgacgag tacatcattc acttttttctt cacaaccggc acggaactcg ctcgggctgg    3000
ccccggtgca tttttttaaat acccgcgaga atagagttg atcgtcaaaa ccaacattgc    3060
gaccgacggt ggcgataggc atccgggtgg tgctcaaaag cagcttcgcc tggctgatac    3120
gttggtcctc gcgccagctt aagacgctaa tccctaactg ctggcggaaa agatgtgaca    3180
gacgcgacgg cgacaagcaa acatgctgtg cgacgctggc gatacattac cctgttatcc    3240
```

```
ctagatgaca ttaccctgtt atcccagatg acattaccct gttatcccta gatgacatta    3300
ccctgttatc cctagatgac atttaccctg ttatccctag atgacattac cctgttatcc    3360
cagatgacat taccctgtta tcccagatca cattaccctg ttatcccaga tgacataccc    3420
tgttatccct agatgacatt accctgttat cccagatgac attaccctgt tatccctaga    3480
tacattaccc tgttatccca gatgacatac cctgttatcc ctagatgaca ttaccctgtt    3540
atcccagatg acattaccct gttatcccta gatacattac cctgttatcc cagatgacat    3600
accctgttat ccctagatga cattaccctg ttatcccaga tgacattacc ctgttatccc    3660
tagatacatt accctgttat cccagatgac ataccctgtt atccctagat gacattaccc    3720
tgttatccca gatgacatta ccctgttatc cctagataca ttaccctgtt atcccagatg    3780
acataccctg ttatccctag atgacattac cctgttatcc cagatgacat taccctgtta    3840
tccctagata cattaccctg ttatcccaga tgacataccc tgttatccct agatgacatt    3900
accctgttat cccagataaa ctcaatgatg atgatgatga tggtcgagac tcagcggccg    3960
cggtgccagg gcgtgccctt gggctcccgg gcgcgactat aagctgcgag caacttcac     4020
ttgggtatgc cggcggtagc gctgagggcc tatttcccat gattccttca tatttgcata    4080
tacgatacaa ggctgttaga gagataattg gaattaattt gactgtaaac acaaagatat    4140
tagtacaaaa tacgtgacgt agaaagtaat aatttcttgg gtagtttgca gttttaaaat    4200
tatgttttaa aatggactat catatgctta ccgtaacttg aaagtatttc gatttcttgg    4260
ctttatatat cttgtggaaa ggacgaaaca ccgggtcttc gagaagacct gtttttagagc   4320
tagaaatcgt ggttcgcacc gactcggtgc cacagcaagt taaaataagg ctagtccgtt    4380
atcaacttga aaaagtggca ccgagtcggt gcttttttga attcgctagc taggtcttga    4440
aaggagtggg aattggctcc ggtgcccgtc agtgggcaga gcgcacatcg cccacagtcc    4500
ccgagaagtt gggggggaggg gtcggcaatt gatccggtgc ctagagaagg tggcgcgggg    4560
taaactggga aagtgatgtc gtgtactggc tccgccttt tcccgagggt ggggagaac     4620
cgtatataag tgcagtagtc gccgtgaacg ttctttttcg caacgggttt gccgccagaa    4680
cacaggaccg gttctagagc gctgccacca tggacaagaa gtacagcatc ggcctggaca    4740
tcggcaccaa ctctgtgggc tgggccgtga tcaccgacga gtacaaggtg cccgccaaga    4800
aattcaaggt gctgggcaac accgaccggc acagcatcaa gaagaacctg atcggagccc    4860
tgctgttcga cagcggcgaa acagccgagg ccacccggct gaagagaacc gccagaagaa    4920
gatacaccag acgaaagaac cggatctgct atctgcaaga gatcttcagc aacgagatgg    4980
ccaaggtgga cgacagcttc ttccacagac tggaagagtc cttcctggtg gaagaggata    5040
agaagcacga gcggcacccc atcttcggca acatcgtgga cgaggtggcc taccacgaga    5100
agtaccccac catctaccac ctgagaaaga aactggtgga cagcaccgac aaggccgacc    5160
tgcggctgat ctatctggcc ctggcccaca tgatcaagtt ccggggccac ttcctgatcg    5220
agggcgacct gaaccccgac aacagcgacg tggacaagct gttcatccag ctggtgcaga    5280
cctacaacca gctgttcgag gaaaaccca tcaacgccag cggcgtggac gccaaggcca    5340
tcctgtctgc cagactgagc aagagcagac ggctggaaaa tctgatcgcc cagctgcccg    5400
gcgagaagaa gaatggcctg ttcggaaacc tgattgccct gagcctgggc ctgacccca   5460
acttcaagag caacttcgac ctggccgagg atgccaaact gcagctgagc aaggacacct    5520
acgacgacga cctggacaac ctgctggccc agatcggaga ccagtacgcc gacctgttc    5580
tggccgccaa gaacctgtcc gacgccatcc tgctgagcga catcctgaga gtgaacaccg    5640
agatcaccaa ggccccctg agcgcctcta tgatcaagag atacgacgag caccaccagg    5700
acctgaccct gctgaaagct ctcgtgcggc agcagctgcc tgaagtac aaagagattt     5760
tcttcgacca gagcaagaac ggctacgccg gctacattga cggcggagcc agccaggaag    5820
agttctacaa gttcatcaag cccatcctgg aaaagatgga cggcaccgag gaactgctcg    5880
tgaagctgaa cagagaggac ctgctgcgga agcagcggac cttcgacaac ggcagcatcc    5940
cccaccagat ccacctggga gagctgcacg ccattctgcg gcggcaggaa gatttttacc    6000
cattcctgaa ggacaaccgg gaaaagatcg agaagatctt gaccttccgc atccccact    6060
acgtgggccc tctggccagg ggaaacagca gattcgcctg gatgaccaga aagagcgagg    6120
aaaccatcac ccccctggaac ttcgaggaag tggtggacaa gggcgcttcc gcccagagct    6180
tcatcgagcg gatgaccaac ttcgataaga acctgcccaa cgagaaggtg ctgcccaagc    6240
acagcctgct gtacgagtac ttcaccgtgt ataacgagct gaccaaagtg aaatacgtga    6300
ccgagggaat gagaaagccc gccttcctga gcggcgagca gaaaaaggcc atcgtgacc    6360
tgctgttcaa gaccaaccgg aaagtgaccg tgaagcagct gaaagaggac tacttcaaga    6420
aaatcgagtg cttcgactcc gtggaaatct ccggcgtgga gatcggttc aacgcctccc    6480
tgggcacata ccacgatctg ctgaaaatta tcaaggacaa ggacttcctg gacaatgagg    6540
aaaacgagga cattctggaa gatatcgtgc tgaccctgac actgtttgag gacagagagg    6600
tgatcgagga acggctgaaa acctatgccc ctgttcga cgacaaagtg atgaagcagc    6660
tgaagcggcg gagatacacc ggctgggca ggctgagccg gaagctgatc aacggcatcc     6720
gggacaagca gtccggcaag acaatcctgg atttcctgaa gtccgacggc ttcgccaaca    6780
gaaacttcat gcagctgatc cacgacgaca gcctgacctt taaagaggac atccagaaag    6840
cccaggtgtc cggccagggc gatagcctgc acgagcacat tgccaatctg gccggcagcc    6900
ccgccattaa gaagggcatc ctgcagacag tgaaggtggt ggacgagctc gtgaaagtga    6960
tgggccggca caagcccgag aacatcgtga tcgaaatggc cagagaaaac cagaccaccc    7020
agaagggaca gaagaacagc cgcgagagga tgaagcggat cgaagagggc atcaaagagc    7080
tgggcagcca gatcctgaaa gaacaccccg tggaaaacac ccagctgcag aacgagaagc    7140
tgtacctgta ctacctgcag aatgggcggg atatgtacgt ggaccaggaa ctggacatca    7200
accggctgtc cgactacgat gtggaccata tcgtgcctca gagctttctg aaggacgact    7260
ccatcgacaa caaggtgctg accagaagcg acaagaaccg gggcaagagc gacaacgtgc    7320
cctccgaaga ggtcgtgaag aagatgaaga actactgctg gcagctgctg aacgccaagc    7380
tgattcccca gagaaagttc gacaatctga ccaaggccga gaggggcggc ctgagcgaac    7440
tggataagc cggcttcatc aagagacagc tggtggaaac ccggcagatc acaaagcacg    7500
tggcacagat cctggactcc cggatgaaca ctaagtacga cgagaatgac aagctgatcc    7560
gggaagtgaa agtgatcacc ctgaagtcca agctggtgtc cgatttccgg aaggatttcc    7620
agttttacaa agtgcgcgag atcaacaact accaccacgc ccacgacgcc tactgaacg    7680
ccgtcgtggg aaccgccctg atcaaaaagt accctaagct ggaaagcgag ttcgtgtacg    7740
gcgactacaa ggtgtacgac gtgcggaaga tgatcgccaa gagcgagcag gaaatcggca    7800
aggctaccgc caagtactc ttctacagca acatcatgaa cttttttcaag accgagatta    7860
ccctggccaa cggcgagatc cggaagcggc ctctgatcga gacaaacggc gaaaccgggg    7920
agatcgtgtg ggataagggc cgggattttg ccaccgtgcg gaaagtgctg agcatgcccc    7980
```

```
aagtgaatat cgtgaaaaag accgaggtgc agacaggcgg cttcagcaaa gagtctatcc 8040
tgcccaagag gaacagcgat aagctgatcg ccagaaagaa ggactgggac cctaagaagt 8100
acggcggctt cgacagcccc accgtggcct attctgtgct ggtggtggcc aaagtggaaa 8160
agggcaagtc caagaaactg aagagtgtga aagagctgct ggggatcacc atcatgaaa  8220
gaagcagctt cgagaagaat cccatcgact ttctgaagc  caagggctac aaagaagtga 8280
aaaaggacct gatcatcaag ctgcctaagt actccctgtt cgagctgaa  aacggccgga 8340
agagaatgct ggcctctgcc ggcgaactgc agaagggaaa cgaactgcc  ctgccctcca 8400
aatatgtgaa cttcctgtac ctggccagcc actatgagaa gctgaagggc tcccccgagg 8460
ataatgagca gaaacagctg tttgtggaac agcacaagca ctacctggac gagatcatcg 8520
agcagatcag cgagttctcc aagagagtga tcctggccga cgctaatctg gacaaagtgc 8580
tgtccgccta caacaagcac cgggataagc ccatcagaga gcaggccgag aatatcatcc 8640
acctgtttac cctgaccaat ctgggagccc ctgccgcctt caagtacttt gacaccacca 8700
tcgaccggaa gaggtacacc agcaccaaag aggtgctgga cgccaccctg atccaccaga 8760
gcatcaccgg cctgtacgag acacggatcg acctgtctca gctgggaggc gacaagcgc  8820
ctgccgccac aaagaaggct ggacaggcta agaagaagaa agattacaaa gacgatgacg 8880
ataagtaact agagctcgct gatcagcctc gactgtgcct tctagttgcc agccatctgt 8940
tgtttgcccc tccccgtgc  cttccttgac cctggaaggt gccactccca ctgtcctttc 9000
ctaataaaat gaggaaattg catcgcattg tctgagtagg tgtcattcta ttctgggggg 9060
tggggtgggg caggacagca aggggagga  ttgggaagag aatagcaggc atgctgggga 9120
ctgaggcgga aagaaccagc tgtggaatgt gtgtcagtta gggtgtggaa agtccccagg 9180
ctccccagca ggcagaagta tgcaaagcat gcatctcaat tagtcagcaa ccaggtgtgg 9240
aaagtcccca ggctccccag caggcagaag tatgcaaagc atgcatctca attagtcagc 9300
aaccatagtc ccgcccctaa ctccgcccat cccgcccta  actccgccca gttccgccca 9360
ttctccgccc catggctgac taattttttt tatttatgca gaggccgagg ccgcctcggc 9420
ctctgagcta ttccagaagt agtgaggagg ctttttgga  ggcctaggct tttgcaaaaa 9480
gcttgggccc gccccaactg gggtaacctt tgagttctct cagttggggg           9530
```

SEQ ID NO: 391        moltype = DNA  length = 5722
FEATURE               Location/Qualifiers
misc_feature       1..5722
                      note = Description of Artificial Sequence: Synthetic
                      polynucleotide
source                 1..5722
                      mol_type = other DNA
                      organism = synthetic construct
SEQUENCE: 391

```
tgatcccctg cgccatcaga tccttggcgg cgagaaagcc atccagttta ctttgcaggg 60
cttcccaacc ttaccagagg gcgccccagc tggcaattgc ggttcgcttg ctgtccataa 120
aaccgcccag tctagctatc gccatgtaag cccactgcaa gctacctgct ttctctttgc 180
gcttgcgttt tccccttgtcc agatagccca gtagctgaca ttcatccggg gtcagcaccg 240
tttctgcgga ctggctttct acgtgctcga ggggggccaa acggtctcca gcttggctgt 300
tttggcggat gagagaagat tttcagcctg atacagatta aatcagaacg cagaagcggt 360
ctgataaaac agaatttgcc tggcggcagt agcgcggtgg tcccacctga ccccatgccg 420
aactcagaag tgaaacgccg tagcgccgat ggtagtgtgg ggtctcccca tgcgagagta 480
gggaactgcc aggcatcaaa taaaacgaaa ggctcagtcg aaagactggg cctttcgttt 540
tatctgttgt ttgtcggtga acgctctcct gagtaggaca aatccgccgg agcggattt  600
gaacgttgcg aagcaacggc ccggagggtg cgggcaggga cgcccgccat aaactgccag 660
gcatcaaatt aagcagaagg ccatcctgac ggatggcctt tttgcgtttc tacaaactct 720
tttgtttatt tttctaaata cattcaaata tgtatccgct catgaccaaa atcccttaac 780
gtgagttttc gttccactga gcgtcagacc ccgtagaaaa gatcaaagga tcttcttgag 840
atcctttttt tctgcgcgta atctgctgct tgcaaacaaa aaaaccaccg ctaccagcgg 900
tggtttgttt gccggatcaa gagctaccaa ctctttttcc gaaggtaact ggcttcagca 960
gagcgcagat accaaatact gtccttctag tgtagccgta gttaggccac cacttcaaga 1020
actctgtagc accgcctaca tacctcgctc tgctaatcct gttaccagtg gctgctgcca 1080
gtggcgataa gtcgtgtctt accgggttgg actcaagacg atagttaccg gataaggcgc 1140
agcggtcggg ctgaacgggg ggttcgtgca cacagcccag cttggagcga acgacctaca 1200
ccgaactgag atacctacag cgtgagctat gagaaagcgc cacgcttccc gaagggagaa 1260
aggcggacag gtatccggta agcggcaggg tcggaacagg agagcgcacg agggagcttc 1320
caggggaaa  cgcctggtat ctttatagtc ctgtcgggtt tcgccacctc tgacttgagc 1380
gtcgattttt gtgatgctcg tcagggggc  ggagcctatg gaaaaacgcc agcaacgcgg 1440
cctttttacg gttcctggcc ttttgctggc cttttgctca catgttcttt cctgcgttat 1500
cccctgattc tgtggataac cgtattaccg cctttgagtg agctgatacc gctcgccgca 1560
gccgaacgac cgagcgcagc gagtcagtga gcgaggaagc ggaagagcgc ctgatgcggt 1620
attttctcct tacgcatctg tgcggtattt cacaccgcat ctcagtacaa 1680
tctgctctga tgccgcatag ttaagccagt atacactccg ctatcgctac gtgactgggt 1740
catggctgcg ccccgacacc cgccaacacc cgctgacgcg ccctgacggg cttgtctgct 1800
cccggcatcc gcttacagac aagctgtgac cgtctccggg agctgcatgt gtcagaggtt 1860
ttcaccgtca tcaccgaaac gcgcgaggca gcagatcaat tcgcgcgcga aggcgaagcg 1920
gcatgcataa tgtgcctgtc aaatggacga agcagggatt ctgcaaaccc tatgctactc 1980
cgtcaagccg tcaattgtct gattcgttac caattatgac aacttgacgg ctacatcatt 2040
cacttttct  tcacaaccgg cacgaactc  gctcgggctg ccccggtgc  atttttaaa  2100
tacccgcgag aaatagagtt gatcgtcaaa accaacattg cgaccgacgg tggcgatagg 2160
catccggggtg tgctcaaaaa gcagcttcgc ctggctgata cgttggtcct cgcgccagct 2220
taagacgcta atccctaact gctggcggaa aagatgtgac gccacaagca 2280
aacatgctgt gcgacgctgg cgatacatta cccgttatc  cctagatgac attaccctgt 2340
tatcccagat gacattaccc tgttatccct agatgacatt accctgttat ccctagtgac 2400
catttaccct gttatcccta gatgacatta cccctgttatc ccagatgaca ttaccctgtt 2460
atccctagat acattaccct gttatcccag atgcataccc ctgttatccc tagatgacat 2520
taccctgtta tcccagatga cattaccctg ttatccctag atacattacc ctgttatccc 2580
```

```
agatgacata   ccctgttatc   cctagatgac   attaccctgt   tatcccagat   gacattaccc   2640
tgttatccct   agatacatta   ccctgttatc   ccagatgaca   taccctgtta   tccctagatg   2700
acattaccct   gttatcccag   atgacattac   cctgttatcc   ctagatacat   taccctgtta   2760
tcccagatga   cataccctgt   tatccctaga   tgacattacc   ctgttatccc   agatgacatt   2820
accctgttat   ccctagatac   attaccctgt   tatcccagat   gacataccct   gttatccccta  2880
gatgacatta   ccctgttatc   ccagatgaca   ttaccctgtt   atccctagat   acattaccct   2940
gttatcccag   atgacatacc   ctgttatccc   tagatgacat   taccctgtta   tcccagataa   3000
actcaatgat   gatgatgatg   atggtcgaga   ctcagcggcc   gcggtgccag   ggcgtgccct   3060
tgggctcccc   gggcgcggtc   ctttgggcgc   taactgcgtg   cgcgctggga   attggcgcta   3120
attgcgcgtg   cgcgctggga   ctcaaggcgc   taactgcgcg   tgcgttctgg   ggcccggggt   3180
gccgcggcct   gggctggggc   gaaggcgggc   tcggccggaa   ggggtggggt   cgccgcggct   3240
cccgggcgct   tgcgcgcact   tcctgcccga   gccgctggcc   gcccgagggt   gtggccgctg   3300
cgtgcgcgcg   cgccgacccg   gcgctgtttg   aaccgggcgg   aggcggggct   ggcgcccggt   3360
tgggaggggg   ttggggcctg   gcttcctgcc   gcgcgccggg   gggacgcctc   cgaccagtgt   3420
ttgccttttta  tggtaataac  gcggccggcc  cggcttcctt  tgtccccaat  ctgggcgcgc   3480
gccggcgccc   cctggcggcc   taaggactcg   gcgcgccgga   agtggccagg   gcggggcga   3540
cctcggctca   cagcgcgccc   ggctattctc   gcagctcgcc   accatgcccg   ccatgaagat   3600
cgagtgccgc   atcaccggca   ccctgaacgg   cgtggagttc   agcttcaagg   tcgggcggaga  3660
gggcacccc   gagcagggcc   gcatgaccaa   caagatgaag   agcaccaaag   gcgccctgac   3720
cttcagcccc   tacctgctga   gccacgtgat   gggctacggc   ttctaccact   cggcaccta   3780
ccccagcggc   tacgagaacc   ccttcctgca   cgccatcaac   aacggcggct   acaccaacac   3840
ccgcatcgag   aagtacgagg   acggcggcgt   gctgcacgtg   agcttcagct   accgctacga   3900
ggccggccgc   gtgatcggcg   acttcaaggt   ggtgggcacc   ggcttccccg   aggacagcgt   3960
gatcttcacc   gacaagatca   tccgcagcaa   cgccaccgtg   gagcacctgc   acccatgggg   4020
cgataacgtg   ctggtgggca   gcttcgcccg   caccttcagc   ctgcgcgacg   gcggctacta   4080
cagcttcgtg   gtggacagcc   acatgcactt   caagagccgc   atccaccca   gcatcctgca   4140
gaacgggggc   cccatgttcg   ccttccgccg   cgtggaggag   ctgcagacca   acaccgagct   4200
gggcatcgtg   gagtaccagc   acgccttcaa   gaccccatc   gccttcgcca   gatctcgagc   4260
tcgaaccatg   gatgatgata   tcgccgcgct   cgtcgtcgac   aacggctccg   gcatgtgcaa   4320
ggccggcttc   gcgggcgacg   atgcccccg   ggccgtcttc   ccctccatcg   tggggcgcc   4380
caggcaccag   gtaggggagc   tggctgggtg   gggcagcccc   gggagcgggc   gggaggcaag   4440
ggcgctttct   ctgcacagga   gcctccggt   tccggggtg   ggggctgcgc   ccgtgctcag   4500
ggcttcttgt   cctttccttc   cagggcgtg   atggtgggca   tgggtcagaa   ggattcctat   4560
gtgggcgacg   aggccagag   caagagaggc   atcctcaccc   tgaagtaccc   catcgagcag   4620
ggcatcgtca   ccaactggga   cgacatggag   aaaatctggc   accacaccttt  ctacaatgag   4680
ctgcgtgtgg   ctcccgagga   gcaccccgtg   ctgctgaccg   aggccccct   gaaccccaag   4740
gccaaccgcg   agaagatgac   ccagccccaa   ctggggtaac   ctttgagttc   tctcagttgg   4800
gggtaatcag   catcatgatg   tggtaccaca   tcatgatgct   gattataaga   atgcggccgc   4860
cacactctag   tggatctcga   gttaataatt   cagaagaact   cgtcaagaag   gcgatagaag   4920
gcgatgcgct   gcgaatcggg   agcggcgata   ccgtaaagca   cgaggaagcg   gtcagcccat   4980
tcgccgccaa   gctcttcagc   aatatcacgg   gtagccaacg   ctatgtcctg   atagcggtcc   5040
gccacaccca   gccggccaca   gtcgatgaat   ccagaaaagc   ggccattttc   caccatgata   5100
ttcggcaagc   aggcatcgcc   atgggtcacg   acagatcct   ggtactcggg   catgctcgcc   5160
ttgagcctgg   cgaacagttc   ggctggcgcg   agccctgat   gctcttcgtc   cagatcatcc   5220
tgatcgacaa   gaccggcttc   catccgagta   cgtgctcgct   cgatgcgatg   tttcgcttgg   5280
tggtcgaatg   ggcaggtagc   cggatcaagc   gtatgcagcc   gccgcattgc   atcagccatg   5340
atggatactt   tctcggcagg   agcaaggtgt   agatgacatg   ccgatcagca   cccggcactt   5400
cgcccaatag   cagccagtcc   cttcccgctt   cagtgacaac   gtcgagcaca   gctgcgcaag   5460
gaacgcccgt   cgtggccagc   cacgatagcc   gcgctgcctc   gtcttgcagt   tcattcaggg   5520
caccggacag   gtcggtcttg   acaaaagaa   ccgggcgccc   ctgcgctgac   agccggaaca   5580
cggcggcatc   agagcagccg   attgtctgtt   gtgcccagtc   atagccgaat   agcctctcca   5640
cccaagcggc   cggagaacct   gcgtgcaatc   catcttgttc   aatcatgcga   aacgatcctc   5700
atcctgtctc   ttgatcagag   ct                                              5722
```

SEQ ID NO: 392   moltype = DNA length = 15424
FEATURE     Location/Qualifiers
misc_feature   1..15424
        note = Description of Artificial Sequence: Synthetic
        polynucleotide
source      1..15424
        mol_type = other DNA
        organism = synthetic construct
SEQUENCE: 392

```
tcgacggtat   cgataagctt   gatatcgaat   tcctgcagcc   cggggatcc   actagttcta   60
gagcggccgc   caccgcggtg   gagctccagc   ttttgttccc   tttagtgagg   gttaatttcg   120
agcttggcgt   aatcatggtc   atagctgttt   cctgtgtgaa   attgttatcc   gctcacaatt   180
ccacacaaca   tacgagccgg   aagcataaag   tgtaaagcct   ggggtgccta   atgagtgagc   240
taactcacat   taattgcgtt   gcgctcactg   cccgctttcc   agtcgggaaa   cctgtcgtgc   300
cagctgcatt   aatgaatcgg   ccaacgcgcg   gggagaggcg   gtttgcgtat   tgggcgctct   360
tccgcttcct   cgctcactga   ctcgctgcgc   tcggtcgttc   ggctgcggcg   agcggtatca   420
gctcactcaa   aggcggtaat   acggttatcc   acagaatcag   gggataacgc   aggaaagaac   480
atgtgagcaa   aaggccagca   aaaggccagg   aaccgtaaaa   aggccgcgtt   gctggcgttt   540
ttccataggc   tccgcccccc   tgacgagcat   cacaaaaatc   gacgctcaag   tcagaggtgg   600
cgaaacccga   caggactata   aagataccag   gcgtttcccc   ctggaagctc   cctcgtgcgc   660
tctcctgttc   cgaccctgcc   gcttaccgga   tacctgtccg   cctttctccc   ttcgggaagc   720
gtggcgcttt   ctcatagctc   acgctgtagg   tatctcagtt   cggtgtaggt   cgttcgctcc   780
aagctgggct   gtgtgcacga   accccccgtt   cagcccgacc   gctgcgcctt   atccggtaac   840
tatcgtcttg   agtccaaccc   ggtaagacac   gacttatcgc   cactggcagc   agccactggt   900
aacaggatta   gcagagcgag   gtatgtaggc   ggtgctacag   agttcttgaa   gtggtggcct   960
```

```
aactacggct acactagaag gacagtattt ggtatctgcg ctctgctgaa gccagttacc   1020
ttcggaaaaa gagttggtag ctcttgatcc ggcaaacaaa ccaccgctgg tagcggtggt   1080
tttttttgttt gcaagcagca gattacgcgc agaaaaaaag gatctcaaga agatcctttg   1140
atcttttcta cggggtctga cgctcagtgg aacgaaaact cacgttaagg gattttggtc   1200
atgagattat caaaaaggat cttcacctag atccttttaa attaaaaatg aagttttaaa   1260
tcaatctaaa gtatatatga gtaaacttgg tctgacagtt accaatgctt aatcagtgag   1320
gcacctatct cagcgatctg tctatttcgt tcatccatag ttgcctgact ccccgtcgtg   1380
tagataacta cgatacggga gggcttacca tctggcccca gtgctgcaat gataccgcga   1440
gacccacgct caccggctcc agatttatca gcaataaacc agccagccgg aagggccgag   1500
cgcagaagtg gtcctgcaac tttatccgcc tccatccagt ctattaattg ttgccgggaa   1560
gctagagtaa gtagttcgcc agttaatagt ttgcgcaacg ttgttgccat tgctacaggc   1620
atcgtggtgt cacgctcgtc gtttggtatg gcttcattca gctccggttc caacgatca   1680
aggcgagtta catgatcccc catgttgtgc aaaaaagcgg ttagctcctt cggtcctccg   1740
atcgttgtca gaagtaagtt ggccgcagtg ttatcactca tggttatggc agcactgcat   1800
aattctctta ctgtcatgcc atccgtaaga tgcttttctg tgactggtga gtactcaacc   1860
aagtcattct gagaatagtg tatgcggcga ccgagttgct cttgcccggc gtcaatacgg   1920
gataataccg cgccacatag cagaacttta aaagtgctca tcattggaaa acgttcttcg   1980
gggcgaaaac tctcaaggat cttaccgctg ttgagatcca gttcgatgta acccactcgt   2040
gcacccaact gatcttcagc atcttttact ttcaccagcg tttctgggtg agcaaaaaca   2100
ggaaggcaaa atgccgcaaa aaagggaata agggcgacac ggaaatgttg aatactcata   2160
ctcttccttt ttcaatatta ttgaagcatt tatcagggtt attgtctcat gagcggatac   2220
atatttgaat gtatttagaa aaataaacaa ataggggttc cgcgcacatt tccccgaaaa   2280
gtgccacctg acgtctaaga aaccattatt atcatgacat taacctataa aaataggcgt   2340
atcacgaggc cctttcgtct tcaagaattc tcatgtttga cagcttatca tcgataagct   2400
ttaatgcggt agtttatcac agttaaattg ctaacgcagt caggcaccgt gtatgaaatc   2460
taacaatgcg ctcatcgtca tcctcggcac cgtcaccctg gatgctgtag gcataggctt   2520
ggttatgccg gtactgccgg gcctcttgcg ggatatcgtc cattccgaca gcatcgccag   2580
tcactatggc gtgctgctag cgctatatgc gttgatgcaa tttctatgcg cacccgttct   2640
cggagcactg tccgaccgct ttggccgccg cccagtcctg ctcgcttcgc tacttggagc   2700
cactactgac tacgcgatca tggcgaccac acccgtcctg tggatccggc gcacaccaaa   2760
aacgtcactt ttgccacatc cgtcgcttac atgtgttccg ccacacttgc aacatcacac   2820
ttccgccaca ctactacgtc acccgcccg ttccacgcc ccgcgccacg tcacaaactc   2880
cacccctca ttatcatatt ggcttcaatc caaaataaat catcaataat ataccttatt   2940
ttggattgaa gccaatatga taatgagggg gtggagtttg tgacgtggcg cggggcgtgg   3000
gaacgggcg ggtgacgtag gttttagggc ggagtaactt gtatgtgttg ggaattgtag   3060
ttttcttaaa atgggaagtt acgtaacgtg ggaaaacgga agtgacgatt tgaggaagtt   3120
gtgggttttt tggctttcgt ttctgggcgt aggttcgcgt gcggttttct gggtgttttt   3180
tgtggacttt aaccgttacg tcattttttta gtcctatata tactcgctct gcacttggcc   3240
ctttttaca ctgtgactga ttgagctggt gccgtgtcga gtggtgtttt tttaataggt   3300
tttcttttttt actggtaagg ctgactgtta ggctgccgct gtgaagcgct gtatgttgtt   3360
ctggagcggg agggtgctat tttgcctagg caggagggtt tttcaggtgt ttatgtgttt   3420
ttctctccta ttaattttgt tatacctcct atgggggctg taatgttgtc tctacgcctg   3480
cgggtatgta ttcccccggg tcatttcggt cgcttttttag cactgaccga tgaatcaacc   3540
tgatgtgttt accgagtctt acattatgac tccggacatg accgaggagc tgtcggtggt   3600
gcttttaat cacggtgacc agttttttta cggtcacgcc ggcatggccg tagtccgtct   3660
tatgcttata agggttgttt ttcctgttgt aagacaggct tctaatgttt aaatgttttt   3720
ttgttatttt attttgtgtt tatgcagaaa cccgcagaca tgtttgagag aaaaatggtg   3780
tcttttctg tggtggttcc ggagcttacc tgcctttatc tgcatgagca tgactacgat   3840
gtgctttctt ttttgcgcga ggctttgcct gattttttga gcagcaccctt gcattttata   3900
tcgccgccca tgcaacaaag cttacatcgg ggctacgctg gttagcatag ctccgagtat   3960
gcgtgtcata atcagtgtgg gttctttttgt caaggttcct ggcggggaag tggccgagat   4020
ggtccgtgca gacctgcacg attatgttca gctggccctg cgaagggacc tacgggatcg   4080
cggtattttt gttaatgttc cgcttttgaa tcttatacag gtctgtgagg aacctgaatt   4140
tttgcaatca tgattcgctg cttgaggctg aaggtggagg gcgctctgga gcagatttttt   4200
acaatggccg gacttaatat tcgggatttg cttagagata tattgagaag gtggcgagat   4260
gagaattatt tgggcatggt tgaaggtgct ggaatgttta tagaggagat tcaccctgaa   4320
gggtttagcc tttacgtcca cttggacgtg agggccgttt gccttttgga agccattgtg   4380
caacatctta caaatgccat tatctgttct ttggctgtag agtttgacca cgccaccgga   4440
ggggagcgcg ttcacttaat agatcttcat tttgaggtttt tggataatct tttggaataa   4500
aaaaaaaac atggttcttc cagctcttcc cgctcctccc gtgtgtgact cgcagaacga   4560
atgtgtaggt tggctgggtg tggcttattc tgcggtggtg gatgttatca gggcagcggc   4620
gcatgaagga gtttacatag aacccgaagc caggggcgc ctggatgctt tgagagagtg   4680
gatatactac aactactaca cagagcgatc taagcggcga gaccggagac gcagatctgt   4740
ttgtcacgcc cgcaccttgt tttgcttcag gaaatatgac tacgtccggc gttccattg   4800
gcatgacact acgaccaaca cgatctcggt tgtctcggcg cactccgtac agtagggatc   4860
gtctacctcc ttttgagaca gaaacccgcg ctaccatact ggaggatcat ccgctgctgc   4920
ccgaatgtaa cactttgaca atgcacaacg tgagttacgt gcgaggtctt ccctgcagtg   4980
tgggatttac gctgattcag gaatggggttg ttccctggga tatggttcta acgcggggagg   5040
agcttgtaat cctgaggaag tgtatgcacg tgtgcctgtg tggtgccaac attgatatca   5100
tgacgagcat gatgatccat ggttacgagt cctgggctct ccactgtcat tgttccagtc   5160
ccggttccct gcagtgtata gccggcgggc aggttttggc cagctggttt aggatggtgg   5220
tggatggcgc catgtttaat cagaggttta tatggtaccg ggaggtggtg aattacaaca   5280
tgccaaaaga ggtaatgttt atgtccagcg tgtttatgag gggtcgccac ttaatctacc   5340
tgccttgtg gtatgatggc cacgtgggtt ctgtcgtcct gccatgagc tttggataca   5400
gcgccttgca ctgtgggatt ttgaacaata ttgtggtgcc gtgctgcagt tactgtgctg   5460
atttaagtga gatcagggtg cgctgctgtg cccggaggac aaggcgcctt atgctgcggg   5520
cggtgcgaat catcgctgag gagaccactg ccatgttgta ttcctgcagg acggagcggc   5580
ggcggcagca gtttattcgc gcgctgctgc agcaccaccg cccctatcctg atgcacgatt   5640
atgactctac ccccatgtag gcgtggactt ctccttcgcg gcccgttaag caaccgcaag   5700
```

```
ttggacagca gcctgtggct cagcagctgg acagcgacat gaacttaagt gagctgcccg   5760
gggagtttat taatatcact gatgagcgtt tggctcgaca ggaaaccgtg tggaatataa   5820
cacctaagaa tatgtctgtt acccatgata tgatgctttt taaggccagc cggggagaaa   5880
ggactgtgta ctctgtgtgt tgggagggag gtggcaggtt gaatactagg gttctgtgag   5940
tttgattaag gtacggtgat ctgtataagc tatgtggtgg tggggctata ctactgaatg   6000
aaaaatgact tgaaattttc tgcaattgaa aaataaacac gttgaaacat aacacaaacg   6060
attctttatt cttgggcaat gtatgaaaaa gtgtaagagg atgtggcaaa tatttcatta   6120
atgtagttgt ggccagacca gtcccatgaa aatgacatag agtatgcact tggagttgtg   6180
tctcctgttt cctgtgtacc gtttagtgta atggttagtg ttacaggttt agtttttgtct  6240
ccgtttaagt aaacttgact gacaatgtta cttttggcag ttttaccgtg agattttgga   6300
taagctgata ggttaggcat aaatccaaca gcgtttgtat aggctgtgcc ttcagtaaga   6360
tctccatttc taaagttcca atattctggg tccaggaagg aattgtttag tagcactcca   6420
ttttcgtcaa atcttataat aagatgagca ctttgaactg ttccagatat tggagccaaa   6480
ctgcctttaa cagccaaaac tgaaactgta gcaagtattt gactgccaca ttttgttaag   6540
accaaagtga gtttagcatc tttctctgca tttagtctac agtaggaga tggagctggt    6600
gtggtccaca aagttagctt atcattattt ttgtttccta ctgtaatggc acctgtgctg   6660
tcaaaactaa ggccagttcc tagtttagga accatagcct tgtttgaatc aaattctagg   6720
ccatggccaa tttttgtttt gaggggattt gtgtttggtg cattaggtga accaaattca   6780
agcccatctc ctgcattaat ggctatggct gtagcgtcaa acatcaaccc cttggcagtg   6840
cttaggttaa cctcaagctt tttggaattg tttgaagctg taaacaagta aaggcctttg   6900
ttgtagttaa tatccaagtt gtgggctgag tttataaaaa gagggccctg tcctagtctt   6960
agatttagtt ggttttgagc atcaaacgga taactaacat caagtataag gcgtctgttt   7020
tgagaatcaa tccttagtcc tcctgctaca ttaagttgta tattgccttg tgaatcaaaa   7080
cccaaggctc cagtaacttt agtttgcaag gaagtattat taatagtcac acctggacca   7140
gttgctacgg tcaaagtgtt taggtcgtct gttacatgca aaggagcccc gtactttagt   7200
cctagtttc cattttgtgt ataaatgggc tctttcaagt caatgcccaa gctaccagtg    7260
gcagtagtta gaggggggtga ggcagtgata gtaagggtac tgctatcggt ggtggtgagg  7320
gggcctgatg tttgcagggc tagctttcct tctgacactg tgaggggtcc ttgggtggca   7380
atgctaagtt tggagtcgtg cacggttagc ggggcctgtg attgcatggt gagtgtgttg   7440
cccgcgacca ttagagggtgc ggcggcagcc acagttgggg cttctgaggt aactgtgagg  7500
ggtgcagata tttccaggtt tatgtttgac ttggtttttt tgagaggtgg gctcacagtg   7560
gttacatttt gggaggtaag gttgccggcc tcgtccagag agaggccgtt gcccattttg   7620
agcgcaagca tgccattgga ggtaactaga ggttcggata ggcgcaaaga gagtaccca    7680
gggggactct cttgaaaccc attgggggat acaaagggag gagtaagaaa aggcacagtt   7740
ggaggaccgg tttccgtgtc atatggatac acggggttga aggtatcttc agacggtctt   7800
gcgcgcttca tctgcaacaa catgaagata gtgggtgcgg atggacagga acaggaggaa   7860
actgacattc catttagatt gtggagaaag tttgcagcca ggaggaagct gcaataccag   7920
agctgggagg agggcaagga ggtgctgctg aataaactgg acagaaattt gctaactgat   7980
tttaagtaag tgatgcttta ttatttttttt ttattagtta aagggaataa gatcccccggg  8040
tactctagtt aattaactag aggatcttga tgtaatccaa ggttaggaca gttgcaaatc   8100
acagtgagaa cacagggtcc cctgtcccgc tcaactagca gggggcgctg ggtaaactcc   8160
cgaatcaggc tacgggcaag ctctccctgg gcggtaagcc ggacgccgtg cgccgggccc   8220
tcgatatgat cctcgggcaa ttcaaagtag caaaactcac cggagtcgcg gcgcaaagcat 8280
ttgtggcggc gacagtggac caggtgtttc aggcgcagtt gctctgcctc tccacttaac   8340
attcagtcgt agccgtccgc cgagtccttt accgcgtcaa agttaggaat aaattgatcc   8400
ggatagtggc cgggaggtcc cgagaagggg ttaaagtaga ccgatggcac aaactcctca   8460
ataaattgca gagttccaat gcctccagag cgccgctcag aggacgaggt ctgcagagtt   8520
aggattgcct gacgaggcgt gaatgaagga cggccggcgc cgccgatctg aaatgtcccg   8580
tccgacggga gaccaagcga ggagctcacc gactcgtcgt tgagctgaat acctcgccct   8640
ctgattgtca ggtgagttat accctgcccg ggcgaccgca ccctgtgacg aaagccgccc   8700
gcaagctgcg cccctgagtt agtcatctga acttcggcct gggcgtctct gggaagtacc   8760
acagtggtgg gagcgggact ttcctggtac accaggtgcag cgggccaact acggggatta  8820
aggttattac gaggtgtggt ggtaatagcc gcctgttcca agagaattcg gtttcggtgg    8880
gcgcggattc cgttgacccg ggatatcatg tgggtcccg cgctcatgta gtttattcgg    8940
gttgagtagt cttgggcagc tccagccgca agtcccattt gtggctggta actccacatg   9000
taggcgtgg gaatttcctt gctcataatg gcgctgacga caggtctgg gcgcgggtgt     9060
ggccgctgga gatgacgtag ttttcgcgct taaatttgag aaaggggcgcg aaactagtcc   9120
ttaagagtca gcgcgcagta tttactgaag agagcctccg cgtcttccag cgtgcgcgca   9180
agctgatctt cgcttttgtg atacaggcag ctgcgggtga gggatcgcag agacctgttt   9240
tttattttca gctcttgttc ttggcccctg ctctgttgaa atatagcata cagagtggga   9300
aaaatcctgt ttctaagctc gcgggtcgat acggggttcgt tgggcgccag acgcagcgct   9360
cctcctcctg ctgctgccgc cgctgtggat tccttgggct ttgtcagagt cttgctatcc   9420
ggtcgccttt gcttctgtgt ggccgctgct gttgctgccg ctgccgctgc cgccggtgca   9480
gtatggctg tagagatgac ggtagtaatg caggatgtta cgggggaagg cgaccgagg   9540
atggtagaga agaaagcggc gggcgaagga gatgttgccc ccacagtctt gcaagcaagc   9600
aactatggcg ttcttgtgcc cgcgccatga gcggtagcct tggcgctgtt gttgctcttg   9660
ggctaacggc ggcggctgct tggacttacc ggccctggtt ccagtggtgt cccatctacg   9720
gttgggtcgg cgaacgggca gtgccggcgg cgcctgagga gcggaggttg tagccatgg    9780
ggaaccggtt gccgatttct gggggcgccgg cgaggggaag cgaccgagg gtgacggtgt   9840
ttcgtctgac acctcttcga cctcggaagc ttcctcgtct aggctctccc agtcttccat   9900
catgtcctcc tcctcctcgt ccaaaacctc ctctgcctga ctgtcccagt attcctcctc   9960
gtccgtgggg gcggcggca gctgcagctt cttttgggt gccatcctgg gaagcaaggg    10020
cccgcggctg ctgctgatag ggctgcgcg gcggggggat tgggttgagc tcctcgccgg   10080
actgggggtc caagtaaacc ccccgtccct ttcgtagcaa aaacttttgg cgggcttttgt  10140
tgatggcttg caattggcca agaatgtggc cctgggtaat gacgcaggcg gtaagctccg   10200
catttgcggg gcgggattgg tcttcgtaga acctaatctc gtgggcgtgg tagtcctcag   10260
gtacaaattt gcgaaggtaa gccgacgtcc acagcccgg agtgagtttc aaccccggag   10320
ccgcggactt ttcgtcaggc gagggaccct gcagctcaaa ggtaccgata atttgacttt   10380
cgttaagcag ctgcgaattg caaaccaggg agcggtgcgg ggtgcatagg ttgcagcgac   10440
```

```
agtgacactc cagtagaccg tcaccgctca cgtcttccat tatgtcagag tggtaggcaa   10500
ggtagttggc tagctgcaga aggtagcagt ggccccaaag cggcggaggg cattcgcggt   10560
acttaatggg cacaaagtcg ctaggaagtg cacagcaggt ggcgggcaag attcctgagc   10620
gctctaggat aaagttccta aagttctgca acatgctttg actggtgaag tctggcagac   10680
cctgtgcag ggttttaagc aggcgttcgg ggaaaatgat gtccgccagg tgcgcggcca   10740
cggagcgctc gttgaaggcc gtccataggt ccttcaagtt ttgctttagc agtttctgca   10800
gctccttgag gttgcactcc tccaagcact gctgccaaac gcccatggcc gtctgccagg   10860
tgtagcatag aaataagtaa acgcagtcgc ggacgtagtc gcggcgcgcc tcgcccttga   10920
gcgtggaatg aagcacgttt tgcccaaggc ggttttcgtg caaaattcca aggtaggaga   10980
ccaggttgca gagctccacg ttggagatct tgcaggcctg gcgtacgtag ccctgtcgaa   11040
aggtgtagtg caatgtttcc tctagcttgc gctgcatctc cgggtcagca aagaaccgct   11100
gcatgcactc aagctccacg gtaacgagca ctgcggccat cattagtttg cgtcgctcct   11160
ccaagtcggc aggctcgcgc gtttgaagcc agcgcgctag ctgctcgtcg ccaactgcgg   11220
gtaggccctc ctctgtttgt tcttgcaaat ttgcatccct ctccagggc tgcgcacggc   11280
gcacgatcag ctcactcatg actgtgctca tgaccttggg gggtaggtta agtgccgggt   11340
aggcaaagtg ggtgacctcg atgctgcgtt ttagtacggc taggcgcgcg ttgtcaccct   11400
cgagttccac caacactcca gagtgacttt cattttcgct gttttcctgt tgcagagcgt   11460
ttgccgcgcg cttctcgtcg cgtccaagac cctcaaagat ttttggcact tcgttgagcg   11520
aggcgatatc aggtatgaca gcgccctgcc gcaaggccag ctgcttgtcc gctcggctgc   11580
ggttggcacg gcaggatagg ggtatcttgc agttttggaa aaagatgtga taggtggcaa   11640
gcacctctgg cacggcaaat acggggtaga agttgaggcg cgggttgggc tcgcatgtgc   11700
cgtttttcttg gcgttgggg ggtacgcgcg gtgagaatag ggtggcgttcg taggcaaggc   11760
tgacatccgc tatggcgagg ggcacatcgc tgcgctcttg caacgcgtcg cagataatgg   11820
cgcactggcg ctgcagatgc ttcaacagca cgtcgtctcc cacatctagg tagtcgccat   11880
gccttccgtc ccccgcccg acttgttcct cgtttgcctc tgcgttgtcc tggtcttgct   11940
ttttatcctc tgttggtact gagcggtcct cgtcgtcttt gcttacaaaa cctgggtct   12000
gctcgataat cacttcctcc tcctcaagcc ggggtgcctc gacggggaag gtggtaggcg   12060
cgttggcgg atcggtggag gcggtggtgg cgaactcaga gggggcggtt aggctgtcct   12120
tcttctcgac tgactccatg atctttttct gcctatagga aaggaaatg gccagtcggg   12180
aagaggagca gcgcgaaacc accccgagc gcggacgcgg tgcgcgcga cgtcccccaa   12240
ccatggagga cgtgtcgtcc ccgtcccgt cgccgccgcc tccccgggcg ccccccaaaaa   12300
agcggatgag gcggcgtatc gagtccgagg acgaggaaga ctcatcacaa gacgcgctgg   12360
tgccgcgcac acccagcccg cggccatcga cctcggcggc ggatttggcc attgcgccca   12420
agaagaaaaa gaagcgccct tctcccaagc ccgagcgccg gccatcacca gaggtaatcg   12480
tggacagcga ggaagaaaga gaagatgtgg cgctacaaat ggtgggtttc agcaacccac   12540
cggtgctaat caagcatggc aaaggaggta agcgcacagt gcggcggctg aatgaagacg   12600
acccagtggc gcgtggtatg cggacgcaag aggaagagga agagccccagc gaagcggaaa   12660
gtgaaattac ggtgatgaac ccgctgagtg tgccgatcgt gtctgcgtgg gagaagggca   12720
tgaggctgc gcgcgcgctg atggacaagt accacgtgga taacgatcta aaggcgaact   12780
tcaaactact gcctgaccaa gtggaagctc tggcggccgt atgcaagacc tggctgaacg   12840
aggagcaccg cgggttgcag ctgacctca ccagcaacaa gaccttttgtg acgatgatgg   12900
ggcgattcct gcaggcgtac ctgcagtcgt ttgcagaggt gacctacaag catcacgagc   12960
ccacgggcgc gcgttgtgg ctgcaccgct gcgctgagat cgaaggcgag cttaagtgtc   13020
tacacggaag cattatgata aataaggagc acgtgattga aatggatgtg acgagcgaaa   13080
acgggcagcg cgcgctgaag gagcagtcta gcaaggccaa gatcgtgaag aaccggtggg   13140
gccgaaatgt ggtgcagatc tccaacaccg acgcaaggtg ctgcgtgcac gacgcggcct   13200
gtccggccaa tcagttttcc ggcaagtctt gcggcaatgt ctttctctgaa ggcgcaaagg   13260
ctcaggtggc ttttaagcag atcaaggctt ttatgcaggc gctgtatcct aacgcccaga   13320
ccgggcacgg tcacctttg atgccactac ggtgcgagtg caactcaaag cctgggcacg   13380
cgcccttttt gggaaggcag ctaccaaagt tgactccgtt cgccctgagc aacgcggagg   13440
acctggacgg ggatctgatc tccgacaaga gcgtgctggc cagcgtgcac caccccgcgc   13500
tgatagtgtt ccagtgctgc aaccctgtgt atcgcaactc gcgcgcgcag ggcggaggcc   13560
ccaactgcga cttcaagata tcggcgcccc acctgctaaa cgcgttggtg atggtgcgca   13620
gcctgtggag tgaaaacttc accgagctgc cgcggatggt tgtgcctgag tttaagtgga   13680
gcactaaaca ccagtatcgc aacgtgtccc tgccagtggc gcatagcgat gcgcggcaga   13740
acccctttga ttttaaacg gcgcagacgg caagggtggg ggtaaataat caccccgagg   13800
tgtacaaata aaagcatttg cctttattga aagtgtctct agtacattat ttttacatgt   13860
ttttcaagtg acaaaaagaa gtggcgctcc taatctgcgc actgtggctg cggaagtagg   13920
gcgagtggcg ctccaggaag ctgtagagct gttcctggtt gcgacgcagg gtggctgta   13980
cctggggact gttgagcatg gagttgggta ccccggtaat aaggttcatg gtggggttgt   14040
gatccatggg agtttggggc cagttggcaa aggcgtggag aaacatgcag cagaatagtc   14100
cacaggcggc cgagttgggc ccctgtacg tttgggtgga cttttccagc gttatacagc   14160
ggtcggggga agaagcaatg gcgctacggc gcaggagtga ctcgtactca aactggtaaa   14220
cctgcttgag tcgctggtca gaaaagccaa agggctcaaa gaggtagcat gtttttgagt   14280
gcgggttcca ggcaaaggcc atccagtgta cgccccagt ctcggtccga gactcgaacc   14340
gggggtcccg cgactcaacc cttggaaaat aaccctccgg ctacagggag cgagccactt   14400
aatgctttgc ctttccagcc taaccgctta cgctgcgcgc ggccagtggc caaaaaagct   14460
agcgcagcag ccgccgcgcc tggaaggaag ccaaaaggaag cactccccg ttgtctgacg   14520
tcgcacacct gggttcgaca cgcggggcggt aaccgcatga atcacggcgg acggccggat   14580
acggggctcg aacccggtc gtccgccatg atacccttgc gaatttatcc accagaccac   14640
ggaagagtgc ccgcttacag gctctccttt tgcacggtag agcgtcaacg attgcgcgcg   14700
cctgaccggc cagagcgtcc cgaccatgga gcacttttg ccgctgcgca acatctggaa   14760
ccgcgtccgc gactttccgc gcgcctccac caccgccgcc ggcatcacct ggatgtccag   14820
gtacatctac ggatatcatc gccttatgtt ggaagatctc cccccggag ccccggccac   14880
cctacgctgg cccctctacc gccagccgcc gccgcacttt ttggtgggat accagtacct   14940
ggtgcggact tgcaacgact acgtatttga ctcgagggct tactcgcgtc tcaggtcacc   15000
cgagctctcg cagccgggtc accagaccgt taactggtcc gttatggcca actgcactta   15060
caccatcaac acgggcgcat accaccgctt tgtggacatg gatgacttcc agtctaccct   15120
cacgcaggtg cagcaggcca tattagccga gcgcgttgtc gccgacctag ccctgcttca   15180
```

```
gccgatgagg ggcttcgggg tcacacgcat gggaggaaga gggcgccacc tacggccaaa   15240
ctccgccgcc gccgcagcga tagatgcaag agatgcagga caagaggaag gagaagaaga   15300
agtgccggta gaaaggctca tgcaagacta ctacaaagac ctgcgccgat gtcaaaacga   15360
agcctggggc atggccgacc gcctgcgcat tcagcaggcc ggacccaagg acatggtgct   15420
tctg                                                                15424

SEQ ID NO: 393       moltype = DNA  length = 3849
FEATURE              Location/Qualifiers
misc_feature         1..3849
                     note = Description of Artificial Sequence: Synthetic
                     polynucleotide
source               1..3849
                     mol_type = other DNA
                     organism = synthetic construct
SEQUENCE: 393
cggcgtcaat acgggataat accgcgccac atagcagaac tttaaaagtg ctcatcattg   60
gaaaacgttc ttcggggcga aaactctcaa ggatcttacc gctgttgaga tccagttcga   120
tgtaacccac tcgtgcaccc aactgatctt cagcatcttt tactttcacc agcgttctg   180
ggtgagcaaa aacaggaagg caaaatgccg caaaaaaggg aataagggcg cacggaaat   240
gttgaatact catactcttc cttttcaat attattgaag catttatcag ggttattgtc   300
tcatgagcgg atacatattt gaatgtattt agaaaaataa acaaatagg gttccgcgca   360
catttccccg aaaagtgcca cctaaattgt aagcgttaat attttgttaa aattcgcgtt   420
aaatttttgt taaatcagct cattttttaa ccaataggcc gaaatcggca aaatccctta   480
taaatcaaaa gaatagaccg agataggggt gagtgttgtt ccagtttgga acaagagtcc   540
actattaaag aacgtggact ccaacgtcaa agggcgaaaa accgtctatc agggcgatgg   600
cccactacgt gaaccatcac cctaatcaag ttttttgga tcgaggtgcc gtaaagcact   660
aaatcggaac cctaaaggga gccccgatt tagagcttga cggggaaagc cggcgaacgt   720
ggcgagaaag gaagggaaga aagcgaaagg agcgggcgct agggcgctgg caagtgtagc   780
ggtcacgctg cgcgtaacca ccacacccgc cgcgcttaat gcgccgctac agggcgcgtc   840
ccattcgcca ttcaggctgc gcaactgttg ggaagggcga tcggtgcggg cctcttcgct   900
attacgccag ctgcgcgctc gctcgctcac tgaggccgcc cgggcaaagc ccgggcgtcg   960
ggcgaccttt ggtcgcccgg cctcagtgag cgagcgagcg cgcagagagg gagtggccaa   1020
ctccatcact agggggttcct tgtagttaat gattaaccccg ccatgctact tatctacgta   1080
gccatgctct aggaagagta ccattgacgt caataatgac gtatgttccc atagtaacgc   1140
caatagggac tttccattga cgtcaatggg tggagtattt acggtaaact gcccacttgg   1200
cagtacatca agtgtatcag tggtttgtct ggtcaaccac cgcggtctca gtggtgtacg   1260
gtacaaaccc agctaccggt cgccaccatg cccgccatga agatcgagtg ccgcatcacc   1320
ggcacccctga acggcgtgga gttcgagctg gtgggcggcg gagagggcac ccccgagcag   1380
ggccgcatga ccaacaagat gaagagcacc aaaggcgcgc tgaccttcag cccctacctg   1440
ctgagccacg tgatgggcta cggcttctac cacttcggca cctacccag cggctacgag   1500
aacccccttcc tgcacgccat caacaacggc ggctacacca caccccgcat cgagaagtac   1560
gaggacggcg gcgtgctgca cgtgagcttc agctaccgct acgaggccgg ccgcgtgatc   1620
ggcgacttca aggtggtggg caccgacttc cccgaggaca gcgtgatctt caccgacaag   1680
atcatccgca gcaacgccac cgtggagcac ctgcacccca tgggcgataa cgtgctggtg   1740
ggcagcttcg cccgcacctt cagcctgcgc gacggcggct actacagctt cgtggtggac   1800
agccacatgc acttcaagag cgccatccac cccagcatcc tgcagaacgg ggccccatg   1860
ttcgccttcc gccgcgtgga ggagctgcac agcaacaccg agtggggcat ctggagtac   1920
cagcacgcct tcaagacccc catcgccttc gccagatctc gagctcgatg agtttggaca   1980
aaccacaact agaatgcagt gaaaaaaatg ctttatttgt gaaattttgtg atgctattgc   2040
tttattttgtg ggccccggat cttcctagag catggctacg tagataagta gcatggcggg   2100
ttaatcatta actacaagga acccctagtg atggagttgg ccactccctc tctgcgcgct   2160
cgctcgctca ctgaggccgg gcgaccaaag gtcgcccgac gcccgggctt tgcccgggcg   2220
gcctcagtga gcgagcgagc gcgcagctgc attaatgaat cggccaacgc gcggggagag   2280
gcggtttgcg tattgggcgc tcttccgctt cctcgctcac tgactcgctg cgctcggtcg   2340
ttcggctgcg gcgagcggta tcagctcact caaaggcggt aatacggtta tccacagaat   2400
caggggataa cgcaggaaag aacatgtgag caaaaggcca gcaaaaggcc aggaaccgta   2460
aaaaggccgc gttgctggcg ttttttccata ggctccgccc cctgacgag catcacaaaa   2520
atcgacgctc aagtcagagg tggcgaaacc cgacaggact ataaagatac caggcgtttc   2580
ccctggaag ctccctcgtg cgctctcctg ttccgaccct gccgcttacc ggatacctgt   2640
ccgccttcct cccttcggaa gcgtggcgc tttctcatag ctcacgctgt aggtatctca   2700
gttcggtgta ggtcgttcgc tccaagctgg gctgtgtgca cgaaccccc gttcagcccg   2760
accgctgcgc cttatccggt aactatcgtc ttgagtccaa cccggtaaga cacgacttat   2820
cgccactggc agcagccact ggtaacagga ttagcagagc gaggtatgta ggcggtgcta   2880
cagagttctt gaagtggtgg cctaactacg gctacactag aagaacagta tttggtatct   2940
gcgctctgct gaagccagtt accttcggaa aaagagttgg tagctcttga tccggcaaac   3000
aaaccaccgc tggtagcggt ggtttttttg tttgcaagca gcagattacg cgcagaaaaa   3060
aaggatctca agaagatcct ttgatctttt ctacggggtc tgacgctcag tggaacgaaa   3120
actcacgtta agggattttg gtcatgagat tatcaaaaag gatcttcacc tagatccttt   3180
taaattaaaa atgaagtttt aaatcaatct aaagtatata tgagtaaact tggtctgaca   3240
gttaccaatg cttaatcagt gaggcaccta tctcagcgat ctgtctattt cgttcatcca   3300
tagttgcctg actccccgtc gtgtagataa ctacgatacg ggagggctta ccatctggcc   3360
ccagtgctgc aatgataccg cgagacccac gctcaccggc tccagattta tcagcaataa   3420
accagccagc cggaagggcc gagcgcagaa gtggtcctgc aactttatcc gcctccatcc   3480
agtctattaa ttgttgccgg gaagctagag taagtagttc gccagttaat agtttgcgca   3540
acgttgttgc cattgctaca ggcatcgtgg tgtcacgctc gtcgtttggt atggcttcat   3600
tcagctccgg ttcccaacga tcaaggcgag ttacatgatc cccccatgttg tgcaaaaaag   3660
cggttagctc cttcggtcct ccgatcgttg tcagaagtaa gttggccgca gtgttatcac   3720
tcatggttat ggcagcactg cataattctc ttactgtcat gccatccgta agatgctttt   3780
ctgtgactgg tgagtactca accaagtcat tctgagaata gtgtatgcgg cgaccgagtt   3840
```

```
                                            gctcttgcc                                            3849

SEQ ID NO: 394          moltype = DNA   length = 7336
FEATURE                 Location/Qualifiers
misc_feature            1..7336
                        note = Description of Artificial Sequence: Synthetic
                        polynucleotide
source                  1..7336
                        mol_type = other DNA
                        organism = synthetic construct
SEQUENCE: 394
atgccggggt tttacgagat tgtgattaag gtccccagcg accttgacga gcatctgccc   60
ggcatttctg acagctttgt gaactgggtg gccgagaagg aatgggagtt gccgccagat  120
tctgacatgg atctgaatct gattgagcag gcacccctga ccgtggccga gaagctgcag  180
cgcgactttc tgacgaatg gcgccgtgtg agtaaggccc cggaggctct tttctttgtg   240
caatttgaga agggagagag ctacttccac atgcacgtgc tcgtgaaaac caccggggtg  300
aaatccatgg tttttgggacg tttcctgagt cagattcgcg aaaaactgat tcagagaatt  360
taccgcggga tcgagccgac tttgccaaac tggttcgtca tcacaaagac cagaaatggc  420
gccggaggcg ggaacaaggt ggtgatgag tgctacatcc ccaattactt gctccccaaa   480
acccagcctg agctccagtg ggcgtggact aatatggaac agtatttaag cgcctgtttg  540
aatctcacgg agcgtaaacg gttggtgcg cagcatctga cgcacgtgtc gcagacgcag   600
gagcagaaca aagagaataa gaatcccaat tctgatgcgc cggtgatcag atcaaaaact  660
tcagccaggt acatggagct ggtcgggtgg ctcgtggaca aggggattac ctcggagaag  720
cagtggatcc aggaggacca ggcctcatac atctccttca atgcggcctc caactcgcgg  780
tcccaaatca aggctgcctt ggacaatgcg ggaaagatta tgagcctgac taaaaccgcc  840
cccgactacc tggtgggcca gcagcccgtg gaggacattt ccagcaatcg gatttataaa  900
attttggaac taaacgggta cgatcccaa tatgcggctt ccgtcttttct gggatgggcc   960
acgaaaaagt tcggcaagag gaacaccatc tggctgtttg gcctgcaac taccggggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggga aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacgaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt ggatgactg catctttgaa 1860
caataatga tttaaatcag gtatggctgc cgatggttat cttccagatt ggctcgagga 1920
caacctctct gagggcattc gcgagtggtg ggcgctgaaa cctggagccc cgaagcccaa 1980
agccaaccag caaaagcagg acgacggccg ggtctggtg cttcctggct acaagtacct 2040
cggacccttc aacggactcg acaaggggga gcccgtcaac gcggcggacg cagcggccct 2100
cgagcacgac aaggcctacg accagcagct gcaggcgggc gacaatccgt acctgcggta 2160
taaccacgcc gacgccgagt ttcaggagc tctgcaagaa gatacgtctt ttgggggcaa 2220
cctcgggcga gcagtcttcc aggccaagaa gcgggttctc gaacctctcg gtctggttga 2280
ggaaggcgct aagacggctc ctggaaagaa gagaccggta gagccatcac ccagcgttc 2340
tccagactcc tctacgggca tcggcaagaa aggccaagac cccgccagaa aaagactcaa 2400
ttttggtcag actggcgact cagagtcagt tccagaccct caacctctcg gagaacctcc 2460
agcagcccc tctggtgtgg gacctaatac aatggctgca ggcggtggcg caccaatggc 2520
agacaataac gaaggcgccg acggagtggg tagttcctcg ggaaattggc attgcgattc 2580
cacatggctg ggcgacagag tcatcaccac cagcacccga acctgggtcc tgcccactta 2640
caacaaccac ctctacaagc aaatctccaa cgggacatcg ggaggagcca ccaacgacaa 2700
cacctacttc ggctacagca ccccctgggg gtattttgac tttaacagat tccactgcca 2760
cttttcacca cgtgactggc agcgactcat caacaacaac tggggattcc ggccccaagag 2820
actcagcttc aagctcttca acatccaggt caaggaggtc acgcagaatg aaggcaccaa 2880
gaccatcgcc aataacctca ccagcaccat ccaggtgttt acggactcgg agtaccagct 2940
gccgtacgtt ctcggctctg cccaccaggg ctgcctgcct ccgttcccgg cggacgtgtt 3000
catgattccc cagtacggct acctaacact caacaacggt agtcaggccg tgggacgctc 3060
ctccttctac tgcctggaat actttccttc gcagatgctg agaaccggca acaacttcca 3120
gtttacttac accttcgagg acgtgcctttt ccacagcagc tacgcccaca gccagagctt 3180
ggaccggctg atgaatcctc tgattgacca gtacctgtac tacttgtctc ggactcaaac 3240
aacaggaggc acggcaaata cgcagactct gggcttcagc caaggtgggc ctaatacaat 3300
ggccaatcag gcaaagaact ggctgccagg acctgttac cgccaacaac gcgtctcaac 3360
gacaaccggg caaaacaaca tagcaactt tgcctggact gctgggacca aataccatct 3420
gaatggtaga aattcattgg ctaatcctgg catcgctatg gcaacacaa aagacgacga 3480
ggagcgtttt tttcccagta acgggatcct gattttggc aaacaaaatg ctgccagaga 3540
caatgcggat tacagcgatg tcatgctcac cagcgaggaa gaaatcaaa ccactaaccc 3600
tgtggctaca gaggaatacg gtatcgtggc agataacttg cagcagcaaa acacggctcc 3660
tcaaattgga actgtcaaca gccagggggc cttaccggt atggtctggc agaaccggga 3720
cgtgtacctg caggtccca tctgggcaa gattcctcac acggacggca acttccaccc 3780
gtctccgctg atgggcggct ttggcctgaa acatcctccg cctcagatcc tgatcaagaa 3840
cacgcctgta cctgcggatc ctcgaccac cttcaaccag tcaaagctga actctttcat 3900
cacgcaatac agcaccggac aggtcagcgt ggaaattgaa tggagctgc agaaggaaa 3960
cagcaagcgc tggaacccg agatccagta cacctccaac tactacaaat ctacaagtgt 4020
ggactttgct gttaatacag aaggcgtgta ctctgaaccc cgcccattg caccccgtta 4080
```

```
cctcacccgt aatctgtaat tgcctgttaa tcaataaacc ggttgattcg tttcagttga   4140
actttggtct ctgcgaaggg cgaattcgtt taaacctgca ggactagagg tcctgtatta   4200
gaggtcacgt gagtgttttg cgacattttg cgacaccatg tggtcacgct gggtatttaa   4260
gcccgagtga gcacgcaggg tctccatttt gaagcgggag gtttgaacgc gcagccgcca   4320
agccgaattc tgcagatatc catcacactg gcggccgctc gactagagcg gccgccaccg   4380
cggtggagct ccagcttttg ttcccttag tgagggttaa ttgcgcgctt ggcgtaatca   4440
tggtcatagc tgtttcctgt gtgaaattgt tatccgctca caattccaca acatacga   4500
gccgaagca taaagtgtaa agcctggggt gcctaatgag tgagctaact cacattaatt   4560
gcgttgcgct cactgcccgc tttccagtcg ggaaacctgt cgtgccagct gcattaatga   4620
atcggccaac gcgcggggag aggcggtttg cgtattgggc gctcttccgc ttcctcgctc   4680
actgactcgc tgcgctcggt cgttcggctg cggcgagcgg tatcagctca ctcaaaggcg   4740
gtaatacggt tatccacaga atcagggat aacgcaggaa agaacatgtg agcaaaaggc   4800
cagcaaaagg ccaggaaccg taaaaaggcc gcgttgctgg cgtttttcca taggctccgc   4860
cccctgacg agcatcacaa aaatcgacgc tcaagtcaga ggtggcgaaa cccgacagga   4920
ctataaagat accaggcgtt tcccctgga agctccctcg tgcgctctcc tgttccgacc   4980
ctgccgctta ccggatacct gtccgccttt ctccccttcgg gaagcgtggc gctttctcat   5040
agctcacgct gtaggtatct cagttcggtg taggtcgttc gctccaagct gggctgtgtg   5100
cacgaacccc ccgttcagcc cgaccgctgc gccttatccg gtaactatcg tcttgagtcc   5160
aacccggtaa gacacgactt atcgccactg gcagcagcca ctggtaacag gattagcaga   5220
gcgaggtatg taggcggtgc tacagagttc ttgaagtggt ggcctaacta cggctacact   5280
agaagaacag tatttggtat ctgcgctctg ctgaagccag ttaccttcgg aaaaagagtt   5340
ggtagctctt gatccggcaa acaaaccacc gctggtagcg gtggtttttt tgtttgcaag   5400
cagcagatta cgcgcagaaa aaaaggatct caagaagatc ctttgatctt ttctacgggg   5460
tctgacgctc agtggaacga aaactcacgt taagggattt tggtcatgag attatcaaaa   5520
aggatcttca cctagatcct tttaaattaa aaatgaagtt ttaaatcaat ctaaagtata   5580
tatgagtaaa cttggtctga cagttaccaa tgcttaatca gtgaggcacc tatctcagcg   5640
atctgtctat ttcgttcatc catagttgcc tgactcccg tcgtgtagat aactacgata   5700
cgggagggct taccatctgg ccccagtgct gcaatgatac cgcgagaccc acgctcaccg   5760
gctccagatt tatcagcaat aaaccagcca gccggaaggg ccgagcgcag aagtggtcct   5820
gcaactttat ccgcctccat ccagtctatt aattgttgcc ggggagctag agtaagtagt   5880
tcgccagtta atagtttgcg caacgttgtt gccattgcta caggcatcgt ggtgtcacgc   5940
tcgtcgtttg gtatggcttc attcagctcc ggttcccaac gatcaaggcg agttacatga   6000
tcccccatgt tgtgcaaaaa agcggttagc tccttcggtc ctccgatcgt tgtcagaagt   6060
aagttggccg cagtgttatc actcatggtt atggcagcac tgcataattc tcttactgtc   6120
atgccatccg taagatgctt ttctgtgact ggtgagtact caaccaagtc attctgagaa   6180
tagtgtatgc ggcgaccgag ttgctcttgc ccggcgtcaa tacgggataa taccgcgcca   6240
catagcagaa ctttaaaagt gctcatcatt ggaaaacgtt cttcggggcg aaaactctca   6300
aggatcttac cgctgttgag atccagttcg atgtaaccca ctcgtgcacc caactgatct   6360
tcagcatctt ttactttcac cagcgtttct gggtgagcaa aaacaggaag gcaaaatgcc   6420
gcaaaaaagg gaataagggc gacacggaaa tgttgaatac tcatactctt cctttttcaa   6480
tattattgaa gcatttatca gggttattgt ctcatgagcg gatacatatt tgaatgtatt   6540
tagaaaaata aacaaatagg ggttccgcgc acatttcccc gaaaagtgcc acctaaattg   6600
taagcgttaa tattttgtta aaattcgcgt taaattttta ttaaatcagc tcattttta   6660
accaataggc cgaaatcggc aaaatccctt ataaatcaaa agaatagacc gagatagggt   6720
tgagtgttgt tccagtttgg aacaagagtc cactattaaa gaacgtggac tccaacgtca   6780
aagggcgaaa aaccgtctat cagggcgatg gcccactacg tgaaccatca ccctaatcaa   6840
gttttttggg gtcgaggtgc cgtaaagcac taaatcagaa cccctaaaggg agcccccgat   6900
ttagagcttg acggggaaag ccggcgaacg tggcgagaaa ggaagggaag aaagcgaaag   6960
gagcgggcgc tagggcgctg gcaagtgtag cggtcacgct gcgcgtaacc accacacccg   7020
ccgcgcttaa tgcgccgcta cagggcgcgt cccattcgcc attcaggctg cgcaactgtt   7080
gggaagggcg atcggtgcgg gcctcttcgc tattacgcca ggtgcgaaa ggggatgtg   7140
ctgcaaggcg attaagttgg gtaacgccca ggttttccca gtcacgacgt tgtaaaacga   7200
cggccagtga gcgcgcgtaa tacgactcac tataggcga attgggtacc gggcccccc   7260
tcgatcgagg tcgacggtat cggggagct cgcagggtct ccattttgaa gcgggaggtt   7320
tgaacgcgca gccgcc                                                   7336
```

SEQ ID NO: 395         moltype = DNA   length = 969
FEATURE                Location/Qualifiers
misc_feature        1..969
                           note = Description of Artificial Sequence: Synthetic
                           polynucleotide
source                 1..969
                           mol_type = other DNA
                           organism = synthetic construct
SEQUENCE: 395

```
ccccaactgg ggtaaccttt gggctccccg ggcgcgacta aagctgcga gcaacttcac    60
ttgggtatgc cggcggtagc gcttaccgtt cgtataatgt atgctatacg aagttatccg   120
aagccgctag cggtggtttg tctggtcaac caccgcggtc tcagtggtgt acggtacaaa   180
cccagctacc ggtcgccacc atgcccgcca tgaagatgca gtgccgcatc accggcaccc   240
tgaacggcgt ggagttcgag ctggtgggcg gcggagaggg cacccccgag cagggccgca   300
tgaccaacaa gatgaagagc accaaggcg ccctgacctt cagccctac ctgctgagcc   360
acgtgatggg ctacggcttc taccacttcg gcacctaccc cagcggctac gagaacccct   420
tcctgcacgc catcaacaac ggcggctaca caacacccg catcgagaag tacgaggacg   480
gcggcgtgct gcacgtgagc ttcagctacc gctacgaggc gtcggcatcg acggccgcat   540
tcaaggtggt gggcaccggc ttccccgagg acagcgtgat cttcaccgac aagatcatcc   600
gcagcaacgc caccgtggag cacctgcacc ccatgggcga taacgtgctg gtgggcagct   660
tcgcccgcac cttcagcctg cgcgacgcg gctactacag cttcgtggtg gacagccaca   720
tgcacttcaa gagcgccatc caccccagca tcctgcagaa cggggccc atgttcgcct   780
tccgccgcgt ggaggagctg cacagcaaca ccgagctggg catcgtggag taccagcacg   840
```

```
ccttcaagac ccccatcgcc ttcgccagat ctcgagctcg atgagtttgg acaaaccaca    900
actagaatgc agtgaaaaaa atgctttatt tgtgaaattt gtgatgctat tgctttattt    960
gtgggcccg                                                            969
```

SEQ ID NO: 396         moltype = DNA  length = 4769
FEATURE                Location/Qualifiers
misc_feature        1..4769
                        note = Description of Artificial Sequence: Synthetic
                        polynucleotide
source                  1..4769
                        mol_type = other DNA
                        organism = synthetic construct

```
SEQUENCE: 396
tgatcccctg cgccatcaga tccttggcgg cgagaaagcc atccagttta ctttgcaggg      60
cttcccaacc ttaccagagg gcgcccccagc tggcaattcc ggttcgcttg ctgtccataa    120
aaccgcccag tctagctatc gccatgtaag cccactgcaa gctacctgct ttctctttgc    180
gcttgcgttt tcccttgtcc agatagccca gtagctgaca ttcatccggg gtcagcaccg    240
tttctgcgga ctggctttct acgtgctcga gggggccaa acggtctcca gcttggctgt    300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactgaa gcctttcgttt    540
tatctgttgt ttgtcggtga acgctctcct gagtaggaca aatccgccgg gagcggattt    600
gaacgttgcg aagcaacggc ccggagggtg gcgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atccttttt tctgcgcgta atctgctgct tgcaaacaaa aaaaccaccg ctaccagcgg    900
tggtttgttt gccggatcaa gagctaccaa ctcttttttcc gaaggtaact ggcttcagca    960
gagcgcagat accaaatact gtccttctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
agcggtcggg ctgaacgggg ggttcgtgca cacagcccag cttggagcga acgacctaca   1200
ccgaactgag atacctacag cgtgagctat gagaaagcgc cacgcttccc gaaggagaa   1260
aggcggacag gtatccggta agcggcaggg tcggaacagg agagcgcacg agggagcttc   1320
caggggggaaa cgcctggtat ctttatagtc ctgtcgggtt tcgccaccctc tgacttgagc   1380
gtcgattttt gtgatgctcg tcagggggggc ggagcctatg gaaaaacgcc agcaacgcgg   1440
ccttttttacg gttcctggcc ttttgctggc cttttgctca catgttcttt cctgcgttat   1500
cccctgattc tgtggataac cgtattaccg cctttgagtg agctgatacc gctcgccgca   1560
gccgaacgac cgagcgcagc gagtcagtga gcgaggaagc ggaagagcgc ctgatgcggt   1620
attttctcct tacgcatctg tgcggtattt cacaccgcat atggtgcact ctcagtacaa   1680
tctgctctga tgccgcatag ttaagccagt atacactccg ctatcgctac gtgactgggt   1740
catggcgtgcg ccccgacacc cgccaacacc cgctgacgcg ccctgacggg cttgtctgct   1800
cccggcatcc gcttacagac aagctgtgac cgtctccggg agctgcatgt gtcagaggtt   1860
ttcaccgtca tcaccgaaac gcgcgaggca gcagatcaat tcgcgcgcga aggcgaagcg   1920
gcatgcataa tgtgcctgtc aaatggacga agcagggatt ctgcaaaccc tatgctactc   1980
cgtcaagccg tcaattgtct gattcgttac caattatgac aacttgacgg ctacatcatt   2040
cacttttttct tcacaaccgg cacggaactc gctcgggctg gccccggtgc attttttaaa   2100
tacccgcgag aaatagagtt gatcgtcaaa accaacattg cgaccgacgg tggcgatagg   2160
catccggggtg gtgctcaaaa gcagcttcgc ctggctgata cgttggtcct cgcgccagct   2220
taagacgcta atccctaact gctggcgaa aagatgtgac agacgcgacg gcgacaagca   2280
aacatgctgt gcgacgctgg cgatacatta ccctgttatc cctagatgac attaccctgt   2340
tatcccagat gacattaccc tgttatcccct agatgacatt accctgttat ccctagatga   2400
catttacccct gttatcccta tgatgacatta ccctgttatc ccagatgaca ttaccctgtt   2460
atccctagat acattaccct gttatcccag atgacatacc tgttatccca tagatgacat   2520
taccctgtta tcccagatga cattaccctg ttatcctag atacattacc ctgttatccc   2580
agatgacata ccctgttatc cctagatgac attaccctgt tatcccagat gacattaccc   2640
tgttatccct agatacatta ccctgttatc cagatgacat accctgttatcc ctagatg    2700
acattaccct gttatcccag atgacattac cctgttatcc ctagatacatt accctgtta   2760
tcccagatga catacctgt tatcccagat gacattacct gttatccca gatgacatt   2820
accctgttat ccctagatac attaccctgt tatcccagat gacataccct gttatccta   2880
gatgacatta ccctgttatc ccagatgaca ttaccctgtt atcctagat acattacct   2940
gttatcccag atgacatacc ctgttatccc tagatgacat accctgtta tcccagataa   3000
actcaatgat gatgatgatg atggtcgaga ctcagcggcc aggcgtgcct gggctcccc   3060
gggcgcgatg cccgccatga gatcgagtg ccgcatcacc ggcaccctga acggcgtgga   3120
gttcgagctg gtgggcgcg gagagggcac cccgagcag ggccgcatga ccaacaagat   3180
gaagagcacc aaaggcgccc tgaccttcag cccctacctg ctgagccacg tgatgggcta   3240
cggcttctac cacttggca cctaccccag cggctacgag aaccctcc tgcacgccat   3300
caacaacggc tgctacacca acaccagac cgagaagtac gaggacggcc tgcgtgctgca   3360
cgtgagcttc agctaccgct acgaggccgg ccgcgtgatc ggcgacttca aggtggtggg   3420
gaccggcttc cccgaggaca cgtgatctt caccgacaag atcatccgca gcaacgccac   3480
cgtggagcac ctgcacccca tgggcgataa cgtgctggtg ggcagcttcg cccgcacctt   3540
cagcctgcgc gacggcgct actacagctt cgtggtggac agccacatgc acttcaagag   3600
gccgcatcac cccagcatcc tgcagaacga ggcccatg ttcgcctcc gccgcgtgga   3660
ggagctgcac agcaacaccc agctggggag cgtgagtac cagcacgcct tcaagacccc   3720
catcgccttc gccagatctc agctcgagg tggtttgtct ggtcaaccac cgcggtctca   3780
gtggtgtacg gtacaaaccc accccaactg gggtaacctt tgagttctct cagttggggg   3840
taatcagcat catgatgtgg taccacatca tgatgctgat tataagaatg   3900
cggccgccac actctagtgg atctcgagtt aataattcag aagaactcgt caagaaggcg   3960
```

```
atagaaggcg atgcgctgcg aatcgggagc ggcgataccg taaagcacga ggaagcggtc    4020
agcccattcg ccgccaagct cttcagcaat atcacgggta gccaacgcta tgtcctgata    4080
gcggtccgcc acaccagcc ggccacagtc gatgaatcca gaaaagcggc cattttccac     4140
catgatattc ggcaagcagg catcgccatg ggtcacgacg atcctcgc cgtcgggcat      4200
gctcgccttg agcctggcga acagttcggc tggcgcgagc ccctgatgct cttcgtccga    4260
atcatcctga tcgacaagac cggcttccat ccgagtacgt gctcgctcga tgcgatgttt    4320
cgcttggtgg tcgaatgggc aggtagccgg atcaagcgta tgcagccgcc gcattgcatc    4380
agccatgatg gatactttct cggcaggagc aaggtgtaga tgacatggag atcctgcccc    4440
ggcacttcgc ccaatagcag ccagtccctt cccgcttcag tgacaacgtc gagcacagct    4500
gcgcaaggaa cgcccgtcgt ggccagccac gatagccgag ctgcctcgtc ttgcagttca    4560
ttcagggcac cggacaggtc ggtcttgaca aaaagaaccg ggcgccctg cgctgacagc     4620
cggaacacgg cggcatcaga gcagccgatt gtctgttgtg cccagtcata gccgaatagc    4680
ctctccaccc aagcggccgg agaacctgcg tgcaatccat cttgttcaat catgcgaaac    4740
gatcctcatc ctgtctcttg atcagagct                                     4769

SEQ ID NO: 397           moltype = DNA   length = 797
FEATURE                  Location/Qualifiers
misc_feature             1..797
                         note = Description of Artificial Sequence: Synthetic
                         polynucleotide
source                   1..797
                         mol_type = other DNA
                         organism = synthetic construct
SEQUENCE: 397
ccccaactgg ggtaaccttt gggctccccg ggcgcgatgg tgagcaaggg cgaggaggat     60
aacatggcca tcatcaagga gttcatgcgc ttcaaggtgc acatggaggg ctccgtgaac    120
ggccacgagt tcgagatcga gggcgagggc gagggccgcc cctacgaggg cacccagacc    180
gccaagctga aggtgaccaa gggtggcccc ctgcccttcg cctgggacat cctgtcccct    240
cagttcatgt acggctccaa ggcctacgtg aagcaccccg ccgacatccc cgactacttg    300
aagctgtcct tccccgaggg cttcaagtgg gagcgcgtga tgaacttcga ggacggcggc    360
gtggtgaccg tgacccagga ctcctccctg caggacggcg agttcatcta caaggtgaag    420
ctgcgcggca ccaacttccc ctccgacggc cccgtaatgc agaagaagac catgggctgg    480
gaggcctcct ccgagcggat gtaccccgag gacggcgccc tgaagggcga gatcaagcag    540
aggctgaagc tgaaggacgg cggccactac tgacgctgagg tcaagaccac ctacaaggcc    600
aagaagcccg tgcagctgcc cggcgcctac aacgtcaaca tcaagttgga catcacctcc    660
cacaacgagg actacaccat cgtggaacag tacgaacgcg ccgagggccg ccactccacc    720
ggcggcatgg acgagctgta caagggtggt ttgtctggtc aaccaccgcg agctcagtgg    780
tgtacggtac aaaccca                                                   797

SEQ ID NO: 398           moltype = DNA   length = 815
FEATURE                  Location/Qualifiers
misc_feature             1..815
                         note = Description of Artificial Sequence: Synthetic
                         polynucleotide
source                   1..815
                         mol_type = other DNA
                         organism = synthetic construct
SEQUENCE: 398
ccccaactgg ggtaaccttt gggctccccg ggcgcggccg ccaccatggt gtccaagggt     60
gaggaacttt taccggagt ggtgccgata ctggtagagc tggatggcga cgtaaacggg     120
cacaagttca gtgtacgggg agagggcgag ggcgacgcta cgaatgggaa attgactttg    180
aaatttattt gcaccacggg caaattgccg gtcccgtggc caactttggt tacgaccttg    240
acctatggcg ttcagtgttt ctcacggtac ccagaccaca tgaaacagca tgactttttt    300
aagtcagcga tgccggaggg atatgtgcaa gaacggacta tctcatttaa agatgatggc    360
acatataaga caagagcgga agtcaaattc gaagggggaca ccctcgtcaa tcgaatagaa    420
ctcaagggaa tagacttcaa agaagatggt aatatactgg ggcacaaact cgaatacaat    480
ttcaacagtc ataacgtcta catcactgcc gacaaacaaa aaaatgggat caaagcgaac    540
ttcaaaatcc gacataatgt cgaggatggg agcgtccaac tggcagacca ttaccagcaa    600
aatactccaa taggtgatgg tccagtgctt ttgccagata atcattatct tagctatcag    660
agcaagttga gtaaggatcc gaatgaaaag cgagatcaca tggtcttgct ggagtttgtt    720
acggcggctg gtatcacact tggtatggat gaattgtaca agggtggttt gtctggtcaa    780
ccaccgcgga ctcagtggtg tacggtacaa accca                               815

SEQ ID NO: 399           moltype = DNA   length = 1660
FEATURE                  Location/Qualifiers
misc_feature             1..1660
                         note = Description of Artificial Sequence: Synthetic
                         polynucleotide
source                   1..1660
                         mol_type = other DNA
                         organism = synthetic construct
SEQUENCE: 399
ccccaactgg ggtaaccttt gggctccccg ggcgcggcca ccatgaaatg ggttactttc     60
atatctctgt tgtttttgtt ttcctctagt tccagggcca tgccgtcttc tgtctcgtgg    120
ggcatcctcc tgctggcagg cctgtgctgc ctggtccctg tctccctggc tgaggatccc    180
cagggagatg ctgcccagaa gacagataca tccaccatg atcaggatca cccaaccttc    240
aacaagatca cccccaacct ggctgagttc gccttcagcc tataccgcca gctggcacac    300
cagtccaaca gcaccaatat cttcttctcc ccagtgagca tcgctacagc ctttgcaatg    360
ctctccctgg ggaccaaggc tgacactcac gatgaaatcc tggagggcct gaatttcaac    420
```

```
ctcacggaga ttccggaggc tcagatccat gaaggcttcc aggaactcct ccgtaccctc    480
aaccagccag acagccagct ccagctgacc accggcaatg gcctgttcct cagcgagggc    540
ctgaagctag tggataagtt tttggaggat gttaaaaagt tgtaccactc agaagccttc    600
actgtcaact tcggggacac cgaagaggcc aagaaacaga tcaacgatta cgtggagaag    660
ggtactcaag ggaaaattgt ggatttggtc aaggagctag acagagacac agttttttgct   720
ctggtgaatt acatcttctt taaaggcaaa tgggagagac cctttgaagt caaggacacc    780
gaggaagagg acttccacgt ggaccaggtg accaccgtga aggtgcctat gatgaagcgt    840
ttaggcatgt ttaacatcca gcactgtaag aagctgtcca gctgggtgct gctgatgaaa    900
tacctgggca atgccaccgc catcttcttc ctgcctgata ggggaaaact acagcacctg    960
gaaaatgaac tcacccacga tatcatcacc aagttcctgg aaaatgaaga cagaaggtct   1020
gccagcttac atttacccaa actgtccatt actggaacct atgatctgaa gagcgtcctg   1080
ggtcaactgg gcatcactaa ggtcttcagc aatgggctg acctctccgg ggtcacagag    1140
gaggcacccc tgaagctctc caaggccgtg cataaggctg tgctgaccat cgacgagaaa   1200
gggactgaag ctgctggggc catgtttta gaggccatac ccatgtctat cccccccgag    1260
gtcaagttca acaaacccct tgtcttctta atgattgaac aaaataccaa gtctcccctc   1320
ttcatgggaa aagtggtgaa tcccacccaa aaataagaat tctaactaga gctcgctgat   1380
cagcctcgac tgtgccttct agttgccagc catctgttgt ttgcccctcc cccgtgcctt   1440
ccttgaccct ggaaggtgcc actcccactg tcctttccta ataaaatgag gaaattgcat   1500
cgcattgtct gagtaggtgt cattctattc tggggggtgg ggtggggcag gacagcaagg   1560
gggaggattg ggaagagaat agcaggcatg ctggggagcg agctcgaggt ggtttgtctg   1620
gtcaaccacc gcggtctcag tggtgtacgg tacaaaccca                          1660

SEQ ID NO: 400        moltype = DNA  length = 4906
FEATURE               Location/Qualifiers
misc_feature          1..4906
                      note = Description of Artificial Sequence: Synthetic
                       polynucleotide
source                1..4906
                      mol_type = other DNA
                      organism = synthetic construct
SEQUENCE: 400
ccccaactgg ggtaaccttt gggctccccg ggcgcggcca ccatgaaatg ggttactttc     60
atatctctgt tgtttttgtt ttcctctagt tccaggccca tgacgaggat tttgacagct    120
ttcaaagtgg tgaggacact gaagactggt tttggcttta ccaatgtgac tgcacaccaa    180
aaatggaaat tttcaagacc tggcatcagg ctccttctg tcaaggcaca gacagcacac     240
attgtcctgg aagatggaac taagatgaaa ggttactcct ttggccatcc atcctctgtt    300
gctggtgaag tggttttaa tactggcctg ggagggtacc cagaagctat tactgaccct    360
gcctacaaag gacagattct cacaatggcc aaccctatta ttgggaatgg tggagctcct    420
gatactactg ctctgatga actgggactt agcaaatatt tggagtctaa tggaatcaag    480
gtttcaggtt tgctggtgct ggattatagt aaagactaca accactggct ggctaccaag    540
agtttagggc aatggctaca ggaagaaaag gttcctgcaa tttatggagt ggacacaaga    600
atgctgacta aaataattcg ggataagggt accatgcttg gaagattga atttgaaggt    660
cagcctgtgg attttgtgga tccaaataaa cagaatttga ttgctgaggt ttcaaccaag   720
gatgtcaaag tgtacggcaa aggaaacccc acaaaagtgg tagctgtaga ctgtgggatt   780
aaaaacaatg taatccgcct gctagtaaag cgaggagctg aagtgcactt agttccctgg   840
aaccatgatt tcaccaagat ggagtatgat gggattttga tcgcgggagg accggggaac   900
ccagctcttg cagaaccact aattcagaat gtcagaagaa ttttggaggt tgatgccaag   960
gagccattgt ttggaatcag tacaggaaac ttaataacag gattggctgc tggtgccaaa   1020
acctacaaga tgtccatggc caacagaggg cagaatcagc ctgttttgaa tatcacaaac   1080
aaacaggctt tcattactgc tcagaatcat ggctatgcct ggacaacac cctccctgct   1140
ggctggaaac cacttttttgt gaatgtcaac gatcaaacaa atgaggggat tatgcatgag  1200
agcaaaccct tcttcgctgt gcagttccac ccagaggtca ccccgggccg aatagacact   1260
gagtacctgt tgattccttt ttctcactg ataaagaaag gaaaagctac caccattaca    1320
tcagtcttac cgaagccagc actagttgca tctcggttg aggtttccaa agtccttatt    1380
ctaggatcag gaggtctgtc cattggtcag gctggagaat ttgattactc aggatctcaa   1440
gctgtaaaag ccatgaagga agaaaatgtc aaaactgttc tgatgaaccc aaacattgca   1500
tcagtccaga ccaatgaggt gggcttaaag caagcggata ctgtctactt tcttcccatc   1560
accccctcagt ttgtcacaga ggtcatcaag gcagaacagc cagatgggtt aattctgggc   1620
atgggtggcc agacagctct gaactgtgga gtggaactat tcaagagagg tgtgctcaag   1680
gaatatggtg tgaaagtcct gggaacttca gttgagtcca ttatgctac ggaagacaag    1740
cagctgtttt cagataaact aaatgagatc aatgaaaaga ttgctccaag ttttgcagtg   1800
gaatcgattg aggatgcact gaaggcagca gacaccattg ctacccagt gatgatccgt   1860
tccgcctatg cactgggtgg gttaggctca ggcatctgtc caacagaga ctttgatg     1920
gacctcagca caaaggcctt tgctatgacc aaccaaattc tggtggagaa gtcagtgaca  1980
ggttggaaag aaaatagaata tgaagtggtt cgagatgctg atgacaattg tgtcactgtc   2040
tgttaacatga aaaatgttga tgccatgggt gttcacacag gtgactcagt tgtgtggct    2100
cctgcccaga cactctccaa tgccgagttt cagatgttga cgtacttc aatcaatgtt     2160
gttcgccact gggcattgt gggtgaatgc aacattcagt ttgccctgc tcctacctca    2220
atggaatact gcatcattga agtgaatgcc agactgctgc gaagctctgc tctggcctca   2280
aaagccactg gctacccatt ggcattcatt gctgcaaaga ttgccctagg aatcccactt   2340
ccagaaatta gaacgtcgt atccgggaag acatcagcct gttttgaacc tagcctggat   2400
tacatggtca ccaagattcc ccgctgggat cttgaccgtt tcatggaac atctagccga    2460
attggtagct ctatgaaaag tgtaggagag gtcatggcta ttggtcgtac ctttgaggag   2520
agtttccaga aagctttacg gatgtgccac ccatctatag aaggtttcac tccccgttcc   2580
ccaatgaaca aagaatggcc atctaattta gatcttagaa aagagttgtc tgaaccaagc   2640
agcacgcgta tctatgccat tgccaaggcc attgatgaca catgtccct tgatgagatt    2700
gagaagctca catacattga caagtggttt tgtataagga tgcgtgatat tttaaacatg    2760
gaaaagacac tgaaggcct caacagtgag tccatgacag aagaaccct gaaagggca     2820
aaggagattg ggttctcaga taagcagatt tcaaaatgcc ttgggctcac tgaggcccag   2880
```

```
acaagggagc tgaggttaaa gaaaaacatc caccctt999 ttaaacagat tgatacactg 2940
gctgcagaat acccatcagt aacaaactat ctctatgtta cctacaatgg tcaggagcat 3000
gatgtcaatt tgatgacca tggaatgatg gtgctaggct gtggtccata tcacattggc 3060
agcagtgtgg aatttgattg gtgtgctgtc tctagtatcc gcacactgcg tcaacttggc 3120
aagaagacgg tggtggtgaa ttgcaatcct gagactgtga gcacagactt tgatgagtgt 3180
gacaaactgt actttgaaga gttgtccttg gagagaatcc tagacatcta ccatcaggag 3240
gcatgtggtg gctgcatcat atcagttgga ggccagattc caaacaacct ggcagttcct 3300
ctatacaaga atggtgtcaa gatcatgggc acaagccccc tgcagatcga cagggctgag 3360
gatcgctcca tcttctcagc tgtcttggat gagctgaagg tggctcaggc acctt999aa 3420
gctgttaata ctttgaatga agcactggaa tttgcaaagt ctgtggacta cccctgcttg 3480
ttgaggcctt cctatgtttt gagtgggtct gctatgaatg tggtattctc tgaggatgag 3540
atgaaaaaat tcctagaaga ggcgactaga gtttctcagg agcacccagt ggtgctgaca 3600
aaatttgttg aaggggcccg agaagtagaa atggacgctg ttggcaaaga tggaagggtt 3660
atctctctcatg ccatctctga acatgttgaa gatgcaggtg tccactcggg aggatgccact 3720
ctgatgctgc ccacacaaac catcagccaa ggggccattg aaaaggtgaa ggatgctacc 3780
cggaagattg caaaggcttt tgccatctct ggtccattca acgtccaatt tcttgtcaaa 3840
ggaaatgatg tcttggtgat tgagtgtaac ttgagagctt ctcgatcctt cccctttgtt 3900
tccaagactc ttggggttga cttcattgat gtggccacca aggtgatgat tggagagaat 3960
gttgatgaga aacatcttcc aacattggac catcccataa ttcctgctga ctatgttgca 4020
attaaggctc ccatgttttc ctggccccgg ttagggatg ctgaccccat tctgagatgt 4080
gagatggctt ccactggaga ggtggcttgc tttggtgaag gtattcatac agccttccta 4140
aaggcaatgc tttccacagg atttaagata ccccagaaag gcctcctgat aggcatccag 4200
caatcattcc ggccaagatt ccttggtgtg gctgaacaat tacacaatga aggtttcaag 4260
ctgtttgcca cggaagccac atcagactgg ctcaacgcca acaatgtccc tgccacccca 4320
gtggcatggc cgtctcaaga aggacagaat cccagcctct cttccatcag aaaattgatt 4380
agagatggca gcattgacct agtgattaac cttcccaaca acaacactaa atttgtccat 4440
gataattatg tgattcggag gacagctgtt gatagtggaa tccctctcct cactaatttt 4500
caggtgacca aactttttgc tgaagctgtg cagaaatctc gcaaggtgga ctccaagagt 4560
cttttccact acaggcagta cagtgctgga aaagcagcat aggaattcta actagagctc 4620
gctgatcagc ctcgactgtg ccttctagtt gccagccatc tgttgtttgc ccctccccg 4680
tgccttcctt gaccctggaa ggtgccactc ccactgtcct ttcctaataa aatgaggaaa 4740
ttgcatcgca ttgtctgagt aggtgtcatt ctattctggg gggtggggtg gggcaggaca 4800
gcaaggggga ggattgggaa gagaaatagca ggcatgctgg ggagcgagct cgaggtggtt 4860
tgtctggtca accaccgcgg tctcagtggt gtacggtaca aaccca      4906

SEQ ID NO: 401          moltype = DNA   length = 4882
FEATURE                 Location/Qualifiers
misc_feature            1..4882
                        note = Description of Artificial Sequence: Synthetic
                        polynucleotide
source                  1..4882
                        mol_type = other DNA
                        organism = synthetic construct
SEQUENCE: 401
ccccaactgg ggtaaccttt gggctccccg ggcgcgacta taagctgcga gcaacttcac   60
ttgggtatgc cggcggtagc gcttaccgtt cgtataatgt atgctatacg aagttatccg  120
aagccgctag cggtggtttg tctggtcaac caccgcgtc tcagtggtgt acggtacaaa  180
cccacccgag agaccatgca gaggtcgcct ctggaaaagg ccagcgttgt ctccaaactt  240
ttctttagct ggactagacc cataccttcgt aaaggataca gacagcgcct ggaattgtca  300
gacatatacc aaatcccttc tgttgattct gctgacaatc tatctgaaaa attggaaaga  360
gaatgggata gagagctggc ttcaaagaaa aatcctaaca tcattaatgc ccttcggcga  420
tgttttttct ggagatttat gttctatgga atctttttat atttagggga agtcaccaaa  480
gcagtacagc ctctccttact gggaagaatc atagcttcct atgacccgga taacaaggag  540
gaacgctcta tcgcgattta tctaggcata ggcttatgcc ttctctttat tgtgaggaca  600
ctgctcctac acccagccat tttttgcctt catcacattg gaatgcagat gagaatagct  660
atgtttagtt tgatttataa gaagacttta aagctgtcaa gccgtgttct agataaaata  720
agtattggac aacttgttag tctcctttcc aacaacctga caaatttga tgaaggactt  780
gcattggcac atttcgtgtg gatcgctcct ttgcaagtgg cactcctcat ggggctaatc  840
tgggagttgt tacaggcgtc tgccttctgt ggacttggtt tcctgatagt ccttgccctt  900
tttcaggctg ggctagggag aatgatgatg aagtacagaa atcagagagc tgggaagatc  960
agtgaaagac ttgtgattac ctcagaaatg attgaaaata tccaatctgt taaggcatac 1020
tgctgggaag aagcaatgga aaaaatgatt gaaaacttaa gacaaacaga actgaaactg 1080
actcggaagg cagcctatgt gagatacttc aatagctcag cctcttcttc tcagggttc 1140
tttgtggtgt ttttatctgt gcttcccact gcactaatca aaggaatcat cctcccggaaa 1200
atattcacca ccatctcatt ctgcattgtt ctgcgcatgc cggtcactcg gcaatttccc 1260
tgggctgtac aaacatggta tgactctctt ggagcaataa acaaaataca ggatttctta 1320
caaaagcaag aatataagac attggaatat aacttaacga ctacagaagt agtgatggag 1380
aatgtaacag ccttctggga ggagggattt ggggaattta ttgagaaagc aaaacaaaac 1440
aataacaata gaaaaacttc taatggtgat gacagcctct tcttcagtaa tttctcactt 1500
cttggtactc ctgtcctgaa agatattaat ttcaagatag aaagaggaca gttgttggcg 1560
gttgctggat ccactggagc aggcaagact tcacttctaa tggtgattat gggagaactg 1620
gagccttcag agggtaaaat taagcacagt ggaagaattt cattctgttc tcagtttcc 1680
tggattatgc ctggcaccat taagaaaaat atcatctttg gtgtttccta tgatgaatat 1740
agagaa gcgtcatcaa agcatgccaa ctagaaggag acatctccaa gttttgagag 1800
aaagacaata tagttcttgg agaaggtgga atcacactga gtgaggtca acgagcaaga 1860
atttctttag caagagcagt atacaaagat gctgatttgt atttattaga ctctcctttt 1920
ggatacctag acgtattgac tgagaaggag atcttcgagt cctgcgtttg caagcttatg 1980
gccaataaga caagaatcct ggttacaagt aagatggagc cctgaagaa ggccgataag 2040
attctgatcc tgcacgaggg atcttcatac ttctacggca ctttcagcga gcttcagaac 2100
```

```
ttgcaacctg atttctctag caagcttatg ggctgcgact cctttgatca gttctctgcc  2160
gagcgtcgca actccattct gaccgaaaca ctgcataggt tttccctcga gggcgacgca  2220
ccagtgtctt ggactgagac taagaagcag agcttcaagc aaaccggcga attcggtgag  2280
aagagaaaga acagtatcct gaaccccatt aattcaattc ggaagttcag tatcgttcag  2340
aaaacgcctc ttcagatgaa cgggattgag gaagactcag acgaaccgct tgaaaggcga  2400
ctctcattgg ttcctgacag tgaacaaggg gaagctattc tcccccggat ttcagtaatt  2460
tccacaggtc cgactctgca agcccggaga agacaatccg tgttgaatct tatgacccat  2520
tccgtgaatc agggggcaaaa tatccataga aagactactg cctctacgag gaaggtatcc  2580
cttgcaccccc aagccaatct gacggagctc gacatctact ctcgccgcct gtcccaggag  2640
acaggactgg agattagcga ggagatcaat gaagaggatc tgaaagaatg tttcttcgac  2700
gacatggaat ccatccctgc cgtcacgacg tggaatacct atttgcgtta catcacggta  2760
cataaaagtc tgatattcgt cctgatctgg tgtcttgtga tcttcctcgc tgaagtcgca  2820
gccagcctgg tcgttctttg gctgctcggg aatacccct tgcaggataa gggaaactcc  2880
accccactct ggaacaatag ttacgccgtc atcattactt ccacttcctc atactacgta  2940
ttctatatat atgtcggggt cgctgataca ctgctggcca tgggcttctt tcgcggcctg  3000
ccgctcgtcc acacgctgat aactgtctcc aagatcttgc atcataagat gctgcactca  3060
gtgctgcagg ctccaatgag tacactgaat actcttaagg ctggcggcat cctgaaccgc  3120
tttagtaagg acatcgccat acttgacgat ctcttgcccc tgacaatctt cgattttatt  3180
caactccttt tgatcgttat cggggcgatc gctgtggttg ctgtgttgca gccatatata  3240
ttcgtagcta ctgttcccgt catcgtcgcg ttcatcatgc tccgtgccta ctttctgcag  3300
acgtcccaac agctgaagca gctcgagagc gagggacggt cccccatatt tacgcacttg  3360
gtaactagtc tgaaggggct gtggactctg agagcatttg gtcgacaacc atatttcgag  3420
accctctttc ataaggcccct caacctgcac accgcgaatt ggtttctgta tttgagtacg  3480
ttgcggtggt ttcagatgcg catcgagatg atattcgtga tattcttcat cgcagtcaca  3540
tttatcagca tcctgactac gggcgaggga gagggtcgcg tgggcatcat actcacgctc  3600
gctataaaca ttatgagcac cctgcaatgg gccgtgaata gctctatcga cgttgacagt  3660
cttatgcgat ctgtgagccg agtctttaag ttcattgaca tgccaacaga aggtaaacct  3720
accaagtcaa ccaaaccata caagaatggc caactctcga aagttatgat tattgagaat  3780
tcacacgtga agaaagatga catctggccc tcagggggcc aaatgactgt caaagatctc  3840
acagcaaaat acacagaagg tggaaatgcc atattagaga acatttcctt ctcaataagt  3900
cctggccaga gggtgggcct cttgggaaga actggatcag ggaagagtac tttgttatca  3960
gcttttttga gactactgaa cactgaagga gaaatccaga tcgatggtgt gtcttgggat  4020
tcaataactt tgcaacagtg gaggaaagcc tttggagtga taccacagaa agtatttatt  4080
ttttctggaa catttagaaa aaacttggat ccctatgaac agtggagtga tcaagaaata  4140
tggaaagttg cagatgaggt tgggctcaga tctgtgatag aacagttttcc tgggaagctt  4200
gactttgtcc ttgtgatgg gggctgtgtc ctaagccatg ccacaagca gttgatgtgc  4260
ttggctagat ctgttctcag taaggcgaag atcttgctgc ttgatgaacc cagtgctcat  4320
ttggatccag taacatacca aataattaga agaactctaa aacaagcatt tgctgattgc  4380
acagtaattc tctgtgaaca caggataaga gcaatgctga aatgccaaca atttttggtc  4440
atagaagaga acaaagtgcg gcagtacgat tccatccaga aactgctgaa cgagagggc  4500
ctcttccggc aagccatcag cccctccgac agggtgaagc tctttccca ccggaactca  4560
agcaagtgca agtctaagcc ccagattgct gctctgaaaa ggagacaga agaaggtg  4620
caagatacaa ggcttagac ccgctgatca gcctcgactg tgccttctag tgccagcca  4680
tctgttgttt gcccctcccc cgtgccttcc ttgaccctgg aaggtgccac tcccactgtc  4740
ctttcctaat aaaatgagaa aattgcatcg cattgtctga gtaggtgtca ttctattctg  4800
gggggtgggg tggggcagga cagcaagggg gaggattggg aagacaatag caggcatgct  4860
ggggatgcgg tgggctctat gg                                           4882

SEQ ID NO: 402       moltype = DNA  length = 1594
FEATURE              Location/Qualifiers
misc_feature         1..1594
                     note = Description of Artificial Sequence: Synthetic
                     polynucleotide
source               1..1594
                     mol_type = other DNA
                     organism = synthetic construct
SEQUENCE: 402
ccccaactgg ggtaaccttt gggctccccg ggcgcggttc cggatccgga gagggcaggg    60
gatctctcct tacttgtggc gacgtggagg agaaccccgg ccccatgagc atcggctcc   120
tgtgctgtgc agccttgtct ctcctgtggg caggtccagt gaatgctggt gtcactcaga   180
ccccaaaatt ccaggtcctg aagacaggac agagcatgac actgcagtgt gcccaggata   240
tgaaccatga atacatgtcc tggtatcgac aagacccagg catggggctg aggctgattc   300
attactcagt tggtgctggt atcactgacc aaggagaagt ccccaatggc tacaatgtct   360
ccagatcaac cacagaggat ttcccgctca ggctgctgtc tccagacat   420
ctgtgtactt ctgtgccagc agttacgtcg ggaacaccgg ggagctgttt tttgagaag   480
gctctaggct gaccgtactg gaggacctga aaacgtgtt cccacccgag gtcgctgtgt   540
ttgagccatc agaagcagag atctcccaca cccaaaaggc cacactggta tgcctggcca   600
caggcttcta ccccgaccac gtggagctga gctggtgggt gaatgggaag gaggtgcaca   660
gtggggtcag cacagacccg cagcccctca aggagcagcc cgccctcaat gactccagat   720
actgcctgag cagccgcctg agggtctcgg ccacctgctg gcagaacccc cgcaaccact   780
tccgctgtca agtccagttc tacgggctct cggagaatga cgagtggacc aggatagg   840
ccaaacccgt cacccagatc gtcagcgccg aggcctgggg tagagcagac tgtggcttca   900
cctccgagtc ttaccagcaa ggggtcctgt ctgccaccat cctctatgag atcttgctag   960
ggaaggccac cttgtatgcc gtgctggtca gtgccctggt gctgatggcc atggtcaaga  1020
gaaaggattc cagaggccgg gccaagcggt ccggatccgg agccaccaac ttcagcctgc  1080
tgaagcaggc cggcgacgtg gaggagaacc ccgggcccat ggagccctc ttgggcctgc  1140
ttatcctttg gctgcagctg caatgggtga gcagcaaaca ggaggtgacg cagattcctg  1200
cagctctgag tgtcccagaa ggagaaaact ggttctcaa ctgcagtttc actgatagcg  1260
ctatttacaa ccctccagtg gtttaggcagg accctgggaa aggtctcaca tctctgttgc  1320
```

```
ttattcagtc aagtcagaga gagcaaacaa gtggaagact taatgcctcg ctggataaat   1380
catcaggacg tagtacttta tacattgcag cttctcagcc tggtgactca gccacctacc   1440
tctgtgctgt gaggcccctg tacggaggaa gctacatacc tacatttgga agaggaacca   1500
gccttattgt tcatccgtat atccagaacc ctgaccctgc gggtggtttg tctggtcaac   1560
caccgcggtc tcagtggtgt acggtacaaa ccca                               1594

SEQ ID NO: 403           moltype = DNA   length = 19
FEATURE                  Location/Qualifiers
misc_feature             1..19
                         note = Description of Artificial Sequence: Synthetic
                          oligonucleotide
source                   1..19
                         mol_type = other DNA
                         organism = synthetic construct
SEQUENCE: 403
ttgagcgggc ccccaccgt                                                 19

SEQ ID NO: 404           moltype = DNA   length = 393
FEATURE                  Location/Qualifiers
misc_feature             1..393
                         note = Description of Artificial Sequence: Synthetic
                          polynucleotide
source                   1..393
                         mol_type = other DNA
                         organism = synthetic construct
SEQUENCE: 404
atgactcact atcaggcctt gcttttggac acggaccggg tccagttcgg accggtggta    60
gccctgaacc cggctacgct gctcccactg cctgaggaag ggctgcaaca caactgcctt   120
gatgggacag gtggcggtgg tgtcaccgtc aagttcaagt acaagggtga ggaacttgaa   180
gttgatatta gcaaaatcaa gaaggtttgg cgcgttggta aaatgatatc ttttacttat   240
gacgacaacg gcaagacagg tagaggggca gtgtctgaga aagacgcccc caaggagctg   300
ttgcaaatgt tggaaaagtc tgggaaaaag tctggcggct caaaaagaac cgccgacggc   360
agcgaattcg agcccaagaa gaagaggaaa gtc                                393

SEQ ID NO: 405           moltype = DNA   length = 11
FEATURE                  Location/Qualifiers
misc_feature             1..11
                         note = Description of Artificial Sequence: Synthetic probe
source                   1..11
                         mol_type = other DNA
                         organism = synthetic construct
SEQUENCE: 405
cgacgacggc g                                                         11

SEQ ID NO: 406           moltype = DNA   length = 16
FEATURE                  Location/Qualifiers
misc_feature             1..16
                         note = Description of Artificial Sequence: Synthetic probe
source                   1..16
                         mol_type = other DNA
                         organism = synthetic construct
SEQUENCE: 406
tttatttgtg ggcccg                                                    16

SEQ ID NO: 407           moltype = DNA   length = 15
FEATURE                  Location/Qualifiers
misc_feature             1..15
                         note = Description of Artificial Sequence: Synthetic probe
source                   1..15
                         mol_type = other DNA
                         organism = synthetic construct
SEQUENCE: 407
tcgagtgccg catca                                                     15

SEQ ID NO: 408           moltype = DNA   length = 17
FEATURE                  Location/Qualifiers
misc_feature             1..17
                         note = Description of Artificial Sequence: Synthetic probe
source                   1..17
                         mol_type = other DNA
                         organism = synthetic construct
SEQUENCE: 408
aaagtggtga ggacact                                                   17

SEQ ID NO: 409           moltype = DNA   length = 15
FEATURE                  Location/Qualifiers
misc_feature             1..15
                         note = Description of Artificial Sequence: Synthetic probe
source                   1..15
```

```
                        mol_type = other DNA
                        organism = synthetic construct
SEQUENCE: 409
aacccacccg agaga                                                     15

SEQ ID NO: 410          moltype = DNA   length = 66
FEATURE                 Location/Qualifiers
misc_feature            1..66
                        note = Description of Artificial Sequence: Synthetic
                        oligonucleotide
source                  1..66
                        mol_type = other DNA
                        organism = synthetic construct
SEQUENCE: 410
ggaagcggag ctactaactt cagcctgctg aagcaggctg gcgacgtgga ggagaaccct     60
ggacct                                                               66

SEQ ID NO: 411          moltype = DNA   length = 45
FEATURE                 Location/Qualifiers
misc_feature            1..45
                        note = Description of Artificial Sequence: Synthetic
                        oligonucleotide
source                  1..45
                        mol_type = other DNA
                        organism = synthetic construct
SEQUENCE: 411
gggggaggag gttctggagg cggaggctcc ggaggcggag ggtca                    45

SEQ ID NO: 412          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 412
ggaggtggcg ggagc                                                     15

SEQ ID NO: 413          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 413
cccgcaccag cgcct                                                     15

SEQ ID NO: 414          moltype = DNA   length = 45
FEATURE                 Location/Qualifiers
misc_feature            1..45
                        note = Description of Artificial Sequence: Synthetic
                        oligonucleotide
source                  1..45
                        mol_type = other DNA
                        organism = synthetic construct
SEQUENCE: 414
gaggcagctg ccaaggaagc cgctgccaag gaggcggccg caaag                    45

SEQ ID NO: 415          moltype = DNA   length = 48
FEATURE                 Location/Qualifiers
misc_feature            1..48
                        note = Description of Artificial Sequence: Synthetic
                        oligonucleotide
source                  1..48
                        mol_type = other DNA
                        organism = synthetic construct
SEQUENCE: 415
agtgggagcg agaccctgg gactagcgag tcagctacac ccgaaagc                  48

SEQ ID NO: 416          moltype = DNA   length = 54
FEATURE                 Location/Qualifiers
misc_feature            1..54
                        note = Description of Artificial Sequence: Synthetic
                        oligonucleotide
source                  1..54
                        mol_type = other DNA
```

```
                            organism = synthetic construct
SEQUENCE: 416
gggggggtcag gtggatccgg cggaagtggc ggatccggtg gatctggcgg cagt          54

SEQ ID NO: 417          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 417
gaagctgctg ctaag                                                     15

SEQ ID NO: 418          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 418
GSGATNFSLL KQAGDVEENP GP                                             22

SEQ ID NO: 419          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 419
GGGGSGGGGS GGGGS                                                     15

SEQ ID NO: 420          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 420
GGGGS                                                                 5

SEQ ID NO: 421          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 421
PAPAP                                                                 5

SEQ ID NO: 422          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 422
EAAAKEAAAK EAAAK                                                     15

SEQ ID NO: 423          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 423
SGSETPGTSE SATPES                                                    16

SEQ ID NO: 424          moltype = AA  length = 18
FEATURE                 Location/Qualifiers
REGION                  1..18
                        note = Description of Artificial Sequence: Synthetic peptide
```

```
source                  1..18
                        mol_type = protein
                        organism = synthetic construct
SEQUENCE: 424
GGSGGSGGSG GSGGSGGS                                                  18

SEQ ID NO: 425          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 425
EAAAK                                                                5

SEQ ID NO: 426          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 426
GLSGQPPRSP SSGSSG                                                    16

SEQ ID NO: 427          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 427
GGLSGQPPRS PSSGSSG                                                   17

SEQ ID NO: 428          moltype = RNA  length = 88
FEATURE                 Location/Qualifiers
misc_feature            1..88
                        note = Description of Artificial Sequence: Synthetic
                        oligonucleotide
source                  1..88
                        mol_type = other RNA
                        organism = synthetic construct
SEQUENCE: 428
gacgagcgcg gcgatatcat catccatggc cggatgatcc tgacgacgga gaccgccgtc   60
gtcgacaagc cggcctgagc tgcgagaa                                      88

SEQ ID NO: 429          moltype = RNA  length = 20
FEATURE                 Location/Qualifiers
misc_feature            1..20
                        note = Description of Artificial Sequence: Synthetic
                        oligonucleotide
source                  1..20
                        mol_type = other RNA
                        organism = synthetic construct
SEQUENCE: 429
gaagccggcc ttgcacatgc                                                20

SEQ ID NO: 430          moltype = DNA  length = 95
FEATURE                 Location/Qualifiers
source                  1..95
                        mol_type = unassigned DNA
                        organism = Homo sapiens
SEQUENCE: 430
gcgcgcccgg ctattctcgc agctcaccat ggatgatgat atcgccgcgc tcgtcgtcga   60
caacggctcc ggcatgtgca aggccggctt cgcgg                              95

SEQ ID NO: 431          moltype = RNA  length = 20
FEATURE                 Location/Qualifiers
misc_feature            1..20
                        note = Description of Artificial Sequence: Synthetic
                        oligonucleotide
source                  1..20
                        mol_type = other RNA
                        organism = synthetic construct
SEQUENCE: 431
accactcgac gctcttatcg                                                20
```

SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

CROSS REFERENCE TO RELATED APPLICATIONS

This application is a continuation of U.S. application Ser. No. 18/066,223, filed Dec. 14, 2022, which is a continuation of U.S. application Ser. No. 17/649,308, filed Jan. 28, 2022, which is a continuation of U.S. application Ser. No. 17/451,734, filed Oct. 21, 2021, which claims the benefit of U.S. Provisional Patent Application Ser. No. 63/222,550, filed Jul. 16, 2021 and U.S. Provisional Patent Application Ser. No. 63/094,803, filed Oct. 21, 2020. The entire contents of the above-referenced patent applications are incorporated by reference in their entirety herein.

SEQUENCE LISTING

The instant application contains a Sequence Listing which has been submitted electronically in XML format and is hereby incorporated by reference in its entirety. Said XML file, created on Dec. 14, 2022, is named 737607_083474_016CON2_SL_ST26v2.xml and is 775,000 bytes in size.

FIELD OF DISCLOSURE

The subject matter disclosed herein is generally directed to systems, methods, and compositions for site-specific genetic engineering using Programmable Addition via Site-Specific Targeting Elements (PASTE) for the treatment of diseases and diagnostics.

BACKGROUND

Editing genomes using the RNA-guided DNA targeting principle of CRISPR-Cas (Clustered Regularly Interspaced Short Palindromic Repeats-CRISPR associated proteins) immunity has been widely exploited and has become a powerful genome editing means for a wide variety of applications. The main advantage of CRISPR-Cas system lies in the minimal requirement for programmable DNA interference: an endonuclease, such as a Cas9, Cas12, or any programmable nucleases, guided by a customizable dual-RNA structure. Cas9 is a multi-domain enzyme that uses an HNH nuclease domain to cleave the target strand. The CRISPR/Cas9 protein-RNA complex is localized on the target by a guide RNA (guide RNA), then cleaved to generate a DNA double strand break (dsDNA break, DSB). After cleavage, DNA repair mechanisms are activated to repair the cleaved strand. Repair mechanisms are generally from one of two types: non-homologous end joining (NHEJ) or homologous recombination (HR). In general, NHEJ dominates the repair, and, being error prone, generates random indels (insertions or deletions) causing frame shift mutations, among others. In contrast, HR has a more precise repairing capability and is potentially capable of incorporating the exact substitution or insertion. To enhance HR, several techniques have been tried, for example: combination of fusion proteins of Cas9 nuclease with homology-directed repair (HDR) effectors to enforce their localization at DSBs, introducing an overlapping homology arm, or suppression of NHEJ. Most of these techniques rely on the host DNA repair systems.

Recently, new guided editors have been developed, such as guided prime editors (PE) PE1, PE2, and PE3, e.g., Liu, D. et al., Nature 2019, 576, 149-157. These PEs are reverse transcriptase (RT) fused with Cas 9 H 840A nickase (Cas9n (H840A)), and the genome editing is achieved using a prime-editing guide RNA (pegRNA). Despite these developments, programmable gene integration is still generally dependent on cellular pathways or repair processes.

Therefore, there is a need for more effective tools for gene editing and delivery.

SUMMARY

The present disclosure provides a method of site-specific integration of a nucleic acid into a cell genome. The method comprises incorporating an integration site at a desired location in the cell genome by introducing into the cell a DNA binding nuclease linked to a reverse transcriptase domain, wherein the DNA binding nuclease comprises a nickase activity; and a guide RNA (gRNA) comprising a primer binding sequence linked to an integration sequence, wherein the gRNA interacts with the DNA binding nuclease and targets the desired location in the cell genome, wherein the DNA binding nuclease nicks a strand of the cell genome and the reverse transcriptase domain incorporates the integration sequence of the gRNA into the nicked site, thereby providing the integration site at the desired location of the cell genome. The method further comprises integrating the nucleic acid into the cell genome by introducing into the cell a DNA or RNA strand comprising the nucleic acid linked to a sequence that is complementary or associated to the integration site, and an integration enzyme, wherein the integration enzyme incorporates the nucleic acid into the cell genome at the integration site by integration, recombination, or reverse transcription of the sequence that is complementary or associated to the integration site, thereby introducing the nucleic acid into the desired location of the cell genome of the cell.

In some embodiments, the gRNA can be hybridized to a complementary strand of the cell genome to the genomic strand that is nicked by the DNA binding nuclease.

In some embodiments, the integration enzyme can be introduced as a peptide or a nucleic acid encoding the same.

In some embodiments, the DNA binding nuclease can be introduced as a peptide or a nucleic acid encoding the same.

In some embodiments, the DNA or RNA strand comprising the nucleic acid can be introduced into the cell as a minicircle, a plasmid, mRNA or a linear DNA.

In some embodiments, the DNA or RNA strand comprising the nucleic acid can be between 1000 bp and 10,000 bp.

In some embodiments, the DNA or RNA strand comprising the nucleic acid can be more than 10,000 bp.

In some embodiments, the DNA or RNA strand comprising the nucleic acid can be less than 1000 bp.

In some embodiments, the DNA comprising the nucleic acid can be introduced into the cell as a minicircle.

In some embodiment, the minicircle cannot comprise sequences of a bacterial origin.

In some embodiments, the DNA binding nuclease can be linked to a reverse transcriptase domain and the integration enzyme can be linked via a linker. The linker can be cleavable. The linker can be non-cleavable. The linker can be replaced by two associating binding domains of the DNA binding nuclease linked to a reverse transcriptase.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the integration site can be selected from an attB site, an attP site, an attL site, an attR site, a lox71 site a Vox site, or a FRT site.

In some embodiments, the DNA binding nuclease comprising a nickase activity can be selected from Cas9-D10A, Cas9-H840A, and Cas12a/b nickase.

In some embodiments, the reverse transcriptase domain can be selected from the group consisting of Moloney Murine Leukemia Virus (M-MLV) reverse transcriptase domain, transcription xenopolymerase (RTX), avian myeloblastosis virus reverse transcriptase (AMV-RT), and *Eubacterium rectale* maturase RT (MarathonRT).

In some embodiments, the reverse transcriptase domain can comprise a mutation relative to the wild-type sequence.

In some embodiments, the M-MLV reverse transcriptase domain can comprise one or more mutations selected from the group consisting of D200N, T306K, W313F, T330P and L603W.

In some embodiments, the method can further comprise introducing a second nicking guide RNA (ngRNA). The ngRNA can direct nicking at 90 bases downstream of the gRNA nick on a complementary strand.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced into a cell in a single reaction.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced using a virus, a RNP, an mRNA, a lipid, or a polymeric nanoparticle.

In some embodiments, the nucleic acid can be a reporter gene. The reporter gene can be a fluorescent protein.

In some embodiments, the cell can be a dividing cell.

In some embodiments, the cell can be a non-dividing cell.

In some embodiments, the desired location in the cell genome can be the locus of a mutated gene.

In some embodiments, the nucleic acid can be a degradation tag for programmable knockdown of proteins in the presence of small molecules.

In some embodiments, the cell can be a mammalian cell, a bacterial cell or a plant cell.

In some embodiments, nucleic acid can be a T-cell receptor (TCR), a chimeric antigen receptor (CAR), an interleukin, a cytokine, or an immune checkpoint gene for integration into a T-cell or natural killer (NK) cell. The TCR, the CAR, the interleukin, the cytokine, or the immune checkpoint gene can be incorporated into the target site of the T-cell or NK cell genome using a minicircle DNA.

In some embodiments, the nucleic acid can be a beta hemoglobin (HBB) gene and the cell can be a hematopoietic stem cell (HSC). The HBB gene can be incorporated into the target site in the HSC genome using a minicircle DNA. The nucleic acid can be a gene responsible for beta thalassemia or sickle cell anemia.

In some embodiments, the nucleic acid can be a metabolic gene. The metabolic gene can be involved in alpha-1 antitrypsin deficiency or ornithine transcarbamylase (OTC) deficiency. The metabolic gene can be a gene involved in inherited diseases.

In some embodiments, the nucleic acid can be a gene involved in an inherited disease or an inherited syndrome. The inherited disease can be cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

The present disclosure provides a vector comprising a nucleic acid encoding a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the linker can comprise two associating binding domains of the DNA binding nuclease linked to a reverse transcriptase.

In some embodiments, the integration enzyme can comprise a conditional activation domain or conditional expression domain.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, MarathonRT, or a RTX. The reverse transcriptase can be a modified M-MLV reverse transcriptase relative to the wildtype M-MLV reverse transcriptase. The M-MLV reverse transcriptase domain can comprise one or more of the mutations selected from the group consisting of D200N, T306K, W313F, T330P and L603W.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the recombinase or integrase can be Bxb1 or a mutant thereof.

The present disclosure provides a cell comprising a vector comprising a nucleic acid encoding a DNA binding nuclease comprising a nickase activity C-terminally linked to a reverse transcriptase linked to an integration enzyme via a linker. The cell further comprises a gRNA comprising a primer binding sequence, an integration sequence, and a guide sequence, wherein the gRNA can interact with the encoded nuclease comprising a nickase activity. The cell further comprising a DNA minicircle comprising a nucleic acid and a sequence recognized by the encoded integrase, recombinase, or reverse transcriptase. The cell further comprising a nicking guide RNA (ngRNA) capable of binding the encoded nuclease comprising a nickase activity, and wherein the ngRNA targets a sequence away from the gRNA.

In some embodiments, the minicircle cannot comprise a sequence of bacterial origin.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA binding nuclease comprising a nickase activity can be selected from the group consisting of Cas9-D10A, Cas9-H840A and Cas12a.

In some embodiments, the reverse transcriptase can be a M-MLV reverse transcriptase. The reverse transcriptase can be a modified M-MLV reverse transcriptase. The amino acid sequence of the M-MLV reverse transcriptase can comprise one or more mutations selected from the group consisting of D200N, T306K, W313F, T330P, and L603W.

In some embodiments, the cell can further comprise introducing ngRNA to the cell. The ngRNA can be a +90 ngRNA. The +90 ngRNA can direct nicking at 90 bases downstream of the gRNA nick on a complementary strand.

The present disclosure provides a polypeptide comprising a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, a MarathonRT, or a XRT. The reverse transcriptase can be a modified M-MLV relative to a wild-type M-MLV reverse transcriptase. The M-MLV reverse transcriptase domain can comprise one or more of mutations selected from the group consisting of D200N, T306K, W313F, T330P, and L603W.

In some embodiments, the integration enzyme can be selected from group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

The present disclosure provides a gRNA that specifically binds to a DNA binding nuclease comprising nickase activity, the gRNA comprising a primer binding site, which hybridizes to a nicked DNA strand, a recognition site for an integration enzyme, and a target recognition sequence recognizing a target site in a cell genome and hybridizing to a genomic strand complementary to the strand that is nicked by the DNA binding nuclease.

In some embodiments, the DNA binding nuclease comprising a nickase activity can be selected from the group consisting of Cas9-D10A, Cas9-H840A, and Cas12a/b.

In some embodiments, the primer binding site can hybridize to the 3' end of the nicked DNA strand.

In some embodiments, the recognition site for the integration enzyme can be selected from an attB site, an attP site, an attL site, an attR site, a lox71 site, and a FRT site.

In some embodiments, the recognition site for the integration enzyme can be a Bxb1 site.

The present disclosure provides a method of site-specific integration of two or more nucleic acids into a cell genome. The method comprises incorporating two integration sites at desired locations in the cell genome by introducing into the cell a DNA binding nuclease linked to a reverse transcriptase domain, wherein the DNA binding nuclease comprises a nickase activity, and two guide RNAs (gRNAs), each comprising, a primer binding sequence, linked to a unique integration sequence, wherein the gRNA interacts with the DNA binding nuclease and targets the desired locations in the cell genome, wherein the DNA binding nuclease nicks a strand of the cell genome and the reverse transcriptase domain incorporates each of the integration sequence of the gRNA into the nicked site, thereby providing the integration site at the desired locations of the cell genome. The method further comprises integrating the nucleic acid by introducing into the cell two or more DNA or RNA comprising the nucleic acids, wherein each DNA is flanked by orthogonal integration sites, and an integration enzyme, wherein the integration enzyme incorporates the nucleic acids into the cell genome at the integration sites by integrase, recombinase, or reverse transcriptase of the sequence that is complementary or associated to the integration site, thereby introducing the nucleic acids into the desired locations of the cell genome of the cell.

In some embodiments, each of the two different integration sites inserted into the cell genome can be attB sequences comprising different palindromic or non-palindromic central dinucleotide.

In some embodiments, each of the two different integration sites inserted into the cell genome can be attP sequences comprising different palindromic or non-palindromic central dinucleotide.

In some embodiments, the integration enzyme can enable each of the two or more DNA or RNA comprising the nucleic acids to directionally enable integration of the nucleic acids into a genome via recombination of a pair of orthogonal attB site sequence and an attP site sequence.

In some embodiments, the integration enzyme can be selected from the group consisting of Cre, Dre, Vika, Bxb1, φC31, RDF, FLP, φBT1, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R1, R2, R3, R4, R5, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA comprising genes can be genes involved in a cell maintenance pathway, cell-division, or a signal transduction pathway.

In some embodiments, the reverse transcriptase domain can comprise Moloney Murine Leukemia Virus (M-MLV) reverse transcriptase domain, transcription xenopolymerase (RTX), avian myeloblastosis virus reverse transcriptase (AMV-RT), or *Eubacterium rectale* maturase RT (MarathonRT).

In some embodiments, the DNA binding nuclease comprising a nickase activity can be selected from the group consisting of Cas9-D10A, Cas9-H840A, and Cas12a/b.

In some embodiments, the pair of an attB site sequence and an attP site sequence can be selected from the group consisting of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34 and SEQ ID NO: 35 and SEQ ID NO: 36.

The present disclosure provides a cell comprising a vector comprising a nucleic acid encoding a DNA binding nuclease comprising a nickase activity, wherein the DNA binding nuclease is C-terminally linked to a reverse transcriptase, wherein the reverse transcriptase is linked to a recombinase or integrase via a linker. The cell further comprises two guide RNAs (gRNAs) comprising a primer binding sequence, an integration sequence and a guide sequence, wherein the gRNA can interact with the encoded DNA binding nuclease comprising a nickase activity. The cell further comprises two or more DNA or RNA strands comprising a nucleic acid and a pair of flanking attB site sequence and an attP site sequence recognized by the encoded integrase or recombinase. The cell optionally further comprises a nicking guide RNA (ngRNA) capable of binding the encoded nuclease comprising a nickase activity, and wherein the ngRNA targets a sequence away from the gRNA.

The present disclosure provides a cell comprising a modified genome, wherein the modification comprises incorporation of two orthogonal integration sites within the cell genome by introducing into the cell a: vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA.

The present disclosure provides a method of integrating two or more nucleic acids into the cell genome of cell of claim 90, the method comprising introducing into the cell: two or more DNA, each comprising a nucleic acid and a pair of flanking orthogonal integration site sequences; an integration enzyme that can recognize the integration site sequence enabling directional linking of the two or more DNA comprising nucleic acid; and enabling incorporation of the nucleic acids into the cell genome by integrating the 5' orthogonal integration sequence of the first DNA with the first genomic integration sequence and 3' orthogonal integration sequence of the last DNA with the last genomic integration sequence, thereby incorporating the two or more nucleic acids into the cell genome.

The present disclosure provides a cell comprising a modified genome, wherein the modification comprises incorporation of two orthogonal integration sites within the cell genome by introducing into the cell: a vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA; two or more DNA or RNA comprising the nucleic acids, wherein each DNA is flanked by orthogonal integration sites; and an integration enzyme, wherein the integration enzyme incorporates the nucleic acids into the cell genome at the integration sites.

BRIEF DESCRIPTION OF THE DRAWINGS

Aspects, features, benefits and advantages of the embodiments described herein will be apparent with regard to the following description, appended claims, and accompanying drawings where:

FIG. 28A shows fluorescent images of the GFP tagging of ACTB and SUPT16H genes with PASTE according to embodiments of the present teachings;

FIG. 28B shows fluorescent images of the GFP tagging of NOLC1 and SRRM2 genes with PASTE according to embodiments of the present teachings;

FIG. 28C shows fluorescent images of the GFP tagging of LMNB1 and DEPDC4 genes with PASTE according to embodiments of the present teachings;

FIG. 28F shows fluorescent images of two single cells with multiplexed gene tagging of ACTB (EGFP) and NOLC1 (mCherry) using PASTE according to embodiments of the present teachings;

FIG. 28G shows fluorescent images two single cells with multiplexed gene tagging of ACTB (EGFP) and LMNB1 (mCherry) using PASTE according to embodiments of the present teachings;

FIG. 29E discloses SEQ ID NOS 428-431, respectively, in order of appearance;

FIG. 31A shows a schematic of various parameters that affect PASTE integration of ~1 kb GFP insert, wherein on the pegRNA, the PBS, RT, and attB lengths can alter the efficiency of attB insertion, and nicking guide selection also affects overall gene integration efficiency according to embodiments of the present teachings;

FIG. 34E shows the endogenous protein tagging with GFP via PASTE by in-frame endogenous gene tagging at the NOLC1 loci and LAMNB loci according to embodiments of the present teachings;

FIG. 40C shows the validation of ddPCR assays for detecting editing at predicted PASTE ACTB Cas9 guide off-target sites using synthetic amplicons according to embodiments of the present teachings;

FIG. 40D shows the validation of ddPCR assays for detecting editing at predicted HITI ACTB Cas9 guide off-target sites using synthetic amplicons according to embodiments of the present teachings;

FIG. 41A shows a number of significant differentially regulated genes in HEK293FT cells expressing Bxb1 integrase, PASTE targeting ACTB integration of EGFP, or Prime editing targeting ACTB for EGFP insertion without Bxb1 expression according to embodiments of the present teachings;

Figure 41A:
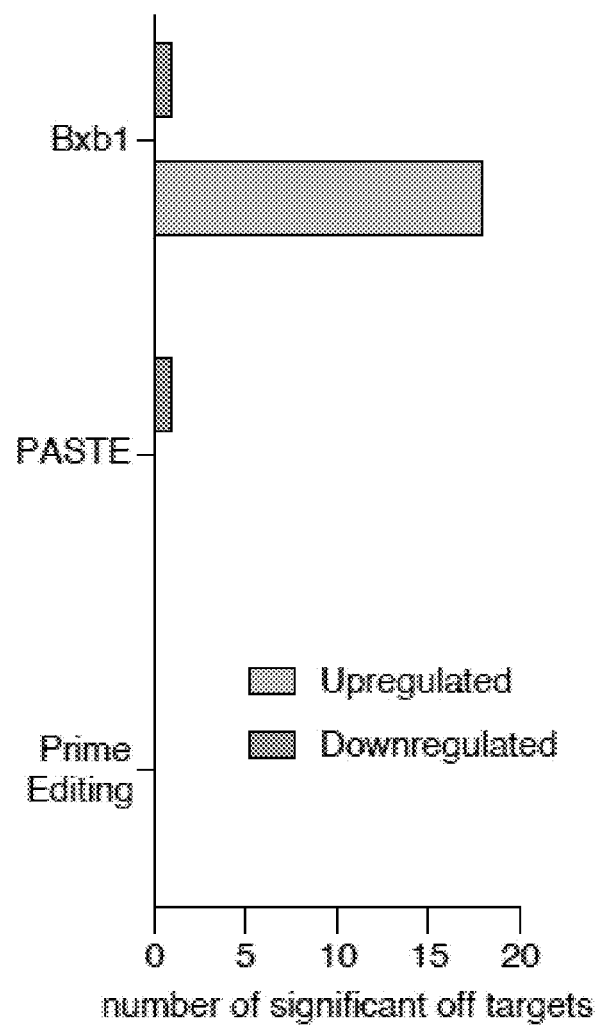
Figure 41B:
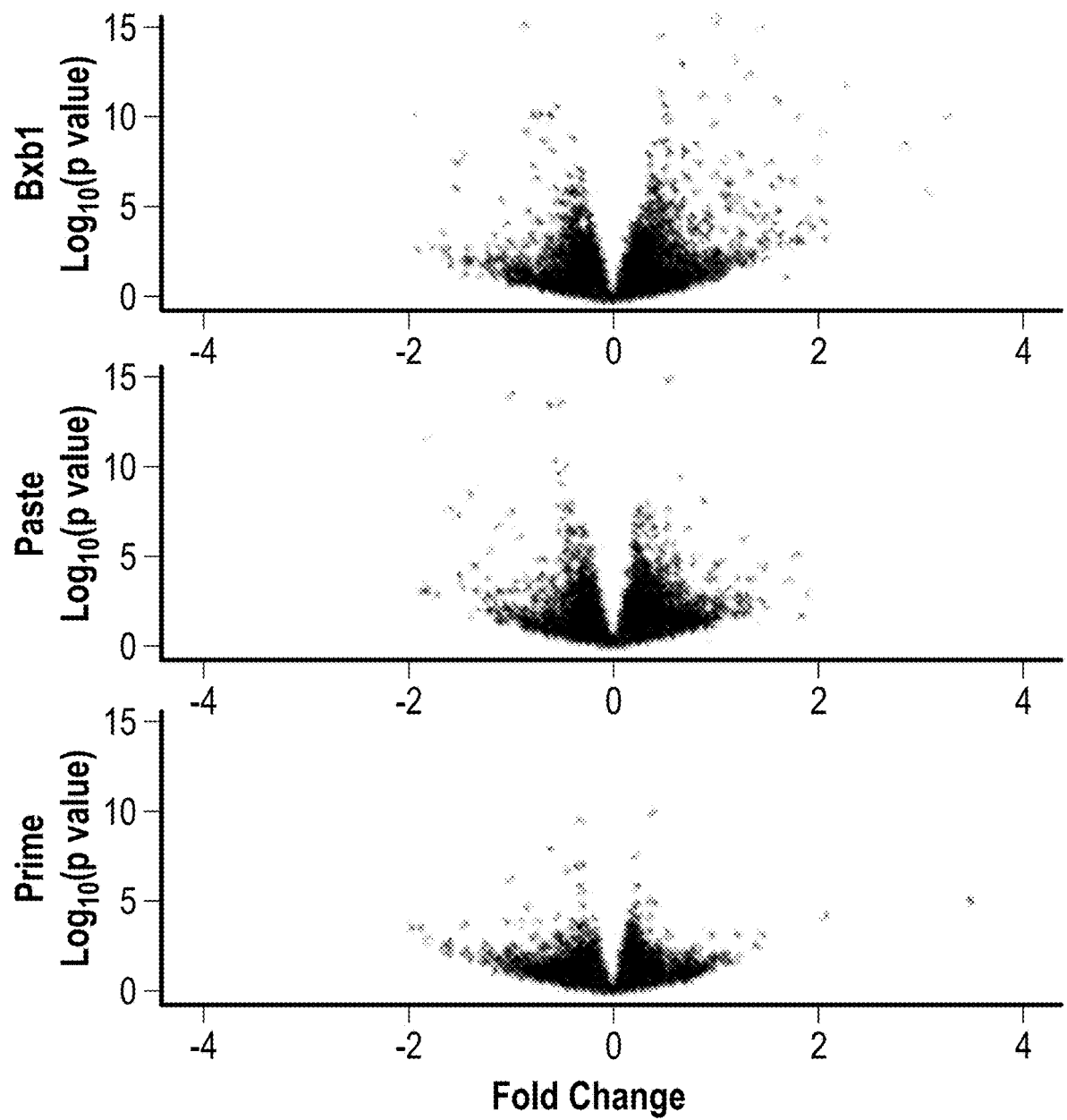
Figure 41C:
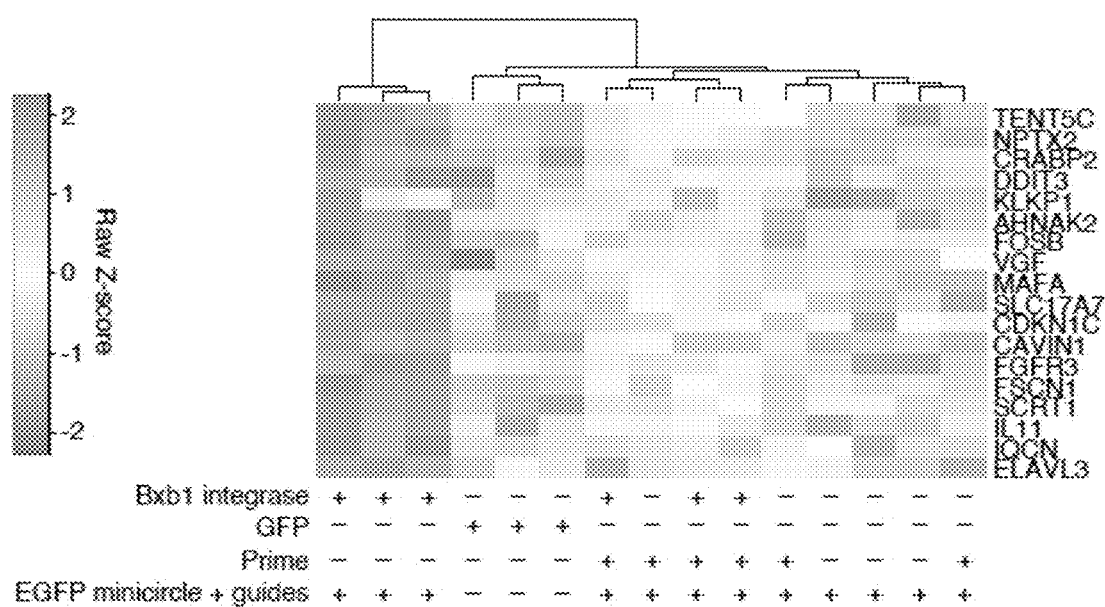
Figure 42A:
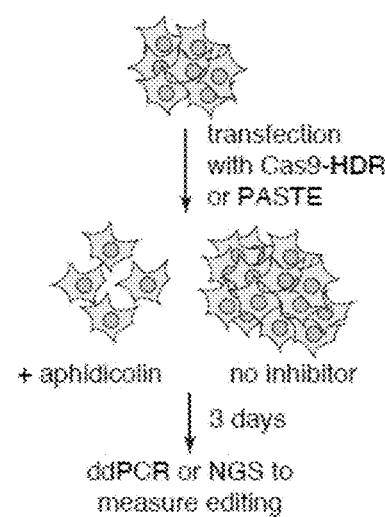
Figure 42B:
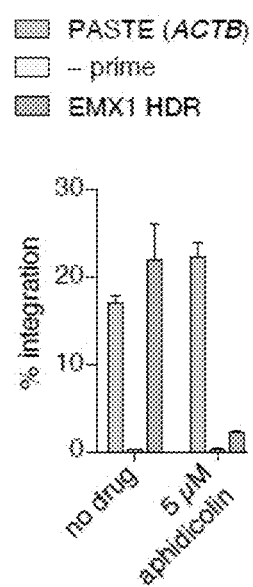
Figure 42C:
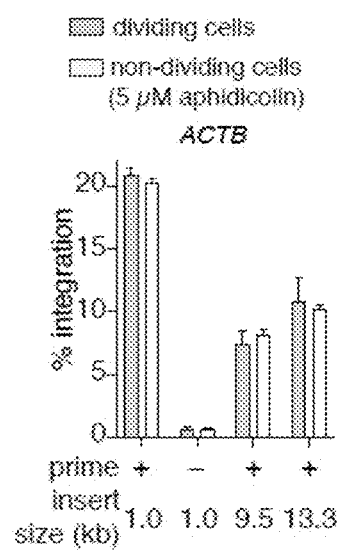
Figure 42D:
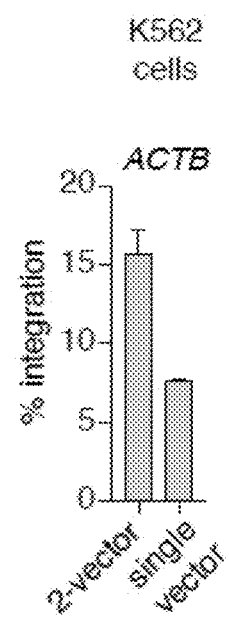
Figure 42E:
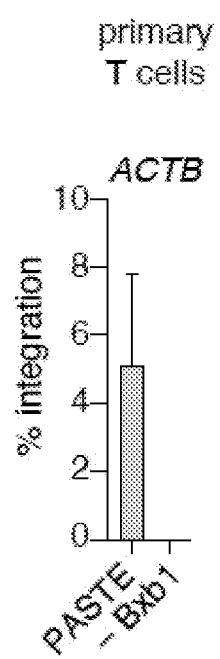
Figure 42F:
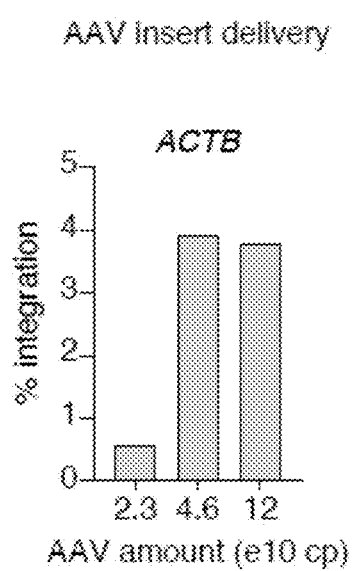
Figure 42G:
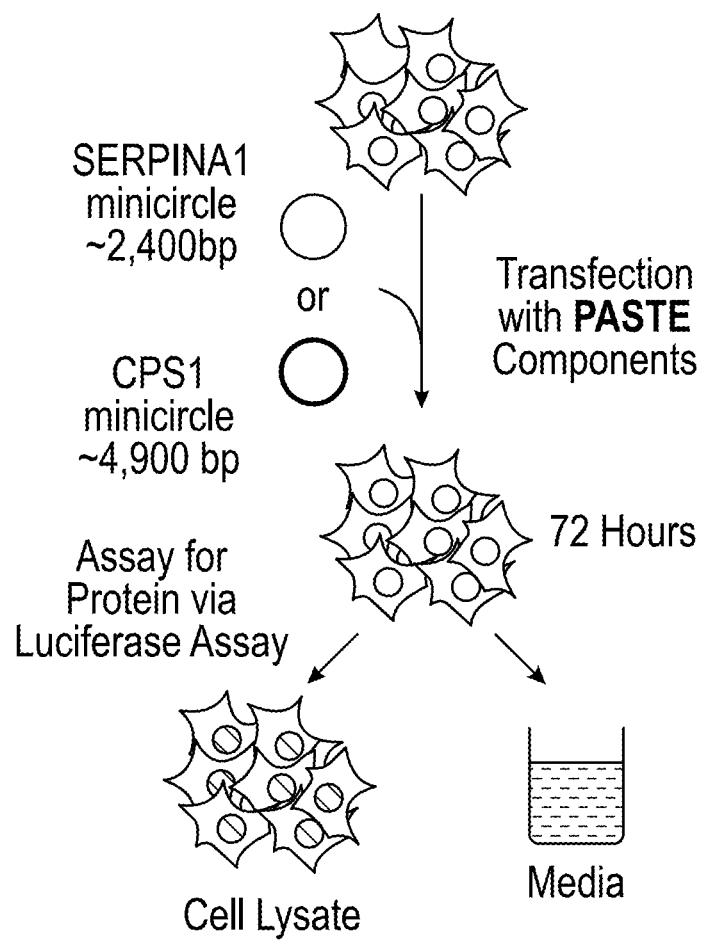
Figure 42H:
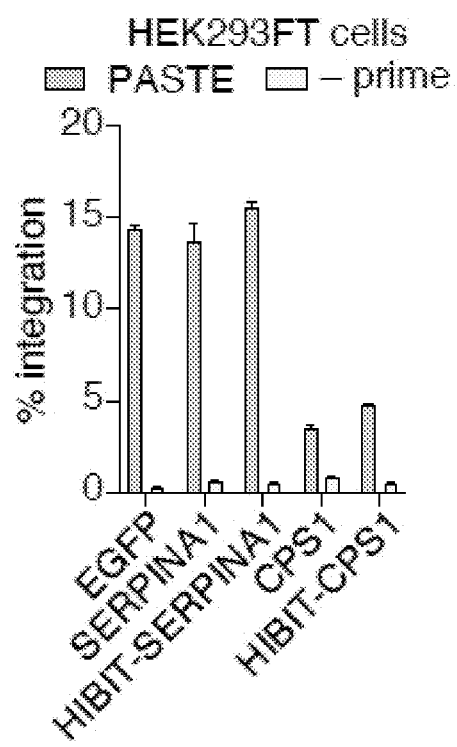
Figure 42I:
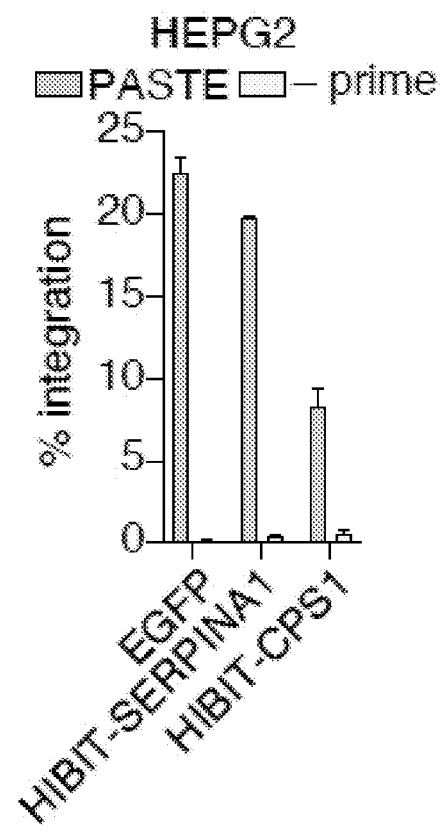
Figure 42J:
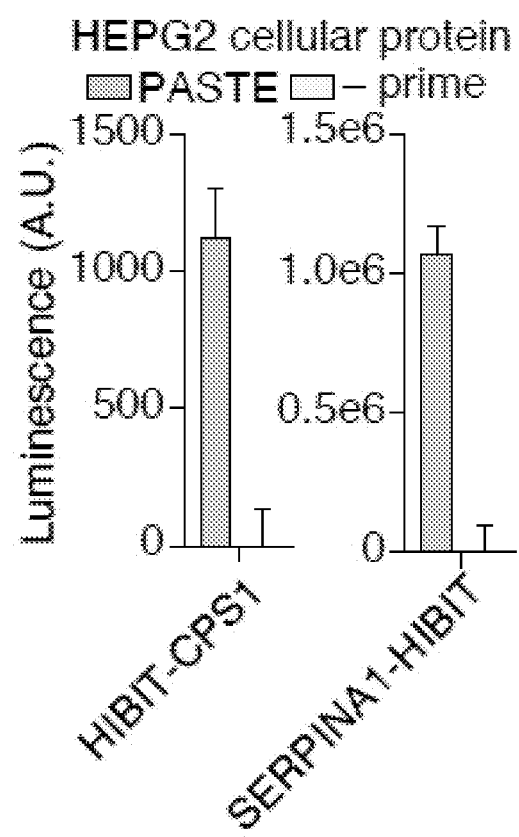
Figure 42K:
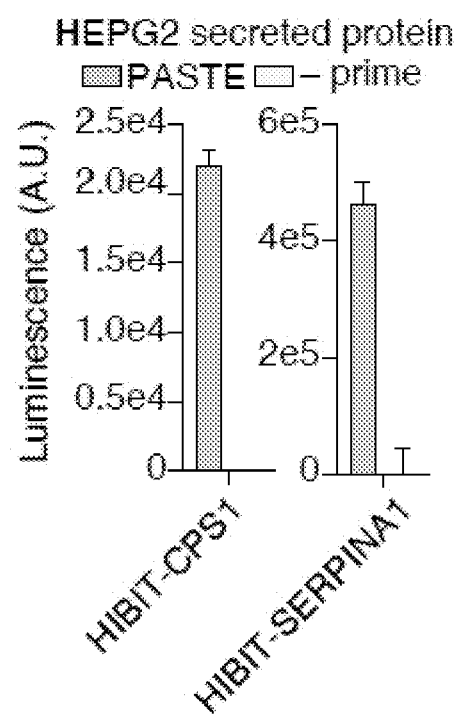
Figure 43A:
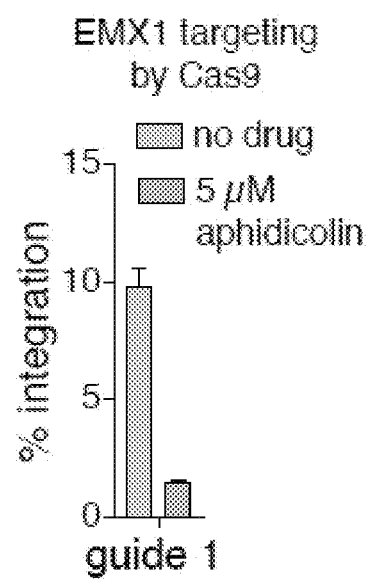
Figure 43B:
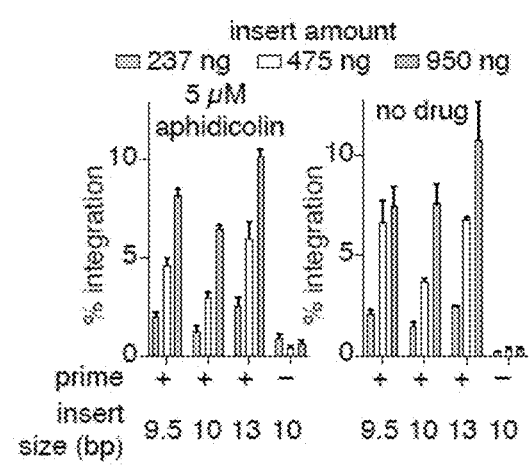
Figure 43C:
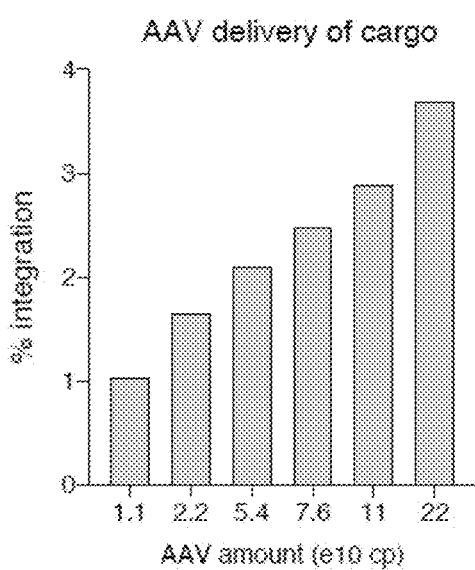
Figure 44A:
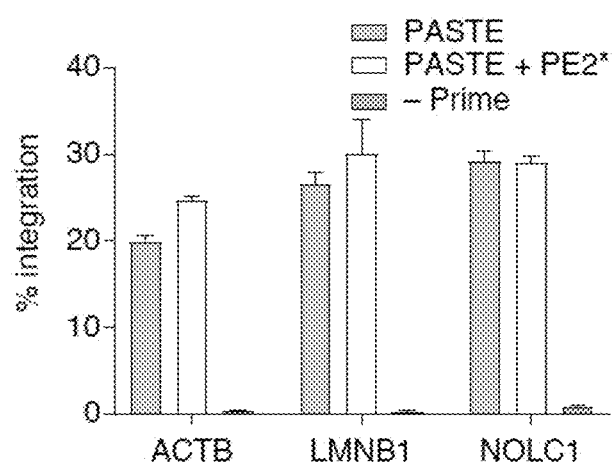
Figure 44B:
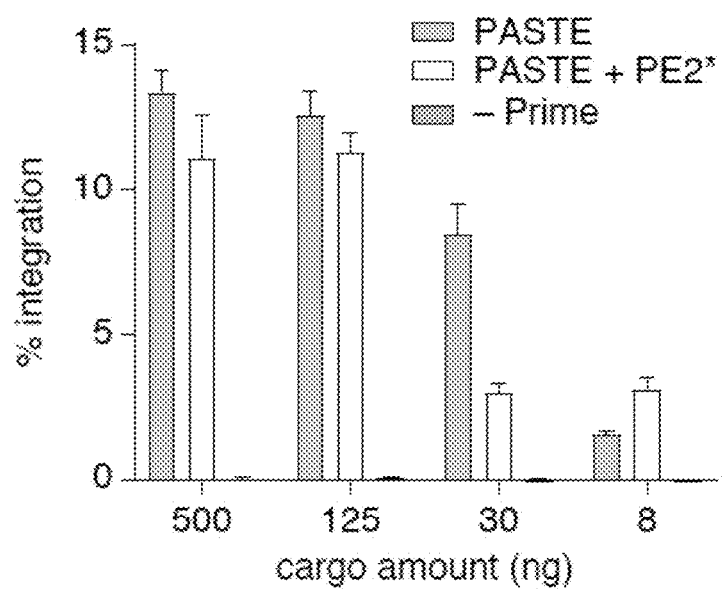
Figure 45:
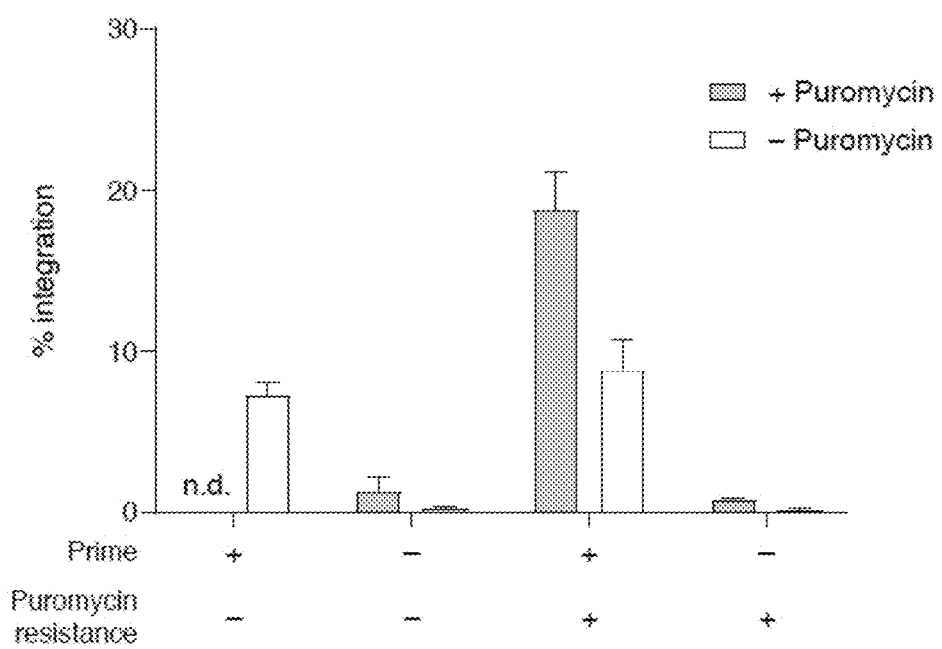
Figure 46A:
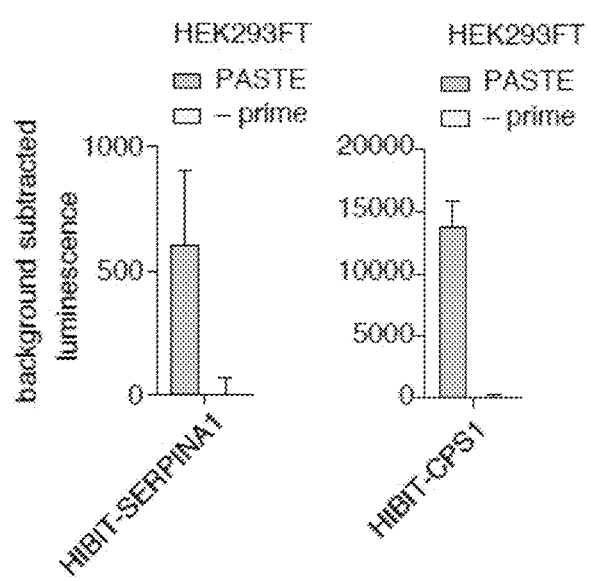
Figure 46B:
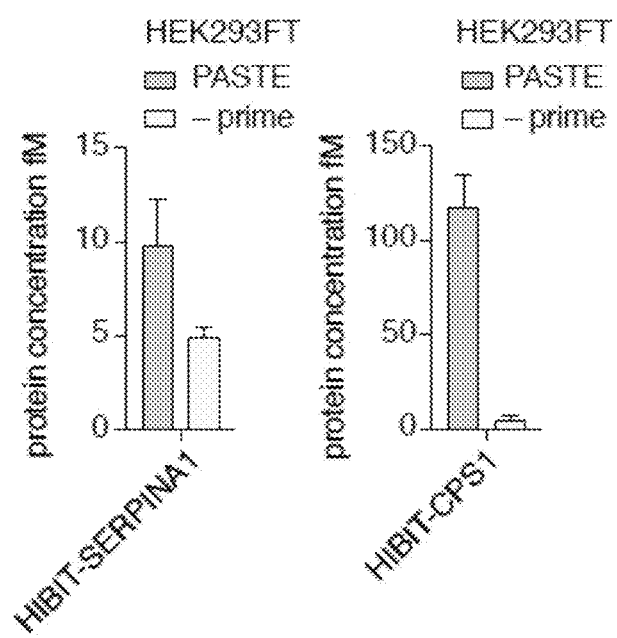
Figure 47A:
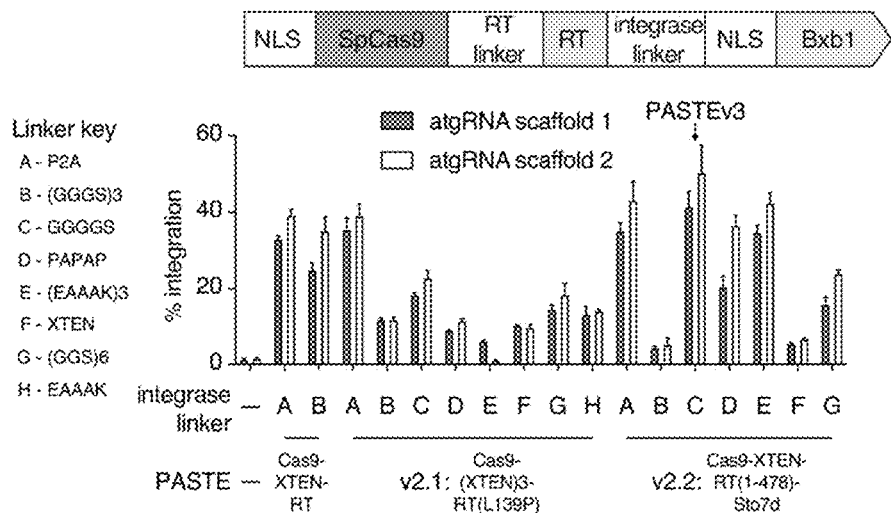
Figure 47B:
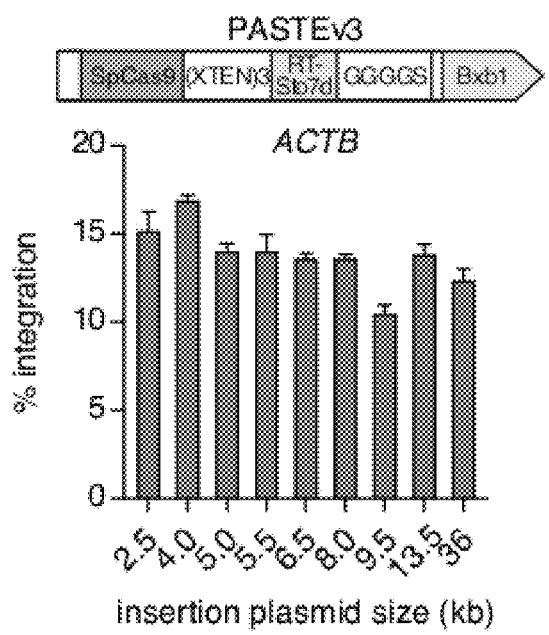
Figure 48A:
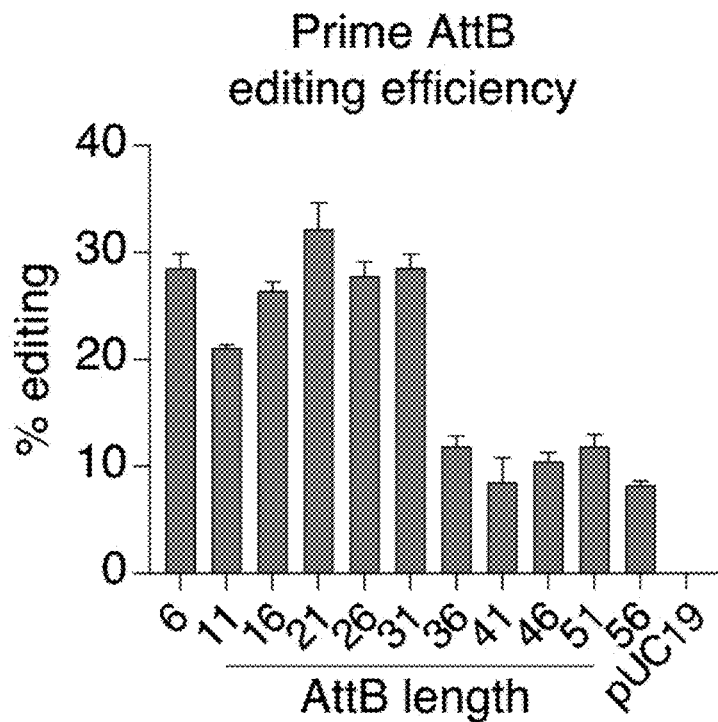
Figure 48B:
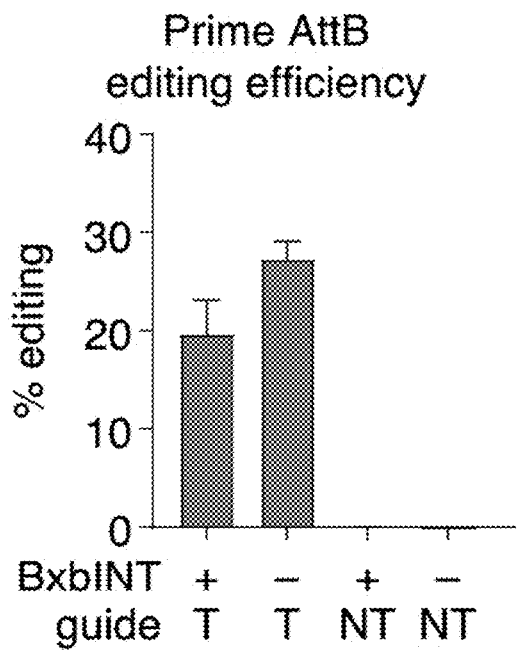
Figure 48C:
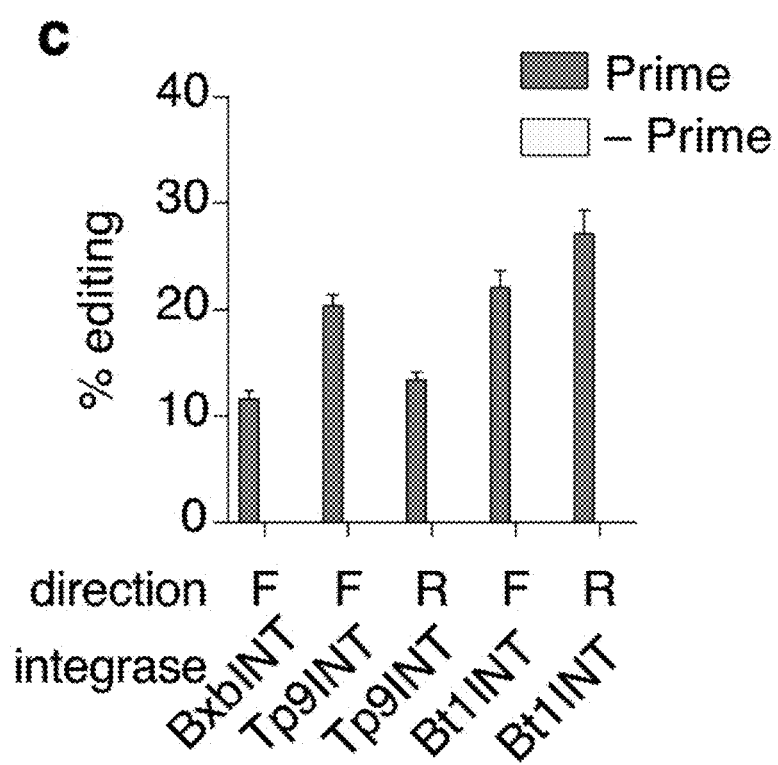
Figure 48D:
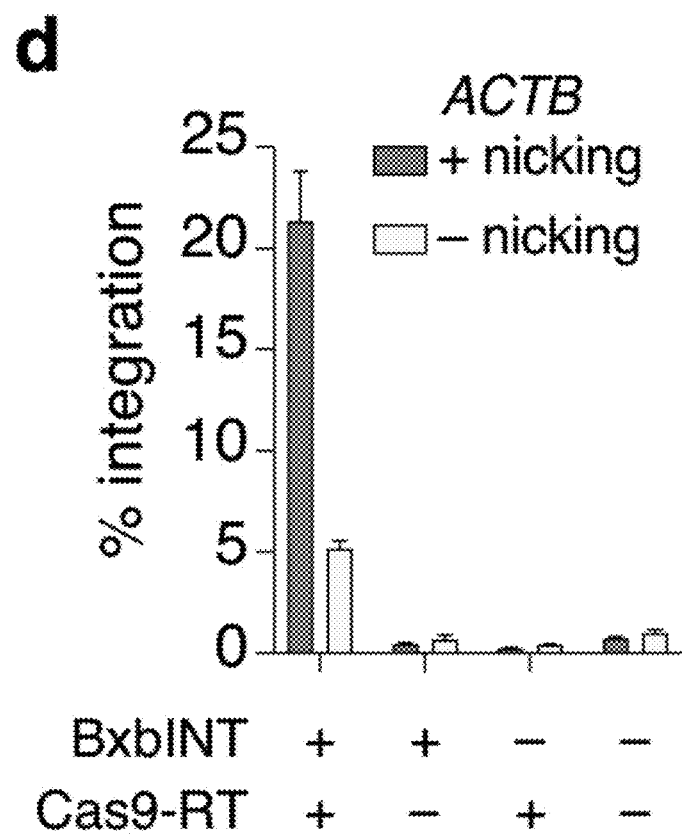

FIG. 41B shows Volcano plots depicting the fold expression change of sequenced mRNAs versus significance (p-value), wherein each dot represents a unique mRNA transcript and significant transcripts are shaded according to either upregulation (red) or downregulation (blue), and wherein fold expression change is measured against ACTB-targeting guide-only expression (including cargo) according to embodiments of the present teachings;

FIG. 41C shows top significantly upregulated and down-regulated genes for Bxb1-only conditions, wherein genes are shown with their corresponding Z-scores of counts per million (cpm) for Bxb1 only expression, GFP-only expression, PASTE targeting ACTB for EGFP insertion, Prime targeting ACTB for EGFP expression without Bxb1, and guide/cargo only according to embodiments of the present teachings;

FIG. 42A shows a schematic of PASTE performance in the presence of cell cycle inhibition, wherein cells are transfected with plasmids for insertion with PASTE or Cas9-induced HDR and treated with aphidicolin to arrest cell division, and wherein the efficiency of PASTE and HDR are read out with ddPCR or amplicon sequencing respectively according to embodiments of the present teachings;

FIG. 42B shows the editing efficiency of single mutations by HDR at EMX1 locus with two Cas9 guides in the presence or absence of cell division read out with amplicon sequencing according to embodiments of the present teachings;

FIG. 42C shows the integration efficiency of various sized GFP inserts up to 13.3 kb at the ACTB locus with PASTE in the presence or absence of cell division according to embodiments of the present teachings;

FIG. 42D shows the PASTE editing efficiency with two vector (PE2 and Bxb1) and single vector (PE2-P2A-Bxb1) designs in K562 cells according to embodiments of the present teachings;

FIG. 42E shows the PASTE editing efficiency with single vector (PE2-P2A-Bxb1) designs in primary human T cells according to embodiments of the present teachings;

FIG. 42F shows the integration efficiency of therapeutically relevant genes at the ACTB locus according to embodiments of the present teachings;

FIG. 42G shows a schematic of protein production assay for PASTE-integrated transgene, wherein SERPINA1 and CPS1 transgenes are tagged with HIBIT luciferase for readout with both ddPCR and luminescence according to embodiments of the present teachings;

FIG. 42H shows the integration efficiency of SERPINA1 and CPS1 transgenes in HEK293FT cells at the ACTB locus according to embodiments of the present teachings;

FIG. 42I shows the integration efficiency of SERPINA1 and CPS1 transgenes in HepG2 cells at the ACTB locus according to embodiments of the present teachings;

FIG. 42J shows the intracellular levels of SERPINA1-HIBIT and CPS1-HIBIT in HepG2 cells according to embodiments of the present teachings;

FIG. 42K shows the secreted levels of SERPINA1-HIBIT and CPS1-HIBIT in HepG2 cells according to embodiments of the present teachings;

FIG. 43A shows the HDR mediated editing of the EMX1 locus that is significantly diminished in non-dividing HEK293FT cells blocked by 5 μM aphidicolin treatment according to embodiments of the present teachings;

FIG. 43B shows the effect of insert minicircle DNA amount on PASTE-mediated insertion at the ACTB locus in dividing and nondividing HEK293FT cells blocked by 5 μM aphidicolin treatment according to embodiments of the present teachings;

FIG. 43C shows the PASTE integration of GFP at the ACTB locus with the GFP template delivered via AAV, showing dose dependence of integration efficiency according to embodiments of the present teachings;

FIG. 44A shows the PASTE integration activity at three endogenous loci comparing the normal PASTE SV40 NLS to a c-Myc NLS/variable bi-partite SV40 NLS design according to embodiments of the present teachings;

FIG. 44B shows the PASTE integration activity at the ACTB locus with different GFP minicircle template amounts comparing the normal PASTE SV40 NLS to a c-Myc NLS/variable bi-partite SV40 NLS design according to embodiments of the present teachings;

FIG. 45 shows the improvement of the PASTE editing activity using a puromycin growth selection marker according to embodiments of the present teachings;

FIG. 46A shows the integration of SERPINA1 and CPS1 genes that are HIBIT tagged as measured by a protein expression luciferase assay according to embodiments of the present teachings;

FIG. 46B shows the integration of SERPINA1 and CPS1 genes that are HIBIT tagged as measured by a protein expression luciferase assay normalized to a standardized HIBIT ladder, enabling accurate quantification of protein levels according to embodiments of the present teachings;

FIG. 47A shows optimization of PASTE constructs with a panel of linkers and reverse transcriptase (RT) modifications for EGFP integration at the ACTB locus, according to embodiments of the present teachings;

FIG. 47B shows the effect of cargo size on PASTE insertion efficiency at the endogenous ACTB target. Cargos were transfected with fixed molar amounts, according to embodiments of the present teachings;

FIG. 48A shows prime editing efficiency for the insertion of different length BxbINT AttB sites at ACTB, according to embodiments of the present teachings;

FIG. 48B shows prime editing efficiency for the insertion of a BxbINT AttB site at ACTB with targeting and non-targeting guides, according to embodiments of the present teachings;

FIG. 48C shows prime editing efficiency for the insertion of different integrases' (Bxb1, Tp9, and Bt1) AttB sites at ACTB. Both orientations of landing sites are profiled (F, forward; R, reverse), according to embodiments of the present teachings;

FIG. 48D shows PASTE editing efficiency for the insertion of EGFP at ACTB with and without a nicking guide, according to embodiments of the present teachings; and FIG. 49A shows optimization of PASTE editing by dosage titration and protein optimization. PASTE integration efficiency of EGFP at ACTB measured with different doses of a single-vector delivery of components.

FIG. 49B PASTE integration efficiency of EGFP at ACTB measured with different ratios of a single-vector delivery of components to the EGFP template vector.

FIG. 49C PASTE integration efficiency of EGFP at ACTB with different RT domain fusions.

FIG. 49D PASTE integration efficiency of EGFP at ACTB with different RT domain fusions and linkers.

FIG. 49E PASTE integration efficiency of EGFP at ACTB with mutant RT domains.

FIG. 49F PASTE integration efficiency of EGFP at ACTB with mutated BxbINT domains.

FIG. 50A Insertion templates delivered via AAV transduction. PASTE editing machinery was delivered via transfection, and templates were co-delivered via AAV dosing at levels indicated.

FIG. 50B Schematic of AdV delivery of the complete PASTE system with three viral vectors.

FIG. 50C Integration efficiency of AdV delivery of integrase, guides, and cargo in HEK293FT and HepG2 cells. BxbINT and guide RNAs or cargo were delivered either via plasmid transfection (Pl), AdV transduction (AdV), or omitted (-). SpCas9-RT was only delivered as plasmid or omitted.

FIG. 50D AdV delivery of all PASTE components in HEK293FT and HepG2 cells.

FIG. 50E Schematic of mRNA and synthetic guide delivery of PASTE components.

FIG. 50F Delivery of PASTE system components with mRNA and synthetic guides, paired with either AdV or plasmid cargo.

FIG. 50G Delivery of circular mRNA with synthetic guides and either AdV or plasmid cargo.

FIG. 50H PASTE editing efficiency with single vector designs in primary human T cells.

FIG. 50I PASTE editing efficiency with single vector designs in primary human hepatocytes.

Figure 51A:
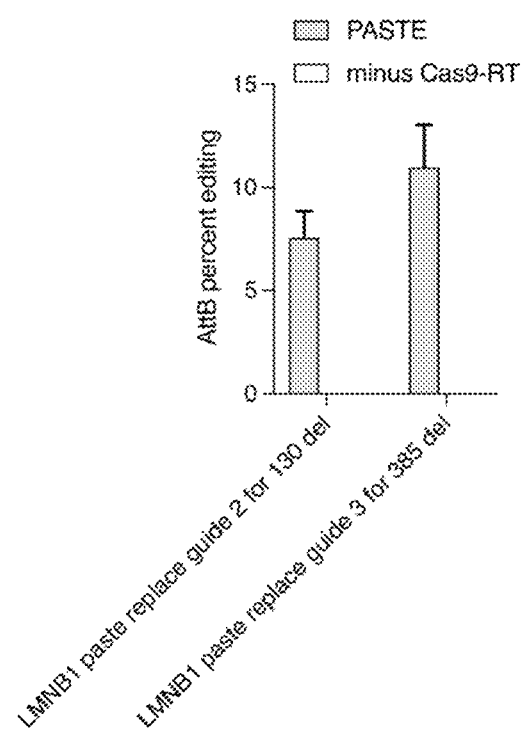

FIG. 51A PASTE editing efficiency at the LMNB1 locus with 130 bp and 385 bp deletions of the first exon of LMNB1 with combined insertion of an attB sequence.

Figure 51B:
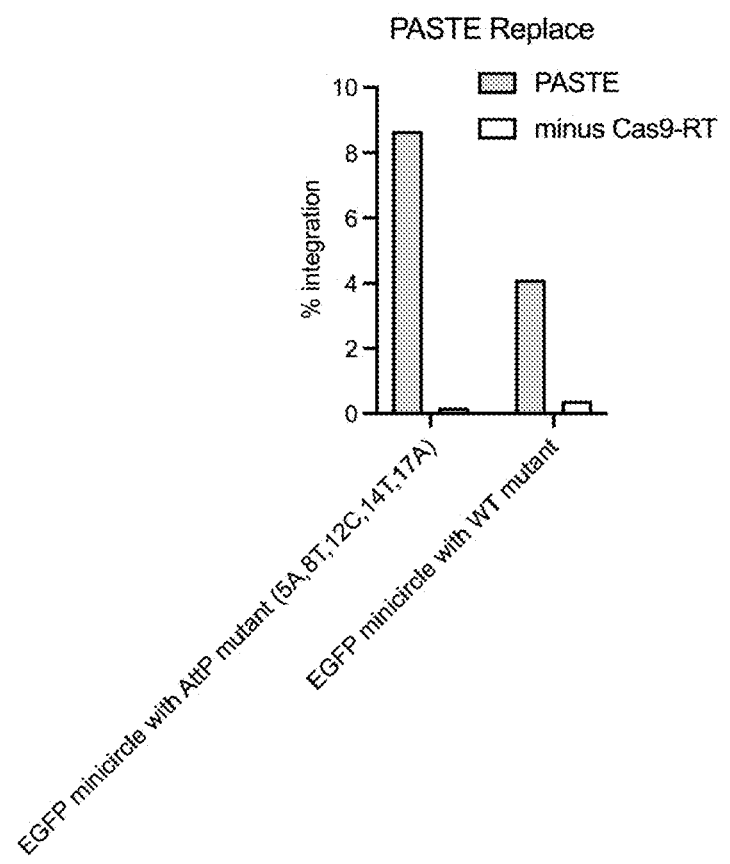

FIG. 51B PASTE editing efficiency with a 130 bp deletion of the first exon of LMNB1 with a combined insertion of a 967 bp cargo using the PASTE system.

DETAILED DESCRIPTION

It will be appreciated that for clarity, the following discussion will describe various aspects of embodiments of the applicant's teachings. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular feature, structures or characteristics may be combined in any suitable manner, as would be apparent to a person skilled in the art from this disclosure, in one or more embodiments.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an," and "the" include both singular and plural referents unless the context clearly dictates otherwise. Thus, for example, reference to "a cell" includes a plurality of such cells.

As used herein, the term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, the term "about" or "approximately" refers to a measurable value such as a parameter, an amount, a temporal duration, and the like, are meant to encompass variations of and from the specified value, such as variations of +/-10% or less, +/-5% or less, +/-1% or less, +/-0.5% or less, and +/-0.1% or less of and from the specified value, insofar such variations are appropriate to perform in the disclosure. It is to be understood that the value to which the modifier "about" or "approximately" refers is itself also specifically, and preferably, disclosed.

It is noted that all publications and references cited herein are expressly incorporated herein by reference in their entirety. The publications discussed herein are provided solely for their disclosure prior to the filing date of the present application. Nothing herein is to be construed as an admission that the present disclosure is not entitled to antedate such publication. Further, the dates of publication provided may be different from the actual publication dates which may need to be independently confirmed.

Overview

Figure 1:
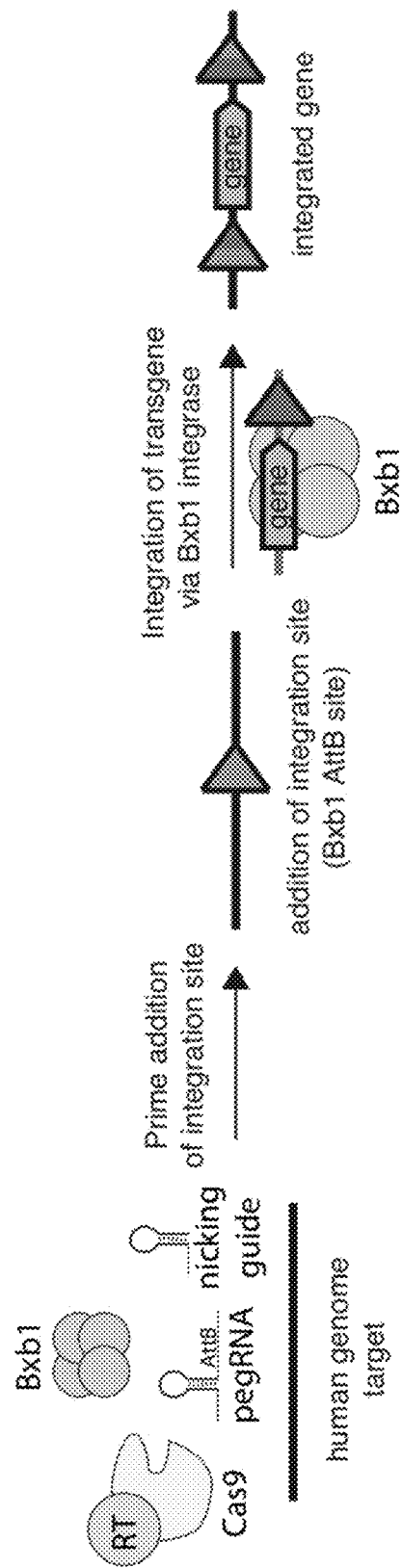
FIG. 1 shows a schematic diagram of a concept of Programmable Addition via Site-Specific Targeting Elements (PASTE) according to embodiments of the present teachings.

The embodiments disclosed herein provide non-naturally occurring or engineered systems, methods, and compositions for site-specific genetic engineering using Programmable Addition via Site-Specific Targeting Elements (PASTE). A schematic diagram illustrating the concept of PASTE is shown in FIG. 1. As discussed in more details below, PASTE comprises the addition of an integration site into a target genome followed by the insertion of one or more genes of interest or one or more nucleic acid sequences of interest at the site. This process can be done as one or more reactions in a cell. The addition of the integration site into the target genome is done using gene editing technologies that include for example, without limitation, prime editing, recombinant adeno-associated virus (rAAV)-mediated nucleic acid integration, transcription activator-like effector nucleases (TALENS), and zinc finger nucleases (ZFNs). The integration of the transgene at the integration site is done using integrase technologies that include for example, without limitation, integrases, recombinases and reverse transcriptases. The necessary components for the site-specific genetic engineering disclosed herein comprise at least one or more nucleases, one or more gRNA, one or more integration enzymes, and one or more sequences that are complementary or associated to the integration site and linked to the one or more genes of interest or one or more nucleic acid sequences of interest to be inserted into the cell genome.

An advantage of the non-naturally occurring or engineered systems, methods, and compositions for site-specific genetic engineering disclosed herein is programmable insertion of large elements without reliance on DNA damage responses.

Another advantage of the non-naturally occurring or engineered systems, methods, and compositions for site-specific genetic engineering disclosed herein is facile multiplexing, enabling programmable insertion at multiple sites.

Another advantage of the non-naturally occurring or engineered systems, methods, and compositions for site-specific genetic engineering disclosed herein is scalable production and delivery through minicircle templates.

Prime Editing

The present disclosure provides non-naturally occurring or engineered systems, methods, and compositions for site-specific genetic engineering using gene editing technologies, such as prime editing, to add an integration site into a target genome. Prime editing will be discussed in more details below.

Figure 2:
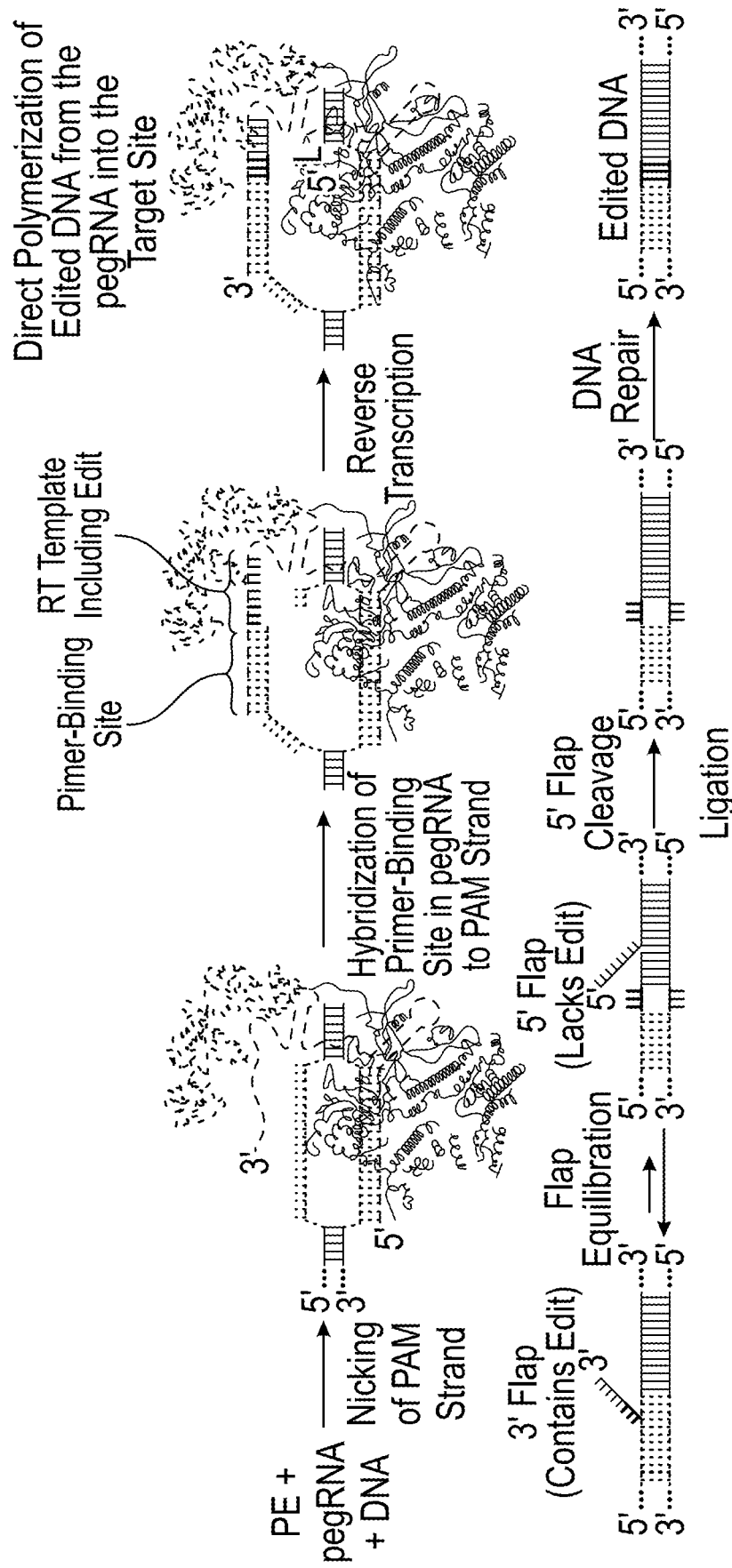
FIG. 2 shows a schematic diagram of a prime editing process according to embodiments of the present teachings.

Prime editing is a versatile and precise genome editing method that directly writes new genetic information into a specified DNA site. A schematic diagram illustrating the concept of prime editing is shown in FIG. 2. See, Anzalone, A. V., et al. "Search-and-replace genome editing without double-strand breaks or donor DNA," Nature 576, 149-157 (2019). Prime editing uses a catalytically-impaired Cas9 endonuclease that is fused to an engineered reverse transcriptase (RT) and programmed with a prime-editing guide RNA (pegRNA). The skilled person in the art would appreciate that the pegRNA both specifies the target site and encodes the desired edit. The catalytically-impaired Cas9 endonuclease also comprises a Cas9 nickase that is fused to the reverse transcriptase. During genetic editing, the Cas9 nickase part of the protein is guided to the DNA target site by the pegRNA. The reverse transcriptase domain then uses the pegRNA to template reverse transcription of the desired edit, directly polymerizing DNA onto the nicked target DNA strand. The edited DNA strand replaces the original DNA strand, creating a heteroduplex containing one edited strand and one unedited strand. Afterward, the prime editor (PE) guides resolution of the heteroduplex to favor copying the edit onto the unedited strand, completing the process.

The prime editors refer to a Moloney Murine Leukemia Virus (M-MLV) reverse transcriptase (RT) fused to a Cas9 H840A nickase. Fusing the RT to the C-terminus of the Cas9 nickase may result in higher editing efficiency. Such a complex is called PE1. The Cas9(H840A) can also be linked to a non-M-MLV reverse transcriptase such as a AMV-RT or XRT (Cas9(H840A)-AMV-RT or XRT). In some embodiments, Cas 9(H840A) can be replaced with Cas12a/b or Cas9(D10A). A Cas9 (wild type), Cas9(H840A), Cas9 (D10A) or Cas 12a/b nickase fused to a pentamutant of M-MLV RT (D200N/L603W/T330P/T306K/W313F), having up to about 45-fold higher efficiency is called PE2. In some embodiments, the M-MLV RT comprise one or more of the mutations: Y8H, P51L, S56A, S67R, E69K, V129P, L139P, T197A, H204R, V223H, T246E, N249D, E286R, Q291I, E302K, E302R, F309N, M320L, P330E, L435G, L435R, N454K, D524A, D524G, D524N, E562Q, D583N, H594Q, E607K, D653N, and L671P. In some embodiments, the reverse transcriptase can also be a wild-type or modified transcription xenopolymerase (RTX), avian myeloblastosis virus reverse transcriptase (AMV-RT), Feline Immunodeficiency Virus reverse transcriptase (FIV-RT), FeLV-RT (Feline leukemia virus reverse transcriptase), HIV-RT (Human Immunodeficiency Virus reverse transcriptase), or *Eubacterium rectale* maturase RT (MarathonRT). PE3 involves nicking the non-edited strand, potentially causing the cell to remake that strand using the edited strand as the template to induce HR. The nicking of the non-edited strand can involve the use of a nicking guide RNA (ngRNA).

Nicking the non-edited strand can increase editing efficiency. For example, nicking the non-edited strand can increase editing efficiency by about 1.1 fold, about 1.3 fold, about 1.5 fold, about 1.7 fold, about 1.9 fold, about 2.1 fold, about 2.3 fold, about 2.5 fold, about 2.7 fold, about 2.9 fold, about 3.1 fold, about 3.3 fold, about 3.5 fold, about 3.7 fold, about 3.9 fold, 4.1 fold, about 4.3 fold, about 4.5 fold, about 4.7 fold, about 4.9 fold, or any range that is formed from any two of those values as endpoints.

Although the optimal nicking position varies depending on the genomic site, nicks positioned 3' of the edit about 40-90 bp from the pegRNA-induced nick can generally increase editing efficiency without excess indel formation. The prime editing practice allows starting with non-edited strand nicks about 50 bp from the pegRNA-mediated nick, and testing alternative nick locations if indel frequencies exceed acceptable levels.

As used herein, the term "guide RNA" (gRNA) and the like refer to a RNA that guide the insertion or deletion of one or more genes of interest or one or more nucleic acid sequences of interest into a target genome. The gRNA can also refer to a prime editing guide RNA (pegRNA), a nicking guide RNA (ngRNA), and a single guide RNA (sgRNA). In some embodiments, the term "gRNA molecule" refers to a nucleic acid encoding a gRNA. In some embodiments, the gRNA molecule is naturally occurring. In some embodiments, a gRNA molecule is non-naturally occurring. In some embodiments, a gRNA molecule is a synthetic gRNA molecule. A gRNA can target a nuclease or a nickase such as Cas9, Cas 12a/b, Cas9 (H840A) or Cas9 (D10A) molecule to a target nucleic acid or sequence in a genome. In some embodiments, the gRNA can bind to a DNA nickase bound to a reverse transcriptase domain. A "modified gRNA," as used herein, refers to a gRNA molecule that has an improved half-life after being introduced into a cell as compared to a non-modified gRNA molecule after being introduced into a cell. In some embodiments, the guide RNA can facilitate the addition of the insertion site sequence for recognition by integrases, transposases, or recombinases.

Figure 24A:
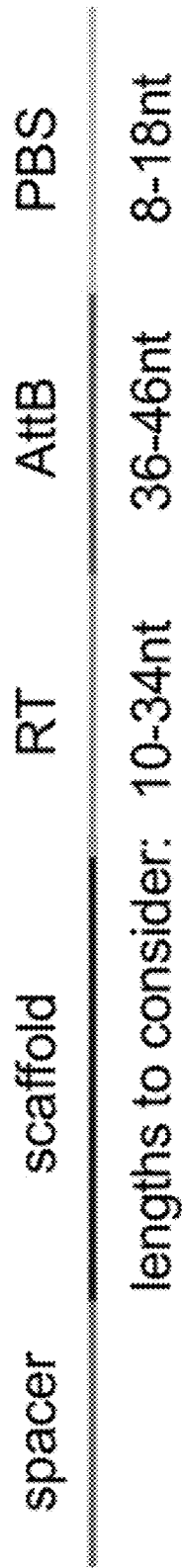
FIG. 24A shows a schematic of the design parameters for the pegRNA according to embodiments of the present teachings.

As used herein, the term "prime-editing guide RNA" (pegRNA) and the like refer to an extended single guide RNA (sgRNA) comprising a primer binding site (PBS), a reverse transcriptase (RT) template sequence, and an integration site sequence that can be recognized by recombinases, integrases, or transposases. Exemplary design parameters for pegRNA are shown in FIG. 24A. For example, the PBS can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or more nt. For example, the PBS can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or any range that is formed from any two of those values as endpoints. For example, the RT template sequence can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or more nt. For example, the RT template sequence can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or any range that is formed from any two of those values as endpoints.

During genome editing, the primer binding site allows the 3' end of the nicked DNA strand to hybridize to the pegRNA, while the RT template serves as a template for the synthesis of edited genetic information. The pegRNA is capable for instance, without limitation, of (i) identifying the target nucleotide sequence to be edited and (ii) encoding new genetic information that replaces the targeted sequence. In some embodiments, the pegRNA is capable of (i) identifying the target nucleotide sequence to be edited and (ii) encoding an integration site that replaces the targeted sequence.

Figure 24B:
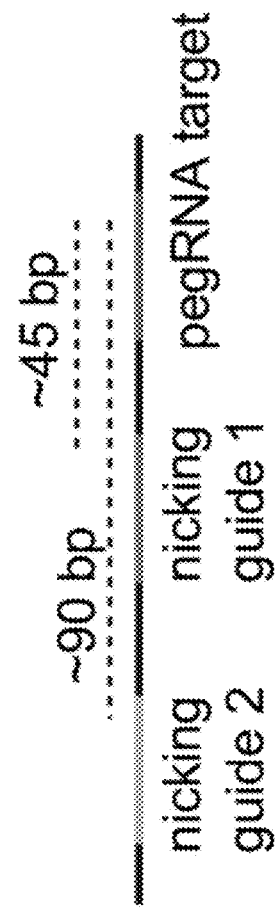
FIG. 24B shows a schematic of the design parameters for nicking guide RNA according to embodiments of the present teachings.

As used herein, the term "nicking guide RNA" (ngRNA) and the like refer to an RNA sequence that can nick a strand such as an edited strand and a non-edited strand. Exemplary design parameters for ngRNA are shown in FIG. 24B. The ngRNA can induce nicks at about 1 or more nt away from the site of the gRNA-induced nick. For example, the ngRNA can nick at least at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or more nt away from the site of the gRNA induced nick. In some embodiments, the ngRNA comprises SEQ ID NO: 75 with guide sequence SEQ ID NO: 74. As used herein, the terms "reverse transcriptase" and "reverse transcriptase domain" refer to an enzyme or an enzymatically active domain that can reverse a RNA transcribe into a complementary DNA. The reverse transcriptase or reverse transcriptase domain is a RNA dependent DNA polymerase. Such reverse transcriptase domains encompass, but are not limited to, a M-MLV reverse transcriptase, or a modified reverse transcriptase such as, without limitation, Superscript® reverse transcriptase (Invitrogen; Carlsbad, California), Superscript® VILO™ cDNA synthesis (Invitrogen; Carlsbad, California), RTX, AMV-RT, and Quantiscript Reverse Transcriptase (Qiagen, Hilden, Germany).

The pegRNA-PE complex disclosed herein recognizes the target site in the genome and the Cas9 for example nicks a protospacer adjacent motif (PAM) strand. The primer binding site (PBS) in the pegRNA hybridizes to the PAM strand. The RT template operably linked to the PBS, containing the edit sequence, directs the reverse transcription of the RT template to DNA into the target site. Equilibration between the edited 3' flap and the unedited 5' flap, cellular 5' flap cleavage and ligation, and DNA repair results in stably edited DNA. To optimize base editing, a Cas9 nickase can be used to nick the non-edited strand, thereby directing DNA repair to that strand, using the edited strand as a template.

Integrase Technologies

The present disclosure provides non-naturally occurring or engineered systems, methods, and compositions for site-specific genetic engineering using integrase technologies. Integrase technologies will be discussed in more details below.

The integrase technologies used herein comprise proteins or nucleic acids encoding the proteins that direct integration of a gene of interest or nucleic acid sequence of interest into an integration site via a nuclease such as a prime editing nuclease. The protein directing the integration can be an enzyme such as integration enzyme. The integration enzyme can be an integrase that incorporates the genome or nucleic acid of interest into the cell genome at the integration site by integration. The integration enzyme can be a recombinase that incorporates the genome or nucleic acid of interest into the cell genome at the integration site by recombination. The integration enzyme can be a reverse transcriptase that incorporates the genome or nucleic acid of interest into the cell genome at the integration site by reverse transcription. The integration enzyme can be a retrotransposase that incorporates the genome or nucleic acid of interest into the cell genome at the integration site by retrotransposition.

As used herein, the term "integration enzyme" refers to an enzyme or protein used to integrate a gene of interest or nucleic acid sequence of interest into a desired location or at the integration site, in the genome of a cell, in a single reaction or multiple reactions. Example of integration enzymes include for example, without limitation, Cre, Dre, Vika, Bxb1, φC31, RDF, FLP, φBT1, RI, R2, R3, R4, R5, TP901-1, A118, φFC1, φC1, MR11, TG1, φ370.1, WO, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, (φRV, and retrotransposases encoded by R2, L1, Tol2 Tc1, Tc3, Mariner (Himar 1), Mariner (mos 1), and Minos. In some embodiments, the term "integration enzyme" refers to a nucleic acid (DNA or RNA) encoding the above-mentioned enzymes. In some embodiments, the Cre recombinase is expressed from a Cre recombinase expression plasmid (SEQ ID NO: 71).

Mammalian expression plasmids can be found in Table 1 below.

TABLE 1

| Name | Full Description | SEQ ID NOS: |
| --- | --- | --- |
| PE2-Bxb1 Single Vector | pCMV-PE2-P2A- Bxb1 | (SEQ ID NO: 381) |
| PE2 prime editor | pCMV-PE2/ Addgene #132775 | (SEQ ID NO: 382) |
| PE2*-Bxb1 Single Vector | New NLS pCMV-PE2-P2A-Bxb1 | (SEQ ID NO: 383) |

TABLE 1-continued

| Name | Full Description | SEQ ID NOS: |
|---|---|---|
| PASTEv3 | pCMV-SpCas9-XTEN-RT(1-478)-Sto7d-GGGGS-BxbINT | (SEQ ID NO: 384) |
| ACTB pegRNA | ACTB N-term PBS 13 RT 29 attB 46 pegRNA | (SEQ ID NO: 385) |
| ACTB Nicking +48 | ACTB N-term Nicking guide 1 +48 guide | (SEQ ID NO: 386) |
| Bxb1 integrase | pCAG-NLS-HA-Bxb1 integrase/Addgene #51271 | (SEQ ID NO: 387) |
| TP901-1 Integrase | TP901-1 Integrase | (SEQ ID NO: 388) |
| PhiBT Integrase | PhiBT Integrase | (SEQ ID NO: 389) |
| HDR sgRNA guide | Minicircle U6-sgRNA EFS-SpCas9 | (SEQ ID NO: 390) |
| HDR EGFP cargo | Cas9 HDR template site with EGFP | (SEQ ID NO: 391) |
| AAV helper plasmid | PDF6 AAV helper plasmid | (SEQ ID NO: 392) |
| AAV EGFP donor | GFP AAV donor plasmid | (SEQ ID NO: 393) |
| AAV2/8 | AAV2/8 capsid protein | (SEQ ID NO: 394) |

273 Minicircle cargo gene maps can be found in Table 2 below.

TABLE 2

| Name | Full Description | SEQ ID NOS: |
|---|---|---|
| Cargo EGFP | Parent minicircle plasmid - Cargo EGFP with attP Bxb1 site | (SEQ ID NO: 76) |
| Cargo EGFP post cleavage | Cargo EGFP with attP Bxb1 site - post minicircle cleavage | (SEQ ID NO: 395) |
| Cargo EGFP for fusion | Parent minicircle plasmid - Cargo EGFP with attP Bxb1 site for fusion | (SEQ ID NO: 396) |
| mCherry Cargo post cleavage | Cargo mCherry with attP Bxb1 site - post minicircle cleavage | (SEQ ID NO: 397) |
| YFP Cargo post cleavage | Cargo YFP with attP Bxb1 site - post minicircle cleavage | (SEQ ID NO: 398) |
| SERPINA1 Cargo post cleavage | Cargo SERPINA1 with attP Bxb1 site - post minicircle cleavage | (SEQ ID NO: 399) |
| CPS1 Cargo post cleavage | Cargo CPS1 with attP Bxb1 site - post minicircle cleavage | (SEQ ID NO: 400) |
| CFTR Cargo | Parent minicircle plasmid - Cargo CFTR with attP Bxb1 site | (SEQ ID NO: 401) |
| NYESO TCR Cargo post cleavage | Cargo NYESO TCR with attP Bxb1 site - post minicircle cleavage | (SEQ ID NO: 402) |

In some embodiments, the serine integrase φC31 from φC31 phage is use as integration enzyme. The integrase φC31 in combination with a pegRNA can be used to insert the pseudo attP integration site (SEQ ID NO: 78). A DNA minicircle containing a gene or nucleic acid of interest and attB (SEQ ID NO: 3) site can be used to integrate the gene or nucleic acid of interest into the genome of a cell. This integration can be aided by a co-transfection of an expression vector having the (φC31 integrase.

As used herein, the term "integrase" refers to a bacteriophage derived integrase, including wild-type integrase and any of a variety of mutant or modified integrases. As used herein, the term "integrase complex" may refer to a complex comprising integrase and integration host factor (IF). As used herein, the term "integrase complex" and the like may also refer to a complex comprising an integrase, an integration host factor, and a bacteriophage λ-derived excisionase (Xis).

As used herein, the term "recombinase" and the like refer to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R1, R2, R3, R4, R5, φRV1, φFC1, MR11, A118, U153, and gp29. Examples of serine recombinases also include, without limitation, recombinases Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, and BxZ2 from Mycobacterial phages. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange.

Recombinases have numerous applications, including the creation of gene knockouts/knock-ins and gene therapy applications. See, e.g., Brown et al., "Serine recombinases as tools for genome engineering." *Methods*, 2011; 53(4): 372-9; Hirano et al., "Site-specific recombinases as tools for heterologous gene integration." *Appl. Microbiol. Biotechnol.* 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12): 4088-107; Venken and Bellen, "Genome-wide manipulations of *Drosophila melanogaster* with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Creating a new biological era." *J. Zhejiang Univ. Sci. B.* 2012; 13(7):511-24; Karpenshif and Bernstein, "From yeast to mammals: recent advances in genetic control of homologous recombination." *DNA Repair (Amst).* 2012; 1; 11(10):781-8; the entire contents of each are hereby incorporated by reference in their entirety.

The recombinases provided herein are not meant to be exclusive examples of recombinases that can be used in embodiments of the disclosure. The methods and compositions of the disclosure can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety).

Other examples of recombinases that are useful in the systems, methods, and compositions described herein are known to those of skill in the art, and any new recombinase that is discovered or generated is expected to be able to be used in the different embodiments of the disclosure.

As used herein, the term "retrotransposase" and the like refer to an enzyme, or combination of one or more enzymes, wherein at least one enzyme has a reverse transcriptase domain. Retrotransposases are capable of inserting long sequences (e.g., over 3000 nucleotides) of heterologous nucleic acid into a genome. Examples of retrotransposases include for example, without limitation, retrotransposases encoded by elements such as R2, L1, Tol2 Tc1, Tc3, Mariner (Himar 1), Mariner (mos 1), Minos, and any mutants thereof.

In some embodiments, the one or more genes of interest or one or more nucleic acid sequences of interest are inserted into a desired location in a genome using a RNA fragment, such as a retrotransposon, encoding the nucleic acid linked to a complementary or associated integration site. The insertion of the nucleic acid of interest into a location in the desired location in the genome using a retrotransposon is aided by a retrotransposase.

The gene and nucleic acid sequence of interest disclosed herein can be any gene and nucleic acid sequence that are known in the art. The gene and nucleic acid sequence of interest can be for therapeutic and/or diagnostic uses. Examples of genes of interest include, without limitation, GBA, BTK, ADA, CNGB3, CNGA3, ATF6, GNAT2, ABCA1, ABCA7, APOE, CETP, LIPC, MMP9, PLTP, VTN, ABCA4, MFSD8, TLR3, TLR4, ERCC6, HMCN1, HTRA1, MCDR4, MCDR5, ARMS2, C2, C3, CFB, CFH, JAGI, NOTCH2, CACNA1F, SERPINA1, TTR, GSN, B2M, APOA2, APOA1, OSMR, ELP4, PAX6, ARG, ASL, PITX2, FOXC1, BBS1, BBS10, BBS2, BBS9, MKKS, MKS1, BBS4, BBS7, TTC8, ARL6, BBS5, BBS12, TRIM32, CEP290, ADIPORI, BBIP1, CEP19, IFT27, LZTFL1, DMD, BEST1, HBB, CYP4V2, AMACR, CYP7B1, HSD3B7, AKR1D1, OPNISW, NR2F1, RLBP1, RGS9, RGS9BP, PROM1, PRPH2, GUCY2D, CACD, CHM, ALAD, ASS1, SLC25A13, OTC, ACADVL, ETFDH, TMEM67, CC2D2A, RPGRIP1L, KCNV2, CRX, GUCA1A, CERKL, CDHR1, PDE6C, TTLL5, RPGR, CEP78, C21orf2, C80RF37, RPGRIP1, ADAM9, POC1B, PITPNM3, RAB28, CACNA2D4, AIPL1, UNC119, PDE6H, OPN1LW, RIMS1, CNNM4, IFT81, RAX2, RDH5, SEMA4A, CORD17, PDE6B, GRK1, SAG, RHO, CABP4, GNB3, SLC24A1, GNAT1, GRM6, TRPM1, LRIT3, TGFBI, TACSTD2, KRT12, OVOL2, CPS1, UGT1A1, UGT1A9, UGT1A8, UGT1A7, UGT1A6, UGT1A5, UGT1A4, CFTR, DLD, EFEMP1, ABCC2, ZNF408, LRP5, FZD4, TSPAN12, EVR3, APOB, SLC2A2, LOC106627981, GBA1, NR2E3, OAT, SLC40A1, F8, F9, UROD, CPOX, HFE, JH, LDLR, EPHX1, TJP2, BAAT, NBAS, LARS1, HAMP, HJV, RS1, ADAMTS18, LRAT, RPE65, LCA5, MERTK, GDF6, RD3, CCT2, CLUAP1, DTHD1, NMNAT1, SPATA7, IFT140, IMPDH1, OTX2, RDH12, TULP1, CRB1, MT-ND4, MT-ND1, MT-ND6, BCKDHA, BCKDHB, DBT, MMAB, ARSB, GUSB, NAGS, NPC1, NPC2, NDP, OPA1, OPA3, OPA4, OPA5, RTN4IP1, TMEM126A, OPA6, OPA8, ACO2, PAH, PRKCSH, SEC63, GAA, UROS, PPOX, HPX, HMOX1, HMBS, MIR223, CYP1B1, LTBP2, AGXT, ATP8B1, ABCB11, ABCB4, FECH, ALAS2, PRPF31, RP1, EYS, TOPORS, USH2A, CNGA1, C2ORF71, RP2, KLHL7, ORF1, RP6, RP24, RP34, ROM1, ADGRA3, AGBL5, AHR, ARHGEF18, CA4, CLCC1, DHDDS, EMC1, FAM161A, HGSNAT, HK1, IDH3B, KIAA1549, KIZ, MAK, NEURODI, NRL, PDE6A, PDE6G, PRCD, PRPF3, PRPF4, PRPF6, PRPF8, RBP3, REEP6, SAMD11, SLC7A14, SNRNP200, SPP2, ZNF513, NEK2, NEK4, NXNL1, OFD1, RP1L1, RP22, RP29, RP32, RP63, RP9, RGR, POMGNT1, DHX38, ARL3, COL2A1, SLCO1B1, SLCO1B3, KCNJ13, TIMP3, ELOVL4, TFR2, FAH, HPD, MYO7A, CDH23, PCDH15, DFNB31, GPR98, USH1C, USH1G, CIB2, CLRN1, HARS, ABHD12, ADGRV1, ARSG, CEP250, IMPG1, IMPG2, VCAN, G6PC1, ATP7B and any derivatives thereof.

As used here, the terms "retrotransposons," "jumping genes," "jumping nucleic acids," and the like refer to cellular movable genetic elements dependent on reverse transcription. The retrotransposons are of non-replication competent cellular origin, and are capable of carrying a foreign nucleic acid sequence. The retrotransposons can act as parasites of retroviruses, retaining certain classical hallmarks, such as long terminal repeats (LTR), retroviral primer binding sites, and the like. However, the naturally occurring retrotransposons usually do not contain functional retroviral structure genes, which would normally be capable of recombining to yield replication competent viruses. Some retrotransposons are examples of so-called "selfish DNA", or genetic information, which encodes nothing except the ability to replicate itself. The retrotransposon may do so by utilizing the occasional presence of a retrovirus or a retrotransposase within the host cell, efficiently packaging itself within the viral particle, which transports it to the new host genome, where it is expressed again as RNA. The information encoded within that RNA is potentially transported with the jumping gene. A retrotransposon can be a DNA transposon or a retrotransposon, including a LTR retrotransposon or a non-LTR retrotransposon.

Non-long terminal repeat (LTR) retrotransposons are a type of mobile genetic elements that are widespread in eukaryotic genomes. They include two classes: the apurinic/apyrimidinic endonuclease (APE)-type and the restriction enzyme-like endonuclease (RLE)-type. The APE class retrotransposons are comprised of two functional domains: an endonuclease/DNA binding domain, and a reverse transcriptase domain. The RLE class are comprised of three functional domains: a DNA binding domain, a reverse transcription domain, and an endonuclease domain. The reverse transcriptase domain of non-LTR retrotransposon functions by binding an RNA sequence template and reverse transcribing it into the host genome's target DNA. The RNA sequence template has a 3' untranslated region which is specifically bound to the transposase, and a variable 5' region generally having Open Reading Frame(s) ("ORF") encoding transposase proteins. The RNA sequence template may also comprise a 5' untranslated region which specifically binds the retrotransposase. In some embodiments, a non-LTR transposons can include a LINE retrotransposon, such as L1, and a SINE retrotransposon, such as an Alu sequence. Other examples include for example, without limitation, RI, R2, R3, R4, and R5 retro-transposons (Moss, W. N. et al., *RNA Biol.* 2011, 8(5), 714-718; and Burke, W. D. et al., *Molecular Biology and Evolution* 2003, 20(8), 1260-1270). The transposon can be autonomous or non-autonomous.

LTR retrotransposons, which include retroviruses, make up a significant fraction of the typical mammalian genome, comprising about 8% of the human genome and 10% of the mouse genome. Lander et al., 2001, *Nature* 409, 860-921; Waterson et al., 2002, Nature 420, 520-562. LTR elements include retrotransposons, endogenous retroviruses (ERVs), and repeat elements with HERV origins, such as SINE-R. LTR retrotransposons include two LTR sequences that flank a region encoding two enzymes: integrase and retrotransposase.

ERVs include human endogenous retroviruses (HERVs), the remnants of ancient germ-cell infections. While most HERV proviruses have undergone extensive deletions and mutations, some have retained ORFS coding for functional proteins, including the glycosylated env protein. The env gene confers the potential for LTR elements to spread between cells and individuals. Indeed, all three open reading frames (pol, gag, and env) have been identified in humans, and evidence suggests that ERVs are active in the germline. See, e.g., Wang et al., 2010, *Genome Res.* 20, 19-27. Moreover, a few families, including the HERV-K (HML-2) group, have been shown to form viral particles, and an apparently intact provirus has recently been discovered in a small fraction of the human population. See, e.g., Bannert and Kurth, 2006, Proc. Natl. Acad. USA 101, 14572-14579.

LTR retrotransposons insert into new sites in the genome using the same steps of DNA cleavage and DNA strand-transfer observed in DNA transposons. In contrast to DNA transposons, however, recombination of LTR retrotransposons involves an RNA intermediate. LTR retrotransposons make up about 8% of the human genome. See, e.g., Lander et al., 2001, *Nature* 409, 860-921; Hua-Van et al., 2011, Biol. Dir. 6, 19.

Integration Site

The present disclosure provides non-naturally occurring or engineered systems, methods, and compositions for site-specific genetic engineering via the addition of an integration site into a target genome. The integration site will be discussed in more details below.

As used herein, the term "integration site" refers to the site within the target genome where one or more genes of interest or one or more nucleic acid sequences of interest are inserted. Examples of integration sites include for example, without limitation, a lox71 site (SEQ ID NO: 1), attB sites (SEQ ID NO: 3 and SEQ ID NO: 43), attP sites (SEQ ID NO: 4 and SEQ ID NO: 44), an attL site (SEQ ID NO: 67), an attR site (SEQ ID NO: 68), a Vox site (SEQ ID NO: 69), a FRT site (SEQ ID NO: 70), or a pseudo attP site (SEQ ID NO: 78). The integration site can be inserted into the genome or a fragment thereof of a cell using a nuclease, a gRNA, and/or an integration enzyme. The integration site can be inserted into the genome of a cell using a prime editor such as, without limitation, PE1, PE2, and PE3, wherein the integration site is carried on a pegRNA. The pegRNA can target any site that is known in the art. Examples of cites targeted by the pegRNA include, without limitation, ACTB, SUPT16H, SRRM2, NOLC1, DEPDC4, NES, LMNB1, AAVS1 locus, CC10, CFTR, SERPINA1, ABCA4, and any derivatives thereof. The complementary integration site may be operably linked to a gene of interest or nucleic acid sequence of interest in an exogenous DNA or RNA. In some embodiments, one integration site is added to a target genome. In some embodiments, more than one integration sites are added to a target genome.

To insert multiple genes or nucleic acids of interest, two or more integration sites are added to a desired location. Multiple DNA comprising nucleic acid sequences of interest are flanked orthogonal to the integration sequences, such as, without limitation, attB and attP. An integration site is "orthogonal" when it does not significantly recognize the recognition site or nucleotide sequence of a recombinase. Thus, one attB site of a recombinase can be orthogonal to an attB site of a different recombinase. In addition, one pair of attB and attP sites of a recombinase can be orthogonal to another pair of attB and attP sites recognized by the same recombinase. A pair of recombinases are considered orthogonal to each other, as defined herein, when there is recognition of each other's attB or attP site sequences.

The lack of recognition of integration sites or pairs of sites by the same recombinase or a different recombinase can be less than about 30%. In some embodiments, the lack of recognition of integration sites or pairs of sites by the same recombinase or a different recombinase can be less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, about 1%, or any range that is formed from any two of those values as endpoints. The crosstalk can be less than about 30%. In some embodiments, the crosstalk is less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, less than about 1%, or any range that is formed from any two of those values as endpoints.

In some embodiments, the attB and/or attP site sequences comprise a central dinucleotide sequence. It has been shown that, for example, the central dinucleotide can be changed to GA from GT and that only GA containing attB/attP sites interact and will not cross react with GT containing sequences. In some embodiments, the central dinucleotide is selected from the group consisting of AG, AC, TG, TC, CA, CT, GA, AA, TT, CC, GG, AT, TA, GC, CG and GT.

As used herein, the term "pair of an attB and attP site sequences" and the like refer to attB and attP site sequences that share the same central dinucleotide and can recombine. This means that in the presence of one serine integrase as many as six pairs of these orthogonal alt sites can recombine (attPTT will specifically recombine with attBTT, attPTC will specifically recombine with attBTC, and so on).

In some embodiments, the central dinucleotide is nonpalindromic. In some embodiments, the central dinucleotide is palindromic. In some embodiments, a pair of an attB site sequence and an attP site sequence are used in different DNA encoding genes of interest or nucleic acid sequences of interest for inducing directional integration of two or more different nucleic acids.

The Table 3 below shows examples of pairs of attB site sequence and attP site sequence with different central dinucleotide (CD).

TABLE 3

| Pair | attB | attP | CD |
|---|---|---|---|
| 1 | SEQ ID NO: 5 | SEQ ID NO: 6 | TT |
| 2 | SEQ ID NO: 7 | SEQ ID NO: 8 | AA |
| 3 | SEQ ID NO: 9 | SEQ ID NO: 10 | CC |
| 4 | SEQ ID NO: 11 | SEQ ID NO: 12 | GG |
| 5 | SEQ ID NO: 13 | SEQ ID NO: 14 | TG |
| 6 | SEQ ID NO: 15 | SEQ ID NO: 16 | GT |
| 7 | SEQ ID NO: 17 | SEQ ID NO: 18 | CT |
| 8 | SEQ ID NO: 19 | SEQ ID NO: 20 | CA |
| 9 | SEQ ID NO: 21 | SEQ ID NO: 22 | TC |
| 10 | SEQ ID NO: 23 | SEQ ID NO: 24 | GA |
| 11 | SEQ ID NO: 25 | SEQ ID NO: 26 | AG |
| 12 | SEQ ID NO: 27 | SEQ ID NO: 28 | AC |
| 13 | SEQ ID NO: 29 | SEQ ID NO: 30 | AT |
| 14 | SEQ ID NO: 31 | SEQ ID NO: 32 | GC |
| 15 | SEQ ID NO: 33 | SEQ ID NO: 34 | CG |
| 16 | SEQ ID NO: 35 | SEQ ID NO: 36 | TA |

Paste

The present disclosure provides non-naturally occurring or engineered systems, methods, and compositions for site-specific genetic engineering using PASTE. PASTE will be discussed in more details below.

The site-specific genetic engineering disclosed herein is for the insertion of one or more genes of interest or one or more nucleic acid sequences of interest into a genome of a cell. In some embodiments, the gene of interest is a mutated gene implicated in a genetic disease such as, without limitation, a metabolic disease, cystic fibrosis, muscular dystrophy, hemochromatosis, Tay-Sachs, Huntington disease, Congenital Deafness, Sickle cell anemia, Familial hypercholesterolemia, adenosine deaminase (ADA) deficiency, X-linked SCID (X-SCID), and Wiskott-Aldrich syndrome (WAS). In some embodiments, the gene of interest or nucleic acid sequence of interest can be a reporter gene upstream or downstream of a gene for genetic analyses such as, without limitation, for determining the expression of a gene. In some embodiments, the reporter gene is a GFP template (SEQ ID NO: 76) or a *Gaussia* Luciferase (G-Luciferase) template (SEQ ID NO: 77) In some embodiments, the gene of interest or nucleic acid sequence of interest can be used in plant genetics to insert genes to enhance drought tolerance, weather hardiness, and increased yield and herbicide resistance in plants. In some embodiments, the gene of interest or nucleic acid sequence of interest can be used for site-specific insertion of a protein (e.g., a lysosomal enzyme), a blood factor (e.g., Factor I, II, V, VII, X, XI, XII or XIII), a membrane protein, an exon, an intracellular protein (e.g., a cytoplasmic protein, a nuclear protein, an organellar protein such as a mitochondrial protein or lysosomal protein), an extracellular protein, a structural protein, a signaling protein, a regulatory protein, a transport protein, a sensory protein, a motor protein, a defense protein, or a storage protein, an anti-inflammatory signaling molecules into cells for treatment of immune diseases, including but not limited to arthritis, psoriasis, lupus, coeliac disease, glomerulonephritis, hepatitis, and inflammatory bowel disease.

The size of the inserted gene or nucleic acid can vary from about 1 bp to about 50,000 bp. In some embodiments, the size of the inserted gene or nucleic acid can be about 1 bp, 10 bp, 50 bp, 100 bp, 150 bp, 200 bp, 250 bp, 300 bp, 350 bp, 400 bp, 600 bp, 800 bp, 1000 bp, 1200 bp, 1400 bp, 1600 bp, 1800 bp, 2000 bp, 2200 bp, 2400 bp, 2600 bp, 2800 bp, 3000 bp, 3200 bp, 3400 bp, 3600 bp, 3800 bp, 4000 bp, 4200 bp, 4400 bp, 4600 bp, 4800 bp, 5000 bp, 5200 bp, 5400 bp, 5600 bp, 5800 bp, 6000 bp, 6200 bp, 6400 bp, 6600 bp, 6800 bp, 7000 bp, 7200 bp, 7400 bp, 7600 bp, 7800 bp, 8000 bp, 8200 bp, 8400 bp, 8600 bp, 8800 bp, 9000 bp, 9200 bp, 9400 bp, 9600 bp, 9800 bp, 10,000 bp, 10,200 bp, 10,400 bp, 10,600 bp, 10,800 bp, 11,000 bp, 11,200 bp, 11,400 bp, 11,600 bp, 11,800 bp, 12,000 bp, 14,000 bp, 16,000 bp, 18,000 bp, 20,000 bp, 30,000 bp, 40,000 bp, 50,000 bp, or any range that is formed from any two of those values as endpoints.

In some embodiments, the site-specific engineering using the gene of interest or nucleic acid sequence of interest disclosed herein is for the engineering of T cells and NKs for tumor targeting or allogeneic generation. These can involve the use of receptor or CAR for tumor specificity, anti-PD1 antibody, cytokines like IFN-gamma, TNF-alpha, IL-15, IL-12, IL-18, IL-21, and IL-10, and immune escape genes.

In the present disclosure, the site-specific insertion of the gene of interest or nucleic acid of interest is performed through Programmable Addition via Site-Specific Targeting Elements (PASTE). Components for inserting a gene of interest or a nucleic acid of interest using PASTE are for example, without limitation, a nuclease, a gRNA adding the integration site, a DNA or RNA strand comprising the gene or nucleic acid linked to a sequence that is complementary or associated to the integration site, and an integration enzyme. Components for inserting a gene of interest or a nucleic acid of interest using PASTE are for example, without limitation, a prime editor expression, pegRNA adding the integration site, nicking guide RNA, integration enzyme (Cre or serine recombinase), transgene vector comprising the gene of interest or nucleic acid sequence of interest with gene and integration signal. The nuclease and prime editor integrate the integration site into the genome. The integration enzyme integrates the gene of interest into the integration site. In some embodiments, the transgene vector comprising the gene or nucleic acid sequence of interest with gene and integration signal is a DNA minicircle devoid of bacterial DNA sequences. In some embodiments, the transgenic vector is a eukaryotic or prokaryotic vector.

As used herein, the term "vector" or "transgene vector" refers to a recombinant DNA molecule containing a desired coding sequence and appropriate nucleic acid sequences necessary for the expression of the operably linked coding sequence in a host organism. Nucleic acid sequences necessary for expression in prokaryotes usually include for example, without limitation, a promoter, an operator (optional), a ribosome binding site, and/or other sequences. Eukaryotic cells are generally known to utilize promoters (constitutive, inducible or tissue specific), enhancers, and termination and polyadenylation signals, although some elements may be deleted and other elements added without sacrificing the necessary expression. The transgenic vector may encode the PE and the integration enzyme, linked to each other via a linker. The linker can be a cleavable linker. For example, transgenic vector encoding the PE and the integration enzyme, linked to each other via a linker is pCMV PE2 P2A Cre comprises SEQ ID NO: 73. In some embodiments, the linker can be a non-cleavable linker. In some embodiments the nuclease, prime editor, and/or integration enzyme can be encoded in different vectors.

Figure 12:
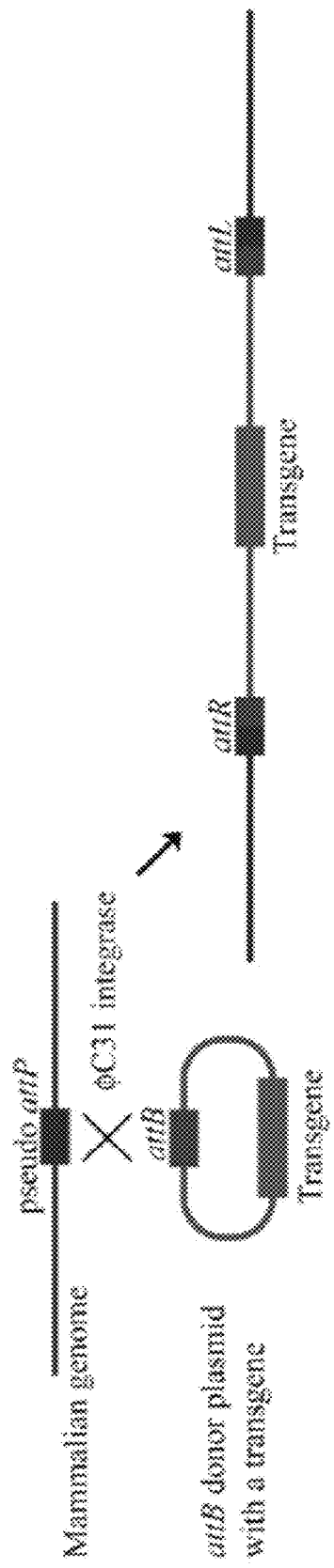
FIG. 12 shows a schematic diagram of the using φC31 as the integration enzyme, according to embodiments of the present teachings.
Figure 13:
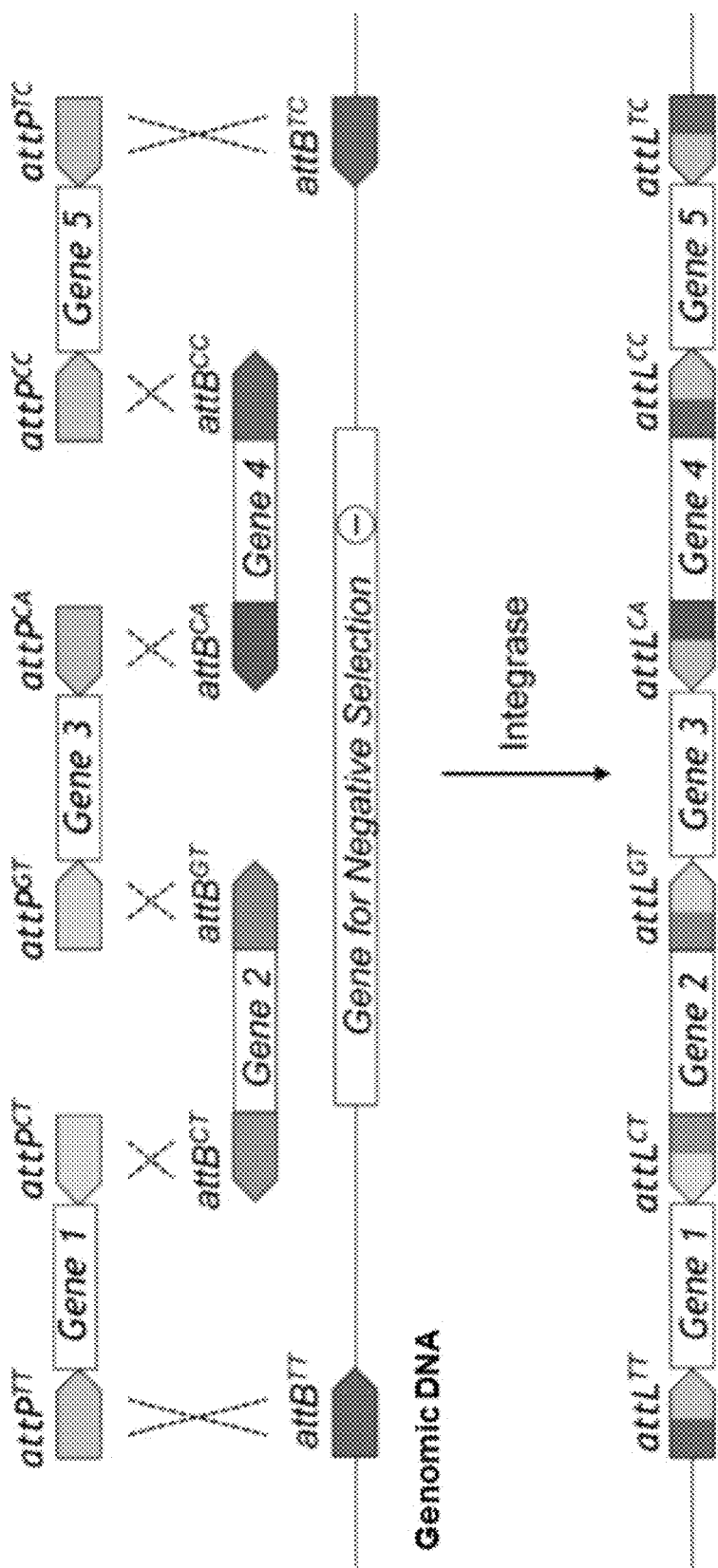
FIG. 13 shows a schematic diagram of multiplexing involving inserting multiple genes of interest in multiple loci using unique guide RNAs that incorporated exterior flanking attB sites according to embodiments of the present teachings.

A method of inserting multiple genes or nucleic acid sequences of interest into a single site according to embodiments of the present disclosure is illustrated in FIG. 12. In some embodiments, multiplexing involves inserting multiple genes of interest in multiple loci using unique pegRNA as illustrated in FIG. 13 (Merrick, C. A. et al., *ACS Synth. Biol.* 2018, 7, 299-310). The insertion of multiple genes of interest or nucleic acids of interest into a cell genome, referred herein as "multiplexing," is facilitated by incorporation of the complementary 5' integration site to the 5' end of the DNA or RNA comprising the first nucleic acid and 3' integration site to the 3' end of the DNA or RNA comprising the last nucleic acid. In some embodiments, the number of genome of interest or amino acid sequences of interest that are inserted into a cell genome using multiplexing can be about 1, 2, 3, 4, 5, 6, 7, 8, 9 10, 11, 12, 13, 14, 15, 16, 17, 18, 19, 20, 21, 22, 23, 24, 25, or any range that is formed from any two of those values as endpoints.

In some embodiments, multiplexing allows integration of for example, signaling cascade, over-expression of a protein of interest with its cofactor, insertion of multiple genes mutated in a neoplastic condition, or insertion of multiple CARs for treatment of cancer.

In some embodiments, the integration sites may be inserted into the genome using non-prime editing methods such as rAAV mediated nucleic acid integration, TALENS and ZFNs. A number of unique properties make AAV a promising vector for human gene therapy (Muzyczka, CURRENT TOPICS IN MICROBIOLOGY AND IMMUNOL-OGY, 158:97-129 (1992)). Unlike other viral vectors, AAVs have not been shown to be associated with any known human disease and are generally not considered pathogenic. Wild type AAV is capable of integrating into host chromosomes in a site-specific manner M. Kotin et al., PROC. NATL. ACAD. SCI, USA, 87:2211-2215 (1990); R. J. Samulski, EMBO 10(12):3941-3950 (1991)). Instead of creating a double-stranded DNA break, AAV stimulates endogenous homologous recombination to achieve the DNA modification. Further, transcription activator-like effector nucleases (TALENs) and Zinc-finger nucleases (ZFNs) for genome editing and introducing targeted DSBs. The specificity of TALENs arises from two polymorphic amino acids, the so-called repeat variable diresidues (RVDs) located at positions 12 and 13 of a repeated unit. TALENS are linked to FokI nucleases, which cleaves the DNA at the desired locations. ZFNs are artificial restriction enzymes for custom site-specific genome editing. Zinc fingers themselves are transcription factors, where each finger recognizes 3-4 bases. By mixing and matching these finger modules, researchers can customize which sequence to target.

As used herein, the terms "administration," "introducing," or "delivery" into a cell, a tissue, or an organ of a plasmid, nucleic acids, or proteins for modification of the host genome refers to the transport for such administration, introduction, or delivery that can occur in vivo, in vitro, or ex vivo. Plasmids, DNA, or RNA for genetic modification can be introduced into cells by transfection, which is typically accomplished by chemical means (e.g., calcium phosphate transfection, polyethyleneimine (PEI) Or lipofection), physical means (electroporation or microinjection), infection (this typically means the introduction of an infectious agent such as a virus (e.g., a baculovirus expressing the AAV Rep gene)), transduction (in microbiology, this refers to the stable infection of cells by viruses, or the transfer of genetic material from one microorganism to another by viral factors (e.g., bacteriophages)). Vectors for the expression of a recombinant polypeptide, protein or oligonucleotide may be obtained by physical means (e.g., calcium phosphate transfection, electroporation, microinjection, or lipofection) in a cell, a tissue, an organ or a subject. The vector can be delivered by preparing the vector in a pharmaceutically acceptable carrier for the in vitro, ex vivo, or in vivo delivery to the carrier.

As used herein, the term "transfection" refers to the uptake of an exogenous nucleic acid molecule by a cell. A cell is "transfected" when an exogenous nucleic acid has been introduced into the cell membrane. The transfection can be a single transfection, co-transfection, or multiple transfection. Numerous transfection techniques are generally known in the art. See, for example, Graham et al. (1973) Virology, 52: 456. Such techniques can be used to introduce one or more exogenous nucleic acid molecules into a suitable host cell.

In some embodiments, the exogenous nucleic acid molecule and/or other components for gene editing are combined and delivered in a single transfection. In other embodiments, the exogenous nucleic acid molecule and/or other components for gene editing are not combined and delivered in a single transfection. In some embodiments, exogenous nucleic acid molecule and/or other components for gene editing are combined and delivered in a single transfection to comprise for example, without limitation, a prime editing vector, a landing site such as a landing site containing pegRNA, a nicking guide such as a nicking guide for stimulating prime editing, an expression vector such as an expression vector for a corresponding integrase or recombinase, a minicircle DNA cargo such as a minicircle DNA cargo encoding for green fluorescent protein (GFP), any derivatives thereof, and any combinations thereof. In some embodiments, the gene of interest or amino acid sequence of interest can be introduced using liposomes. In some embodiments, the gene of interest or amino acid sequence of interest can be delivered using suitable vectors for instance, without limitation, plasmids and viral vectors. Examples of viral vectors include, without limitation, adeno-associated viruses (AAV), lentiviruses, adenoviruses, other viral vectors, derivatives thereof, or combinations thereof. The proteins and one or more guide RNAs can be packaged into one or more vectors, e.g., plasmids or viral vectors. In some embodiments, the delivery is via nanoparticles or exosomes. For example, exosomes can be particularly useful in delivery RNA.

In some embodiments, the prime editing inserts the landing site with efficiencies of at least about 1%, at least about 5%, at least about 10%, at least about 15%, at least about, at least about 20%, at least about 25%, at least about 30%, at least about 35%, at least about 40%, at least about 45%, or at least about 50%. In some embodiments, the prime editing inserts the landing site(s) with efficiencies of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, or any range that is formed from any two of those values as endpoints.

Sequences

Sequences of enzymes, guides, integration sites, and plasmids can be found in Table 4 below.

TABLE 4

| SEQ ID NO/ DESCRIPTION/ SOURCE | SEQUENCE |
| --- | --- |
| SEQ ID NO: 1 Lox71 (Artificial sequence) | ATAACTTCGTATAATGTATGCTATACGAACGGTA |
| SEQ ID NO: 2 Lox66 (Artificial sequence) | TACCGTTCGTATAATGTATGCTATACGAAGTTAT |
| SEQ ID NO: 3 attB (Artificial sequence) | GGCCGGCTTGTCGACGACGGCGGTCTCCGTCGTCAGGATCATCCG G |
| SEQ ID NO: 4 attP (Artificial Sequence) | CCGGATGATCCTGACGACGGAGACCGCCGTCGTCGACAAGCCGGC C |
| SEQ ID NO: 5 attB-TT (Artificial Sequence) | GGCTTGTCGACGACGGCGTTCTCCGTCGTCAGGATCAT |
| SEQ ID NO: 6 attP-TT (Artificial Sequence) | GTGGTTTGTCTGGTCAACCACCGCGTTCTCAGTGGTGTACGGTACA AACCCA |
| SEQ ID NO: 7 attB-AA (Artificial Sequence) | GGCTTGTCGACGACGGCGAACTCCGTCGTCAGGATCAT |
| SEQ ID NO: 8 attP-AA (Artificial Sequence) | GTGGTTTGTCTGGTCAACCACCGCGAACTCAGTGGTGTACGGTAC AAACCCA |
| SEQ ID NO: 9 attB-CC (Artificial Sequence) | GGCTTGTCGACGACGGCGCCCTCCGTCGTCAGGATCAT |
| SEQ ID NO: 10 attP-CC (Artificial Sequence) | GTGGTTTGTCTGGTCAACCACCGCGCCCTCAGTGGTGTACGGTACA AACCCA |
| SEQ ID NO: 11 attB-GG (Artificial Sequence) | GGCTTGTCGACGACGGCGGGCTCCGTCGTCAGGATCAT |
| SEQ ID NO: 12 attP-GG (Artificial Sequence) | GTGGTTTGTCTGGTCAACCACCGCGGGCTCAGTGGTGTACGGTAC AAACCCA |
| SEQ ID NO: 13 attB-TG (Artificial Sequence) | GGCTTGTCGACGACGGCGTGCTCCGTCGTCAGGATCAT |

TABLE 4-continued

| SEQ ID NO/<br>DESCRIPTION/<br>SOURCE | SEQUENCE |
|---|---|
| SEQ ID NO: 14<br>attP-TG<br>(Artificial Sequence) | GTGGTTTGTCTGGTCAACCACCGCGTGCTCAGTGGTGTACGGTACA<br>AACCCA |
| SEQ ID NO: 15<br>attB-GT<br>(Artificial Sequence) | GGCTTGTCGACGACGGCGGTCTCCGTCGTCAGGATCAT |
| SEQ ID NO: 16<br>attP-GT<br>(Artificial Sequence) | GTGGTTTGTCTGGTCAACCACCGCGGTCTCAGTGGTGTACGGTACA<br>AACCCA |
| SEQ ID NO: 17<br>attB-CT<br>(Artificial Sequence) | GGCTTGTCGACGACGGCGCTCTCCGTCGTCAGGATCAT |
| SEQ ID NO: 18<br>attP-CT<br>(Artificial Sequence) | GTGGTTTGTCTGGTCAACCACCGCGCTCTCAGTGGTGTACGGTACA<br>AACCCA |
| SEQ ID NO: 19<br>attB-CA<br>(Artificial Sequence) | GGCTTGTCGACGACGGCGCACTCCGTCGTCAGGATCAT |
| SEQ ID NO: 20<br>attP-CA<br>(Artificial Sequence) | GTGGTTTGTCTGGTCAACCACCGCGCACTCAGTGGTGTACGGTACA<br>AACCCA |
| SEQ ID NO: 21<br>attB-TC<br>(Artificial Sequence) | GGCTTGTCGACGACGGCGTCCTCCGTCGTCAGGATCAT |
| SEQ ID NO: 22<br>attP-TC<br>(Artificial Sequence) | GTGGTTTGTCTGGTCAACCACCGCGTCCTCAGTGGTGTACGGTACA<br>AACCCA |
| SEQ ID NO: 23<br>attB-GA<br>(Artificial Sequence) | GGCTTGTCGACGACGGCGGACTCCGTCGTCAGGATCAT |
| SEQ ID NO: 24<br>attP-GA<br>(Artificial Sequence) | GTGGTTTGTCTGGTCAACCACCGCGGACTCAGTGGTGTACGGTAC<br>AAACCCA |
| SEQ ID NO: 25<br>attB-AG<br>(Artificial Sequence) | GGCTTGTCGACGACGGCGAGCTCCGTCGTCAGGATCAT |
| SEQ ID NO: 26<br>attP-AG<br>(Artificial Sequence) | GTGGTTTGTCTGGTCAACCACCGCGAGCTCAGTGGTGTACGGTAC<br>AAACCCA |
| SEQ ID NO: 27<br>attB-AC<br>(Artificial Sequence) | GGCTTGTCGACGACGGCGACCTCCGTCGTCAGGATCAT |
| SEQ ID NO: 28<br>attP-AC<br>(Artificial Sequence) | GTGGTTTGTCTGGTCAACCACCGCGACCTCAGTGGTGTACGGTACA<br>AACCCA |
| SEQ ID NO: 29<br>attB-AT<br>(Artificial Sequence) | GGCTTGTCGACGACGGCGATCTCCGTCGTCAGGATCAT |
| SEQ ID NO: 30<br>attP-AT<br>(Artificial Sequence) | GTGGTTTGTCTGGTCAACCACCGCGATCTCAGTGGTGTACGGTACA<br>AACCCA |
| SEQ ID NO: 31<br>attB-GC<br>(Artificial Sequence | GGCTTGTCGACGACGGCGGCCTCCGTCGTCAGGATCAT |
| SEQ ID NO: 32<br>attP-GC<br>(Artificial Sequence) | GTGGTTTGTCTGGTCAACCACCGCGGCCTCAGTGGTGTACGGTACA<br>AACCCA |

TABLE 4-continued

| SEQ ID NO/<br>DESCRIPTION/<br>SOURCE | SEQUENCE |
| --- | --- |
| SEQ ID NO: 33<br>attB-CG<br>(Artificial Sequence) | GGCTTGTCGACGACGGCGCGCTCCGTCGTCAGGATCAT |
| SEQ ID NO: 34<br>attP-CG<br>(Artificial Sequence) | GTGGTTTGTCTGGTCAACCACCGCGCGCTCAGTGGTGTACGGTACA<br>AACCCA |
| SEQ ID NO: 35<br>attB-TA<br>(Artificial Sequence) | GGCTTGTCGACGACGGCGTACTCCGTCGTCAGGATCAT |
| SEQ ID NO: 36<br>attP-TA<br>(Artificial Sequence) | GTGGTTTGTCTGGTCAACCACCGCGTACTCAGTGGTGTACGGTACA<br>AACCCA |
| SEQ ID NO: 37<br>C31-attB<br>(Artificial Sequence) | TGCGGGTGCCAGGGCGTGCCCTTGGGCTCCCCGGGCGCGTACTCC |
| SEQ ID NO: 38<br>C31-attP<br>(Artificial Sequence) | GTGCCCCAACTGGGGTAACCTTTGAGTTCTCTCAGTTGGGGG |
| SEQ ID NO: 39<br>R4-attB<br>(Artificial Sequence) | GCGCCCAAGTTGCCCATGACCATGCCGAAGCAGTGGTAGAAGGGC<br>ACCGGCAGACAC |
| SEQ ID NO: 40<br>R4-attP<br>(Artificial Sequence) | AGGCATGTTCCCCAAAGCGATACCACTTGAAGCAGTGGTACTGCT<br>TGTGGGTACACTCTGCGGGTGATGA |
| SEQ ID NO: 41<br>BT1-attB<br>(Artificial Sequence) | GTCCTTGACCAGGTTTTTGACGAAAGTGATCCAGATGATCCAGCTC<br>CACACCCCGAACGC |
| SEQ ID NO: 42<br>BT1-attP<br>(Artificial Sequence) | GGTGCTGGGTTGTTGTCTCTGGACAGTGATCCATGGGAAACTACTC<br>AGCACCACCAATGTTCC |
| SEQ ID NO: 43<br>Bxb-attB<br>(Artificial Sequence) | TCGGCCGGCTTGTCGACGACGGCGGTCTCCGTCGTCAGGATCATCC<br>GGGC |
| SEQ ID NO: 44<br>Bxb-attP<br>(Artificial Sequence) | GTCGTGGTTTGTCTGGTCAACCACCGCGGTCTCAGTGGTGTACGGT<br>ACAAACCCCGAC |
| SEQ ID NO: 45<br>TG1-attB<br>(Artificial Sequence) | GATCAGCTCCGCGGGCAAGACCTTCTCCTTCACGGGGTGGAAGGT<br>C |
| SEQ ID NO: 46<br>TG1-attP<br>(Artificial Sequence) | TCAACCCCGTTCCAGCCCAACAGTGTTAGTCTTTGCTCTTACCCAG<br>TTGGGCGGGATAGCCTGCCCG |
| SEQ ID NO: 47<br>C1-attB<br>(Artificial Sequence) | AACGATTTTCAAAGGATCACTGAATCAAAAGTATTGCTCATCCAC<br>GCGAAATTTTTC |
| SEQ ID NO: 48<br>C1-attP<br>(Artificial Sequence) | AATATTTTAGGTATATGATTTTGTTTATTAGTGTAAATAACACTAT<br>GTACCTAAAAT |
| SEQ ID NO: 49<br>C370-attB<br>(Artificial Sequence) | TGTAAAGGAGACTGATAATGGCATGTACAACTATACTCGTCGGTA<br>AAAAGGCA |
| SEQ ID NO: 50<br>C370-attP<br>(Artificial Sequence) | TAAAAAAATACAGCGTTTTTCATGTACAACTATACTAGTTGTAGTG<br>CCTAAA |
| SEQ ID NO: 51<br>K38-attB<br>(Artificial Sequence) | GAGCGCCGGATCAGGGAGTGGACGGCCTGGGAGCGCTACACGCT<br>GTGGCTGCGGTC |

TABLE 4-continued

| SEQ ID NO/<br>DESCRIPTION/<br>SOURCE | SEQUENCE |
|---|---|
| SEQ ID NO: 52<br>K38-attP<br>(Artificial Sequence) | CCCTAATACGCAAGTCGATAACTCTCCTGGGAGCGTTGACAACTT<br>GCGCACCCTGA |
| SEQ ID NO: 53<br>RB-attB<br>(Artificial Sequence) | TCTCGTGGTGGTGGAAGGTGTTGGTGCGGGGTTGGCCGTGGTCGA<br>GGTGGGGTGGTGGTAGCCATTCG |
| SEQ ID NO: 54<br>RV-attP<br>(Artificial Sequence) | GCACAGGTGTAGTGTATCTCACAGGTCCACGGTTGGCCGTGGACT<br>GCTGAAGAACATTCCACGCCAGGA |
| SEQ ID NO: 55<br>SPBC-attB<br>(Artificial Sequence) | AGTGCAGCATGTCATTAATATCAGTACAGATAAAGCTGTATCTCCT<br>GTGAACACAATGGGTGCCA |
| SEQ ID NO: 56<br>SPBC-attP<br>(Artificial Sequence) | AAAGTAGTAAGTATCTTAAAAAACAGATAAAGCTGTATATTAAGA<br>TACTTACTAC |
| SEQ ID NO: 57<br>TP901-attB<br>(Artificial Sequence) | TGATAATTGCCAACACAATTAACATCTCAATCAAGGTAAATGCTTT<br>TTCGTTTT |
| SEQ ID NO: 58<br>TP901-attP<br>(Artificial Sequence) | AATTGCGAGTTTTTATTTCGTTTATTTCAATTAAGGTAACTAAAAA<br>ACTCCTTT |
| SEQ ID NO: 59<br>Wβ-attB<br>(Artificial Sequence) | AAGGTAGCGTCAACGATAGGTGTAACTGTCGTGTTTGTAACGGTA<br>CTTCCAACAGCTGGCGTTTCAGT |
| SEQ ID NO: 60<br>Wβ-attP<br>(Artificial Sequence) | TAGTTTTAAAGTTGGTTATTAGTTACTGTGATATTTATCACGGTAC<br>CCAATAACCAATGAATATTTGA |
| SEQ ID NO: 61<br>A118-attB<br>(Artificial Sequence) | TGTAACTTTTTCGGATCAAGCTATGAAGGACGCAAAGAGGGAACT<br>AAACACTTAATT |
| SEQ ID NO: 62<br>A118-attP<br>(Artificial Sequence) | TTGTTTAGTTCCTCGTTTTCTCTCGTTGGAAGAAGAAGAAACGAGA<br>AACTAAAATTA |
| SEQ ID NO: 63<br>BL3-attB<br>(Artificial Sequence) | CAACCTGTTGACATGTTTCCACAGACAACTCACGTGGAGGTAGTC<br>ACGGCTTTTACGTTAGTT |
| SEQ ID NO: 64<br>BL3-attP<br>(Artificial Sequence) | GAGAATACTGTTGAACAATGAAAAACTAGGCATGTAGAAGTTGTT<br>TGTGCACTAACTTTAA |
| SEQ ID NO: 65<br>MR11-attB<br>(Artificial Sequence) | ACAGGTCAACACATCGCAGTTATCGAACAATCTTCGAAAATGTAT<br>GGAGGCACTTGTATCAATATAGGATGTATACCTTCGAAGCACTT<br>GTACATGATGGATTAGAAGGCAAATCCTTT |
| SEQ ID NO: 66<br>MR11-attP<br>(Artificial Sequence) | CAAAATAAAAAACATTGATTTTTATTAACTTCTTTTGTGCGGAACT<br>ACGAACAGTTCATTAATACGAAGTGTACAAACTTCCATACAAAAA<br>TAACCACGACAATTAAGACGTGGTTTCTA |
| SEQ ID NO: 67<br>attL<br>(Artificial Sequence) | ATTATTTCTCACCCTGA |
| SEQ ID NO: 68<br>attR<br>(Artificial Sequence) | ATCATCTCCCACCCGGA |
| SEQ ID NO: 69<br>Vox<br>(Artificial Sequence) | AATAGGTCTG AGAACGCCCA TTCTCAGACG TATT |
| SEQ ID NO: 70<br>FRT<br>(Artificial Sequence) | GAAGTTCCTATAC TTTCTAGA GAATAGGAACTTC |

TABLE 4-continued

| SEQ ID NO/<br>DESCRIPTION/<br>SOURCE | SEQUENCE |
| --- | --- |
| SEQ ID NO: 71<br>Cre recombinase<br>expression plasmid<br>(Artificial Sequence) | GGTCGACATTGATTATTGACTAGTTATTAATAGTAATCAATTACGG<br>GGTCATTAGTTCATAGCCCATATATGGAGTTCCGCGTTACATAACT<br>TACGGTAAATGGCCCGCCTGGCTGACCGCCCAACGACCCCCGCCC<br>ATTGACGTCAATAATGACGTATGTTCCCATAGTAACGCCAATAGG<br>GACTTTCCATTGACGTCAATGGGTGGAGTATTTACGGTAAACTGCC<br>CACTTGGCAGTACATCAAGTGTATCATATGCCAAGTACGCCCCCTA<br>TTGACGTCAATGACGGTAAATGGCCCGCCTGGCATTATGCCCAGT<br>ACATGACCTTATGGGACTTTCCTACTTGGCAGTACATCTACGTATT<br>AGTCATCGCTATTACCATGGTCGAGGTGAGCCCCACGTTCTGCTTC<br>ACTCTCCCCATCTCCCCCCCCTCCCCACCCCCAATTTTGTATTTATT<br>TATTTTTTAATTATTTTGTGCAGCGATGGGGGCGGGGGGGGGGGG<br>GGCGCGCGCCAGGCGGGGGGGGGGGGGGGGGGGGGGGGGG<br>GGGGGGGCGGGGGGGGGGGCGGCAGCCAATCAGAGCGGCGCGC<br>TCCGAAAGTTTCCTTTTATGGCGAGGCGGCGGCGGCGGCGGCCCT<br>ATAAAAAGCGAAGCGCGCGGCGGGCGGGAGTCGCTGCGCGCTGC<br>CTTCGCCCCGTGCCCCGCTCCGCCGCCGCCTCGCGCCGCCCGCCCC<br>GGCTCTGACTGACCGCGTTACTCCCACAGGTGAGCGGGCGGGACG<br>GCCCTTCTCCTCCGGGCTGTAATTAGCGCTTGGTTTAATGACGGCT<br>TGTTTCTTTTCTGTGGCTGCGTGAAAGCCTTGAGGGGCTCCGGGAG<br>GGCCCTTTGTGCGGGGGGAGCGGCTCGGGGGGTGCGTGCGTGTGT<br>GTGTGCGTGGGGAGCGCCGCGTGCGGCTCCGCGCTGCCCGGCGGC<br>TGTGAGCGCTGCGGGCGCGGCGCGGGGCTTTGTGCGCTCCGCAGT<br>GTGCGCGAGGGGAGCGCGGCCGGGGCGGTGCCCCGCGGTGCGG<br>GGGGGGCTGCGAGGGGAACAAAGGCTGCGTGCGGGGTGTGTGCG<br>TGGGGGGGTGAGCAGGGGGTGTGGGCGCGTCGGTCGGGCTGCAA<br>CCCCCCCTGCACCCCCCTCCCCGAGTTGCTGAGCACGGCCCGGCTT<br>CGGGTGCGGGGCTCCGTACGGGGCGTGGCGCGGGGCTCGCCGTGC<br>CGGGCGGGGGTGGCGGCAGGTGGGGGTGCCGGGCGGGGCGGGG<br>CCGCCTCGGGCCGGGAGGGCTCGGGGGAGGGGCGCGGCGGCCC<br>CCGGAGCGCCGGCGGCTGTCGAGGCGCGGCGAGCCGCAGCCATTG<br>CCTTTTATGGTAATCGTGCGAGAGGGCGCAGGGACTTCCTTTGTCC<br>CAAATCTGTGCGGAGCCGAAATCTGGGAGGCGCCGCCGCACCCCC<br>TCTAGCGGGCGCGGGGCGAAGCGGTGCGGCGCCGGCAGGAAGGA<br>AATGGGCGGGGAGGGCCTTCGTGCGTCGCCGCGCCGCCGTCCCCT<br>TCTCCCTCTCCAGCCTCGGGGCTGTCCGCGGGGGGACGGCTGCCTT<br>CGGGGGGGACGGGGCAGGGCGGGGTTCGGCTTCTGGCGTGTGACC<br>GGCGGCTCTAGAGCCTCTGCTAACCATGTTCATGCCTTCTTCTTTTT<br>CCTACAGCTCCTGGGCAACGTGCTGGTTATTGTGCTGTCTCATCAT<br>TTTGGCAAAGAATTCTGAGCCGCCACCATGGCCAATTTACTGACC<br>GTACACCAAAATTTGCCTGCATTACCGGTCGATGCAACGAGTGAT<br>GAGGTTCGCAAGAACCTGATGGACATGTTCAGGGATCGCCAGGCG<br>TTTTCTGAGCATACCTGGAAAATGCTTCTGTCCGTTTGCCGGTCGT<br>GGGCGGCATGGTGCAAGTTGAATAACCGGAAATGGTTTCCCGCAG<br>AACCTGAAGATGTTCGCGATTATCTTCTATATCTTCAGGCGCGCGG<br>TCTGGCAGTAAAAACTATCCAGCAACATTTGGGCCAGCTAAACAT<br>GCTTCATCGTCGGTCCGGGCTGCCACGACCAAGTGACAGCAATGC<br>TGTTTCACTGGTTATGCGGCGGATCCGAAAAGAAAACGTTGATGC<br>CGGTGAACGTGCAAAACAGGCTCTAGCGTTCGAACGCACTGATTT<br>CGACCAGGTTCGTTCACTCATGGAAAATAGCGATCGCTGCCAGGA<br>TATACGTAATCTGGCATTTCTGGGGATTGCTTATAACACCCTGTTA<br>CGTATAGCCGAAATTGCCAGGATCAGGGTTAAAGATATCTCACGT<br>ACTGACGGTGGGAGAATGTTAATCCATATTGGCAGAACGAAAACG<br>CTGGTTAGCACCGCAGGTGTAGAGAAGGCACTTAGCCTGGGGGTA<br>ACTAAACTGGTCGAGCGATGGATTTCCGTCTCTGGTGTAGCTGATG<br>ATCCGAATAACTACCTGTTTTGCCGGGTCAGAAAAAATGGTGTTG<br>CCGCGCCATCTGCCACCAGCCAGCTATCAACTCGCGCCCTGGAAG<br>GGATTTTTGAAGCAACTCATCGATTGATTTACGGCGCTAAGGATG<br>ACTCTGGTCAGAGATACCTGGCCTGGTCTGGACACAGTGCCCGTG<br>TCGGAGCCGCGCGAGATATGGCCCGCGCTGGAGTTTCAATACCGG<br>AGATCATGCAAGCTGGTGGCTGGACCAATGTAAATATTGTCATGA<br>ACTATATCCGTAACCTGGATAGTGAAACAGGGGCAATGGTGCGCC<br>TGCTGGAAGATGGCGATGGACCGGTGGAACAAAAACTTATTTCTG<br>AAGAAGATCTGTGATAGCGGCCGCACTCCTCAGGTGCAGGCTGCC<br>TATCAGAAGGTGGTGGCTGGTGTGGCCAATGCCCTGGCTCACAAA<br>TACCACTGAGATCTTTTTCCCTCTGCCAAAAATTATGGGGACATCA<br>TGAAGCCCCTTGAGCATCTGACTTCTGGCTAATAAAGGAAATTTAT<br>TTTCATTGCAATAGTGTGTTGGAATTTTTTGTGTCTCTCACTCGGAA<br>GGACATATGGGAGGGCAAATCATTTAAAACATCAGAATGAGTATT<br>TGGTTTAGAGTTTGGCAACATATGCCCATATGCTGGCTGCCATGAA<br>CAAAGGTTGGCTATAAAGAGGTCATCAGTATATGAAACAGCCCCC<br>TGCTGTCCATTCCTTATTCCATAGAAAAGCCTTGACTTGAGGTTAG<br>ATTTTTTTTATATTTTGTTTTGTGTTATTTTTTCTTTAACATCCCTA<br>AAATTTTCCTTACATGTTTTACTAGCCAGATTTTTCCTCCTCTCCTG<br>ACTACTCCCAGTCATAGCTGTCCCTCTTCTCTTATGGAGATCCCTC<br>GACCTGCAGCCCAAGCTTGGCGTAATCATGGTCATAGCTGTTTCCT<br>GTGTGAAATTGTTATCCGCTCACAATTCCACACAACATACGAGCC |

TABLE 4-continued

| SEQ ID NO/<br>DESCRIPTION/<br>SOURCE | SEQUENCE |
|---|---|
| | GGAAGCATAAAGTGTAAAGCCTGGGGTGCCTAATGAGTGAGCTAA<br>CTCACATTAATTGCGTTGCGCTCACTGCCCGCTTTCCAGTCGGGAA<br>ACCTGTCGTGCCAGCGGATCCGCATCTCAATTAGTCAGCAACCAT<br>AGTCCCGCCCCTAACTCCGCCCATCCCGCCCCTAACTCCGCCCAGT<br>TCCGCCCATTCTCCGCCCCATGGCTGACTAATTTTTTTATTTATGC<br>AGAGGCCGAGGCCGCCTCGGCCTCTGAGCTATTCCAGAAGTAGTG<br>AGGAGGCTTTTTTGGAGGCCTAGGCTTTTGCAAAAAGCTAACTTGT<br>TTATTGCAGCTTATAATGGTTACAAATAAAGCAATAGCATCACAA<br>ATTTCACAAATAAAGCATTTTTTTCACTGCATTCTAGTTGTGGTTTG<br>TCCAAACTCATCAATGTATCTTATCATGTCTGGATCCGCTGCATTA<br>ATGAATCGGCCAACGCGCGGGGAGAGGCGGTTTGCGTATTGGGCG<br>CTCTTCCGCTTCCTCGCTCACTGACTCGCTGCGCTCGGTCGTTCGG<br>CTGCGGCGAGCGGTATCAGCTCACTCAAAGGCGGTAATACGGTTA<br>TCCACAGAATCAGGGGATAACGCAGGAAAGAACATGTGAGCAAA<br>AGGCCAGCAAAAGGCCAGGAACCGTAAAAAGGCCGCGTTGCTGG<br>CGTTTTTCCATAGGCTCCGCCCCCCTGACGAGCATCACAAAAATCG<br>ACGCTCAAGTCAGAGGTGGCGAAACCCGACAGGACTATAAAGAT<br>ACCAGGCGTTTCCCCCTGGAAGCTCCCTCGTGCGCTCTCCTGTTCC<br>GACCCTGCCGCTTACCGGATACCTGTCCGCCTTTCTCCCTTCGGGA<br>AGCGTGGCGCTTTCTCATAGCTCACGCTGTAGGTATCTCAGTTCGG<br>TGTAGGTCGTTCGCTCCAAGCTGGGCTGTGTGCACGAACCCCCCGT<br>TCAGCCCGACCGCTGCGCCTTATCCGGTAACTATCGTCTTGAGTCC<br>AACCCGGTAAGACACGACTTATCGCCACTGGCAGCAGCCACTGGT<br>AACAGGATTAGCAGAGCGAGGTATGTAGGCGGTGCTACAGAGTTC<br>TTGAAGTGGTGGCCTAACTACGGCTACACTAGAAGAACAGTATTT<br>GGTATCTGCGCTCTGCTGAAGCCAGTTACCTTCGGAAAAAGAGTT<br>GGTAGCTCTTGATCCGGCAAACAAACCACCGCTGGTAGCGGTGGT<br>TTTTTTGTTTGCAAGCAGCAGATTACGCGCAGAAAAAAAGGATCT<br>CAAGAAGATCCTTTGATCTTTTCTACGGGGTCTGACGCTCAGTGGA<br>ACGAAAACTCACGTTAAGGGATTTTGGTCATGAGATTATCAAAAA<br>GGATCTTCACCTAGATCCTTTTAAATTAAAAATGAAGTTTTAAATC<br>AATCTAAAGTATATATGAGTAAACTTGGTCTGACAGTTACCAATG<br>CTTAATCAGTGAGGCACCTATCTCAGCGATCTGTCTATTTCGTTCA<br>TCCATAGTTGCCTGACTCCCCGTCGTGTAGATAACTACGATACGGG<br>AGGGCTTACCATCTGGCCCCAGTGCTGCAATGATACCGCGAGACC<br>CACGCTCACCGGCTCCAGATTTATCAGCAATAAACCAGCCAGCCG<br>GAAGGGCCGAGCGCAGAAGTGGTCCTGCAACTTTATCCGCCTCCA<br>TCCAGTCTATTAATTGTTGCCGGGAAGCTAGAGTAAGTAGTTCGC<br>AGTTAATAGTTTGCGCAACGTTGTTGCCATTGCTACAGGCATCGTG<br>GTGTCACGCTCGTCGTTTGGTATGGCTTCATTCAGCTCCGGTTCCC<br>AACGATCAAGGCGAGTTACATGATCCCCCATGTTGTGCAAAAAAG<br>CGGTTAGCTCCTTCGGTCCTCCGATCGTTGTCAGAAGTAAGTTGGC<br>CGCAGTGTTATCACTCATGGTTATGGCAGCACTGCATAATTCTCTT<br>ACTGTCATGCCATCCGTAAGATGCTTTTCTGTGACTGGTGAGTACT<br>CAACCAAGTCATTCTGAGAATAGTGTATGCGGCGACCGAGTTGCT<br>CTTGCCCGGCGTCAATACGGGATAATACCGCGCCACATAGCAGAA<br>CTTTAAAAGTGCTCATCATTGGAAAACGTTCTTCGGGGCGAAAAC<br>TCTCAAGGATCTTACCGCTGTTGAGATCCAGTTCGATGTAACCCAC<br>TCGTGCACCCAACTGATCTTCAGCATCTTTTACTTTCACCAGCGTTT<br>CTGGGTGAGCAAAAACAGGAAGGCAAAATGCCGCAAAAAAGGGA<br>ATAAGGGCGACACGGAAATGTTGAATACTCATACTCTTCCTTTTTC<br>AATATTATTGAAGCATTTATCAGGGTTATTGTCTCATGAGCGGATA<br>CATATTTGAATGTATTTAGAAAAATAAACAAATAGGGGTTCCGCG<br>CACATTTCCCCGAAAAGTGCCACCTG |
| SEQ ID NO: 72<br>GFP-Lox66 Cre<br>expression plasmid<br>(Artificial Sequence) | AGCTCTGATCAAGAGACAGGATGAGGATCGTTTCGCATGATTGAA<br>CAAGATGGATTGCACGCAGGTTCTCCGGCCGCTTGGGTGGAGAGG<br>CTATTCGGCTATGACTGGGCACAACAGACAATCGGCTGCTCTGAT<br>GCCGCCGTGTTCCGGCTGTCAGCGCAGGGGCGCCCGGTTCTTTTTG<br>TCAAGACCGACCTGTCCGGTGCCCTGAATGAACTGCAAGACGAGG<br>CAGCGCGGCTATCGTGGCTGGCCACGACGGGCGTTCCTTGCGCAG<br>CTGTGCTCGACGTTGTCACTGAAGCGGGAAGGGACTGGCTGCTAT<br>TGGGCGAAGTGCCGGGGCAGGATCTCCTGTCATCTCACCTTGC<br>TCCTGCCGAGAAAGTATCCATCATGGCTGATGCAATGCGGCGGCT<br>GCATACGCTTGATCCGGCTACCTGCCCATTCGACCACCAAGCGAA<br>ACATCGCATCGAGCGAGCACGTACTCGGATGGAAGCCGGTCTTGT<br>CGATCAGGATGATCTGGACGAAGAGCATCAGGGGCTCGCGCCAGC<br>CGAACTGTTCGCCAGGCTCAAGGCGAGCATGCCCGACGGCGAGGA<br>TCTCGTCGTGACCCATGGCGATGCCTGCTTGCCGAATATCATGGTG<br>GAAAATGGCCGCTTTTCTGGATTCATCGACTGTGGCCGGCTGGGTG<br>TGGCGGACCGCTATCAGGACATAGCGTTGGCTACCCGTGATATTG<br>CTGAAGAGCTTGGCGGCGAATGGGCTGACCGCTTCCTCGTGCTTTA<br>CGGTATCGCCGCTCCCGATTCGCAGCGCATCGCCTTCTATCGCCTT<br>CTTGACGAGTTCTTCTGAATTATTAACTCGAGATCCACTAGAGTGT<br>GGCGGCCGCATTCTTATAATCAGCATCATGATGTGGTACCACATCA<br>TGATGCTGATTACCCCCAACTGAGAGAACTCAAAGGTTACCCCAG |

TABLE 4-continued

| SEQ ID NO/<br>DESCRIPTION/<br>SOURCE | SEQUENCE |
|---|---|
| | TTGGGGGGGCCCACAAATAAAGCAATAGCATCACAAATTTCACA |
| | AATAAAGCATTTTTTTCACTGCATTCTAGTTGTGGTTTGTCCAAAC |
| | TCATCGAGCTCGAGATCTGGCGAAGGCGATGGGGGTCTTGAAGGC |
| | GTGCTGGTACTCCACGATGCCCAGCTCGGTGTTGCTGTGCAGCTCC |
| | TCCACGCGGCGGAAGGCGAACATGGGGCCCCCGTTCTGCAGGATG |
| | CTGGGGTGGATGGCGCTCTTGAAGTGCATGTGGCTGTCCACCACG |
| | AAGCTGTAGTAGCCGCCGTCGCGCAGGCTGAAGGTGCGGGCGAAG |
| | CTGCCCACCAGCACGTTATCGCCCATGGGGTGCAGGTGCTCCACG |
| | GTGGCGTTGCTGCGGATGATCTTGTCGGTGAAGATCACGCTGTCCT |
| | CGGGGAAGCCGGTGCCCACCACCTTGAAGTCGCCGATCACGCGGC |
| | CGGCCTCGTAGCGGTAGCTGAAGCTCACGTGCAGCACGCCGCCGT |
| | CCTCGTACTTCTCGATGCGGGTGTTGGTGTAGCCGCCGTTGTTGAT |
| | GGCGTGCAGGAAGGGGTTCTCGTAGCCGCTGGGGTAGGTGCCGAA |
| | GTGGTAGAAGCCGTAGCCCATCACGTGGCTCAGCAGGTAGGGGCT |
| | GAAGGTCAGGGCGCCTTTGGTGCTCTTCATCTTGTTGGTCATGCGG |
| | CCCTGCTCGGGGGTGCCCTCTCCGCCGCCCACCAGCTCGAACTCCA |
| | CGCCGTTCAGGGTGCCGGTGATGCGGCACTCGATCTTCATGGCGG |
| | GCATGGTGGCGACCGGTAGCGCTAGCGGCTTCGGATAACTTCGTA |
| | TAGCATACATTATACGAACGGTAAGCGCTACCGCCGGCATACCCA |
| | AGTGAAGTTGCTCGCAGCTTATAGTCGCGCCCGGGGAGCCCAAGG |
| | GCACGCCCTGGCACCGCGGCCGCTGAGTCTCGACCATCATCATCA |
| | TCATCATTGAGTTTATCTGGGATAACAGGGTAATGTCATCTAGGGA |
| | TAACAGGGTATGTCATCTGGGATAACAGGGTAATGTATCTAGGGA |
| | TAACAGGGTAATGTCATCTGGGATAACAGGGTAATGTCATCTAGG |
| | GATAACAGGGTATGTCATCTGGGATAACAGGGTAATGTATCTAGG |
| | GATAACAGGGTAATGTCATCTGGGATAACAGGGTAATGTCATCTA |
| | GGGATAACAGGGTATGTCATCTGGGATAACAGGGTAATGTATCTA |
| | GGGATAACAGGGTAATGTCATCTGGGATAACAGGGTAATGTCATC |
| | TAGGGATAACAGGGTATGTCATCTGGGATAACAGGGTAATGTATC |
| | TAGGGATAACAGGGTAATGTCATCTGGGATAACAGGGTAATGTCA |
| | TCTAGGGATAACAGGGTATGTCATCTGGGATAACAGGGTAATGTA |
| | TCTAGGGATAACAGGGTAATGTCATCTGGGATAACAGGGTAATGT |
| | CATCTAGGGATAACAGGGTATGTCATCTGGGATAACAGGGTAATG |
| | TATCTAGGGATAACAGGGTAATGTCATCTGGGATAACAGGGTAAT |
| | GTCATCTAGGGATAACAGGGTAAATGTCATCTAGGGATAACAGGG |
| | TAATGTCATCTAGGGATAACAGGGTAATGTCATCTGGGATAACAG |
| | GGTAATGTCATCTAGGGATAACAGGGTAATGTATCGCCAGCGTCG |
| | CACAGCATGTTTGCTTGTCGCCGTCGCGTCTGTCACATCTTTTCCG |
| | CCAGCAGTTAGGGATTAGCGTCTTAAGCTGGCGCGAGGACCAACG |
| | TATCAGCCAGGCGAAGCTGCTTTTGAGCACCACCCGGATGCCTAT |
| | CGCCACCGTCGGTCGCAATGTTGGTTTTGACGATCAACTCTATTTC |
| | TCGCGGGTATTTAAAAAATGCACCGGGGCCAGCCCGAGCGAGTTC |
| | CGTGCCGGTTGTGAAGAAAAAGTGAATGATGTAGCCGTCAAGTTG |
| | TCATAATTGGTAACGAATCAGACAATTGACGGCTTGACGGAGTAG |
| | CATAGGGTTTGCAGAATCCCTGCTTCGTCCATTTGACAGGCACATT |
| | ATGCATGCCGCTTCGCCTTCGCGCGCGAATTGATCTGCTGCCTCGC |
| | GCGTTTCGGTGATGACGGTGAAAACCTCTGACACATGCAGCTCCC |
| | GGAGACGGTCACAGCTTGTCTGTAAGCGGATGCCGGGAGCAGACA |
| | AGCCCGTCAGGGCGCGTCAGCGGGTGTTGGCGGGTGTCGGGCGC |
| | AGCCATGACCCAGTCACGTAGCGATAGCGGAGTGTATACTGGCTT |
| | AACTATGCGGCATCAGAGCAGATTGTACTGAGAGTGCACCATATG |
| | CGGTGTGAAATACCGCACAGATGCGTAAGGAGAAAATACCGCATC |
| | AGGCGCTCTTCCGCTTCCTCGCTCACTGACTCGCTGCGCTCGGTCG |
| | TTCGGCTGCGGCGAGCGGTATCAGCTCACTCAAAGGCGGTAATAC |
| | GGTTATCCACAGAATCAGGGGATAACGCAGGAAAGAACATGTGA |
| | GCAAAAGGCCAGCAAAAGGCCAGGAACCGTAAAAAGGCCGCGTT |
| | GCTGGCGTTTTTCCATAGGCTCCGCCCCCCTGACGAGCATCACAAA |
| | AATCGACGCTCAAGTCAGAGGTGGCGAAACCCGACAGGACTATAA |
| | AGATACCAGGCGTTTCCCCCTGGAAGCTCCCTCGTGCGCTCTCCTG |
| | TTCCGACCCTGCCGCTTACCGGATACCTGTCCGCCTTTCTCCCTTCG |
| | GGAAGCGTGGCGCTTTCTCATAGCTCACGCTGTAGGTATCTCAGTT |
| | CGGTGTAGGTCGTTCGCTCCAAGCTGGGCTGTGTGCACGAACCCC |
| | CCGTTCAGCCCGACCGCTGCGCCTTATCCGGTAACTATCGTCTTGA |
| | GTCCAACCCGGTAAGACACGACTTATCGCCACTGGCAGCAGCCAC |
| | TGGTAACAGGATTAGCAGAGCGAGGTATGTAGGCGGTGCTACAGA |
| | GTTCTTGAAGTGGTGGCCTAACTACGGCTACACTAGAAGGACAGT |
| | ATTTGGTATCTGCGCTCTGCTGAAGCCAGTTACCTTCGGAAAAAGA |
| | GTTGGTAGCTCTTGATCCGGCAAACAAACCACCGCTGGTAGCGGT |
| | GGTTTTTTTGTTTGCAAGCAGCAGATTACGCGCAGAAAAAAAGGA |
| | TCTCAAGAAGATCCTTTGATCTTTTCTACGGGGTCTGACGCTCAGT |
| | GGAACGAAAACTCACGTTAAGGGATTTTGGTCATGAGCAGATACA |
| | TATTTGAATGTATTTAGAAAAATAAACAAAAGAGTTTGTAGAAAC |
| | GCAAAAAGGCCATCCGTCAGGATGGCCTTCTGCTTAATTTGATGCC |
| | TGGCAGTTTATGGCGGGCGTCCTGCCCGCCACCCTCCGGGCCGTTG |
| | CTTCGCAACGTTCAAATCCGCTCCCGGCGGATTTGTCCTACTCAGG |
| | AGAGCGTTCACCGACAAACAACAGATAAAACGAAAGGCCCAGTC |

TABLE 4-continued

| SEQ ID NO/<br>DESCRIPTION/<br>SOURCE | SEQUENCE |
|---|---|
| | TTTCGACTGAGCCTTTCGTTTTATTTGATGCCTGGCAGTTCCCTACT<br>CTCGCATGGGGAGACCCCACACTACCATCGGCGCTACGGCGTTTC<br>ACTTCTGAGTTCGGCATGGGGTCAGGTGGGACCACCGCGCTACTG<br>CCGCCAGGCAAATTCTGTTTTATCAGACCGCTTCTGCGTTCTGATT<br>TAATCTGTATCAGGCTGAAAATCTTCTCTCATCCGCCAAAACAGCC<br>AAGCTGGAGACCGTTTGGCCCCCCTCGAGCACGTAGAAAGCCAGT<br>CCGCAGAAACGGTGCTGACCCCGGATGAATGTCAGCTACTGGGCT<br>ATCTGGACAAGGGAAAACGCAAGCGCAAAGAGAAAGCAGGTAGC<br>TTGCAGTGGGCTTACATGGCGATAGCTAGACTGGGCGGTTTTATG<br>GACAGCAAGCGAACCGGAATTGCCAGCTGGGGCGCCCTCTGGTAA<br>GGTTGGGAAGCCCTGCAAAGTAAACTGGATGGCTTTCTCGCCGCC<br>AAGGATCTGATGGCGCAGGGGATCA |
| SEQ ID NO: 73<br>pCMV PE2 P2A Cre<br>plasmid<br>(Artificial Sequence) | ACGCGTTGACATTGATTATTGACTAGTTATTAATAGTAATCAATTA<br>CGGGGTCATTAGTTCATAGCCCATATATGGAGTTCCGCGTTACATA<br>ACTTACGGTAAATGGCCCGCCTGGCTGACCGCCCAACGACCCCCG<br>CCCATTGACGTCAATAATGACGTATGTTCCCATAGTAACGCCAATA<br>GGGACTTTCCATTGACGTCAATGGGTGGAGTATTTACGGTAAACT<br>GCCCACTTGGCAGTACATCAAGTGTATCATATGCCAAGTACGCCC<br>CCTATTGACGTCAATGACGGTAAATGGCCCGCCTGGCATTATGCCC<br>AGTACATGACCTTATGGGACTTTCCTACTTGGCAGTACATCTACGT<br>ATTAGTCATCGCTATTACCATGGTGATGCGGTTTTGGCAGTACATC<br>AATGGGCGTGGATAGCGGTTTGACTCACGGGGATTTCCAAGTCTC<br>CACCCCATTGACGTCAATGGGAGTTTGTTTTGGCACCAAAATCAAC<br>GGGACTTTCCAAAATGTCGTAACAACTCCGCCCCATTGACGCAAA<br>TGGGCGGTAGGCGTGTACGGTGGGAGGTCTATATAAGCAGAGCTG<br>GTTTAGTGAACCGTCAGATCCGCTAGAGATCCGCGGCCGCTAATA<br>CGACTCACTATAGGGAGAGCCGCCACCATGAAACGGACAGCCGAC<br>GGAAGCGAGTTCGAGTCACCAAAGAAGAAGCGGAAAGTCGACAA<br>GAAGTACAGCATCGGCCTGGACATCGGCACCAACTCTGTGGGCTG<br>GGCCGTGATCACCGACGAGTACAAGGTGCCCAGCAAGAAATTCAA<br>GGTGCTGGGCAACACCGACCGGCACAGCATCAAGAAGAACCTGAT<br>CGGAGCCCTGCTGTTCGACAGCGGCGAAACAGCCGAGGCCACCCG<br>GCTGAAGAGAACCGCCAGAAGAAGATACACCAGACGGAAGAACC<br>GGATCTGCTATCTGCAAGAGATCTTCAGCAACGAGATGGCCAAGG<br>TGGACGACAGCTTCTTCCACAGACTGGAAGAGTCCTTCCTGGTGG<br>AAGAGGATAAGAAGCACGAGCGGCACCCCATCTTCGGCAACATCG<br>TGGACGAGGTGGCCTACCACGAGAAGTACCCCACCATCTACCACC<br>TGAGAAAGAAACTGGTGGACAGCACCGACAAGGCCGACCTGCGG<br>CTGATCTATCTGGCCCTGGCCCACATGATCAAGTTCCGGGGCCACT<br>TCCTGATCGAGGGCGACCTGAACCCCGACAACAGCGACGTGGACA<br>AGCTGTTCATCCAGCTGGTGCAGACCTACAACCAGCTGTTCGAGG<br>AAAACCCCATCAACGCCAGCGGCGTGGACGCCAAGGCCATCCTGT<br>CTGCCAGACTGAGCAAGAGCAGACGGCTGGAAAATCTGATCGCCC<br>AGCTGCCCGGCGAGAAGAAGAATGGCCTGTTCGGAAACCTGATTG<br>CCCTGAGCCTGGGCCTGACCCCCAACTTCAAGAGCAACTTCGACC<br>TGGCCGAGGATGCCAAACTGCAGCTGAGCAAGGACACCTACGACG<br>ACGACCTGGACAACCTGCTGGCCCAGATCGGCGACCAGTACGCCG<br>ACCTGTTTCTGGCCGCCAAGAACCTGTCCGACGCCATCCTGCTGAG<br>CGACATCCTGAGAGTGAACACCGAGATCACCAAGGCCCCCCTGAG<br>CGCCTCTATGATCAAGAGATACGACGAGCACCACCAGGACCTGAC<br>CCTGCTGAAAGCTCTCGTGCGGCAGCAGCTGCCTGAGAAGTACAA<br>AGAGATTTTCTTCGACCAGAGCAAGAACGGCTACGCCGGCTACAT<br>TGACGGCGGAGCCAGCCAGGAAGAGTTCTACAAGTTCATCAAGCC<br>CATCCTGGAAAAGATGGACGGCACCGAGGAACTGCTCGTGAAGCT<br>GAACAGAGAGGACCTGCTGCGGAAGCAGCGGACCTTCGACAACG<br>GCAGCATCCCCCACCAGATCCACCTGGGAGAGCTGCACGCCATTC<br>TGCGGCGGCAGGAAGATTTTTACCCATTCCTGAAGGACAACCGGG<br>AAAAGATCGAGAAGATCCTGACCTTCCGCATCCCCTACTACGTGG<br>GCCCTCTGGCCAGGGGAAACAGCAGATTCGCCTGGATGACCAGAA<br>AGAGCGAGGAAACCATCACCCCCTGGAACTTCGAGGAAGTGGTGG<br>ACAAGGGCGCTTCCGCCCAGAGCTTCATCGAGCGGATGACCAACT<br>TCGATAAGAACCTGCCCAACGAGAAGGTGCTGCCCAAGCACAGCC<br>TGCTGTACGAGTACTTCACCGTGTATAACGAGCTGACCAAAGTGA<br>AATACGTGACCGAGGGAATGAGAAAGCCCGCCTTCCTGAGCGGCG<br>AGCAGAAAAAGGCCATCGTGGACCTGCTGTTCAAGACCAACCGGA<br>AAGTGACCGTGAAGCAGCTGAAAGAGGACTACTTCAAGAAAATC<br>GAGTGCTTCGACTCCGTGGAAATCTCCGGCGTGGAAGATCGGTTC<br>AACGCCTCCCTGGGCACATACCACGATCTGCTGAAAATTATCAAG<br>GACAAGGACTTCCTGGACAATGAGGAAAACGAGGACATTCTGGA<br>AGATATCGTGCTGACCCTGACACTGTTTGAGGACAGAGAGATGAT<br>CGAGGAACGGCTGAAAACCTATGCCCACCTGTTCGACGACAAAGT<br>GATGAAGCAGCTGAAGCGGCGGAGATACACCGGCTGGGGCAGGC<br>TGAGCCGGAAGCTGATCAACGGCATCCGGGACAAGCAGTCCGGCA<br>AGACAATCCTGGATTTCCTGAAGTCCGACGGCTTCGCCAACAGAA<br>ACTTCATGCAGCTGATCCACGACGACAGCCTGACCTTTAAAGAGG |

TABLE 4-continued

| SEQ ID NO/<br>DESCRIPTION/<br>SOURCE | SEQUENCE |
|---|---|
| | ACATCCAGAAAGCCCAGGTGTCCGGCCAGGGCGATAGCCTGCACG<br>AGCACATTGCCAATCTGGCCGGCAGCCCCGCCATTAAGAAGGGCA<br>TCCTGCAGACAGTGAAGGTGGTGGACGAGCTCGTGAAAGTGATGG<br>GCCGGCACAAGCCCGAGAACATCGTGATCGAAATGGCCAGAGAG<br>AACCAGACCACCCAGAAGGGACAGAAGAACAGCCGCGAGAGAAT<br>GAAGCGGATCGAAGAGGGCATCAAAGAGCTGGGCAGCCAGATCC<br>TGAAAGAACACCCCGTGGAAAACACCCAGCTGCAGAACGAGAAG<br>CTGTACCTGTACTACCTGCAGAATGGGCGGGATATGTACGTGGAC<br>CAGGAACTGGACATCAACCGGCTGTCCGACTACGATGTGGACGCT<br>ATCGTGCCTCAGAGCTTTCTGAAGGACGACTCCATCGACAACAAG<br>GTGCTGACCAGAAGCGACAAGAACCGGGGCAAGAGCGACAACGT<br>GCCCTCCGAAGAGGTCGTGAAGAAGATGAAGAACTACTGGCGGC<br>AGCTGCTGAACGCCAAGCTGATTACCCAGAGAAAGTTCGACAATC<br>TGACCAAGGCCGAGAGAGGCGGCCTGAGCGAACTGGATAAGGCC<br>GGCTTCATCAAGAGACAGCTGGTGGAAACCCGGCAGATCACAAAG<br>CACGTGGCACAGATCCTGGACTCCCGGATGAACACTAAGTACGAC<br>GAGAATGACAAGCTGATCCGGGAAGTGAAAGTGATCACCCTGAA<br>GTCCAAGCTGGTGTCCGATTTCCGGAAGGATTTCCAGTTTTACAAA<br>GTGCGCGAGATCAACAACTACCACCACGCCCACGACGCCTACCTG<br>AACGCCGTCGTGGGAACCGCCCTGATCAAAAAGTACCCTAAGCTG<br>GAAAGCGAGTTCGTGTACGGCGACTACAAGGTGTACGACGTGCGG<br>AAGATGATCGCCAAGAGCGAGCAGGAAATCGGCAAGGCTACCGC<br>CAAGTACTTCTTCTACAGCAACATCATGAACTTTTTCAAGACCGAG<br>ATTACCCTGGCCAACGGCGAGATCCGGAAGCGGCCTCTGATCGAG<br>ACAAACGGCGAAACCGGGGAGATCGTGTGGGATAAGGGCCGGGA<br>TTTTGCCACCGTGCGGAAAGTGCTGAGCATGCCCCAAGTGAATAT<br>CGTGAAAAAGACCGAGGTGCAGACAGGCGGCTTCAGCAAAGAGT<br>CTATCCTGCCCAAGAGGAACAGCGATAAGCTGATCGCCAGAAAGA<br>AGGACTGGGACCCTAAGAAGTACGGCGGCTTCGACAGCCCCACCG<br>TGGCCTATTCTGTGCTGGTGGTGGCCAAAGTGGAAAAGGGCAAGT<br>CCAAGAAACTGAAGAGTGTGAAAGAGCTGCTGGGGATCACCATCA<br>TGGAAAGAAGCAGCTTCGAGAAGAATCCCATCGACTTTCTGGAAG<br>CCAAGGGCTACAAAGAAGTGAAAAAGGACCTGATCATCAAGCTG<br>CCTAAGTACTCCCTGTTCGAGCTGGAAAACGGCCGGAAGAGAATG<br>CTGGCCTCTGCCGGCGAACTGCAGAAGGGAAACGAACTGGCCCTG<br>CCCTCCAAATATGTGAACTTCCTGTACCTGGCCAGCCACTATGAGA<br>AGCTGAAGGGCTCCCCCGAGGATAATGAGCAGAAACAGCTGTTTG<br>TGGAACAGCACAAGCACTACCTGGACGAGATCATCGAGCAGATCA<br>GCGAGTTCTCCAAGAGAGTGATCCTGGCCGACGCTAATCTGGACA<br>AAGTGCTGTCCGCCTACAACAAGCACCGGGATAAGCCCATCAGAG<br>AGCAGGCCGAGAATATCATCCACCTGTTTACCCTGACCAATCTGG<br>GAGCCCCTGCCGCCTTCAAGTACTTTGACACCACCATCGACCGGA<br>AGAGGTACACCAGCACCAAAGAGGTGCTGGACGCCACCCTGATCC<br>ACCAGAGCATCACCGGCCTGTACGAGACACGGATCGACCTGTCTC<br>AGCTGGGAGGTGACTCTGGAGGATCTAGCGGAGGATCCTCTGGCA<br>GCGAGACACCAGGAACAAGCGAGTCAGCAACACCAGAGAGCAGT<br>GGCGGCAGCAGCGGCGGCAGCAGCACCCTAAATATAGAAGATGA<br>GTATCGGCTACATGAGACCTCAAAAGAGCCAGATGTTTCTCTAGG<br>GTCCACATGGCTGTCTGATTTTCCTCAGGCCTGGGCGGAAACCGG<br>GGGCATGGGACTGGCAGTTCGCCAAGCTCCTCTGATCATACCTCTG<br>AAAGCAACCTCTACCCCCGTGTCCATAAAACAATACCCCATGTCA<br>CAAGAAGCCAGACTGGGGATCAAGCCCCACATACAGAGACTGTTG<br>GACCAGGGAATACTGGTACCCTGCCAGTCCCCTGGAACACGCCC<br>CTGCTACCCGTTAAGAAACCAGGGACTAATGATTATAGGCCTGTC<br>CAGGATCTGAGAGAAGTCAACAAGCGGGTGGAAGACATCCACCC<br>CACCGTGCCCAACCCTTACAACCTCTTGAGCGGGCTCCCACCGTCC<br>CACCAGTGGTACACTGTGCTTGATTTAAAGGATGCCTTTTTCTGCC<br>TGAGACTCCACCCCACCAGTCAGCCTCTCTTCGCCTTTGAGTGGAG<br>AGATCCAGAGATGGGAATCTCAGGACAATTGACCTGGACCAGACT<br>CCCACAGGGTTTCAAAAACAGTCCCACCCTGTTTAATGAGGCACT<br>GCACAGAGACCTAGCAGACTTCCGGATCCAGCACCCAGACTTGAT<br>CCTGCTACAGTACGTGGATGACTTACTGCTGGCCGCCACTTCTGAG<br>CTAGACTGCCAACAAGGTACTCGGGCCTGTTACAAACCCTAGGG<br>AACCTCGGGTATCGGGCCTCGGCCAAGAAAGCCCAAATTTGCCAG<br>AAACAGGTCAAGTATCTGGGGTATCTTCTAAAAGAGGGTCAGAGA<br>TGGCTGACTGAGGCCAGAAAAGAGACTGTGATGGGGCAGCCTACT<br>CCGAAGACCCCTCGACAACTAAGGGAGTTCCTAGGGAAGGCAGGC<br>TTCTGTCGCCTCTTCATCCCTGGGTTTGCAGAAATGGCAGCCCCCC<br>TGTACCCTCTCACCAAACCGGGGACTCTGTTTAATTGGGGCCCAGA<br>CCAACAAAAGGCCTATCAAGAAATCAAGCAAGCTCTTCTAACTGC<br>CCCAGCCCTGGGGTTGCCAGATTTGACTAAGCCCTTTGAACTCTTT<br>GTCGACGAGAAGCAGGGCTACGCCAAAGGTGTCCTAACGCAAAA<br>ACTGGGACCTTGGCGTCGGCCGGTGGCCTACCTGTCCAAAAAGCT<br>AGACCCAGTAGCAGCTGGGTGGCCCCCTTGCCTACGGATGGTAGC<br>AGCCATTGCCGTACTGACAAAGGATGCAGGCAAGCTAACCATGGG<br>ACAGCCACTAGTCATTCTGGCCCCCCATGCAGTAGAGGCACTAGT |

TABLE 4-continued

| SEQ ID NO/ DESCRIPTION/ SOURCE | SEQUENCE |
|---|---|
| | CAAACAACCCCCCGACCGCTGGCTTTCCAACGCCCGGATGACTCA CTATCAGGCCTTGCTTTTGGACACGGACCGGGTCCAGTTCGGACCG GTGGTAGCCCTGAACCCGGCTACGCTGCTCCCACTGCCTGAGGAA GGGCTGCAACACAACTGCCTTGATATCCTGGCCGAAGCCCACGGA ACCCGACCCGACCTAACGGACCAGCCGCTCCCAGACGCCGACCAC ACCTGGTACACGGATGGAAGCAGTCTCTTACAAGAGGGACAGCGT AAGGCGGGAGCTGCGGTGACCACCGAGACCGAGGTAATCTGGGCT AAAGCCCTGCCAGCCGGGACATCCGCTCAGCGGGCTGAACTGATA GCACTCACCCAGGCCCTAAAGATGGCAGAAGGTAAGAAGCTAAAT GTTTATACTGATAGCCGTTATGCTTTTGCTACTGCCCATATCCATG GAGAAATATACAGAAGGCGTGGGTGGCTCACATCAGAAGGCAAA GAGATCAAAATAAAGACGAGATCTTGGCCCTACTAAAAGCCCTC TTTCTGCCCAAAAGACTTAGCATAATCCATTGTCCAGGACATCAAA AGGGACACAGCGCCGAGGCTAGAGGCAACCGGATGGCTGACCAA GCGGCCCGAAAGGCAGCCATCACAGAGACTCCAGACACCTCTACC CTCCTCATAGAAAATTCATCACCCTCTGGCGGCTCAAAAGAACC GCCGACGGCAGCGAATTCGAGCCCAAGAAGAAGAGGAAAGTCGG AAGCGGAGCTACTAACTTCAGCCTGCTGAAGCAGGCTGGCGACGT GGAGGAGAACCCTGGACCTAATTTACTGACCGTACACCAAATTT GCCTGCATTACCGGTCGATGCAACGAGTGATGAGGTTCGCAAGAA CCTGATGGACATGTTCAGGGATCGCCAGGCGTTTTCTGAGCATACC TGGAAAATGCTTCTGTCCGTTTGCCGGTCGTGGGCGGCATGGTGCA AGTTGAATAACCGGAAATGGTTTCCCGCAGAACCTGAAGATGTTC GCGATTATCTTCTATATCTTCAGGCGCGCGGTCTGGCAGTAAAAAC TATCCAGCAACATTTGGGCCAGCTAAACATGCTTCATCGTCGGTCC GGGCTGCCACGACCAAGTGACAGCAATGCTGTTTCACTGGTTATG CGGCGGATCCGAAAAGAAAACGTTGATGCCGGTGAACGTGCAAA ACAGGCTCTAGCGTTCGAACGCACTGATTTCGACCAGGTTCGTTCA CTCATGGAAAATAGCGATCGCTGCCAGGATATACGTAATCTGGCA TTTCTGGGGATTGCTTATAACACCCTGTTACGTATAGCCGAAATTG CCAGGATCAGGGTTAAAGATATCTCACGTACTGACGGTGGGAGAA TGTTAATCCATATTGGCAGAACGAAAACGCTGGTTAGCACCGCAG GTGTAGAGAAGGCACTTAGCCTGGGGGTAACTAAACTGGTCGAGC GATGGATTTCCGTCTCTGGTGTAGCTGATGATCCGAATAACTACCT GTTTTGCCGGGTCAGAAAAAATGGTGTTGCCGCGCCATCTGCCAC CAGCCAGCTATCAACTCGCGCCCTGGAAGGGATTTTTGAAGCAAC TCATCGATTGATTTACGGCGCTAAGGATGACTCTGGTCAGAGATA CCTGGCCTGGTCTGGACACAGTGCCCGTGTCGGAGCCGCGCGAGA TATGGCCCGCGCTGGAGTTTCAATACCGGAGATCATGCAAGCTGG TGGCTGGACCAATGTAAATATTGTCATGAACTATATCCGTAACCTG GATAGTGAAACAGGGGCAATGGTGCGCCTGCTGGAAGATGGCGAT TAATTTAAACCCGCTGATCAGCCTCGACTGTGCCTTCTAGTTGCCA GCCATCTGTTGTTTGCCCCTCCCCCGTGCCTTCCTTGACCCTGGAA GGTGCCACTCCCACTGTCCTTTCCTAATAAAATGAGAAATTGCAT CGCATTGTCTGAGTAGGTGTCATTCTATTCTGGGGGGTGGGGTGGG GCAGGACAGCAAGGGGGAGGATTGGGAAGACAATAGCAGGCATG CTGGGGATGCGGTGGGCTCTATGGCTTCTGAGGCGGAAAGAACCA GCTGGGGCTCGATACCGTCGACCTCTAGCTAGAGCTTGGCGTAAT CATGGTCATAGCTGTTTCCTGTGTGAAATTGTTATCCGCTCACAAT TCCACACAACATACGAGCCGGAAGCATAAAGTGTAAAGCCTAGGG TGCCTAATGAGTGAGCTAACTCACATTAATTGCGTTGCGCTCACTG CCCGCTTTCCAGTCGGGAAACCTGTCGTGCCAGCTGCATTAATGAA TCGGCCAACGCGCGGGAGAGGCGGTTTGCGTATTGGGCGCTCTT CCGCTTCCTCGCTCACTGACTCGCTGCGCTCGGTCGTTCGGCTGCG GCGAGCGGTATCAGCTCACTCAAAGGCGGTAATACGGTTATCCAC AGAATCAGGGGATAACGCAGGAAAGAACATGTGAGCAAAAGGCC AGCAAAAGGCCAGGAACCGTAAAAAGGCCGCGTTGCTGGCGTTTT TCCATAGGCTCCGCCCCCCTGACGAGCATCACAAAAATCGACGCT CAAGTCAGAGGTGGCGAAACCCGACAGGACTATAAAGATACCAG GCGTTTCCCCCTGGAAGCTCCCTCGTGCGCTCTCCTGTTCCGACCC TGCCGCTTACCGGATACCTGTCCGCCTTTCTCCCTTCGGGAAGCGT GGCGCTTTCTCATAGCTCACGCTGTAGGTATCTCAGTTCGGTGTAG GTCGTTCGCTCCAAGCTGGGCTGTGTGCACGAACCCCCCGTTCAGC CCGACCGCTGCGCCTTATCCGGTAACTATCGTCTTGAGTCCAACCC GGTAAGACACGACTTATCGCCACTGGCAGCAGCCACTGGTAACAG GATTAGCAGAGCGAGGTATGTAGGCGGTGCTACAGAGTTCTTGAA GTGGTGGCCTAACTACGGCTACACTAGAAGAACAGTATTTGGTAT CTGCGCTCTGCTGAAGCCAGTTACCTTCGGAAAAAGAGTTGGTAG CTCTTGATCCGGCAAACAAACCACCGCTGGTAGCGGTGGTTTTTTT GTTTGCAAGCAGCAGATTACGCGCAGAAAAAAAGGATCTCAAGA AGATCCTTTGATCTTTTCTACGGGGTCTGACGCTCAGTGGAACGAA AACTCACGTTAAGGGATTTTGGTCATGAGATTATCAAAAAGGATC TTCACCTAGATCCTTTTAAATTAAAAATGAAGTTTTAAATCAATCT AAAGTATATATGAGTAAACTTGGTCTGACAGTTACCAATGCTTAAT CAGTGAGGCACCTATCTCAGCGATCTGTCTATTTCGTTCATCCATA GTTGCCTGACTCCCCGTCGTGTAGATAACTACGATACGGGAGGGC |

TABLE 4-continued

| SEQ ID NO/ DESCRIPTION/ SOURCE | SEQUENCE |
|---|---|
| | TTACCATCTGGCCCCAGTGCTGCAATGATACCGCGAGACCCACGC
TCACCGGCTCCAGATTTATCAGCAATAAACCAGCCAGCCGGAAGG
GCCGAGCGCAGAAGTGGTCCTGCAACTTTATCCGCCTCCATCCAGT
CTATTAATTGTTGCCGGGAAGCTAGAGTAAGTAGTTCGCCAGTTA
ATAGTTTGCGCAACGTTGTTGCCATTGCTACAGGCATCGTGGTGTC
ACGCTCGTCGTTTGGTATGGCTTCATTCAGCTCCGGTTCCCAACGA
TCAAGGCGAGTTACATGATCCCCCATGTTGTGCAAAAAAGCGGTT
AGCTCCTTCGGTCCTCCGATCGTTGTCAGAAGTAAGTTGGCCGCAG
TGTTATCACTCATGGTTATGGCAGCACTGCATAATTCTCTTACTGT
CATGCCATCCGTAAGATGCTTTTCTGTGACTGGTGAGTACTCAACC
AAGTCATTCTGAGAATAGTGTATGCGGCGACCGAGTTGCTCTTGCC
CGGCGTCAATACGGGATAATACCGCGCCACATAGCAGAACTTTAA
AAGTGCTCATCATTGGAAAACGTTCTTCGGGGCGAAAACTCTCAA
GGATCTTACCGCTGTTGAGATCCAGTTCGATGTAACCCACTCGTGC
ACCCAACTGATCTTCAGCATCTTTTACTTTCACCAGCGTTTCTGGG
TGAGCAAAAACAGGAAGGCAAAATGCCGCAAAAAAGGGAATAAG
GGCGACACGGAAATGTTGAATACTCATACTCTTCCTTTTTCAATAT
TATTGAAGCATTTATCAGGGTTATTGTCTCATGAGCGGATACATAT
TTGAATGTATTTAGAAAAATAAACAAATAGGGGTTCCGCGCACAT
TTCCCCGAAAAGTGCCACCTGACGTCGACGGATCGGGAGATCGAT
CTCCCGATCCCCTAGGGTCGACTCTCAGTACAATCTGCTCTGATGC
CGCATAGTTAAGCCAGTATCTGCTCCCTGCTTGTGTGTTGGAGGTC
GCTGAGTAGTGCGCGAGCAAATTTAAGCTACAACAAGGCAAGGC
TTGACCGACAATTGCATGAAGAATCTGCTTAGGGTTAGGCGTTTTG
CGCTGCTTCGCGATGTACGGGCCAGATAT |
| SEQ ID NO: 74
+90 ngRNA guide sequence
(Artificial Sequence) | GTCAACCAGTATCCCGGTGC |
| SEQ ID NO: 75
+90 ngRNA
(Artificial Sequence) | GTCAACCAGTATCCCGGTGCGTTTTAGAGCTAGAAATAGCAAGTT
AAAATAAGGCTAGTCCGTTATCAACTTGAAAAAGTGGCACCGAGT
CGGTGC |
| SEQ ID NO: 76
GFP minicircle template (before cleavage into a minicircle)
(Artificial Sequence) | TGATCCCCTGCGCCATCAGATCCTTGGCGGCGAGAAAGCCATCCA
GTTTACTTTGCAGGGCTTCCCAACCTTACCAGAGGGCGCCCCAGCT
GGCAATTCCGGTTCGCTTGCTGTCCATAAAACCGCCCAGTCTAGCT
ATCGCCATGTAAGCCCACTGCAAGCTACCTGCTTTCTCTTTGCGCT
TGCGTTTTCCCTTGTCCAGATAGCCCAGTAGCTGACATTCATCCGG
GGTCAGCACCGTTTCTGCGGACTGGCTTTCTACGTGCTCGAGGGGG
GCCAAACGGTCTCCAGCTTGGCTGTTTTGGCGGATGAGAGAAGAT
TTTCAGCCTGATACAGATTAAATCAGAACGCAGAAGCGGTCTGAT
AAAACAGAATTTGCCTGGCGGCAGTAGCGCGGTGGTCCCACCTGA
CCCCATGCCGAACTCAGAAGTGAAACGCCGTAGCGCCGATGGTAG
TGTGGGGTCTCCCCATGCGAGAGTAGGGAACTGCCAGGCATCAAA
TAAAACGAAAGGCTCAGTCGAAAGACTGGGCCTTTCGTTTTATCT
GTTGTTTGTCGGTGAACGCTCTCCTGAGTAGGACAAATCCGCCGG
GAGCGGATTTGAACGTTGCGAAGCAACGGCCCGGAGGGTGGCGG
GCAGGACGCCCGCCATAAACTGCCAGGCATCAAATTAAGCAGAAG
GCCATCCTGACGGATGGCCTTTTTGCGTTTCTACAAACTCTTTTGTT
TATTTTTCTAAATACATTCAAATATGTATCCGCTCATGACCAAAAT
CCCTTAACGTGAGTTTTCGTTCCACTGAGCGTCAGACCCCGTAGAA
AAGATCAAAGGATCTTCTTGAGATCCTTTTTTTCTGCGCGTAATCT
GCTGCTTGCAAACAAAAAAACCACCGCTACCAGCGGTGGTTTGTT
TGCCGGATCAAGAGCTACCAACTCTTTTTCCGAAGGTAACTGGCTT
CAGCAGAGCGCAGATACCAAATACTGTCCTTCTAGTGTAGCCGTA
GTTAGGCCACCACTTCAAGAACTCTGTAGCACCGCCTACATACCTC
GCTCTGCTAATCCTGTTACCAGTGGCTGCTGCCAGTGGCGATAAGT
CGTGTCTTACCGGGTTGGACTCAAGACGATAGTTACCGGATAAGG
CGCAGCGGTCGGGCTGAACGGGGGGTTCGTGCACACAGCCCAGCT
TGGAGCGAACGACCTACACCGAACTGAGATACCTACAGCGTGAGC
TATGAGAAAGCGCCACGCTTCCCGAAGGGAGAAAGGCGGACAGG
TATCCGGTAAGCGGCAGGGTCGGAACAGGAGAGCGCACGAGGGA
GCTTCCAGGGGGAAACGCCTGGTATCTTTATAGTCCTGTCGGGTTT
CGCCACCTCTGACTTGAGCGTCGATTTTTGTGATGCTCGTCAGGGG
GGCGGAGCCTATGGAAAAACGCCAGCAACGCGGCCTTTTTACGGT
TCCTGGCCTTTTGCTGGCCTTTTGCTCACATGTTCTTTCCTGCGTTA
TCCCCTGATTCTGTGGATAACCGTATTACCGCCTTTGAGTGAGCTG
ATACCGCTCGCCGCAGCCGAACGACCGAGCGCAGCGAGTCAGTGA
GCGAGGAAGCGGAAGAGCGCCTGATGCGGTATTTTCTCCTTACGC
ATCTGTGCGGTATTTCACACCGCATATGGTGCACTCTCAGTACAAT
CTGCTCTGATGCCGCATAGTTAAGCCAGTATACACTCCGCTATCGC
TACGTGACTGGGTCATGGCTGCGCCCCGACACCCGCCAACACCCG
CTGACGCGCCCTGACGGGCTTGTCTGCTCCCGGCATCCGCTTACAG
ACAAGCTGTGACCGTCTCCGGGAGCTGCATGTGTCAGAGGTTTTC |

TABLE 4-continued

| SEQ ID NO/<br>DESCRIPTION/<br>SOURCE | SEQUENCE |
|---|---|
| | ACCGTCATCACCGAAACGCGCGAGGCAGCAGATCAATTCGCGCGC<br>GAAGGCGAAGCGGCATGCATAATGTGCCTGTCAAATGGACGAAGC<br>AGGGATTCTGCAAACCCTATGCTACTCCGTCAAGCCGTCAATTGTC<br>TGATTCGTTACCAATTATGACAACTTGACGGCTACATCATTCACTT<br>TTTCTTCACAACCGGCACGGAACTCGCTCGGGCTGGCCCCGGTGC<br>ATTTTTTAAATACCCGCGAGAAATAGAGTTGATCGTCAAAACCAA<br>CATTGCGACCGACGGTGGCGATAGGCATCCGGGTGGTGCTCAAAA<br>GCAGCTTCGCCTGGCTGATACGTTGGTCCTCGCGCCAGCTTAAGAC<br>GCTAATCCCTAACTGCTGGCGGAAAAGATGTGACAGACGCGACGG<br>CGACAAGCAAACATGCTGTGCGACGCTGGCGATACATTACCCTGT<br>TATCCCTAGATGACATTACCCTGTTATCCCAGATGACATTACCCTG<br>TTATCCCTAGATGACATTACCCTGTTATCCCTAGATGACATTTACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATAAACTCAA<br>TGATGATGATGATGATGGTCGAGACTCAGCGGCCGCGGTGCCAGG<br>GCGTGCCCTTGGGCTCCCCGGGCGCGACTATAAGCTGCGAGCAAC<br>TTCACTTGGGTATGCCGGCGGTAGCGCTTACCGTTCGTATAATGTA<br>TGCTATACGAAGTTATCCGAAGCCGCTAGCGGTGGTTTGTCTGGTC<br>AACCACCGCGGTCTCAGTGGTGTACGGTACAAACCCAGCTACCGG<br>TCGCCACCATGCCCGCCATGAAGATCGAGTGCCGCATCACCGGCA<br>CCCTGAACGGCGTGGAGTTCGAGCTGGTGGGCGGCGGAGAGGGC<br>ACCCCCGAGCAGGGCCGCATGACCAACAAGATGAAGAGCACCAA<br>AGGCGCCCTGACCTTCAGCCCCTACCTGCTGAGCCACGTGATGGG<br>CTACGGCTTCTACCACTTCGGCACCTACCCCAGCGGCTACGAGAA<br>CCCCTTCCTGCACGCCATCAACAACGGCGGCTACACCAACACCCG<br>CATCGAGAAGTACGAGGACGGCGGCGTGCTGCACGTGAGCTTCAG<br>CTACCGCTACGAGGCCGGCCGCGTGATCGGCGACTTCAAGGTGGT<br>GGGCACCGGCTTCCCCGAGGACAGCGTGATCTTCACCGACAAGAT<br>CATCCGCAGCAACGCCACCGTGGAGCACCTGCACCCCATGGGCGA<br>TAACGTGCTGGTGGGCAGCTTCGCCCGCACCTTCAGCCTGCGCGA<br>CGGCGGCTACTACAGCTTCGTGGTGGACAGCCACATGCACTTCAA<br>GAGCGCCATCCACCCCAGCATCCTGCAGAACGGGGGCCCCATGTT<br>CGCCTTCCGCCGCGTGGAGGAGCTGCACAGCAACACCGAGCTGGG<br>CATCGTGGAGTACCAGCACGCCTTCAAGACCCCCATCGCCTTCGCC<br>AGATCTCGAGCTCGATGAGTTTGGACAAACCACAACTAGAATGCA<br>GTGAAAAAAATGCTTTATTTGTGAAATTTGTGATGCTATTGCTTTA<br>TTTGTGGGCCCGCCCCAACTGGGGTAACCTTTGAGTTCTCTCAGTT<br>GGGGGGTAATCAGCATCATGATGTGGTACCACATCATGATGCTGAT<br>TATAAGAATGCGGCCGCCACACTCTAGTGGATCTCGAGTTAATAA<br>TTCAGAAGAACTCGTCAAGAAGGCGATAGAAGGCGATGCGCTGCG<br>AATCGGGAGCGGCGATACCGTAAAGCACGAGGAAGCGGTCAGCC<br>CATTCGCCGCCAAGCTCTTCAGCAATATCACGGGTAGCCAACGCT<br>ATGTCCTGATAGCGGTCCGCCACACCCAGCCGGCCACAGTCGATG<br>AATCCAGAAAAGCGGCCATTTTCCACCATGATATTCGGCAAGCAG<br>GCATCGCCATGGGTCACGACGAGATCCTCGCCGTCGGGCATGCTC<br>GCCTTGAGCCTGGCGAACAGTTCGGCTGGCGCGAGCCCCTGATGC<br>TCTTCGTCCAGATCATCCTGATCGACAAGACCGGCTTCCATCCGAG<br>TACGTGCTCGCTCGATGCGATGTTTCGCTTGGTGGTCGAATGGGCA<br>GGTAGCCGGATCAAGCGTATGCAGCCGCCGCATTGCATCAGCCAT<br>GATGGATACTTTCTCGGCAGGAGCAAGGTGTAGATGACATGGAGA<br>TCCTGCCCCGGCACTTCGCCCAATAGCAGCCAGTCCCTTCCCGCTT<br>CAGTGACAACGTCGAGCACAGCTGCGCAAGGAACGCCCGTCGTGG<br>CCAGCCACGATAGCCGCGCTGCCTCGTCTTGCAGTTCATTCAGGGC<br>ACCGGACAGGTCGGTCTTGACAAAAAGAACCGGGCGCCCCTGCGC<br>TGACAGCCGGAACACGGCGGCATCAGAGCAGCCGATTGTCTGTTG<br>TGCCCAGTCATAGCCGAATAGCCTCTCCACCCAAGCGGCCGGAGA<br>ACCTGCGTGCAATCCATCTTGTTCAATCATGCGAAACGATCCTCAT<br>CCTGTCTCTTGATCAGAGCT |
| SEQ ID NO: 77<br>Gaussia Luciferase<br>minicircle template<br>(Artificial Sequence) | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT<br>TGCGTTTTCCCTTGTCCAGATAGCCCAGTAGCTGACATTCATCCGG<br>GGTCAGCACCGTTTCTGCGGACTGGCTTTCTACGTGCTCGAGGGGG |

TABLE 4-continued

| SEQ ID NO/<br>DESCRIPTION/<br>SOURCE | SEQUENCE |
|---|---|
| | GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT<br>TATTTTTCTAAATACATTCAAATATGTATCCGCTCATGACCAAAAT<br>CCCTTAACGTGAGTTTTCGTTCCACTGAGCGTCAGACCCCGTAGAA<br>AAGATCAAAGGATCTTCTTGAGATCCTTTTTTTCTGCGCGTAATCT<br>GCTGCTTGCAAACAAAAAAACCACCGCTACCAGCGGTGGTTTGTT<br>TGCCGGATCAAGAGCTACCAACTCTTTTTCCGAAGGTAACTGGCTT<br>CAGCAGAGCGCAGATACCAAATACTGTCCTTCTAGTGTAGCCGTA<br>GTTAGGCCACCACTTCAAGAACTCTGTAGCACCGCCTACATACCTC<br>GCTCTGCTAATCCTGTTACCAGTGGCTGCTGCCAGTGGCGATAAGT<br>CGTGTCTTACCGGGTTGGACTCAAGACGATAGTTACCGGATAAGG<br>CGCAGCGGTCGGGCTGAACGGGGGGTTCGTGCACACAGCCCAGCT<br>TGGAGCGAACGACCTACACCGAACTGAGATACCTACAGCGTGAGC<br>TATGAGAAAGCGCCACGCTTCCCGAAGGGAGAAAGGCGGACAGG<br>TATCCGGTAAGCGGCAGGGTCGGAACAGGAGAGCGCACGAGGGA<br>GCTTCCAGGGGAAACGCCTGGTATCTTTATAGTCCTGTCGGGTTT<br>CGCCACCTCTGACTTGAGCGTCGATTTTTGTGATGCTCGTCAGGGG<br>GGCGGAGCCTATGGAAAAACGCCAGCAACGCGGCCTTTTTACGGT<br>TCCTGGCCTTTTGCTGGCCTTTTGCTCACATGTTCTTTCCTGCGTTA<br>TCCCCTGATTCTGTGGATAACCGTATTACCGCCTTTGAGTGAGCTG<br>ATACCGCTCGCCGCAGCCGAACGACCGAGCGCAGCGAGTCAGTGA<br>GCGAGGAAGCGGAAGAGCGCCTGATGCGGTATTTTCTCCTTACGC<br>ATCTGTGCGGTATTTCACACCGCATATGGTGCACTCTCAGTACAAT<br>CTGCTCTGATGCCGCATAGTTAAGCCAGTATACACTCCGCTATCGC<br>TACGTGACTGGGTCATGGCTGCGCCCCGACACCCGCCAACACCCG<br>CTGACGCGCCCTGACGGGCTTGTCTGCTCCCGGCATCCGCTTACAG<br>ACAAGCTGTGACCGTCTCCGGGAGCTGCATGTGTCAGAGGTTTTC<br>ACCGTCATCACCGAAACGCGCGAGGCAGCAGATCAATTCGCGCGC<br>GAAGGCGAAGCGGCATGCATAATGTGCCTGTCAAATGGACGAAGC<br>AGGGATTCTGCAAACCCTATGCTACTCCGTCAAGCCGTCAATTGTC<br>TGATTCGTTACCAATTATGACAACTTGACGGCTACATCATTCACTT<br>TTTCTTCACAACCGGCACGGAACTCGCTCGGGCTGGCCCCGGTGC<br>ATTTTTTAAATACCCGCGAGAAATAGAGTTGATCGTCAAAACCAA<br>CATTGCGACCGACGGTGGCGATAGGCATCCGGGTGGTGCTCAAAA<br>GCAGCTTCGCCTGGCTGATACGTTGGTCCTCGCGCCAGCTTAAGAC<br>GCTAATCCCTAACTGCTGGCGGAAAAGATGTGACAGACGCGACGG<br>CGACAAGCAAACATGCTGTGCGACGCTGGCGATACATTACCCTGT<br>TATCCCTAGATGACATTACCCTGTTATCCCAGATGACATTACCCTG<br>TTATCCCTAGATGACATTACCCTGTTATCCCTAGATGACATTTACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATAAACTCAA<br>TGATGATGATGATGGTCGAGACTCAGCGGCCGCGGTGCCAGG<br>GCGTGCCCTTGGGCTCCCCGGGCGCGACTATAAGCTGCGAGCAAC<br>TTCACTTGGGTATGCCGGCGGTAGCGCTTACCGTTCGTATAATGTA<br>TGCTATACGAAGTTATCCGAAGCCGCTAGCGGTGGTTTGTCTGGTC<br>AACCACCGCGGTCTCAGTGGTGTACGGTACAAACCCACTACCGGT<br>CGCCACCATGGGAGTCAAAGTTCTGTTTGCCCTGATCTGCATCGCT<br>GTGGCCGAGGCCAAGCCCACCGAGAACAACGAAGACTTCAACATC<br>GTGGCCGTGGCCAGCAACTTCGCGACCACGGATCTCGATGCTGAC<br>CGCGGGAAGTTGCCCGGCAAGAAGCTGCCGCTGGAGGTGCTCAAA<br>GAGATGGAAGCCAATGCCCGGAAAGCTGGCTGCACCAGGGGCTGT<br>CTGATCTGCCTGTCCCACATCAAGTGCACGCCCAAGATGAAGAAG<br>TTCATCCCAGGACGCTGCCACACCTACGAAGGCGACAAAGAGTCC<br>GCACAGGGCGGCATAGGCGAGGCGATCGTCGACATTCCTGAGATT<br>CCTGGGTTCAAGGACTTGGAGCCCATGGAGCAGTTCATCGCACAG<br>GTCGATCTGTGTGTGGACTGCACAACTGGCTGCCTCAAAGGGCTT<br>GCCAACGTGCAGTGTTCTGACCTGCTCAAGAAGTGGCTGCCGCAA |

TABLE 4-continued

| SEQ ID NO/<br>DESCRIPTION/<br>SOURCE | SEQUENCE |
|---|---|
| | CGCTGTGCGACCTTTGCCAGCAAGATCCAGGGCCAGGTGGACAAG<br>ATCAAGGGGGCCGGTGGTGACTAAGCGGAGCTCGATGAGTTTGGA<br>CAAACCACAACTAGAATGCAGTGAAAAAAATGCTTTATTTGTGAA<br>ATTTGTGATGCTATTGCTTTATTTGTGGGCCCGCCCCAACTGGGGT<br>AACCTTTGAGTTCTCTCAGTTGGGGGTAATCAGCATCATGATGTGG<br>TACCACATCATGATGCTGATTATAAGAATGCGGCCGCCACACTCT<br>AGTGGATCTCGAGTTAATAATTCAGAAGAACTCGTCAAGAAGGCG<br>ATAGAAGGCGATGCGCTGCGAATCGGGAGCGGCGATACCGTAAA<br>GCACGAGGAAGCGGTCAGCCCATTCGCCGCCAAGCTCTTCAGCAA<br>TATCACGGGTAGCCAACGCTATGTCCTGATAGCGGTCCGCCACAC<br>CCAGCCGGCCACAGTCGATGAATCCAGAAAAGCGGCCATTTTCCA<br>CCATGATATTCGGCAAGCAGGCATCGCCATGGGTCACGACGAGAT<br>CCTCGCCGTCGGGCATGCTCGCCTTGAGCCTGGCGAACAGTTCGG<br>CTGGCGCGAGCCCCTGATGCTCTTCGTCCAGATCATCCTGATCGAC<br>AAGACCGGCTTCCATCCGAGTACGTGCTCGCTCGATGCGATGTTTC<br>GCTTGGTGGTCGAATGGGCAGGTAGCCGGATCAAGCGTATGCAGC<br>CGCCGCATTGCATCAGCCATGATGGATACTTTCTCGGCAGGAGCA<br>AGGTGTAGATGACATGGAGATCCTGCCCCGGCACTTCGCCCAATA<br>GCAGCCAGTCCCTTCCCGCTTCAGTGACAACGTCGAGCACAGCTG<br>CGCAAGGAACGCCCGTCGTGGCCAGCCACGATAGCCGCGCTGCCT<br>CGTCTTGCAGTTCATTCAGGGCACCGGACAGGTCGGTCTTGACAA<br>AAAGAACCGGGCGCCCCTGCGCTGACAGCCGGAACACGGCGGCA<br>TCAGAGCAGCCGATTGTCTGTTGTGCCCAGTCATAGCCGAATAGC<br>CTCTCCACCCAAGCGGCCGGAGAACCTGCGTGCAATCCATCTTGTT<br>CAATCATGCGAAACGATCCTCATCCTGTCTCTTGATCAGAGCT |
| SEQ ID NO: 78<br>pseudo attP site<br>(Artificial sequence) | CCCCAACTGGGGTAACCTTTGAGTTCTCTCAGTTGGGG |
| SEQ ID NO: 79<br>Albumin-pegRNA-<br>SERPIN<br>(Artificial Sequence) | GACTGAAACTTCACAGAATAGTTTTAGAGCTAGAAATAGCAAGTT<br>AAAATAAGGCTAGTCCGTTATCAACTTGAAAAAGTGGCACCGAGT<br>CGGTGCTTGGGATAGTTATGAATTCAATCTTCAACCCTATCCGGAT<br>GATCCTGACGACGGAGACCGCCGTCGTCGACAAGCCGGCCTCTGT<br>GAAGTTTCAGTCA |
| SEQ ID NO: 80<br>Albumin-pegRNA-<br>CPS1<br>(Artificial Sequence) | GACTGAAACTTCACAGAATAGTTTTAGAGCTAGAAATAGCAAGTT<br>AAAATAAGGCTAGTCCGTTATCAACTTGAAAAAGTGGCACCGAGT<br>CGGTGCTTGGGATAGTTATGAATTCAATCTTCAACCCTATCCGGAT<br>GATCCTGACGACGGAGACCGCCGTCGTCGACAAGCCGGCCTCTGT<br>GAAGTTTC |
| SEQ ID NO: 81<br>34 bp lox71 pegRNA<br>(Artificial Sequence) | GGCCCAGACTGAGCACGTGAGTTTTAGAGCTAGAAATAGCAAGTT<br>AAAATAAGGCTAGTCCGTTATCAACTTGAAAAAGTGGCACCGAGT<br>CGGTGCTGGAGGAAGCAGGGCTTCCTTTCCTCTGCCATCATACCGT<br>TCGTATAGCATACATTATACGAAGTTATCGTGCTCAGTCTG |
| SEQ ID NO: 82<br>34 bp lox66 pegRNA<br>(Artificial Sequence) | GGCCCAGACTGAGCACGTGAGTTTTAGAGCTAGAAATAGCAAGTT<br>AAAATAAGGCTAGTCCGTTATCAACTTGAAAAAGTGGCACCGAGT<br>CGGTGCTGGAGGAAGCAGGGCTTCCTTTCCTCTGCCATCAATAACT<br>TCGTATAGCATACATTATACGAACGGTACGTGCTCAGTCTG |
| SEQ ID NO: 83<br>gRNA<br>(Artificial Sequence) | GGCCCAGACTGAGCACGTGA |
| SEQ ID NO: 84<br>ACTB N-term PBS<br>13 RT 29 attB 46<br>(original length)<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAGACCGCCGTCGTCGACAAGCCGGCCTGAGCTGCGA<br>GAA |
| SEQ ID NO: 85<br>ACTB N-term<br>PBS_13 RT_29_with<br>TP901-1 minimal<br>attB f pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGCACAATTAACATCTCAATCAAGGTAAATGCTTGAGCTGCGAG<br>AA |
| SEQ ID NO: 86<br>ACTB N-term<br>PBS_13 RT_29_with<br>TP901-1 minimal<br>attB rc pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGAGCATTTACCTTGATTGAGATGTTAATTGTGTGAGCTGCGAGA<br>A |

TABLE 4-continued

| SEQ ID NO/ DESCRIPTION/ SOURCE | SEQUENCE |
|---|---|
| SEQ ID NO: 87 ACTB N-term PBS_13_RT_29_with PhiBT1 minimal attB f pegRNA (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGCAGGTTTTTGACGAAAGTGATCCAGATGATCCAGTGAGCTGC GAGAA |
| SEQ ID NO: 88 ACTB N-term PBS_13_RT_29_with PhiBT1 minimal attB rc pegRNA (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGCTGGATCATCTGGATCACTTTCGTCAAAAACCTGTGAGCTGCG AGAA |
| SEQ ID NO: 89 ACTB N-term Nicking guide 1 +48 guide (Artificial Sequence) | GAAGCCGGCCTTGCACATGCGTTTTAGAGCTAGAAATAGCAAGT TAAAATAAGGCTAGTCCGTTATCAACTTGAAAAAGTGGCACCGA GTCGGTGC |
| SEQ ID NO: 90 ACTB N-term PBS_18_RT_16_with_L ox71_Cre pegRNA (Artificial Sequence) | GAAGCCGGCCTTGCACATGCGTTTTAGAGCTAGAAATAGCAAGT TAAAATAAGGCTAGTCCGTTATCAACTTGAAAAAGTGGCACCGA GTCGGTGCATATCATCATCCATGGTACCGTTCGTATAGCATACAT TATACGAAGTTATTGAGCTGCGAGAATAGCC |
| SEQ ID NO: 91 ACTB N-term PBS_13_RT_29_with_L ox71_Cre pegRNA (Artificial Sequence) | GAAGCCGGCCTTGCACATGCGTTTTAGAGCTAGAAATAGCAAGT TAAAATAAGGCTAGTCCGTTATCAACTTGAAAAAGTGGCACCGA GTCGGTGCGACGAGCGCGGCGATATCATCATCCATGGTACCGTT CGTATAGCATACATTATACGAAGTTATTGAGCTGCGAGAA |
| SEQ ID NO: 92 ACTB N-term PBS 13 RT 34 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCGACGACGAGCGCGGCGATATCATCATCCATGGCCGAT GATCCTGACGACGGAGACCGCCGTCGTCGACAAGCCGGCCTGAGC TGCGAGAA |
| SEQ ID NO: 93 ACTB N-term PBS 13 RT 26 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGAGCGCGGCGATATCATCATCCATGGCCGGATGATCCTGA CGACGGAGACCGCCGTCGTCGACAAGCCGGCCTGAGCTGCGAGAA |
| SEQ ID NO: 94 ACTB N-term PBS 13 RT 23 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCCGCGGCGATATCATCATCCATGGCCGGATGATCCTGACGAC GGAGACCGCCGTCGTCGACAAGCCGGCCTGAGCTGCGAGAA |
| SEQ ID NO: 95 ACTB N-term PBS 13 RT 20 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGGCGATATCATCATCCATGGCCGGATGATCCTGACGACGG AGACCGCCGTCGTCGACAAGCCGGCCTGAGCTGCGAGAA |
| SEQ ID NO: 96 ACTB N-term PBS 13 RT 16 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCATATCATCATCCATGGCCGGATGATCCTGACGACGGAGAC CGCCGTCGTCGACAAGCCGGCCTGAGCTGCGAGAA |
| SEQ ID NO: 97 ACTB N-term PBS 18 RT 34 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCGACGACGAGCGCGGCGATATCATCATCCATGGCCGAT GATCCTGACGACGGAGACCGCCGTCGTCGACAAGCCGGCCTGAGC TGCGAGAATAGCC |
| SEQ ID NO: 98 ACTB N-term PBS 18 RT 29 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCGGATGATCC TGACGACGGAGACCGCCGTCGTCGACAAGCCGGCCTGAGCTGCGA GAATAGCC |

TABLE 4-continued

| SEQ ID NO/ DESCRIPTION/ SOURCE | SEQUENCE |
|---|---|
| SEQ ID NO: 99 ACTB N-term PBS 18 RT 16 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCATATCATCATCCATGGCCGGATGATCCTGACGACGGAGAC CGCCGTCGTCGACAAGCCGGCCTGAGCTGCGAGAATAGCC |
| SEQ ID NO: 100 LMNB1 N-term PBS 13 RT 39 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCTGCCCATCCGCGGCGGCACGGGGGTCGCAGTCGCCA TGCCGGATGATCCTGACGACGGAGACCGCCGTCGTCGACAAGCC GGCCCGGGCGGCGGAGA |
| SEQ ID NO: 101 LMNB1 N-term PBS 13 RT 34 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCATCCGCGGCGGCACGGGGGTCGCAGTCGCCATGCCG GATGATCCTGACGACGGAGACCGCCGTCGTCGACAAGCCGGCCC GGGCGGCGGAGA |
| SEQ ID NO: 102 LMNB1 N-term PBS 13 RT 29 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGCGGCGGCACGGGGGTCGCAGTCGCCATGCCGGATGA TCCTGACGACGGAGACCGCCGTCGTCGACAAGCCGGCCCGGGCG GCGGAGA |
| SEQ ID NO: 103 LMNB1 N-term PBS 13 RT 24 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGGCACGGGGGTCGCAGTCGCCATGCCGGATGATCCTG ACGACGGAGACCGCCGTCGTCGACAAGCCGGCCCGGGCGGCGGA GA |
| SEQ ID NO: 104 LMNB1 N-term PBS 13 RT 19 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGGGGGTCGCAGTCGCCATGCCGGATGATCCTGACGAC GGAGACCGCCGTCGTCGACAAGCCGGCCCGGGCGGCGGAGA |
| SEQ ID NO: 105 LMNB1 N-term PBS 18 RT 39 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCTGCCCATCCGCGGCGGCACGGGGGTCGCAGTCGCCA TGCCGGATGATCCTGACGACGGAGACCGCCGTCGTCGACAAGCC GGCCCGGGCGGCGGAGACAGCG |
| SEQ ID NO: 106 LMNB1 N-term PBS 18 RT 34 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCATCCGCGGCGGCACGGGGGTCGCAGTCGCCATGCCG GATGATCCTGACGACGGAGACCGCCGTCGTCGACAAGCCGGCCC GGGCGGCGGAGACAGCG |
| SEQ ID NO: 107 LMNB1 N-term PBS 18 RT 29 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGCCGGATGATC CTGACGACGGAGACCGCCGTCGTCGACAAGCCGGCCCGGGCGGCG GAGACAGCG |
| SEQ ID NO: 108 LMNB1 N-term PBS 18 RT 24 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGGCACGGGGGTCGCAGTCGCCATGCCGGATGATCCTG ACGACGGAGACCGCCGTCGTCGACAAGCCGGCCCGGGCGGCGGA GACAGCG |
| SEQ ID NO: 109 LMNB1 N-term PBS 18 RT 19 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGGGGGTCGCAGTCGCCATGCCGGATGATCCTGACGAC GGAGACCGCCGTCGTCGACAAGCCGGCCCGGGCGGCGGAGACAG CG |
| SEQ ID NO: 110 LMNB1 N-term Nicking guide 1 +46 (Artificial Sequence) | GCGTGGTGGGCCGCCAGCGGTTTTAGAGCTAGAAATAGCAAGT TAAAATAAGGCTAGTCCGTTATCAACTTGAAAAAGTGGCACCGA GTCGGTGC |
| SEQ ID NO: 111 ACTB N-term PBS 13 RT 29 attB 42 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGGATGATCCTG ACGACGGAGACCGCCGTCGTCGACAAGCCGGTGAGCTGCGAGAA |

TABLE 4-continued

| SEQ ID NO/<br>DESCRIPTION/<br>SOURCE | SEQUENCE |
|---|---|
| SEQ ID NO: 112<br>ACTB N-term PBS<br>13 RT 29 attB 40<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGATGATCCTGA<br>CGACGGAGACCGCCGTCGTCGACAAGCCGTGAGCTGCGAGAA |
| SEQ ID NO: 113<br>ACTB N-term PBS<br>13 RT 29 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGATGATCCTGAC<br>GACGGAGACCGCCGTCGTCGACAAGCCTGAGCTGCGAGAA |
| SEQ ID NO: 114<br>ACTB N-term PBS<br>13 RT 29 attB 36<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGATCCTGACG<br>ACGGAGACCGCCGTCGTCGACAAGCTGAGCTGCGAGAA |
| SEQ ID NO: 115<br>LMNB1 N-term PBS<br>13 RT 29 attB 44<br>pegRNA v2<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGCGGATGATCC<br>TGACGACGGAGACCGCCGTCGTCGACAAGCCGGCCGGGCGGCGG<br>AGA |
| SEQ ID NO: 116<br>LMNB1 N-term PBS<br>13 RT 29 attB 42<br>pegRNA v2<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGGGATGATCCT<br>GACGACGGAGACCGCCGTCGTCGACAAGCCGGCGGGCGGCGGAG<br>A |
| SEQ ID NO: 117<br>LMNB1 N-term PBS<br>13 RT 29 attB 40<br>pegRNA v2<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGGATGATCCTG<br>ACGACGGAGACCGCCGTCGTCGACAAGCCGCGGGCGGCGGAGA |
| SEQ ID NO: 118<br>LMNB1 N-term PBS<br>13 RT 29 attB 38<br>pegRNA v2<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGATGATCCTGA<br>CGACGGAGACCGCCGTCGTCGACAAGCCCGGGCGGCGGAGA |
| SEQ ID NO: 119<br>NOLC1 N-term PBS<br>18 RT 29 attB 46<br>pegRNA<br>(Artificial Sequence) | GCGTATTGCCTGGAGGATGGGTTTTAGAGCTAGAAATAGCAAGT<br>TAAAATAAGGCTAGTCCGTTATCAACTTGAAAAAGTGGCACCGA<br>GTCGGTGCGAACCACGCGGCGAATGCCGGCGTCCGCCCCGGATG<br>ATCCTGACGACGGAGACCGCCGTCGTCGACAAGCCGGCCTCCTC<br>CAGGCAATACGCG |
| SEQ ID NO: 120<br>NOLC1 N-term PBS<br>13 RT 29 attB 46<br>pegRNA<br>(Artificial Sequence) | GCGTATTGCCTGGAGGATGGGTTTTAGAGCTAGAAATAGCAAGTT<br>AAAATAAGGCTAGTCCGTTATCAACTTGAAAAAGTGGCACCGAGT<br>CGGTGCGAACCACGCGGCGAATGCCGGCGTCCGCCCCGGATGATC<br>CTGACGACGGAGACCGCCGTCGTCGACAAGCCGGCCTCCTCCAGG<br>CAAT |
| SEQ ID NO: 121<br>NOLC1 N-term PBS<br>13 RT 29 attB 44<br>pegRNA<br>(Artificial Sequence) | GCGTATTGCCTGGAGGATGGGTTTTAGAGCTAGAAATAGCAAGT<br>TAAAATAAGGCTAGTCCGTTATCAACTTGAAAAAGTGGCACCGA<br>GTCGGTGCGAACCACGCGGCGAATGCCGGCGTCCGCCCGGATGA<br>TCCTGACGACGGAGACCGCCGTCGTCGACAAGCCGGCTCCTCCA<br>GGCAAT |
| SEQ ID NO: 122<br>NOLC1 N-term PBS<br>13 RT 29 attB 42<br>pegRNA<br>(Artificial Sequence) | GCGTATTGCCTGGAGGATGGGTTTTAGAGCTAGAAATAGCAAGT<br>TAAAATAAGGCTAGTCCGTTATCAACTTGAAAAAGTGGCACCGA<br>GTCGGTGCGAACCACGCGGCGAATGCCGGCGTCCGCCGGATGAT<br>CCTGACGACGGAGACCGCCGTCGTCGACAAGCCGGTCCTCCAGG<br>CAAT |
| SEQ ID NO: 123<br>NOLC1 N-term PBS<br>13 RT 29 attB 40<br>pegRNA<br>(Artificial Sequence) | GCGTATTGCCTGGAGGATGGGTTTTAGAGCTAGAAATAGCAAGT<br>TAAAATAAGGCTAGTCCGTTATCAACTTGAAAAAGTGGCACCGA<br>GTCGGTGCGAACCACGCGGCGAATGCCGGCGTCCGCCGATGATC<br>CTGACGACGGAGACCGCCGTCGTCGACAAGCCGTCCTCCAGGCA<br>AT |

TABLE 4-continued

| SEQ ID NO/<br>DESCRIPTION/<br>SOURCE | SEQUENCE |
|---|---|
| SEQ ID NO: 124<br>NOLC1 N-term PBS<br>13 RT 29 attB 38<br>pegRNA<br>(Artificial Sequence) | GCGTATTGCCTGGAGGATGGGTTTTAGAGCTAGAAATAGCAAGTT<br>AAAATAAGGCTAGTCCGTTATCAACTTGAAAAAGTGGCACCGAG<br>TCGGTGCGAACCACGCGGCGAATGCCGGCGTCCGCCATGATCCT<br>GACGACGGAGACCGCCGTCGTCGACAAGCCTCCTCCAGGCAAT |
| SEQ ID NO: 125<br>NOLC1 nicking<br>guide - 43<br>(Artificial Sequence) | GAGCCGAGCACGAGGGGATACGTTTTAGAGCTAGAAATAGCAAGT<br>TAAAATAAGGCTAGTCCGTTATCAACTTGAAAAAGTGGCACCGAG<br>TCGGTGC |
| SEQ ID NO: 126<br>ACTB N-term PBS<br>13 RT 20 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGGCGATATCATCATCCATGGATGATCCTGACGACGGAGAC<br>CGCCGTCGTCGACAAGCCTGAGCTGCGAGAA |
| SEQ ID NO: 127<br>ACTB N-term PBS<br>13 RT 15 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTATCATCATCCATGGATGATCCTGACGACGGAGACCGCCG<br>TCGTCGACAAGCCTGAGCTGCGAGAA |
| SEQ ID NO: 128<br>ACTB N-term PBS<br>13 RT 10 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTCATCCATGGATGATCCTGACGACGGAGACCGCCGTCGTC<br>GACAAGCCTGAGCTGCGAGAA |
| SEQ ID NO: 129<br>ACTB N-term PBS 9<br>RT 20 attB 38<br>pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGGCGATATCATCATCCATGGATGATCCTGACGACGGAG<br>ACCGCCGTCGTCGACAAGCCTGAGCTGCG |
| SEQ ID NO: 130<br>ACTB N-term PBS 9<br>RT 15 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTATCATCATCCATGGATGATCCTGACGACGGAGACCGCCG<br>TCGTCGACAAGCCTGAGCTGCG |
| SEQ ID NO: 131<br>ACTB N-term PBS 9<br>RT 10 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTCATCCATGGATGATCCTGACGACGGAGACCGCCGTCGTC<br>GACAAGCCTGAGCTGCG |
| SEQ ID NO: 132<br>LMNB1 N-term PBS<br>13 RT 20 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCGGGGGTCGCAGTCGCCATGATGATCCTGACGACGGA<br>GACCGCCGTCGTCGACAAGCCCGGGCGGCGGAGA |
| SEQ ID NO: 133<br>LMNB1 N-term PBS<br>13 RT 15 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGTCGCAGTCGCCATGATGATCCTGACGACGGAGACCG<br>CCGTCGTCGACAAGCCCGGGCGGCGGAGA |
| SEQ ID NO: 134<br>LMNB1 N-term PBS<br>13 RT 10 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCAGTCGCCATGATGATCCTGACGACGGAGACCGCCGTC<br>GTCGACAAGCCCGGGCGGCGGAGA |
| SEQ ID NO: 135<br>LMNB1 N-term PBS<br>9 RT 20 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCCGGGGGTCGCAGTCGCCATGATGATCCTGACGACGGAGA<br>CCGCCGTCGTCGACAAGCCCGGGCGGCG |

TABLE 4-continued

| SEQ ID NO/ DESCRIPTION/ SOURCE | SEQUENCE |
|---|---|
| SEQ ID NO: 136 LMNB1 N-term PBS 9 RT 15 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGTCGCAGTCGCCATGATGATCCTGACGACGGAGACCG CCGTCGTCGACAAGCCCGGGCGGCG |
| SEQ ID NO: 137 LMNB1 N-term PBS 9 RT 10 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCAGTCGCCATGATGATCCTGACGACGGAGACCGCCGTCGT CGACAAGCCCGGGCGGCG |
| SEQ ID NO: 138 SUPT16H N-term PBS 13 RT 24 Bxb1- GT_Initial length (Artificial Sequence) | GAGAAGCGGCGTCCGGGGCTAGTTTTAGAGCTAGAAATAGCAAGT TAAAATAAGGCTAGTCCGTTATCAACTTGAAAAAGTGGCACCGAG TCGGTGCTCTTTGTCCAGAGTCACAGCCATACCGGATGATCCTGAC GACGGAGACCGCCGTCGTCGACAAGCCGGCCCCCCGGACGCCGC |
| SEQ ID NO: 139 SRRM2 N-term PBS 13 RT 24 Bxb1 Initial length (Artificial Sequence) | GGGCACGGGGCCATGTACAAGTTTTAGAGCTAGAAATAGCAAGT TAAAATAAGGCTAGTCCGTTATCAACTTGAAAAAGTGGCACCGA GTCGGTGCGGCGTCGGCAGCCCGATCCCGTTGCCGGATGATCCT GACGACGGAGACCGCCGTCGTCGACAAGCCGGCCTACATGGCCC CGT |
| SEQ ID NO: 140 DEPDC4 N-term PBS 18 RT 24 Bxb1 Initial length (Artificial Sequence) | GTGTCAGGTGGGGCGGGGCTAGTTTTAGAGCTAGAAATAGCAAG TTAAAATAAGGCTAGTCCGTTATCAACTTGAAAAAGTGGCACCG AGTCGGTGCGCTGGCTCCTCCCCTGGCACCATACCGGATGATCCT GACGACGGAGACCGCCGTCGTCGACAAGCCGGCCCCCCGCCCCA CCTGACAC |
| SEQ ID NO: 141 NES N-term PBS 13 RT 29 Bxb1 Initial length (Artificial Sequence) | GAGTGGGTCAGACGAGCAGGAGTTTTAGAGCTAGAAATAGCAAGT TAAAATAAGGCTAGTCCGTTATCAACTTGAAAAAGTGGCACCGAG TCGGTGCGATGGAGGGCTGCATGGGGAGGAGTCGCCGGATGATC CTGACGACGGAGACCGCCGTCGTCGACAAGCCGGCCTGCTCGTCT GACC |
| SEQ ID NO: 142 SUPT16H nicking guide -53 (Artificial Sequence) | GCAGCCACCCGCTCTCGGCCCGTTTTAGAGCTAGAAATAGCAAG TTAAAATAAGGCTAGTCCGTTATCAACTTGAAAAAGTGGCACCG AGTCGGTGC |
| SEQ ID NO: 143 SRRM2 N-term nicking guide 1 +87 (Artificial Sequence) | GTGTAGTCAGGCCGCTCACCCGTTTTAGAGCTAGAAATAGCAAG TTAAAATAAGGCTAGTCCGTTATCAACTTGAAAAAGTGGCACCG AGTCGGTGC |
| SEQ ID NO: 144 DEPDC4 N-term Nicking guide 1 +59 (Artificial Sequence) | GCTGACAAGTCTACGGAACCTGTTTTAGAGCTAGAAATAGCAAG TTAAAATAAGGCTAGTCCGTTATCAACTTGAAAAAGTGGCACCG AGTCGGTGC |
| SEQ ID NO: 145 NES N-term Nicking guide 2 +79 (Artificial Sequence) | GCTCCTCCAGCGCCTTGACCGTTTTAGAGCTAGAAATAGCAAGTTA AAATAAGGCTAGTCCGTTATCAACTTGAAAAAGTGGCACCGAGTC GGTGC |
| SEQ ID NO: 146 HITI_ACTB_guide (Artificial Sequence) | GCTATTCTCGCAGCTCACCA |
| SEQ ID NO: 147 HITI_SUPTH16_guide (Artificial Sequence) | AGAAGCGGCGTCCGGGGCTA |
| SEQ ID NO: 148 HITI_SRRM2_guide (Artificial Sequence) | GGGCACGGGGCCATGTACAA |
| SEQ ID NO: 149 HITI_NOLC1_guide (Artificial Sequence) | GCGTATTGCCTGGAGGATGG |
| SEQ ID NO: 150 HITI_DEPDC4_guide (Artificial Sequence) | TGTCAGGTGGGGCGGGGCTA |

TABLE 4-continued

| SEQ ID NO/<br>DESCRIPTION/<br>SOURCE | SEQUENCE |
|---|---|
| SEQ ID NO: 151<br>HITI_NES_guide<br>(Artificial Sequence) | AGTGGGTCAGACGAGCAGGA |
| SEQ ID NO: 152<br>HITI_LMNB1_guide<br>(Artificial Sequence) | GCTGTCTCCGCCGCCCGCCA |
| SEQ ID NO: 153<br>HDR Cas9 ACTB<br>guide<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGC |
| SEQ ID NO: 154<br>ACTB N-term PBS<br>13 RT 29 attB<br>original length<br>pegRNAs for<br>dinucleotides<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAXXCGCCGTCGTCGACAAGCCGGCCTGAGCTGCGA<br>GAA<br>XX: CG, GC, AT, TA, GG, TT, GA, AG, CC, TC, CT, AA, TG, GT, CA, or<br>AC |
| SEQ ID NO: 155<br>ACTB N-term PBS<br>13 RT 29 pegRNA<br>with attB 46 GT for<br>fusion<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGCCGGATGATCCT<br>GACGACGGAGACCGCCGTCGTCGACAAGCCGGCCTGAGCTGCGAG<br>AA |
| SEQ ID NO: 156<br>ACTB N-term PBS<br>13 RT 29 pegRNA<br>with attB 46 CT for<br>multiplexing<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGCCGGATGATCCT<br>GACGACGGAGAGCGCCGTCGTCGACAAGCCGGCCTGAGCTGCGA<br>GAA |
| SEQ ID NO: 157<br>NOLC1 N-term PBS<br>18 RT 29 pegRNA<br>with attB 46 GA for<br>multiplexing<br>(Artificial Sequence) | GCGTATTGCCTGGAGGATGGGTTTTAGAGCTAGAAATAGCAAGTT<br>AAAATAAGGCTAGTCCGTTATCAACTTGAAAAAGTGGCACCGAGT<br>CGGTGCGAACCACGCGGCGAATGCCGGCGTCCGCCCCGGATGATC<br>CTGACGACGGAGTCCGCCGTCGTCGACAAGCCGGCCTCCTCCAGG<br>CAATACGCG |
| SEQ ID NO: 158<br>LMNB1 N-term PBS<br>18 RT 29 pegRNA<br>with attB 46 AG for<br>multiplexing<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGCCGGATGATC<br>CTGACGACGGAGCTCGCCGTCGTCGACAAGCCGGCCCGGGCGGCG<br>GAGACAGCG |
| SEQ ID NO: 159<br>EMX1 Cas9 guide 1<br>(Artificial Sequence) | GTCACCTCCAATGACTAGGG |
| SEQ ID NO: 160<br>EMX1 Cas9 guide 2<br>(Artificial Sequence) | GGGCAACCACAAACCCACGA |
| SEQ ID NO: 161<br>ACTB N-term PBS<br>13 RT 29 attB 56 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCTATGCCGGAT<br>GATCCTGACGACGGAGTCCGCCGTCGTCGACAAGCCGGCCCTAGC<br>TGAGCTGCGAGAA |
| SEQ ID NO: 162<br>ACTB N-term PBS<br>13 RT 29 attB 51 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGCCGGATGAT<br>CCTGACGACGGAGTCCGCCGTCGTCGACAAGCCGGCCCTATGAGC<br>TGCGAGAA |
| SEQ ID NO: 163<br>ACTB N-term PBS<br>13 RT 29 attB 46 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAGTCCGCCGTCGTCGACAAGCCGGCCTGAGCTGCGA<br>GAA |

TABLE 4-continued

| SEQ ID NO/ DESCRIPTION/ SOURCE | SEQUENCE |
| --- | --- |
| SEQ ID NO: 164 ACTB N-term PBS 13 RT 29 attB 41 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGGATGATCCTG ACGACGGAGTCCGCCGTCGTCGACAAGCCGTGAGCTGCGAGAA |
| SEQ ID NO: 165 ACTB N-term PBS 13 RT 29 attB 36 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGATCCTGACG ACGGAGTCCGCCGTCGTCGACAAGCTGAGCTGCGAGAA |
| SEQ ID NO: 166 ACTB N-term PBS 13 RT 29 attB 31 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGATCCTGACGAC GGAGTCCGCCGTCGTCGACATGAGCTGCGAGAA |
| SEQ ID NO: 167 ACTB N-term PBS 13 RT 29 attB 26 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCTGACGACGG AGTCCGCCGTCGTCGTGAGCTGCGAGAA |
| SEQ ID NO: 168 ACTB N-term PBS 13 RT 29 attB 21 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGACGACGGAG TCCGCCGTCGTGAGCTGCGAGAA |
| SEQ ID NO: 169 ACTB N-term PBS 13 RT 29 attB 16 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGACGACGGAGTC CGCCGTGAGCTGCGAGAA |
| SEQ ID NO: 170 ACTB N-term PBS 13 RT 29 attB 11 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGACGGAGTCCG TGAGCTGCGAGAA |
| SEQ ID NO: 171 ACTB N-term PBS 13 RT 29 attB 6 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCGGAGTTGAGC TGCGAGAA |
| SEQ ID NO: 172 ACTB N-term PBS_18_RT_34_with_L ox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAATAG CC |
| SEQ ID NO: 173 ACTB N-term PBS_18_RT_29_with_L ox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCGACGAGCGCGGCGATATCATCATCCATGGTACCGTTCGT ATAGCATACATTATACGAAGTTATTGAGCTGCGAGAATAGCC |
| SEQ ID NO: 174 ACTB N-term PBS_13_RT_34_with_L ox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAA |
| SEQ ID NO: 175 ACTB N-term PBS_13_RT_16_with_L ox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCATATCATCATCCATGGTACCGTTCGTATAGCATACATTAT ACGAAGTTATTGAGCTGCGAGAA |

TABLE 4-continued

| SEQ ID NO/ DESCRIPTION/ SOURCE | SEQUENCE |
|---|---|
| SEQ ID NO: 176 ACTB N-term Nicking guide 2 +93 guide (Artificial Sequence) | CCCCACGATGGAGGGGAAGAGTTTTAGAGCTAGAAATAGCAAGTT AAAATAAGGCTAGTCCGTTATCAACTTGAAAAAGTGGCACCGAGT CGGTGC |
| SEQ ID NO: 177 LMNB1 N-term Nicking guide 2 +87 guide (Artificial Sequence) | CCTTCTCCTGGAGCCGCGACGTTTTAGAGCTAGAAATAGCAAGTT AAAATAAGGCTAGTCCGTTATCAACTTGAAAAAGTGGCACCGAGT CGGTGC |

Sequences of insertion sites can be found in Table 4 below.

TABLE 4

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attP_GT_ original_site (Artificial Sequence) | 178 | GTGGTTTGTCTGGTC AACCACCGCGGTCT CAGTGGTGTACGGT ACAAACCCA | 179 | TGGGTTTGTACCGTA CACCACTGAGACCG CGGTGGTTGACCAG ACAAACCAC |
| Bxb1_attP_C G_site (Artificial Sequence) | 180 | GTGGTTTGTCTGGTC AACCACCGCGCGCT CAGTGGTGTACGGT ACAAACCCA | 181 | TGGGTTTGTACCGTA CACCACTGAGCGCG CGGTGGTTGACCAG ACAAACCAC |
| Bxb1_attP_G C_site (Artificial Sequence) | 182 | GTGGTTTGTCTGGTC AACCACCGCGGCCT CAGTGGTGTACGGT ACAAACCCA | 183 | TGGGTTTGTACCGTA CACCACTGAGGCCG CGGTGGTTGACCAG ACAAACCAC |
| Bxb1_attP_AT_ site (Artificial Sequence) | 184 | GTGGTTTGTCTGGTC AACCACCGCGATCT CAGTGGTGTACGGT ACAAACCCA | 185 | TGGGTTTGTACCGTA CACCACTGAGATCG CGGTGGTTGACCAG ACAAACCAC |
| Bxb1_attP_TA_ site (Artificial Sequence) | 186 | GTGGTTTGTCTGGTC AACCACCGCGTACT CAGTGGTGTACGGT ACAAACCCA | 187 | TGGGTTTGTACCGTA CACCACTGAGTACG CGGTGGTTGACCAG ACAAACCAC |
| Bxb1_attP_G G_site (Artificial Sequence) | 188 | GTGGTTTGTCTGGTC AACCACCGCGGGCT CAGTGGTGTACGGT ACAAACCCA | 189 | TGGGTTTGTACCGTA CACCACTGAGCCCG CGGTGGTTGACCAG ACAAACCAC |
| Bxb1_attP_TT_ site (Artificial Sequence) | 190 | GTGGTTTGTCTGGTC AACCACCGCGTTCTC AGTGGTGTACGGTA CAAACCCA | 191 | TGGGTTTGTACCGTA CACCACTGAGAACG CGGTGGTTGACCAG ACAAACCAC |
| Bxb1_attP_G A_site (Artificial Sequence) | 192 | GTGGTTTGTCTGGTC AACCACCGCGGACT CAGTGGTGTACGGT ACAAACCCA | 193 | TGGGTTTGTACCGTA CACCACTGAGTCCG CGGTGGTTGACCAG ACAAACCAC |
| Bxb1_attP_A G_site (Artificial Sequence) | 194 | GTGGTTTGTCTGGTC AACCACCGCGAGCT CAGTGGTGTACGGT ACAAACCCA | 195 | TGGGTTTGTACCGTA CACCACTGAGCTCG CGGTGGTTGACCAG ACAAACCAC |
| Bxb1_attP_CC_ site (Artificial Sequence) | 196 | GTGGTTTGTCTGGTC AACCACCGCGCCCT CAGTGGTGTACGGT ACAAACCCA | 197 | TGGGTTTGTACCGTA CACCACTGAGGGCG CGGTGGTTGACCAG ACAAACCAC |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attP_TC_ site (Artificial Sequence) | 198 | GTGGTTTGTCTGGTC AACCACCGCGTCCTC AGTGGTGTACGGTA CAAACCCA | 199 | TGGGTTTGTACCGTA CACCACTGAGGACG CGGTGGTTGACCAG ACAAACCAC |
| Bxb1_attP_CT_ site (Artificial Sequence) | 200 | GTGGTTTGTCTGGTC AACCACCGCGCTCTC AGTGGTGTACGGTA CAAACCCA | 201 | TGGGTTTGTACCGTA CACCACTGAGAGCG CGGTGGTTGACCAG ACAAACCAC |
| Bxb1_attP_A A_site (Artificial Sequence) | 202 | GTGGTTTGTCTGGTC AACCACCGCGAACT CAGTGGTGTACGGT ACAAACCCA | 203 | TGGGTTTGTACCGTA CACCACTGAGTTCGC GGTGGTTGACCAGA CAAACCAC |
| Bxb1_attP_C A_site (Artificial Sequence) | 204 | GTGGTTTGTCTGGTC AACCACCGCGCACT CAGTGGTGTACGGT ACAAACCCA | 205 | TGGGTTTGTACCGTA CACCACTGAGTGCG CGGTGGTTGACCAG ACAAACCAC |
| Bxb1_attP_A C_site (Artificial Sequence) | 206 | GTGGTTTGTCTGGTC AACCACCGCGACCT CAGTGGTGTACGGT ACAAACCCA | 207 | TGGGTTTGTACCGTA CACCACTGAGGTCG CGGTGGTTGACCAG ACAAACCAC |
| Bxb1_attP_TG_ site (Artificial Sequence) | 208 | GTGGTTTGTCTGGTC AACCACCGCGTGCT CAGTGGTGTACGGT ACAAACCCA | 209 | TGGGTTTGTACCGTA CACCACTGAGCACG CGGTGGTTGACCAG ACAAACCAC |
| Bxb1_attB_46_ GT original_site (Artificial Sequence) | 210 | GGCCGGCTTGTCGA CGACGGCGGTCTCC GTCGTCAGGATCATC CGG | 211 | CCGGATGATCCTGA CGACGGAGACCGCC GTCGTCGACAAGCC GGCC |
| Bxb1_attB_46_ AA_site (Artificial Sequence) | 212 | GGCCGGCTTGTCGA CGACGGCGAACTCC GTCGTCAGGATCATC CGG | 213 | CCGGATGATCCTGA CGACGGAGTTCGCC GTCGTCGACAAGCC GGCC |
| Bxb1_attB_46_ GA_site (Artificial Sequence) | 214 | GGCCGGCTTGTCGA CGACGGCGGACTCC GTCGTCAGGATCATC CGG | 215 | CCGGATGATCCTGA CGACGGAGTCCGCC GTCGTCGACAAGCC GGCC |
| Bxb1_attB_46_ CA_site (Artificial Sequence) | 216 | GGCCGGCTTGTCGA CGACGGCGCACTCC GTCGTCAGGATCATC CGG | 217 | CCGGATGATCCTGA CGACGGAGTGCGCC GTCGTCGACAAGCC GGCC |
| Bxb1_attB_46_ TA_site (Artificial Sequence) | 218 | GGCCGGCTTGTCGA CGACGGCGTACTCC GTCGTCAGGATCATC CGG | 219 | CCGGATGATCCTGA CGACGGAGTACGCC GTCGTCGACAAGCC GGCC |
| Bxb1_attB_46_ AG_site (Artificial Sequence) | 220 | GGCCGGCTTGTCGA CGACGGCGAGCTCC GTCGTCAGGATCATC CGG | 221 | CCGGATGATCCTGA CGACGGAGCTCGCC GTCGTCGACAAGCC GGCC |
| Bxb1_attB_46_ GG_site (Artificial Sequence) | 222 | GGCCGGCTTGTCGA CGACGGCGGGCTCC GTCGTCAGGATCATC CGG | 223 | CCGGATGATCCTGA CGACGGAGCCCGCC GTCGTCGACAAGCC GGCC |
| Bxb1_attB_46_ CG_site (Artificial Sequence) | 224 | GGCCGGCTTGTCGA CGACGGCGCGCTCC GTCGTCAGGATCATC CGG | 225 | CCGGATGATCCTGA CGACGGAGCGCGCC GTCGTCGACAAGCC GGCC |

TABLE 4-continued

| DESCRIPTION/ SOURCE | FORWARD SEQUENCE (5'-3') SEQ ID NO | Sequence | REVERSE SEQUENCE (5'-3') SEQ ID NO | Sequence |
|---|---|---|---|---|
| Bxb1_attB_46_ TG_site (Artificial Sequence) | 226 | GGCCGGCTTGTCGA CGACGGCGTGCTCC GTCGTCAGGATCATC CGG | 227 | CCGGATGATCCTGA CGACGGAGCACGCC GTCGTCGACAAGCC GGCC |
| Bxb1_attB_46_ AC_site (Artificial Sequence) | 228 | GGCCGGCTTGTCGA CGACGGCGACCTCC GTCGTCAGGATCATC CGG | 229 | CCGGATGATCCTGA CGACGGAGGTCGCC GTCGTCGACAAGCC GGCC |
| Bxb1_attB_46_ GC_site (Artificial Sequence) | 230 | GGCCGGCTTGTCGA CGACGGCGGCCTCC GTCGTCAGGATCATC CGG | 231 | CCGGATGATCCTGA CGACGGAGGCCGCC GTCGTCGACAAGCC GGCC |
| Bxb1_attB_46_ CC_site (Artificial Sequence) | 232 | GGCCGGCTTGTCGA CGACGGCGCCCTCC GTCGTCAGGATCATC CGG | 233 | CCGGATGATCCTGA CGACGGAGGGCGCC GTCGTCGACAAGCC GGCC |
| Bxb1_attB_46_ TC_site (Artificial Sequence) | 234 | GGCCGGCTTGTCGA CGACGGCGTCCTCC GTCGTCAGGATCATC CGG | 235 | CCGGATGATCCTGA CGACGGAGGACGCC GTCGTCGACAAGCC GGCC |
| Bxb1_attB_46_ AT_site (Artificial Sequence) | 236 | GGCCGGCTTGTCGA CGACGGCGATCTCC GTCGTCAGGATCATC CGG | 237 | CCGGATGATCCTGA CGACGGAGATCGCC GTCGTCGACAAGCC GGCC |
| Bxb1_attB_46_ CT_site (Artificial Sequence) | 238 | GGCCGGCTTGTCGA CGACGGCGCTCTCC GTCGTCAGGATCATC CGG | 239 | CCGGATGATCCTGA CGACGGAGAGCGCC GTCGTCGACAAGCC GGCC |
| Bxb1_attB_46_ TT_site (Artificial Sequence) | 240 | GGCCGGCTTGTCGA CGACGGCGTTCTCCG TCGTCAGGATCATCC GG | 241 | CCGGATGATCCTGA CGACGGAGAACGCC GTCGTCGACAAGCC GGCC |
| Bxb1_attB_38_ GT_site (Artificial Sequence) | 242 | GGCTTGTCGACGAC GGCGGTCTCCGTCGT CAGGATCAT | 243 | ATGATCCTGACGAC GGAGACCGCCGTCG TCGACAAGCC |
| Bxb1_attB_38_ AA_site (Artificial Sequence) | 244 | GGCTTGTCGACGAC GGCGAACTCCGTCG TCAGGATCAT | 245 | ATGATCCTGACGAC GGAGTTCGCCGTCGT CGACAAGCC |
| Bxb1_attB_38_ GA_site (Artificial Sequence) | 246 | GGCTTGTCGACGAC GGCGGACTCCGTCG TCAGGATCAT | 247 | ATGATCCTGACGAC GGAGTCCGCCGTCG TCGACAAGCC |
| Bxb1_attB_38_ CA_site (Artificial Sequence) | 248 | GGCTTGTCGACGAC GGCGCACTCCGTCGT CAGGATCAT | 249 | ATGATCCTGACGAC GGAGTGCGCCGTCG TCGACAAGCC |
| Bxb1_attB_38_ TA_site (Artificial Sequence) | 250 | GGCTTGTCGACGAC GGCGTACTCCGTCGT CAGGATCAT | 251 | ATGATCCTGACGAC GGAGTACGCCGTCG TCGACAAGCC |
| Bxb1_attB_38_ AG_site (Artificial Sequence) | 252 | GGCTTGTCGACGAC GGCGAGCTCCGTCG TCAGGATCAT | 253 | ATGATCCTGACGAC GGAGCTCGCCGTCG TCGACAAGCC |
| Bxb1_attB_38_ GG_site (Artificial Sequence) | 254 | GGCTTGTCGACGAC GGCGGGCTCCGTCG TCAGGATCAT | 255 | ATGATCCTGACGAC GGAGCCCGCCGTCG TCGACAAGCC |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attB_38_CG_site (Artificial Sequence) | 256 | GGCTTGTCGACGACGGCGCGCTCCGTCGTCAGGATCAT | 257 | ATGATCCTGACGACGGAGCGCGCCGTCGTCGACAAGCC |
| Bxb1_attB_38_TG_site (Artificial Sequence) | 258 | GGCTTGTCGACGACGGCGTGCTCCGTCGTCAGGATCAT | 259 | ATGATCCTGACGACGGAGCACGCCGTCGTCGACAAGCC |
| Bxb1_attB_38_AC_site (Artificial Sequence) | 260 | GGCTTGTCGACGACGGCGACCTCCGTCGTCAGGATCAT | 261 | ATGATCCTGACGACGGAGGTCGCCGTCGTCGACAAGCC |
| Bxb1_attB_38_GC_site (Artificial Sequence) | 262 | GGCTTGTCGACGACGGCGGCCTCCGTCGTCAGGATCAT | 263 | ATGATCCTGACGACGGAGGCCGCCGTCGTCGACAAGCC |
| Bxb1_attB_38_CC_site (Artificial Sequence) | 264 | GGCTTGTCGACGACGGCGCCCTCCGTCGTCAGGATCAT | 265 | ATGATCCTGACGACGGAGGGCGCCGTCGTCGACAAGCC |
| Bxb1_attB_38_TC_site (Artificial Sequence) | 266 | GGCTTGTCGACGACGGCGTCCTCCGTCGTCAGGATCAT | 267 | ATGATCCTGACGACGGAGGACGCCGTCGTCGACAAGCC |
| Bxb1_attB_38_AT_site (Artificial Sequence) | 268 | GGCTTGTCGACGACGGCGATCTCCGTCGTCAGGATCAT | 269 | ATGATCCTGACGACGGAGATCGCCGTCGTCGACAAGCC |
| Bxb1_attB_38_CT_site (Artificial Sequence) | 270 | GGCTTGTCGACGACGGCGCTCTCCGTCGTCAGGATCAT | 271 | ATGATCCTGACGACGGAGAGCGCCGTCGTCGACAAGCC |
| Bxb1_attB_38_TT_site (Artificial Sequence) | 272 | GGCTTGTCGACGACGGCGTTCTCCGTCGTCAGGATCAT | 273 | ATGATCCTGACGACGGAGAACGCCGTCGTCGACAAGCC |
| Cre Lox 66 site (Artificial Sequence) | 274 | TACCGTTCGTATAATGTATGCTATACGAAGTTAT | 275 | ATAACTTCGTATAGCATACATTATACGAACGGTA |
| Cre Lox 71 site (Artificial Sequence) | 276 | ATAACTTCGTATAATGTATGCTATACGAACGGTA | 277 | TACCGTTCGTATAGCATACATTATACGAAGTTAT |
| TP901-1 minimal attB site (Artificial Sequence) | 278 | TTTACCTTGATTGAGATGTTAATTGTG | 279 | CACAATTAACATCTCAATCAAGGTAAA |
| TP901-1 minimal attP site (Artificial Sequence) | 280 | GCGAGTTTTTATTTCGTTTATTTCAATTAAGGTAACTAAAAAACTCCTTT | 281 | AAAGGAGTTTTTTAGTTACCTTAATTGAAATAAACGAAATAAAACTCGC |
| PhiBT1 minimal attB site (Artificial Sequence) | 282 | CTGGATCATCTGGATCACTTTCGTCAAAAACCTG | 283 | CAGGTTTTTGACGAAAGTGATCCAGATGATCCAG |

TABLE 4-continued

| | FORWARD SEQUENCE (5'-3') | | REVERSE SEQUENCE (5'-3') | |
|---|---|---|---|---|
| DESCRIPTION/ SOURCE | SEQ ID NO | Sequence | SEQ ID NO | Sequence |
| PhiBT1 minimal attP site (Artificial Sequence) | 284 | TTCGGGTGCTGGGTT GTTGTCTCTGGACAG TGATCCATGGGAAA CTACTCAGCACCA | 285 | TGGTGCTGAGTAGTT TCCCATGGATCACTG TCCAGAGACAACAA CCCAGCACCCGAA |

Sequences of Bxb1 and RT mutants can be found in Table 6 below.

TABLE 6

| SEQ ID NO/ DESCRIPTION/ SOURCE | FORWARD SEQUENCE (5'-3') |
|---|---|
| SEQ ID NO: 286 Bxb1_mut_V368A (Artificial Sequence) | AAAAGTGTGGGCTGCAGGATCTGA |
| SEQ ID NO: 287 Bxb1_mut_E379A (Artificial Sequence) | GGAGCTGGCAGCTGTCAATGCC |
| SEQ ID NO: 288 Bxb1_mut_E383A (Artificial Sequence) | AGTCAATGCCGCTCTCGTGGA |
| SEQ ID NO: 403 RT_mut_L139P (Artificial Sequence) | TTGAGCGGGCCCCCACCGT |
| SEQ ID NO: 289 RT_mut_E562Q (Artificial Sequence) | CAGCGGGCTCAGCTGATAGCA |
| SEQ ID NO: 290 RT_mut_D653N (Artificial Sequence) | CGGATGGCTAACCAAGCGGCC |
| SEQ ID NO: 404 RT(1-478)_Sto7d fusion | atgactcactatcaggccttgcttttggacacggaccgggtccagttcggaccggtggtagccctgaaccc ggctacgctgctcccactgcctgaggaagggctgcaacacaactgccttgatGGGACAGGTGG CGGTGGTGTCACCGTCAAGTTCAAGTACAAGGGTGAGGAACTT GAAGTTGATATTAGCAAAATCAAGAAGGTTTGGCGCGTTGGTA AAATGATATCTTTTACTTATGACGACAACGGCAAGACAGGTAG AGGGGCAGTGTCTGAGAAAGACGCCCCCAAGGAGCTGTTGCAA ATGTTGGAAAAGTCTGGGAAAAAGtctggcggctcaaaaagaaccgccgacgg cagcgaattcgagcccaagaagaagaggaaagtc |

Sequences of primers, probes and restriction enzymes used in ddPCR readout can be found in Table 7 below.

TABLE 7

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| ACTB | GFP (pDY0186) | 291 | CCCG GCTTC CTTTG TCC | 292 | GAAC TCCAC GCCG TTCA | /56- FAM/C C GGC TTG T/ZEN/ C GAC GAC GGC G/3IAB kFQ/ | 405 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| ACTB | TP90-1 GFP (pDY0333) | 293 | CCCGGCTTCCTTTGTCC | 294 | AACCACAACTAGAATGCAGTGA | /56-FAM/TG CTATTGC/ZEN/T TTATTTGTGGGCCCG/3IABkFQ/ | 406 | None |
| ACTB | TP90-1 rc GFP (pDY0334) | 295 | CCCGGCTTCCTTTGTCC | 296 | GAACTCCACGCCGTTCA | /56-FAM/CC ATGAAGA/ZEN/T CGAGTGCCGCATCA/3IABkFQ/ | 407 | None |
| ACTB | PhiBT1 GFP (pDY0367) | 297 | CCCGGCTTCCTTTGTCC | 298 | AACCACAACTAGAATGCAGTGA | /56-FAM/TG CTATTGC/ZEN/T TTATTTGTGGGCCCG/3IABkFQ/ | 406 | None |
| ACTB | PhiBT1 rc GFP (pDY0368) | 299 | CCCGGCTTCCTTTGTCC | 300 | GAACTCCACGCCGTTCA | /56-FAM/CC ATGAAGA/ZEN/T CGAGTGCCGCATCA/3IABkFQ/ | 407 | None |
| LMNB1 | GFP (pDY0186) | 301 | TCCTTATCACGGTCCCGCTCG | 302 | GAACTCCACGCCGTTCA | /56-FAM/CC ATGAAGA/ZEN/T CGAGTGCCGCATCA/3IABkFQ/ | 407 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| NOLC1 | GFP (pDY0186) | 303 | CGTCGACAACGGTAGTG | 304 | GAACTCCACGCCGTTCA | /56-FAM/CC ATG AAG A/ZEN/T CGA GTG CCG CAT CA/3IABkFQ/ | 407 | Eco91I, HindIII |
| SUPT16 H | GFP (pDY0186) | 305 | TCGCGTGATTCTCGGAAC | 306 | GAACTCCACGCCGTTCA | /56-FAM/C C ATG AAG A/ZEN/T CGA GTG CCG CAT CA/3IABkFQ/ | 407 | Eco91I, HindIII |
| SRRM2 | GFP (pDY0186) | 307 | GGGCGGTAAGTGGTTAGTTT | 308 | GAACTCCACGCCGTTCA | /56-FAM/CC ATG AAG A/ZEN/T CGA GTG CCG CAT CA/3IABkFQ/ | 407 | Eco91I, HindIII |
| DEPDC4 | GFP (pDY0186) | 309 | AAGAGGCGGAGCCAGTA | 310 | GAACTCCACGCCGTTCA | /56-FAM/CC ATG AAG A/ZEN/T CGA GTG CCG CAT CA/3IABkFQ/ | 407 | Eco91I, HindIII |
| NES | GFP (pDY0186) | 311 | CTCCCTTCTCCCGGTGCCC | 312 | GAACTCCACGCCGTTCA | /56-FAM/C GGC TTG T/ZEN/C GAC GAC GGC G/3IABkFQ/ | 405 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| ACTB | ACTB HITI template GFP (pDY0219) | 313 | CCGGGCTTCCTTTGTCC | 314 | GCCGTCCACGCCGTTCA | /56-FAM/CCATGAAGA/ZEN/TCGAGTGCCGCATCA/3IABkFQ/ | 407 | Eco91I |
| SRRM2 | SRRM2 HITI template GFP (aRY0182_A2) | 315 | GGGCGGTAAGTGGTTAGTTT | 316 | GAACTCCACGCCGTTCA | /56-FAM/CCATGAAGA/ZEN/TCGAGTGCCGCATCA/3IABkFQ/ | 407 | Eco91I |
| NOLC1 | NOLC1 HITI template GFP (aRY0182_A3) | 317 | CGTCGACAACGGTAGTG | 318 | GAACTCCACGCCGTTCA | /56-FAM/CCATGAAGA/ZEN/TCGAGTGCCGCATCA/3IABkFQ/ | 407 | Eco91I |
| DEPDC4 | DEPDC4 HITI template GFP (aRY0182_A5) | 319 | AAGAGGCGGAGCCAGTA | 320 | GAACTCCACGCCGTTCA | /56-FAM/CCATGAAGA/ZEN/TCGAGTGCCGCATCA/3IABkFQ/ | 407 | Eco91I |
| NES | NES HITI template GFP (aRY0182_A7) | 321 | CTCCCTTCTCCCGGTGCCC | 322 | GAACTCCACGCCGTTCA | /56-FAM/CCATGAAGA/ZEN/TCGAGTGCCGCATCA/3IABkFQ/ | 407 | Eco91I |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| LMNB1 | LMNB1 HITI template GFP (aRY0182_A4) | 323 | TCCTTATCACGGTCCCGCTCG | 324 | GAACTCCACGCCGTTCA | /56-FAM/CCATGAAGA/ZEN/TCGAGTGCCGCATCA/3IABkFQ/ | 407 | Eco91I |
| ACTB | SERPINA (pDY0298) | 325 | CCCGGCTTCCTTTGTCC | 326 | GGCCTGCCAGCAGGAGGA | /56-FAM/CCGGCTTGT/ZEN/CGACGACGGCG/3IABkFQ/ | 405 | EcoRI, XhoI, HindIII |
| ACTB | CPS1 (pDY299) | 327 | CCCGGCTTCCTTTGTCC | 328 | GGTGTGCAGTCACATTGGTAAAGCC | /56-FAM/ACAGCTTTC/ZEN/AAAGTGGTGAGGACACT/3IABkFQ/ | 408 | XhoI, HindIII |
| ACTB | CFTR (pDY0373) | 329 | CCCGGCTTCCTTTGTCC | 330 | GATGGGTCTAGTCCAGCTAAAG | /56-FAM/TACGGTACA/ZEN/AACCCACCCGAGAGA/3IABkFQ/ | 409 | Eco91I, HindIII |
| ACTB | NYESO TRAC (pDY0318) | 331 | CCCGGCTTCCTTTGTCC | 332 | GAGAGACAAGGCTGCACA | /56-FAM/TACGGTACA/ZEN/AACCCACCCGAGAGA/3IABkFQ/ | 409 | Eco47III, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| NC_0000 03 | GFP (pDY0186) | 333 | CCAGGTGAGAGTCAGGGTAGTGTTCA | 334 | GAACTCCACGCCGTTCA | /56-FAM/CCGGCTTGT/ZEN/CGACGACGGCG/3IABkFQ/ | 405 | Eco91I, HindIII |
| NC_0000 02 | GFP (pDY0186) | 335 | AGGGACCTTTGCCTGTGTGAGTC | 336 | GAACTCCACGCCGTTCA | /56-FAM/CCGGCTTGT/ZEN/CGACGACGGCG/3IABkFQ/ | 405 | Eco91I, HindIII |
| NC_0000 09 | GFP (pDY0186) | 337 | TCAGCTCTGTGCTGAGGCGAA | 338 | GAACTCCACGCCGTTCA | /56-FAM/CCGGCTTGT/ZEN/CGACGACGGCG/3IABkFQ/ | 405 | Eco91I, HindIII |
| chr6:149045959 | GFP (pDY0186) | 339 | AAGCCATCTCCCAGAATATCTGCTTAGAAATG | 340 | GAACTCCACGCCGTTCA | /56-FAM/CCGGCTTGT/ZEN/CGACGACGGCG/3IABkFQ/ | 405 | Eco91I, HindIII |
| chr16:18607730 | GFP (pDY0186) | 341 | GAGAGGAGCAACAGTGAGCATGATG | 342 | GAACTCCACGCCGTTCA | /56FAM/CCGGCTTGT/ZEN/CGACGACGGCG/3IABkFQ/ | 405 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| chr6:149045959 | ACTB HITI template GFP (pDY0219) | 343 | AAGCCATCTCCCAGAATATCTGCTTAGAAATG | 344 | GAACTCCACGCCGTTCA | /56 FAM/CCGGCTTGT/ZEN/CGACGACGGCG/3IABkFQ/ | 405 | Eco91I |
| chr16:18607730 | ACTB HITI template GFP (pDY0219) | 345 | GAGAGGAGCAACAGTGAGCATGATG | 346 | GAACTCCACGCCGTTCA | /56-FAM/CCGGCTTGT/ZEN/CGACGACGGCG/3IABkFQ/ | 405 | Eco91I |
| ACTB | CAG_Kozak_bGH_therapeutic_genes generic minicircle | 347 | CCCGGCTTCCTTTGTCC | 348 | GGCTATGAACTAATGACCCCGT | /56-FAM/CCGGCTTGT/ZEN/CGACGACGGCG/3IABkFQ/ | 405 | Eco91I, HindIII |
| ACTB | Hibit-SERPINA (pDY0405) | 349 | CCCGGCTTCCTTTGTCC | 350 | GGCCTGCCAGCAGGAGGA | /56-FAM/CCGGCTTGT/ZEN/CGACGACGGCG/3IABkFQ/ | 405 | EcoRI, XhoI, HindIII |
| ACTB | Hibit-CPS1 (pDY406) | 351 | CCCGGCTTCCTTTGTCC | 352 | GGTGTGCAGTCACATTGGTAAAGCC | /56-FAM/ACAGCTTTC/ZEN/AAAGTGGTGAGGACACT/3IABkFQ/ | 408 | XhoI, HindIII |

Sequences of primers used for NGS readout can be found in Table 8 below.

TABLE 8

| SEQ ID NO/ DESCRIPTION/ SOURCE | ID | SEQUENCE (5'-3') |
|---|---|---|
| SEQ ID NO: 353 N-term ACTB Tn5 readout F 1 (Artificial Sequence) | PD0966 | ACACTCTTTCCCTACACGACGCTCTTCCGATCTCCGAC CTCGGC TCACAGCG |
| SEQ ID NO: 354 N-term ACTB Tn5 readout F 2 (Artificial Sequence) | PD0967 | ACACTCTTTCCCTACACGACGCTCTTCCGATCTACCGA CCTCGG CTCACAGCG |
| SEQ ID NO: 355 N-term ACTB Tn5 readout F 3 (Artificial Sequence) | PD0968 | ACACTCTTTCCCTACACGACGCTCTTCCGATCTGACCG ACCTCG GCTCACAGCG |
| SEQ ID NO: 356 N-term ACTB Tn5 readout F 4 (Artificial Sequence) | PD0969 | ACACTCTTTCCCTACACGACGCTCTTCCGATCTTGACC GACCTC GGCTCACAGCG |
| SEQ ID NO: 357 N-term ACTB Tn5 readout F 5 (Artificial Sequence) | PD0970 | ACACTCTTTCCCTACACGACGCTCTTCCGATCTCTGAC CGACCT CGGCTCACAGCG |
| SEQ ID NO: 358 N-term ACTB Tn5 readout F 6 (Artificial Sequence) | PD0971 | ACACTCTTTCCCTACACGACGCTCTTCCGATCTACTGA CCGACC TCGGCTCACAGCG |
| SEQ ID NO: 359 N-term ACTB Tn5 readout F 7 (Artificial Sequence) | PD0972 | ACACTCTTTCCCTACACGACGCTCTTCCGATCTTACTG ACCGAC CTCGGCTCACAGCG |
| SEQ ID NO: 360 N-term ACTB Tn5 readout F 8 (Artificial Sequence) | PD0973 | ACACTCTTTCCCTACACGACGCTCTTCCGATCTGTACT GACCGA CCTCGGCTCACAGCG |
| SEQ ID NO: 361 ACTB N-term NGS R for Cas14 indels (Artificial Sequence) | FP0952 | GTGACTGGAGTTCAGACGTGTGCTCTTCCGATCTCCAC CCAGCC AGCTCCC |
| SEQ ID NO: 362 NGS EMX1 Forward 1 (Artificial Sequence) | PD0313 | ACACTCTTTCCCTACACGACGCTCTTCCGATCTCCGGT GGCGCAT TGCCAC |
| SEQ ID NO: 363 NGS EMX1 Forward 2 (Artificial Sequence) | PD0314 | ACACTCTTTCCCTACACGACGCTCTTCCGATCTACCGG TGGCGCA TTGCCAC |
| SEQ ID NO: 364 NGS EMX1 Forward 3 (Artificial Sequence) | PD0315 | ACACTCTTTCCCTACACGACGCTCTTCCGATCTGACCG GTGGCGC ATTGCCAC |
| SEQ ID NO: 365 NGS EMX1 Forward 4 (Artificial Sequence) | PD0316 | ACACTCTTTCCCTACACGACGCTCTTCCGATCTTGACC GGTGGCG CATTGCCAC |
| SEQ ID NO: 366 NGS EMX1 Forward 5 (Artificial Sequence) | PD0317 | ACACTCTTTCCCTACACGACGCTCTTCCGATCTCTGAC CGGTGGC GCATTGCCAC |

TABLE 8-continued

| SEQ ID NO/ DESCRIPTION/ SOURCE | ID | SEQUENCE (5'-3') |
|---|---|---|
| SEQ ID NO: 367 NGS EMX1 Forward 6 (Artificial Sequence) | PD0318 | ACACTCTTTCCCTACACGACGCTCTTCCGATCTACTGA CCGGTGG CGCATTGCCAC |
| SEQ ID NO: 368 NGS EMX1 Forward 7 (Artificial Sequence) | PD0319 | ACACTCTTTCCCTACACGACGCTCTTCCGATCTTACTG ACCGGTG GCGCATTGCCAC |
| SEQ ID NO: 369 NGS EMX1 Forward 8 (Artificial Sequence) | PD0320 | ACACTCTTTCCCTACACGACGCTCTTCCGATCTGTACT GACCGGT GGCGCATTGCCAC |
| SEQ ID NO: 370 NGS EMX1 Reverse (Artificial Sequence) | PD0321 | GTGACTGGAGTTCAGACGTGTGCTCTTCCGATCTCAGA GTCCAGC TTGGGCCCA |

Sequences of off-target sites can be found in Table 9 below.

TABLE 9

| SEQ ID NO/ DESCRIPTION/ SOURCE | SEQUENCE (5'-3') |
|---|---|
| SEQ ID NO: 371 Cas9_chr6:149045959 (Artificial Sequence) | GATATTTTCCCAGCTCACCA |
| SEQ ID NO: 372 Cas9_chr16:18607730 (Artificial Sequence) | TCTATTCTCCCAGCTCCCCA |
| SEQ ID NO: 373 Bxb1_NC_000002 (Artificial Sequence) | AGCGGCTTCTGTCTCTGTGAGTGAGCTGGCGGTCTCCGTC |
| SEQ ID NO: 374 Bxb1_NC_000003 (Artificial Sequence) | GACTAGCCCACGCTCCGGTTCTGAGCCGCGACGGCGGTCTCCG |
| SEQ ID NO: 375 Bxb1_NC_000009 (Artificial Sequence) | CCCAGGGTCCCATGCGCTCCCCGGCCCTGACGGCGGTCTCC |

Linker sequences in Table 10 below.

TABLE 10

| Description | Sequence (5'-3') | Amino acid sequence |
|---|---|---|
| A - P2A | GGAAGCGGAGCTACTAACTTCAGCCT GCTGAAGCAGGCTGGCGACGTGGAGG AGAACCCTGGACCT (SEQ ID NO: 410) | GSGATNFSLLKQAGDVEENPGP (SEQ ID NO: 418) |
| B - (GGGS)3 | GGGGGAGGAGGTTCTGGAGGCGGAGG CTCCGGAGGCGGAGGGTCA (SEQ ID NO: 411) | GGGGSGGGSGGGGS (SEQ ID NO: 419) |
| C - GGGGS | GGAGGTGGCGGGAGC (SEQ ID NO: 412) | GGGGS (SEQ ID NO: 420) |

TABLE 10-continued

| Description | Sequence (5'-3') | Amino acid sequence |
| --- | --- | --- |
| D - PAPAP | CCCGCACCAGCGCCT (SEQ ID NO: 413) | PAPAP (SEQ ID NO: 421) |
| E - (EAAAK)3 | GAGGCAGCTGCCAAGGAAGCCGCT GCCAAGGAGGCGGCCGCAAAG (SEQ ID NO: 414) | EAAAKEAAAKEAAAK (SEQ ID NO: 422) |
| F - XTEN | AGTGGGAGCGAGACCCCTGGGACT AGCGAGTCAGCTACACCCGAAAGC (SEQ ID NO: 415) | SGSETPGTSESATPES (SEQ ID NO: 423) |
| G - (GGS)6 | GGGGGGTCAGGTGGATCCGGCGG AAGTGGCGGATCCGGTGGATCGG CGGCAGT (SEQ ID NO: 416) | GGSGGSGGSGGSGGSGGS (SEQ ID NO 424) |
| H - EAAAK | GAAGCTGCTGCTAAG (SEQ ID NO: 417) | EAAAK (SEQ ID NO: 425) |

Exemplary fusion sequences in Table 11 below.

| Description | Sequence |
| --- | --- |
| SpCas9-XTEN-RT(1-478)-Sto7d-GGGGS-BxbINT Amino acid SEQ ID NO: 376 | MKRTADGSEFESPKKKRKVDKKYSIGLDIGTNSVGWAVITDEYKVPS KKFKVLGNTDRHSIKKNLIGALLFDSGETAEATRLKRTARRRYTRR KNRICYLQEIFSNEMAKVDDSFFHRLEESFLVEEDKKHERHPIFGNI VDEVAYHEKYPTIYHLRKKLVDSTDKADLRLIYLALAHMIKFRGHF LIEGDLNPDNSDVDKLFIQLVQTYNQLFEENPINASGVDAKAILSAR LSKSRRLENLIAQLPGEKKNGLFGNLIALSLGLTPNFKSNFDLAEDA KLQLSKDTYDDDLDNLLAQIGDQYADLFLAAKNLSDAILLSDILRVN TEITKAPLSASMIKRYDEHHQDLTLLKALVRQQLPEKYKEIFFDQS KNGYAGYIDGGASQEEFYKFIKPILEKMDGTEELLVKLNREDLLRK QRTFDNGSIPHQIHLGELHAILRRQEDFYPFLKDNREKIEKILTFRIP YYVGPLARGNSRFAWMTRKSEETITPWNFEEVVDKGASAQSFIER MTNFDKNLPNEKVLPKHSLLYEYFTVYNELTKVKYVTEGMRKPAF LSGEQKKAIVDLLFKTNRKVTVKQLKEDYFKKIECFDSVEISGVED RFNASLGTYHDLLKIIKDKDFLDNEENEDILEDIVLTLTLFEDREMIE ERLKTYAHLFDDKVMKQLKRRRYTGWGRLSRKLINGIRDKQSGK TILDFLKSDGFANRNFMQLIHDDSLTFKEDIQKAQVSGQGDSLHEHI ANLAGSPAIKKGILQTVKVVDELVKVMGRHKPENIVIEMARENQTT QKGQKNSRERMKRIEEGIKELGSQILKEHPVENTQLQNEKLYLYYL QNGRDMYVDQELDINRLSDYDVDAIVPQSFLKDDSIDNKVLTRSDK NRGKSDNVPSEEVVKKMKNYWRQLLNAKLITQRKFDNLTKAERG GLSELDKAGFIKRQLVETRQITKHVAQILDSRMNTKYDENDKLIRE VKVITLKSKLVSDFRKDFQFYKVREINNYHHAHDAYLNAVVGTALI KKYPKLESEFVYGDYKVYDVRKMIAKSEQEIGKATAKYFFYSNIMN FFKTEITLANGEIRKRPLIETNGETGEIVWDKGRDFATVRKVLSMP QVNIVKKTEVQTGGFSKESILPKRNSDKLIARKKDWDPKKYGGFDS PTVAYSVLVVAKVEKGKSKKLKSVKELLGITIMERSSFEKNPIDFLE AKGYKEVKKDLIIKLPKYSLFELENGRKRMLASAGELQKGNELAL PSKYVNFLYLASHYEKLKGSPEDNEQKQLFVEQHKHYLDEIIEQISE FSKRVILADANLDKVLSAYNKHRDKPIREQAENIIHLFTLTNLGAPA AFKYFDTTIDRKRYTSTKEVLDATLIHQSITGLYETRIDLSQLGGDS GGSSGGSSGSETPGTSESATPESSGSETPGTSESATPESSGSETPGTSESAT PESSGGSSGGSSTLNIEDEYRLHETSKEPDVSLGSTWLSDFPQAWAET GGMGLAVRQAPLIIPLKATSTPVSIKQYPMSQEARLGIKPHIQRLLD QGILVPCQSPWNTPLLPVKKPGTNDYRPVQDLREVNKRVEDIHPTV PNPYNLLSGPPPSHQWYTVLDLKDAFFCLRLHPTSQPLFAFEWRDP EMGISGQLTWTRLPQGFKNSPTLFNEALHRDLADFRIQHPDLILLQ YVDDLLLAATSELDCQQGTRALLQTLGNLGYRASAKKAQICQKQV KYLGYLLKEGQRWLTEARKETVMGQPTPKTPRQLREFLGKAGFC RLFIPGFAEMAAPLYPLTKPGTLFNWGPDQQKAYQEIKQALLTAPA LGLPDLTKPFELFVDEKQGYAKGVLTQKLGPWRRPVAYLSKKLDP VAAGWPPCLRMVAAIAVLTKDAGKLTMGQPLVILAPHAVEALVK QPPDRWLSNARMTHYQALLLDTDRVQFGPVVALNPATLLPLPEEG LQHNCLDGTGGGVTVKFKYKGEELEVDISKIKKVWRVGKMISFT YDDNGKTGRGAVSEKDAPKELLQMLEKSGKKSGGSKRTADGSEFE PKKKRKVGGGGSPKKKRKVYPYDVPDYAGSRALVVIRLSRVTDATTS PERQLESCQQLCAQRGWDVVGVAEDLDVSGAVDPFDRKRRPNLAR WLAFEEQPFDVIVAYRVDRLTRSIRHLQQLVHWAEDHKKLVVSAT EAHFDTTTPFAAVVIALMGTVAQMELEAIKERNRSAAHFNIRAGKY RGSLPPWGYLPTRVDGEWRLVPDPVQRERILEVYHRVVDNHEPLH LVAHDLNRRGVLSPKDYFAQLQGREPQGREWSATALKRSMISEAM LGYATLNGKTVRDDDGAPLVRAEPILTREQLEALRAELVKTSRAKP AVSTPSLLLRVLFCAVCGEPAYKFAGGGRKHPYRCRSMGFPKHC |

| Description | Sequence |
|---|---|
| | GNGTVAMAEWDAFCEEQVLDLLGDAERLEKVWVAGSDSAVELAE VNAELVDLTSLIGSPAYRAGSPQREALDARIAALAARQEELEGLEAR PSGWEWRETGQRFGDWWREQDTAAKNTWLRSMNVRLTFDVRGG LTRTIDFGDLQEYEQHLRLGSVVERLHTGMS |
| SpCas9-XTEN-RT(1-478)-Sto7d-GGGGS-BxbINT Nucleic acid SEQ ID NO: 377 | ATGAAACGGACAGCCGACGGAAGCGAGTTCGAGTCACCAAAGAAG AAGCGGAAAGTCGACAAGAAGTACAGCATCGGCCTGGACATCGGCA CCAACTCTGTGGGCTGGGCCGTGATCACCGACGAGTACAAGGTGCC CAGCAAGAAATTCAAGGTGCTGGGCAACACCGACCGGCACAGCATC AAGAAGAACCTGATCGGAGCCCTGCTGTTCGACAGCGGCGAAACAG CCGAGGCCACCCGGCTGAAGAGAACCGCCAGAAGAAGATACACCA GACGGAAGAACCGGATCTGCTATCTGCAAGAGATCTTCAGCAACGA GATGGCCAAGGTGGACGACAGCTTCTTCCACAGACTGGAAGAGTCC TTCCTGGTGGAAGAGGATAAGAAGCACGAGCGGCACCCCATCTTCG GCAACATCGTGGACGAGGTGGCCTACCACGAGAAGTACCCCACCAT CTACCACCTGAGAAAGAAACTGGTGGACAGCACCGACAAGGCCGAC CTGCGGCTGATCTATCTGGCCCTGGCCCACATGATCAAGTTCCGGGG CCACTTCCTGATCGAGGGCGACCTGAACCCCGACAACAGCGACGTG GACAAGCTGTTCATCCAGCTGGTGCAGACCTACAACCAGCTGTTCGA GGAAAACCCCATCAACGCCAGCGGCGTGGACGCCAAGGCCATCCTG TCTGCCAGACTGAGCAAGAGCAGACGGCTGGAAAATCTGATCGCCC AGCTGCCCGGCGAGAAGAAGAATGGCCTGTTCGGAAACCTGATTGC CCTGAGCCTGGGCCTGACCCCCAACTTCAAGAGCAACTTCGACCTGG CCGAGGATGCCAAACTGCAGCTGAGCAAGGACACCTACGACGACGA CCTGGACAACCTGCTGGCCCAGATCGGCGACCAGTACGCCGACCTG TTTCTGGCCGCCAAGAACCTGTCCGACGCCATCCTGCTGAGCGACAT CCTGAGAGTGAACACCGAGATCACCAAGGCCCCCCTGAGCGCCTCT ATGATCAAGAGATACGACGAGCACCACCAGGACCTGACCCTGCTGA AAGCTCTCGTGCGGCAGCAGCTGCCTGAGAAGTACAAAGAGATTTT CTTCGACCAGAGCAAGAACGGCTACGCCGGCTACATTGACGGCGGA GCCAGCCAGGAAGAGTTCTACAAGTTCATCAAGCCCATCCTGGAAA AGATGGACGGCACCGAGGAACTGCTCGTGAAGCTGAACAGAGAGG ACCTGCTGCGGAAGCAGCGGACCTTCGACAACGGCAGCATCCCCCA CCAGATCCACCTGGGAGAGCTGCACGCCATTCTGCGGCGGCAGGAA GATTTTTACCCATTCCTGAAGGACAACCGGGAAAAGATCGAGAAGA TCCTGACCTTCCGCATCCCCTACTACGTGGGCCCTCTGGCCAGGGGA AACAGCAGATTCGCCTGGATGACCAGAAAGAGCGAGGAAACCATCA CCCCCTGGAACTTCGAGGAAGTGGTGGACAAGGGCGCTTCCGCCCA GAGCTTCATCGAGCGGATGACCAACTTCGATAAGAACCTGCCCAAC GAGAAGGTGCTGCCCAAGCACAGCCTGCTGTACGAGTACTTCACCG TGTATAACGAGCTGACCAAAGTGAAATACGTGACCGAGGGAATGAG AAAGCCCGCCTTCCTGAGCGGCGAGCAGAAAAAGGCCATCGTGGAC CTGCTGTTCAAGACCAACCGGAAAGTGACCGTGAAGCAGCTGAAAG AGGACTACTTCAAGAAAATCGAGTGCTTCGACTCCGTGGAAATCTCC GGCGTGGAAGATCGGTTCAACGCCTCCCTGGGCACATACCACGATC TGCTGAAAATTATCAAGGACAAGGACTTCCTGGACAATGAGGAAAA CGAGGACATTCTGGAAGATATCGTGCTGACCCTGACACTGTTTGAGG ACAGAGAGATGATCGAGGAACGGCTGAAAACCTATGCCCACCTGTT CGACGACAAAGTGATGAAGCAGCTGAAGCGGCGGAGATACACCGG CTGGGGCAGGCTGAGCCGGAAGCTGATCAACGGCATCCGGGACAAG CAGTCCGGCAAGACAATCCTGGATTTCCTGAAGTCCGACGGCTTCGC CAACAGAAACTTCATGCAGCTGATCCACGACGACAGCCTGACCTTT AAAGAGGACATCCAGAAAGCCCAGGTGTCCGGCCAGGGCGATAGCC TGCACGAGCACATTGCCAATCTGGCCGGCAGCCCCGCCATTAAGAA GGGCATCCTGCAGACAGTGAAGGTGGTGGACGAGCTCGTGAAAGTG ATGGGCCGGCACAAGCCCGAGAACATCGTGATCGAAATGGCCAGAG AGAACCAGACCACCCAGAAGGGACAGAAGAACAGCCGCGAGAGAA TGAAGCGGATCGAAGAGGGCATCAAGGAGCTGGGCAGCCAGATCCT GAAAGAACACCCCGTGGAAAACACCCAGCTGCAGAACGAGAAGCT GTACCTGTACTACCTGCAGAATGGGCGGGATATGTACGTGGACCAG GAACTGGACATCAACCGGCTGTCCGACTACGATGTGGACGCTATCG TGCCTCAGAGCTTTCTGAAGGACGACTCCATCGACAACAAGGTGCT GACCAGAAGCGACAAGAACCGGGGCAAGAGCGACAACGTGCCCTC CGAAGAGGTCGTGAAGAAGATGAAGAACTACTGGCGGCAGCTGCTG AACGCCAAGCTGATTACCCAGAGAAAGTTCGACAATCTGACCAAGG CCGAGAGAGGCGGCCTGAGCGAACTGGATAAGGCCGGCTTCATCAA GAGACAGCTGGTGGAAACCCGGCAGATCACAAAGCACGTGGCACA GATCCTGGACTCCCGGATGAACACTAAGTACGACGAGAATGACAAG CTGATCCGGGAAGTGAAAGTGATTACCCTGAAGTCCAAGCTGGTGT CCGATTTCCGGAAGGATTTCCAGTTTTACAAAGTGCGCGAGATCAAC AACTACCACCACGCCCACGACGCCTACCTGAACGCCGTCGTGGGAA CCGCCCTGATCAAAAAGTACCCTAAGCTGGAAAGCGAGTTCGTGTA CGGCGACTACAAGGTGTACGACGTGCGGAAGATGATCGCCAAGAGC GAGCAGGAAATCGGCAAGGCTACCGCCAAGTACTTCTTCTACAGCA ACATCATGAACTTTTTCAAGACCGAGATTACCCTGGCCAACGGCGA GATCCGGAAGCGGCCTCTGATCGAGACAAACGGCGAAACCGGGGA GATCGTGTGGGATAAGGGCCGGGATTTTGCCACCGTGCGGAAAGTG |

| Description | Sequence |
|---|---|
| | CTGAGCATGCCCCAAGTGAATATCGTGAAAAAGACCGAGGTGCAGA |
| | CAGGCGGCTTCAGCAAAGAGTCTATCCTGCCCAAGAGGAACAGCGA |
| | TAAGCTGATCGCCAGAAAGAAGGACTGGGACCCTAAGAAGTACGGC |
| | GGCTTCGACAGCCCCACCGTGGCCTATTCTGTGCTGGTGGTGGCCAA |
| | AGTGGAAAAGGGCAAGTCCAAGAAACTGAAGAGTGTGAAAGAGCT |
| | GCTGGGGATCACCATCATGGAAAGAAGCAGCTTCGAGAAGAATCCC |
| | ATCGACTTTCTGGAAGCCAAGGGCTACAAAGAAGTGAAAAAGGACC |
| | TGATCATCAAGCTGCCTAAGTACTCCCTGTTCGAGCTGGAAAACGGC |
| | CGGAAGAGAATGCTGGCCTCTGCCGGCGAACTGCAGAAGGGAAACG |
| | AACTGGCCCTGCCCTCCAAATATGTGAACTTCCTGTACCTGGCCAGC |
| | CACTATGAGAAGCTGAAGGGCTCCCCCGAGGATAATGAGCAGAAAC |
| | AGCTGTTTGTGGAACAGCACAAGCACTACCTGGACGAGATCATCGA |
| | GCAGATCAGCGAGTTCTCCAAGAGAGTGATCCTGGCCGACGCTAAT |
| | CTGGACAAAGTGCTGTCCGCCTACAACAAGCACCGGGATAAGCCCA |
| | TCAGAGAGCAGGCCGAGAATATCATCCACCTGTTTACCCTGACCAAT |
| | CTGGGAGCCCCTGCCGCCTTCAAGTACTTTGACACCACCATCGACCG |
| | GAAGAGGTACACCAGCACCAAAGAGGTGCTGGACGCCACCCTGATC |
| | CACCAGAGCATCACCGGCCTGTACGAGACACGGATCGACCTGTCTC |
| | AGCTGGGAGGTGACTCTGGAGGATCTAGCGGAGGATCCTCTGGCAG |
| | CGAGACACCAGGAACAAGCGAGTCAGCAACACCAGAGAGCTCTGGT |
| | AGCGAGACACCCGGTACCAGTGAAAGCGCCACGCCAGAAAGCAGT |
| | GGGAGTGAGACTCCGGGTACATCTGAATCAGCGACACCGGAATCAA |
| | GTGGCGGCAGCAGCGGCGGCAGCAGCACCCTAAATATAGAAGATGA |
| | GTATCGGCTACATGAGACCTCAAAAGAGCCAGATGTTTCTCTAGGGT |
| | CCACATGGCTGTCTGATTTTCCTCAGGCCTGGGCGGAAACCGGGGGC |
| | ATGGGACTGGCAGTTCGCCAAGCTCCTCTGATCATACCTCTGAAAGC |
| | AACCTCTACCCCCGTGTCCATAAAACAATACCCCATGTCACAAGAA |
| | GCCAGACTGGGGATCAAGCCCCACATACAGAGACTGTTGGACCAGG |
| | GAATACTGGTACCCTGCCAGTCCCCCTGGAACACGCCCCTGCTACCC |
| | GTTAAGAAACCAGGGACTAATGATTATAGGCCTGTCCAGGATCTGA |
| | GAGAAGTCAACAAGCGGGTGGAAGACATCCACCCCACCGTGCCCAA |
| | CCCTTACAACCTCTTGAGCGGGCCCCCACCGTCCCACCAGTGGTACA |
| | CTGTGCTTGATTTAAAGGATGCCTTTTTCTGCCTGAGACTCCACCCC |
| | ACCAGTCAGCCTCTCTTCGCCTTTGAGTGGAGAGATCCAGAGATGGG |
| | AATCTCAGGACAATTGACCTGGACCAGACTCCCACAGGGTTTCAAA |
| | AACAGTCCCACCCTGTTTAATGAGGCACTGCACAGAGACCTAGCAG |
| | ACTTCCGGATCCAGCACCCAGACTTGATCCTGCTACAGTACGTGGAT |
| | GACTTACTGCTGGCCGCCACTTCTGAGCTAGACTGCCAACAAGGTAC |
| | TCGGGCCCTGTTACAAACCCTAGGGAACCTCGGGTATCGGGCCTCG |
| | GCCAAGAAAGCCCAAATTTGCCAGAAACAGGTCAAGTATCTGGGGT |
| | ATCTTCTAAAAGAGGGTCAGAGATGGCTGACTGAGGCCAGAAAAGA |
| | GACTGTGATGGGGCAGCCTACTCCGAAGACCCCTCGACAACTAAGG |
| | GAGTTCCTAGGGAAGGCAGGCTTCTGTCGCCTCTTCATCCCTGGGTT |
| | TGCAGAAATGGCAGCCCCCCTGTACCCTCTCACCAAACCGGGGACT |
| | CTGTTTAATTGGGGCCCAGACCAACAAAAGGCCTATCAAGAAATCA |
| | AGCAAGCTCTTCTAACTGCCCCAGCCCTGGGGTTGCCAGATTTGACT |
| | AAGCCCTTTGAACTCTTTGTCGACGAGAAGCAGGGCTACGCCAAAG |
| | GTGTCCTAACGCAAAAACTGGGACCTTGGCGTCGGCCGGTGGCCTA |
| | CCTGTCCAAAAAGCTAGACCCAGTAGCAGCTGGGTGGCCCCCTTGC |
| | CTACGGATGGTAGCAGCCATTGCCGTACTGACAAAGGATGCAGGCA |
| | AGCTAACCATGGGACAGCCACTAGTCATTCTGGCCCCCCATGCAGTA |
| | GAGGCACTAGTCAAACAACCCCCCGACCGCTGGCTTTCCAACGCCC |
| | GGATGACTCACTATCAGGCCTTGCTTTTGGACACGGACCGGGTCCAG |
| | TTCGGACCGGTGGTAGCCCTGAACCCGGCTACGCTGCTCCCACTGCC |
| | TGAGGAAGGGCTGCAACACAACTGCCTTGATGGGACAGGTGGCGGT |
| | GGTGTCACCGTCAAGTTCAAGTACAAGGGTGAGGAACTTGAAGTTG |
| | ATATTAGCAAAATCAAGAAGGTTTGGCGCGTTGGTAAAATGATATC |
| | TTTTACTTATGACGACAACGGCAAGACAGGTAGAGGGGCAGTGTCT |
| | GAGAAAGACGCCCCCAAGGAGCTGTTGCAAATGTTGGAAAAGTCTG |
| | GGAAAAAGTCTGGCGGCTCAAAAAGAACCGCCGACGGCAGCGAATT |
| | CGAGCCCAAGAAGAAGAGGAAAGTCGGAGGTGGCGGGAGCCCAAA |
| | AAAGAAAAGAAAAGTGTATCCCTATGATGTCCCCGATTATGCCGGT |
| | TCAAGAGCCCTGGTCGTGATTAGACTGAGCCGAGTGACAGACGCCA |
| | CCACAAGTCCCGAGAGACAGCTGGAATCATGCCAGCAGCTCTGTGC |
| | TCAGCGGGGTTGGGATGTGGTCGGCGTGGCAGAGGATCTGGACGTG |
| | AGCGGGCCGTCGATCCATTCGACAGAAAGAGGAGGCCCAACCTGG |
| | CAAGATGGCTCGCTTTCGAGGAACAGCCCTTTGATGTGATCGTCGCC |
| | TACAGAGTGGACCGGCTGACCCGCTCAATTCGACATCTCCAGCAGCT |
| | GGTGCATTGGGCTGAGGACCACAAGAAACTGGTGGTCAGCGCAACA |
| | GAAGCCCACTTCGATACTACCACACCTTTTGCCGCTGTGGTCATCGC |
| | ACTGATGGGCACTGTGGCCCAGATGGAGCTCGAAGCTATCAAGGAG |
| | CGAAACAGGAGCGCAGCCCATTTCAATATTAGGGCCGGTAAATACA |
| | GAGGCTCCCTGCCCCCTTGGGGATATCTCCCTACCAGGGTGGATGG |
| | GAGTGGAGACTGGTGCCAGACCCCGTCCAGAGAGAGCGGATTCTGG |
| | AAGTGTACCACAGAGTGGTCGATAACCACGAACCACTCCATCTGGT |
| | GGCACACGACCTGAATAGACGCGGCGTGCTCTCTCCAAAGGATTAT |
| | TTTGCTCAGCTGCAGGGAAGAGAGCCACAGGGAAGAGAATGGAGTG |

| Description | Sequence |
|---|---|
| | CTACTGCACTGAAGAGATCTATGATCAGTGAGGCTATGCTGGGTTAC<br>GCAACACTCAATGGCAAAACTGTCCGGGACGATGACGGAGCCCCTC<br>TGGGTGAGGGCTGAGCCTATTCTCACCAGAGAGCAGCTCGAAGCTCT<br>GCGGGCAGAACTGGTCAAGACTAGTCGCGCCAAACCTGCCGTGAGC<br>ACCCCAAGCCTGCTCCTGAGGGTGCTGTTCTGCGCCGTCTGTGGAGA<br>GCCAGCATACAAGTTTGCCGGCGGAGGGCGCAAACATCCCCGCTAT<br>CGATGCAGGAGCATGGGGTTCCCTAAGCACTGTGGAAACGGGACAG<br>TGGCCATGGCTGAGTGGGACGCCTTTTGCGAGGAACAGGTGCTGGA<br>TCTCCTGGGTGACGCTGAGCGGCTGGAAAAAGTGTGGGTGGCAGGA<br>TCTGACTCCGCTGTGGAGCTGGCAGAAGTCAATGCCGAGCTCGTGG<br>ATCTGACTTCCCTCATCGGATCTCCTGCATATAGAGCTGGGTCCCCA<br>CAGAGAGAAGCTCTGGACGCACGAATTGCTGCACTCGCTGCTAGAC<br>AGGAGGAACTGGAGGGCCTGGAGGCCAGGCCCTCTGGATGGGAGTG<br>GCGAGAAACCGGACAGAGGTTTGGGGATTGGTGGAGGGAGCAGGA<br>CACCGCAGCCAAGAACACATGGCTGAGATCATGAATGTCCGGCTC<br>ACATTCGACGTGCGCGGTGGCCTGACTCGAACCATCGATTTTGGCGA<br>CCTGCAGGAGTATGAACAGCACCTGAGACTGGGGTCCGTGGTCGAA<br>AGACTGCACACTGGGATGTCC |
| SpCas9<br>Amino acid<br>SEQ ID NO: 378 | DKKYSIGLDIGTNSVGWAVITDEYKVPSKKFKVLGNTDRHSIKKNLIGA<br>LLFDSGETAEATRLKRTARRRYTRRKNRICYLQEIFSNEMAKVDDSFFH<br>RLEESFLVEEDKKHERHPIFGNIVDEVAYHEKYPTIYHLRKKLVDSTDK<br>ADLRLIYLALAHMIKFRGHFLIEGDLNPDNSDVDKLFIQLVQTYNQLFE<br>ENPINASGVDAKAILSARLSKSRRLENLIAQLPGEKKNGLFGNLIALSLG<br>LTPNFKSNFDLAEDAKLQLSKDTYDDDLDNLLAQIGDQYADLFLAAKN<br>LSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLN<br>REDLLRKQRTFDNGSIPHQIHLGELHAILRRQEDFYPFLKDNREKIEKILT<br>FRIPYYVGPLARGNSRFAWMTRKSEETITPWNFEEVVDKGASAQSFIER<br>MTNFDKNLPNEKVLPKHSLLYEYFTVYNELTKVKYVTEGMRKPAFLSG<br>EQKKAIVDLLFKTNRKVTVKQLKEDYFKKIECFDSVEISGVEDRFNASL<br>GTYHDLLKIIKDKDFLDNEENEDILEDIVLTLTLFEDREMIEERLKTYAH<br>LFDDKVMKQLKRRRYTGWGRLSRKLINGIRDKQSGKTILDFLKSDGFA<br>NRNFMQLIHDDSLTFKEDIQKAQVSGQGDSLHEHIANLAGSPAIKKGIL<br>QTVKVVDELVKVMGRHKPENIVIEMARENQTTQKGQKNSRERMKRIE<br>EGIKELGSQILKEHPVENTQLQNEKLYLYYLQNGRDMYVDQELDINRL<br>SDYDVDAIVPQSFLKDDSIDNKVLTRSDKNRGKSDNVPSEEVVKKMKN<br>YWRQLLNAKLITQRKFDNLTKAERGGLSELDKAGFIKRQLVETRQITK<br>HVAQILDSRMNTKYDENDKLIREVKVITLKSKLVSDFRKDFQFYKVREI<br>NNYHHAHDAYLNAVVGTALIKKYPKLESEFVYGDYKVYDVRKMIAKS<br>EQEIGKATAKYFFYSNIMNFFKTEITLANGEIRKRPLIETNGETGEIVWD<br>KGRDFATVRKVLSMPQVNIVKKTEVQTGGFSKESILPKRNSDKLIARKK<br>DWDPKKYGGFDSPTVAYSVLVVAKVEKGKSKKLKSVKELLGITIMERS<br>SFEKNPIDFLEAKGYKEVKKDLIIKLPKYSLFELENGRKRMLASAGELQ<br>KGNELALPSKYVNFLYLASHYEKLKGSPEDNEQKQLFVEQHKHYLDEII<br>EQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGD |
| RT(1-478)-Sto7d<br>Amino acid<br>SEQ ID NO: 379 | LNIEDEYRLHETSKEPDVSLGSTWLSDFPQAWAETGGMGLAVRQAPLII<br>PLKATSTPVSIKQYPMSQEARLGIKPHIQRLLDQGILVPCQSPWNTPLLP<br>VKKPGTNDYRPVQDLREVNKRVEDIHPTVPNPYNLLSGPPPSHQWYTV<br>LDLKDAFFCLRLHPTSQPLFAFEWRDPEMGISGQLTWTRLPQGFKNSPT<br>LFNEALHRDLADFRIQHPDLILLQYVDDLLLAATSELDCQQGTRALLQT<br>LGNLGYRASAKKAQICQKQVKYLGYLLKEGQRWLTEARKETVMGQPT<br>PKTPRQLREFLGKAGFCRLFIPGFAEMAAPLYPLTKPGTLFNWGPDQQK<br>AYQEIKQALLTAPALGLPDLTKPFELFVDEKQGYAKGVLTQKLGPWRR<br>PVAYLSKKLDPVAAGWPPCLRMVAAIAVLTKDAGKLTMGQPLVILAP<br>HAVEALVKQPPDRWLSNARMTHYQALLLDTDRVQFGPVVALNPATLL<br>PLPEEGLQHNCLDGTGGGVTVKFKYKGEELEVDISKIKKVWRVGKMI<br>SFTYDDNGKTGRGAVSEKDAPKELLQMLEKSGKKSGGSKRTADGS |
| BxbINT<br>Amino acid<br>SEQ ID NO: 380 | SRALVVIRLSRVTDATTSPERQLESCQQLCAQRGWDVVGVAEDLDVSG<br>AVDPFDRKRRPNLARWLAFEEQPFDVIVAYRVDRLTRSIRHLQQLVHW<br>AEDHKKLVVSATEAHFDTTTPFAAVVIALMGTVAQMELEAIKERNRSA<br>AHFNIRAGKYRGSLPPWGYLPTRVDGEWRLVPDPVQRERILEVYHRVV<br>DNHEPLHLVAHDLNRRGVLSPKDYFAQLQGREPQGREWSATALKRSM<br>ISEAMLGYATLNGKTVRDDDGAPLVRAEPILTREQLEALRAELVKTSRA<br>KPAVSTPSLLLRVLFCAVCGEPAYKFAGGGRKHPYRCRSMGFPKHCG<br>NGTVAMAEWDAFCEEQVLDLLGDAERLEKVWWAGSDSAVELAEVNA<br>ELVDLTSLIGSPAYRAGSPQREALDARIAALAARQEELEGLEARPSGWE<br>WRETGQRFGDWWREQDTAAKNTWLRSMNVRLTFDVRGGLTRTIDFG<br>DLQEYEQHLRLGSVVERLHTGMS |

EXAMPLES

While several experimental Examples are contemplated, these Examples are intended to be non-limiting.

Example 1

CRE Integration Efficiency

Figure 3:
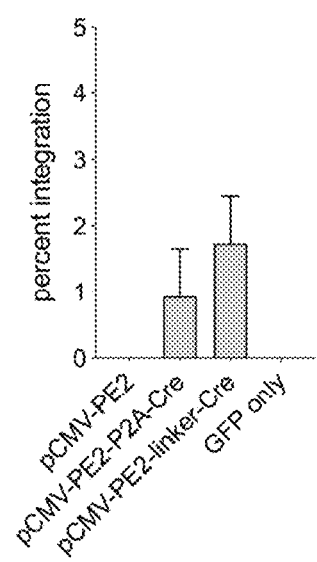
FIG. 3 shows the percent integration of green fluorescent protein (GFP) in the lentiviral integrated lox71 site in HEK293FT cell line in the presence of various plasmids according to embodiments of the present teachings.

The efficiency of the CRE integration was tested. In order to test the efficacy of PASTE with GFP using lox71/lox66/Cre recombinase system, a clonal HEK293FT cell line with lox71 sequence (SEQ ID NO: 1) integrated into the genome using lentivirus was developed. The integration of GFP was tested by transfection of modified HEK293FT cell line with: (1) plus/minus SEQ ID NO: 71 comprising a Cre recombinase expression plasmid, and (2) SEQ ID NO: 72 comprising a GFP template and a lox 66 Cre site of SEQ ID NO: 2. After 72 hours, the percent integration of GFP into the lox71 site was probed. FIG. 3 shows the percent integration of GFP in the lentiviral integrated lox71 site in HEK293FT cell line in the presence of various plasmids. It was observed that pCMV PE2 P2A Cre (SEQ ID NO: 73), a mammalian expression vector with prime editing complex and Cre recombinase linked to PE2 via a cleavable linker or a non-cleavable linker, shows integration of GFP.

Example 2

Figure 4:
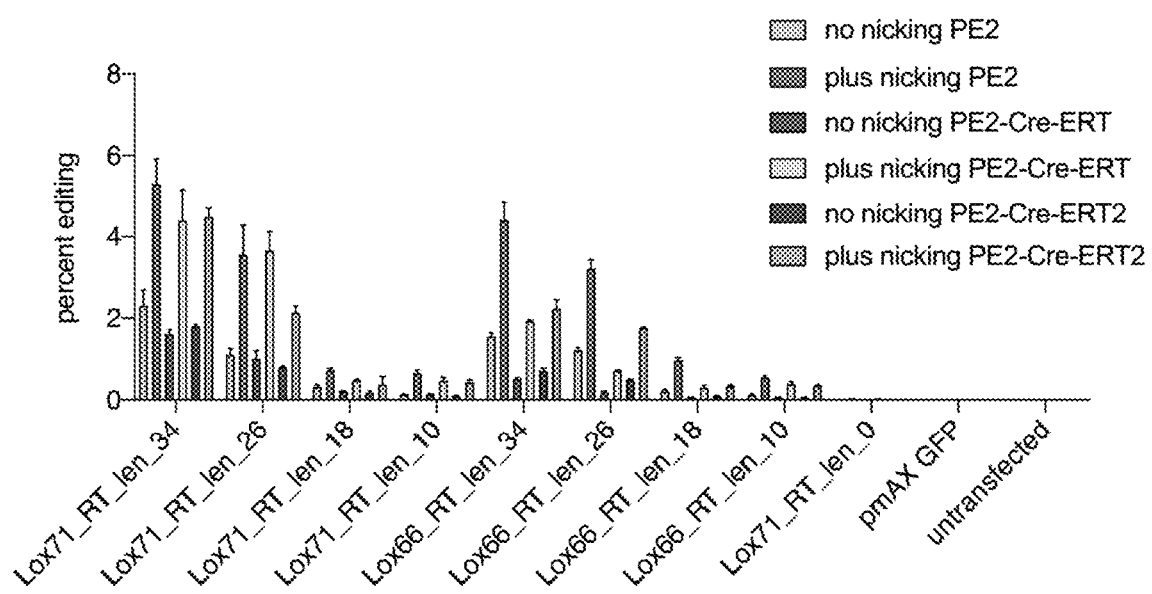
FIG. 4 shows the percent editing of the HEK293FT genome for incorporation of various lengths of lox71 or lox66 according to embodiments of the present teachings.

Programmable Addition Via Site-Specific Targeting Elements (PASTE) with Cre Recombinase—Addition of Lox Site The lox71 (SEQ ID NO: 1) or lox66 (SEQ ID NO: 2) sequence was inserted into the HEK293FT cell genome using prime editing to test integration of GFP into the HEK293FT genome. In order to insert lox71 or lox66 sequence into HEK293FT cell genome, a pegRNA with PBS length of 13 base pairs operably linked to RT region of varying lengths was used. The following plasmids were used in the transfection of HEK293FT cells. The cells were transfected with (1) prime editing construct (PE2) or PE2 with conditional Cre expression, (2) Lox71 or Lox66 pegRNA targeting the HEK3 locus, and (3) plus/minus +90 HEK3 nicking second guide RNA targeting the HEK3 locus (+90 ngRNA). After 72 hours, the percent editing of the HEK293FT genome at the HEK3 locus was probed for incorporation of various lengths of lox71 or lox66 (see FIG. 4). It was observed that 34 base pair lox71 (HEK3 locus guide, SEQ ID NO: 83; and Lox71 pegRNA with RT 34 and PBS 13, SEQ ID NO: 81) with +90 ngRNA (SEQ ID NO: 75) and 34 base pair lox66 (HEK3 locus guide, SEQ ID NO: 83; and Lox66 pegRNA with RT 34 and PBS 13, SEQ ID NO: 82) with +90 ngRNA (SEQ ID NO: 75) had the highest percent editing.

Example 3

PASTE with Cre Recombinase—Integration of Gene

Figure 5A:
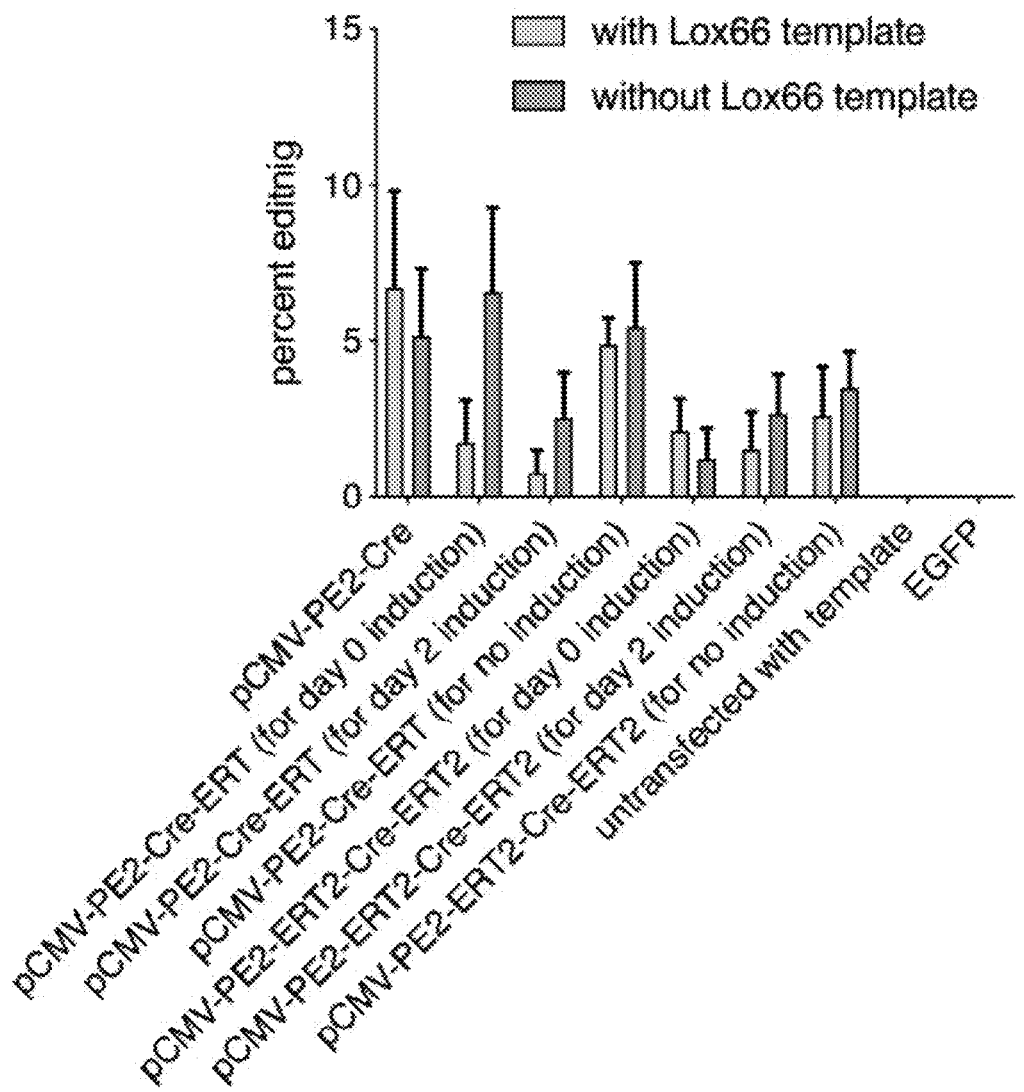
FIG. 5A shows the percent editing of lox71 site with different PE/Cre vectors according to embodiments of the present teachings.
Figure 5B:
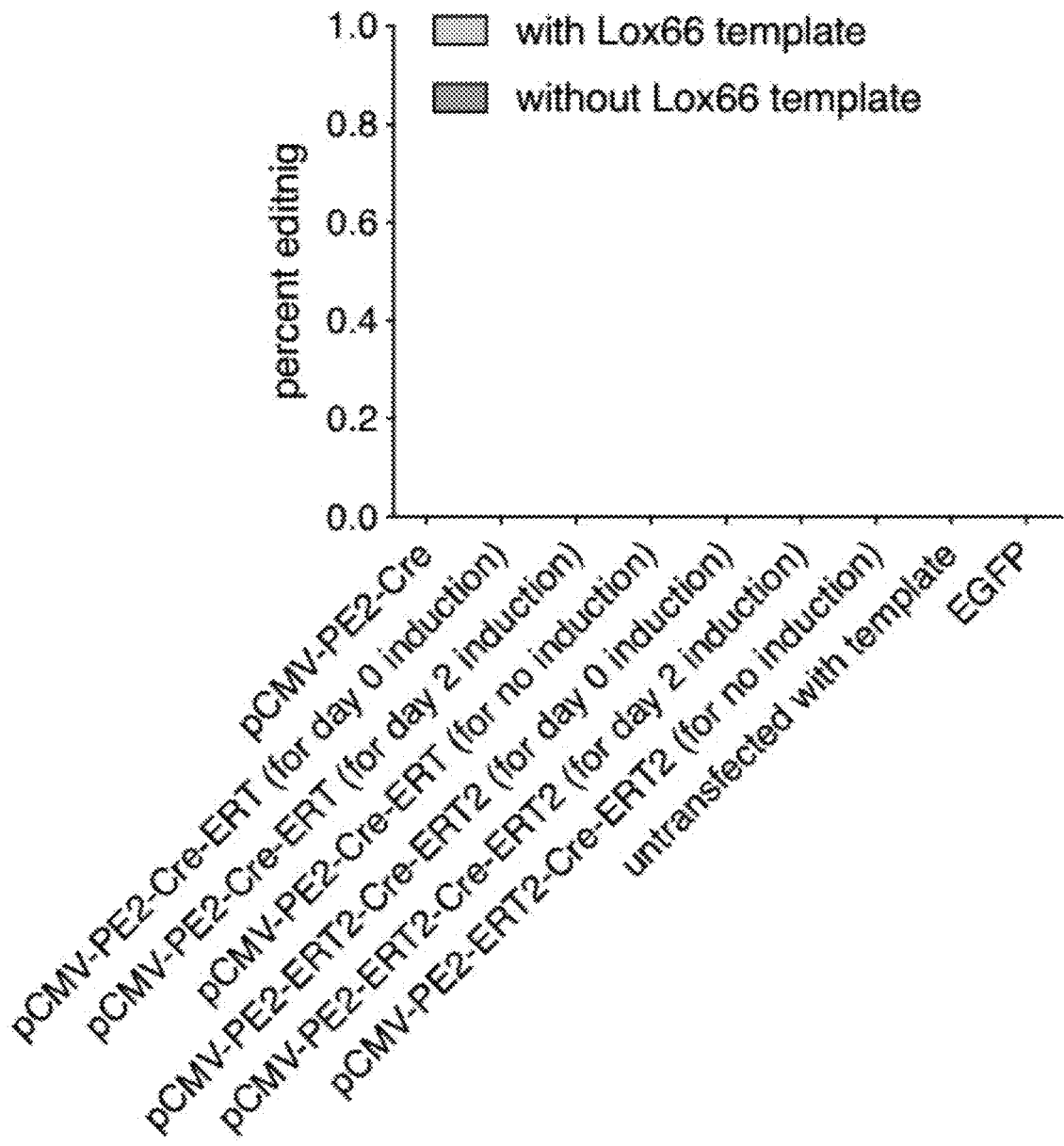
FIG. 5B shows the percent integration of GFP at the lox71 site in HEK293FT cell genome according to embodiments of the present teachings.

The lox71 or lox66 pegRNAs having PBS length of 13 base pairs and insert length of 34 base pairs were used to probe integration of GFP in the HEK293F genome. The PE and Cre were delivered in an inducible expression vectors and induced at day 2. The HEK293FT cells were transfected with the following plasmids: (1) prime editing construct (PE2 or PE2 with conditional Cre expression); (2) Lox71 pegRNA; (3) plus/minus +90 HEK3 nicking guide RNA; and (4) EGFP template with Lox66 site. After 72 hours, the percent editing of lox71 site and percent integration of GFP was probed with or without lox66 site in the presence of various PE/Cre constructs. FIG. 5A summarizes the percent editing of lox71 site with different PE/Cre vectors. FIG. 5B summarizes the percent integration of GFP at the lox71 site in HEK293FT cell genome. It was observed that although the lox71 site was edited in the presence of inducible or non-inducible PE/Cre expression system, there was no GFP integration.

Example 4

Bxb1 Integration Data Lenti Reporter

Figure 6:
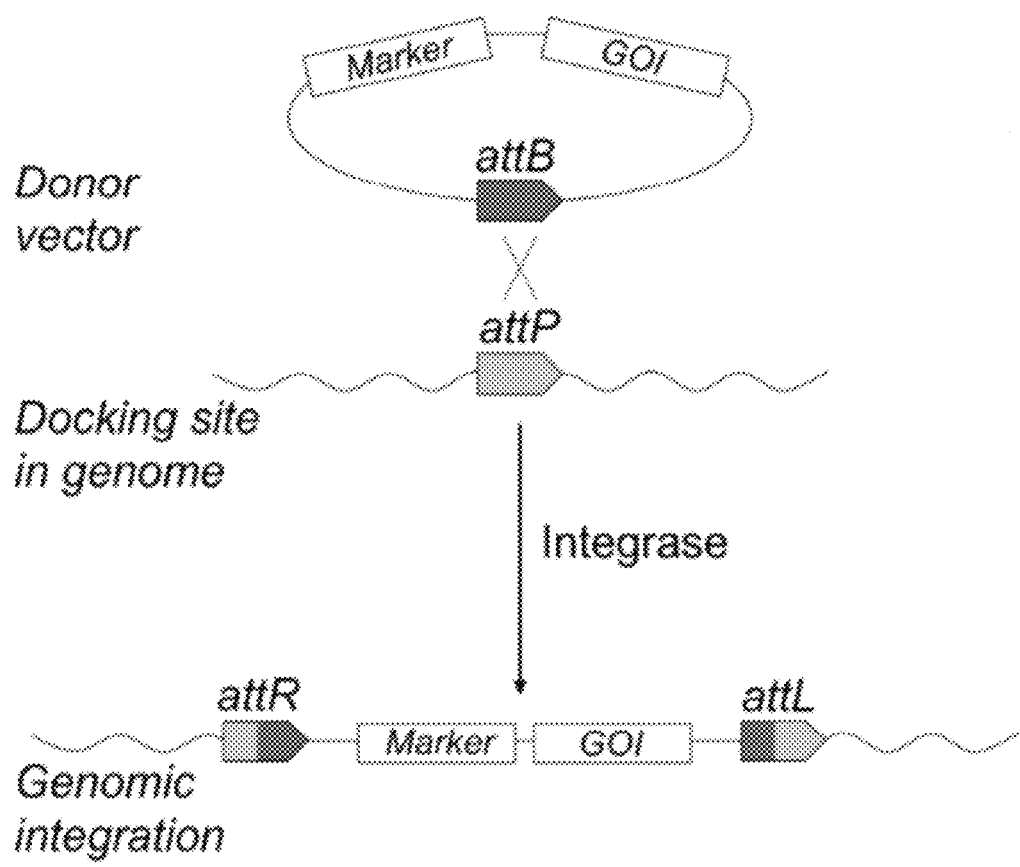
FIG. 6 shows a schematic representation of using Bxb1 to integrate a nucleic acid into the genome according to embodiments of the present teachings.

The integration system was switched to an integrase system that could result in an integration of target genes into a genome with higher efficiency. Serine integrase Bxb1 has been shown to be more active than Cre recombinase and highly efficient in bacteria and mammalian cells for irreversible integration of target genes. FIG. 6 shows a schematic of PASTE methodology using Bxb1 (Merrick, C. A. et al., *ACS Synth. Biol.* 2018, 7, 299-310).

Figure 7:
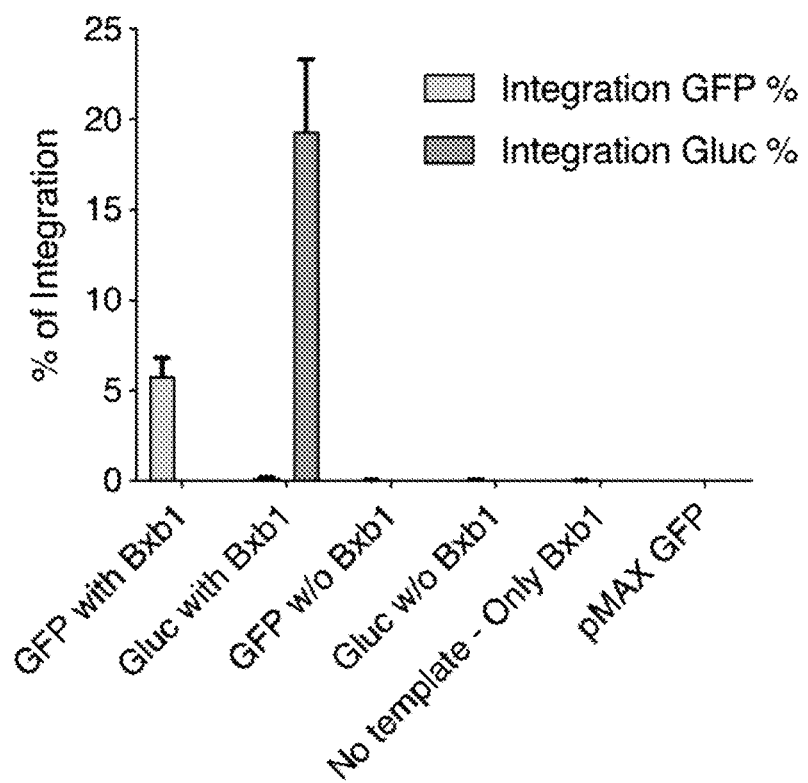
FIG. 7 shows the percent integration of GFP or Gluc into the attB locus using Bxb1 Programmable Addition via Site-Specific Targeting Elements (PASTE) according to embodiments of the present teachings.

To probe the efficiency of the Bxb1 integration system, a clonal HEK293FT cell line with attB Bxb1 site (SEQ ID NO: 3) integrated using lentivirus was developed. The modified HEK293FT cell line was then transferred with the following plasmids: (1) plus/minus Bxb1 expression plasmid and (2) plus/minus GFP (SEQ ID NO: 76) or G-Luc (SEQ ID NO: 77) minicircle template with attP Bxb1 site. After 72 hours, the integration of GFP or Gluc into the attB site in the HEK293FT genome was probed. The percent integrations of GFP or Gluc into the attB locus are shown in FIG. 7. It was observed that GFP and Gluc showed efficient integration into the attB site in HEK293FT cells.

Example 5

Addition of Bxb1 Site to Human Genome Using PRIME

Figure 8:
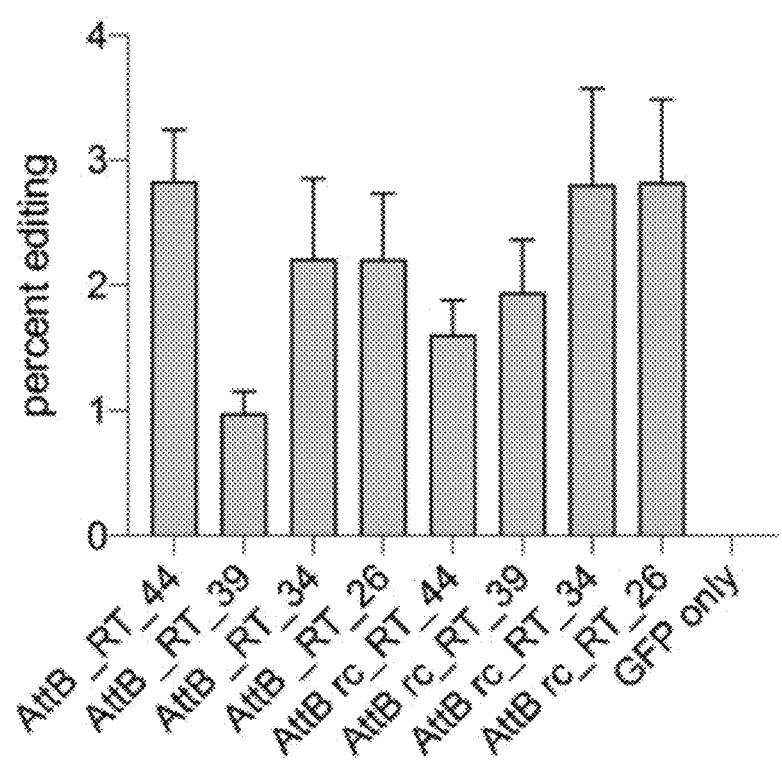
FIG. 8 shows the percent editing of various HEK3 targeting pegRNA Programmable Addition via Site-Specific Targeting Elements (PASTE) according to embodiments of the present teachings.
Figure 9A:
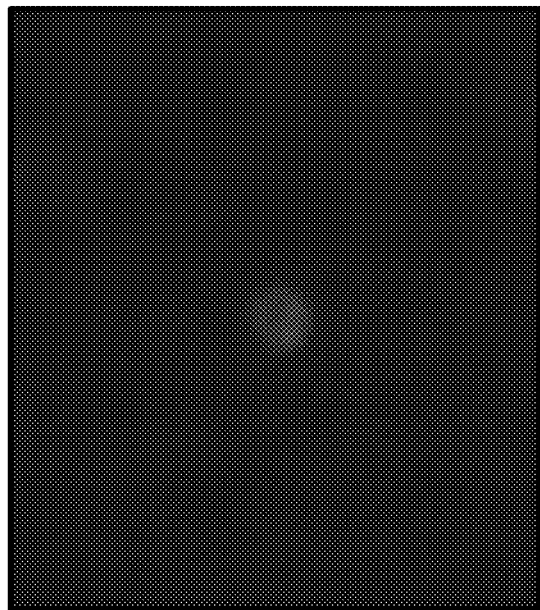
FIG. 9A shows a fluorescent image of cells wherein the SUPT16H marker is tagged with EGFP using PASTE according to embodiments of the present teachings.
Figure 9B:
FIG. 9B shows a fluorescent image of cells wherein the SRRM2 marker is tagged with EGFP using Programmable Addition via Site-Specific Targeting Elements (PASTE) according to embodiments of the present teachings.
Figure 9C:
FIG. 9C shows a fluorescent image of cells wherein the LAMNB1 marker is tagged with EGFP using Programmable Addition via Site-Specific Targeting Elements (PASTE) according to embodiments of the present teachings.
Figure 9D:
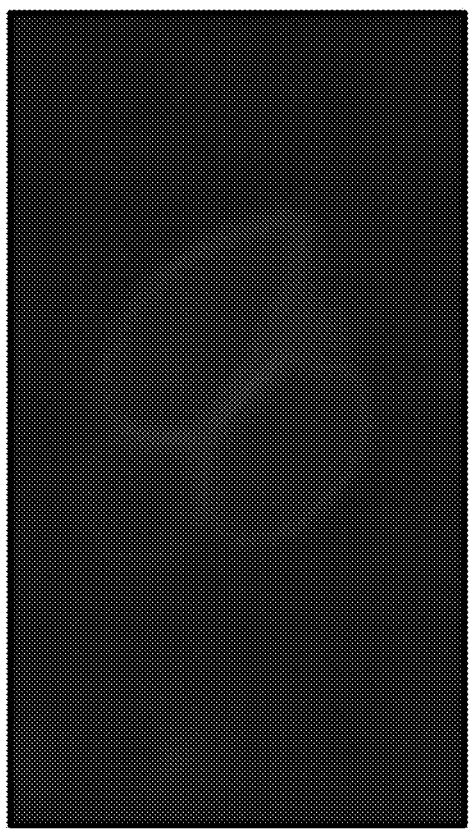
FIG. 9D shows a fluorescent image of cells wherein the NOLC1 marker is tagged with EGFP using Programmable Addition via Site-Specific Targeting Elements (PASTE) according to embodiments of the present teachings.
Figure 9E:
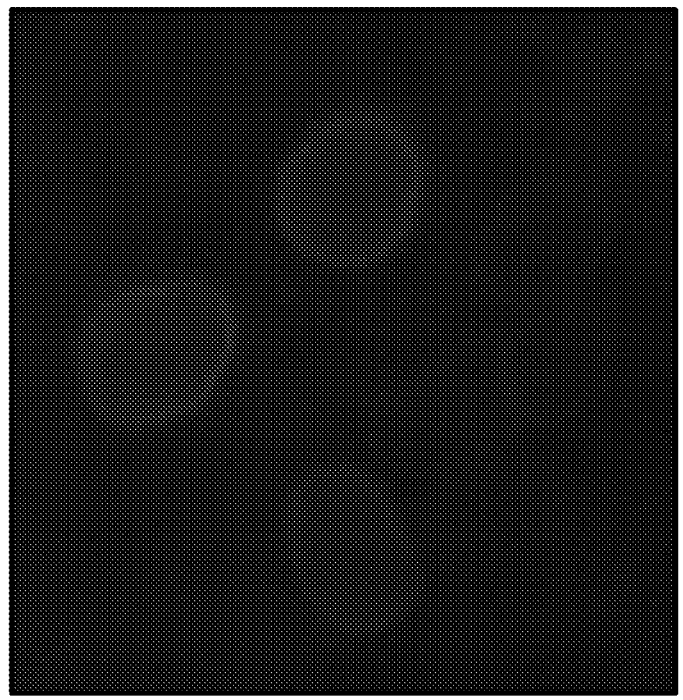
FIG. 9E shows a fluorescent image of cells wherein the NOLC1 marker is tagged with EGFP using Programmable Addition via Site-Specific Targeting Elements (PASTE) according to embodiments of the present teachings.
Figure 9F:
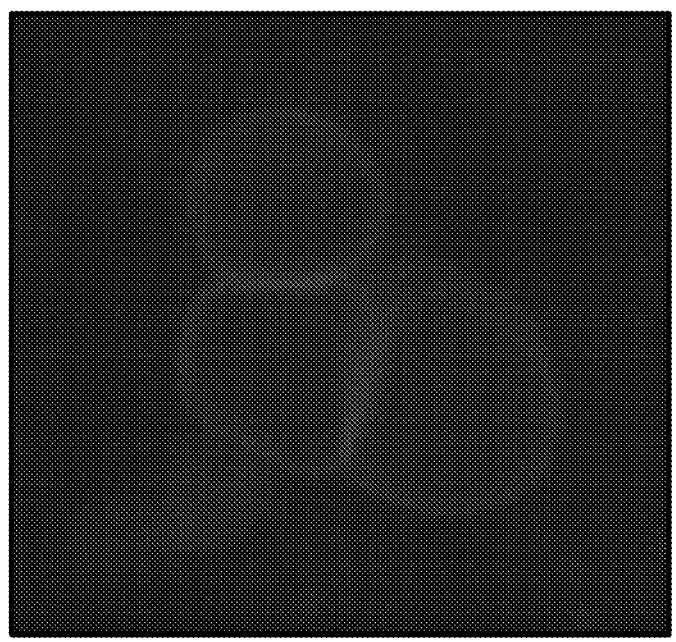
FIG. 9F shows a fluorescent image of cells wherein the NOLC1 marker is tagged with EGFP using Programmable Addition via Site-Specific Targeting Elements (PASTE) according to embodiments of the present teachings.
Figure 9G:
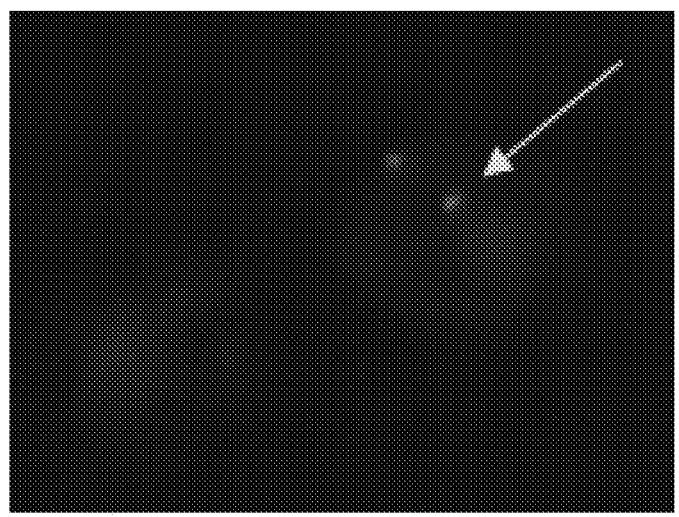
FIG. 9G shows a fluorescent image of cells wherein the DEPDC4 marker is tagged with EGFP using Programmable Addition via Site-Specific Targeting Elements (PASTE) according to embodiments of the present teachings.

The maximum length of attB that can be integrated into a HEK293FT cell line with the best efficiency was probed. To probe the best length of attB (SEQ ID NO: 3) or its reverse complement attP (SEQ ID NO: 4) for prime editing, pegRNAs having PBS length of 13 nt with varying RT homology length were used. The following plasmids were transfected in HEK293FT: (1) prime expression plasmid; (2) HEK3 targeting pegRNA design; and (3) HEK3 +90 nicking guide. After 72 hours, the percent integration of each of the attB construct was probed. FIG. 8 shows the percent editing in each HEK3 targeting pegRNA. It was observed that attB with 44, 34 and 26 base pairs and attB reverse complement with 34 and 26 base pairs showed the highest percent editing.

Integration PASTE was then tested with tagging cell-organelle marker proteins with GFP in HEK29FT cells. PASTE was used to tag SUPT16H, SRRM2, LAMNB1, NOLC1 and DEPDC4 with GFP in different cell-culture wells and to test the usefulness of PASTE in tracking protein localization within the cells using microscopy. FIGS. 9A-9G shows the fluorescent microscopy results for each of the organelles. SUPT16H-GFP was observed to be enriched in the nucleus, SRRM2-GFP was observed to be enriched in the nuclear speckles, LAMNB1-GFP was observed to be enriched in the nuclear membrane, NOLC1-GFP was observed to be enriched in the fibrillar center, and DEPDC4-GFP was observed to be enriched in the aggresome.

Figure 10A:
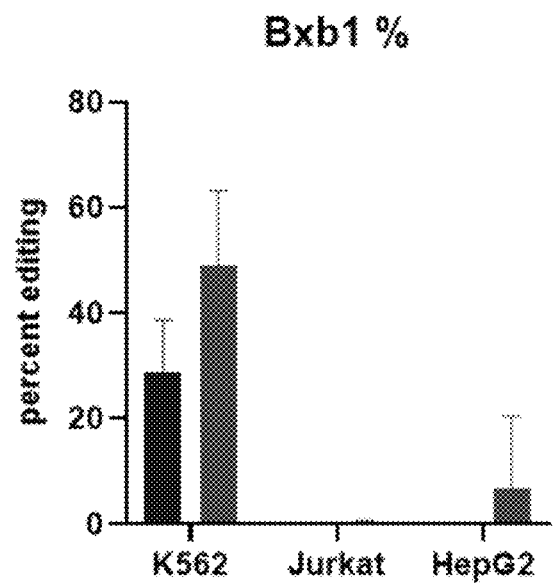
FIG. 10A shows comparisons of lipofectamine aided transfection in blue with electroporation aided transfection in red for the addition of the Bxb1 attB site at the ACTB N-terminal site in the genome using PASTE according to embodiments of the present teachings.
Figure 10B:
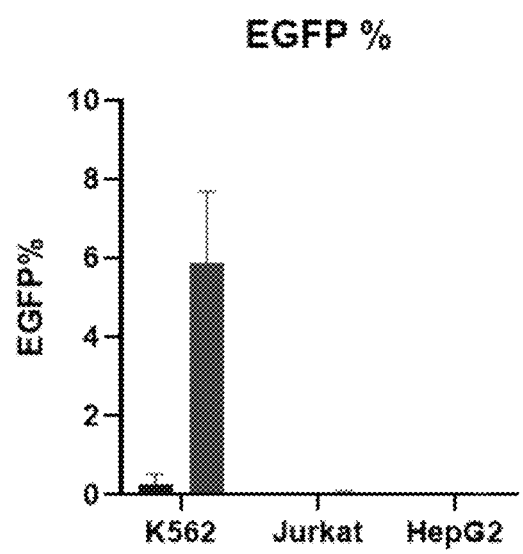
FIG. 10B shows comparisons of lipofectamine aided transfection in blue with electroporation aided transfection in red for EGFP integration at the ACTB N-terminal site in the genome using PASTE according to embodiments of the present teachings.

The transfection of the plasmids can be achieved using electroporation as illustrated in FIGS. 10A-10B.

Example 6

Programmable Integration of Genes with PASTE

Figure 11:
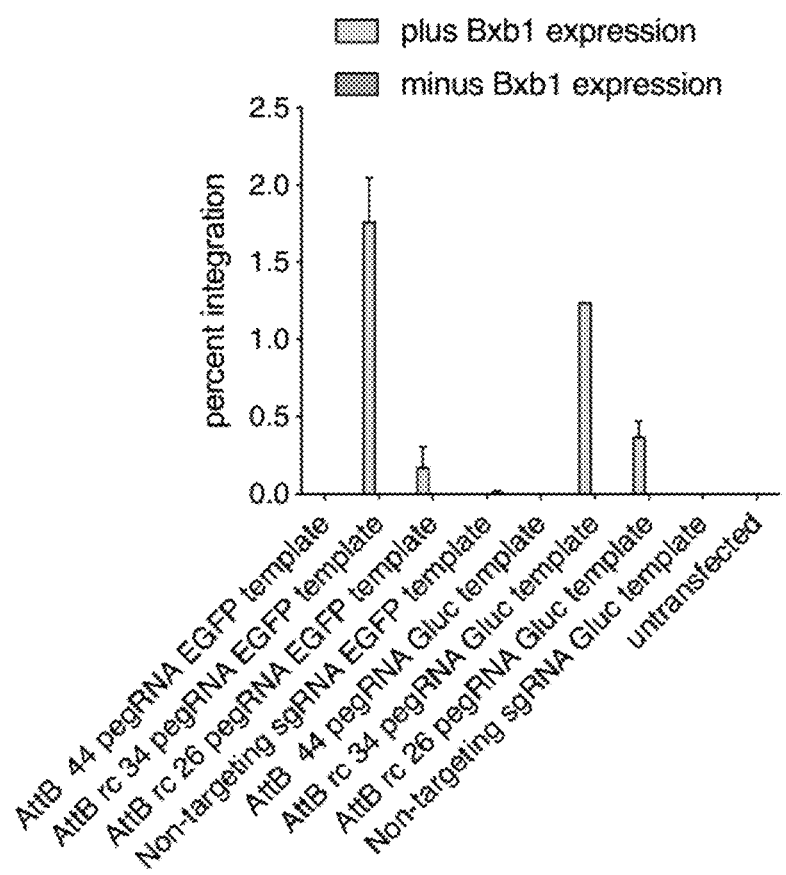
FIG. 11 shows a diagram of the integration of EGFP and Gluc with various HEK3 targeting pegRNAs according to embodiments of the present teachings.

The efficiency of gene integration of Gluc or EGFP with PASTE was tested. To enable gene integration with PASTE, the following HEK3 targeting pegRNAs were used: (1) 44 pegRNA: PBS of 13nt and RT homology of 44nt; (2) 34 pegRNA: PBS of 13nt and RT homology of 34nt; and (3) 26 pegRNA: PBS of 13nt and RT homology of 26nt. A HEK293 cell line was transfected with following plasmids HEK293FT: (1) Prime expression plasmid; (2) Bxb1 expression plasmid; (3) HEK3 targeting pegRNA design; (4) HEK3 +90 nicking guide; and (5) EGFP or Gluc minicircle. After 72 hours, the percent integration of Gluc or EGFP was observed. FIG. 11 shows integration of EGFP and Gluc with each of the tested HEK3 targeting pegRNAs. It was observed that EGFP and Gluc were efficiently integrated using PASTE.

Example 7

PASTE for Integration of Multiple Genes

The PASTE technique for site-specific integration of multiple genes into a cell is facilitated with the use of orthogonal attB and attP sites. Central dinucleotide can be changed to GA from GT, and only GA containing attB/attP sites can interact and do not cross react with GT containing sequences. A screen of dinucleotide combinations to find orthogonal attB/attP pairs for multiplexed PASTE editing can be performed. It has been shown that many orthogonal dinucleotide combinations can be found using a Bxb1 reporter system.

Figure 14A:
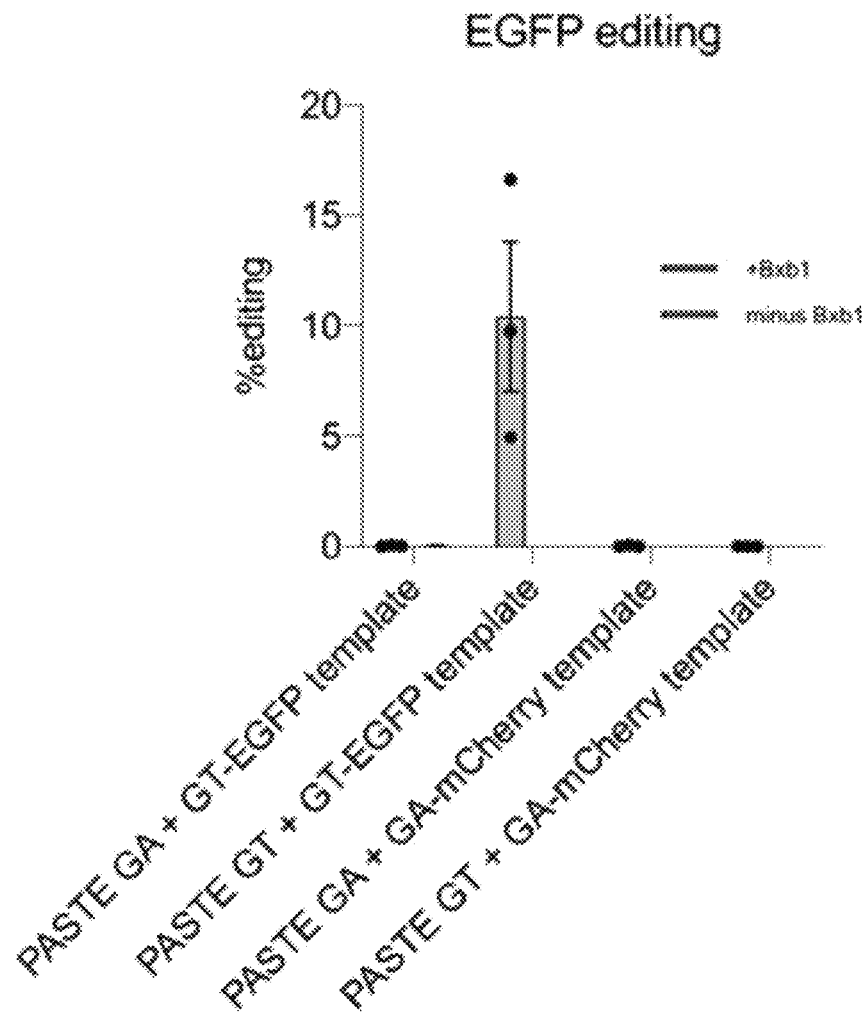
FIG. 14A shows a diagram of the orthogonal editing with the right GT-EGFP according to embodiments of the present teachings.
Figure 14B:
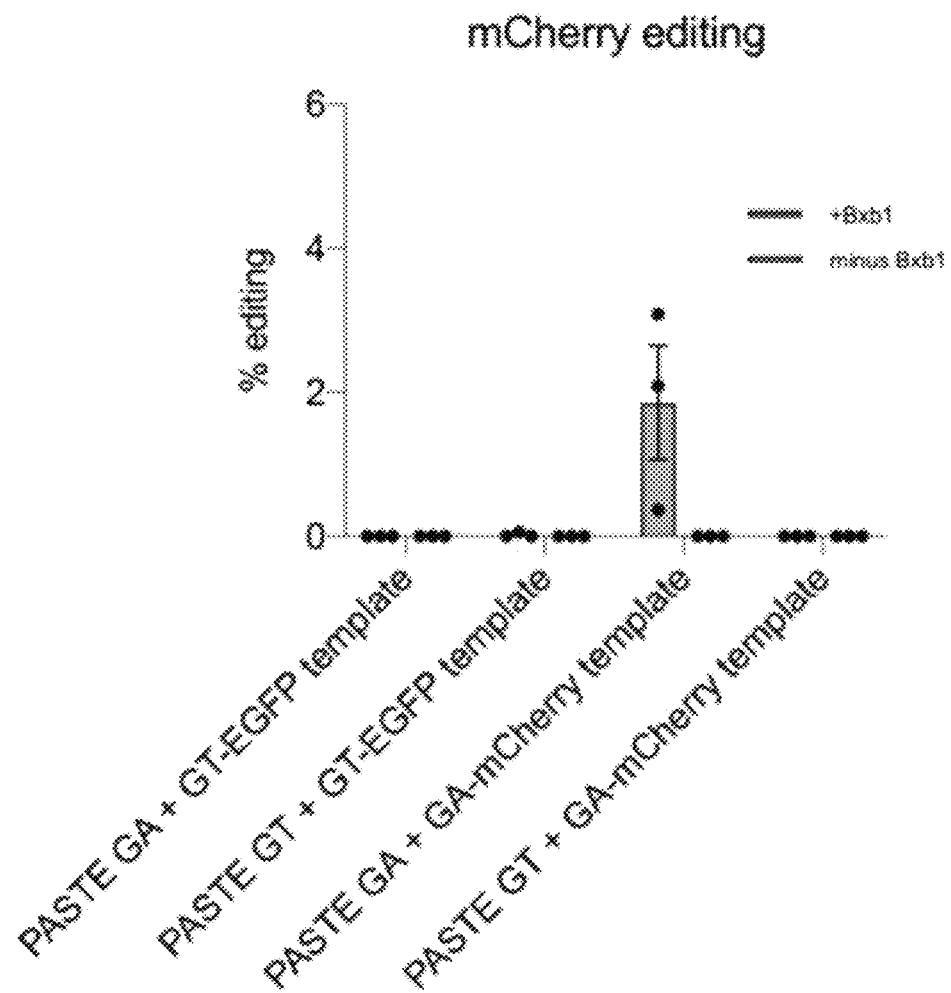
FIG. 14B shows a diagram of the orthogonal editing with the right GA-mCherry according to embodiments of the present teachings.

To test this, attB$^{GT}$ and attB$^{GA}$ dinucleotides for Bxb1 was added at a ACTB site by prime editing. A EGFP-attP$^{GT}$ DNA minicircle and a mCherry-attP$^{GA}$ DNA minicircle was introduced to test the percent EGFP and mCherry editing in the presence or absence of Bxb1. The results of EGFP and mCherry editing are shown in FIGS. 14A-14B.

Orthogonal editing with the right GT-EGFP and GA-mCherry pairs was achieved demonstrating the ability for multiplexed PASTE editing in cells.

Figure 15A:
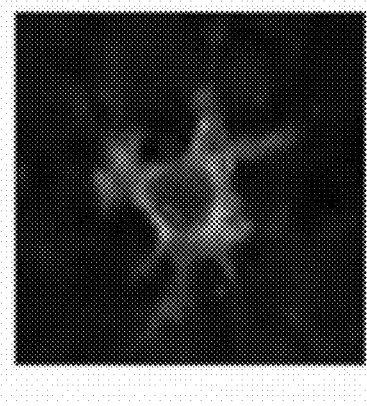
FIG. 15A shows a fluorescent image of a multiplexing of ACTB-EGFP and NOLC1-mCherry according to embodiments of the present teachings
Figure 15B:
FIG. 15B shows a fluorescent image of a multiplexing of ACTB-EGFP and LAMNB1-mCherry according to embodiments of the present teachings.

Two genes were introduced in the same cell using multiplexed PASTE to tag two different genes in a single reaction. EGFP and mCherry were tagged into the loci of ACTB and NOLC1 in a x cell line, in a single reaction. Further, EGFP and mCherry were tagged into the loci of ACTB and LAMNB1. The cells were visualized using fluorescence microscopy. FIGS. 15A-15B show the results of fluorescent microscopy for multiplexed PASTE.

Figure 16A:
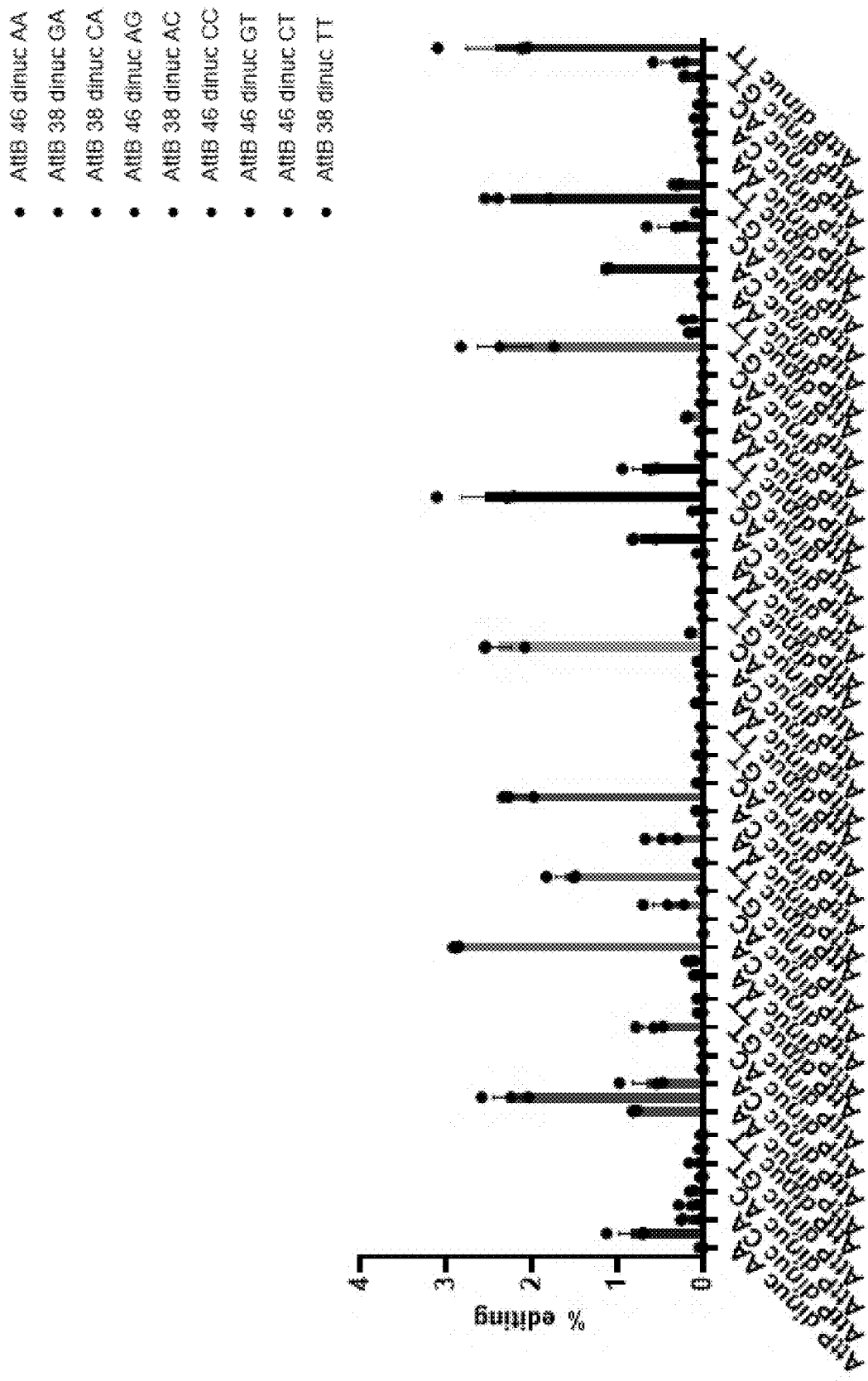
FIG. 16A shows next generation sequencing results of 9×9 attP and attB central dinucleotide variants and their edit percentage wherein the orthogonality of attB/attP combinations for potential multiplexing applications is shown according to embodiments of the present teachings.
Figure 16B:
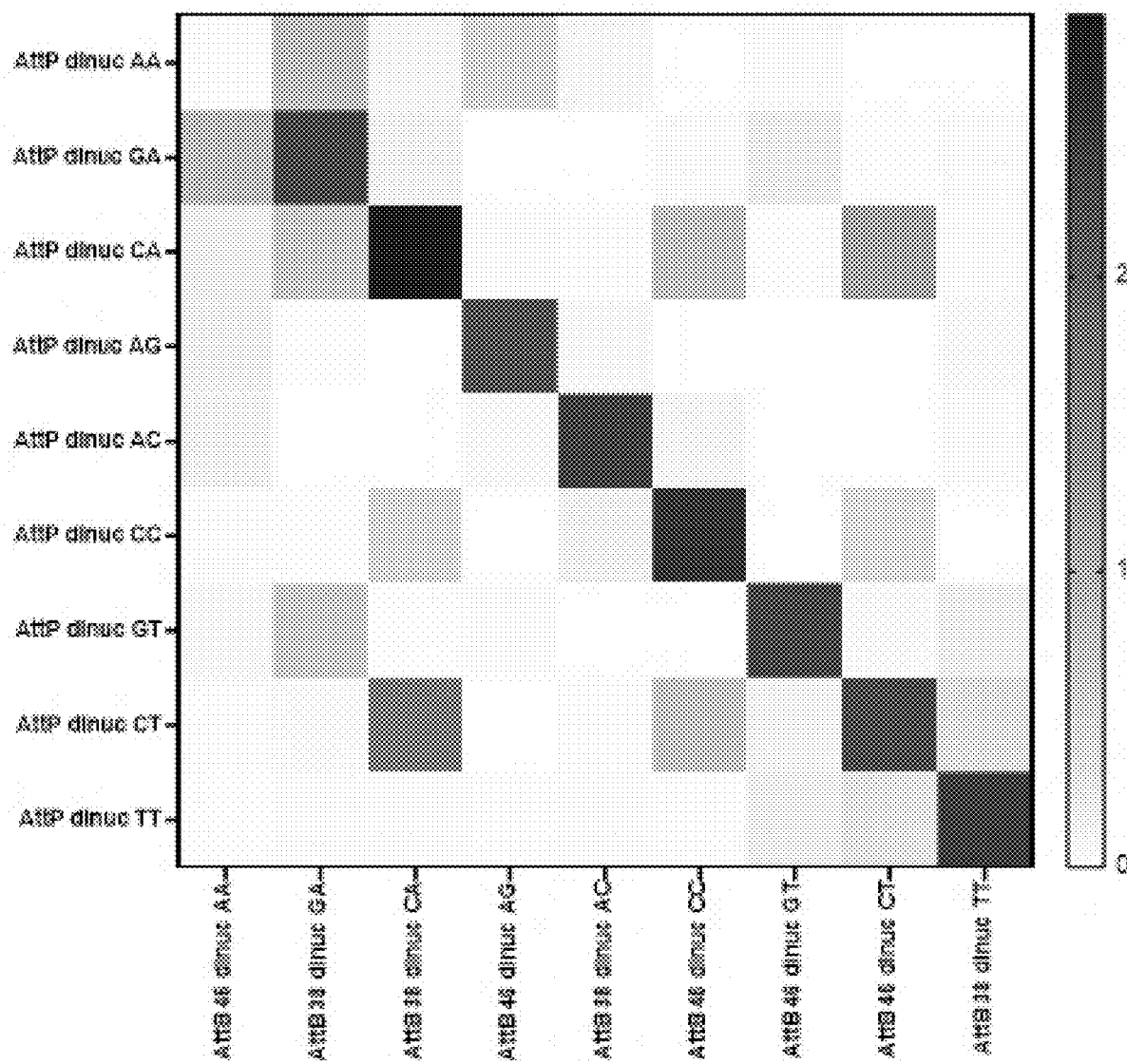
FIG. 16B shows an heatmap of 9×9 attP and attB central dinucleotide variants and their edit percentage according to embodiments of the present teachings.

The ability of multiplexing with 9-different attB and attP central dinucleotides—AA, GA, CA, AG, AC, CC, GT, CT and TT (SEQ ID NOs: 7, 8, 23, 24, 19, 20, 25, 26, 27, 28, 9, 10, 15, 16, 17, 18, 5 and 6)—in a 9×9 cross of attB and attP was tested. The edits were probed using next-generation sequencing. The results of the 9×9 cross of attB and attP central dinucleotides—AA, GA, CA, AG, AC, CC, GT, CT and TT—are shown in FIG. 16A. Only orthogonal pairs of attB and attP show the highest edit percentage. This result is also shown in the heat-map of FIG. 16B.

Example 8

Figure 17:
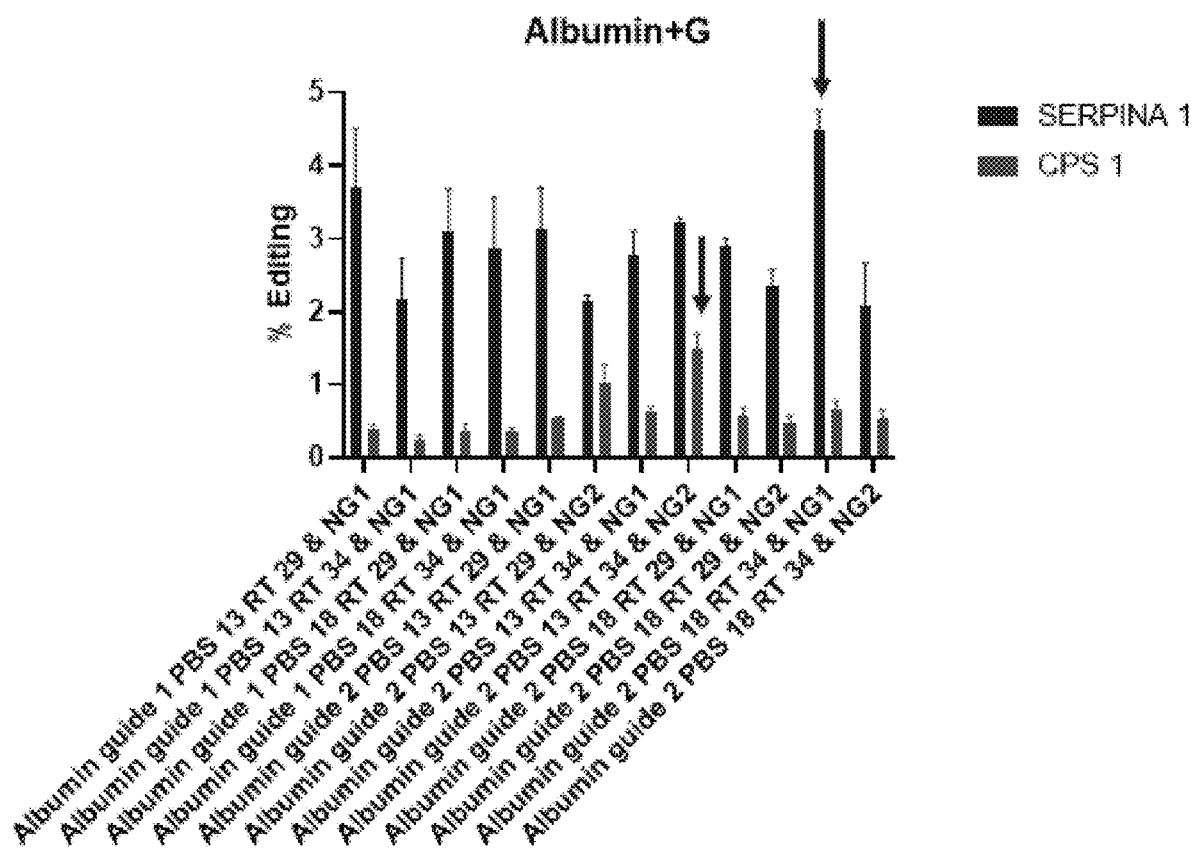
FIG. 17 shows integration of SERPINA and CPS1 into Albumin loci using Albumin guide-pegRNA in HEK293FT cells according to embodiments of the present teachings.

Integration of Albumin and CPS1 into Albumin Locus 12 pegRNAs with albumin guide were linked to PBS and reverse transcriptase sequence of variable length, and different nicking guide RNAs were used to transfect HEK293FT cells. The percent editing in the albumin was probed using next-generation sequencing. The results of prime editing at the albumin locus are shown in FIG. 17. It was observed that SEQ ID NO: 79 showed the highest percent edits with SERPINA1 and SEQ ID NO: 80 showed the highest percent edits with CPS1.

Example 9

Engineering T-Cells

Figure 18:
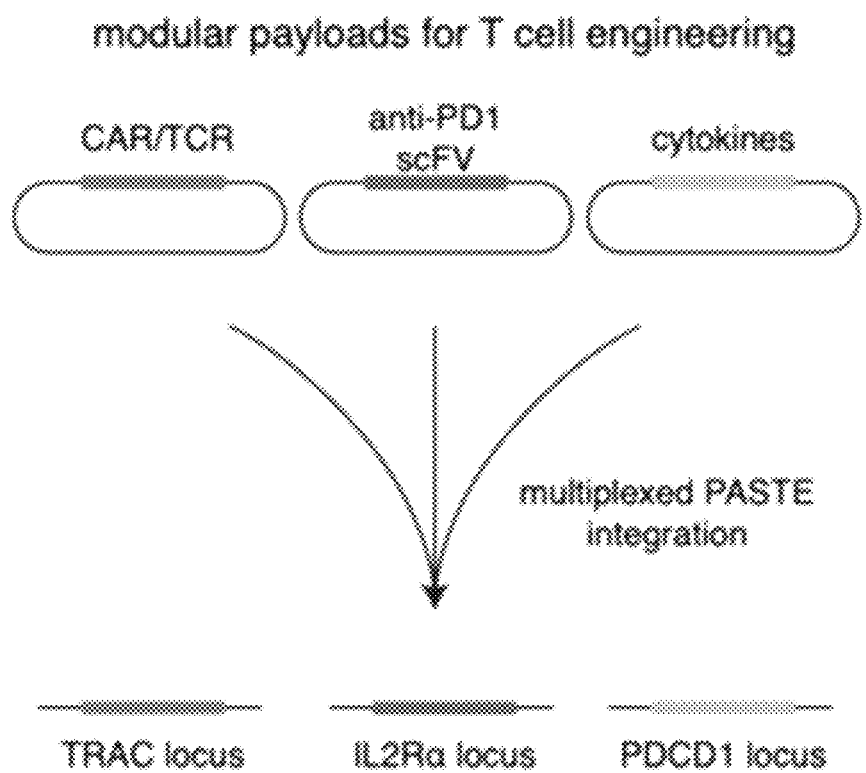
FIG. 18 shows schematics for different nucleic acids for engineering T-cells according to embodiments of the present teachings.

In order to engineer CD8+ T-cells, the efficiency of PASTE delivery and editing in T-cells can be evaluated (FIG. 18). ACTB targeting pegRNA can be used to insert an integration site with an EGFP insertion template. To deliver the PASTE components to CD8+ T-cells, electroporation can be used along with an optimized electroporation protocol for unstimulated T-cells. As multiple plasmids may reduce the efficiency of electroporation, the consolidated PASTE components that use fewer vectors can be applied.

Figure 19:
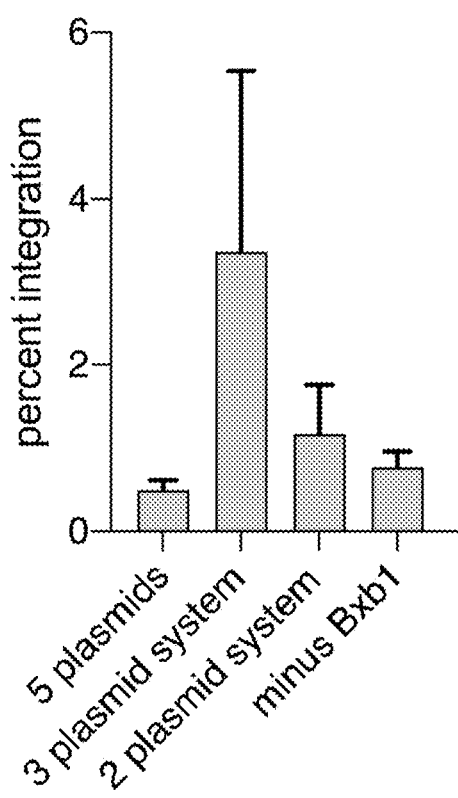
FIG. 19 shows the editing efficiency for EGFP integration at the ACTB locus in primary T-cells according to embodiments of the present teachings.
Figure 20:
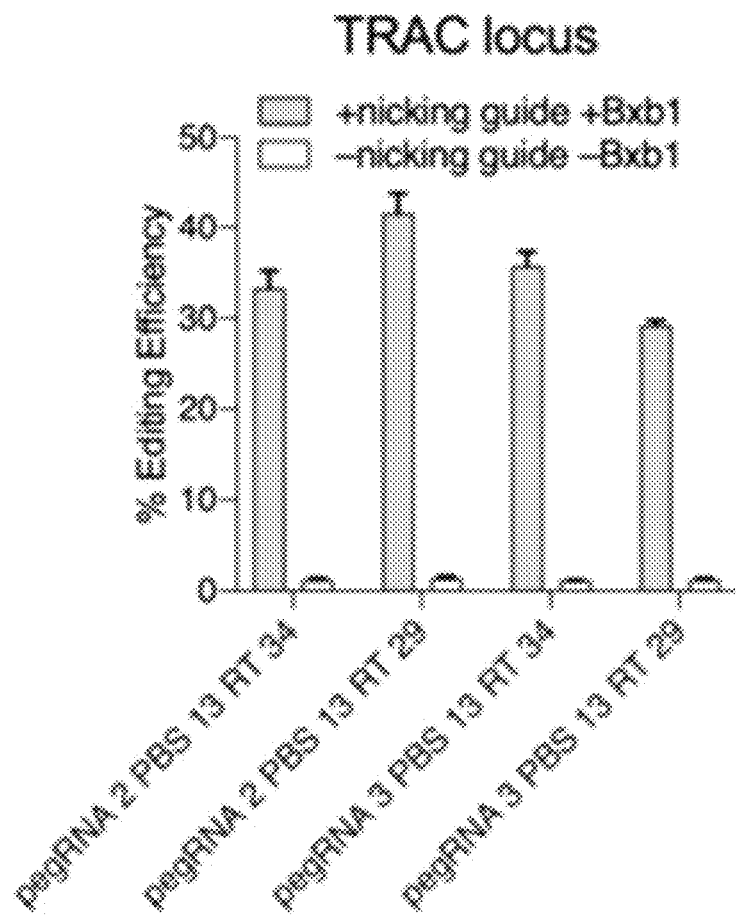
FIG. 20 shows editing in TRAC locus in HEK293FT with different pegRNA according to embodiments of the present teachings.

Five vectors, three vectors, and two vectors PASTE systems show that robust T-cell editing can be achieved with maximal editing using the three-vector approach (FIG. 19). Further, expanded sets of electroporation conditions, including the overall plasmid amounts, cell numbers, and voltage/amperage protocol can be tested. In addition, stimulation of T-cells may influence the efficiency of transduction and PASTE efficiency. Further, CD4+/CD8+ T cell mixtures stimulated with T-Activator CD3/CD28 ligands can have higher PASTE editing efficiency versus unstimulated cells. In order to separate efficiency of PASTE from the overall delivery rate, an mCherry expression cassette on PASTE vectors can be evaluated in order to sort successfully transfected T cells. Once optimized parameters are achieved, a panel of 10 insertion sites with PASTE in T cells, including the TRAC, IL2Rα, and PDCD1 loci, can be evaluated, using different insertions (e.g. EGFP, BFP, and YFP), both in single and multiplexed editing contexts. A tested subset of relevant sites in HEK293FT achieved greater than 40% editing for EGFP insertion (FIG. 20). The PASTE efficiency at TRAC locus with different TCR and CAR constructs can be evaluated. The T-cells can successfully be transfected to achieve insertion of CARs or TCRs.

Example 10

PASTE for CFTR

PASTE for the CFTR locus can be tested in HEK293FT cells to identify top performing pegRNA and nicking designs for human cells. Neuro-2A cells can also be tested to identify top performing pegRNA and nicking designs for mouse cells. The best constructs can be applied for testing in mouse air lung interface (ALI) organoids in vitro or for delivery in pre-clinical models of cystic fibrosis in mice.

Table 12 shows the pegRNA, nicking guide and minicircle DNA characteristics for the CFTR gene modulation.

TABLE 12

| Variables | Characteristics |
|---|---|
| pegRNA | 38 bp shortened minimal attB and normal 46 bp attB sequence with:<br>a. PBS of 17, 13, and 9 nt length, and<br>b. RT of 20, 15, and 10 nt in length |
| Nicking guides | Nicking guide 1 +64 bp Nicking guide 2 +23 bp Nicking guide 3 −60 bp Nicking guide 4 −78 bp (distance is calculated from cut site of pegRNA) |
| Minicircle template | A. CFTR coding sequence alone (~4,454 pb in size)<br>B. CFTR coding sequence plus 5' and 3' UTRs (~6,011 bp in size)<br>(Both minicircles have attP site on them for integration by Bxb1 and a bGH poly A signal) |

Example 11

AttB and EGPF Integration Using PASTE

Figure 21A:
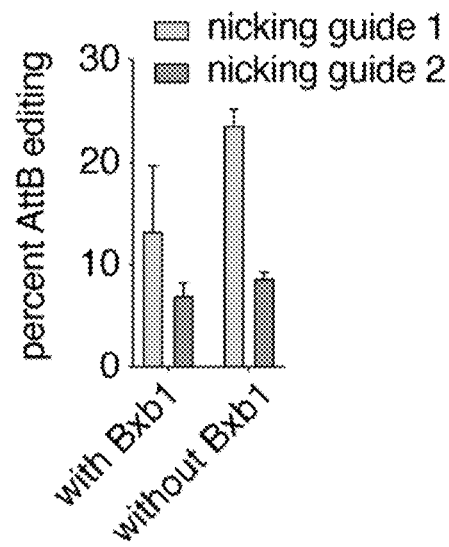
FIG. 21A shows the attB integration at the ACTB locus using nicking guides 1 and 2 according to embodiments of the present teachings.
Figure 21B:
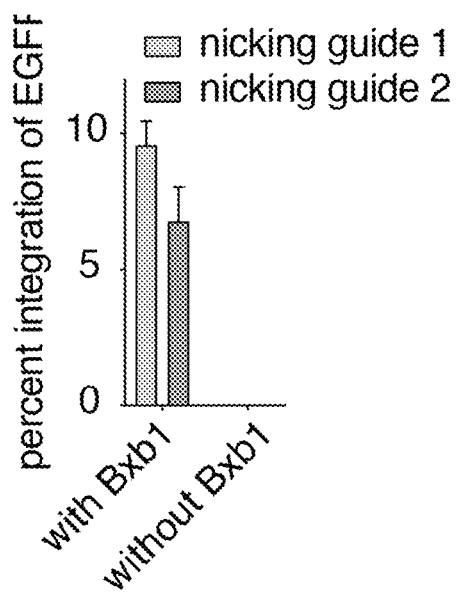
FIG. 21B shows the EGFP integration at the ACTB locus using nicking guides 1 and 2 according to embodiments of the present teachings.
Figure 21C:
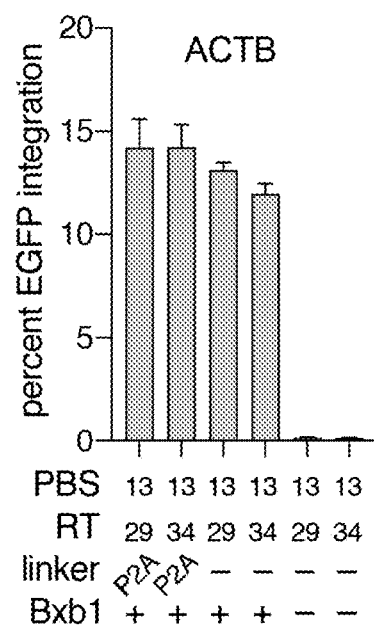
FIG. 21C shows the EGFP integration at an ACTB site according to embodiments of the present teachings.

The efficiency of the integration of attB and EGPF at the ACTB locus was evaluated (FIGS. 21A-21C). To investigate whether Bxb1 can add an EGFP template into this site, a delivery approach using a 5 plasmid system expressing each of the following component was deployed: 1) pegRNA expression, 2) nicking guide expression, 3) Prime expression (Cas9-RT), 4) Bxb1 expression and 5) the insertion template (in this case EGFP). This approach was found to yield editing efficiency of the attB site up to 24% and integration of EGFP ~10% in HEK293FT cells as measured by sequencing (FIGS. 21A-21B). Optimal activity is achieved in 3-4 days and can be performed as a single step transfection or electroporation of all components. Because the EGFP plasmid is designed as a minicircle, allowing removal of all undesired bacterial components, only the desired gene is inserted along with minimal scars from the Bxb1 recombined sites.

To make the tool simpler to use, the Bxb1 can be linked to Prime via a P2A linker to the Cas9-RT fusion, allowing for only a single plasmid to be used for PASTE protein expression rather than two. This optimization can maintain the same level of editing, making it easier to use the tool and deliver it (FIG. 21C).

Example 12

Programmable EGFP Integrations in Different Cell Types

Figure 22A:
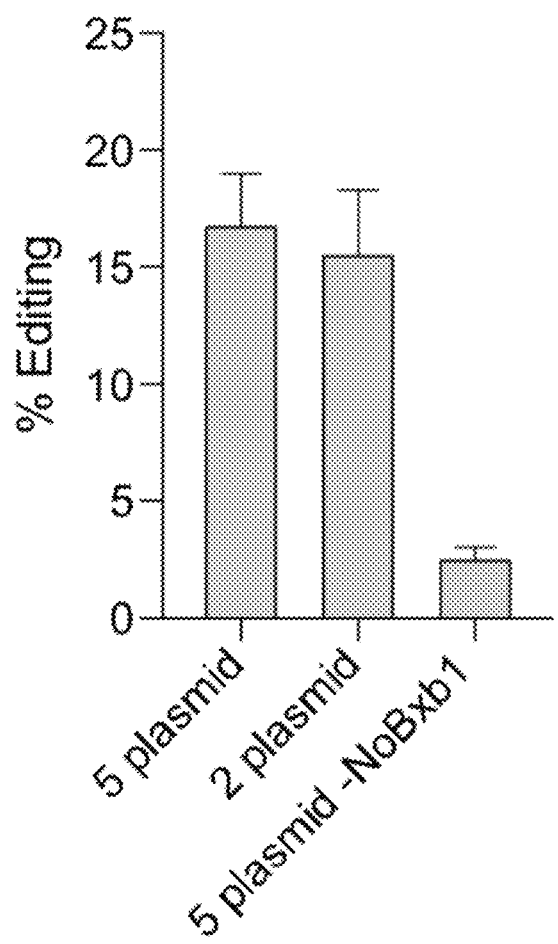
FIG. 22A shows PASTE editing in liver hepatocellular carcinoma cell line HEPG2 according to embodiments of the present teachings.
Figure 22B:
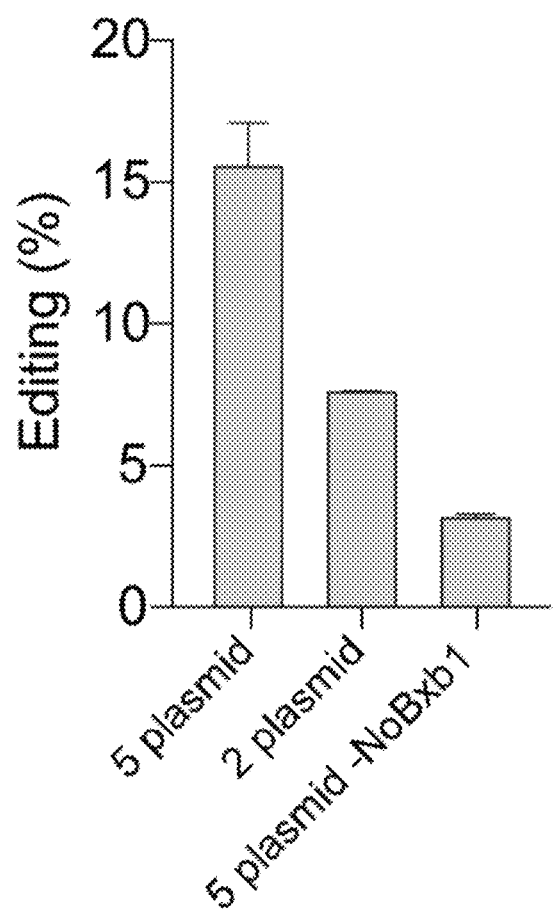
FIG. 22B shows PASTE editing of chronic myelogenous leukemia cell line K562 according to embodiments of the present teachings.

The programmable EGFP integration in liver hepatocellular carcinoma cell line HEPG2 (FIG. 22A) and chronic myelogenous leukemia cell line K562 (FIG. 22B) was evaluated. EGFP integration at the ACTB locus in K562 and HEPG2 cells of about 15% was observed, demonstrating robustness of the platform across cell types.

Example 13

Mutagenesis of Bxb1 for Enhanced PASTE Activity

Figure 23A:
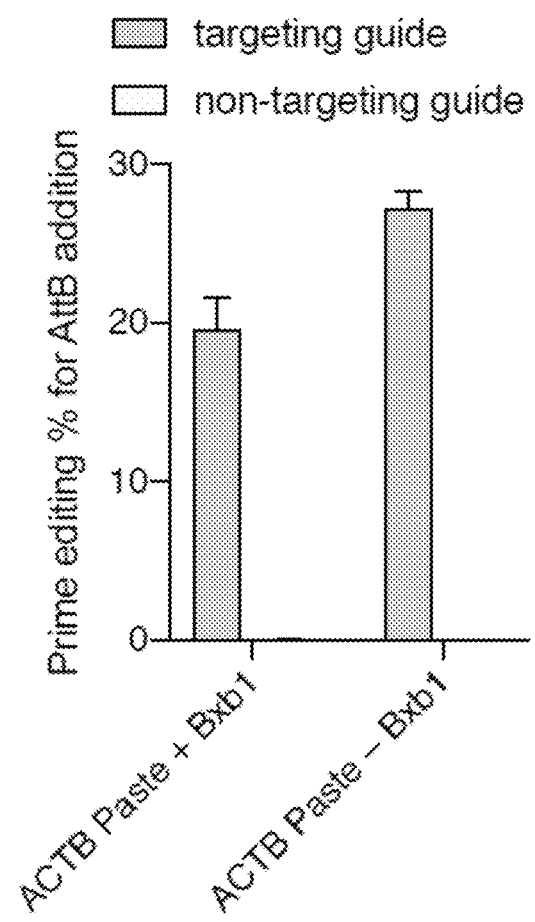
FIG. 23A shows the attB addition with targeting and non-targeting guides according to embodiments of the present teachings.
Figure 23B:
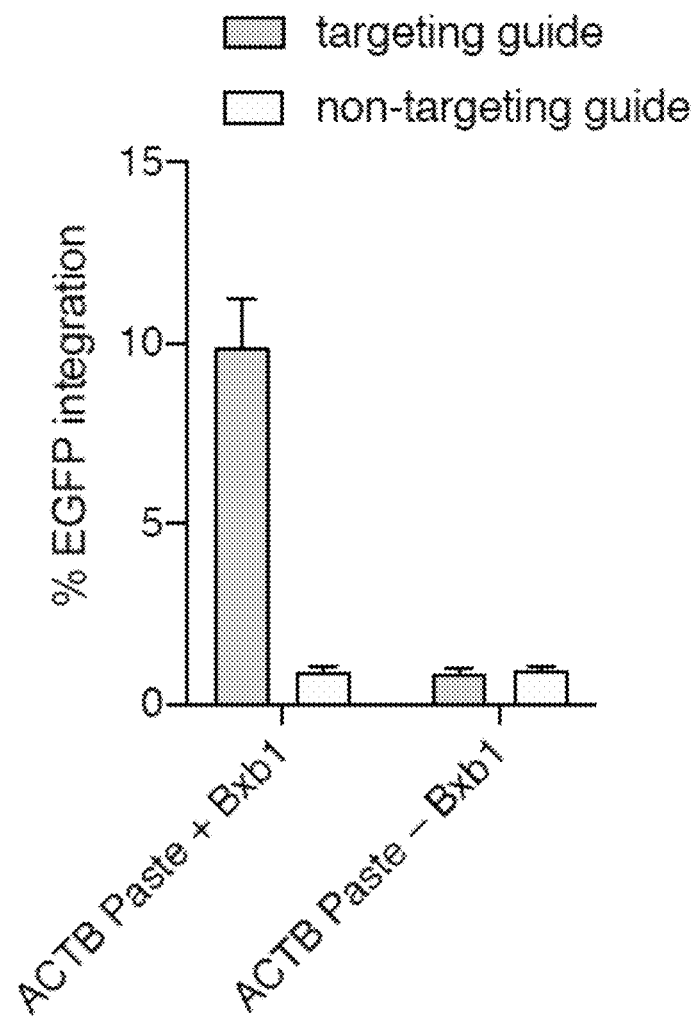
FIG. 23B shows the EGFP integration with targeting and non-targeting guides according to embodiments of the present teachings.
Figure 23C:
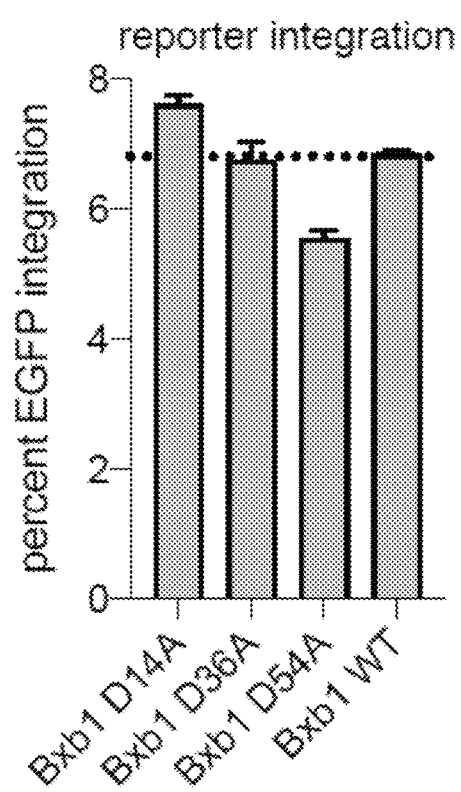
FIG. 23C shows the EGFP integration for mutagenized Bxb1 according to embodiments of the present teachings.

The mutagenesis of Bxb1 for enhanced PASTE activity was evaluated (FIGS. 23A-23C). Two levers for optimizing PASTE activity exist: 1) improving the activity of the integrase and 2) enhancing the Prime addition of the integration sequence. As illustrated in FIGS. 23A-23B, Bxb1 activity can be improved as only about 30% of Bxb1 attB sites that are added by PASTE are integrated into by Bxb1. This illustrates that if the Bxb1 efficiency can be improved, the PASTE can be improved. Furthermore, catalytic residues in the Bxb1 integrase were identified via conservation and structural analyses and Bxb1 mutants were generated to test as part of PASTE. As illustrated in FIG. 23B, the mutations can improve integration by about 20-30%.

Example 14

Figure 25A:
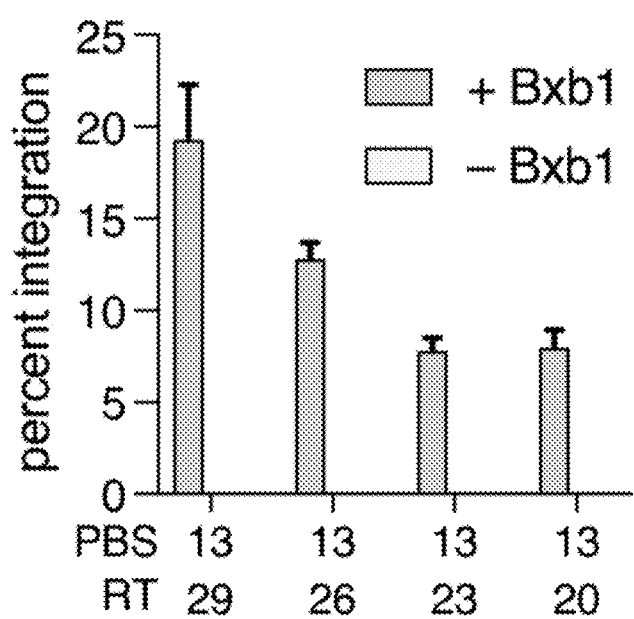
FIG. 25A shows the integration of EGFP at the ACTD locus with different PBS and RT lengths according to embodiments of the present teachings.
Figure 25B:
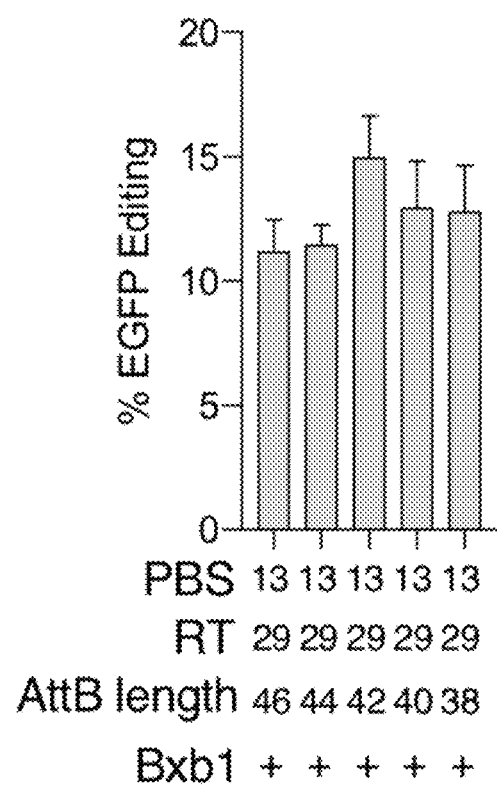
FIG. 25B shows the integration of EGFP at the LMNB1 loci with different PBS and RT lengths according to embodiments of the present teachings.
Figure 25C:
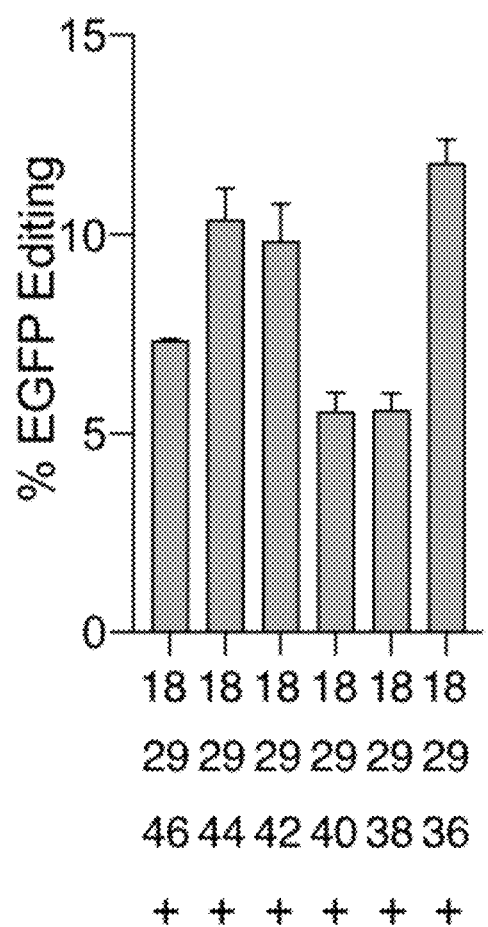
FIG. 25C shows the integration of EGFP at the NOLC1 loci with different PBS and RT lengths according to embodiments of the present teachings.
Figure 25D:
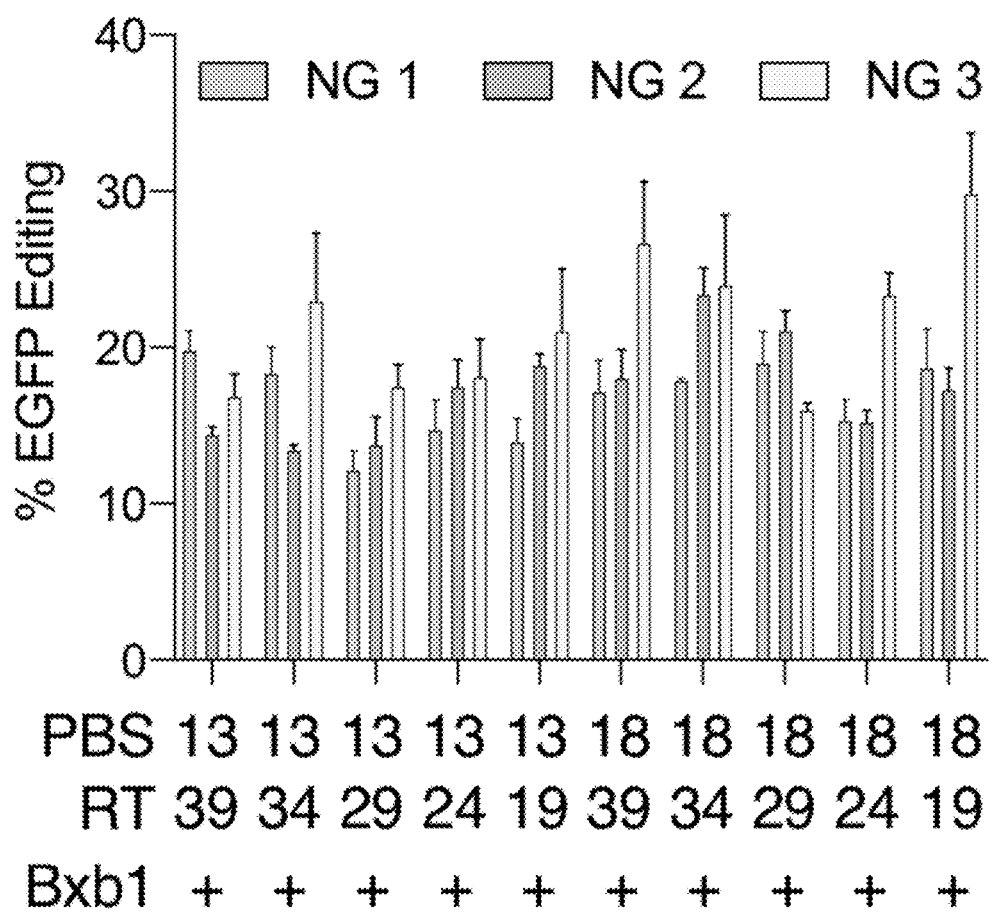
FIG. 25D shows the integration of EGFP at the GRSF1 locus with different PBS and RT lengths and different nicking guides according to embodiments of the present teachings.
Figure 25E:
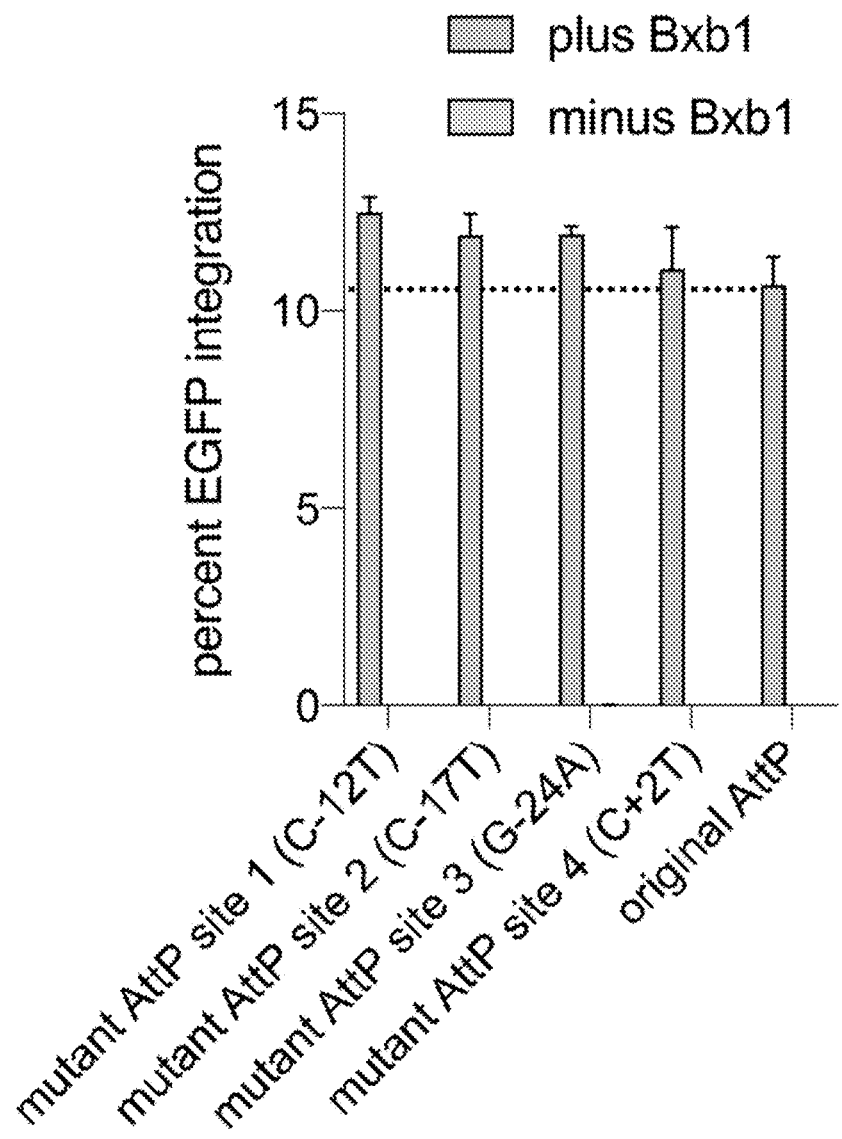
FIG. 25E shows EGFP integration with mutant attP sites according to embodiments of the present teachings.
Figure 25F:
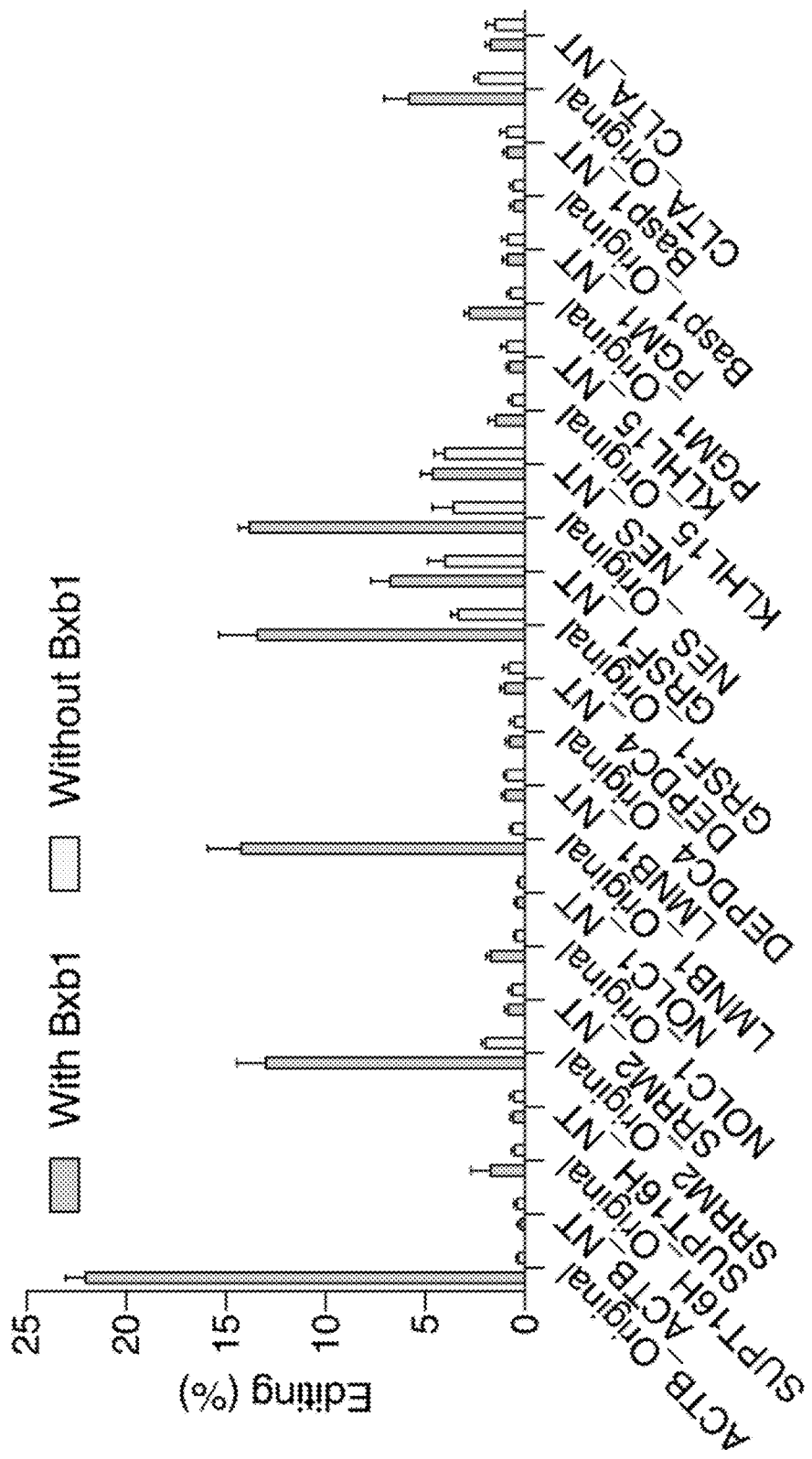
FIG. 25F shows the PASTE editing of an expanded panel of genes according to embodiments of the present teachings.

Effect of the pegRNA PBS and RT Lengths on the Prime Editing Integration Efficiency The effect of the pegRNA PBS and RT lengths on the prime editing integration efficiency was evaluated (FIGS. 25A-25F). It was found that PASTE can be optimized by tuning the PBS and RT lengths at the ACTB locus to achieve editing rates up to about 20% (FIG. 25A). It was found that shortening the attB site can help improve PASTE function as Prime is better at inserting shorter sequences. Further optimization of PBS, RT, and attB lengths showed that optimal designs can be found for insertion upstream of the LMNB1, NOLC1, and GRSF1 loci (FIGS. 25B, 25C, and 25D). Lengths as short as 36nt for attB were found to be still functional for integration into a reporter plasmid (FIGS. 25B and 25C). It was found that the reverse complemented version of the attB sequence was better integrated via Prime editing, suggesting that the sequence of what Prime is inserting matters. EGFP integrations with attP site mutants showed that certain mutants can improve integration efficiency significantly (FIG. 25E). PASTE was also performed with a large panel of genes, inserting EGFP at the N-terminus of ACTB, LMNB1, SUPT16H, SRRM2, NOLC1, KLHL15, GRSF1, DEPDC4, NES, PGM1, CLTA, BASP1, and DNAJC18 (FIG. 25F). Editing rates that are about 5%-40% were found using digital droplet PCR (ddPCR).

Example 15

Comparison of PASTE and HITI On-Target and Off-Target Activities

Figure 26A:
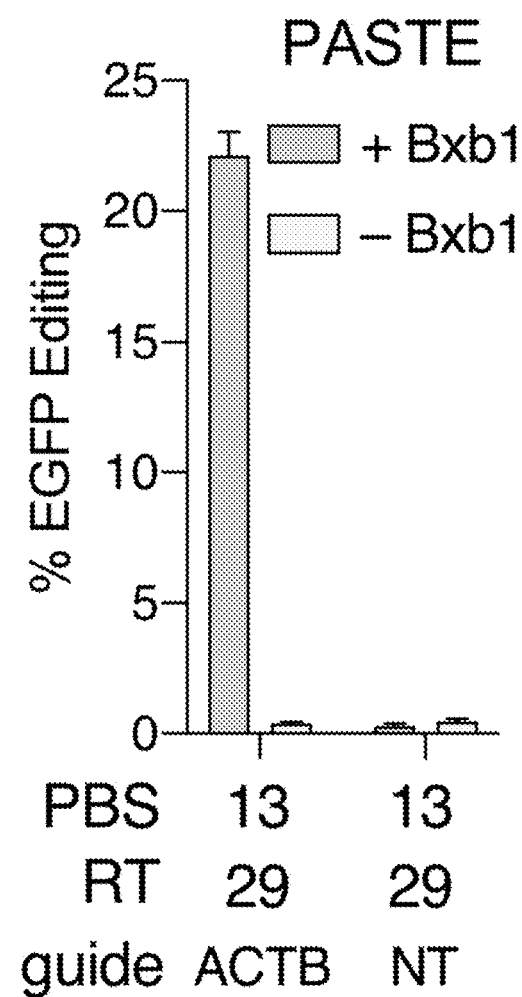
FIG. 26A shows the PASTE EGPF editing at the ACTB locus according to embodiments of the present teachings.
Figure 26B:
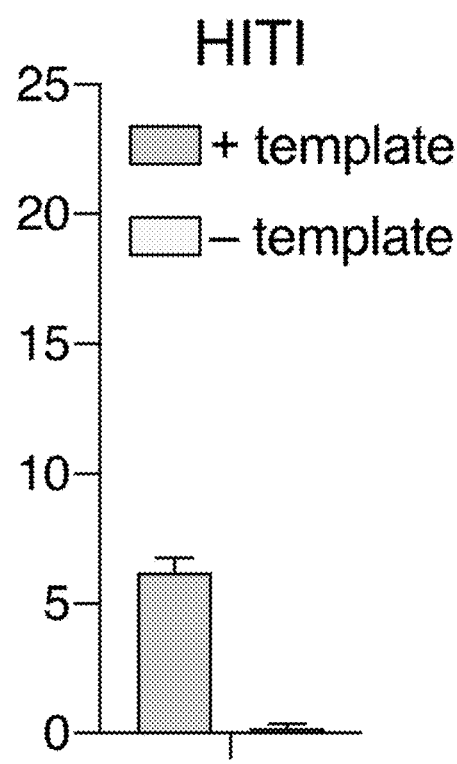
FIG. 26B shows the HITI EGPF editing at the ACTB locus according to embodiments of the present teachings.
Figure 26C:
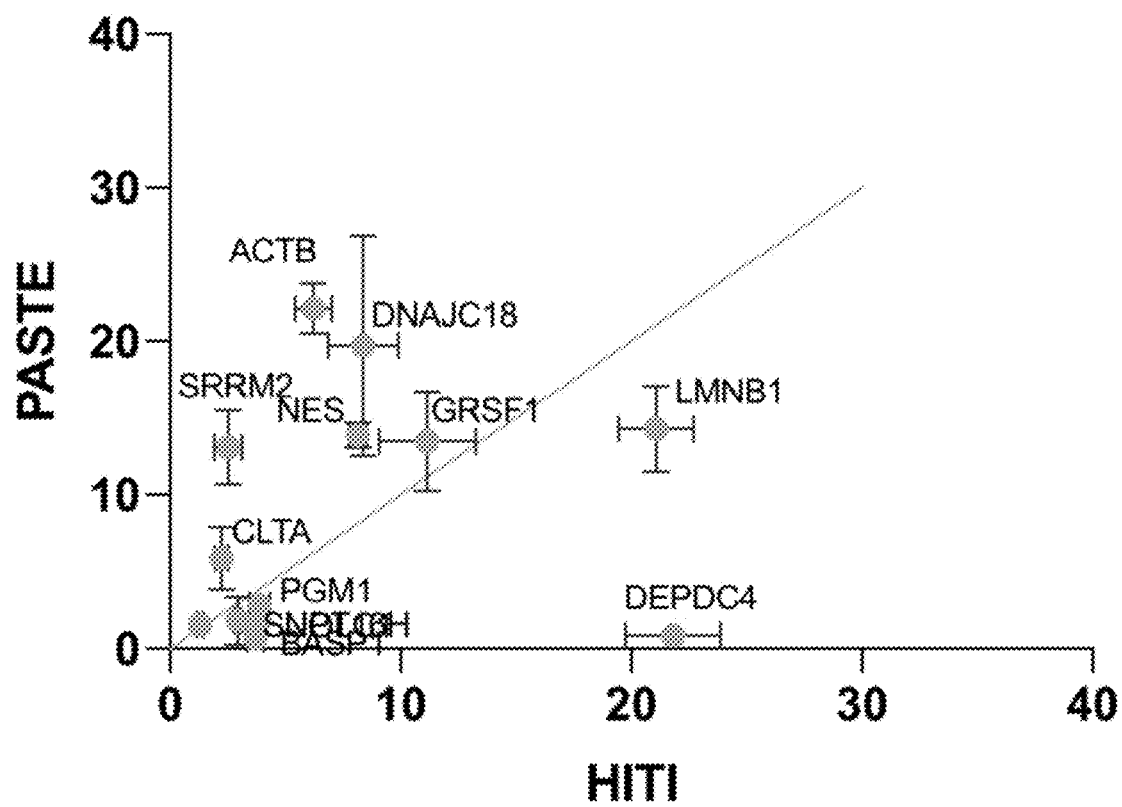
FIG. 26C shows the comparison between the PASTE and HITI editing a panel of 14 genes according to embodiments of the present teachings.
Figure 26D:
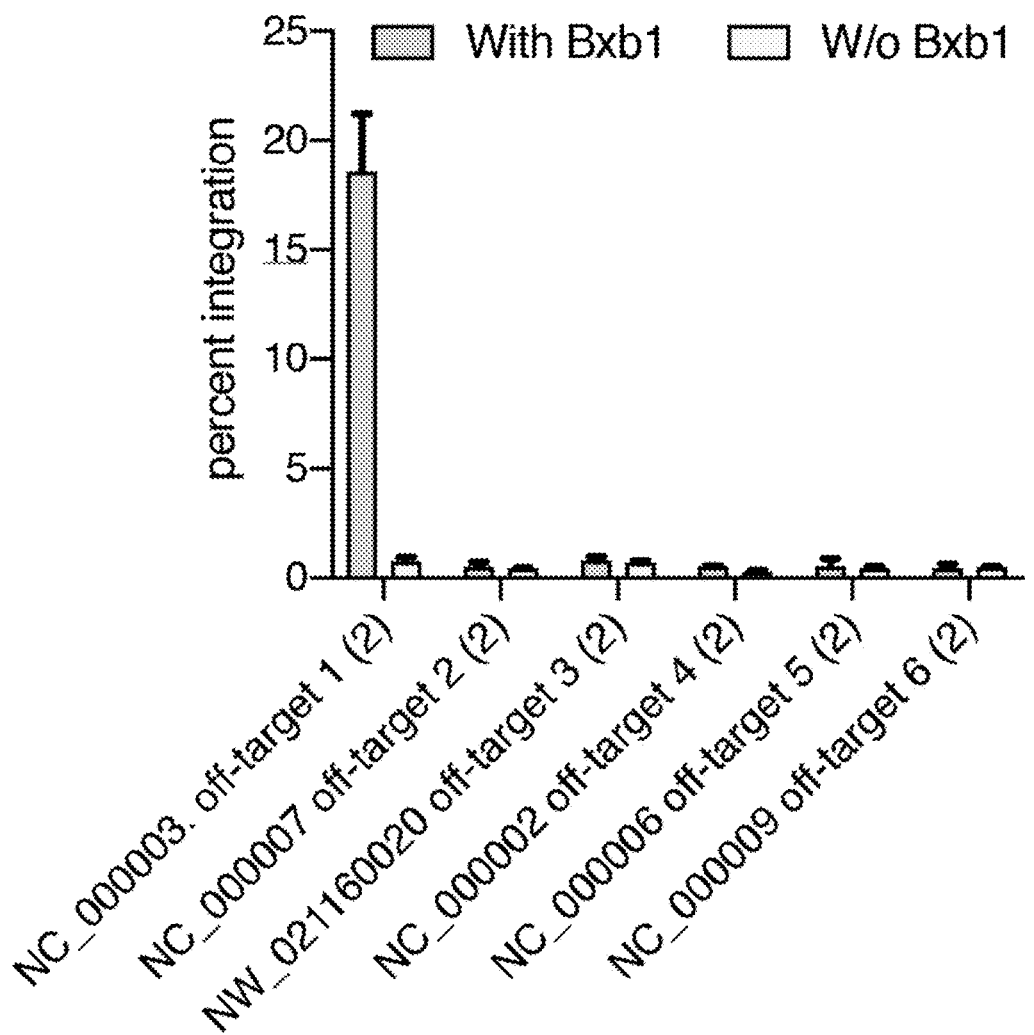
FIG. 26D shows PASTE Bxb1 off-target integrations according to embodiments of the present teachings.
Figure 26E:
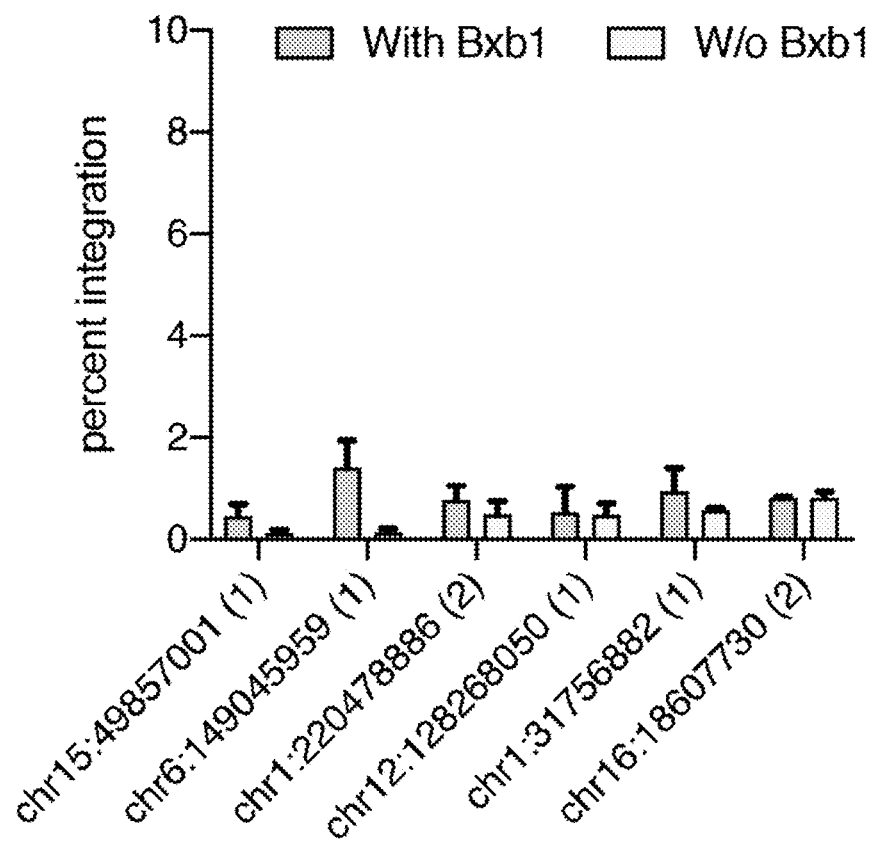
FIG. 26E shows PASTE Cas9 off-target integrations according to embodiments of the present teachings.
Figure 26F:
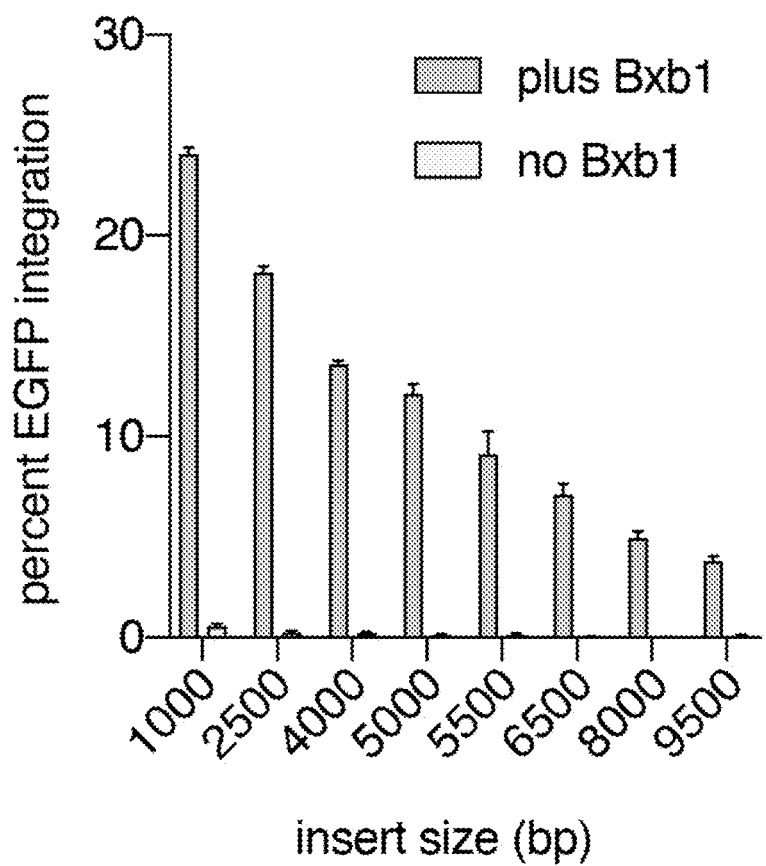
FIG. 26F shows the EGFP integration for gene inserts of different sizes according to embodiments of the present teachings.
Figure 27A:
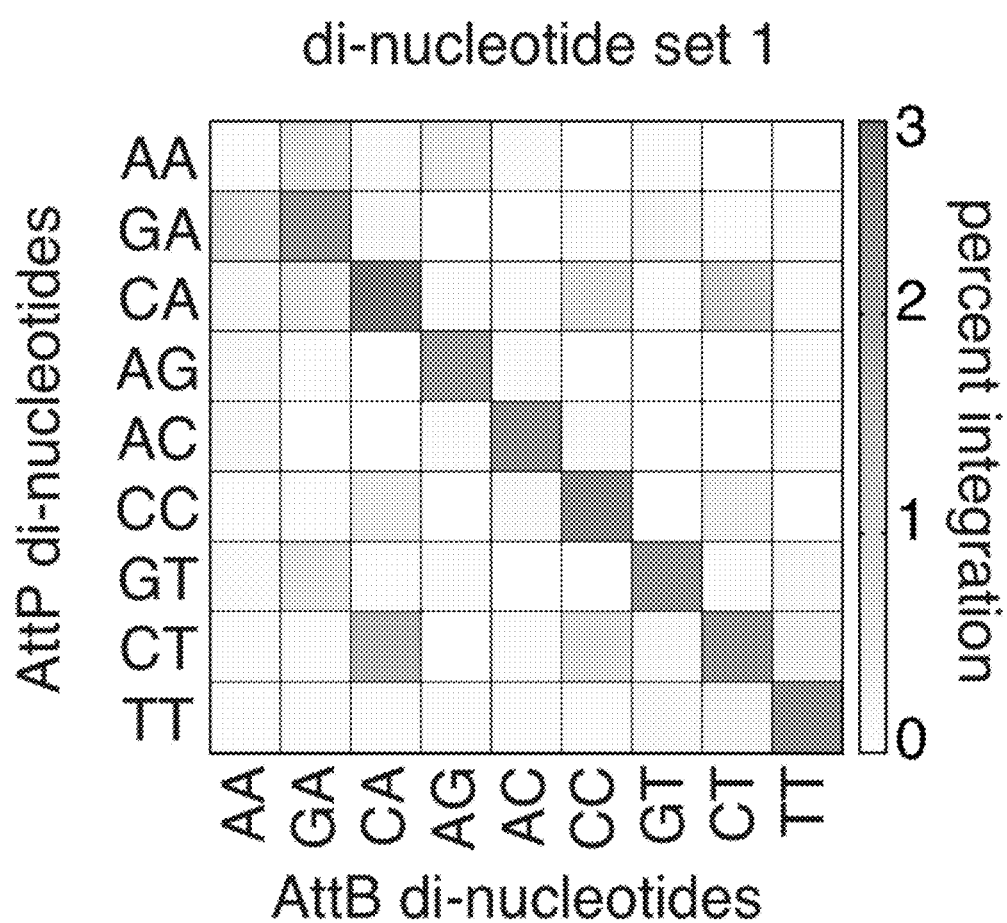
FIG. 27A shows the orthogonality between selected sets of attB and attP sites according to embodiments of the present teachings.
Figure 27B:
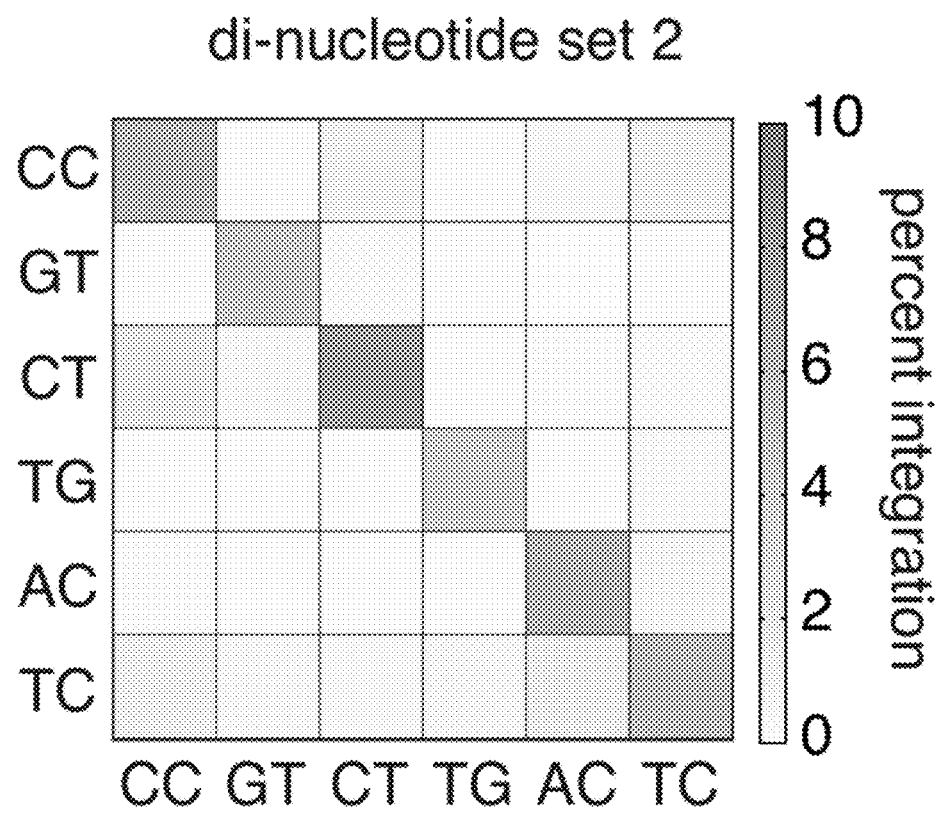
FIG. 27B shows the orthogonality between selected sets of attB and attP sites according to embodiments of the present teachings.
Figure 27C:
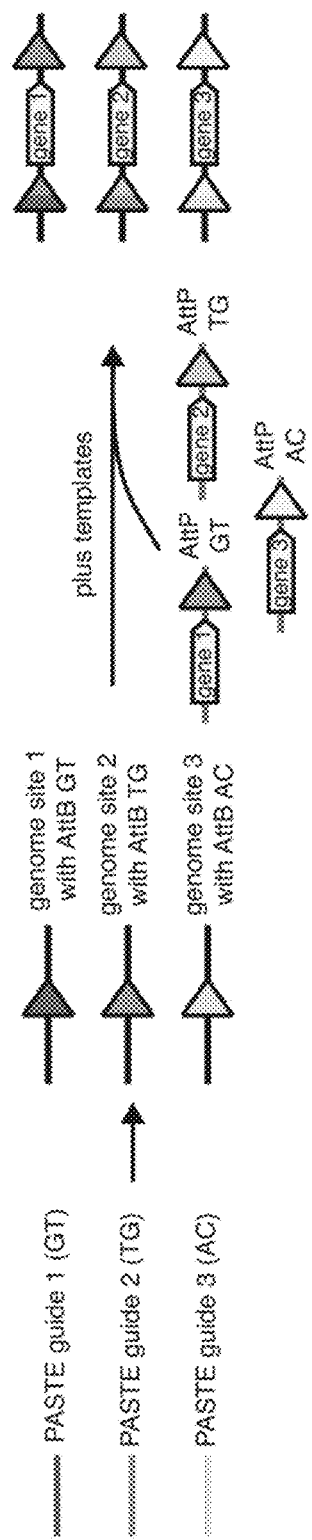
FIG. 27C shows a schematic for the orthogonal PASTE editing using engineered di-nucleotide combinations according to embodiments of the present teachings.

The PASTE and HITI on-target and off-target activities were compared (FIGS. 26A-26F). PASTE and HITI were found to have about 22% and 5% integration efficiencies respectively when using the same guide sequence (FIGS. 26A and 26B). PASTE was found to outperform HITI at most sites when analyzing the editing of 14 genes (FIG. 26C). Using a ddPCR based approach, it was found that PASTE was very specific with minimal off-target activity for Bxb1 off-targets integrations (FIG. 26D) and Cas9 off-targets integrations (FIG. 26E). The analysis of inserts of different sizes showed that PASTE can reliably insert sequences 1kb-10 kb in size (FIG. 26F), revealing the wide range of sequence sizes PASTE is capable of working with. A decrease in insertion efficiency at larger sizes was also observed, which was likely due to the reduction in plasmid delivery to HEK293FT cells at larger plasmid sizes.

Example 16

Multiplexing with PASTE and Orthogonal Di-Nucleotide attB and attP Sites

Multiplexing with PASTE and orthogonal di-nucleotide attB and attP sites was evaluated (FIGS. 28A-28C). Multiple orthogonal combinations were found for mutants of the central di-nucleotide motif (FIGS. 28A and 28B). As illustrated in FIG. 28C, programmable multiplexed gene insertion can be achieved by using these orthogonal combinations with PASTE only delivering different pegRNAs and gene inserts while keeping the protein components the same (FIG. 8C).

Example 17

PASTE Multiplexed Integrations at Endogenous Sites

Figure 28D:
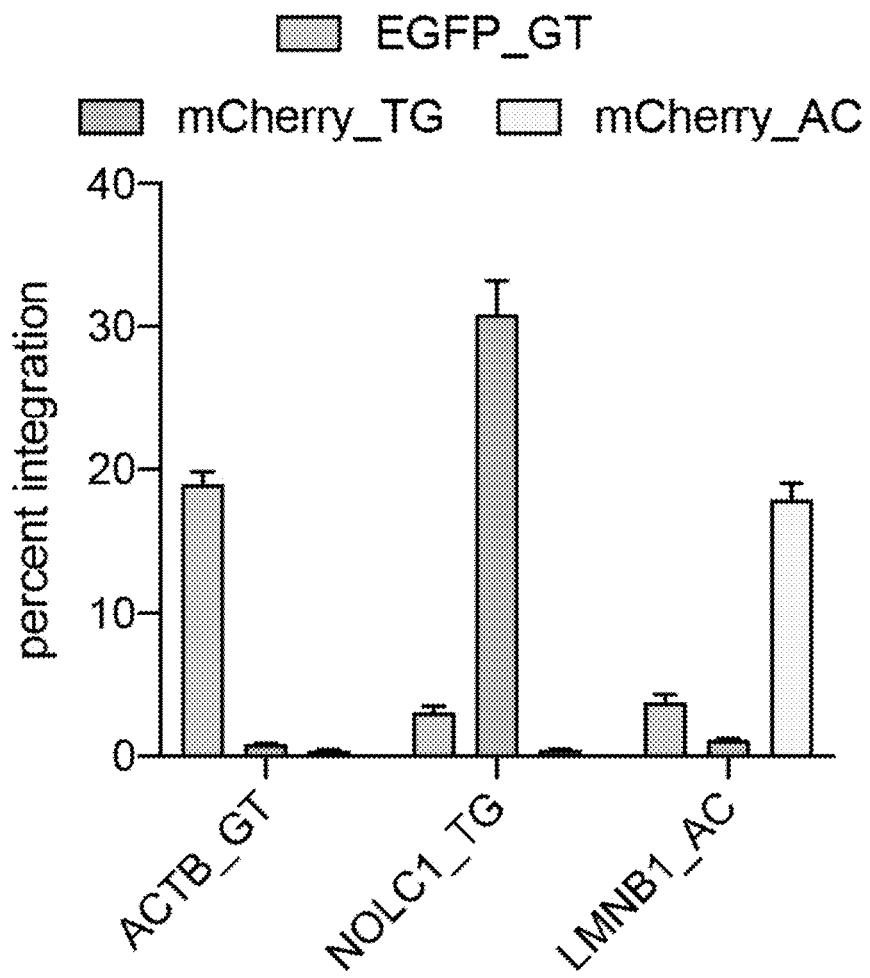
FIG. 28D shows the orthogonal gene integration at three endogenous sites with PASTE according to embodiments of the present teachings.
Figure 28E:
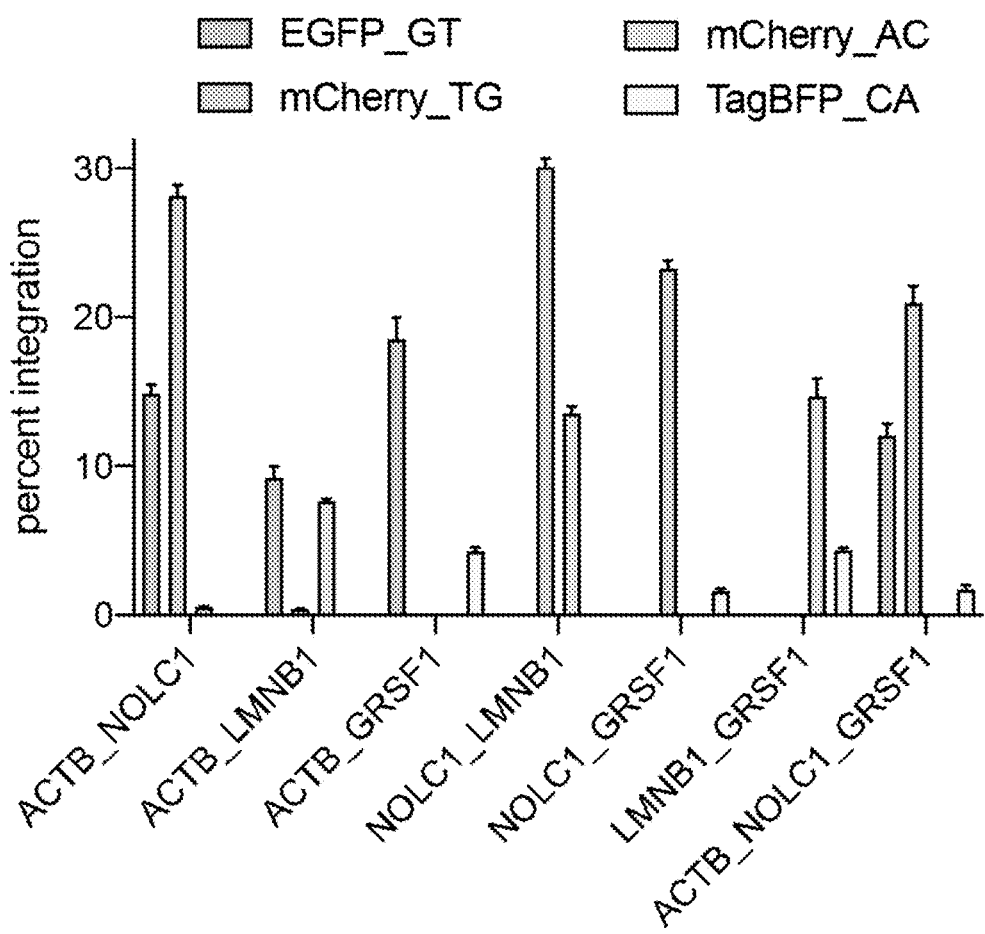
FIG. 28E shows the multiplexed insertion via one-plex, two-plex, and three-plex gene insertion at three endogenous sites via PASTE according to embodiments of the present teachings.

PASTE multiplexed integrations at endogenous sites were evaluated (FIGS. 28A-28G). A reading frame for the attR scar that is left post-integration by Bxb1 that is ideal for a protein linker due to the enrichment of glycines, serines, and prolines in the sequence (GLSGQPPRSPSSGSSG (SEQ ID NO: 426)) was identified. PegRNAs were designed using this linker frame for the resolution of the attR for tagging a number of genes at the N-terminus with EGFP (ACTB, NOLC1, LMNB1, SUPT16H, SRRM2, and DEPDC4). As these genes all have distinct protein localization appearances, microscopy can be used for ascertaining proper gene tagging. PASTE was found to be capable of high-efficiency gene tagging with protein localizations that match the reference images and expected localization of the proteins in the cells (FIGS. 28A-28C). Genes were also tagged in multiplexed fashion to demonstrate the orthogonality of the engineered integration sites. ACTB, LMNB1, NOLC1, and GRSF were targeted with orthogonal pegRNAs carrying GT, TG, AC, and CA, respectively in HEK293FT in groups of single, dual-plexing, and triple-plexing (FIGS. 28D-28E). These dinucleotides were paired with templates carrying EGFP, BFP, and mCherry to allow for multicolor imaging of these labeled genes. The efficiencies of integration for these multiplexing experiments were found to range from about 5%-32%, revealing efficient multiplex integration with PASTE. Using confocal microscopy of these multiplexed integration experiments, cells were found with simultaneous labeling of these different proteins (FIGS. 28F-28G).

Example 18

Combination of CRISPR-Based Genome Editing and Site-Specific Integration

The combination of CRISPR-based genome editing and site-specific integration was evaluated.

Figure 29A:
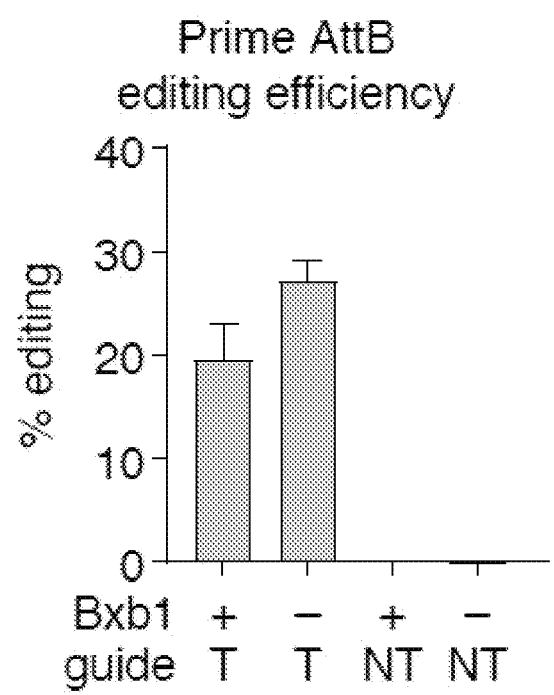
FIG. 29A shows the prime editing efficiency of Bxb1 attB site insertion at the ACTB locus according to embodiments of the present teachings.
Figure 29B:
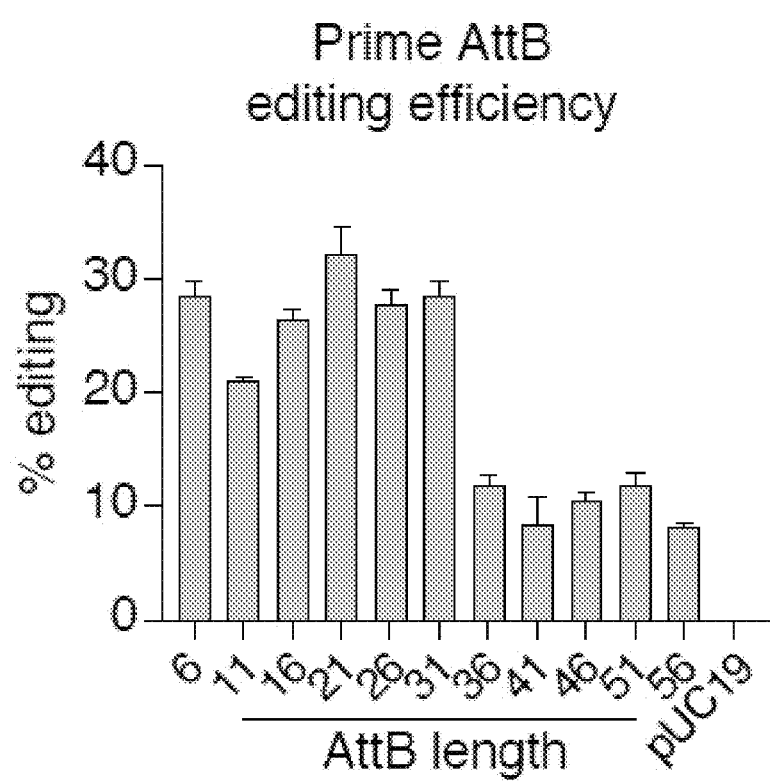
FIG. 29B shows the prime editing efficiency at inserting Bxb1 attB sites of different lengths at the ACTB locus according to embodiments of the present teachings.
Figure 29C:
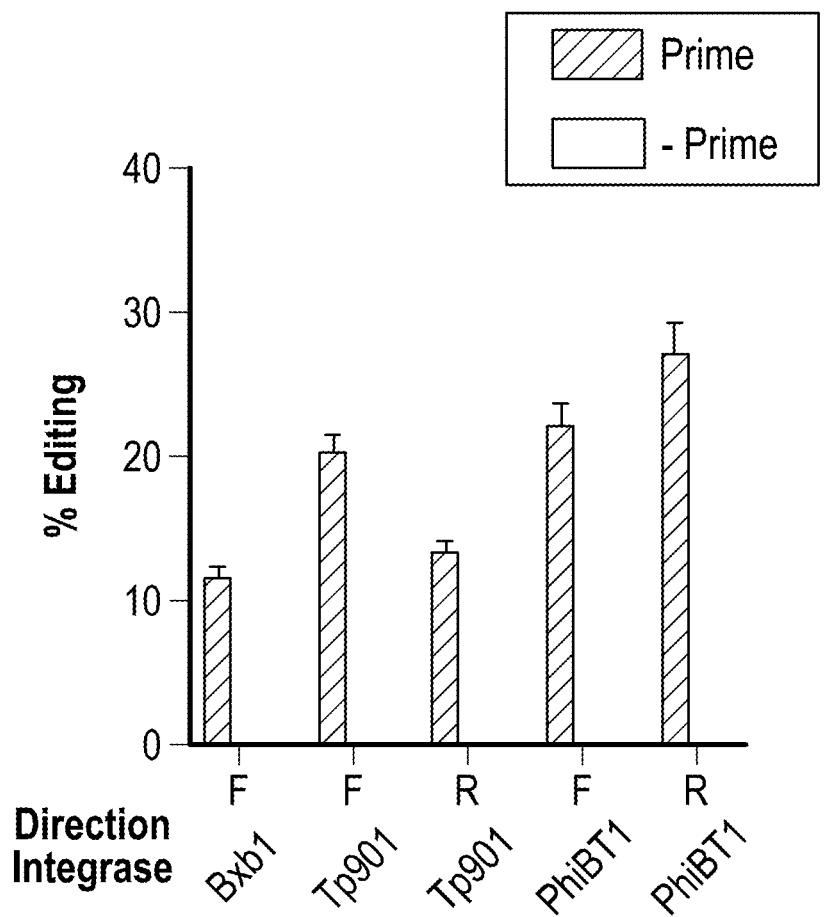
FIG. 29C shows the prime editing efficiency of inserting attB sequences from different integrases, wherein both orientations of landing sites are profiled (F, forward; and R, reverse) according to embodiments of the present teachings.
Figure 29D:
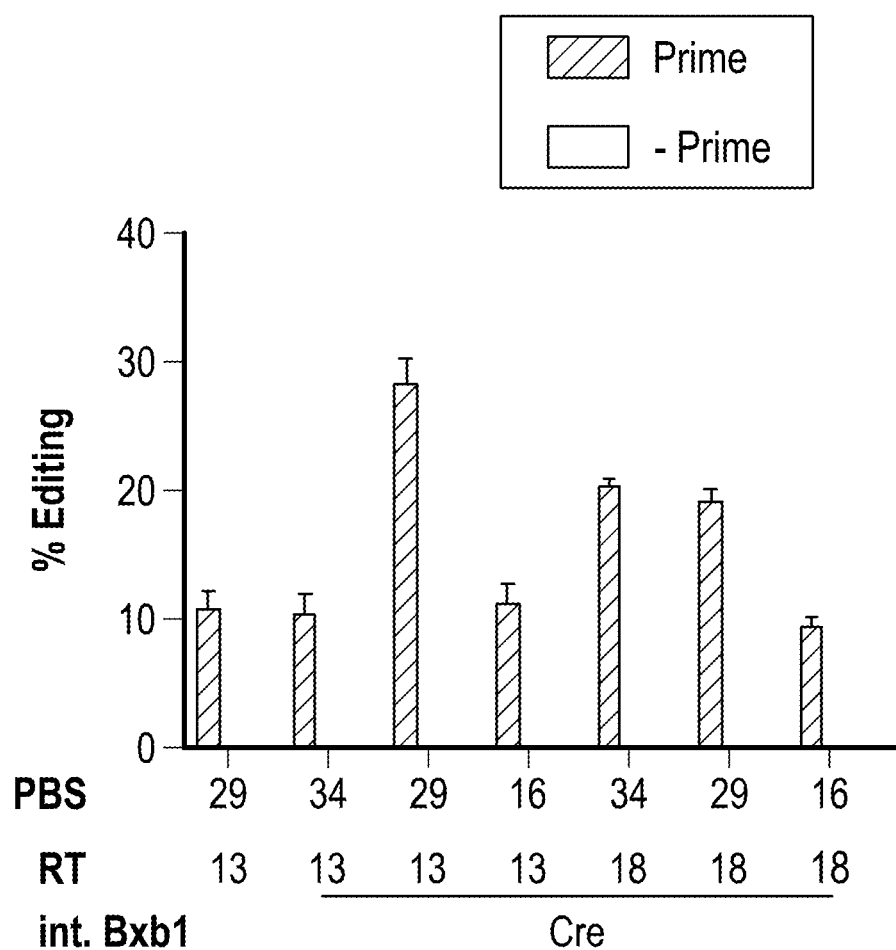
FIG. 29D shows the prime editing efficiency of inserting attB sequences from Bxb1 integrase and Cre recombinase, wherein both orientations of landing sites are profiled (F, forward; and R, reverse) according to embodiments of the present teachings.
Figure 29E:
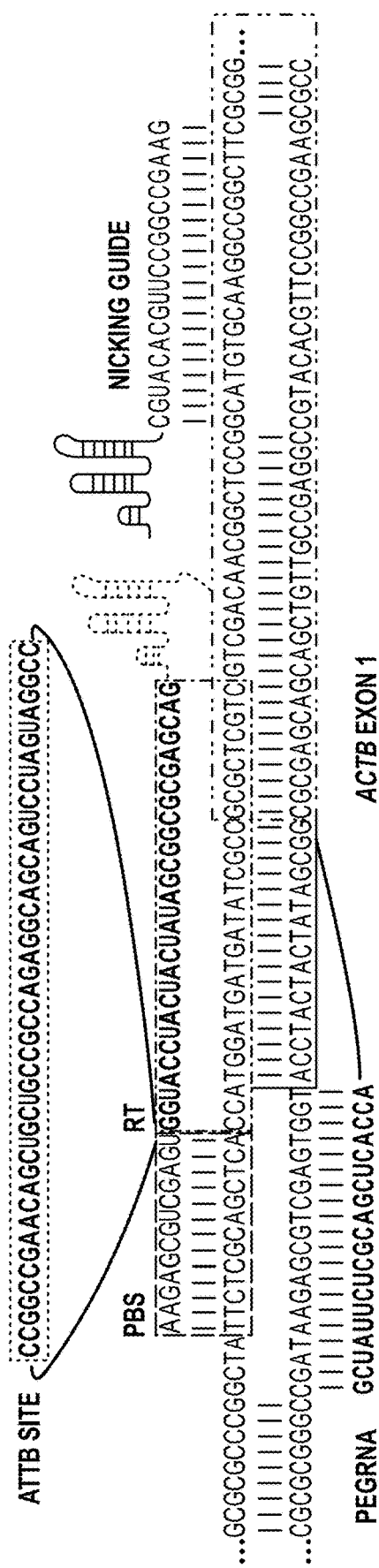
FIG. 29E shows a schematic of PASTE insertion at the ACTB locus showing guide and target sequences according to embodiments of the present teachings.
Figure 29F:
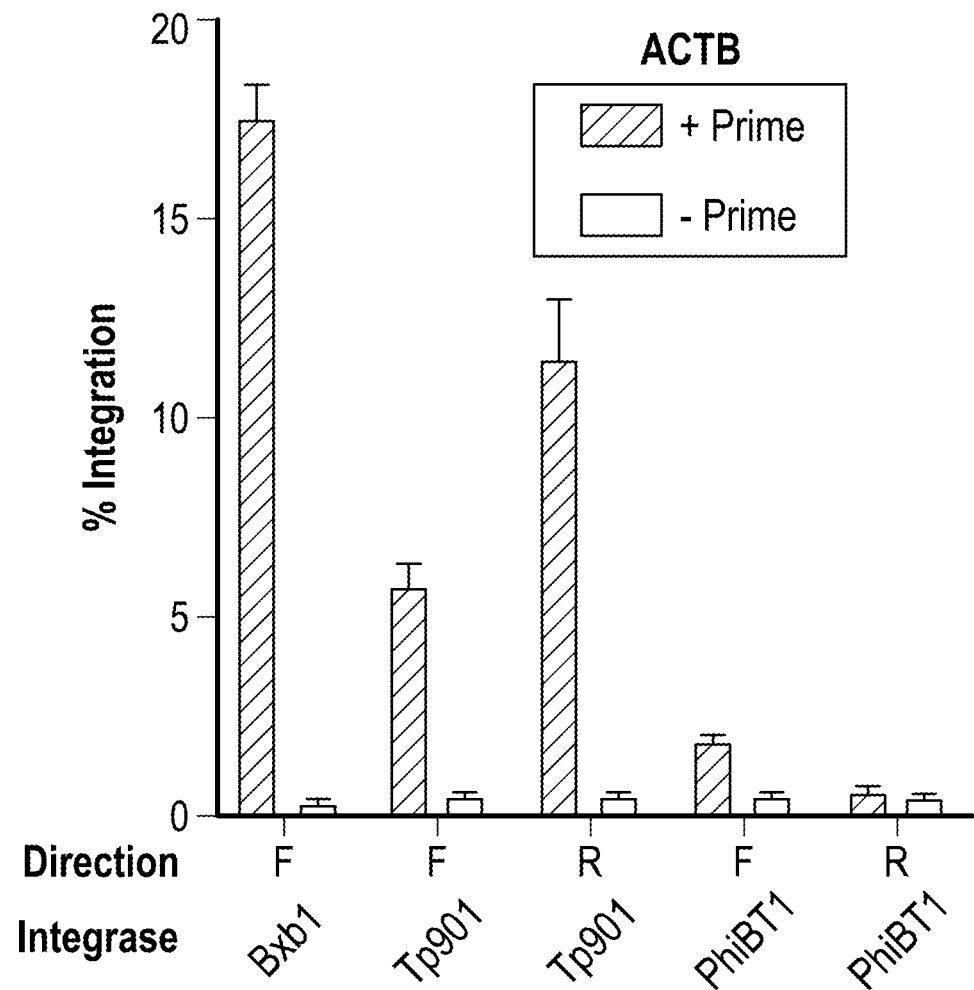
FIG. 29F shows a comparison of PASTE integration efficiency of GFP with a panel of integrases targeting the 5' end of the ACTB locus, wherein both orientations of landing sites are profiled (F, forward; and R, reverse) according to embodiments of the present teachings.
Figure 29G:
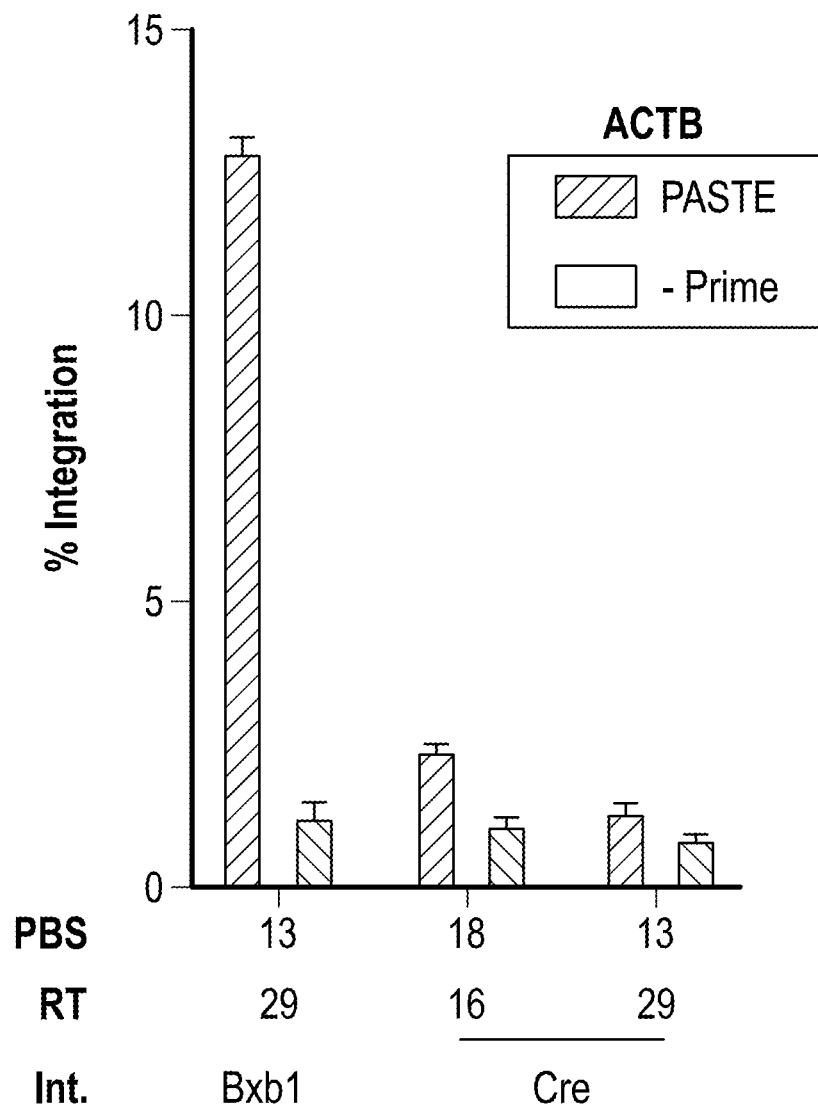
FIG. 29G shows a comparison of GFP cargo integration efficiency between Bxb1 integrases and Cre recombinase according to embodiments of the present teachings.
Figure 29H:
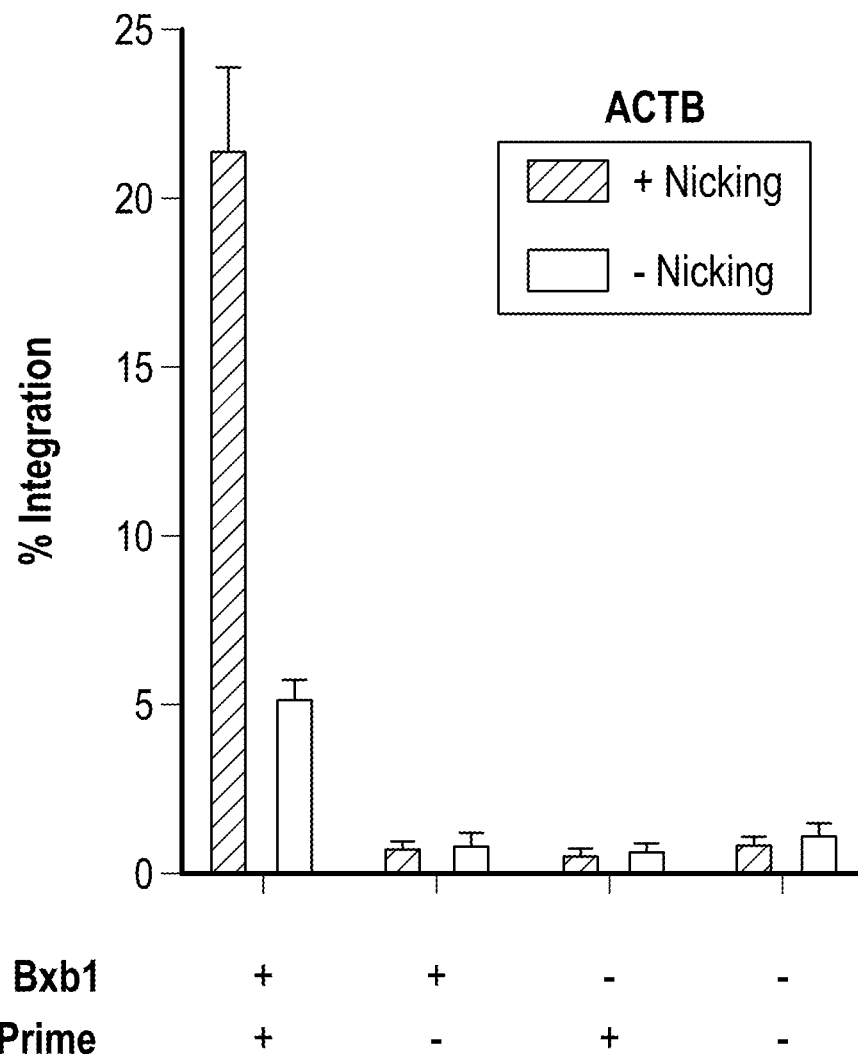
FIG. 29H shows the dependence of PASTE editing activity on different prime and integrase components according to embodiments of the present teachings.
Figure 29I:
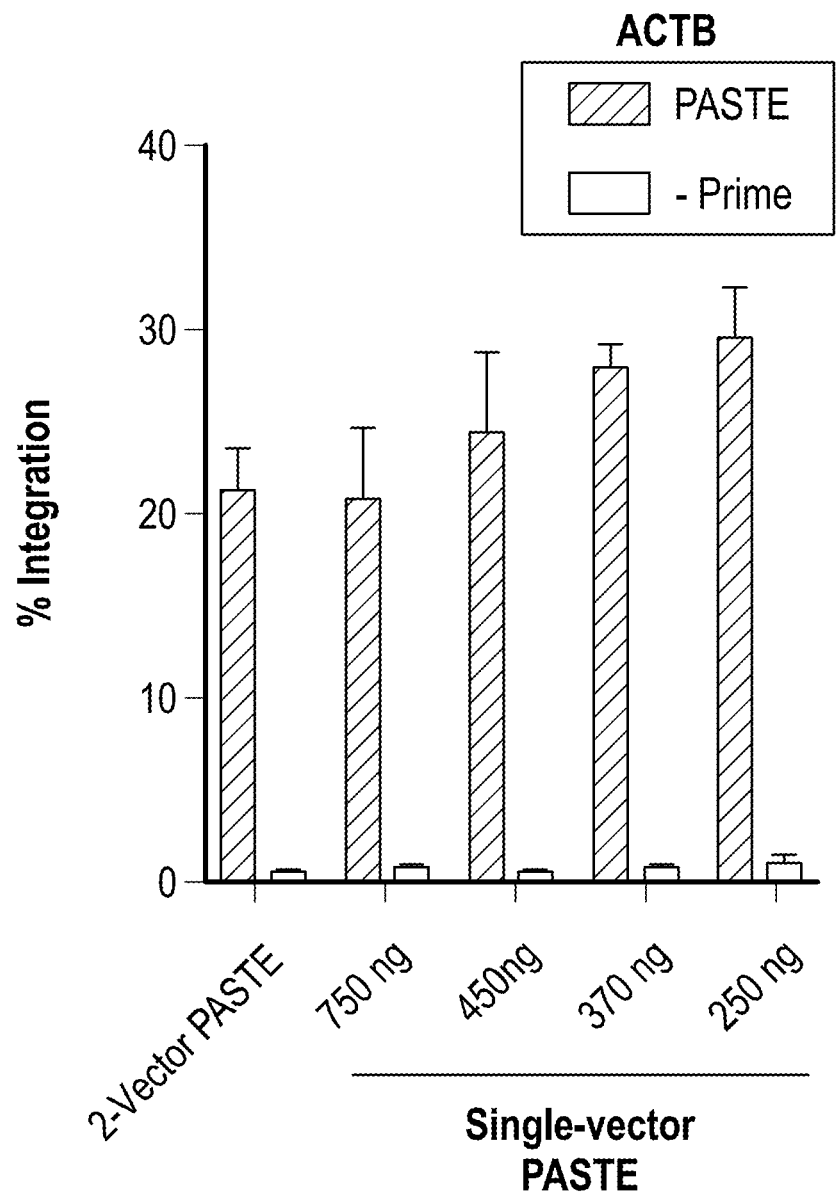
FIG. 29I shows a titration of a single vector PASTE system (SpCas9-RT-P2A-Bxb1) on integrase efficiency according to embodiments of the present teachings.
Figure 29J:
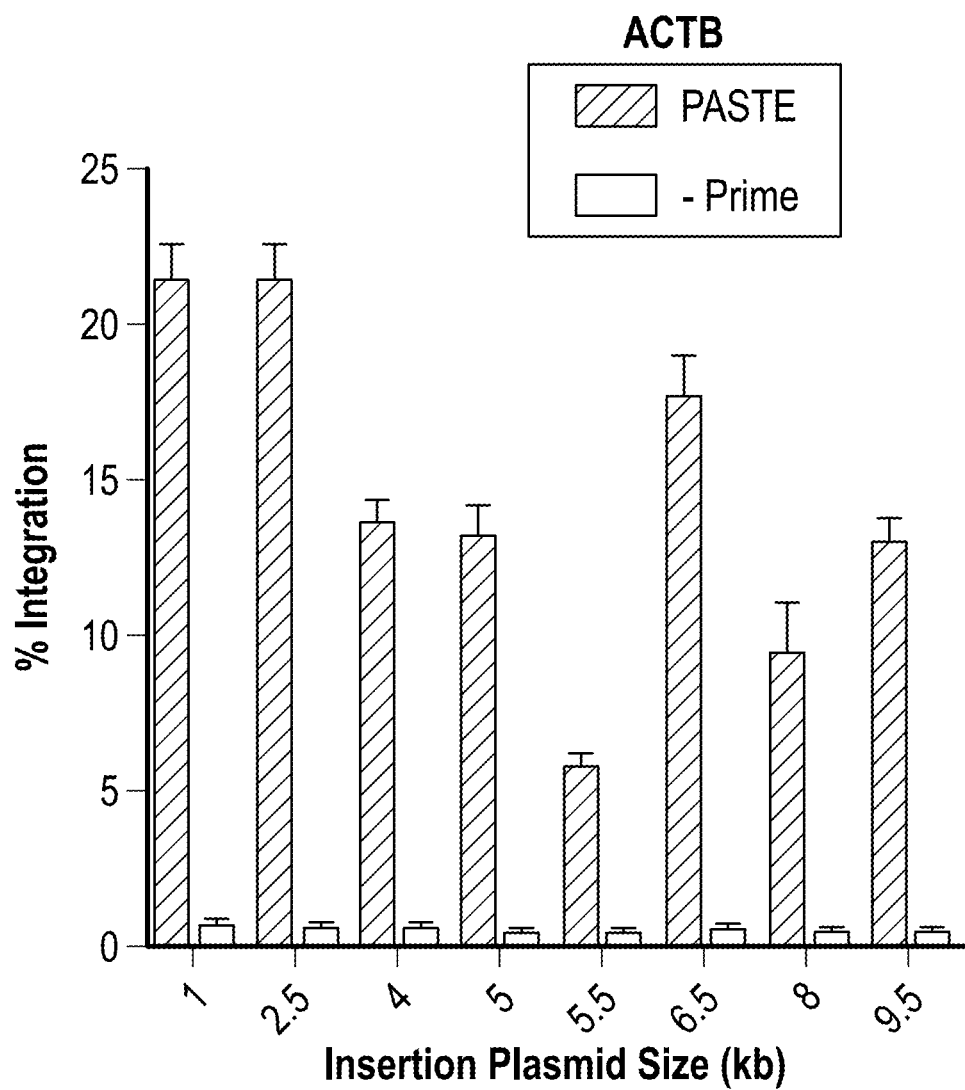
FIG. 29J shows the effect of cargo size on PASTE insertion efficiency at the endogenous ACTB target according to embodiments of the present teachings.
Figure 29K:
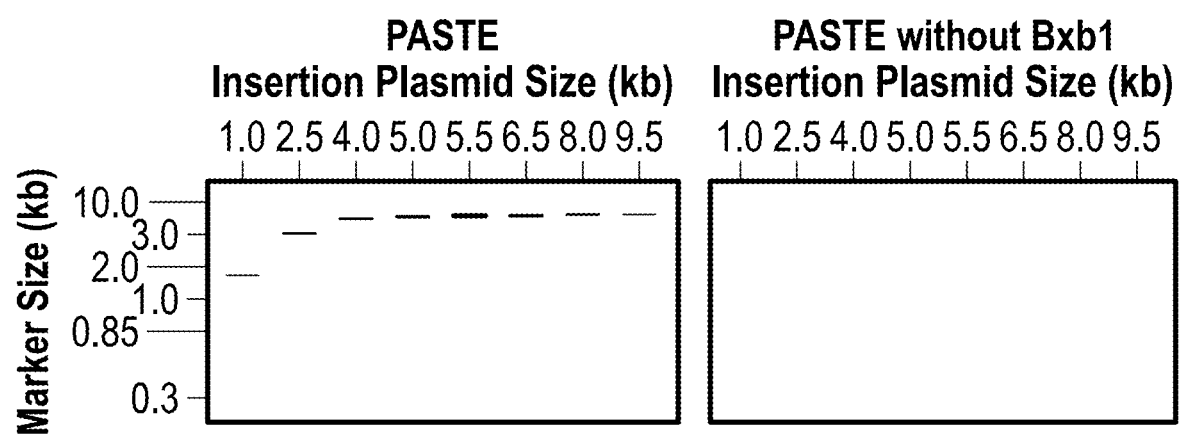
FIG. 29K shows a gel electrophoresis showing complete insertion by PASTE for multiple cargo sizes according to embodiments of the present teachings.
Figure 30A:
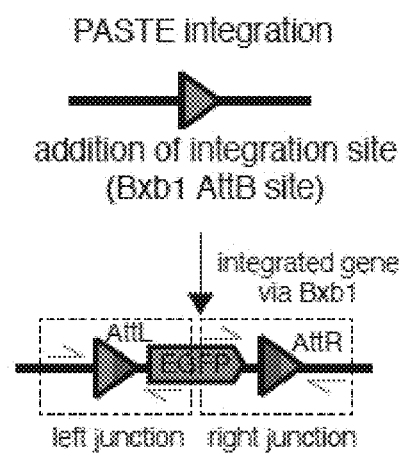
FIG. 30A shows a schematic of PASTE integration, including resulting attR and attL sites that are generated and PCR primers for assaying the integration junctions according to embodiments of the present teachings.
Figure 30B:
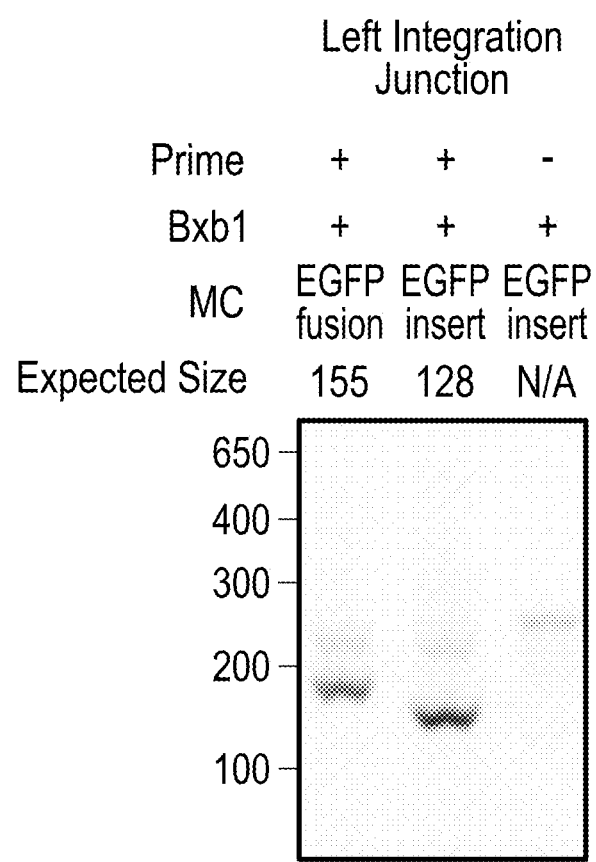
FIG. 30B shows a PCR and gel electrophoresis readout of left integration junction from PASTE insertion of GFP at the ACTB locus, wherein the insertion is analyzed for in-frame and out-of-frame GFP integration experiments as well as for a no prime control and expected sizes of the PCR fragments are shown using the primers shown in the schematic in subpanel FIG. 30A according to embodiments of the present teachings.
Figure 30C:
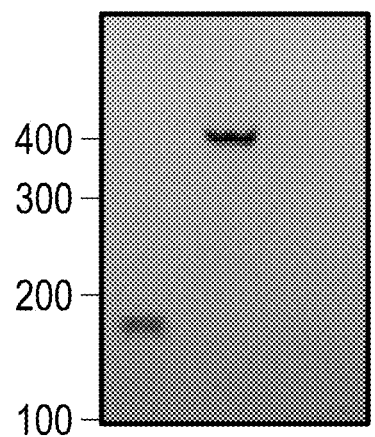
FIG. 30C shows a PCR and gel electrophoresis readout of right integration junction from PASTE insertion of GFP at the ACTB locus, wherein the insertion is analyzed for in-frame and out-of-frame GFP integration experiments as well as for a no prime control and the expected sizes of the PCR fragments are shown using the primers shown in the schematic in subpanel FIG. 30A according to embodiments of the present teachings.
Figure 30D:
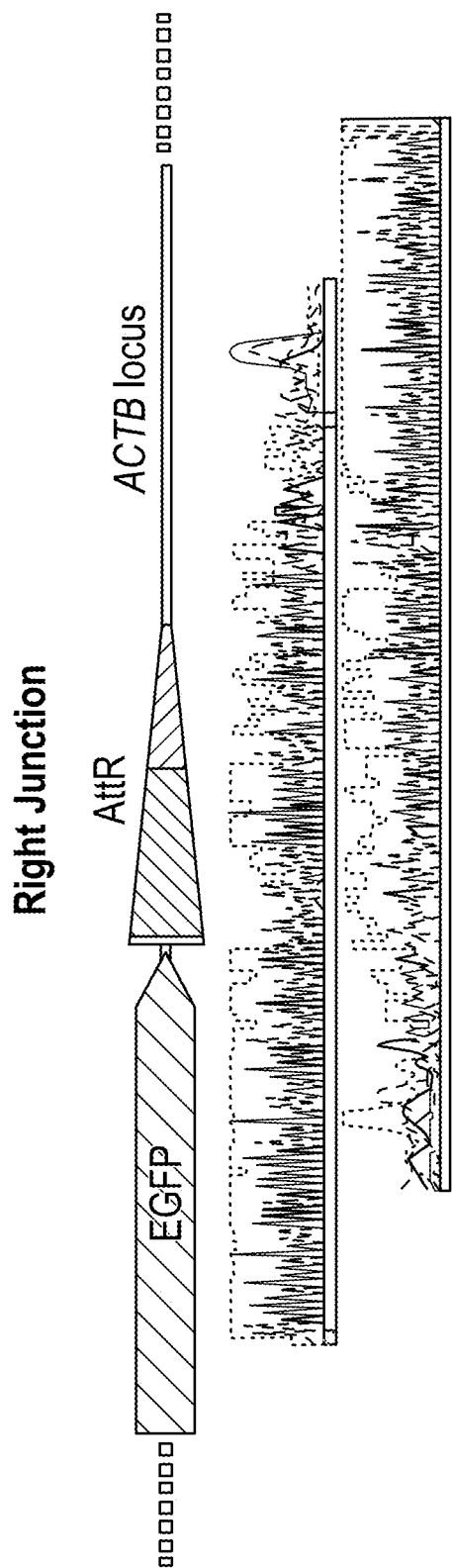
FIG. 30D shows a Sanger sequencing shown for the right integration junction for an in-frame fusion of GFP via PASTE to the N-terminus of ACTB according to embodiments of the present teachings.
Figure 30E:
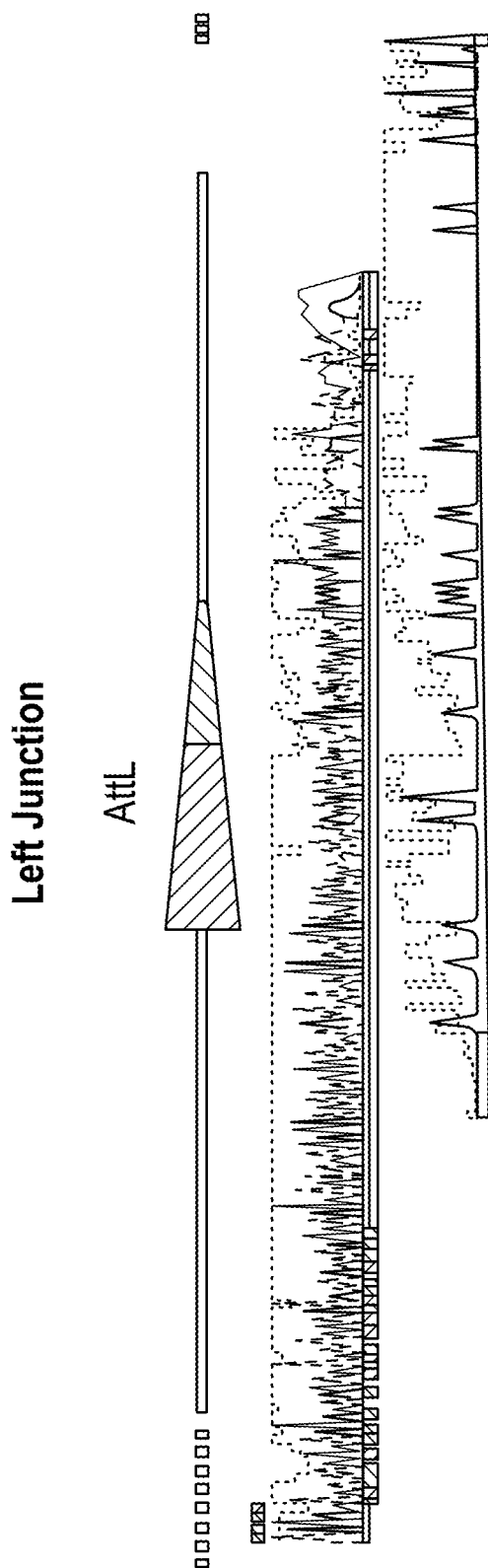
FIG. 30E shows a Sanger sequencing shown for the left integration junction for an in-frame fusion of GFP via PASTE to the N-terminus of ACTB according to embodiments of the present teachings.

PegRNAs containing different attB length truncations were assessed (FIG. 29A). Prime editing was found to be capable of inserting sequences up to 56 bp at the beta-actin (ACTB) gene locus, with higher efficiency at lengths below 31 bp (FIGS. 29A-B) The integration of cognate landing sites was tested for multiple insertion enzymes: Bxb1, TP901, and phiBTI phage serine integrases and Cre recombinase. Prime editing successfully inserted all landing sites tested, with efficiencies between 10-30% (FIGS. 29C-D). To test the complete system, all components were combined and delivered in a single transfection: the prime editing vector, the landing site containing pegRNA, a nicking guide for stimulating prime editing, a mammalian expression vector for the corresponding integrase or recombinase and a 969 bp minicircle DNA cargo encoding green fluorescent protein (GFP) (FIG. 29E). GFP integration rates among the four integrases and recombinases were compared and Bxb1 integrase was found to have the highest integration rate (~20%) at the targeted ACTB locus and require the prime editing nicking guide for optimal performance (FIGS. 29F-H). Finally, to reduce the number of transfected components, Bxb1 was co-expressed with the SpCas9-M-MLV reverse transcriptase (PE2) fusion protein via a P2A protein cleavage site. This combination maintained high GFP insertion efficiency, up to 30% (FIG. 29E). The complete system, PASTE, achieved precise integration of templates as large as 9,500 bp with greater than 10% integration efficiency (FIGS. 29J-K and 26E), with complete integration of the full-length cargo confirmed by Sanger sequencing (FIG. 30A-E).

Example 19

Impact of Prime Editing and Integrase Parameters on PRIME Editing

The impact of prime editing and integrase parameters on the integration efficiency of PRIME editing was assessed.

Figure 31B:
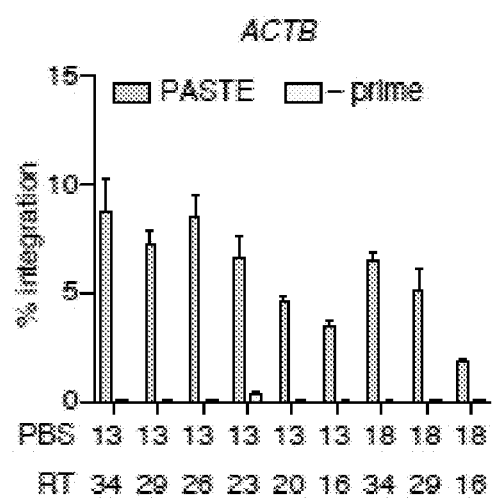
FIG. 31B shows the impact of PBS and RT length on PASTE integration of GFP at the ACTB locus according to embodiments of the present teachings.
Figure 31C:
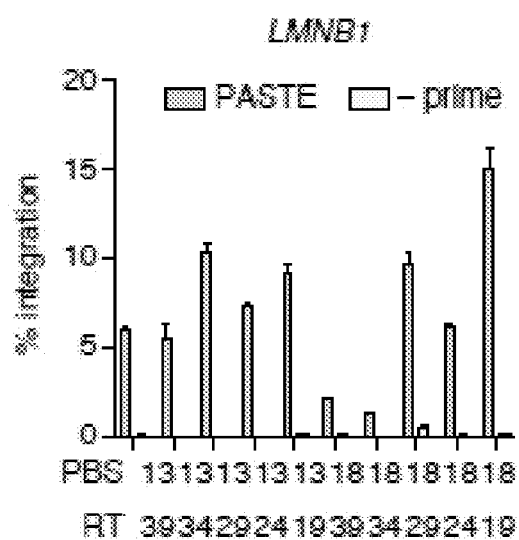
FIG. 31C shows the impact of PBS and RT length on PASTE integration of GFP at the LMNB1 locus according to embodiments of the present teachings.

Relevant pegRNA parameters for PASTE include the primer binding site (PBS), reverse transcription template (RT), and attB site lengths, as well as the relative locations and efficacy of the pegRNA spacer and nicking guide (FIG. 31A). A range of PBS and RT lengths were tested at two loci, ACTB and lamin B1 (LMNB1), and rules governing efficiency were found to vary between loci, with shorter PBS lengths and longer RT designs having higher editing at the ACTB locus (FIG. 31B) and longer PBS and shorter RT designs performing better at LMNB1 (FIG. 31C).

Figure 31D:
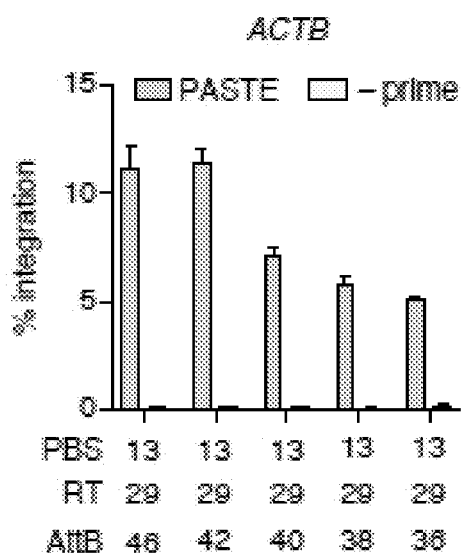
FIG. 31D shows the impact of attB length on PASTE integration of GFP at the ACTB locus according to embodiments of the present teachings.
Figure 31E:
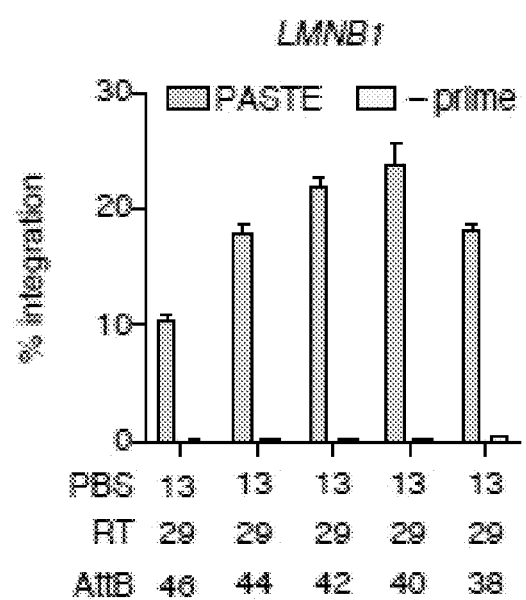
FIG. 31E shows the impact of attB length on PASTE integration of GFP at the LMNB1 locus according to embodiments of the present teachings.
Figure 31F:
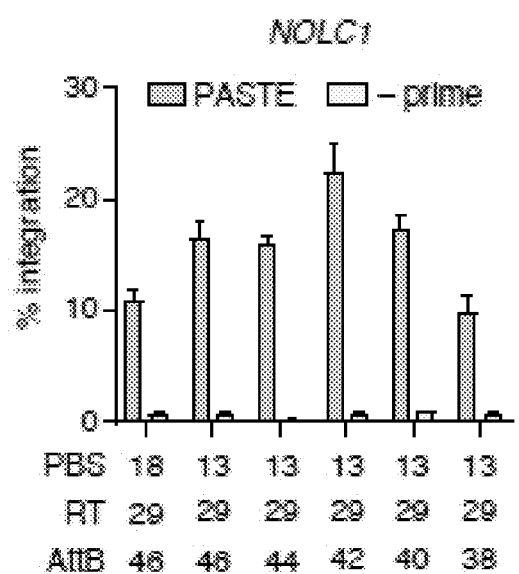
FIG. 31F shows the impact of attB length on PASTE integration of GFP at the NOLC1 locus according to embodiments of the present teachings.

The length of the attB landing site must balance two conflicting factors: the higher efficiency of prime editing for smaller inserts and reduced efficiency of Bxb1 integration at shorter attB lengths. AttB lengths were evaluated at ACTB, LMNB1, and nucleolar phosphoprotein p130 (NOLC1), and the optimal attB length was found to be locus dependent. At the ACTB locus, long attB lengths could be inserted by prime editing (FIG. 29B) and overall PASTE efficiencies for the insertion of GFP were highest for long attB lengths (FIG. 31d). In contrast, intermediate attB lengths had higher overall integration efficiencies (>20%) at LMNB1 (FIG. 31E) and NOLC1 (FIG. 31F), indicating that the increased efficiency of installing shorter attB sequences overcame the reduction of Bxb1 integration at these sites.

Figure 32A:
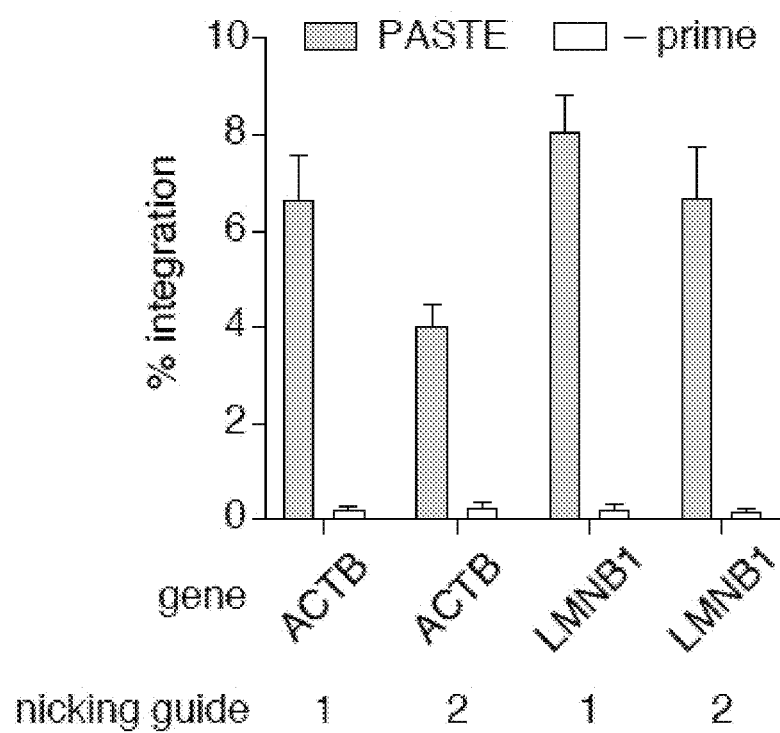
FIG. 32A shows the PASTE insertion efficiency at ACTB and LAMNB loci with two different nicking guide designs according to embodiments of the present teachings.
Figure 32B:
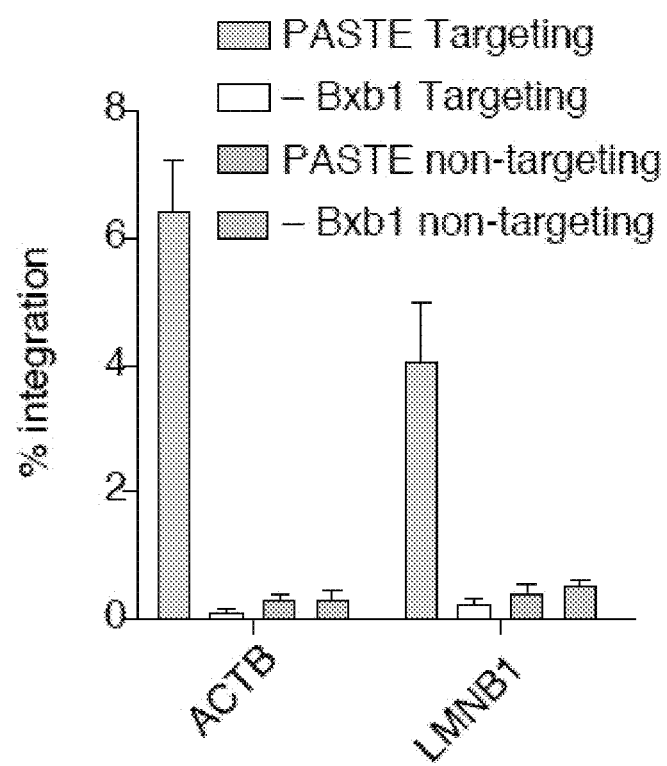
FIG. 32B shows the PASTE editing efficiency at ACTB and LMNB1 with target and non-targeting spacers and matched pegRNAs with and without Bxb1 expression according to embodiments of the present teachings.

The PE3 version of prime editing combines PE2 and an additional nicking guide to bias resolution of the flap intermediate towards insertion. To test the importance of nicking guide selection on PASTE editing, editing at ACTB and LMNB1 loci was tested with two nicking guide positions. Suboptimal nicking guide positions were found to reduce the PASTE efficiency up to 30% (FIG. 32A) in agreement with the 75% reduction of PASTE efficiency in the absence of nicking guide (FIG. 29G). The pegRNA spacer sequence was found to be necessary for PASTE editing, and substitution of the spacer sequence with a non-targeting guide was found to eliminate editing (FIG. 32B).

Figure 33A:
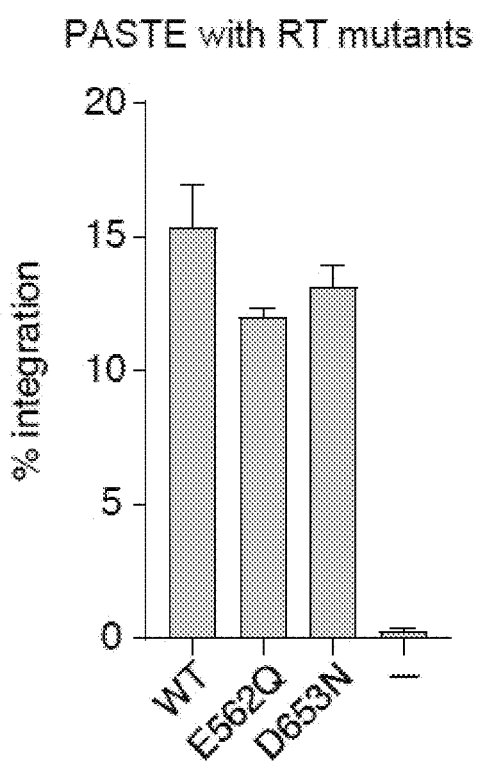
FIG. 33A shows the PASTE integration of GFP at the ACTB locus with different Bxb1 catalytic mutants according to embodiments of the present teachings.
Figure 33B:
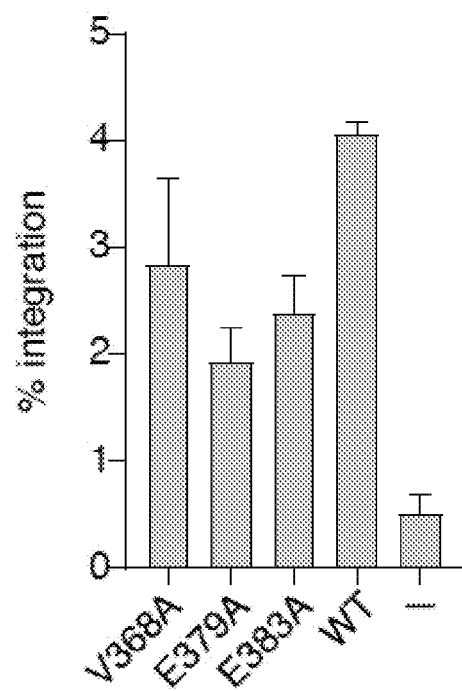
FIG. 33B shows the PASTE integration of GFP at the ACTB locus with different RT catalytic mutants according to embodiments of the present teachings.

Rational mutations were also introduced in both the Bxb1 integrase and reverse transcriptase domain of the PE2 construct to optimize PASTE further. While some of these mutations were well tolerated by PASTE (FIGS. 33A-B), none of them improved PASTE editing efficiency.

Figure 31G:
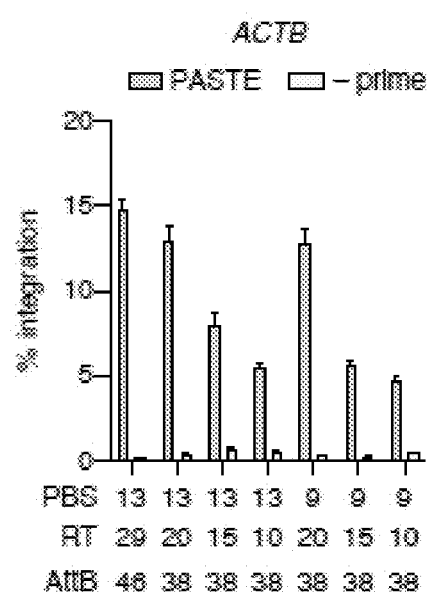
FIG. 31G shows the impact of minimal PBS, RT, and attB lengths on PASTE integration efficiency of GFP at the ACTB locus according to embodiments of the present teachings.
Figure 31H:
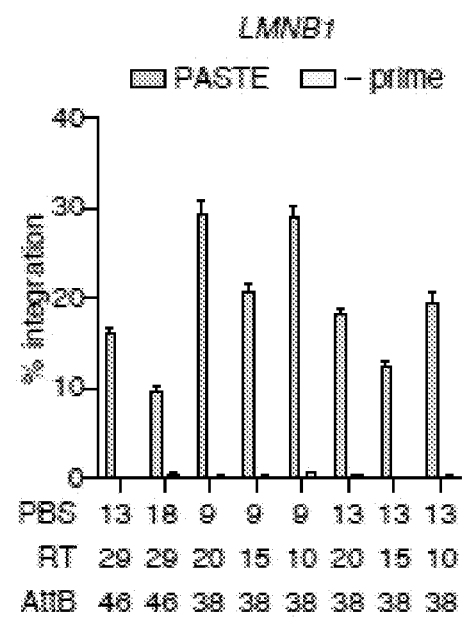
FIG. 31H shows the impact of minimal PBS, RT, and attB lengths on PASTE integration efficiency of GFP at the LAMNB locus according to embodiments of the present teachings.
Figure 31I:
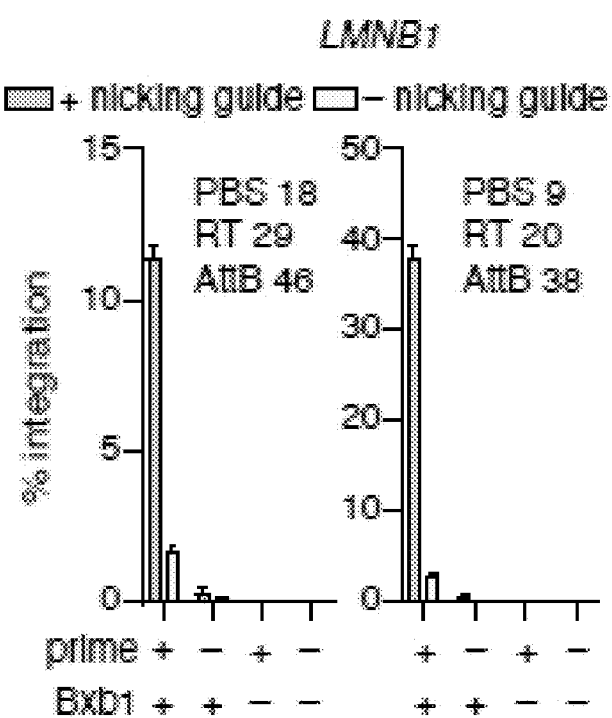
FIG. 31I shows the PASTE integration of GFP at the LMNB1 locus in the presence and absence of nicking guide, prime, and Bxb1 with a minimally compact pegRNA containing a 38 bp attB compared to a longer pegRNA design according to embodiments of the present teachings.

Short RT and PBS lengths can offer additional improvements for editing. A panel of shorter RT and PBS guides were tested at ACTB and LMNB1 loci and while shorter RT and PBS sequences did not increase editing at ACTB (FIG. 31G), it was found that they had improved editing at LMNB1 (FIG. 31H) with best performing guides reaching GFP insertion rates of ~40% (FIG. 31I).

Example 20

PASTE Tagging at Multiple Endogenous Genes

Figure 34A:
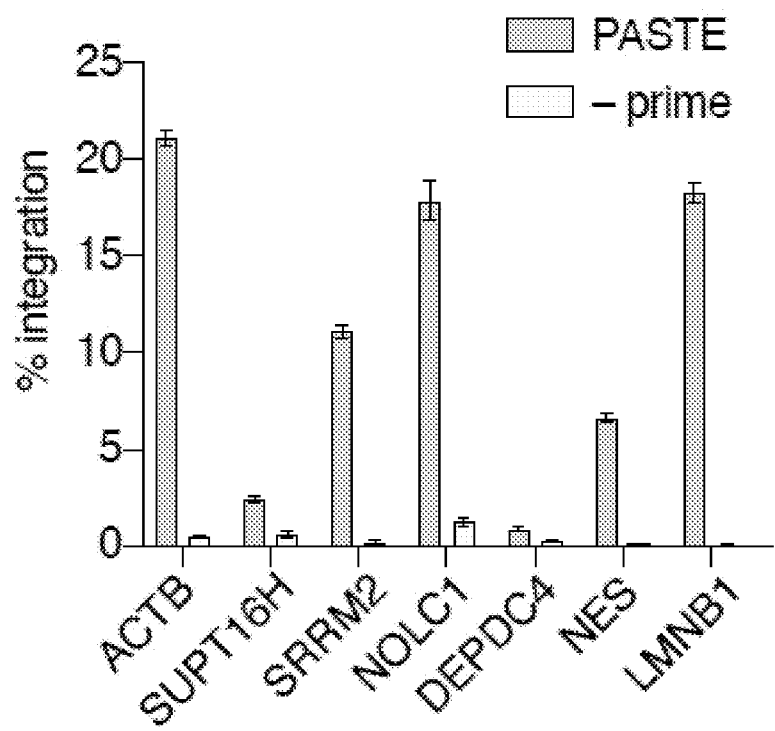
FIG. 34A shows the GFP integration by PASTE at a panel of endogenous genomic loci according to embodiments of the present teachings.
Figure 34B:
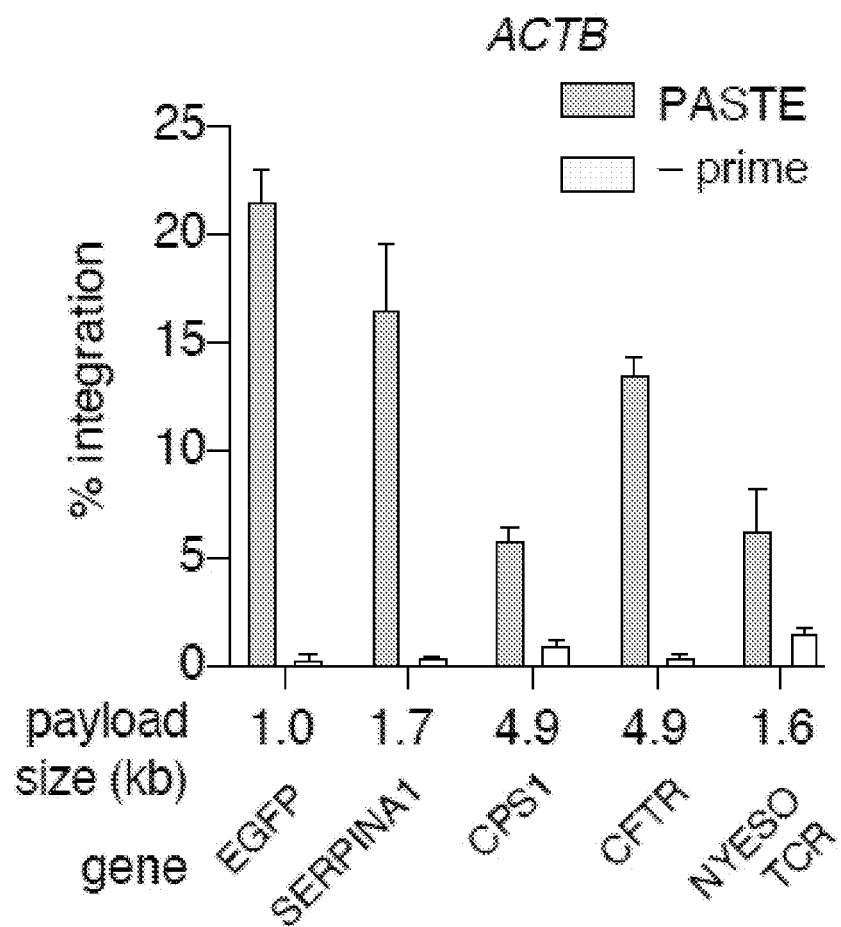
FIG. 34B shows the integration of a panel of different gene cargo at ACTB locus via PASTE according to embodiments of the present teachings.
Figure 34C:
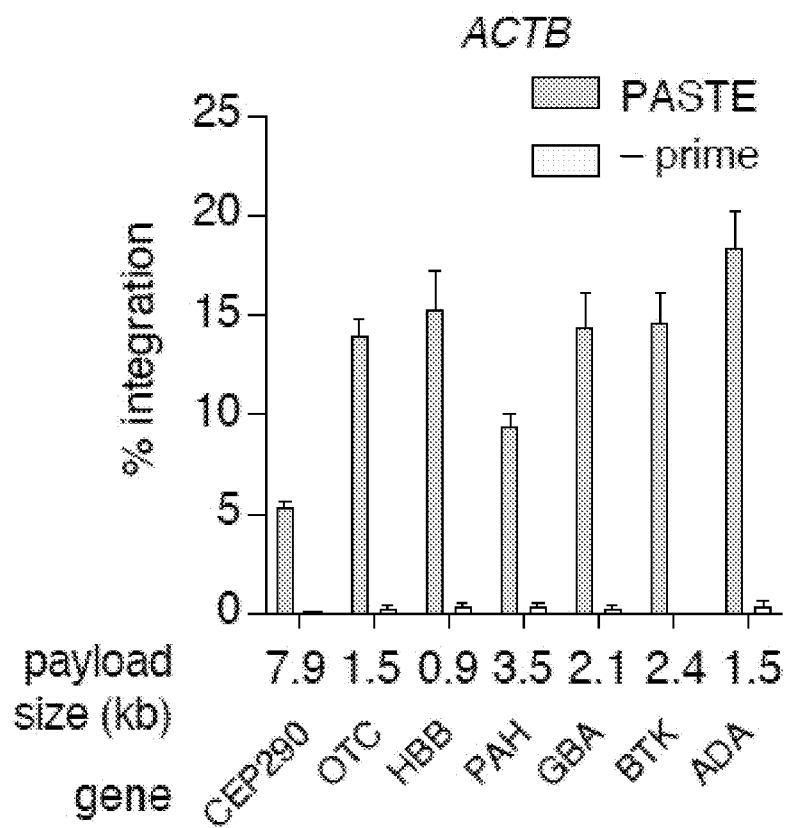
FIG. 34C shows the integration efficiency of therapeutically relevant genes at the ACTB locus according to embodiments of the present teachings.
Figure 35:
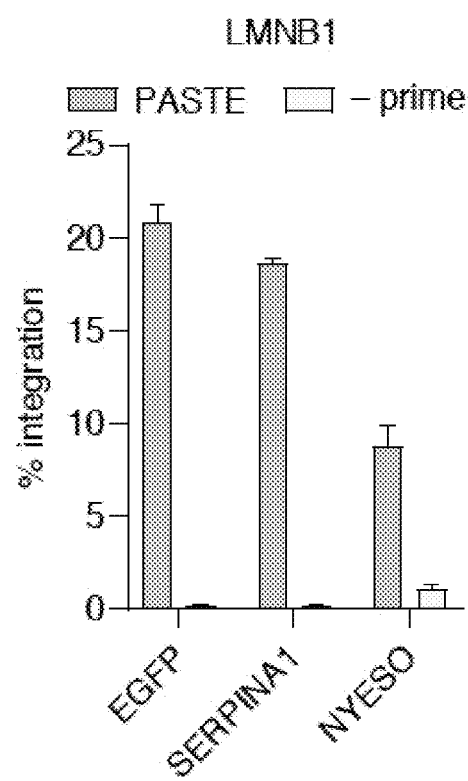
FIG. 35 shows the integration of a panel of different gene cargo at LMNB1 locus via PASTE according to embodiments of the present teachings.

GFP insertion efficiency was measured at seven different gene loci—ACTB, SUPT16H, SRRM2, NOLC1 DEPDC4, NES, and LMNB1—to test the versatility of the PASTE programming. A range of integration rates up to 22% was found (FIG. 34A). Because PASTE does not require homology or sequence similarity on cargo plasmids, integration of diverse cargo sequences is modular and easily scaled across different loci. Six different gene cargos, varying in size from 969 bp to 4906 bp, were tested for insertion at ACTB and LMNB1 loci with PASTE. Integration frequencies between 5% and 22% depending on the gene and insertion locus were found (FIGS. 34B and 35). Additionally, a panel of seven common therapeutic genes, CEP290, OTC, HBB, PAH, GBA, BTK, and ADA was evaluated for insertion at the ACTB locus, and the efficient integration of these cargos were found between 5%-20% (FIG. 34C).

Figure 34D:
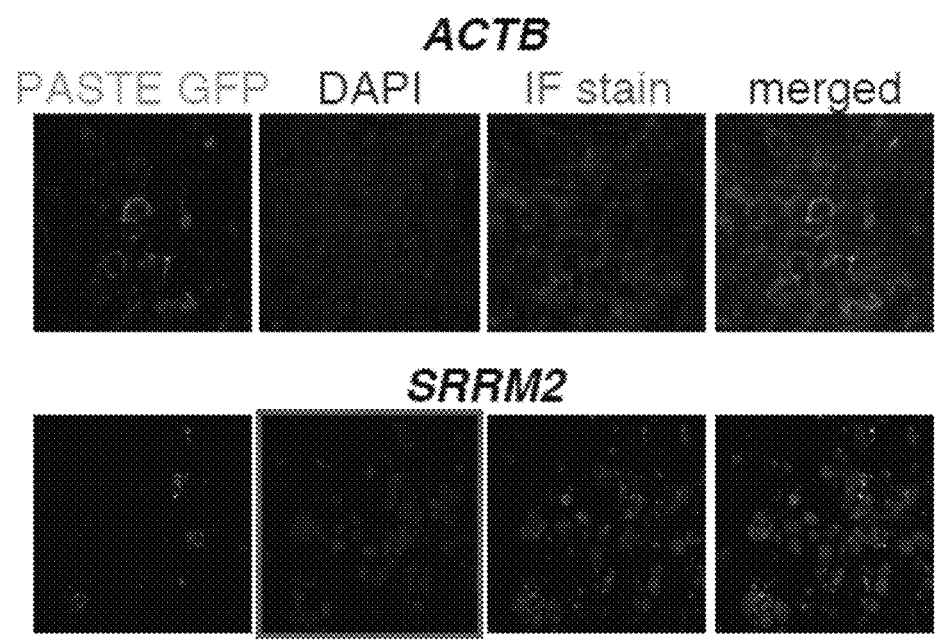
FIG. 34D shows the endogenous protein tagging with GFP via PASTE by in-frame endogenous gene tagging at the ACTB loci and SRRM2 loci according to embodiments of the present teachings.

The precise insertions of PASTE for in-frame protein tagging or expressing cargo without disruption of endogenous gene expression was assessed. As Bxb1 leaves residual sequences in the genome (termed attL and attR) after cargo integration, these genomic scars can serve as protein linkers. The frame of the attR sequence was positioned through strategic placement of the attP on the minicircle cargo, achieving a suitable protein linker, GGLSGQP-PRSPSSGSSG (SEQ ID NO: 427). Using this linker, four genes (ACTB, SRRM2, NOLC1, and LMNB1) were tagged with GFP using PASTE. To assess correct gene tagging, the subcellular location of GFP was compared with the tagged gene product by immunofluorescence. For all four targeted loci, GFP co-localized with the tagged gene product, indicating successful tagging (FIGS. 34D-E).

Example 21

Orthogonal Sequence Preferences for Bxb1 Integration

Figure 36A:
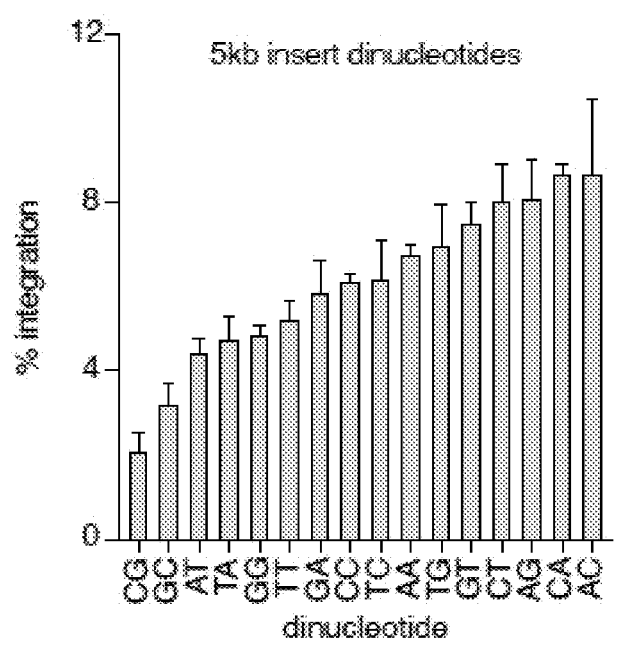
FIG. 36A shows the PASTE integration efficiency for all 16 central dinucleotide attB/attP sequence pairs with a 5 kb GFP template at the ACTB locus according to embodiments of the present teachings.

The central dinucleotide of Bxb1 is involved in the association of attB and attP sites for integration, and changing the matched central dinucleotide sequences can modify integrase activity and provide orthogonality for insertion of two genes. Expanding the set of attB/attP dinucleotides can enable multiplexed gene insertion with PASTE. The efficiency of GFP integration at the ACTB locus with PASTE across all 16 dinucleotide attB/attP sequence pairs was profiled to find optimal attB/attP dinucleotides for PASTE insertion. Several dinucleotides with integration efficiencies greater than the wild-type GT sequence were found (FIG. 36A). A majority of dinucleotides had 75% editing efficiency or greater compared to wild-type attB/attP efficiency, implying that these dinucleotides can be orthogonal channels for multiplexed gene insertion with PASTE.

Figure 36B:
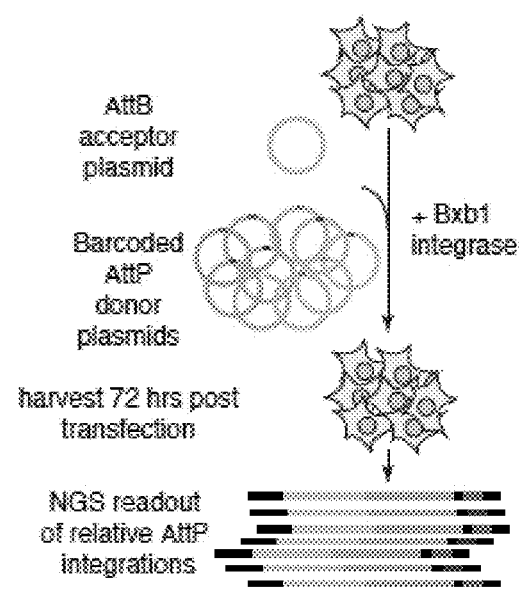
FIG. 36B shows a schematic of the pooled attB/attP dinucleotide orthogonality assay, wherein each attB dinucleotide sequence is co-transfected with a barcoded pool of all 16 attP dinucleotide sequences and Bxb1 integrase, relative integration efficiencies are determined by next generation sequencing of barcodes, and all 16 attB dinucleotides are profiled in an arrayed format with attP pools according to embodiments of the present teachings.
Figure 36C:
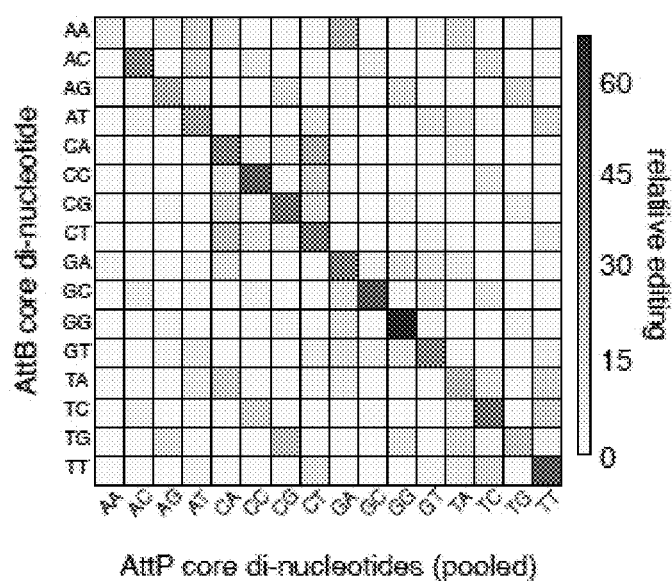
FIG. 36C shows the relative insertion preferences for all possible attB/attP dinucleotide pairs determined by the pooled orthogonality assay according to embodiments of the present teachings.
Figure 37:
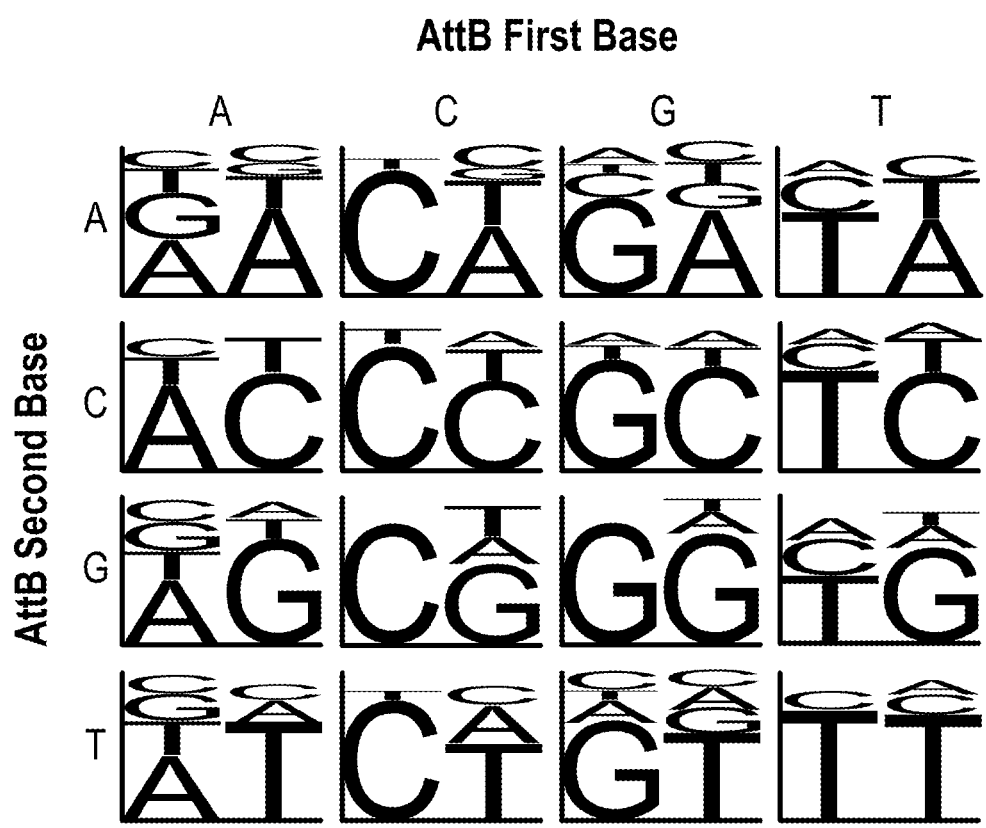
FIG. 37 shows the orthogonality of Bxb1 dinucleotides as measured by a pooled reporter assay, wherein each web logo motif shows the relative integration of different attP sequences in a pool at a denoted attB sequence with the listed dinucleotide according to embodiments of the present teachings.

The specificity of matched and unmatched attB/attP dinucleotide interactions was then assessed. The interactions between all dinucleotide combinations in a scalable fashion using a pooled assay to compare attB/attP integration were profiled (FIG. 36B). By barcoding 16 attP dinucleotide plasmids with unique identifiers, co-transfecting this attP pool with the Bxb1 integrase expression vector and a single attB dinucleotide acceptor plasmid, and sequencing the resulting integration products, the relative integration efficiencies of all possible attB/attP pairs were measured (FIG. 36C). Dinucleotide specificity was found to vary, with some dinucleotides (GG) exhibiting strong self-interaction with negligible crosstalk, and others (AA) showing minimal self-preference. Sequence logos of attP preferences (FIG. 37) revealed that dinucleotides with C or G in the first position have stronger preferences for attB dinucleotide sequences with shared first bases, while other attP dinucleotides, especially those with an A in the first position, have reduced specificity for the first attB base.

Figure 36D:
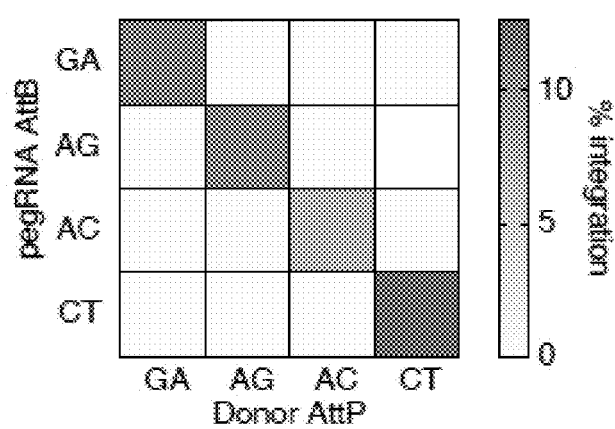
FIG. 36D shows the orthogonality of top 4 attB/attP dinucleotide pairs evaluated for GFP integration with PASTE at the ACTB locus according to embodiments of the present teachings.

GA, AG, AC, and CT dinucleotide pegRNAs were then tested for GFP integration at ACTB, either paired with their corresponding attP cargo or mispaired with the other three dinucleotide attP sequences. All four of the tested dinucleotides efficiently were found to integrate cargo only when paired with the corresponding attB/attP pair, with no detectable integration across mispaired combinations (FIG. 36D).

Example 22

Multiplex Gene Integration with PASTE

Figure 38A:
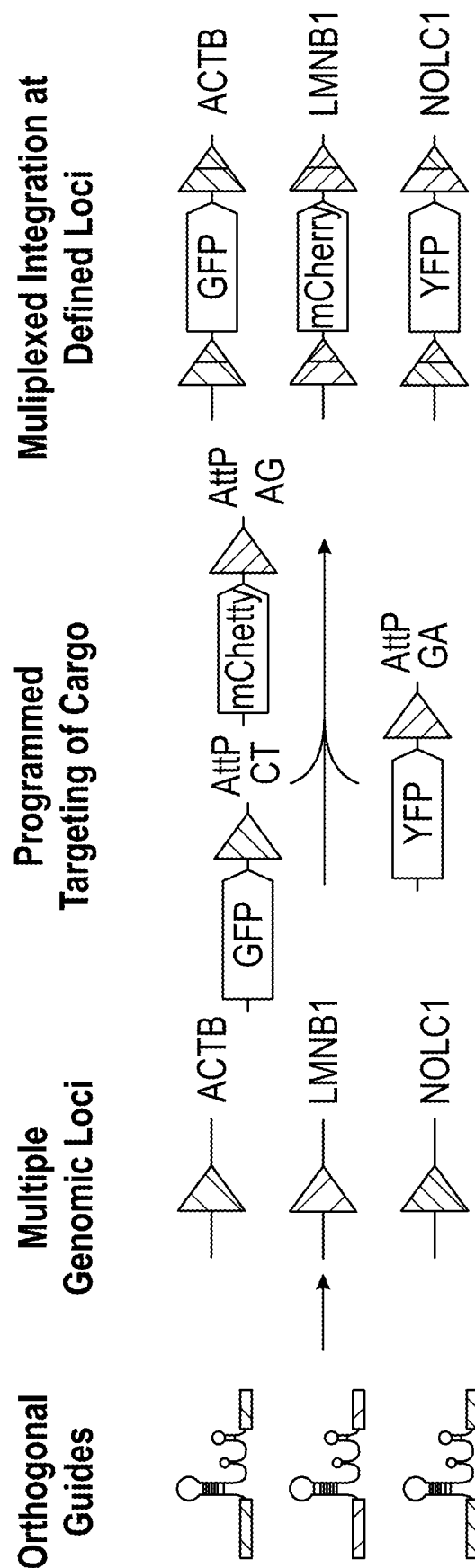
FIG. 38A shows a schematic of multiplexed integration of different cargo sets at specific genomic loci, wherein three fluorescent cargos (GFP, mCherry, and YFP) are inserted orthogonally at three different loci (ACTB, LMNB1, NOLC1) for in-frame gene tagging according to embodiments of the present teachings.
Figure 38B:
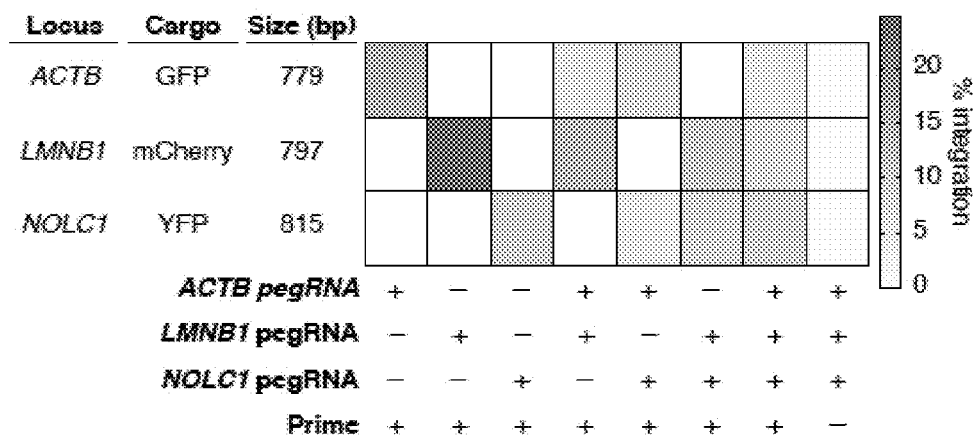
FIG. 38B shows the efficiency of multiplexed PASTE insertion of combinations of fluorophores at ACTB, LMNB1, and NOLC1 loci according to embodiments of the present teachings.

Multiplexing in cells by using orthogonal pegRNAs that direct a matched attP cargo to a specific site in the genome was assessed (FIG. 38A). Selecting the three top dinucleotide attachment site pairs (CT, AG, and GA), pegRNAs that target ACTB (CT), LMNB1 (AG), and NOLC1 (GA) and corresponding minicircle cargo containing GFP (CT), mCherry (AG), and YFP (GA) were designed. Upon co-delivering these reagents to cells, single-plex, dual-plex, and trip-plex editing of all possible combinations of these pegRNAs and cargo in the range of 5%-25% integration was found to be achieved (FIG. 38B).

An application for multiplexed gene integration is for labeling different proteins to visualize intracellular localization and interactions within the same cell. PASTE was used to simultaneously tag ACTB (GFP) and NOLC1 (mCherry) or ACTB (GFP) and LMNB1 (mCherry) in the same cell. No overlap of GFP and mCherry fluorescence was observed and tagged genes were confirmed to be visible in their appropriate cellular compartments, based on the known subcellular localizations of the ACTB, NOLC1 and LMNB1 protein products (FIGS. 15A-B).

Example 23

PASTE Efficiencies Compared with DSB-Based Insertion Methods

PASTE efficiencies were found to exceed comparable DSB-based insertion methods.

Figure 39A:
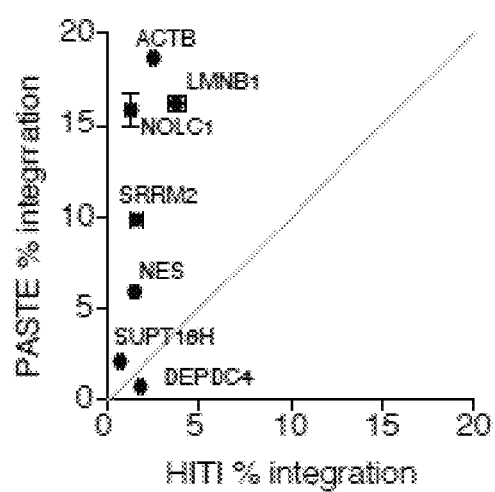
FIG. 39A shows the GFP integration efficiency at a panel of genomic loci by PASTE compared to insertion rates by homology-independent targeted integration (HITI) according to embodiments of the present teachings.
Figure 39B:
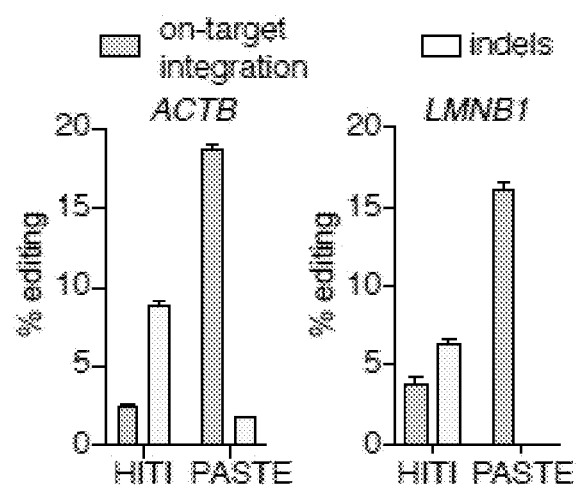
FIG. 39B shows a comparison of unintended indel generation by PASTE and HITI at the ACTB and LMNB1 target sites, wherein the on-target EGFP integration rate observed compared to unintended indels is shown according to embodiments of the present teachings.
Figure 39C:
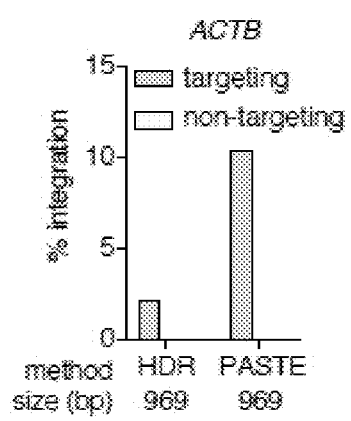
FIG. 39C shows the integration of a GFP template by PASTE at the ACTB locus compared to homology-directed repair (HDR) at the same target, wherein the quantification is by single-cell clone counting, wherein targeting and non-targeting guides were used for HDR insertion, and wherein for PASTE targeting and non-targeting refers to the presence or absence of the SpCas9-RT protein respectively according to embodiments of the present teachings.
Figure 39D:
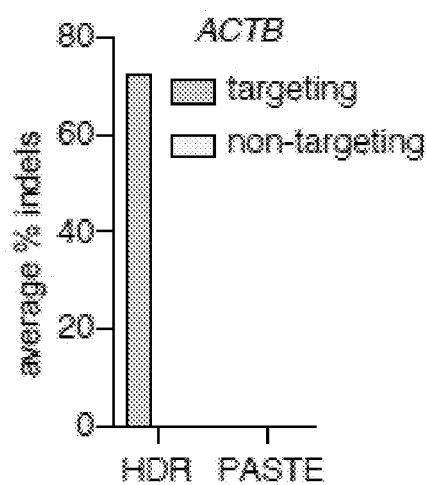
FIG. 39D shows the comparison of unintended indel generation by PASTE and HDR based EGFP insertion at the ACTB target site, wherein the average indel rate measured across all single-cell clones generated is showed according to embodiments of the present teachings.
Figure 40A:
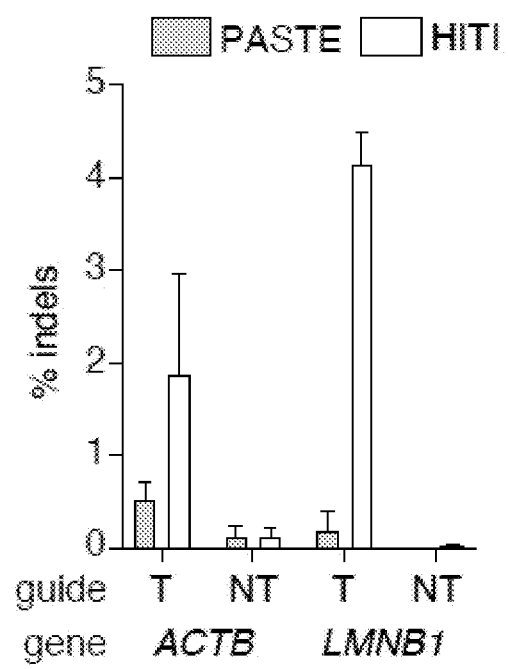
FIG. 40A shows a comparison of indel rates generated by PASTE and HITI mediated insertion of EGFP at the ACTB and LMNB1 loci in HepG2 cells according to embodiments of the present teachings.
Figure 40B:
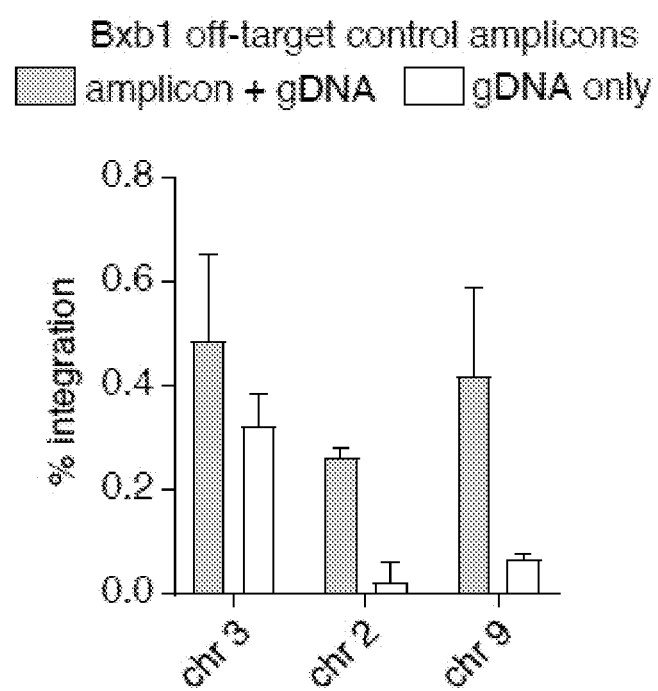
FIG. 40B shows the validation of ddPCR assays for detecting editing at predicted Bxb1 offtarget sites using synthetic amplicons according to embodiments of the present teachings.
Figure 40C:
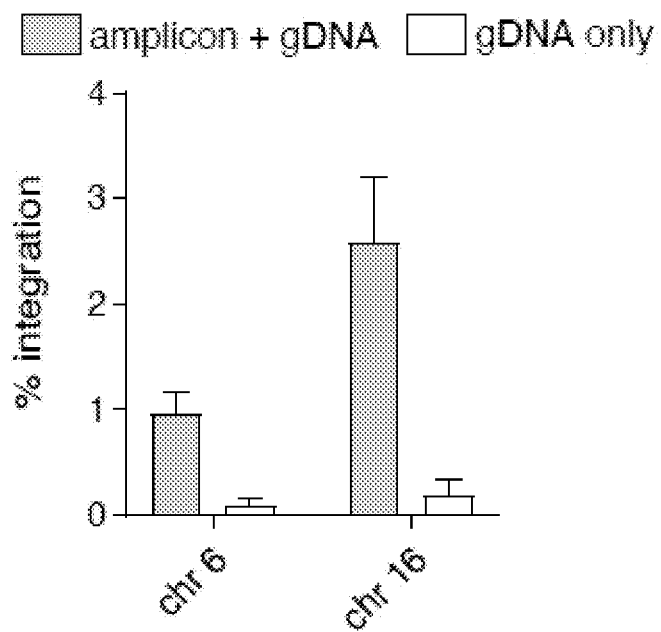
Figure 40D:
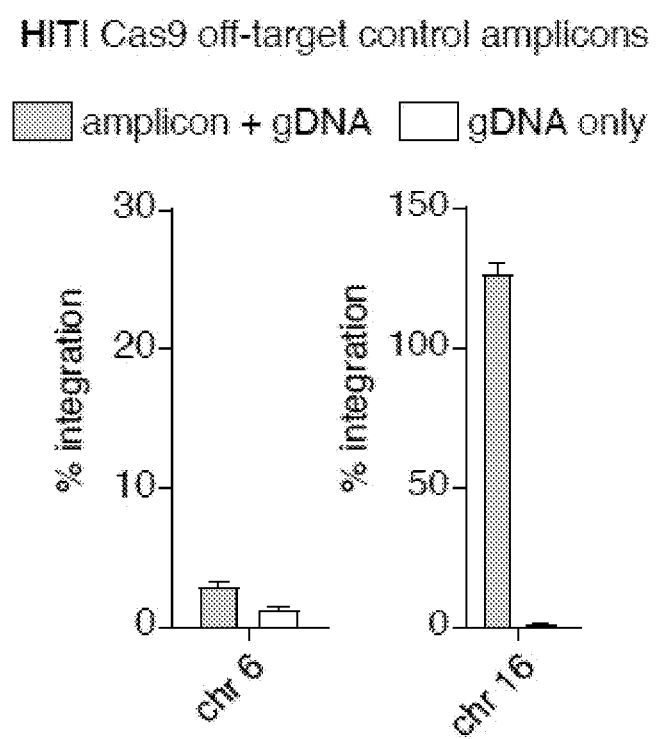

PASTE editing was assessed alongside DSB-dependent gene integration using either NHEJ (i.e., homology-independent targeted integration, HITI) or HDR pathways. PASTE had equivalent or better gene insertion efficiencies than either HITI (FIGS. 39A-B) or HDR (FIGS. 39C-D). On a panel of 7 different endogenous targets, PASTE exceeded HITI editing at 6 out of 7 genes, with similar efficiency for the 7th gene (FIG. 39A). As DSB generation can lead to insertions or deletions (indels) as an alternative and undesired editing outcome, the indel frequency of all three methods was assessed by next-generation sequencing, finding significantly fewer indels generated with PASTE than either HDR or HITI in both HEK293FT and HepG2 cells (FIGS. 39B, 39D and 40A), showcasing the high purity of gene integration outcomes with PASTE.

Example 24

Off-Target Characterization of PASTE and HITI Gene Integration

Figure 39E:
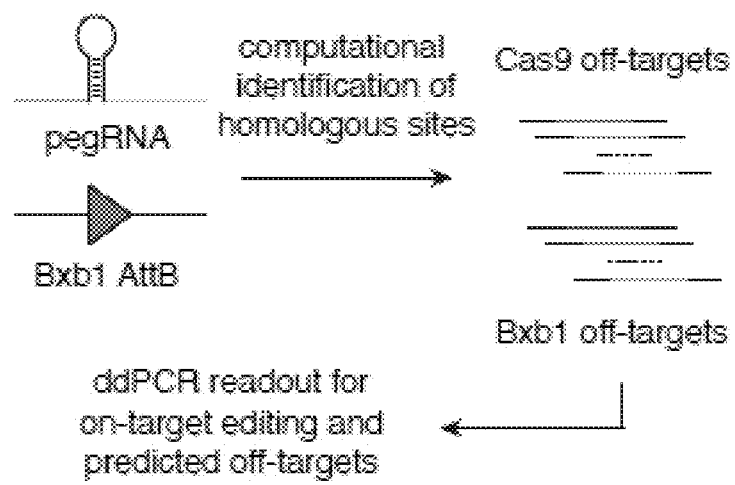
FIG. 39E shows a schematic for Bxb1 and Cas9 off-target identification and a detection assay according to embodiments of the present teachings.
Figure 39F:
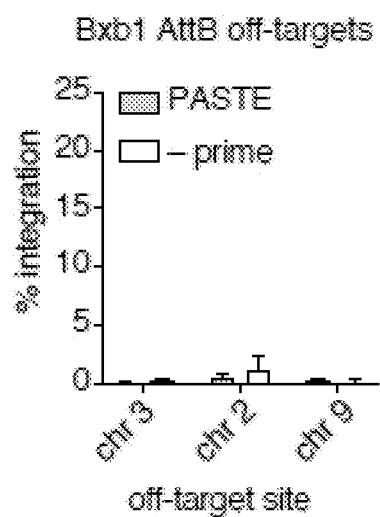
FIG. 39F shows the GFP integration activity at predicted Bxb1 off-target sites in the human genome according to embodiments of the present teachings.
Figure 39G:
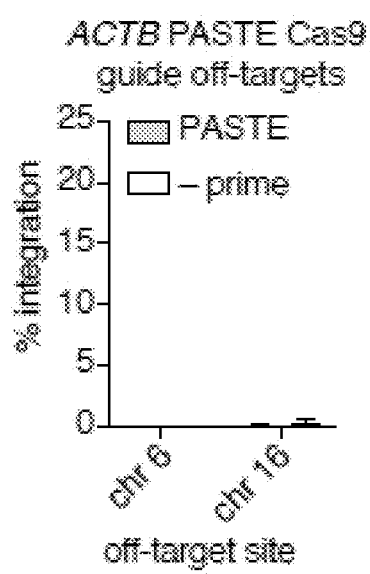
FIG. 39G shows the GFP integrations activity at predicted PASTE ACTB Cas9 guide off target sites according to embodiments of the present teachings.
Figure 39H:
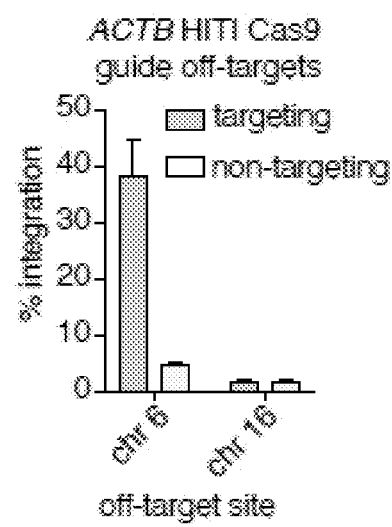
FIG. 39H shows the GFP integration activity at predicted HITI ACTB Cas9 guide off-target sites according to embodiments of the present teachings.

Off-target editing can be used in genome editing technologies. The specificity of PASTE at specific sites was assessed based on off-targets generated by Bxb1 integration into pseudo-attB sites in the human genome and off-targets generated via guide- and Cas9-dependent editing in the human genome (FIG. 39E). While Bxb1 lacks documented integration into the human genome at pseudo-attachment sites, potential sites with partial similarity to the natural Bxb1 attB core sequence were computationally identified. Bxb1 integration by ddPCR across these sites was tested and no off-target activity was found (FIGS. 39F and 40B-D). To assay Cas9 off-targets for the ACTB pegRNA, two potential off-target sites were identified via computational prediction and no off-target integration for PASTE was found (FIGS. 39G and 40A-D), but substantial off-target activity by HITI at one of the sites was found (FIGS. 39H and 40A-D).

Figure 39I:
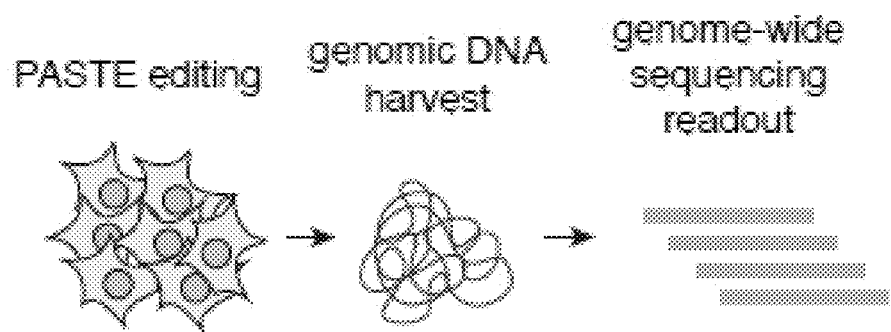
FIG. 39I shows a schematic of next-generation sequencing method to assay genome-wide off-target integration sites by PASTE according to embodiments of the present teachings.
Figure 39J:
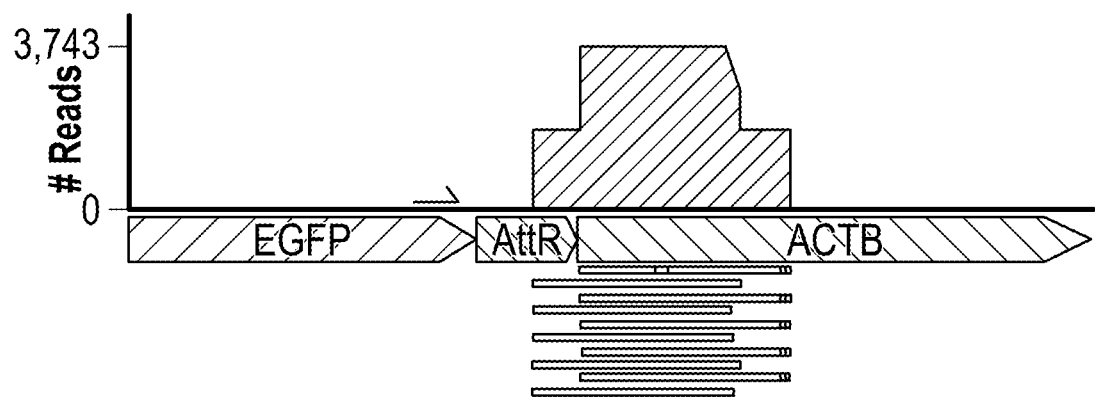
FIG. 39J shows the alignment of reads at the on-target ACTB site using a genome-wide integration assay, wherein expected on-target integration outcomes are shown according to embodiments of the present teachings.
Figure 39K:
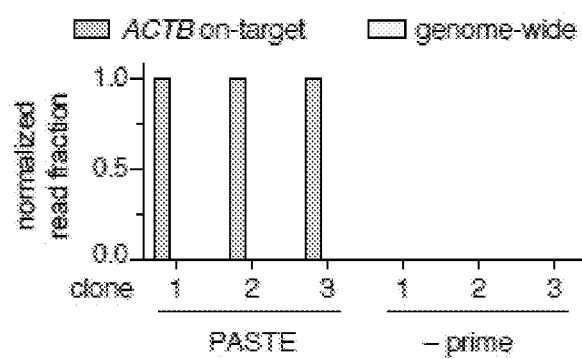
FIG. 39K shows the analysis of on-target and off-target integration events across 3 single-cell clones for PASTE and 3 single-cell clones for no prime condition according to embodiments of the present teachings.
Figure 39L:
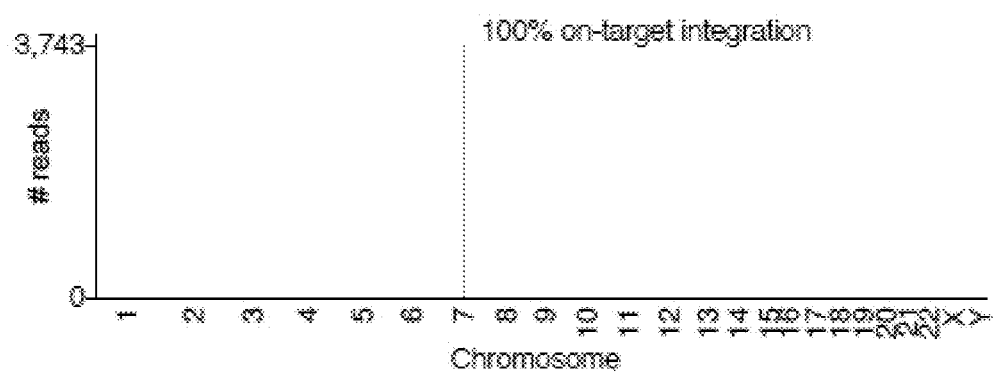
FIG. 39L shows a Manhattan plot of integration events for a representative single-cell clone with PASTE editing, wherein the on-target site is at the ACTB gene on chromosome 7 according to embodiments of the present teachings.

Genome-wide off-targets due to either Cas9 or Bxb1 through tagging and PCR amplification of insert-genomic junctions were additionally assessed (FIG. 39I). Single cell clones were isolated for conditions with PASTE editing and negative controls missing PE2, and deep sequencing of insert genomic junctions from these clones showed all reads aligning to the on-target ACTB site, confirming no off-target genomic insertions (FIGS. 39J-L).

Expression of reverse transcriptases and integrases involved in PASTE can have detrimental effects on cellular health. The complete PASTE system, the corresponding guides and cargo with only PE2, and the corresponding guides and cargo with only Bxb1 were transfected and compared to both GFP control transfections and guides without protein expression via transcriptome-wide RNA sequencing to determine the extent of these effects. While Bxb1 expression in the absence of Prime editing was found to have several significant off targets, the complete PASTE system had only one differentially regulated gene with more than a 1.5-fold change (FIGS. 41A-B). Genes upregulated by Bxb1 overexpression included stress response genes, such as TENT5C and DDIT3, but these changes were not seen in the expression of the PASTE system (FIG. 41C), potentially due to the decreased expression of Bxb1 from the P2A linker on the PASTE construct.

Example 25

PASTE Efficiency in Non-Dividing Cell

PASTE activity in non-dividing cells was assessed. Cas9 and HDR templates or PASTE were transfected into HEK293FT cells and cell division was arrested via aphidicolin treatment (FIG. 42A). In this model of blocked cell division, PASTE was found to maintain a GFP gene integration activity greater than 20% at the ACTB locus whereas HDR-mediated integration was abolished (FIGS. 42B and 43A).

Example 26

Production and Secretion of Therapeutic Transgene

PASTE with larger transgenes and in additional cell lines were assessed.

To evaluate the size limits for therapeutic transgenes, insertion of cargos up to 13.3 kb in length in both dividing and aphidicolin treated cells was assessed. Insertion efficiency greater than 10% was found (FIG. 42C), enabling insertion of ~99.7% of all full-length human cDNA transgenes. To overcome reduction of large insert delivery to cells because of delivery inefficiencies, delivering larger DNA amounts of insert was found to significantly improve gene integration efficiency (FIG. 43B). PASTE editing to additional cell types such as PASTE in the K562 lymphoblast line and in primary human T cells were also assessed. Both PE2-P2A-Bxb1 (PASTE) and separate delivery of PE2 and Bxb1 were found to result in efficient editing in both cell types (FIGS. 42D-E). Lastly, as therapeutic delivery of PASTE in vivo might require viral delivery of the DNA cargo, whether AAV could deliver an attP containing payload that could be integrated into the genome via Bxb1 was evaluated. Targeting the ACTB locus, AAV was found to be capable of delivering the appropriate template for integrase mediated insertion with rates up to 4% in a dose dependent fashion (FIGS. 42F and 43C).

To improve the efficiency of PASTE, PE2* NLS was incorporated for prime editing and improved PASTE integration at multiple loci was found (FIG. 44A). Furthermore, PE2* resulted in more robust integration at lower titrations of cargo plasmid, demonstrating integration at amounts as low as 8 ng of plasmid (FIG. 44B). To combat reductions in PASTE efficiency due to incomplete plasmid delivery, a puromycin resistance gene was co-delivered and found to increase the PASTE efficiency in the presence of drug selection (FIG. 45).

Programmable gene integration provides a modality for expression of therapeutic protein products, and protein production was assessed for therapeutically relevant proteins Alpha-1 antitrypsin (encoded by SERPINA1) and Carbamoyl phosphate synthetase I (encoded by CPS1), involved in the diseases Alpha-1 antitrypsin deficiency and CPS1 deficiency, respectively. By tagging gene products with the luminescent protein subunit HiBiT, the transgene production and secretion were assessed independently in response to PASTE treatment (FIG. 42G). PASTE was transfected with SERPINA1 or CPS1 cargo in HEK293FT cells and a human hepatocellular carcinoma cell line (HepG2) and efficient integration at the ACTB locus was found (FIG. 42H-I). This integration resulted in robust protein expression, intracellular accumulation of transgene products (FIGS. 42J and 46A-B), and secretion of proteins into the media (FIG. 42K).

Example 27

Optimized PASTE Constructs

To optimize complex activity, a panel of protein modifications were screened, including alternative reverse transcriptase fusions and mutations, various linkers between the reverse transcriptase domain and integrase and between the Cas9 and reverse transcriptase domain, and reverse transcriptase and BxbINT domain mutants (FIG. 47A and FIG. 49C-FIG. 49F). A number of protein modifications, including a 48 residue XTEN linker between the Cas9 and reverse transcriptase and the fusion of MMuLV to the Sto7d DNA binding domain (Oscorbin et al. FEBS Lett. 594. 4338-4356. 2020) improved editing efficiency (FIG. 47A and FIG. 49C-FIG. 49D). When these top modifications were combined with a GGGGS linker (SEQ ID NO: 420) between the reverse transcriptase-Sto7d domain and the BxbINT, they produced ~55% gene integration, highlighting the importance of directly recruiting the integrase to the target site (FIG. 47A). This optimized construct was referred to as SpCas9-(XTEN-48)-RT-Sto7d-(GGGGS)-BxbINT. The optimized construct achieved precise integration of templates as large as ~36,000 bp with ~20% integration efficiency (FIG. 47A), with complete integration of the full-length cargo confirmed by Sanger sequencing.

Additionally, pegRNAs containing different AttB length truncations were tested and found that prime editing was capable of inserting sequences up to 56 bp at the beta-actin (ACTB) gene locus, with higher efficiency at lengths below 31 bp (FIG. 48A-FIG. 48B). A panel of multiple enzymes was evaluated, including Bxb1 (i.e., BxbINT), TP901 (i.e., Tp9INT), and phiBTI (i.e., Bt1INT) phage serine integrases. Prime editing successfully inserted all landing sites tested, with efficiencies between 10-30% (FIG. 48C-FIG. 48D)

Example 28

Viral Delivery & In Vivo Editing

In order to package the complete PASTE system in viral vectors, an AdV vector was utilized (FIG. 50B). Adenovirus was evaluated for if it could deliver a suitable template for BxbINT-mediated insertion along with plasmids for SpCas9-RT-BxbINT and guide expression, or AdV delivery of guides and BxbINT with plasmid delivery of SpCas9-RT, finding that 10-20% integration of the ~36 kb adenovirus genome carrying EGFP in HEK293FT and HepG2 cells was achieved (FIG. 50C). Upon packaging and delivering the cargo and PASTE system components across 3 AdV vectors, the complete PASTE system (Cas9-reverse transcriptase, integrase and guide RNAs, or cargo) could be substituted by adenoviral delivery, with integration of up to ~50-60% with viral-only delivery in HEK293FT and HepG2 cells (FIG. 50D).

To further demonstrate PASTE would be amenable for in vivo delivery, an mRNA version of the PASTE protein components was developed as well as chemically-modified synthetic atgRNA and nicking guide against the LMNB1 target (FIG. 50E). Electroporation of the mRNA and guides along with delivery of the template via adenovirus or plasmid yielded high efficiency integration up to ~23% (FIG. 50E-FIG. 50F). More sustained BxbINT expression could allow for integration into newly placed AttB sites in the genome, so circular mRNA expression was tested and found to boost the efficiency of integration to ~30% (FIG. 50G-FIG. 50I).

Example 29

Simultaneous Deletion & Insertion With PASTE

The PASTE system was used to simultaneously delete one sequence and insert another. 130 bp and 385 bp deletions of first exon of LMNB1 with combined insertion of AttB nucleic acid sequence was performed (FIG. 51A). This data shows that it is possible to replace DNA sequence using the PASTE system.

A130 bp deletion of the first exon of LMNB1 with combined insertion of a 967 bp cargo using the PASTE system was also performed.

One of two attP sequences were inserted using the mini circle template that has mutated AttP, as described above. This AttP mutants shows better integration kinetics and efficiency, especially for the shorter AttBs (38-44 bp). The LMNB1 AttB used in this experiment is 38 bp (FIG. 51B).

What is claimed is:

1. A system capable of site-specifically integrating an exogenous nucleic acid into a mammalian cell genome at a desired target site, wherein the system comprises, in a single composition:
   (a) a nucleic acid encoding a DNA binding nickase domain linked to a reverse transcriptase domain;
   (b) a nucleic acid encoding at least two guide RNAs (gRNAs) comprising, from 3' to 5',
      i. a primer binding sequence,
      ii. a sequence complementary to one strand of an integration recognition sequence, and
      iii. a target binding sequence,
      wherein the gRNA is capable of guiding the linked nickase-reverse transcriptase domains to the genomic target site;
   (c) nucleic acid encoding an integration enzyme; and
   (d) an exogenous nucleic acid linked to a sequence that is an integration cognate of the integration recognition sequence.

2. The system of claim 1, wherein the DNA binding nickase domain is linked to the reverse transcriptase domain by in-frame fusion.

3. The system of claim 1, wherein the DNA binding nickase domain is linked to the reverse transcriptase domain by a linker.

4. The system of claim 3, wherein the linker is a peptide fused in-frame between the nickase and reverse transcriptase domains.

5. The system of claim 1, wherein the linked DNA binding nickase-reverse transcriptase domains are further linked to the integration enzyme.

6. The system of claim 1, wherein the DNA binding nickase domain is selected from Cas9-D10A, Cas9-H840A, and Cas12a/b nickase.

7. The system of claim 1, wherein the reverse transcriptase domain is selected from the group consisting of Moloney Murine Leukemia Virus (M-MLV) reverse transcriptase domain, transcription xenopolymerase (RTX), avian myeloblastosis virus reverse transcriptase (AMV-RT), and *Eubacterium rectale* maturase RT.

8. The system of claim 7, wherein the reverse transcriptase domain is a M-MLV reverse transcriptase domain.

9. The system of claim 7, wherein the M-MLV reverse transcriptase domain comprises one or more mutations selected from the group consisting of D200N, T306K, W313F, T330P, and L603W.

10. The system of claim 1, wherein the exogenous nucleic acid is a minicircle, a plasmid, a mRNA, or a linear DNA.

11. The system of claim 9, wherein exogenous nucleic acid is a minicircle.

12. The system of claim 11, wherein the minicircle does not comprise a sequence of a bacterial origin.

13. The system of claim 1, wherein the integration enzyme is selected from the group consisting of Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Te1, Tc3, Mariner Rimar 1, Mariner mos-1, and Minos.

14. The system of claim 13, wherein the integration enzyme is Bxb1.

15. The system of claim 13, wherein the integration recognition sequence is an attB sequence, an attP sequence, a Vox sequence, or a FRT sequence.

16. The system of claim 15, wherein the integration recognition sequence is an attB sequence and the integration cognate is an attP sequence.

17. The system of claim 15, wherein the exogenous nucleic acid encodes:
   a reporter gene;
   a degradation tag for programmable knockdown of proteins in the presence of small molecules;
   a T-cell receptor (TCR), a chimeric antigen receptor (CAR), an interleukin, a cytokine, or an immune checkpoint gene and the mammalian cell is a T-cell or natural killer (NK) cell;
   a beta hemoglobin (HBB) gene and the mammalian cell is a hematopoietic stem cell (HSC);
   a metabolic gene; or
   a gene involved in an inherited disease or syndrome.

18. The system of claim 1, wherein the exogenous nucleic acid is between 1000 bp and 36,000 bp in length.

19. The system of claim 1, wherein the exogenous nucleic acid is more than 36,000 bp in length.

20. The system of claim 1, wherein the exogenous nucleic acid is less than 1000 bp in length.

21. The system of claim 17, wherein the inherited disease is cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

22. The system of claim 1, further comprising a nicking gRNA.

23. The system of claim 1, wherein a)-d) are introduced into the mammalian cell in an adeno-associated virus (AAV) or an adenovirus (AdV).

24. The system of claim 1, wherein the nucleic acid encoding at least two gRNAs comprises a nucleic acid encoding two gRNAs.

25. The system of claim 1, wherein the composition is ex vivo or in vitro.

* * * * *

UNITED STATES PATENT AND TRADEMARK OFFICE
CERTIFICATE OF CORRECTION

| | | |
|---|---|---|
| PATENT NO. | : 11,952,571 B2 | Page 1 of 1 |
| APPLICATION NO. | : 18/487744 | |
| DATED | : April 9, 2024 | |
| INVENTOR(S) | : Abudayyeh et al. | |

It is certified that error appears in the above-identified patent and that said Letters Patent is hereby corrected as shown below:

In the Specification

Column 1, Line 18, after paragraph "CROSS REFERENCE TO RELATED APPLICATIONS" insert heading & paragraph:
--GOVERNMENT SUPPORT
This invention was made with government support under EB031957 awarded by the National Institutes of Health. The government has certain rights in the invention.--

Signed and Sealed this
Eleventh Day of November, 2025

John A. Squires
*Director of the United States Patent and Trademark Office*